United States Patent
Chandrasekhar et al.

(10) Patent No.: US 10,214,519 B2
(45) Date of Patent: Feb. 26, 2019

(54) PHOSPHATIDYLINOSITOL 3-KINASE INHIBITORS

(71) Applicant: Gilead Sciences, Inc., Foster City, CA (US)

(72) Inventors: Jayaraman Chandrasekhar, Redmond, WA (US); Julian Andrew Codelli, Seattle, WA (US); Devan Naduthambi, San Bruno, CA (US); Leena Patel, Seattle, WA (US); Stephane Perreault, Brier, WA (US); Gary Phillips, Issaquah, WA (US); Kassandra F. Sedillo, Seattle, WA (US); Jennifer Anne Treiberg, Redmond, WA (US); Joshua Van Veldhuizen, Seattle, WA (US); William J. Watkins, Saratoga, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/711,957

(22) Filed: Sep. 21, 2017

(65) Prior Publication Data
US 2018/0086747 A1    Mar. 29, 2018

Related U.S. Application Data

(60) Provisional application No. 62/398,774, filed on Sep. 23, 2016.

(51) Int. Cl.
| | |
|---|---|
| *C07D 413/14* | (2006.01) |
| *A61K 31/5377* | (2006.01) |
| *C07D 417/14* | (2006.01) |
| *C07D 405/14* | (2006.01) |
| *C07D 409/14* | (2006.01) |
| *A61K 45/06* | (2006.01) |

(52) U.S. Cl.
CPC ........ *C07D 413/14* (2013.01); *A61K 31/5377* (2013.01); *A61K 45/06* (2013.01); *C07D 405/14* (2013.01); *C07D 409/14* (2013.01); *C07D 417/14* (2013.01); *A61K 2300/00* (2013.01)

(58) Field of Classification Search
CPC .......... C07D 413/14; A61K 31/5377
See application file for complete search history.

(56) References Cited

U.S. PATENT DOCUMENTS

| | | | |
|---|---|---|---|
| 6,060,479 | A | 5/2000 | Chenard et al. |
| 6,369,092 | B1 | 4/2002 | Pamukcu et al. |
| 6,596,723 | B1 | 7/2003 | Watkins et al. |
| 7,071,189 | B2 | 7/2006 | Kawashima et al. |
| 7,476,670 | B2 | 1/2009 | Bordon-Pallier et al. |
| 8,138,183 | B2 | 3/2012 | Pike |
| 8,158,624 | B2 | 4/2012 | Castanedo et al. |
| 8,158,625 | B2 | 4/2012 | Castanedo et al. |
| 8,173,650 | B2 | 5/2012 | Castanedo et al. |
| 8,193,182 | B2 | 6/2012 | Ren et al. |
| 8,288,381 | B2 | 10/2012 | Pei et al. |
| 8,329,910 | B2 | 12/2012 | Chen et al. |
| 8,343,955 | B2 | 1/2013 | Blaquiere et al. |
| 8,362,241 | B2 | 1/2013 | D'Angelo et al. |

(Continued)

FOREIGN PATENT DOCUMENTS

| | | |
|---|---|---|
| EP | 0 884 310 A1 | 12/1998 |
| EP | 0 884 310 B1 | 12/1998 |

(Continued)

OTHER PUBLICATIONS

Ahearn, T.U. et al. (2016, e-pub. Nov. 27, 2015). "A Prospective Investigation of PTEN Loss and ERG Expression in Lethal Prostate Cancer," *JNCI Natl Cancer Inst* 108(2):djv346, 9 pages.

(Continued)

*Primary Examiner* — Golam M Shameem
(74) *Attorney, Agent, or Firm* — Morrison & Foerster LLP

(57) ABSTRACT

The present application provides the compounds of formula I or IA

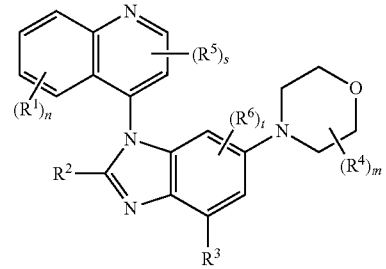

Formula I

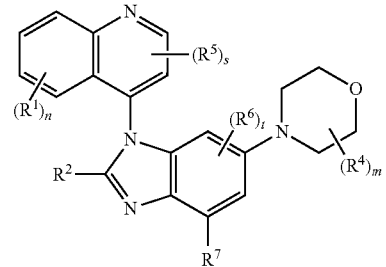

Formula IA or pharmaceutically acceptable salts, isomers, tautomer, or a mixture thereof, wherein s, t, m, n, $R^1$, $R^2$, $R^3$, $R^4$, $R^5$, $R^6$ and $R^7$ are as described herein.

20 Claims, No Drawings

(56) References Cited

U.S. PATENT DOCUMENTS

| | | | |
|---|---|---|---|
| 8,383,620 B2 | 2/2013 | Bayliss et al. | |
| 8,394,796 B2 | 3/2013 | Castanedo et al. | |
| 8,399,460 B2 | 3/2013 | Barlaam et al. | |
| 8,399,690 B2 | 3/2013 | Do et al. | |
| 8,435,988 B2 | 5/2013 | Qu et al. | |
| 8,445,487 B2 | 5/2013 | Castanedo et al. | |
| 8,450,315 B2 | 5/2013 | Castanedo et al. | |
| 8,530,470 B2 | 9/2013 | Barlaam et al. | |
| 8,536,161 B2 | 9/2013 | Ebens, Jr. et al. | |
| 8,569,323 B2 | 10/2013 | Ren et al. | |
| 8,575,183 B2 | 11/2013 | Cushing et al. | |
| 8,586,574 B2 | 11/2013 | Blaquiere et al. | |
| 8,586,739 B2 | 11/2013 | Chen et al. | |
| 8,633,313 B2 | 1/2014 | Cushing et al. | |
| 8,653,098 B2 | 2/2014 | Dotson et al. | |
| 8,673,906 B2 | 3/2014 | Barlaam et al. | |
| 8,686,137 B2 | 4/2014 | Dransfield | |
| 8,716,290 B2 | 5/2014 | Bui et al. | |
| 8,729,074 B2 | 5/2014 | Bo et al. | |
| 8,754,089 B2 | 6/2014 | Cushing et al. | |
| 8,765,940 B2 | 7/2014 | Brown et al. | |
| 8,785,626 B2 | 7/2014 | Blaquiere et al. | |
| 8,846,762 B2 | 9/2014 | Do et al. | |
| 8,852,590 B2 | 10/2014 | Sathyanarayanan et al. | |
| 8,883,799 B2 | 11/2014 | Dotson et al. | |
| 9,029,374 B2 | 5/2015 | Barlaam et al. | |
| 9,029,384 B2 * | 5/2015 | Evarts | C07D 473/34 514/263.21 |
| 9,221,795 B2 * | 12/2015 | Evarts | A61K 31/517 |
| 9,266,878 B2 * | 2/2016 | Evarts | C07D 471/08 |
| 9,499,523 B2 * | 11/2016 | Kim | C07D 487/04 |
| 9,765,060 B2 * | 9/2017 | Evarts | C07D 403/12 |
| 2002/0161014 A1 | 10/2002 | Sadhu et al. | |
| 2003/0220338 A1 | 11/2003 | Watkins et al. | |
| 2003/0229097 A1 | 12/2003 | Watkins et al. | |
| 2004/0116421 A1 | 6/2004 | Kawashima et al. | |
| 2006/0025406 A1 | 2/2006 | Zembower et al. | |
| 2008/0113987 A1 | 5/2008 | Haruta et al. | |
| 2008/0234299 A1 | 9/2008 | Buchstaller et al. | |
| 2009/0197889 A1 | 8/2009 | Winfield | |
| 2009/0264384 A1 | 10/2009 | Didsbury et al. | |
| 2009/0312319 A1 | 12/2009 | Ren et al. | |
| 2009/0318434 A1 | 12/2009 | Blade et al. | |
| 2010/0032593 A1 | 2/2010 | Yarbrough et al. | |
| 2011/0098271 A1 | 4/2011 | Barlaam et al. | |
| 2011/0152277 A1 | 6/2011 | Chen et al. | |
| 2011/0152296 A1 | 6/2011 | Cushing et al. | |
| 2011/0172216 A1 | 7/2011 | Dotson et al. | |
| 2011/0217300 A1 | 9/2011 | Liu et al. | |
| 2011/0245257 A1 | 10/2011 | Cushing et al. | |
| 2011/0275653 A1 | 11/2011 | Chen et al. | |
| 2011/0281897 A1 | 11/2011 | Chen et al. | |
| 2012/0035208 A1 | 2/2012 | Dotson et al. | |
| 2012/0071474 A1 | 3/2012 | Bo et al. | |
| 2012/0094972 A1 | 4/2012 | Brown et al. | |
| 2012/0094997 A1 | 4/2012 | England et al. | |
| 2012/0157306 A1 | 6/2012 | Frackenpohl et al. | |
| 2012/0178736 A1 | 7/2012 | Castanedo et al. | |
| 2012/0178737 A1 | 7/2012 | Shuttleworth et al. | |
| 2012/0190666 A1 | 7/2012 | Bode et al. | |
| 2012/0202785 A1 | 8/2012 | Heald et al. | |
| 2012/0220585 A1 | 8/2012 | Chen et al. | |
| 2012/0220586 A1 | 8/2012 | Chen et al. | |
| 2012/0245169 A1 | 9/2012 | Ren et al. | |
| 2013/0012488 A1 | 1/2013 | Blaquiere et al. | |
| 2013/0029982 A1 | 1/2013 | Castro et al. | |
| 2013/0029984 A1 | 1/2013 | Castro et al. | |
| 2013/0034406 A1 | 2/2013 | Wu | |
| 2013/0035203 A1 | 2/2013 | Arakawa et al. | |
| 2013/0053362 A1 | 2/2013 | Castro et al. | |
| 2013/0079303 A1 | 3/2013 | Andrews et al. | |
| 2013/0079331 A1 | 3/2013 | Blaquire et al. | |
| 2013/0079342 A1 | 3/2013 | Dransfield et al. | |
| 2013/0085131 A1 | 4/2013 | Bui et al. | |
| 2013/0085151 A1 | 4/2013 | Lucas | |
| 2013/0090323 A1 | 4/2013 | Dransfield et al. | |
| 2013/0096134 A1 | 4/2013 | Duquette et al. | |
| 2013/0123263 A1 | 5/2013 | Do et al. | |
| 2013/0129820 A1 | 5/2013 | Bayliss et al. | |
| 2013/0143882 A1 | 6/2013 | Dransfield | |
| 2013/0157977 A1 | 6/2013 | Rivero et al. | |
| 2013/0158026 A1 | 6/2013 | Barlaam et al. | |
| 2013/0225557 A1 | 8/2013 | Castanedo et al. | |
| 2013/0231352 A1 | 9/2013 | Cushing et al. | |
| 2013/0267524 A1 | 10/2013 | Bui et al. | |
| 2013/0267526 A1 | 10/2013 | Chen et al. | |
| 2013/0330765 A1 | 12/2013 | Ebens et al. | |
| 2013/0344061 A1 | 12/2013 | Palombella et al. | |
| 2013/0345217 A1 | 12/2013 | Belvin et al. | |
| 2014/0023661 A1 | 1/2014 | Huang et al. | |
| 2014/0031355 A1 | 1/2014 | Fisher et al. | |
| 2014/0038937 A1 | 2/2014 | Barlaam et al. | |
| 2014/0044706 A1 | 2/2014 | Belvin et al. | |
| 2014/0065136 A1 | 3/2014 | Heald et al. | |
| 2014/0100366 A1 | 4/2014 | Babu et al. | |
| 2014/0135308 A1 | 5/2014 | Blaquiere et al. | |
| 2014/0194419 A1 | 7/2014 | Barlaam et al. | |
| 2014/0206694 A1 | 7/2014 | Bui et al. | |
| 2014/0206700 A1 | 7/2014 | Barlaam et al. | |
| 2014/0275523 A1 | 9/2014 | Angelaud et al. | |
| 2014/0288047 A1 | 9/2014 | Blaquiere et al. | |
| 2014/0309216 A1 | 10/2014 | Folkes et al. | |
| 2014/0336154 A1 | 11/2014 | Do et al. | |
| 2018/0086719 A1 | 3/2018 | Chandrasekhar et al. | |
| 2018/0086768 A1 | 3/2018 | Chandrasekhar et al. | |

FOREIGN PATENT DOCUMENTS

| | | | |
|---|---|---|---|
| EP | 2 397 471 A1 | 12/2011 | |
| FR | 2 851 248 A1 | 8/2004 | |
| FR | 2 851 248 B1 | 8/2004 | |
| KR | 2010-0099459 A | 9/2010 | |
| WO | WO-1993/020078 A1 | 10/1993 | |
| WO | WO-1997/021437 A1 | 6/1997 | |
| WO | WO-2000/012497 A2 | 3/2000 | |
| WO | WO-2000/012497 A3 | 3/2000 | |
| WO | WO-2000/043385 A1 | 7/2000 | |
| WO | WO-2001/019800 A2 | 3/2001 | |
| WO | WO-2001/019800 A3 | 3/2001 | |
| WO | WO-2001/030768 A1 | 5/2001 | |
| WO | WO-2001/040217 A1 | 6/2001 | |
| WO | WO-2001/081346 A2 | 11/2001 | |
| WO | WO-2001/081346 A3 | 11/2001 | |
| WO | WO-2001/098278 A1 | 12/2001 | |
| WO | WO-2002/000651 A2 | 1/2002 | |
| WO | WO-2002/000651 A3 | 1/2002 | |
| WO | WO-2002/088112 A1 | 11/2002 | |
| WO | WO-2003/006447 A2 | 1/2003 | |
| WO | WO-2003/006447 A3 | 1/2003 | |
| WO | WO-2003/026652 A1 | 4/2003 | |
| WO | WO-2003/035075 A1 | 5/2003 | |
| WO | WO-2003/048081 A2 | 6/2003 | |
| WO | WO-2003/048081 A3 | 6/2003 | |
| WO | WO-2003/048158 A1 | 6/2003 | |
| WO | WO-2003/076418 A1 | 9/2003 | |
| WO | WO-2004/010929 A2 | 2/2004 | |
| WO | WO-2004/010929 A3 | 2/2004 | |
| WO | WO-2004/037176 A2 | 5/2004 | |
| WO | WO-2004/037176 A3 | 5/2004 | |
| WO | WO-2004/043913 A2 | 5/2004 | |
| WO | WO-2004/043913 A3 | 5/2004 | |
| WO | WO-2004/073595 A2 | 9/2004 | |
| WO | WO-2004/073595 A3 | 9/2004 | |
| WO | WO-2004/083174 A2 | 9/2004 | |
| WO | WO-2004/083174 A3 | 9/2004 | |
| WO | WO-2004/087053 A2 | 10/2004 | |
| WO | WO-2004/087053 A3 | 10/2004 | |
| WO | WO-2004/111014 A1 | 12/2004 | |
| WO | WO-2005/030129 A2 | 4/2005 | |
| WO | WO-2005/030129 A3 | 4/2005 | |
| WO | WO-2005/030792 A2 | 4/2005 | |
| WO | WO-2005/030792 A3 | 4/2005 | |
| WO | WO-2005/046588 A2 | 5/2005 | |
| WO | WO-2005/046588 A3 | 5/2005 | |

(56) References Cited

FOREIGN PATENT DOCUMENTS

| | | |
|---|---|---|
| WO | WO-2005/051922 A1 | 6/2005 |
| WO | WO-2005/054232 A1 | 6/2005 |
| WO | WO-2005/058834 A2 | 6/2005 |
| WO | WO-2005/058834 A3 | 6/2005 |
| WO | WO-2005/058869 A1 | 6/2005 |
| WO | WO-2005/058871 A1 | 6/2005 |
| WO | WO-2005/058873 A1 | 6/2005 |
| WO | WO-2005/058874 A1 | 6/2005 |
| WO | WO-2005/118555 A1 | 6/2005 |
| WO | WO-2005/113556 A1 | 12/2005 |
| WO | WO-2005/120511 A1 | 12/2005 |
| WO | WO-2005/123696 A1 | 12/2005 |
| WO | WO-2006/004915 A1 | 1/2006 |
| WO | WO-2006/089106 A2 | 8/2006 |
| WO | WO-2006/089106 A3 | 8/2006 |
| WO | WO-2006/095906 A1 | 9/2006 |
| WO | WO-2006/117743 A1 | 11/2006 |
| WO | WO-2006/125555 A2 | 11/2006 |
| WO | WO-2006/125555 A3 | 11/2006 |
| WO | WO-2007/002701 A2 | 1/2007 |
| WO | WO-2007/002701 A3 | 1/2007 |
| WO | WO-2007/024294 A2 | 3/2007 |
| WO | WO-2007/024294 A3 | 3/2007 |
| WO | WO-2007/056155 A1 | 5/2007 |
| WO | WO-2007/076085 A2 | 7/2007 |
| WO | WO-2007/076085 A3 | 7/2007 |
| WO | WO-2007/076087 A2 | 7/2007 |
| WO | WO-2007/076087 A3 | 7/2007 |
| WO | WO-2007/147217 A1 | 12/2007 |
| WO | WO-2008/013987 A2 | 1/2008 |
| WO | WO-2008/013987 A3 | 1/2008 |
| WO | WO-2008/023159 A1 | 2/2008 |
| WO | WO-2008/032033 A1 | 3/2008 |
| WO | WO-2008/032060 A1 | 3/2008 |
| WO | WO-2008/032064 A1 | 3/2008 |
| WO | WO-2008/064018 A1 | 5/2008 |
| WO | WO-2008/070740 A1 | 6/2008 |
| WO | WO-2008/074068 A1 | 6/2008 |
| WO | WO-2008/118454 A2 | 10/2008 |
| WO | WO-2008/118454 A3 | 10/2008 |
| WO | WO-2008/118455 A1 | 10/2008 |
| WO | WO-2008/118468 A1 | 10/2008 |
| WO | WO-2008/140750 A1 | 11/2008 |
| WO | WO-2009/001060 A2 | 12/2008 |
| WO | WO-2009/001060 A3 | 12/2008 |
| WO | WO-2009/002553 A1 | 12/2008 |
| WO | WO-2009/002808 A2 | 12/2008 |
| WO | WO-2009/002808 A3 | 12/2008 |
| WO | WO-2009/007750 A1 | 1/2009 |
| WO | WO-2009/042607 A1 | 4/2009 |
| WO | WO-2009/046448 A1 | 4/2009 |
| WO | WO-2009/053715 A1 | 4/2009 |
| WO | WO-2009/055730 A1 | 4/2009 |
| WO | WO-2009/088986 A1 | 7/2009 |
| WO | WO-2009/088990 A1 | 7/2009 |
| WO | WO-2009/093972 A1 | 7/2009 |
| WO | WO-2009/114874 A2 | 9/2009 |
| WO | WO-2009/114874 A3 | 9/2009 |
| WO | WO-2009/119776 A1 | 10/2009 |
| WO | WO-2009/140128 A2 | 11/2009 |
| WO | WO-2009/140128 A3 | 11/2009 |
| WO | WO-2009/155121 A2 | 12/2009 |
| WO | WO-2009/155121 A3 | 12/2009 |
| WO | WO-2010/003048 A1 | 1/2010 |
| WO | WO-2010/005558 A2 | 1/2010 |
| WO | WO-2010/005558 A3 | 1/2010 |
| WO | WO-2010/006086 A2 | 1/2010 |
| WO | WO-2010/006086 A3 | 1/2010 |
| WO | WO-2010/036380 A1 | 4/2010 |
| WO | WO-2010/057048 A1 | 5/2010 |
| WO | WO-2010/059773 A1 | 5/2010 |
| WO | WO-2010/059788 A1 | 5/2010 |
| WO | WO-2010/096314 A1 | 8/2010 |
| WO | WO-2010/105008 A2 | 9/2010 |
| WO | WO-2010/105008 A3 | 9/2010 |
| WO | WO-2010/126895 A1 | 11/2010 |
| WO | WO-2010/129816 A2 | 11/2010 |
| WO | WO-2010/129816 A3 | 11/2010 |
| WO | WO-2010/132598 A1 | 11/2010 |
| WO | WO-2010/136491 A1 | 12/2010 |
| WO | WO-2010/138577 A1 | 12/2010 |
| WO | WO-2010/138585 A1 | 12/2010 |
| WO | WO-2010/138589 A1 | 12/2010 |
| WO | WO-2010/151735 A2 | 12/2010 |
| WO | WO-2010/151735 A3 | 12/2010 |
| WO | WO-2010/151737 A2 | 12/2010 |
| WO | WO-2010/151737 A3 | 12/2010 |
| WO | WO-2010/151740 A2 | 12/2010 |
| WO | WO-2010/151740 A3 | 12/2010 |
| WO | WO-2010/151740 A4 | 12/2010 |
| WO | WO-2010/151791 A1 | 12/2010 |
| WO | WO-2011/008302 A1 | 1/2011 |
| WO | WO-2011/011550 A1 | 1/2011 |
| WO | WO-2011/022439 A1 | 2/2011 |
| WO | WO-2011/031896 A2 | 3/2011 |
| WO | WO-2011/031896 A3 | 3/2011 |
| WO | WO-2011/041399 A2 | 4/2011 |
| WO | WO-2011/041399 A3 | 4/2011 |
| WO | WO-2011/051704 A1 | 5/2011 |
| WO | WO-2011/075628 A1 | 6/2011 |
| WO | WO-2011/075699 A2 | 6/2011 |
| WO | WO-2011/075699 A3 | 6/2011 |
| WO | WO-2011/078226 A1 | 6/2011 |
| WO | WO-2011/101429 A1 | 8/2011 |
| WO | WO-2011/123751 A2 | 10/2011 |
| WO | WO-2011/123751 A3 | 10/2011 |
| WO | WO-2011/130654 A1 | 10/2011 |
| WO | WO-2011/146882 A1 | 11/2011 |
| WO | WO-2011/150156 A2 | 12/2011 |
| WO | WO-2011/150156 A3 | 12/2011 |
| WO | WO-2012/003264 A1 | 1/2012 |
| WO | WO-2012/003271 A1 | 1/2012 |
| WO | WO-2012/003274 A1 | 1/2012 |
| WO | WO-2012/003278 A1 | 1/2012 |
| WO | WO-2012/003283 A1 | 1/2012 |
| WO | WO-2012/037204 A1 | 3/2012 |
| WO | WO-2012/047538 A1 | 4/2012 |
| WO | WO-2012/054332 A1 | 4/2012 |
| WO | WO-2012/061696 A1 | 5/2012 |
| WO | WO-2012/068343 A1 | 5/2012 |
| WO | WO-2012/082997 A1 | 6/2012 |
| WO | WO-2012/087784 A1 | 6/2012 |
| WO | WO-2012/087938 A1 | 6/2012 |
| WO | WO-2012/107465 A1 | 8/2012 |
| WO | WO-2012/140419 A1 | 10/2012 |
| WO | WO-2013/012915 A1 | 1/2013 |
| WO | WO-2013/012915 A8 | 1/2013 |
| WO | WO-2013/012915 A9 | 1/2013 |
| WO | WO-2013/012918 A1 | 1/2013 |
| WO | WO-2013/078126 A1 | 5/2013 |
| WO | WO-2013/095761 A1 | 6/2013 |
| WO | WO-2013/116562 A1 | 8/2013 |
| WO | WO-2013/152150 A1 | 10/2013 |
| WO | WO-2013/154878 A1 | 10/2013 |
| WO | WO-2013/178569 A1 | 12/2013 |
| WO | WO-2013/186229 A1 | 12/2013 |
| WO | WO-2014/004470 A1 | 1/2014 |
| WO | WO-2014/023083 A1 | 2/2014 |
| WO | WO-2014/114928 A1 | 7/2014 |
| WO | WO-2014/135851 A1 | 9/2014 |
| WO | WO-2014/165815 A2 | 10/2014 |
| WO | WO-2014/165815 A3 | 10/2014 |
| WO | WO-2016/151063 A1 | 9/2015 |
| WO | WO-2015/171725 A1 | 11/2015 |
| WO | WO-2016/064957 A1 | 4/2016 |
| WO | WO-2016/064958 A1 | 4/2016 |
| WO | WO-2017/001645 A1 | 1/2017 |
| WO | WO-2017/001658 A1 | 1/2017 |

(56) References Cited

FOREIGN PATENT DOCUMENTS

| WO | WO-2017/076895 A1 | 5/2017 |
|---|---|---|
| WO | WO-2017/076898 A1 | 5/2017 |

OTHER PUBLICATIONS

Akinleye, A. et al. (2013). "Phosphatidylinositol 3-kinase (PI3K) inhibitors as cancer therapeutics," *Journal of Hematology & Oncology* 6(88):1-17.

Ali, K. et al. (Apr. 16, 2013, e-pub May 7, 2014). "Inactivation of PI(3)K p110d Breaks Regulatory T-cell-Mediated Immune Tolerance to Cancer," *Nature* pp. 1-9.

Amin, A.S. (2012). "Modifiers of Phenotype in Inheritable Arrhythmia Syndromes: From Beside to Cell," Thesis, University of Amsterdam, Faculty of Medicine, 237 pages.

Amzel, L.M. et al. (Sep. 2008, e-pub. Jul. 17, 2008). "Structural Comparisons of Class I Phosphoinositide 3-kinases," *Cancer* 8:665-669.

Antonarakis, E.S. et al. (Dec. 15, 2012). "An Immunohistochemical Signature Comprising PTEN, MYC, and Ki67 Predicts Progression in Prostate Cancer Patients Receiving Adjuvant Docetaxel After Prostatectomy," *Cancer* 118(24):6063-6071.

Asangani, I.A. et al. (2014, e-pub. Apr. 23, 2014). "Therapeutic Targeting of BET Bromodomain Proteins in Castration-Resistant Prostate Cancer," *Nature* pp. 1-18.

At Tard, G. et al. (Jan. 2, 2016, e-pub. Jun. 12, 2015). "Prostate Cancer," *Lancet* 387:70-82.

Barnett, C.M. et al. (2014, e-pub Dec. 18, 2013). "Genetic Profiling to Determine Risk of Relapse-Free Survival in High-Risk Localized Prostate Cancer," *Clin Cancer Res* 20:1306-1312.

Bartok, B. et al. (2014). "Phosphoinositide 3-Kinase δ Regulates Migration and Invasion of Synoviocytes in Rheumatoid Arthritis," *The Journal of Immunology* 192:2063-2070.

Becattini, B. et al. (2011). "PI3Kγ within a Nonhematopoietic Cell Type Negatively Regulates Diet-Induced Thermogenesis and Promotes Obesity and Insulin Resistance," *PNAS* 1-10.

Beltran, L. et al. (Sep. 27, 2011). "Calpain Interacts with Class IA Phosphoinositide 3-kinases Regulating Their Stability and Signaling Activity," *PNAS* 108(39):16217-16222.

Bendell, J.C. et al. (2011, e-pub Dec. 12, 2011). "Phase I, Dose-Escalation Study of BKM120, an Oral Pan-Class I PI3K Inhibitor, in Patients With Advanced Solid Tumors," *J. Clin Oncol.* pp. 1-12.

Bendell, J.C. et al. (Jan. 20, 2012, e-pub. Dec. 12, 2011). "Phase 1, Dose-Escalation Study of BKM120, an Oral Pan-Class I PI3K Inhibitor, in Patients with Advanced Solid Tumors," *J Clin Oncol* 30(3):282-290.

Berenjeno, I.M. et al. (2012). "Both p110α and p110β Isoforms of PI3K can Modulate the Impact off Loss-of-Function of the PTEN Tumour Suppressor," *Biochem J.* 442:151-159.

Berndt, A. et al. (Feb. 2010, e-pub. Jan. 10, 2010).. "The p110δ Structure: Mechanisms for Selectivity and Potency of New PI(3)K Inhibitors," *Nature Chemical Biology* 6:117-306.

Bhavsar, P. et al. (2010, e-pub. Oct. 19, 2009). "Effect of p38 MAPK Inhibition on Corticosteroid Suppression of Cytokine Release in Severe Asthma," *Eur. Respir* J. 35:750-756.

Brass, L.F. (Apr. 2010). "Are MD-PhD Programs Meeting Their Goals? An Analysis of Career Choices Made by Graduates of 24 MD-PhD Programs," *Acad. Med.* 85(4):692-701.

Brasso, K. et al. (2015). "Enzalutamide Antitumour Activity Against Metastatic Castration-resistant Prostate Cancer PrevioUS-ly Treated with Docetaxel and Abiraterone: A Multicentre Analysis," *European Urology* 68:317-324.

Bukong, T.N. et al. (2016). "Inhibition of Spleen Tyrosine Kinase Activation Ameliorates Inflammation, Cell Death, and Steatosis in Alcoholic Liver Disease," *Hepatology* 64(4):1057-1071.

Burger, M.T. et al. (Aug. 26, 2011). "Identification of NVP-BKM120 as a Potent, Selective, Orally Bioavailable Class I PI3 Kinase Inhibitor for Treating Cancer," *ACS Med. Chem. Lett.* 2:774-779.

Burmester, G.R. et al. (Feb. 2014, e-pub. Nov. 12, 2013). "Emerging Cell and Cytokine Targets in Rheumatoid Arthritis," *Nat. Rev. Rheumatol* 10:77-88.

Caino, M.C. et al. (Jun. 29, 2015). "PI3K Therapy Reprograms Mitochondrial Trafficking to Fuel Tumor Cell Invasion," *PNAS* 1-18 (Includes Supporting Information).

Carreira, S. et al. (Sep. 17, 2014). "Tumor Clone Dynamics in Lethal Prostate Cancer," *Cancer* 6(254):254ra125, 11 pages.

Carver, B.S. et al. (May 17, 2011). "Reciprocal Feedback Regulation of PI3K and Androgen Receptor Signaling in PTEN-Deficient Prostate Cancer," *Cancer Cell* 19:575-586.

Cathomas, R. (2012, e-pub. Sep. 12, 2012). "Efficacy of Cetuximab in Metastatic Castration-Resistant Prostate Cancer Might Depend on EGFR and PTEN Expression: Results from a Phase II Trial (SAKK Aug. 2007)," *Clin Cancer Res* 18(21):6049-6057.

Certal, V. et al. (2012). "Discovery and Optimization of New Benzimidazole- and Benzoxazole-Pyrimidone Selective PI3Kβ Inhibitors for the Treatment of Phosphatase and TENsin homologue (PTEN)-Deficient Cancers," *J. Med. Chem.* 18 pages.

Chang, A.J. et al. (Jun. 2014, e-pub. May 20, 2014). "High-Risk Prostate Cancer—Classification and Therapy," *Nat. Rev. Clin. Oncol.* 11:308-323.

Chen, J. et al. (2012). "Imaging primary prostate cancer with 11C-Choline PET/CT: relation to tumour stage, Gleason score and biomarkers of biologic aggressiveness," *Radiol Oncol* 46(3):179-188.

Chen, Y-N. P. et al. (Jul. 7, 2016, e-pub. Jun. 29, 2016). "Allosteric Inhibition of SHP2 Phosphatase Inhibits Cancers Driven by Receptor Tyrosine Kinases," *Nature* 535:148-164.

Choucair, K. et al. (2012). "PTEN genomic deletion predicts prostate cancer recurrence and is associated with low AR expression and transcriptional activity," *BMC Cancer* 12:543, 9 pages.

Ciraolo, E. et al. (PMC Jun. 11, 2009). "Phosphoinositide 3-Kinase p110β activity: Key Role in Metabolism and Mammary Gland Cancer but not Development," *Sci Signal* 1(36):ra3, 22 pages.

Clayton, E. et al. (Sep. 9, 2002). "A Crucial Role for the p110 δ Subunit of Phosphatidylinositol 3-Kinase in B Cell Development and Activation," *J. Exp. Med.* 196(6):753-763.

Clifton, M.C. et al. (Apr. 24, 2015). "A Maltose-Binding Protein FUS-ion Construct Yields a RobUS-t Crystallography Platform for MCL1," *PLOS One* 10(4):1-18.

Constantinides, M.G. et al. (Apr. 17, 2014). "A Committed Precursor to Innate Lymphoid Cells," *Nature* 508:397-410.

Courtney, K.D. et al. (Feb. 20, 2010, e-pub. Jan. 19, 2010). "The PI3K Pathway as Drug Target in Human Cancer," *J Clin Oncol* 28(6):1075-1083.

Crawford, D.E. et al. (Dec. 2015). "Treating Patients with Metastatic Castration Resistant Prostate Cancer: A Comprehensive Review of Available Therapies," *Journal of Urology* 194:1537-1547.

Cuzick, J. et al. (May 21, 2013). "Prognostic Value of PTEN Loss in Men with Conservatively Managed Localised Prostate Cancer," *British Journal of Cancer* 108:2582-2589.

Daye, D. et al. (Mar. 2015). "Challenges and opportunities for reinvigorating the physician-scientist pipeline," *Journal of Clinical Investigation* 125(3):883-887.

De Bono, J.S. et al. (2015). "The Oral CYP17-Lyase (L) Inhibitor VT-464 in Patients With CRPC," Abstract No. 187, Innocrin Precision Therapeutics, Poster, 1 page.

De Laere, B. et al. (2017). "Comprehensive Profiling of the Androgen Receptor in Liquid Biopsies from Castration-resistant Prostate Cancer Reveals Novel Intra-AR Structural Variation and Splice Variant Expression Patterns," *European Urology* 72:192-200.

Deisting, W. et al. (Oct. 28, 2015). "Impact of Diverse Immune Evasion Mechanisms of Cancer Cells on T Cells Engaged by EpCAM/CD3-Bispecific Antibody Construct AMG 110," *PLoS ONE* 10(10):e0141669, 16 pages.

Dienstmann, R. et al. (2014, e-pub. Apr. 18, 2014). "Picking the Point of Inhibition: A Comparative Review of PI3K/AKT/mTOR Pathway Inhibitors," *Molecular Cancer Therapeutics* 13(5):1021-1031.

Dillion, L.M. (2014). "Therapeutic Targeting of Cancers with Loss of PTEN Function," *Current Drug Targets* 15:65-79.

(56) References Cited

OTHER PUBLICATIONS

Dubin, K. (Feb. 2, 2016). "Intestinal Microbiome Analyses Identify Melanoma Patients at Risk for Checkpoint-Blockade-Induced Colitis," *Nature Communications* 7(10391):1-8.
Edgar, K.A. (Feb. 1, 2010, e-pub. Jan. 26, 2010). "Isoform-Specific Phosphoinositide 3-Kinase Inhibitors Exert Distinct Effects in Solid Tumors," *Cancer Res* 70(3):1164-1172.
Edlind, M.P. et al. (2014, published online Apr. 18, 2014). "PI3K-AKT-mTOR signaling in prostate cancer progression and androgen deprivation therapy resistance," *Asian Journal of Andrology* 16:378-386.
Falk, M.J. et al. (Mar. 24, 2016). "Mitochondrial Replacement Techniques—Implications for the Clinical Community," *N. Engl. J. Med.* 374(12):1103-1106.
Ferraldeschi, R. et al. (2014, e-pub. Apr. 2015). "PTEN Protein Loss and Clinical Outcome from Castration-resistant Prostate Cancer Treated with Abiraterone Acetate," *European Urology* 67(4):795-802.
Ferraldeschi, R. et al. (2015, e-pub. May 19, 2014). "Targeting the Androgen Receptor Pathway in Castration-Resistant Prostate Cancer: Progresses and Prospects," *Oncogene* 34:1745-1757.
Fidock, D.A. (2016). "Chemical Diversity Targets Malaria," *Nature* pp. 1-2.
Fujimara, K.E. et al. (Oct. 2016). "Neonatal Gut Microbiota Associates With Childhood Multisensitized Atopy and T Cell Differentiation," *Nature Medicine* 22(10):1187-1191, 8 pages.
Gajewski, T. (Jun. 2016). "Manipulating the Microbiome to Improve the Efficacy of Immunotherapy," *Clinical Advances in Hematology & Oncology* 14(6):424-426.
Ghigo, A. et al. (Aug. 13, 2015). "Phosphoinositide 3-Kinase: Friend and Foe in Cardiovascular Disease," *Frontiers in Pharmacology* 6(169):1-7.
Gibson, K. H. et al. (Nov. 4, 1997). "Epidermal Growth Factor Receptor Tyrosine Kinase: Structure-Activity Relationships and Antitumor Activity of Novel Quinazolines," *Bioorganic & Medicinal Chemistry Letters* 7(21):2723-2728.
Gonzalez-Lopez De Turiso, F. et al. (Sep. 13, 2012, e-pub. Aug. 29, 2012). "Discovery and in Vivo Evaluation of Dual PI3Kβ/δ Inhibitors," *J Med Chem.* 55(17)7667-7685.
Gopalasingam, P. et al. (2015). *SH2 Domain Structures and Interactions,* School of Cancer Sciences, University of Birmingham, Birmingham, UK, 27 pages.
Grasso, C.S. et al. (Jul. 12, 2012, e-pub. May 20, 2012). "The Mutational Landscape of Lethal Castration-Resistant Prostate Cancer," *Nature* 487:239-243.
Gronich, N. et al. (2015). "Tyrosine Kinase Targeting Drugs Associated Congestive Heart Failure: Trastuzumab, Cetuximab, Panitumumab and Sunitinib are Associated With Increased Risk—A Nested Case-Control Study," *CLALIT*, Poster, 1 page.
Guo, X. (Jan. 16, 2014). "Induction of Innate Lymphoid Cell-Derived Interleukin-22 by the Transcription Factor STAT3 Mediates Protection against Intestinal Infection," *Immunity* 40:25-39.
Hancox, U. et al. (Jan. 2015). "Inhibition of PI3Kb Signaling with AZD8186 Inhibits Growth of PTEN-Deficient Breast and Prostate Tumors Alone and in Combination with Docetaxel," *Mol. Cancer Ther.* 14(1):48-58.
Heffron, T.P. et al. (Oct. 10, 2011). "The Rational Design of Phosphoinositide 3-Kinase # Inhibitors that Exhibit Selectivity Over the Phosphoinositide 3-Kinase # Isoform," Journal of Medicinal Chemistry, *J. Med. Chem.* pp. 1-62.
Hinterleitner, R. et al. (May 2016). "A dendritic cell subset designed for oral tolerance," *Nature Immunology* 17(5):474-476.
Hoellenriegel, J. et al. (Sep. 29, 2011, e-pub. Jul. 29, 2011). "The Phosphoinositide 3'-Kinase δ Inhibitor, CAL-101, Inhibits β-cell Receptor Signaling and Chemokine Networks in Chronic Lymphocytic Leukemia," *Blood* 118(13):3603-3612.
Hong, D.S. et al. (2012, e-pub. Jun. 12, 2012). "A Multicenter Phase I Trial of PX-866, an Oral Irreversible Phosphatidylinositol 3-Kinase Inhibitor, in Patients with Advanced Solid Tumors," *Cancer Therapy: Clinical* 18(15):4173-4182.

Hutz, J.E. (Sep. 19, 2011). "Genomewide Analysis of Inherited Variation Associated with Phosphorylation of PI3K/AKT/mTOR Signaling Proteins," *PLOS ONE* 6(9):e24873, 8 pages.
International Search Report dated Nov. 15, 2017, for PCT Application No. PCT/US-2017/052817, filed Sep. 21, 2017, 6 pages.
Ishizuka, I.E. et al. (Mar. 2016). "Single Cell Analysis Defines the Divergence Between the Innate Lymphoid Cell and Lymphoid Tissue Inducer Lineages," *Nat Immunol* 17(3):269-276.
Jabri, B. et al. (Dec. 2015). "IL-15 Functions as a Danger Signal to Regulate Tissue-Resident T Cells and Tissue Destruction," *Nature Reviews Immunol.* 15:771-783.
Jackson, S.P. et al. (2012). "Antithrombotic Phosphoinositide 3-Kinase β Inhibitors in Humans: A 'Shear' Delight!," *J Throm Haemost* 10:2123-2126.
Jarman, M. et al. (1998, e-pub. Dec. 1, 1998). "The 16,17-Double Bond Is Needed for Irreversible Inhibition of Human Cytochrome P45017r by Abiraterone (17-(3-Pyridyl)androsta-5,16-dien-3â-ol) and Related Steroidal Inhibitors," *J. Med. Chem.* 41:5375-5381.
Jia, S. et al. (Aug. 7, 2008, e-pub. Jun. 25, 2008). "Essential Roles of PI(3)K-p110β in Cell Growth, Metabolism and Tumorigenesis," *Nature* 454:776-779, 5 pages.
Jia, S. et al. (Dec. 20, 2012). "Opposing Effects of Androgen Deprivation and Targeted Therapy on Prostate Cancer Prevention," *Cancer Discovery* 3:44-51.
Juric, D. et al. (Feb. 12, 2015, e-pub. Nov. 17, 2014). "Convergent loss of PTEN leads to clinical resistance to a PI(3)Kα inhibitor," *Nature* 518:240-244, 15 pages.
Kato, N. et al. (Oct. 20, 2016, e-pub. Sep. 7, 2016). "Diversity-oriented synthesis yields novel multistage antimalarial Inhibitors," *Nature* 538(7625):344-349.
Knight, Z.A. et al. (May 19, 2006). "A Pharmacological Map of the PI3-K Family Defines a Role for p110α in Insulin Signaling," *Cell* 125:733-747.
Knobbe, C.B. et al. (2008). "The Roles of PTEN in Development, Physiology and Tumorigenesis in Mouse Models: A Tissue-by-Tissue Survey," *Oncogene* 27:5398-5415.
Laurent, P-A. et al. (2015). "Platelet PI3Kβ and GSK3 Regulate Thrombus Stability at a High Shear Rate," *Blood* 125(5):881-888.
Lee, S.H. et al. (Jun. 15, 2010). A Constitutively Activated Form of the p110β Isoform of PI3-Kinase Induces Prostatic Intraepithelial Neoplasia in Mice, *PNAS* 107(24):11002-11007.
Leinonen, K.A. (2013). "Loss of PTEN is Associated with Aggressive Behavior in ERG-Positive Prostate Cancer," *Cancer Epidemiol Biomarkers Prev* 22(12):2333-2344.
Liamis, G. et al. (2010, e-pub Mar. 30, 2010). "Medication-Induced Hypophosphatemia: A Review," *Q J Med.* 103:449-459.
Liu, B.A. et al. (2012, e-pub. May 5, 2012). "The Language of SH2 Domain Interactions Defines Phosphotyrosine-Mediated Signal Transduction," *FEBS Letters* 586:2597-2605.
Lohr, J.G. et al. (2014, e-pub Apr. 20, 2014). "Whole-Exome Sequencing of Circulating Tumor Cells Provides a Window into Metastatic Prostate Cancer," *Nature Biotechnology* 32:479-484, 8 pages.
Lotan, T. et al. (Aug. 30, 2011). "PTEN Protein Loss by Immunostaining: Analytic Validation and Prognostic Indicator for a High Risk Surgical Cohort of Prostate Cancer Patients," *Clin Cancer Res* 17(20):6563-6573, 39 pages.
Manni, M.L. et al. (Sep. 2014, e-pub. Feb. 19, 2014). "The Complex Relationship Between Inflammation and Lung Function in Severe Asthma," *Mucosal Immunol.* 7(5):1186-1198.
Maughan, B.L. et al. (2015). "Androgen pathway resistance in prostate cancer and therapeutic implications," *Expert Opin. Pharmacother.* 16(10):1521-1537.
McCall, P. (2008). "Is PTEN loss associated with clinical outcome measures in human prostate cancer," *British Journal of Cancer* 99:1296-1301.
McDonald, B.D. et al. (Aug. 21, 2014). "Elevated T Cell Receptor Signaling Identifies a Thymic Precursor to the TCRαβ+CD4-CD8β-Intraepithelial Lymphocyte Lineage," *Immunity* 41:219-222.
Mercado, N. et al. (2011). "Nortriptyline Reverses Corticosteroid Insensitivity by Inhibition of Phosphoinositide-3-Kinase-δ$^δ$," *JPET* 337(2):465-471.

(56) References Cited

OTHER PUBLICATIONS

Meshram, H.M. et al. (Jan. 22, 2013). "Synthesis and Cytotoxicity of New Quinoline Derivatives", *Indian Journal of Chemistry* 518(9):1411-1416.

Milewicz, D.M. et al. (2015). "Rescuing the Physician-Scientist Workforce: the Time for Action is Now," *J Clin Invest* 125(10):3742-3747.

Miller, M.S. et al. (Jul. 24, 2014). "Structural basis of nSH2 regulation and lipid binding in PI3Kα" *Oncotarget* 5(14):5198-5208.

Millis, S.Z. et al. (2015). "PI3K/PTEN/Akt/mTOR Pathway Aberrations and Co-Incidence of Hormone Receptors and HER2 in 19,784 Diverse Solid Tumors," U.C. San Diego, Moores Cancer Center, Poster, 1 Page.

Miyamoto, D. T. et al. (2014, e-pub. May 13, 2014). "Circulating Tumour Cells—Monitoring Treatment Response in Prostate Cancer," *Nat. Rev. Clin. Oncol.* 11(7):401-412.

Modena, A. et al. (2015). "Metastic Castration-Resistant Prostate Cancer: Targeting the Mechanisms of Resistance to Abiraterone" *Expert Rev. of Anticancer Ther*. 15(9):1037-1048.

Moore, W.R. et al. (2015). "Direct Effects of the Selective CYP17 Lyase (L) Inhibitor, VT-464, on the Androgen Receptor (AR) and its Oral Activity in an F876L Tumor Mouse Xenograft Model," Innocrin Pharmaceuticals, Inc. et al., Poster, 1 page.

Morlacchi, P. et al. (2014, e-pub. Dec. 4, 2013). "Synthesis and in Vitro Evaluation of a Peptidomimetic Inhibitor Targeting the Src Homology 2 (SH2) Domain of STAT6," *ACS Med. Chem. Lett.* 5:69-72.

Mubanga, M. et al. (e-pub. Nov. 17, 2017). "Dog Ownership and the Risk of Cardiovascular Disease and Death—A Nationwide Cohort Study," *Scientific Reports* 7(15821):1-9.

Muellner, M. et al. (2011, e-pub. Sep. 25, 2011). "A Chemical-Genetic Screen Reveals a Mechanism of Resistance to PI3K Inhibitors in Cancer," *Nature Chemical Biology* 7(11):787-793, 7 pages.

Mulholland, D.J. et al. (Jun. 14, 2011). "Cell Autonomous Role of PTEN in Regulating Castration-Resistant Prostate Cancer Growth," *Cancer Cell* 19(6):792-804.

Mulholland, D.J. et al. (Jun. 14, 2011). "Cell Autonomous Role of PTEN in Regulating Castration-Resistant Prostate Cancer Growth," *Cancer Cell* 19(6):792-804, 26 pages.

Narayanan, S. et al. (Jan. 2016, e-pub. Dec. 8, 2015). "Androgen—Glucocorticoid interactions in the era of Novel Prostate Cancer Therapy," *Nature Reviews Urology* 13:47-60.

Ni, J. et al. (Jan. 2013, May 2012, published online Apr. 12, 2012). "Functional Characterization of an Isoform-Selective Inhibitor of PI3K-p110b as a Potential Anticancer Agent," *Cancer Discovery* 2(5):OF1-OF9.

Ni, J. et al. (Jul. 2016). "Combination Inhibition of PI3K and mTORC1 Yields Durable Remissions in Mice Bearing Orthotopic Patient-Derived Xenografts of HER2-Positive Breast Cancer Brain Metastases," *Nature Medicine* 22(7):723-728.

Noble, M.E.M. et al. (Mar. 19, 2004): "Protein Kinase Inhibitors: Insights Into Drug Design From Structure," *Science* 303:1800-1805.

Oda, K. et al. (Oct. 1, 2008). "PIK3CA Cooperates with Other Phosphatidylinositol 3'-Kinase Pathway Mutations to Effect Oncogenic Transformation," *Cancer Res* 68(19):8127-8136.

Okkenhaug, K. (2013). "Signaling by the Phosphoinositide 3-Kinase Family in Immune Cells," *Annu. Rev. Immunol.* 31:675-704.

Patel, L. et al. (2016, e-pub. Mar. 16, 2016). "2,4,6-Triaminopyrimidine as a Novel Hinge Binder in a Series of PI3Kδ Selective Inhibitors," *J. Med. Chem.* 59:3532-3548.

Peng, W. et al. (Feb. 2016, e-pub. Dec. 8, 2015). "Loss of PTEN Promotes Resistance to T Cell-Mediated Immunotherapy," *Cancer Discov.* 6(2):1-15.

Poulin, P. et al. (Apr. 2013, e-pub. Jan. 18, 2013). "Correlation of Tissue-Plasma Partition Coefficients Between Normal Tissues and Subcutaneous Xenografts of Human Tumor Cell Lines in Mouse as a Prediction Tool of Drug Penetration in Tumors," *Journal of Pharmaceutical Sciences* 102(4):1355-1369.

Pu, Y. et al. (Apr. 6, 2016). "Androgen Receptor Antagonists Compromise T Cell Response Against Prostate Cancer Leading to Early Tumor Relapse," *Science Translational Medicine* 8(333):1-12.

Punnoose, E.A. et al. (2015). "PTEN Loss in Circulating Tumour Cells Correlates with PTEN Loss in Fresh Tumour Tissue from Castration-Resistant Prostate Cancer Patients," *British Journal of Cancer* 113:1225-1233.

Qu, X. et al. (2013). "A Three-Marker FISH Panel Detects More Genetic Aberrations of AR, PTEN and TMPRSS2/ERG in Castration-Resistant or Metastatic Prostate Cancers than in Primary Prostate Tumors," *PLoS ONE* 8(9):e74671, 13 pages.

Raynaud, F.I. et al. (2007). "Pharmacologic Characterization of a Potent Inhibitor of Class I Phosphatidylinositide 3-Kinases," *Cancer Res*. 67(12):5840-5850, 12 pages.

Reid, A. H.M. et al. (2012, e-pub. Mar. 30, 2012). "Novel, gross chromosomal alterations involving PTEN cooperate with allelic loss in prostate cancer," *Modern Pathology* 25:902-910.

Rheault, T.R. et al. (2010). "Heteroaryl-linked 5-(1H-benzimidazol-1-yl)-2-thiophenecarboxamides: Potent inhibitors of polo-like kinase 1 (PLK1) with improved drug-like properties", *Bioorganic & Medicinal Chemistry Letters* 20(15):4587-4592.

Robinson, D. et al. (May 21, 2015). "Integrative Clinical Genomics of Advanced Prostate Cancer," *Cell* 161:1215-1228.

Sawyer, C. et al. (Apr. 1, 2003). "Regulation of Breast Cancer Cell Chemotaxis by the Phosphoinositide 3-Kinase p110δ," *Cancer Res* 63:1667-1675.

Schmit, F. et al. (Apr. 29, 2014, e-pub. Apr. 15, 2014). "PI3K isoform Dependence of PTEN-Deficient Tumors can be Altered by the Genetic Context," *PNAS* 111(17)6395-6400, 10 pages.

Schroeder, B.O. et al. (Oct. 2016). "Signals from the Gut Microbiota to Distant Organs in Physiology and Disease," *Nature Medicine* 22(10):1079-1089.

Schwartz, S. et al. (Jan. 12, 2015). "Feedback Suppression of PI3Kα Signaling in PTEN-Mutated Tumors is Relieved by Selective Inhibition of PI3Kβ," *Cancer Cell* 27:1-14.

Serya, R.A.T et al. (Feb. 2015). "Design, Synthesis and Biological Evaluation of Novel Quinazoline-Based Anti-inflammatory Agents Acting as PDE4B Inhibitors", *Chemical and Pharmaceutical Bulletin* 63(2):102-116.

Shonberg, J. et al. (2015). "GPCR crystal structures: Medicinal chemistry in the pocket," *Bioorg. Med. Chem.* 23(14):3880-3906.

Shutz, M. et al. (Feb. 25, 2016). "Directed Evolution of G Protein Coupled Receptors in Yeast for Higher Functional Production in Eukaryotic Expression Hosts," *Scientific Reports* 6(21508):1-16.

Sircar, K. et al. (2009, e-pub.Mar. 20, 2009). "PTEN Genomic Deletion is Associated with p-Akt and AR Signalling in Poorer Outcome, Hormone Refractory Prostate Cancer," *J. Pathol.* 218:505-513.

Sivan, A. et al. (Nov. 27, 2015). "Commensal *Bifidobacterium* Promotes Antitumor Immunity and Facilitates Anti-PD-L1 Efficacy," *Science* 350(6264):1084-1089.

Smith, G.C. (2012). "Effects of Acutely Inhibiting PI3K Isoforms and mTOR on Regulation of Glucose Metabolism in vivo," *Biochem J.* 442:161-169.

Soifer, H.S. et al. (Feb. 3, 2012). "Direct Regulation of Androgen Receptor Activity by Potent CYP17 Inhibitors in Prostate Cancer Cells," *J. Bio. Chem.* 287(6):3777-3787.

Somoza, J.R. et al. (2015). "*The characterization of idelalisib binding to PI3Kδ*: S0tructural, biochemical and biophysical characterization of idelalisib binding to phosphoinositide 3-kinase δ", Paper, Departments of 1Structural Chemistry and 2Biology, *The American Society for Biochem. and Mol. Bio.*, Gilead Sciences, Inc., Foster City, California, pp. 1-23.

Sopasakis, V.R. et al. (Mar. 3, 2010). "Specific Roles of the p110α Isoform of Phosphatidylinsositol 3-Kinase in Hepatic Insulin Signaling and Metabolic Regulation," *Cell Metab.* 11(3):220-230.

Stevens, R. C. (Jan. 2013). "The GPCR Network: A Large-Scale Collaboration to Determine Human GPCR Structure and Function," *Nature Drug Discovery* 12:25-34.

Stratikopoulos, E.E. et al. (Jun. 8, 2015). "Kinase and BET Inhibitors Together Clamp Inhibition of PI3K Signaling and Overcome Resistance to Therapy," *Cancer Cell* 27:837-851.

(56) References Cited

OTHER PUBLICATIONS

Suárez-Fueyo, A. et al. (e-pub. Jun. 16, 2014). "Inhibition of PI3Kδ Reduces Kidney Infiltration by Macrophages and Ameliorates Systemic Lupus in the Mouse," *J. Immunol.* 193:1-11, 18 pages.
Sung, J. A.M. et al. (Nov. 2015). "Dual-Affinity Re-Targeting proteins direct T cell-mediated cytolysis of latently HIV-infected cells," *J Clin Invest.* 125(11):4077-4090.
Tamburini, S. et al. (Jul. 2016, e-pub. Jul. 7, 2016). "The microbiome in early life: Implications for Health Outcomes," *Nature Medicine* 22(7):713-722.
Tamburino, L. et al. (2012, e-pub. Jan. 11, 2012). "Androgen Receptor (AR) Expression in Prostate Cancer and Progression of the Tumor: Lessons from Cell Lines, Animal Models and Human Specimens," *Steroids* 77:996-1001.
Tautermann, C.S. et al. (2014). "GPCR Structures in Drug Design, Emerging Opportunities with New Structures," *Bioorg. & Medicinal Chem. Lett.* 24:4073-4079.
Torbett, N.E. et al. (Oct. 1, 2008). "A chemical screen in diverse breast cancer cell lines reveals genetic enhancers and suppressors of sensitivity to PI3K isotype-selective inhibition," *Biochem J.* 415(1):97-110.
Toren, P. et al. (2016). "Pre-Clinical Rationale for Combined PI3K and BRD4 Inhibition in Advanced Prostate Cancer," UBC, Vancouver Prostate Center, Poster, 1 page.
Toren, P. et al. (Aug. 1, 2014). "Combination AZD5363 with Enzalutamide Significantly Delays Enzalutamide-resistant Prostate Cancer in Preclinical Models," *European Urology* 67:986-990.
Torti, M. (Jan. 2015). "PI3Kβ Inhibition: All That Glitters is not Gold," *BLOOD* 125(5)750-751, 3 pages.
Vanhaesebroeck, B. et al. (Apr. 2005). "Signalling by PI3K Isoforms: Insights from Gene-Targeted Mice," *TRENDS in Biochemical Sciences* 30(4):194-204.
Vanhaesebroeck, B. et al. (May 2010, e-pub Apr. 9, 2010). "The Emerging Mechanisms of Isoform-Specific PI3K Signaling," *Molecular Cell Biology* 11:329-341.
Walker, E.H. et al. (Nov. 18, 1999). "Structural insights into Phosphoinositide 3-kinase Catalysis and Signaling," *Nature* 402:313-320.
Walker, E.H. et al. (Oct. 2000). "Structural Determinants of Phosphoinositide 3-Kinase Inhibition by Wortmannin, LY294002, Quercetin, Myricetin, and Staurosporine," *Molecular Cell* 6:909-919.
Wang, Q. et al. (2013). "Spatially Distinct Roles of Class Ia PI3K Isoforms in the Development and Maintenance of PTEN Hamartoma Tumor Syndrome," *Genes Dev.* 27:1568-1580.
Watson, P.A. et al. (Dec. 2015, Nov. 13, 2015). "Emerging mechanisms of resistance to androgen receptor inhibitors in prostate cancer," *Cancer* 15:701-711.
Wee, S. et al. (Sep. 2, 2008). "PTEN-deficient cancers depend on PIK3CB," *PNAS* 105(35):13057-13062.
Weigelt, B. et al. (Aug. 31, 2012). "Genomic Determinants of PI3K Pathway Inhibitor Response in Cancer," *Frontiers in Oncology* 2(109):1-16.
Wenzel, S. et al. (2010). "Crystal structure of the human transcription elongation factor DSIF hSpt4 subunit in complex with the hSpt5 dimerization interface," *Biochem J.* 425:373-380.
Wible, B.A. et al. (2005). "HERG-Lite®: A Novel Comprehensive High-Throughput Screen for Drug-Induced hERG Risk," *Journal of Pharmacological and Toxicological Methods* 52:136-145.
Winkler, D.G. et al. (Nov. 21, 2013). "PI3K-δ and PI3K-γ Inhibition by IPI-145 Abrogates Immune Responses and Suppresses Activity in Autoimmune and Inflammatory Disease Models," *Chemistry & Biology* 20:1364-1374.
Wise, H.M. et al. (2017). "Prostate cancer, PI3K, PTEN and prognosis," *Clinical Science* 131:197-210.
Wisler, J. et al. (2012). "Small Molecular Inhibition of the PI3K β Isoform Causes Testicular Toxicity in the Rat," Poster, AMGEN Abstract 2334, 1 page.
Workman, P. et al. (2010, e-pub. Feb. 23, 2010). "Drugging the PI3 Kinome: From Chemical Tools to Drugs in the Clinic" *Cancer Res* 70:2146-2157.
Written Opinion of the International Searching Authority dated Nov. 15, 2017, for PCT Application No. PCT/US-2017/052817, filed Sep. 21, 2017, 6 pages.
Wyatt, A.W. et al. (2015, e-pub. Apr. 20, 2015). "Targeting the Adaptive Molecular Landscape of Castration-Resistant Prostate Cancer," *EMBO Molecular Medicine* 7(7):878-894.
Yap, T.A. (Oct. 2016, e-pub. Jul. 22, 2016). "Drug Discovery in Advanced Prostate Cancer: Translating Biology into Therapy," *Nature Reviews Drug Disc.* 15:699-718.
Yin, L. et al. (Jan. 2014, published online Nov. 26, 2013). "CYP17 Inhibitors—Abiraterone, C17,20-lyase Inhibitors and Multi-Targeting Agents," *Nat Rev Urol.* 11:32-42.
Yoshimoto, M. et al. (2013, e-pub. Sep. 28, 2012). "PTEN Losses Exhibit Heterogeneity in Multifocal Prostatic Adenocarcinoma and are Associated with Higher Gleason Grade," *Modern Pathology* 26:435-447.
Zhang, X. et al. (Mar. 4, 2011). "Structure of Lipid Kinase p110β/p85β Elucidates an UnusualSH2-Domain-Mediated Inhibitory Mechanism," *Molecular Cell* 41:567-578 (and supplemental Information).
Zhao, Z. et al. (Apr. 14, 2014). "Exploration of Type II Binding Mode: A Privileged Approach for Kinase Inhibitor Focused Drug Discovery?," *ACS Chem* 9:1230-1241.
Zhong, J. et al. (Mar. 15, 2014, e-pub. Jan. 30, 2014). "p300 Acetyltransferase Regulates Androgen Receptor Degradation and PTEN-Deficient Prostate Tumorigenesis," *Cancer Res* 74(6):1870-1880.
Zoncu, R. et al. (Jan. 2011, e-pub. Dec. 15, 2010). "mTOR: From Growth Signal Integration to Cancer, Diabetes and Ageing," *Nature Reviews Mol. Cell Biol.* 12:21-35.
Li, Y. et al. (2011). "*PTEN* deletion and heme oxygenase-1 overexpression cooperate in prostate cancer progression and are associated with adverse clinical outcome," *J Pathol* 224:90-100.
Loriot, Y. et al. (May 2015, e-pub. Apr. 15, 2015). "Effect of Enzalutamide on Health-Related Quality of Life, Pain, and Skeletal-Related Events in Asymptomatic and Minimally Symptomatic, Chemotherapy-Naive Patients with Metastatic Castration-Resistant Prostate Cancer (PREVAIL): Results from a Randomised, Phase 3 Trial," *Lancet Oncol* 16:509-521.
Lu, Z. et al. (Apr. 25, 2012). "Suppression of Phosphoinositide 3-Kinase Signaling and Alteration of Multiple Ion Currents in Drug-Induced Long QT Syndrome," *Sci Transl Med* 4(131):131ra50, 11 pages.
Marques, R.B. et al. (2015). "High Efficacy of Combination Therapy Using PI3K/AKT Inhibitors with Androgen Deprivation in Prostate Cancer Preclinical Models," *European Urology* 67:1177-1185.
Mateo, J. et al. (2014, e-pub. Jan. 4, 2014). "Novel Drugs Targeting the Androgen Receptor Pathway in Prostate Cancer," *Cancer Metastasis Rev* 33:567-579.
Zhang, X. et al. (Mar. 4, 2011). "Structure of Lipid Kinase p110β/p85β Elucidates an UnusualSH2-Domain-Mediated Inhibitory Mechanism," Molecular Cell 41: Supplemental.

\* cited by examiner

PHOSPHATIDYLINOSITOL 3-KINASE INHIBITORS

FIELD

The present application relates to novel compounds that selectively inhibit the activities of PI3K isoforms and their uses in therapeutic treatments.

BACKGROUND

Cell signaling via 3'-phosphorylated phosphoinositides has been implicated in a variety of cellular processes, e.g., malignant transformation, growth factor signaling, inflammation, and immunity (Rameh et al., *J. Biol. Chem.*, 274: 8347-8350, 1999). Phosphatidylinositol 3-kinase (PI 3-kinase or PI3K) is responsible for generating these phosphorylated signaling products. PI3K was initially identified as a protein associated with viral oncoproteins and growth factor receptor tyrosine kinases that phosphorylate phosphatidylinositol (PI) and its phosphorylated derivatives at the 3'-hydroxyl of the inositol ring (Panayotou et al., *Trends Cell Biol.*, 2:358-60, 1992).

Three classes of the PI 3-kinase (PI3K) are proposed based on the substrate specificities. Class I PI3Ks phosphorylate phosphatidylinositol (PI), phosphatidylinositol-4-phosphate, and phosphatidylinositol-4,5-biphosphate ($PIP_2$) to produce phosphatidylinositol-3-phosphate (PIP), phosphatidylinositol-3,4-biphosphate, and phosphatidylinositol-3,4,5-triphosphate, respectively. Also, Class II PI3Ks phosphorylate PI and phosphatidylinositol-4-phosphate, and Class III PI3Ks phosphorylate PI.

The initial purification and molecular cloning of PI 3-kinase revealed that it was a heterodimer consisting of p85 and p110 subunits (Otsu et al., *Cell*, 65:91-104, 1991; Hiles et al., *Cell*, 70:419-29, 1992). Later, four distinct Class I PI3Ks were identified and designated as PI3K α, β, δ, and γ isoforms. Each isoform consists of a distinct 110 kDa catalytic subunit and a regulatory subunit. The catalytic subunits of PI3K α, β, and δ (i.e., p110α, p110β, and p110δ, respectively) interacts, individually, with the same regulatory subunit p85, whereas the catalytic subunit of PI3K γ (p110γ) interacts with a distinct regulatory subunit p101.

Studies have also showed that each PI3K isoform has distinct expression pattern. For example, PIK3CA which encodes PI3Kα is frequently mutated in human cancers (Engelman, *Nat. Rev. Cancer*, 9: 550-562, 2009). Also, PI3Kδ is generally expressed in hematopoietic cells. Moreover, PI3K isoforms are shown to be associated with proliferation or survival signaling in cancers, inflammatory, or autoimmune diseases. As each PI3K isoform has different biological function, PI3K isoforms are potential targets to treat cancer or disorder (U.S. Pat. Nos. 6,800,620; 8,435,988; 8,673,906; US Patent Application Publication No. US 2013/0274253).

Therefore, there is a need for developing therapeutic agents that inhibit PI3K isoforms to treat diseases, disorders, or conditions that are mediated by PI3K.

SUMMARY

The present application provides novel compounds that are inhibitors of PI3K isoforms. The application also provides compositions, including pharmaceutical compositions, kits that include the compounds, and methods of using and making the compounds. The compounds provided herein are useful in treating diseases, disorders, or conditions that are mediated by PI3K isoforms. The application also provides compounds for use in therapy. The application further provides compounds for use in a method of treating a disease, disorder, or condition that is mediated by PI3K isoforms. Moreover, the application provides uses of the compounds in the manufacture of a medicament for the treatment of a disease, disorder or condition that is mediated by PI3K isoforms. In typical embodiments, provided are compounds of formula I or IA:

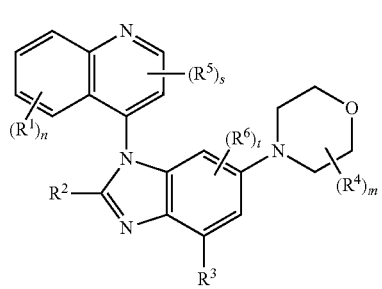

Formula I

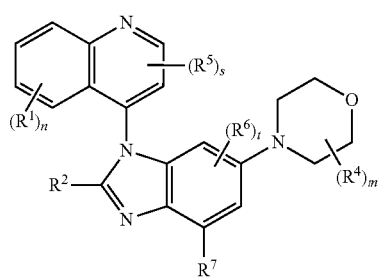

Formula IA wherein n is 1, 2, 3 or 4;
m is 1, 2, 3 or 4;
s is 1 or 2;
t is 1 or 2;
each $R^1$ is independently selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
  wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{100}$;
$R^2$ is selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
  wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{101}$;
$R^3$ is selected from $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
  wherein each $C_{6-10}$ aryl, 5-10 membered heteroaryl and 4-10 membered heterocyclyl is optionally substituted with one to four $R^{102}$;

$R^4$ is selected from hydrogen, $C_{1-6}$ alkyl, $C_{2-6}$ alkenyl, $C_{2-6}$ alkynyl, acyl, $C_{3-8}$ cycloalkyl and $C_{1-6}$ alkyl sulfonyl;

each $R^5$ is independently selected from hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
  wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{103}$;

each $R^6$ is independently selected from hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl or $C_{2-6}$ alkynyl;

$R^7$ is selected from hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl;
  wherein each $C_{1-6}$ alkyl, $C_{2-6}$ alkenyl, $C_{2-6}$ alkynyl is optionally substituted with one to four $R^{102}$;

each $R^a$ and $R^b$ is independently selected from hydrogen, $C_{1-6}$ alkyl, $C_{2-6}$ alkenyl and $C_{2-6}$ alkynyl;
  wherein each $C_{1-6}$ alkyl, $C_{2-6}$ alkenyl, $C_{2-6}$ alkynyl, is optionally substituted with one to four $R^{200}$;

each $R^{100}$, $R^{101}$, $R^{102}$, and $R^{103}$ is independently selected from hydrogen, halo, cyano, hydroxy, amino, oxo, thioxo, vinyl, —C(O)$R^c$, —C(O)O$R^c$, —C(O)N$R^cR^d$, —N($R^c$)C(O)$R^d$, —S(O)N$R^cR^d$, —S(O)$_2$N$R^cR^d$, —S(O)$R^c$, —S(O)$_2R^c$, —N$R^cR^d$, —O$R^c$, —S$R^d$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl;
  wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{201}$;

each $R^c$ and $R^d$ is independently selected from hydrogen, $C_{1-6}$ alkyl, $C_{2-6}$ alkenyl and $C_{2-6}$ alkynyl;

each $R^{200}$ and $R^{201}$ is independently selected from hydrogen, halo, cyano, hydroxy, amino, oxo, thioxo, vinyl, —C(O)$R^e$, —C(O)O$R^e$, —C(O)N$R^eR^f$, —N($R^e$)C(O)$R^f$, —S(O)N$R^eR^f$, —S(O)$_2$N$R^eR^f$, —S(O)$R^e$, —S(O)$_2R^e$, —N$R^eR^f$, —O$R^e$, —S$R^e$, $C_{1-6}$ alkyl, $C_{2-6}$ alkenyl and $C_{2-6}$ alkynyl;

each $R^e$ and $R^f$ is independently selected from hydrogen, $C_{1-6}$ alkyl, $C_{2-6}$ alkenyl and $C_{2-6}$ alkynyl;

or a pharmaceutically acceptable salt, isomer, or a mixture thereof.

In certain embodiments, the PI3K inhibitors are the compounds selected from Table 1, a pharmaceutically acceptable salt, isomer, or a mixture thereof. In additional embodiments, the compound is an (S)-enantiomer. In other embodiments, the compound is an (R)-enantiomer. In other additional embodiments, the compound is an atropisomer.

The application also provides a pharmaceutical composition that comprises a compound of formula (I), a pharmaceutically acceptable salt, isomer, or a mixture thereof, together with at least one pharmaceutically acceptable vehicle. Examples of a pharmaceutically acceptable vehicle may be selected from carriers, adjuvants, and excipients.

Further provided herein is a method of treating a disease, disorder, or condition in a human in need thereof by administering to the human a therapeutically effective amount of a compound of formula (I) or a pharmaceutically acceptable salt, isomer, or a mixture thereof. Further provided is a compound of formula (I) for use in a method of treating a disease, disorder or condition that is mediated by PI3K isoforms. The application also provides the use of a compound of formula (I) in the manufacture of a medicament for the treatment of a disease, disorder or condition that is mediated by PI3K isoforms. In certain embodiments, the disease, disorder, or condition is associated or mediated by PI3K. In some embodiments, the disease, disorder, or condition is an inflammatory disorder. In other embodiments, the disease, disorder, or condition is a cancer.

Also provided herein is a method of inhibiting the activity of a phosphatidylinositol 3-kinase polypeptide by contacting the polypeptide with a compound of formula (I) or a pharmaceutically acceptable salt, isomer, or a mixture thereof.

Further provided is a method of inhibiting excessive or destructive immune reactions, comprising administering an effective amount of a compound of formula (I) or a pharmaceutically acceptable salt, isomer, or a mixture thereof.

Also provided is a method of inhibiting growth or proliferation of cancer cells comprising contacting the cancer cells with an effective amount of a compound of formula (I) or a pharmaceutically acceptable salt, isomer, or a mixture thereof.

Also provided is a kit that includes a compound of formula (I) or a pharmaceutically acceptable salt, isomer, or a mixture thereof. The kit may further comprise a label and/or instructions for use of the compound in treating a disease, disorder, or condition in a human in need thereof. In some embodiments, the disease, disorder, or condition may be associated or mediated by PI3K activity.

Also provided are articles of manufacture that include a compound of formula (I) or a pharmaceutically acceptable salt, isomer, or a mixture thereof, and a container. In one embodiment, the container may be a vial, jar, ampoule, preloaded syringe, or an intravenous bag.

DETAILED DESCRIPTION

The following description sets forth exemplary methods, parameters and the like. Such description is not intended as a limitation on the scope of the present application but is instead provided as exemplary embodiments.

As used herein, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "C$_{u-v}$" indicates that the following group has from u to v carbon atoms. For example, "C$_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms (i.e., C$_{1-8}$ alkyl), 1 to 6 carbon atoms (i.e., C$_{1-6}$ alkyl), or 1 to 4 carbon atoms (i.e., C$_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" includes n-butyl, sec-butyl, isobutyl and t-butyl; "propyl" includes n-propyl and isopropyl.

"Alkenyl" refers to an aliphatic group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Acyl" refers to a group —C(=O)R, wherein R is hydrogen, alkyl, cycloalkyl, heterocycloalkyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one alkenyl). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocycloalkyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl include 1 to 20 ring carbon atoms, 3 to 12 ring carbon atoms, or 3 to 8 carbon ring atoms; and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocycloalkyl" refers to a saturated or unsaturated cyclic alkyl group, with one or more ring heteroatoms independently selected from nitrogen, oxygen and sulfur. The term "heterocycloalkyl" includes heterocycloalkenyl groups (i.e. the heterocycloalkyl group having at least one alkenyl). A heterocycloalkyl may be a single ring or multiple rings wherein the multiple rings may be fused, bridged, or spiro. As used herein, heterocycloalkyl has 2 to 20 ring carbon atoms, 2 to 12 ring carbon atoms, 2 to 10 ring carbon atoms, 2 to 8 ring carbon atoms, 3 to 12 ring carbon atoms, 3 to 8 ring carbon atoms, or 3 to 6 ring carbon atoms; having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include pyrrolidinyl, piperidinyl, piperazinyl, oxetanyl, dioxolanyl, azetidinyl, and morpholinyl.

"Hydroxy" or "hydroxyl" refers to the group —OH.

"Oxo" refers to the group (═O) or (O).

"Sulfonyl" refers to the group —S(O)$_2$R, where R is alkyl, haloalkyl, cycloalkyl, heterocycloalkyl, heteroaryl, or aryl. Examples of sulfonyl are methylsulfonyl, ethylsulfonyl, phenylsulfonyl, and toluenesulfonyl.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. By way of example, there may be one, two, three, four, five, or six substituents. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to substituted aryl (substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocycloalkyl, aryl, and heteroaryl. In additional embodiments, "substituted cycloalkyl" refers to a cycloalkyl group having one or more substituents including alkyl, haloalkyl, heterocycloalkyl, aryl, heteroaryl, alkoxy, halo, hydroxyl; "substituted aryl" refers to an aryl group having one or more substituents including halo, alkyl, haloalkyl, heterocycloalkyl, heteroaryl, alkoxy, and cyano, and "substituted sulfonyl" refers to a group —S(O)$_2$R, in which R is substituted with one or more substituents of alkyl, cycloalkyl, heterocycloalkyl, aryl or heteroaryl. In other embodiments, the one or more substituents may be further substituted with halo, alkyl, haloalkyl, alkoxy, cycloalkyl, heterocycloalkyl, aryl, or heteroaryl, each of which is substituted. In other embodiments, the substituents may be further substituted with halo, alkyl, haloalkyl, alkoxy, cycloalkyl, heterocycloalkyl, aryl, or heteroaryl, each of which is unsubstituted.

List of Abbreviations and Acronyms

| Abbreviation | Meaning |
| --- | --- |
| ° C. | Degree Celsius |
| Ac | Acetyl |
| aq. | Aqueous |
| ATP | Adenosine triphosphate |
| br | Broad |
| BSA | Bovine serum albumin |
| Cbz | Carboxybenzyl |
| COD | Cyclooctadiene |
| COPD | Chronic obstructive pulmonary disease |
| d | Doublet |
| DCE | Dichloroethene |
| DCM | Dichloromethane |
| dd | Doublet of doublets |
| DIEA | Diisopropylethylamine |
| DMF | Dimethylformamide |
| DMSO | Dimethylsulfoxide |
| dt | Doublet-triplet |
| DTT | Dithiothreitol |
| EC$_{50}$ | The half maximal effective concentration |
| eq | Equivalents |
| ES/MS | Electrospray mass spectrometry |
| Et | Ethyl |
| FBS | Fetal bovine serum |
| g | Grams |
| HEPES | 2-[4-(2-hydroxyethyl)piperazin-1-yl]ethanesulfonic acid |
| HPLC | High pressure liquid chromatography |
| hr or h or hrs | Hours |
| Hz | Hertz |
| IBD | Inflammatory bowel disease |
| i-pr | Isopropyl |
| J | Coupling constant (MHz) |
| Kg/kg | Kilogram |
| LCMS | Liquid chromatography-mass spectrometry |
| LPS | Lipopolysaccharide |
| M | Molar |
| m | multiplet |
| M+ | Mass peak |
| M + H+ | Mass peak plus hydrogen |
| Me | Methyl |
| mg | Milligram |
| MHz | Megahertz |
| ml/mL | Milliliter |
| mM | Millimolar |
| mmol | Millimole |
| MOPS | 3-Morpholinopropane-1-sulfonic acid |
| MS | Mass spectroscopy |
| Ms | Mesyl |
| nBu/Bu | Butyl |
| nL | Nanoliter |
| nm | Nanometer |

-continued

| Abbreviation | Meaning |
|---|---|
| NMR | Nuclear magnetic resonance |
| NMP | N-methylpyrrolidinone |
| NP-40 | Nonyl phenoxypolyethoxylethanol |
| Pd—C/Pd/C | Palladium on Carbon |
| Ph | Phenyl |
| q | Quartet |
| q.s. | Quantity sufficient to achieve a stated function |
| RP | Reverse phase |
| rt | Room temperature |
| s | Singlet |
| sat. | Saturated |
| t | Triplet |
| TEA | Triethylamine |
| Tf | Trifluoromethanesulfonyl |
| TFA | Trifluoroacetic acid |
| THF | Tetrahydrofuran |
| TR-FRET | Time-resolved fluorescence energy transfer |
| δ | Chemical shift (ppm) |
| μL/μl | Microliter |
| μM | Micromolar |

Compounds

The present application provides compounds that function as inhibitors of PI3K isoforms. In one aspect, provided are the compounds having the structure of formula I or IA:

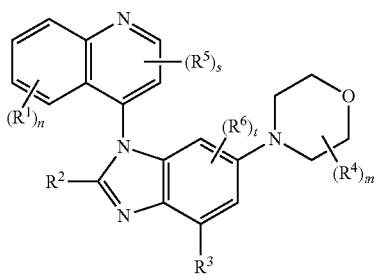

Formula I

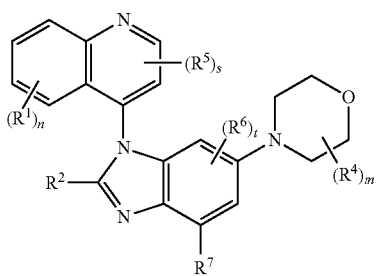

Formula IA wherein n is 1, 2, 3 or 4;
m is 1, 2, 3 or 4;
s is 1 or 2;
t is 1 or 2;
each $R^1$ is independently selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{100}$;
$R^2$ is selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{101}$;
$R^3$ is selected from $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{6-10}$ aryl, 5-10 membered heteroaryl and 4-10 membered heterocyclyl is optionally substituted with one to four $R^{102}$;
$R^4$ is selected from hydrogen, $C_{1-6}$ alkyl, $C_{2-6}$ alkenyl, $C_{2-6}$ alkynyl, acyl, $C_{3-8}$ cycloalkyl and $C_{1-6}$ alkyl sulfonyl;
each $R^5$ is independently selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{103}$;
each $R^6$ is independently selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl or $C_{2-6}$ alkynyl;
each $R^a$ and $R^b$ is independently selected from hydrogen, $C_{1-6}$ alkyl, $C_{2-6}$ alkenyl and $C_{2-6}$ alkynyl;
wherein each $C_{1-6}$ alkyl, $C_{2-6}$ alkenyl, $C_{2-6}$ alkynyl, is optionally substituted with one to four $R^{200}$;
each $R^{100}$, $R^{101}$, $R^{102}$, and $R^{103}$ is independently selected from hydrogen, halo, cyano, hydroxy, amino, oxo, thioxo, vinyl, —C(O)$R^c$, —C(O)OR, —C(O)N$R^c R^d$, —N($R^c$)C(O)$R^d$, —S(O)N$R^c R^d$, —S(O)$_2$N$R^c R^d$, —S(O)$R^c$, —S(O)$_2$R, —N$R^c R^d$, —O$R^c$, —S$R^d$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl;
wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{201}$;
each $R^c$ and $R^d$ is independently selected from hydrogen, $C_{1-6}$ alkyl, $C_{2-6}$ alkenyl and $C_{2-6}$ alkynyl;
each $R^{200}$ and $R^{201}$ is independently selected from hydrogen, halo, cyano, hydroxy, amino, oxo, thioxo, vinyl, —C(O)$R^e$, —C(O)O$R^e$, —C(O)N$R^e R^f$, —N($R^e$)C(O)$R^f$, —S(O)

$NR^eR^f$, $-S(O)_2NR^eR^f$, $-S(O)R^e$, $-S(O)_2R^e$, $-NR^eR^f$, $-OR^e$, $-SR^e$, $C_{1-6}$ alkyl, $C_{2-6}$ alkenyl and $C_{2-6}$ alkynyl;

each $R^e$ and $R^f$ is independently selected from hydrogen, $C_{1-6}$ alkyl, $C_{2-6}$ alkenyl and $C_{2-6}$ alkynyl;

or a pharmaceutically acceptable salt, isomer, or a mixture thereof.

In another aspect, provided are compounds of Formula IB:

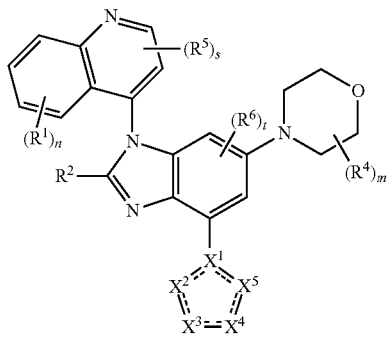

Formula IB wherein n, s, m, t, $R^1$, $R^2$, $R^4$, $R^5$ and $R^6$ are as defined above;

═══ represents a single or double bond;

$X^1$ is N or C;

each $X^2$, $X^3$, $X^4$ and $X^5$ is independently selected from S, O, $CR^{10}$ and $NR^{11}$;

wherein each $R^{10}$ is independently selected from hydrogen, halo, cyano, hydroxy, amino, $-C(O)R^a$, $-C(O)OR^b$, $-C(O)NR^aR^b$, $-N(R^a)C(O)R^b$, $-S(O)NR^aR^b$, $-S(O)_2NR^aR^b$, $-S(O)R^a$, $-S(O)_2R^a$, $-NR^aR^b$, $-OR^a$, $-SR^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{104}$;

wherein each $R^{11}$ is independently selected from absent, hydrogen, halo, cyano, hydroxy, amino, $-C(O)R^a$, $-C(O)OR^b$, $-C(O)NR^aR^b$, $-N(R^a)C(O)R^b$, $-S(O)NR^aR^b$, $-S(O)_2NR^aR^b$, $-S(O)R^a$, $-S(O)_2R^a$, $-NR^aR^b$, $-OR^a$, $-SR^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

alternatively, one $R^{10}$ and one $R^{11}$ group, together with the atoms to which they are attached form a five, six or seven membered fused or bridged ring;

or a pharmaceutically acceptable salt, isomer, or a mixture thereof.

In another aspect, provided are compounds of Formula IC:

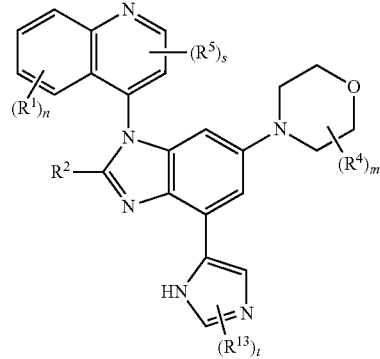

Formula IC wherein n, s, m, t, $R^1$, $R^2$, $R^4$ and $R^5$ are as defined above;

each $R^{13}$ is independently selected from hydrogen, halo, cyano, hydroxy, amino, $-C(O)R^a$, $-C(O)OR^b$, $-C(O)NR^aR^b$, $-N(R^a)C(O)R^b$, $-S(O)NR^aR^b$, $-S(O)_2NR^aR^b$, $-S(O)R^a$, $-S(O)_2R^a$, $-NR^aR^b$, $-OR^a$, $-SR^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

each $R^a$ and $R^b$ is independently selected from hydrogen, $C_{1-6}$ alkyl, $C_{2-6}$ alkenyl and $C_{2-6}$ alkynyl;

wherein each $C_{1-6}$ alkyl, $C_{2-6}$ alkenyl, $C_{2-6}$ alkynyl, is optionally substituted with one to four $R^{200}$;

each $R^{200}$ is independently selected from hydrogen, halo, cyano, hydroxy, amino, oxo, thioxo, vinyl, $-C(O)R^e$, $-C(O)OR^e$, $-C(O)NR^eR^f$, $-N(R^e)C(O)R^f$, $-S(O)NR^eR^f$, $-S(O)_2NR^eR^f$, $-S(O)R^e$, $-S(O)_2R^e$, $-NR^eR^f$, $-OR^e$, $-SR^e$, $C_{1-6}$alkyl, $C_{2-6}$ alkenyl and $C_{2-6}$ alkynyl;

each $R^e$ and $R^f$ is independently selected from hydrogen, $C_{1-6}$ alkyl, $C_{2-6}$ alkenyl and $C_{2-6}$ alkynyl;

or a pharmaceutically acceptable salt, isomer, or a mixture thereof.

In another aspect, provided are compounds of Formula ID:

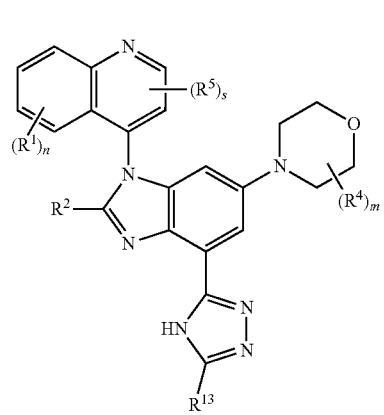

Formula ID wherein n, s, m, $R^1$, $R^2$, $R^4$, $R^5$, and $R^{13}$ are as defined above;

or a pharmaceutically acceptable salt, isomer, or a mixture thereof.

In another aspect, provided are compounds of Formula IE:

Formula IE

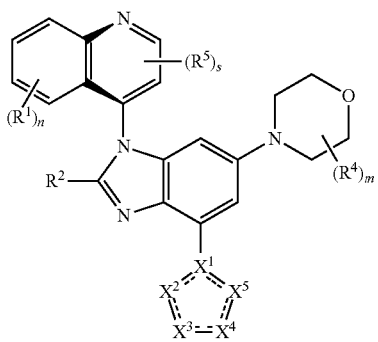

wherein n, s, m, $R^1$, $R^2$, $R^4$, $R^5$, $X^1$, $X^2$, $X^3$, $X^4$ and $X^5$ are as defined above;
or a pharmaceutically acceptable salt, isomer, or a mixture thereof.

In another aspect, provided are compounds of Formula IF:

Formula IF wherein n, s, m, t, $R^1$, $R^2$, $R^4$, $R^5$, and $R^{13}$ are as defined above;
or a pharmaceutically acceptable salt, isomer, or a mixture thereof.

In another aspect, provided are compounds of Formula IG:

Formula IG wherein n, s, m, $R^1$, $R^2$, $R^4$, $R^5$, and $R^{13}$ are as defined above;
or a pharmaceutically acceptable salt, isomer, or a mixture thereof.

In another aspect, provided are compounds of Formula IH:

Formula IH

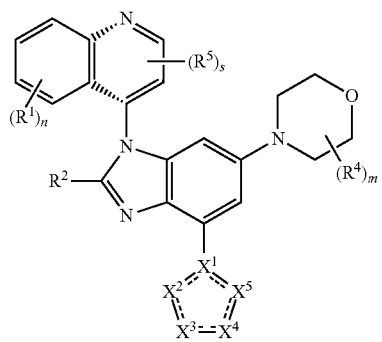

wherein n, s, m, $R^1$, $R^2$, $R^4$, $R^5$, $X^1$, $X^2$, $X^3$, $X^4$ and $X^5$ are as defined above;
or a pharmaceutically acceptable salt, isomer, or a mixture thereof.

In another aspect, provided are compounds of Formula IJ:

Formula IJ

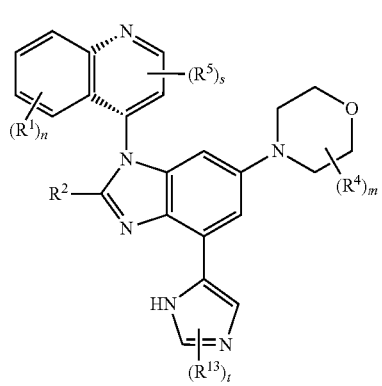

wherein n, s, m, t, $R^1$, $R^2$, $R^4$, $R^5$, and $R^{13}$ are as defined above;
or a pharmaceutically acceptable salt, isomer, or a mixture thereof.

In another aspect, provided are compounds of Formula IK:

Formula IK

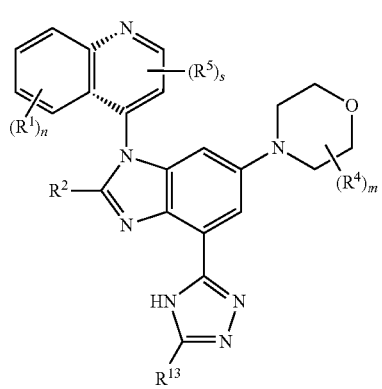

wherein n, s, m, $R^1$, $R^2$, $R^4$, $R^5$, and $R^{13}$ are as defined above;
or a pharmaceutically acceptable salt, isomer, or a mixture thereof.

In another aspect, provided are compounds of Formula (IL) or (IM)

Formula IL

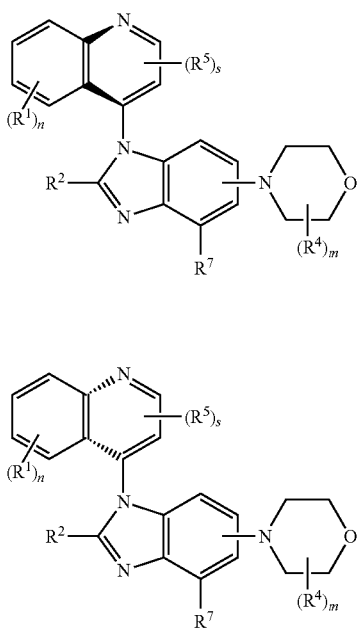

Formula IM wherein n, s, m, $R^1$, $R^2$, $R^4$, $R^5$, and $R^7$ are as defined above;
or a pharmaceutically acceptable salt, isomer, or a mixture thereof.

In certain embodiments, provided is a compound of Formula I, wherein $R^3$ is

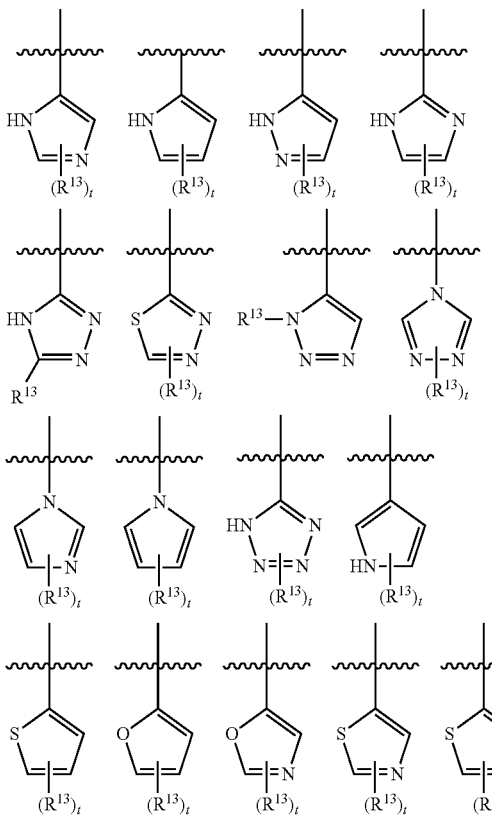

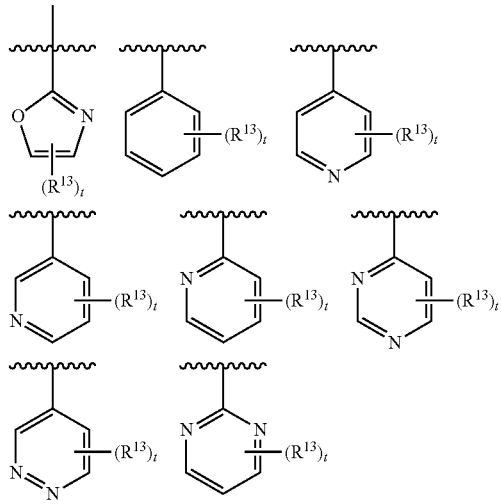

wherein t is 1 or 2;

each $R^{13}$ is independently selected from hydrogen, halo, cyano, hydroxy, amino, oxo, thioxo, vinyl, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

or a pharmaceutically acceptable salt, isomer, or a mixture thereof.

In certain embodiments, provided is a compound of Formula IE or IH, or a pharmaceutically acceptable salt, isomer, or a mixture thereof; wherein the substituent

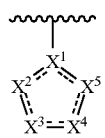

is selected from:

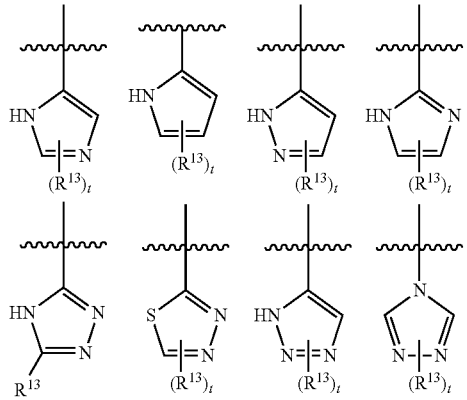

-continued

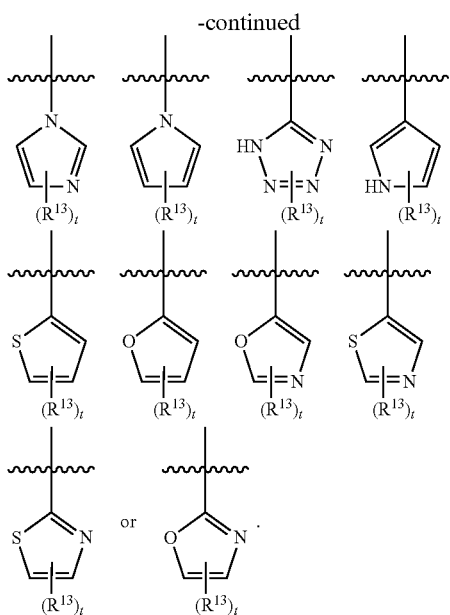

One of skill in the art understands that t=1 for compounds having only one atom available for substitution.

In certain embodiments, provided is a compound of Formula I, IA, IB, IC, ID, IE, IF, IG, IH, IJ, IK, IL or IM, wherein $R^1$ is selected from hydrogen, fluoro, chloro, bromo, iodo, methyl, ethyl, propyl, butyl, fluoromethyl, difluoromethyl, trifluoromethyl, fluoroethyl, difluoroethyl and trifluoroethyl; or a pharmaceutically acceptable salt, isomer, or a mixture thereof.

In certain embodiments, provided is a compound of Formula I, IA, IB, IC, ID, IE, IF, IG, IH, IJ, IK, IL or IM, wherein $R^1$ is fluoro or chloro; or a pharmaceutically acceptable salt, isomer, or a mixture thereof.

In certain embodiments, provided is a compound of Formula I, IA, IB, IC, ID, IE, IF, IG, IH, IJ, IK, IL or IM, wherein $R^2$ is $C_{1-6}$ alkyl, $C_{3-8}$ cycloalkyl, 5-6 membered heteroaryl containing 1 to 3 heteroatoms selected from the group consisting of N, O, and S, and 4-6 membered heterocyclyl containing 1 to 4 heteroatoms selected from the group consisting of N, O, and S; wherein each $C_{1-6}$ alkyl, $C_{3-8}$ cycloalkyl, 5-6 membered heteroaryl and 4-6 membered heterocyclyl is optionally substituted with one to four $R^{101}$; or a pharmaceutically acceptable salt, isomer, or a mixture thereof.

In certain embodiments, provided is a compound of Formula I, IA, IB, IC, ID, IE, IF, IG, IH, IJ, IK, IL or IM, wherein $R^2$ is selected from hydrogen, amino, methyl, ethyl, propyl, isopropyl, butyl, isobutyl, t-butyl, furanyl, tetrahydrofuranyl, oxetanyl, and cyclopropyl; or a pharmaceutically acceptable salt, isomer, or a mixture thereof.

In certain embodiments, provided is a compound of Formula I, IA, IB, IC, ID, IE, IF, IG, IH, IJ, IK, IL or IM, wherein $R^4$ is selected from hydrogen and methyl; or a pharmaceutically acceptable salt, isomer, or a mixture thereof.

In certain embodiments, provided is a compound of Formula I, IA, IB, IC, ID, IE, IF, IG, IH, IJ, IK, IL or IM, wherein $R^5$ is selected from hydrogen, methyl, ethyl, trifluoromethyl, carboxamide, cyano, piperazinyl, cyclopropyl, phenyl and triazolyl; or a pharmaceutically acceptable salt, isomer, or a mixture thereof.

In certain embodiments, provided is a compound of Formula I, IA, IB, IC, ID, IE, IF, IG, IH, IJ, IK, IL or IM, wherein $R^1$ is selected from hydrogen or a substituent selected from the table below:

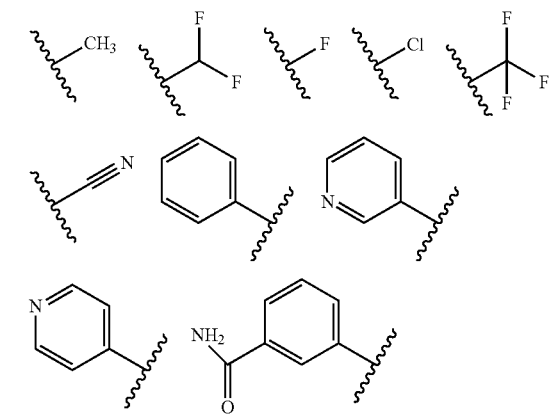

or a pharmaceutically acceptable salt thereof.

In certain embodiments, provided is a compound of Formula I, IA, IB, IC, ID, IE, IF, IG, IH, IJ, IK, IL or IM, wherein $R^2$ is selected from hydrogen or a substituent selected from the table below:

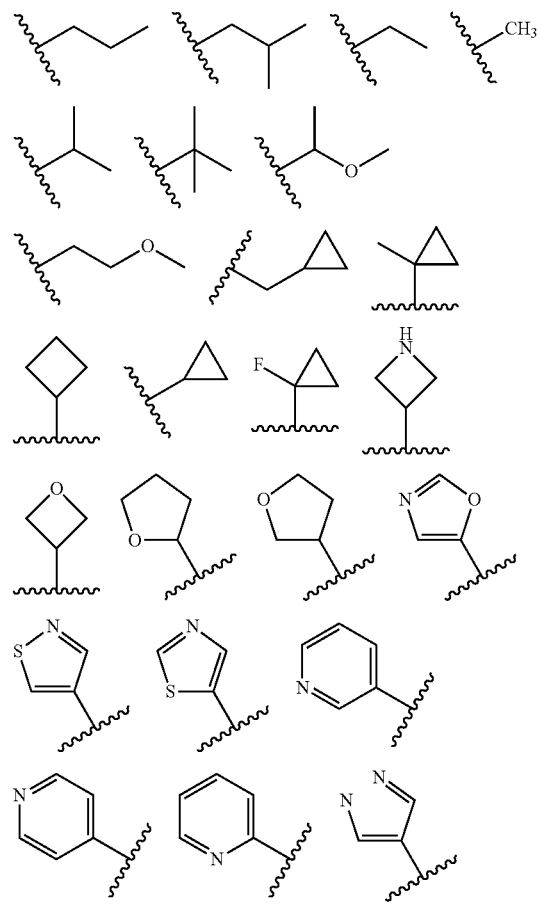

-continued
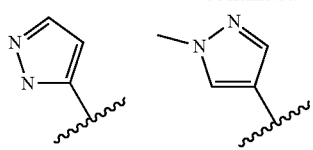
or a pharmaceutically acceptable salt thereof.
In certain embodiments, provided is a compound of Formula I, wherein R³ is selected from hydrogen or a substituent selected from the table below:
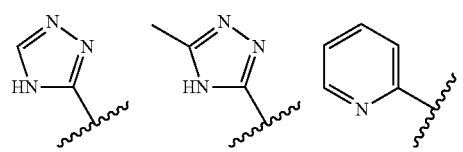
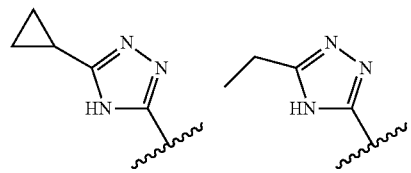
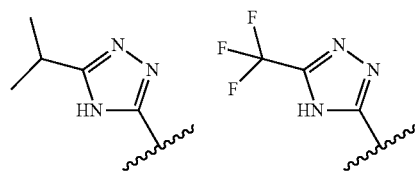
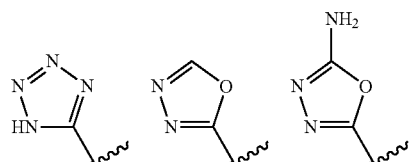
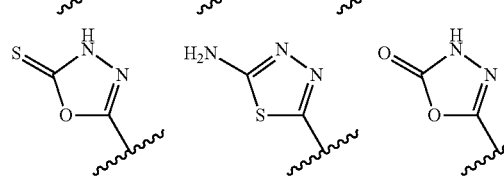
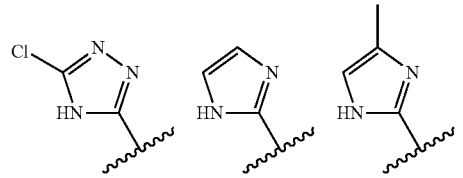
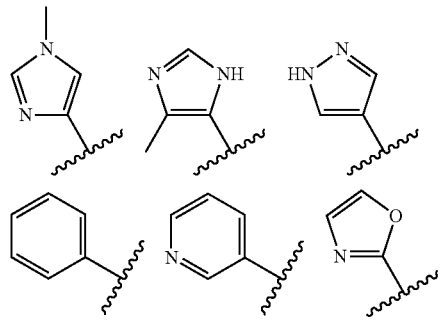
-continued
or a pharmaceutically acceptable salt thereof.

In certain embodiments, provided is a compound of Formula I, IA, IB, IC, ID, IE, IF, IG, IH, IJ, IK, IL or IM, wherein $R^5$ is selected from hydrogen or a substituent selected from the table below:

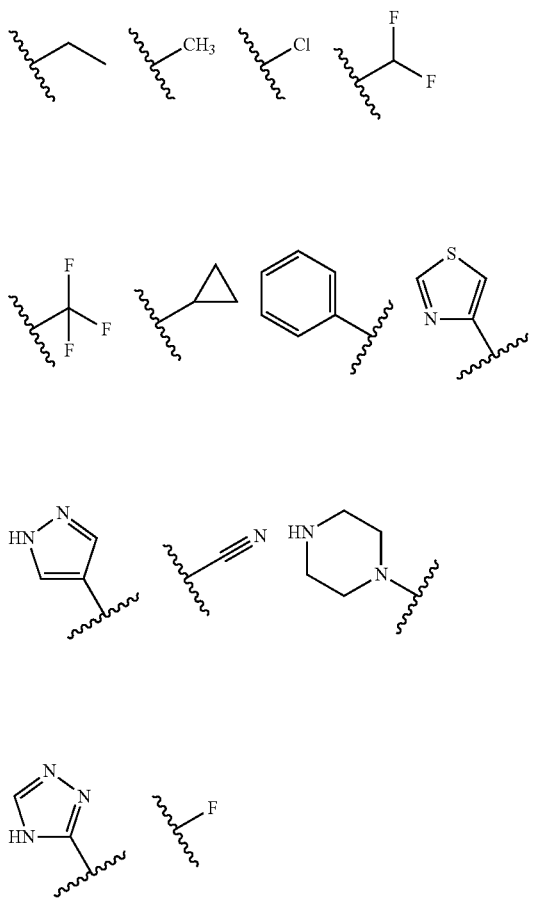

or a pharmaceutically acceptable salt thereof.

In certain embodiments, provided is a compound selected from Table A, or a pharmaceutically acceptable salt, isomer, or a mixture thereof:

TABLE A

| Example | Structure |
|---------|-----------|
| 1 | 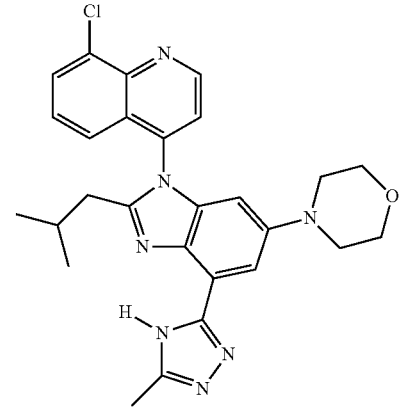 [SMILES: Cc1nnc(-c2cc(N3CCOCC3)cc3c2nc(CC(C)C)n3-c2ccnc3c(Cl)cccc23)[nH]1] |
| 2 | 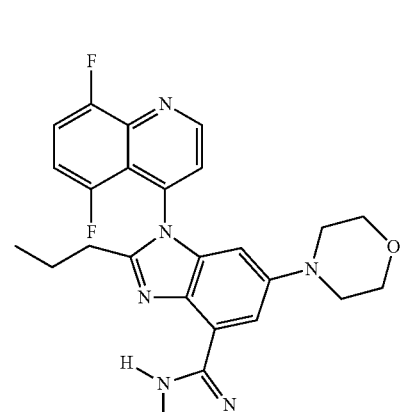 |
| 3 | 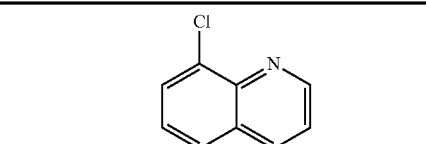 |
| 4 | 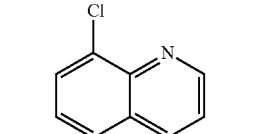 |

TABLE A-continued

| Example | Structure |
|---------|-----------|
| 5 | 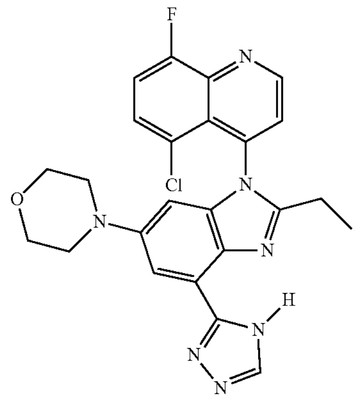 [SMILES: CCc1nc2c(-c3nnc[nH]3)cc(N3CCOCC3)cc2n1-c1ccnc2c(F)ccc(Cl)c12] |
| 6 | 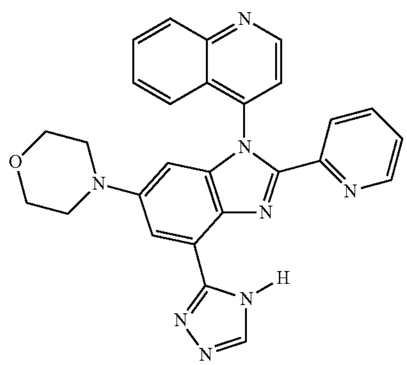 [SMILES: c1ccc(-c2nc3c(-c4nnc[nH]4)cc(N4CCOCC4)cc3n2-c2ccnc3ccccc23)nc1] |
| 7 | 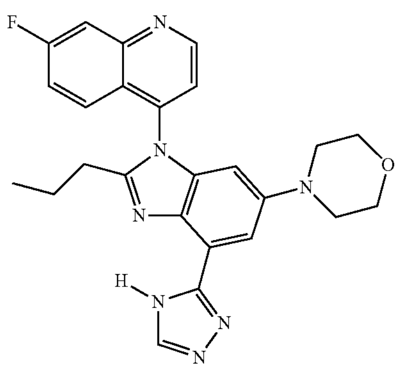 [SMILES: CCCc1nc2c(-c3nnc[nH]3)cc(N3CCOCC3)cc2n1-c1ccnc2cc(F)ccc12] |
| 8 | 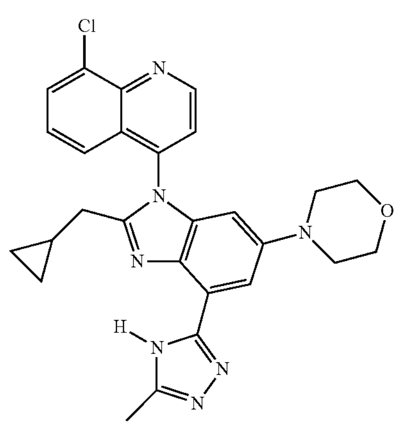 [SMILES: Cc1nnc(-c2cc(N3CCOCC3)cc3c2nc(CC2CC2)n3-c2ccnc3c(Cl)cccc23)[nH]1] |
| 9 | |
| 10 | |
| 11 | |
| 12 | |

TABLE A-continued

| Example | Structure |
|---------|-----------|
| 13 | |
| 14 | |
| 15 | |
| 16 | 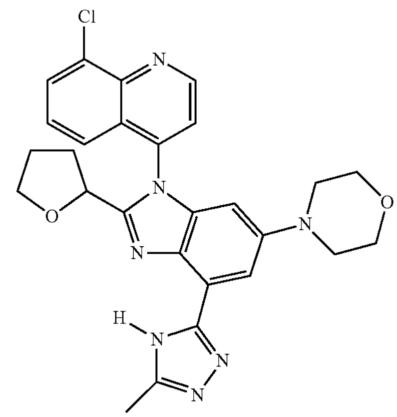 [SMILES: Cc1nnc(-c2cc(N3CCOCC3)cc3c2nc(C2CCCO2)n3-c2ccnc3c(Cl)cccc23)[nH]1] |
| 17 | 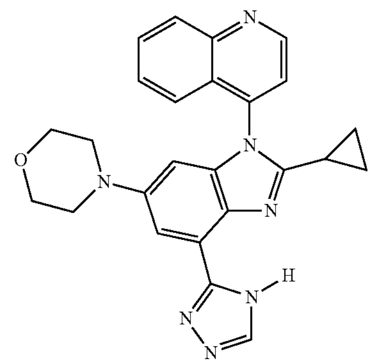 [SMILES: c1ccc2c(-n3c(C4CC4)nc4c(-c5nnc[nH]5)cc(N5CCOCC5)cc43)ccnc2c1] |
| 18 | 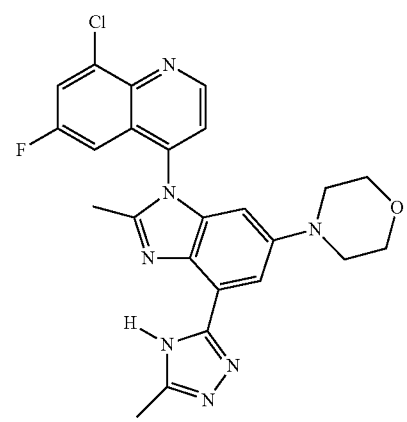 [SMILES: Cc1nnc(-c2cc(N3CCOCC3)cc3c2nc(C)n3-c2ccnc3c(Cl)cc(F)cc23)[nH]1] |
| 19 | 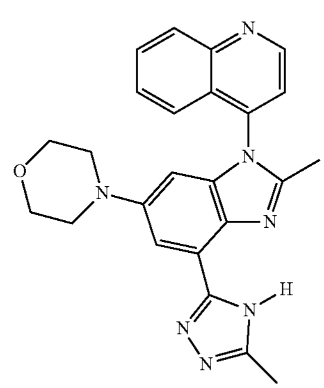 [SMILES: Cc1nnc(-c2cc(N3CCOCC3)cc3c2nc(C)n3-c2ccnc3ccccc23)[nH]1] |

TABLE A-continued

| Example | Structure |
|---------|-----------|
| 20 | 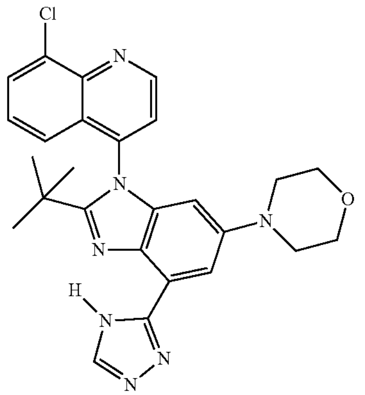 [SMILES: CC(C)(C)c1nc2c(-c3nnc[nH]3)cc(N3CCOCC3)cc2n1-c1ccnc2c(Cl)cccc12] |
| 21 | 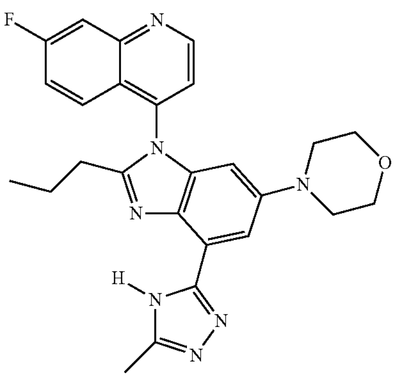 [SMILES: CCCc1nc2c(-c3nnc(C)[nH]3)cc(N3CCOCC3)cc2n1-c1ccnc2cc(F)ccc12] |
| 22 | 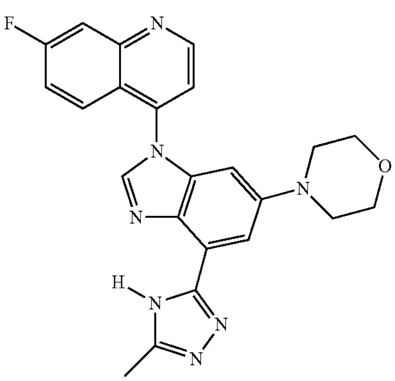 [SMILES: Cc1nnc(-c2cc(N3CCOCC3)cc3c2ncn3-c2ccnc3cc(F)ccc23)[nH]1] |
| 23 | 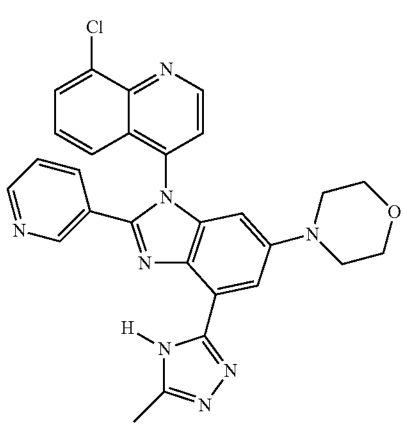 [SMILES: Cc1nnc(-c2cc(N3CCOCC3)cc3c2nc(-c2cccnc2)n3-c2ccnc3c(Cl)cccc23)[nH]1] |
| 24 | |
| 25 | |
| 26 | |
| 27 | |

TABLE A-continued
| Example | Structure |
|---|---|
| 28 | 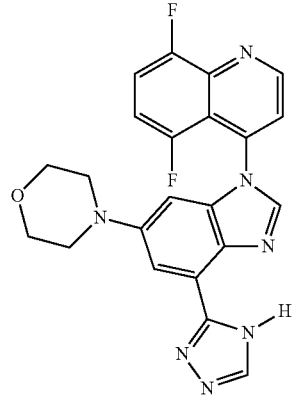 [SMILES: Fc1ccc(F)c2c(-n3cnc4c(-c5nnc[nH]5)cc(N5CCOCC5)cc43)ccnc12] |
| 29 | 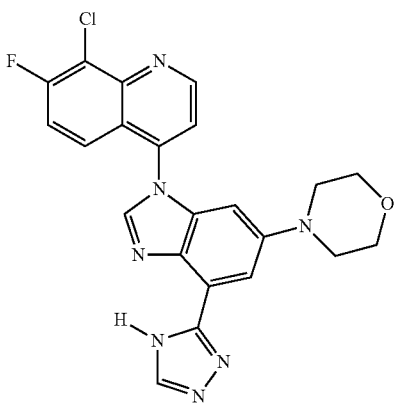 [SMILES: Fc1ccc2c(-n3cnc4c(-c5nnc[nH]5)cc(N5CCOCC5)cc43)ccnc2c1Cl] |
| 30 | 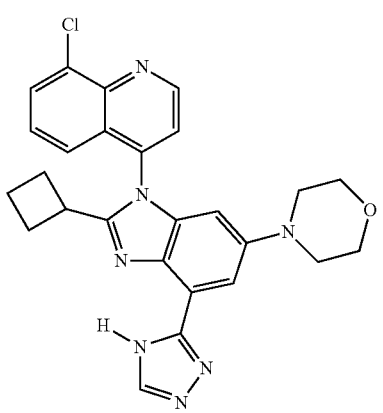 [SMILES: Clc1cccc2c(-n3c(C4CCC4)nc4c(-c5nnc[nH]5)cc(N5CCOCC5)cc43)ccnc12] |
| 31 | 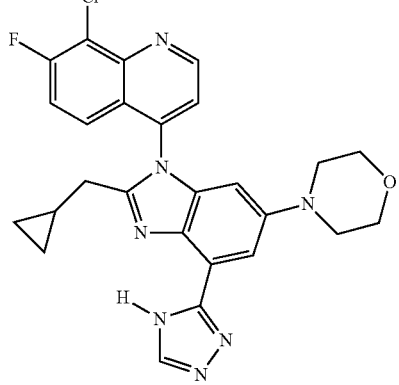 |
| 32 | 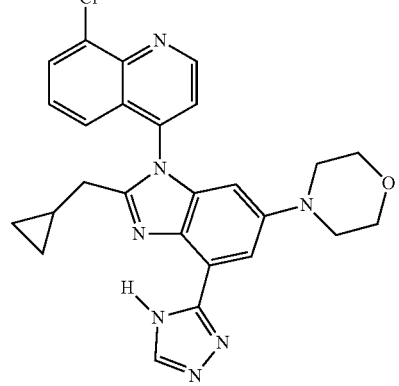 |
| 33 | 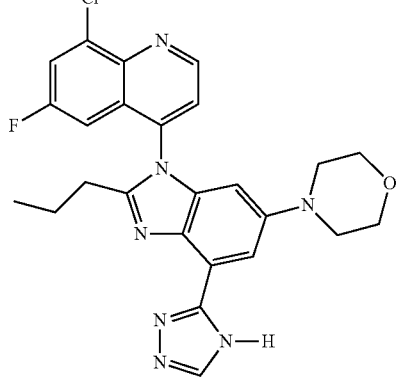 |
| 34 | 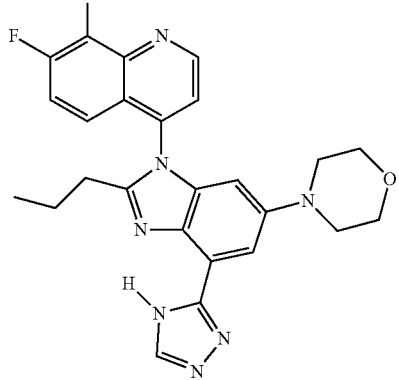 |

TABLE A-continued

| Example | Structure |
|---|---|
| 35 | |
| 36 | |
| 37 | |
| 38 | 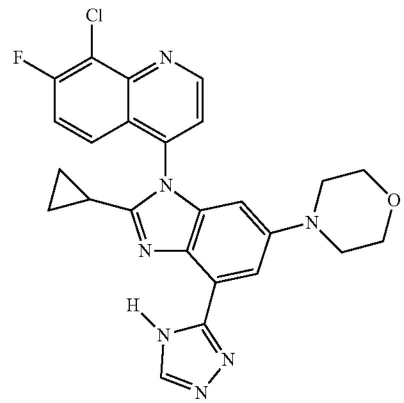 [SMILES: Fc1ccc2c(-n3c(C4CC4)nc4c(-c5nnc[nH]5)cc(N5CCOCC5)cc43)ccnc2c1Cl] |
| 39 | 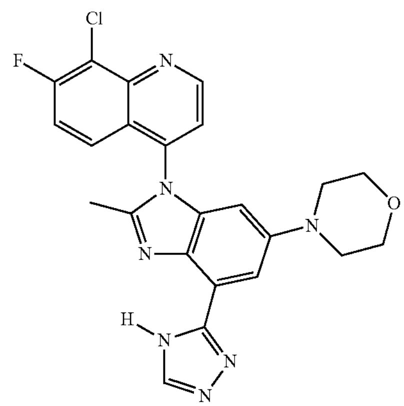 |
| 40 | 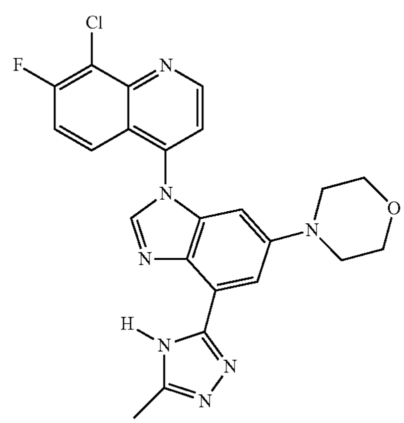 [SMILES: Cc1nnc(-c2cc(N3CCOCC3)cc3c2ncn3-c2ccnc3c(Cl)c(F)ccc23)[nH]1] |
| 41 | 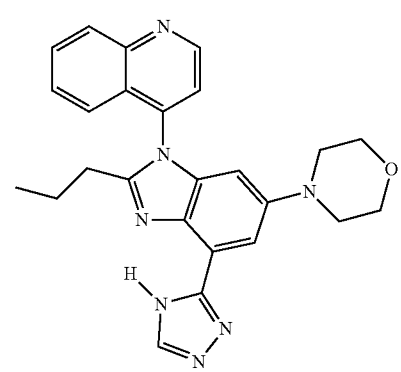 [SMILES: CCCc1nc2c(-c3nnc[nH]3)cc(N3CCOCC3)cc2n1-c1ccnc2ccccc12] |

TABLE A-continued

| Example | Structure |
|---------|-----------|
| 42 | 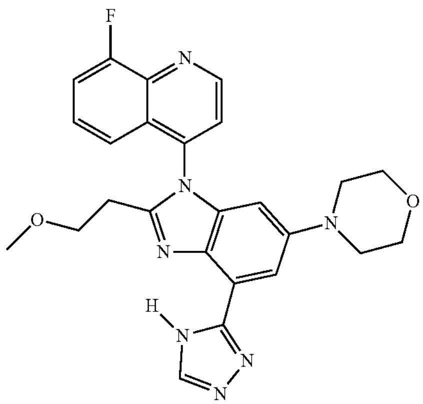 [SMILES: COCCc1nc2c(-c3nnc[nH]3)cc(N3CCOCC3)cc2n1-c1ccnc2c(F)cccc12] |
| 43 | 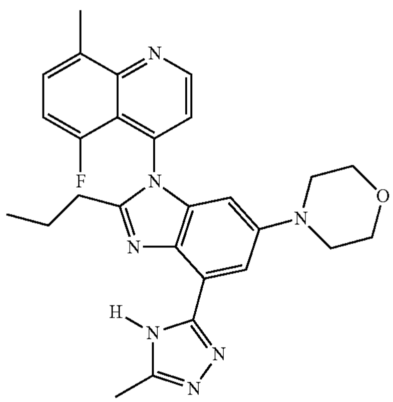 [SMILES: CCCc1nc2c(-c3nnc(C)[nH]3)cc(N3CCOCC3)cc2n1-c1ccnc2c(C)ccc(F)c12] |
| 44 | 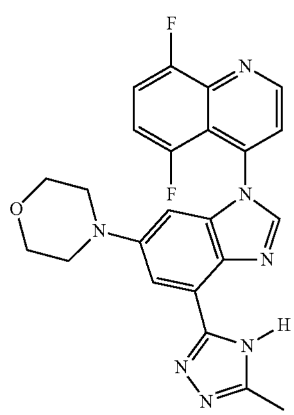 [SMILES: Cc1nnc(-c2cc(N3CCOCC3)cc3c2ncn3-c2ccnc3c(F)ccc(F)c23)[nH]1] |
| 45 | 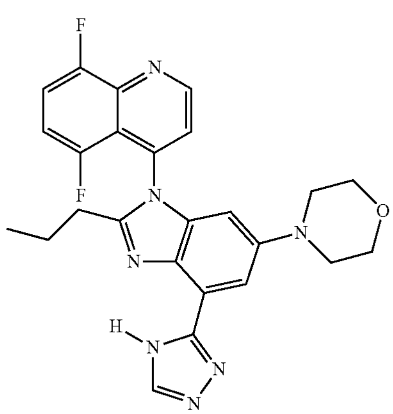 [SMILES: CCCc1nc2c(-c3nnc[nH]3)cc(N3CCOCC3)cc2n1-c1ccnc2c(F)ccc(F)c12] |
| 46 | 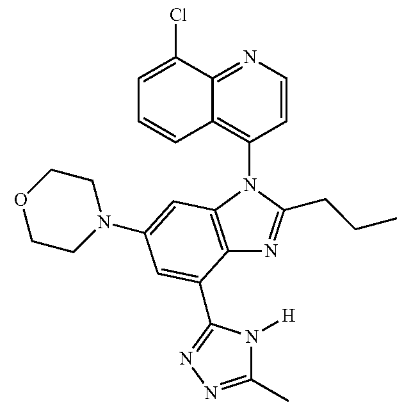 [SMILES: CCCc1nc2c(-c3nnc(C)[nH]3)cc(N3CCOCC3)cc2n1-c1ccnc2c(Cl)cccc12] |
| 47 | 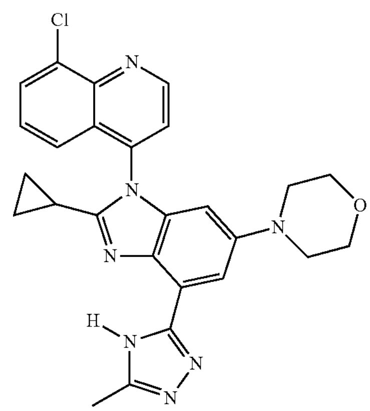 [SMILES: Cc1nnc(-c2cc(N3CCOCC3)cc3c2nc(C2CC2)n3-c2ccnc3c(Cl)cccc23)[nH]1] |
| 48 | 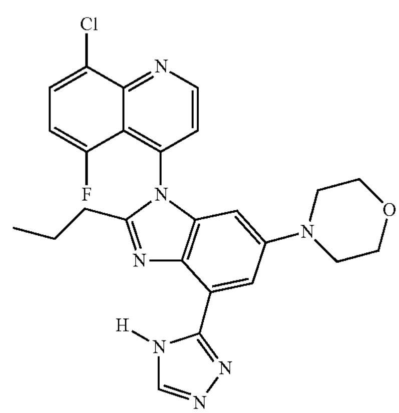 |

TABLE A-continued

| Example | Structure |
|---|---|
| 49 | (7,8-difluoroquinolin-4-yl on N1; 2-propyl; 6-morpholino; 4-(4H-1,2,4-triazol-3-yl) benzimidazole) |
| 50 | (8-chloroquinolin-4-yl on N1; 2-isobutyl; 6-morpholino; 4-(4H-1,2,4-triazol-3-yl) benzimidazole) |
| 51 | (5,8-difluoroquinolin-4-yl on N1; 2-methyl; 6-morpholino; 4-(5-methyl-4H-1,2,4-triazol-3-yl) benzimidazole) |
| 52 | (8-chloro-7-fluoroquinolin-4-yl on N1; 2-methyl; 6-morpholino; 4-(5-methyl-4H-1,2,4-triazol-3-yl) benzimidazole) |
| 53 | (7-fluoroquinolin-4-yl on N1; 6-morpholino; 4-(4H-1,2,4-triazol-3-yl) benzimidazole) |
| 54 | (8-chloroquinolin-4-yl on N1; 2-(1-fluorocyclopropyl); 6-morpholino; 4-(4H-1,2,4-triazol-3-yl) benzimidazole) |
| 55 | (2-ethyl-3-methylquinolin-4-yl on N1; 2-methyl; 6-morpholino; 4-(4H-1,2,4-triazol-3-yl) benzimidazole) |

TABLE A-continued
| Example | Structure |
|---|---|
| 56 | 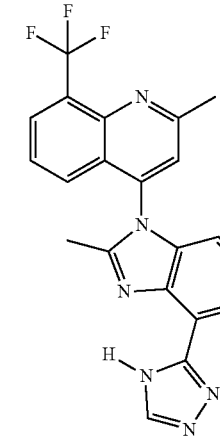 |
| 57 | 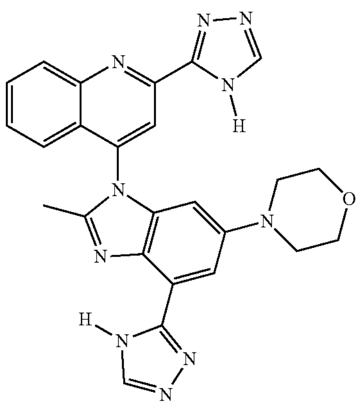 [SMILES: Cc1nc2c(-c3nnc[nH]3)cc(N3CCOCC3)cc2n1-c1cc(-c2nnc[nH]2)nc2ccccc12] |
| 58 | 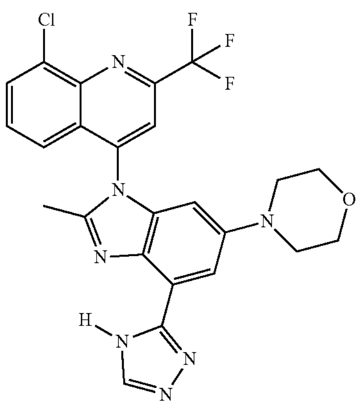 [SMILES: Cc1nc2c(-c3nnc[nH]3)cc(N3CCOCC3)cc2n1-c1cc(C(F)(F)F)nc2c(Cl)cccc12] |
| 59 | 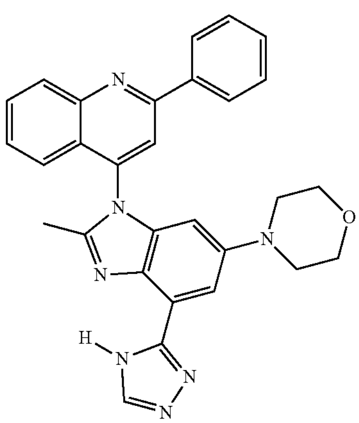 [SMILES: Cc1nc2c(-c3nnc[nH]3)cc(N3CCOCC3)cc2n1-c1cc(-c2ccccc2)nc2ccccc12] |
| 60 | 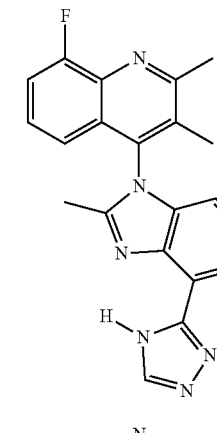 |
| 61 | |
| 62 | |
| 63 | |

TABLE A-continued

| Example | Structure |
|---------|-----------|
| 64 | *(8-chloro-2-methylquinolin-4-yl substituted 2-methyl-6-morpholino-4-(4H-1,2,4-triazol-3-yl)benzimidazole)* |
| 65 | *(3-methylquinolin-4-yl substituted 2-methyl-6-morpholino-4-(4H-1,2,4-triazol-3-yl)benzimidazole)* |
| 66 | *(3-cyclopropylquinolin-4-yl substituted 2-methyl-6-morpholino-4-(4H-1,2,4-triazol-3-yl)benzimidazole)* |
| 67 | *(2-cyanoquinolin-4-yl substituted 2-methyl-6-morpholino-4-(4H-1,2,4-triazol-3-yl)benzimidazole)* |
| 68 | *(8-chloro-3-methylquinolin-4-yl substituted 2-methyl-6-morpholino-4-(4H-1,2,4-triazol-3-yl)benzimidazole)* |
| 69 | *(2-methylquinolin-4-yl substituted 2-methyl-6-morpholino-4-(4H-1,2,4-triazol-3-yl)benzimidazole)* |
| 70 | *(8-chloro-2,3-dimethylquinolin-4-yl substituted 2-methyl-6-morpholino-4-(4H-1,2,4-triazol-3-yl)benzimidazole)* |
| 71 | *(2-methyl-3-ethylquinolin-4-yl substituted 6-morpholino-4-(4H-1,2,4-triazol-3-yl)benzimidazole)* |

TABLE A-continued
| Example | Structure |
|---|---|
| 72 | 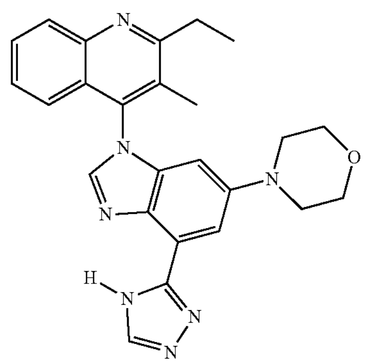 [SMILES: CCc1nc2ccccc2c(-n2cnc3c(-c4nnc[nH]4)cc(N4CCOCC4)cc32)c1C] |
| 73 | 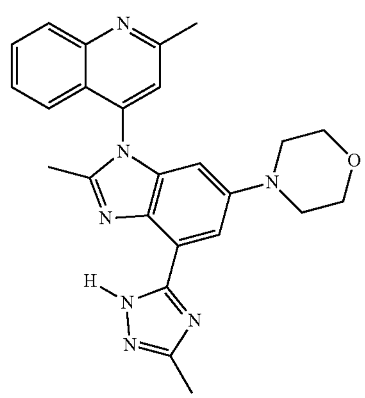 [SMILES: Cc1cc(-n2c(C)nc3c(-c4nc(C)n[nH]4)cc(N4CCOCC4)cc32)c2ccccc2n1] |
| 74 | 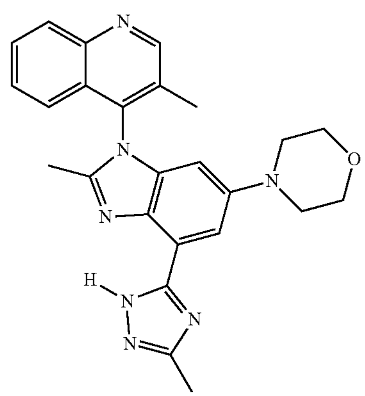 [SMILES: Cc1n[nH]c(-c2cc(N3CCOCC3)cc3c2nc(C)n3-c2c(C)cnc3ccccc23)n1] |
| 75 | 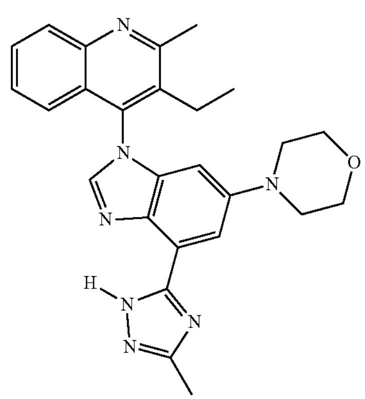 [SMILES: CCc1c(C)nc2ccccc2c1-n1cnc2c(-c3nc(C)n[nH]3)cc(N3CCOCC3)cc21] |
| 76 | |
| 77 | |
| 78 | |
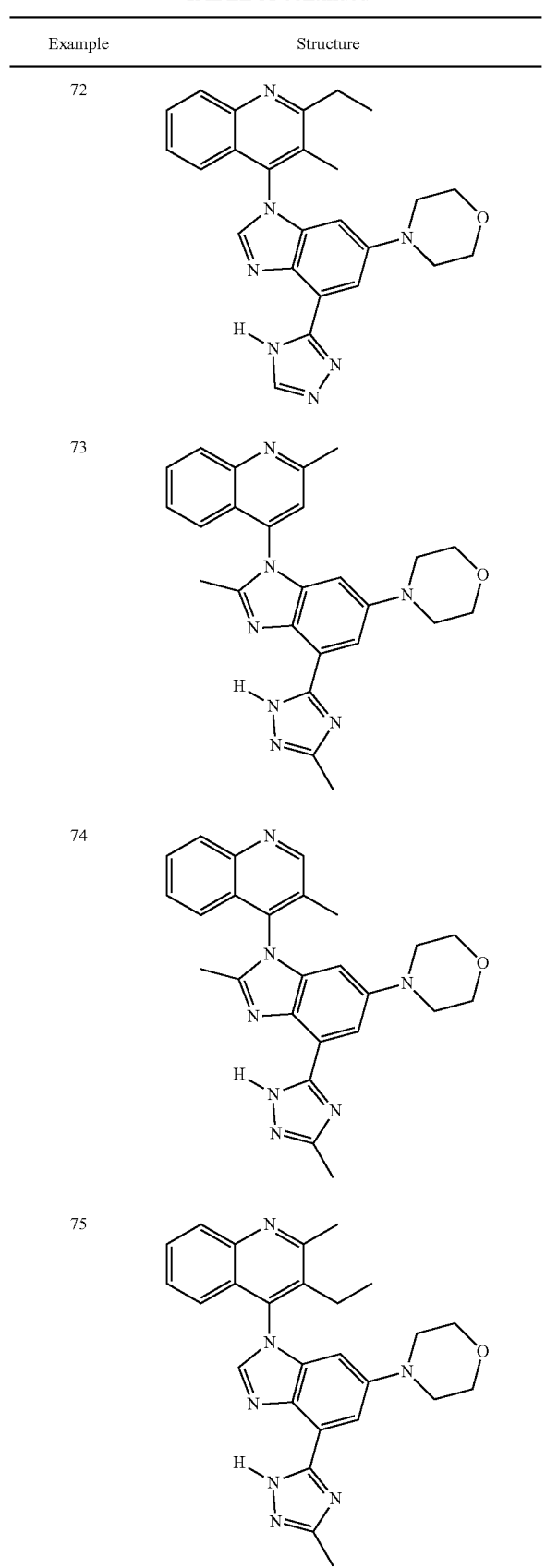
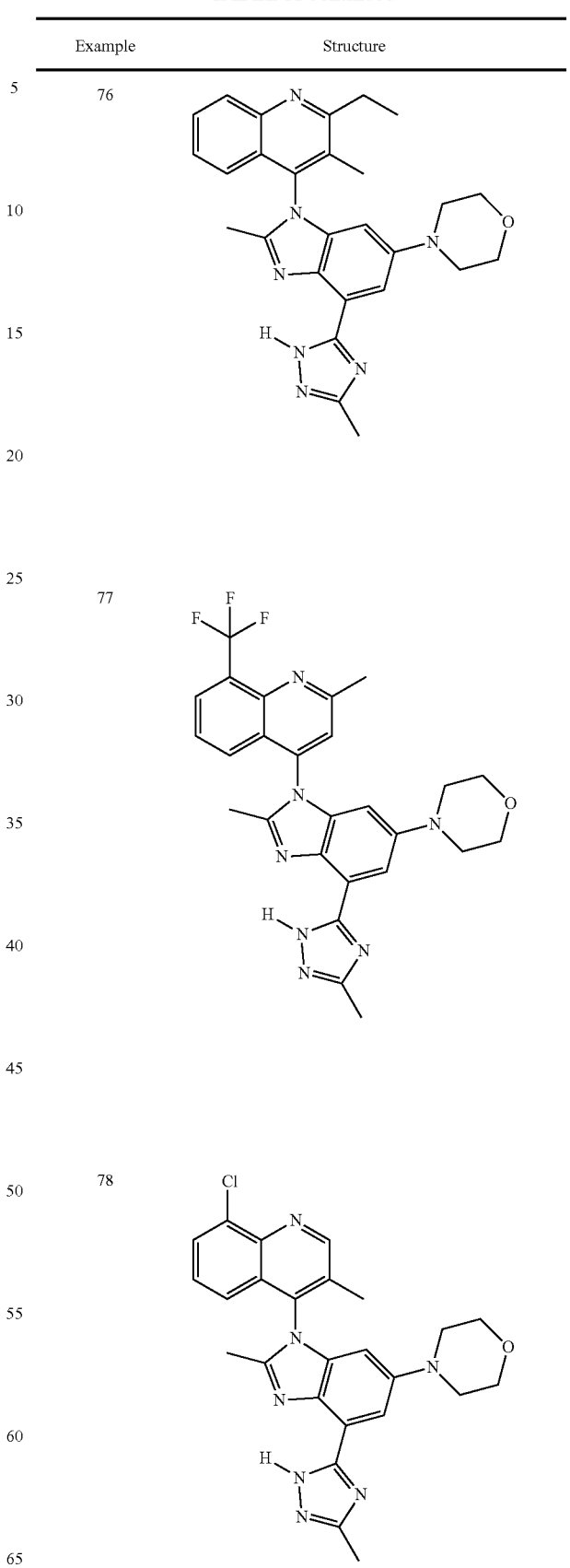

TABLE A-continued
| Example | Structure |
|---|---|
| 79 | 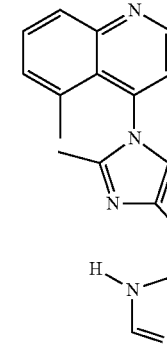 |
| 80 | 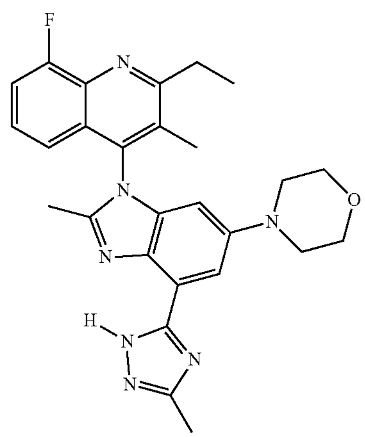 [SMILES: CCc1nc2c(F)cccc2c(-n2c(C)nc3c(-c4nc(C)n[nH]4)cc(N4CCOCC4)cc32)c1C] |
| 81 | 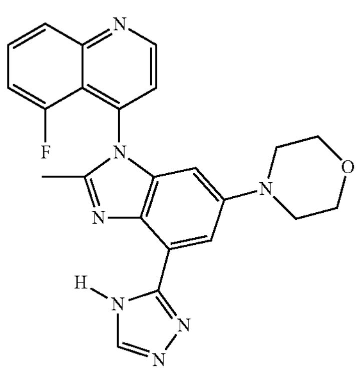 [SMILES: Cc1nc2c(-c3nnc[nH]3)cc(N3CCOCC3)cc2n1-c1ccnc2cccc(F)c12] |
| 82 | 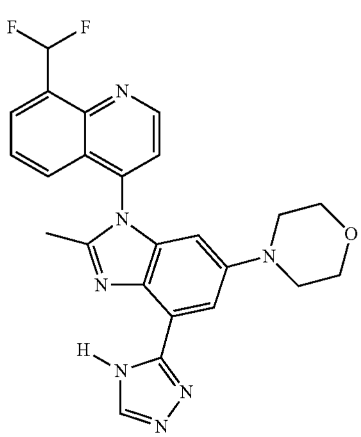 [SMILES: Cc1nc2c(-c3nnc[nH]3)cc(N3CCOCC3)cc2n1-c1ccnc2c(C(F)F)cccc12] |
TABLE A-continued
| Example | Structure |
|---|---|
| 83 | 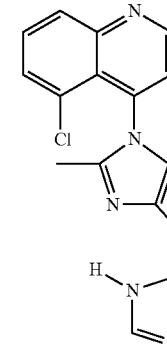 |
| 84 | 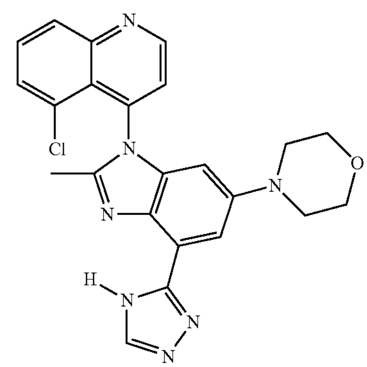 [SMILES: Cc1nc2c(-c3nnc[nH]3)cc(N3CCOCC3)cc2n1-c1ccnc2cccc(Cl)c12] |
| 85 | 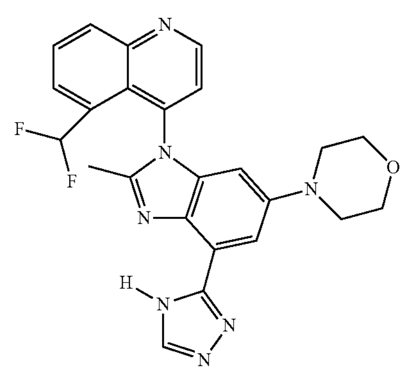 [SMILES: Cc1nc2c(-c3nnc[nH]3)cc(N3CCOCC3)cc2n1-c1ccnc2cccc(C(F)F)c12] |
| 86 | 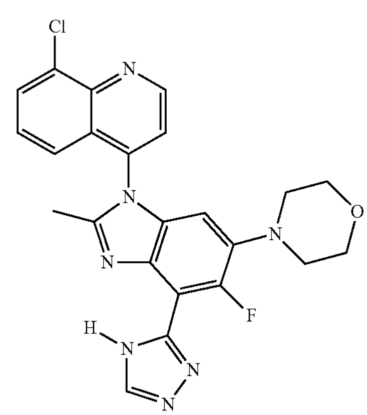 [SMILES: Cc1nc2c(-c3nnc[nH]3)c(F)c(N3CCOCC3)cc2n1-c1ccnc2c(Cl)cccc12] |

TABLE A-continued
| Example | Structure |
|---|---|
| 87 | 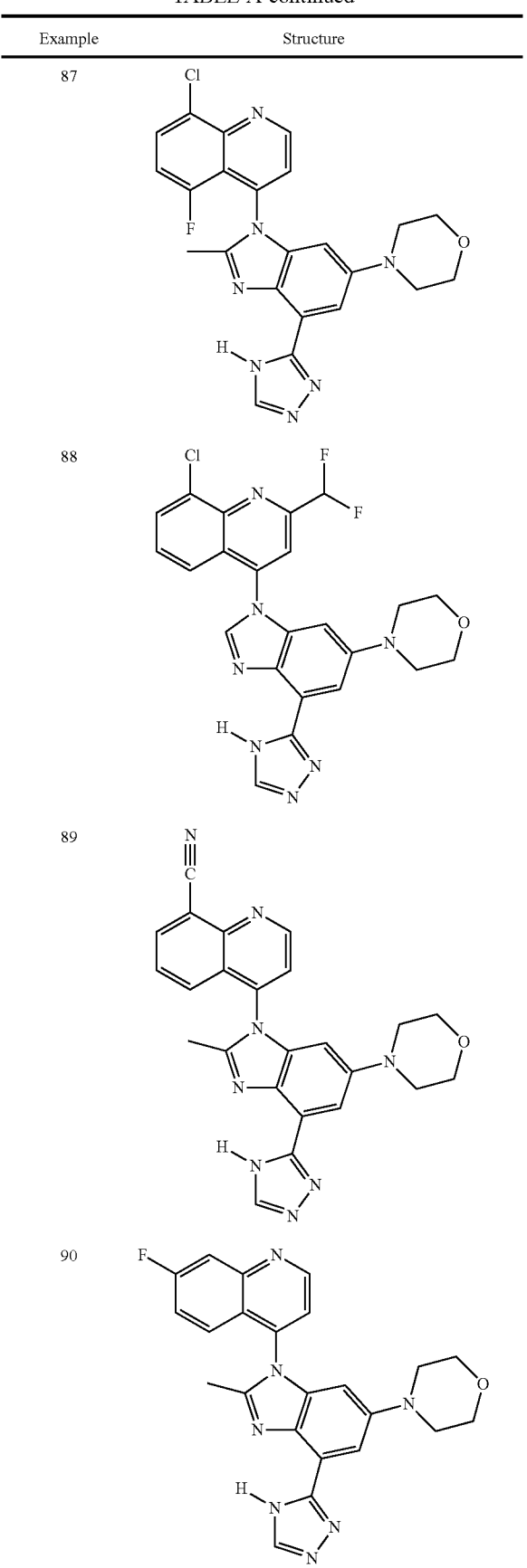 |
| 88 | 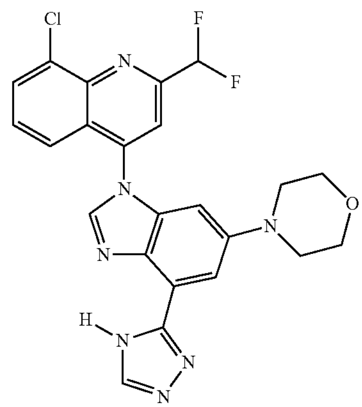 [SMILES: FC(F)c1cc(-n2cnc3c(-c4nnc[nH]4)cc(N4CCOCC4)cc32)c2cccc(Cl)c2n1] |
| 89 | 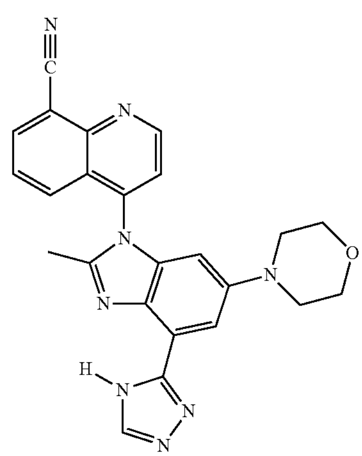 [SMILES: Cc1nc2c(-c3nnc[nH]3)cc(N3CCOCC3)cc2n1-c1ccnc2c(C#N)cccc12] |
| 90 | 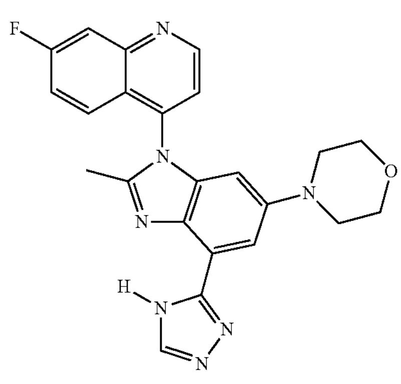 [SMILES: Cc1nc2c(-c3nnc[nH]3)cc(N3CCOCC3)cc2n1-c1ccnc2cc(F)ccc12] |
TABLE A-continued
| Example | Structure |
|---|---|
| 91 | 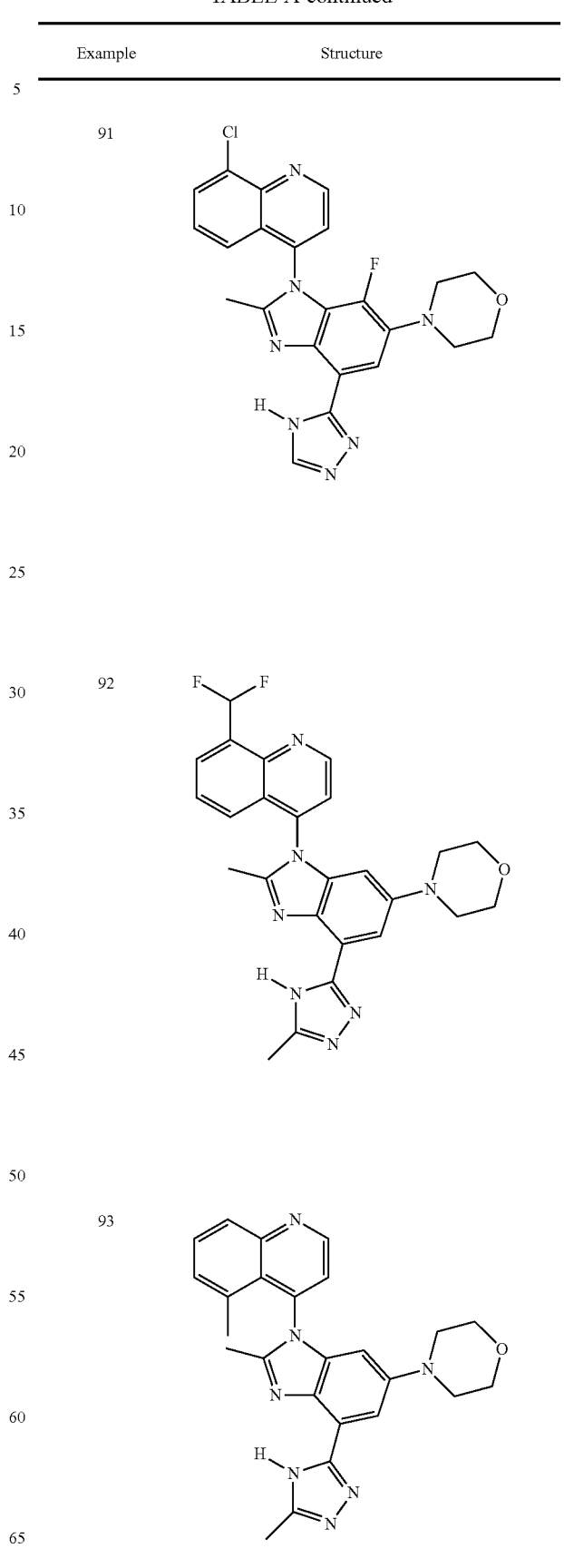 |
| 92 | 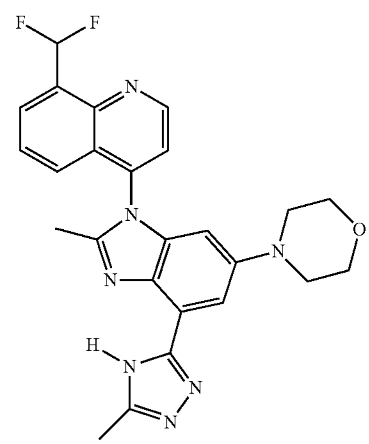 [SMILES: Cc1nnc(-c2cc(N3CCOCC3)cc3c2nc(C)n3-c2ccnc3c(C(F)F)cccc23)[nH]1] |
| 93 | 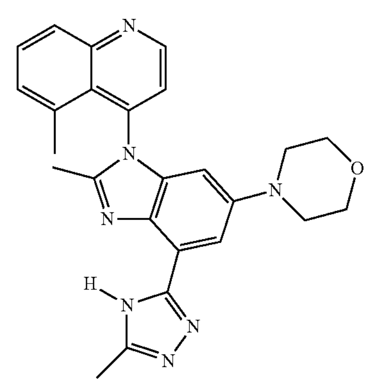 [SMILES: Cc1nnc(-c2cc(N3CCOCC3)cc3c2nc(C)n3-c2ccnc3cccc(C)c23)[nH]1] |

TABLE A-continued
| Example | Structure |
|---|---|
| 94 | 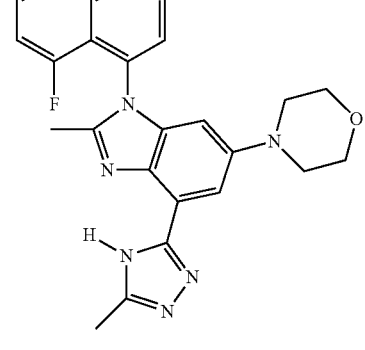 |
| 95 | |
| 96 | |
| 97 | 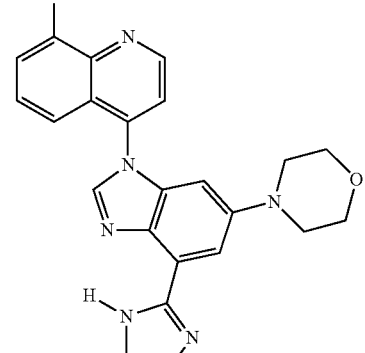 |
| 98 | 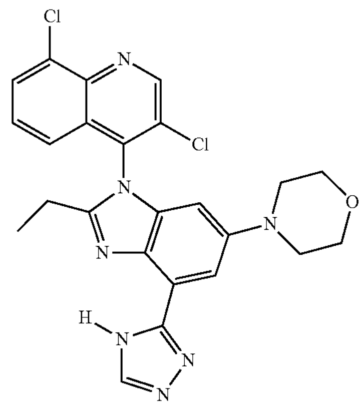 [SMILES: CCc1nc2c(-c3nnc[nH]3)cc(N3CCOCC3)cc2n1-c1c(Cl)cnc2c(Cl)cccc12] |
| 99 | 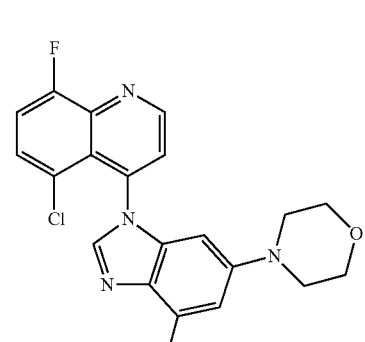 |
| 100 | 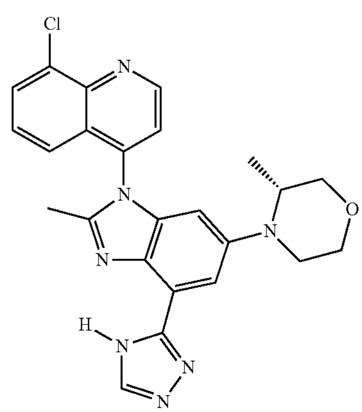 [SMILES: Cc1nc2c(-c3nnc[nH]3)cc(N3CCOC[C@H]3C)cc2n1-c1ccnc2c(Cl)cccc12] |

TABLE A-continued

| Example | Structure |
|---------|-----------|
| 101 | |
| 102 | |
| 103 | |
| 104 | 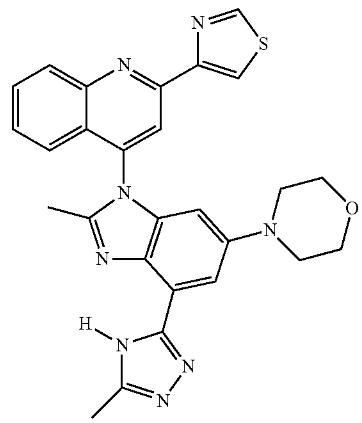 [SMILES: Cc1nnc(-c2cc(N3CCOCC3)cc3c2nc(C)n3-c2cc(-c3cscn3)nc3ccccc23)[nH]1] |
| 105 | 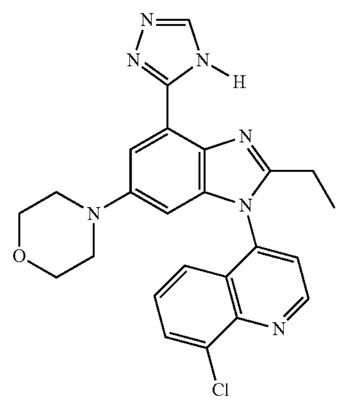 [SMILES: CCc1nc2c(-c3nnc[nH]3)cc(N3CCOCC3)cc2n1-c1ccnc2c(Cl)cccc12] |
| 106 | 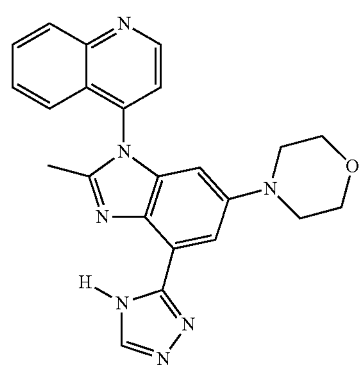 [SMILES: Cc1nc2c(-c3nnc[nH]3)cc(N3CCOCC3)cc2n1-c1ccnc2ccccc12] |
| 107 | 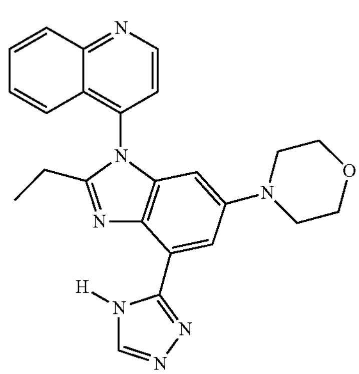 [SMILES: CCc1nc2c(-c3nnc[nH]3)cc(N3CCOCC3)cc2n1-c1ccnc2ccccc12] |

TABLE A-continued
| Example | Structure |
|---------|-----------|
| 108 | 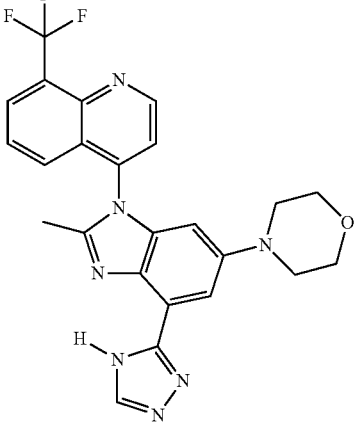 |
| 109 | 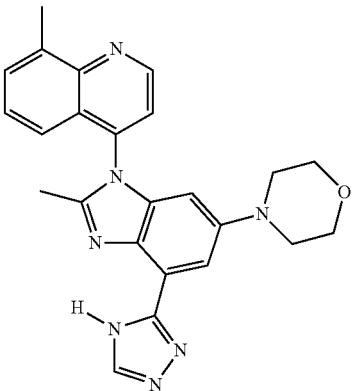 [SMILES: Cc1cccc2c(-n3c(C)nc4c(-c5nnc[nH]5)cc(N5CCOCC5)cc43)ccnc12] |
| 110 | 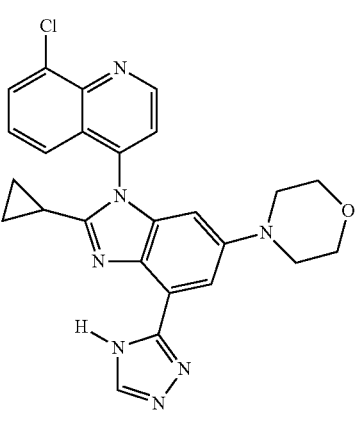 |
TABLE A-continued
| Example | Structure |
|---------|-----------|
| 111 | 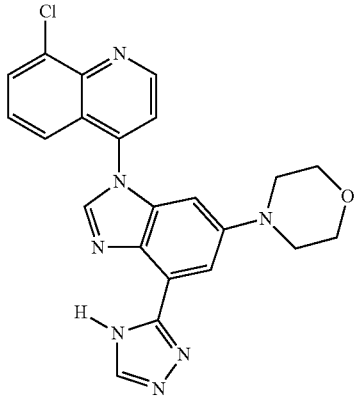 |
| 112 | 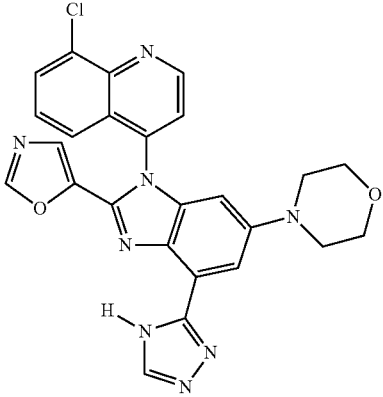 [SMILES: Clc1cccc2c(-n3c(-c4cnco4)nc4c(-c5nnc[nH]5)cc(N5CCOCC5)cc43)ccnc12] |
| 113 | 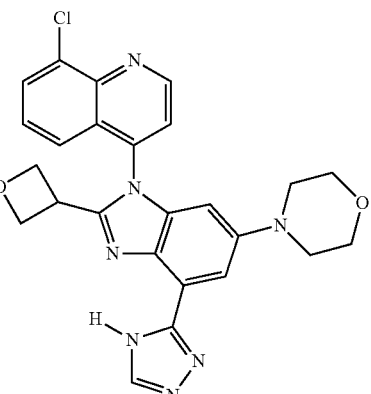 |
| 114 | 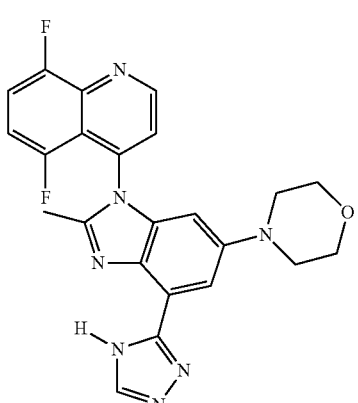 |

TABLE A-continued
| Example | Structure |
|---|---|
| 115 | 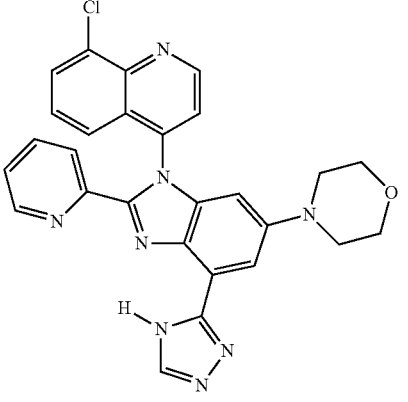 [SMILES: Clc1cccc2c(-n3c(-c4ccccn4)nc4c(-c5nnc[nH]5)cc(N5CCOCC5)cc43)ccnc12] |
| 116 | 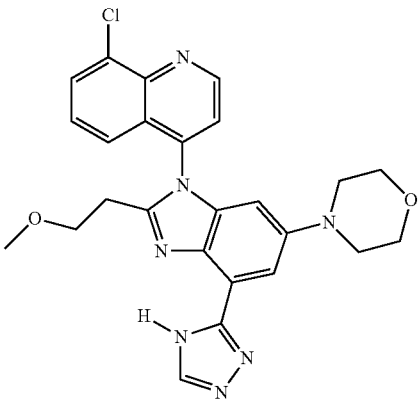 |
| 117 | 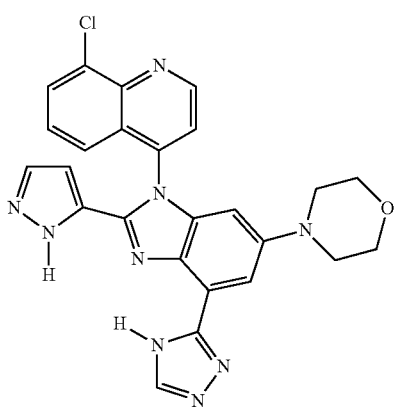 [SMILES: Clc1cccc2c(-n3c(-c4ccn[nH]4)nc4c(-c5nnc[nH]5)cc(N5CCOCC5)cc43)ccnc12] |
| 118 | 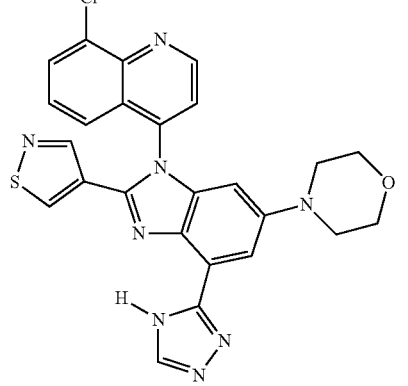 |
| 119 | 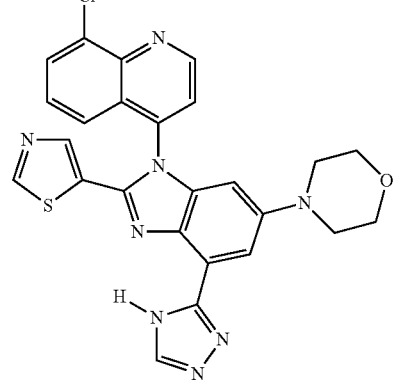 |
| 120 | 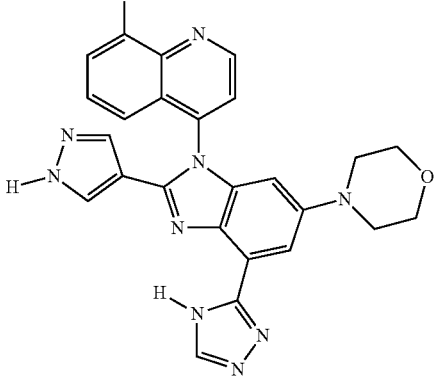 |
| 121 | 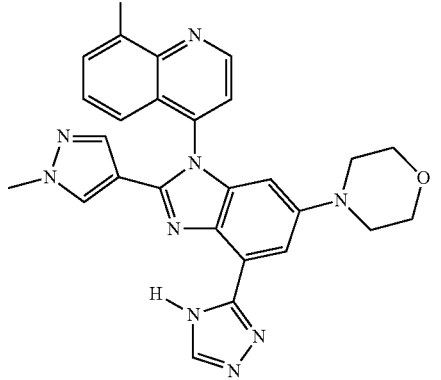 |

TABLE A-continued

| Example | Structure |
|---------|-----------|
| 122 | 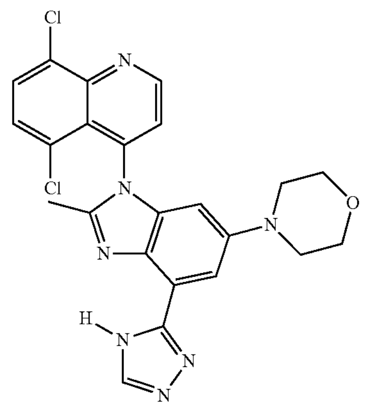 [SMILES: Cc1nc2c(-c3nnc[nH]3)cc(N3CCOCC3)cc2n1-c1ccnc2c(Cl)ccc(Cl)c12] |
| 123 | 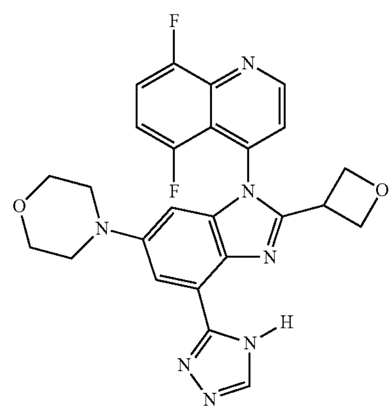 [SMILES: Fc1ccc(F)c2c(-n3c(C4COC4)nc4c(-c5nnc[nH]5)cc(N5CCOCC5)cc43)ccnc12] |
| 124 | 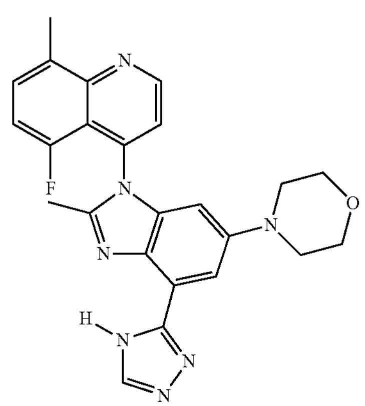 [SMILES: Cc1ccc(F)c2c(-n3c(C)nc4c(-c5nnc[nH]5)cc(N5CCOCC5)cc43)ccnc12] |
| 125 | 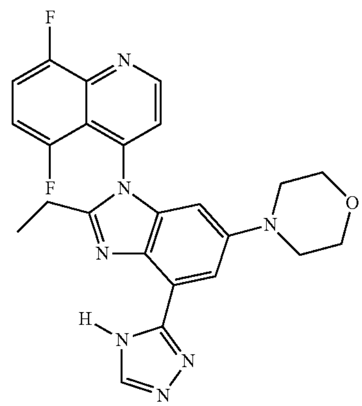 [SMILES: CCc1nc2c(-c3nnc[nH]3)cc(N3CCOCC3)cc2n1-c1ccnc2c(F)ccc(F)c12] |
| 126 | 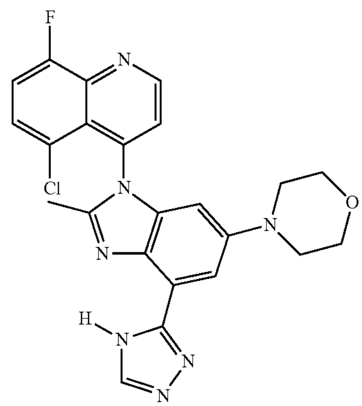 [SMILES: Cc1nc2c(-c3nnc[nH]3)cc(N3CCOCC3)cc2n1-c1ccnc2c(F)ccc(Cl)c12] |
| 127 | 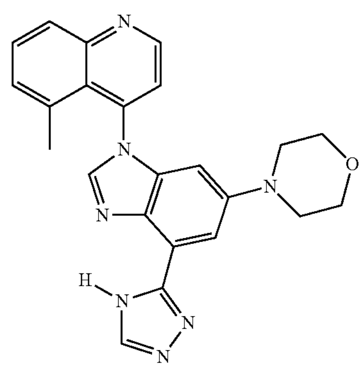 [SMILES: Cc1cccc2nccc(-n3cnc4c(-c5nnc[nH]5)cc(N5CCOCC5)cc43)c12] |
| 128 | 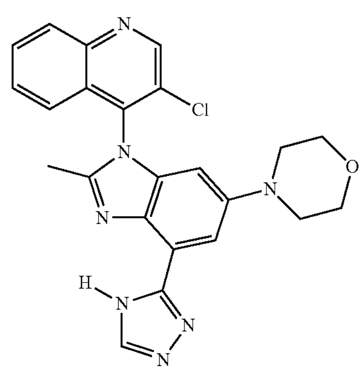 [SMILES: Cc1nc2c(-c3nnc[nH]3)cc(N3CCOCC3)cc2n1-c1c(Cl)cnc2ccccc12] |

TABLE A-continued

| Example | Structure |
|---------|-----------|
| 129 | 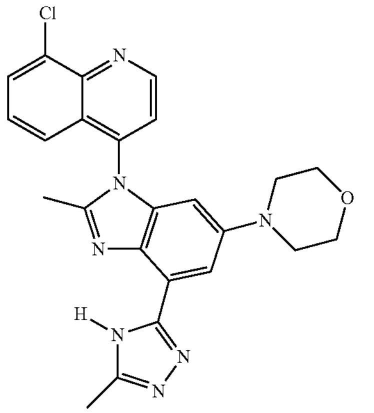 |
| 130 | 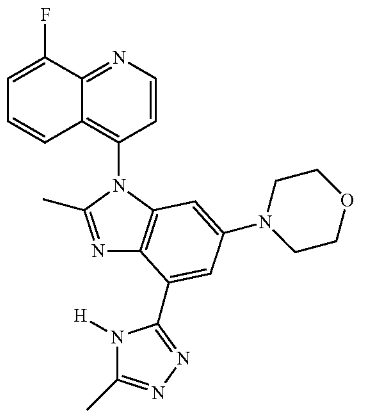 [SMILES: Cc1nnc(-c2cc(N3CCOCC3)cc3c2nc(C)n3-c2ccnc3c(F)cccc23)[nH]1] |
| 131 | 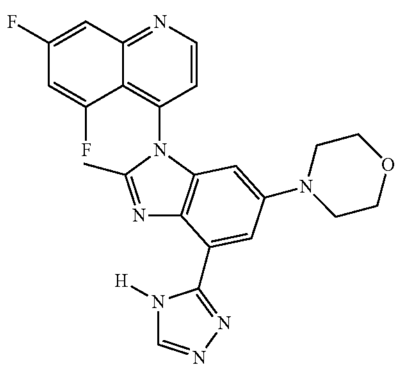 [SMILES: Cc1nc2c(-c3nnc[nH]3)cc(N3CCOCC3)cc2n1-c1ccnc2cc(F)cc(F)c12] |
| 132 | 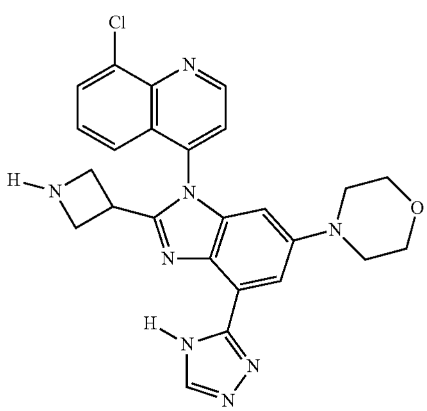 [SMILES: Clc1cccc2c(-n3c(C4CNC4)nc4c(-c5nnc[nH]5)cc(N5CCOCC5)cc43)ccnc12] |
| 133 | |
| 134 | |
| 135 | |

TABLE A-continued
| Example | Structure |
|---|---|
| 136 | 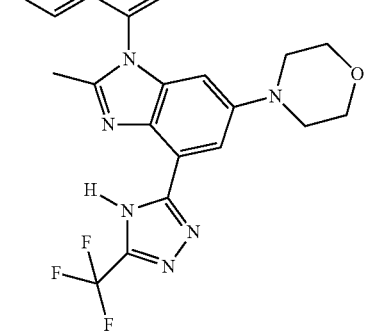 |
| 137 | 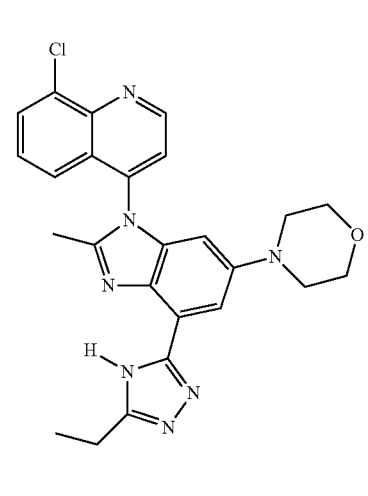 [SMILES: CCc1nnc(-c2cc(N3CCOCC3)cc3c2nc(C)n3-c2ccnc3c(Cl)cccc23)[nH]1] |
| 138 | 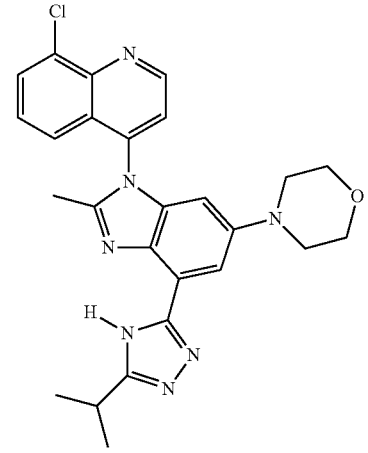 [SMILES: Cc1nc2c(-c3nnc(C(C)C)[nH]3)cc(N3CCOCC3)cc2n1-c1ccnc2c(Cl)cccc12] |
| 139 | 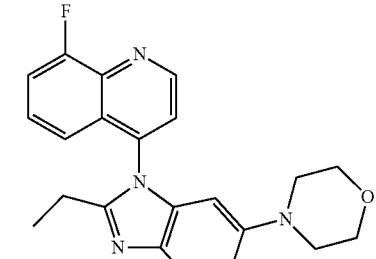 |
| 140 | 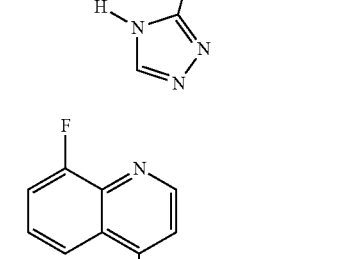 |
| 141 | 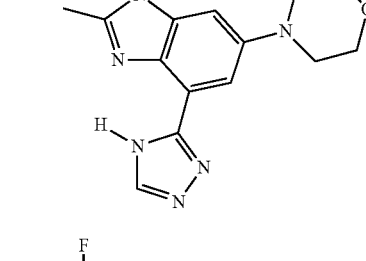 |
| 142 | 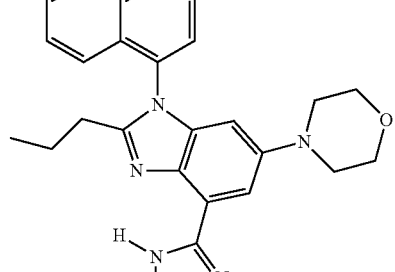 |

TABLE A-continued
| Example | Structure |
|---|---|
| 143 | 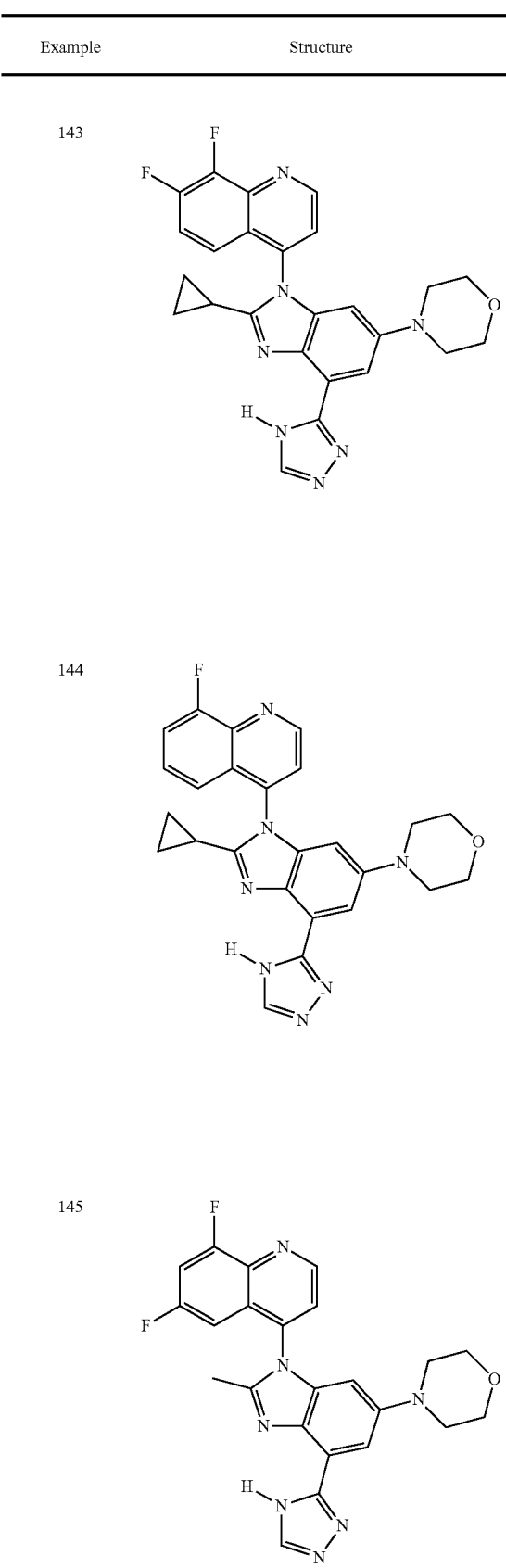 |
| 144 | |
| 145 | |
TABLE A-continued
| Example | Structure |
|---|---|
| 146 | 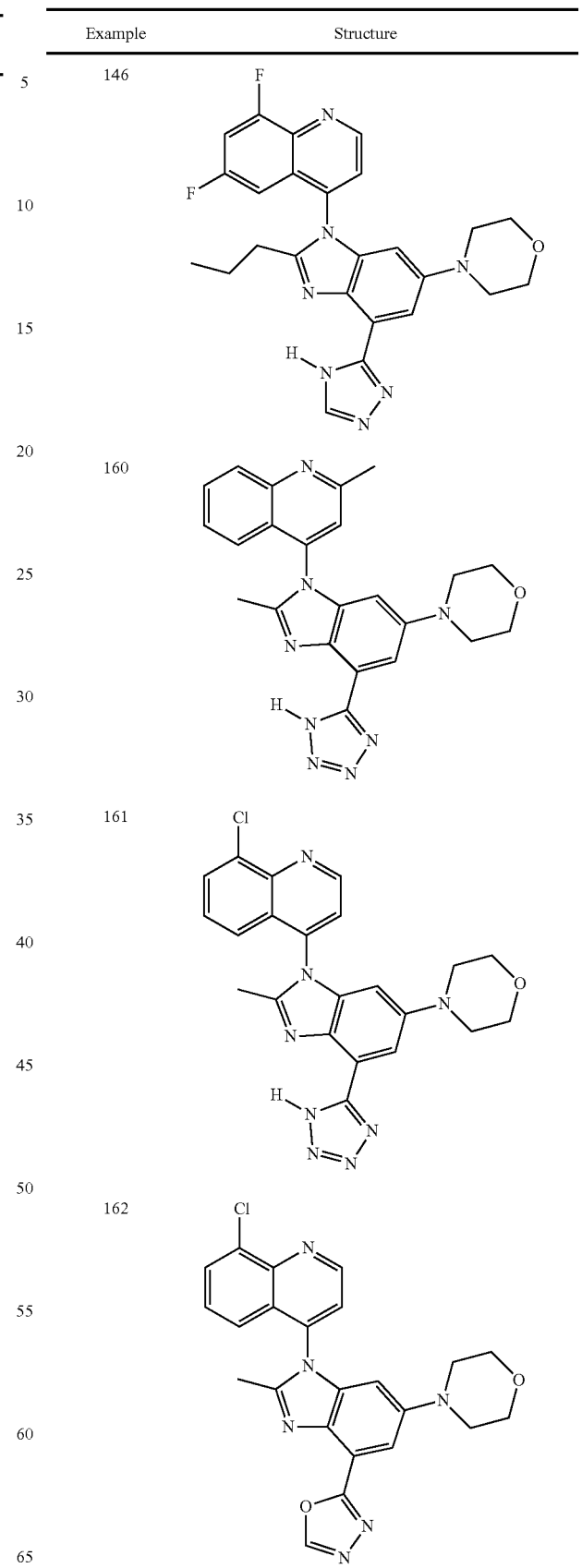 |
| 160 | 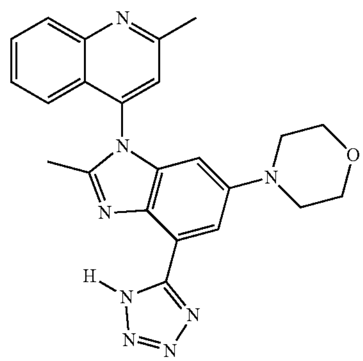 [SMILES: Cc1cc(-n2c(C)nc3c(-c4nnn[nH]4)cc(N4CCOCC4)cc32)c2ccccc2n1] |
| 161 | 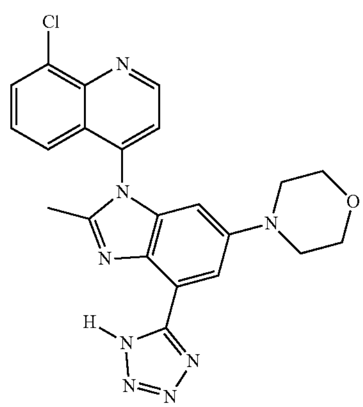 [SMILES: Cc1nc2c(-c3nnn[nH]3)cc(N3CCOCC3)cc2n1-c1ccnc2c(Cl)cccc12] |
| 162 | 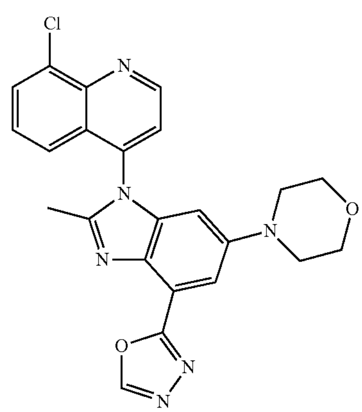 [SMILES: Cc1nc2c(-c3nnco3)cc(N3CCOCC3)cc2n1-c1ccnc2c(Cl)cccc12] |

TABLE A-continued

| Example | Structure |
|---|---|
| 163 | 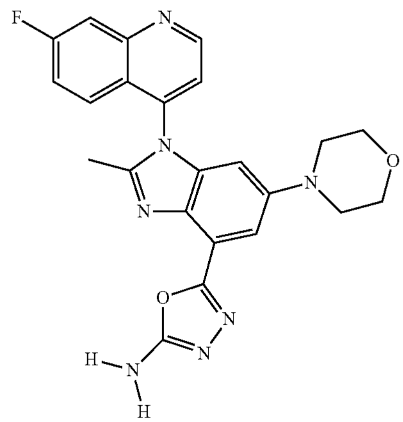 [SMILES: Cc1nc2c(-c3nnc(N)o3)cc(N3CCOCC3)cc2n1-c1ccnc2cc(F)ccc12] |
| 164 | 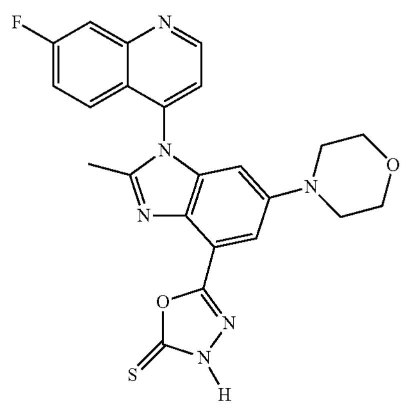 [SMILES: Cc1nc2c(-c3n[nH]c(=S)o3)cc(N3CCOCC3)cc2n1-c1ccnc2cc(F)ccc12] |
| 165 | 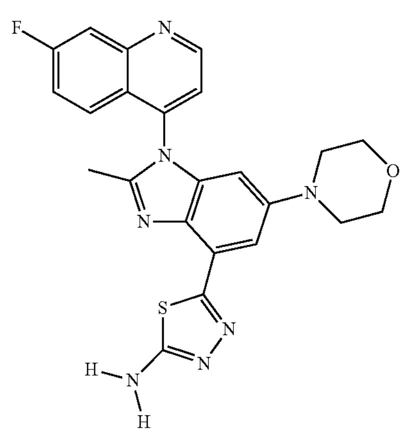 [SMILES: Cc1nc2c(-c3nnc(N)s3)cc(N3CCOCC3)cc2n1-c1ccnc2cc(F)ccc12] |
| 166 | |
| 167 | |
| 168 | |

TABLE A-continued

| Example | Structure |
|---|---|
| 169 | (structure) |
| 170 | (structure) |
| 171 | (structure) |
| 172 | (structure) |
| 173 | (structure) |
| 174 | (structure) |

TABLE A-continued

| Example | Structure |
|---|---|
| 175 | (structure) |
| 176 | (structure) |
| 177 | (structure) |
| 178 | (structure) |
| 179 | (structure) |
| 180 | (structure) |

TABLE A-continued

| Example | Structure |
|---|---|
| 181 | (structure) |
| 182 | (structure) |
| 183 | (structure) |
| 198 | (structure) |
| 199 | (structure) |
| 200 | (structure) |
| 201 | (structure) |

TABLE A-continued
| Example | Structure |
|---------|-----------|
| 202 | 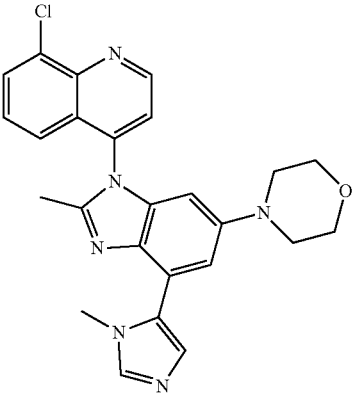 [SMILES: Cc1nc2c(-c3cncn3C)cc(N3CCOCC3)cc2n1-c1ccnc2c(Cl)cccc12] |
| 203 | 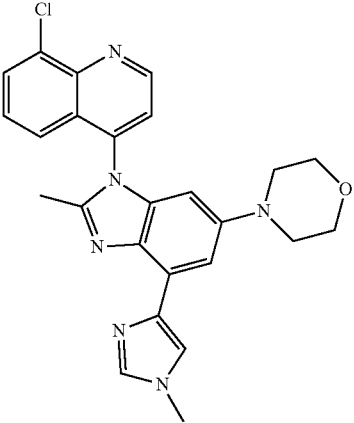 [SMILES: Cc1nc2c(-c3cn(C)cn3)cc(N3CCOCC3)cc2n1-c1ccnc2c(Cl)cccc12] |
| 204 | 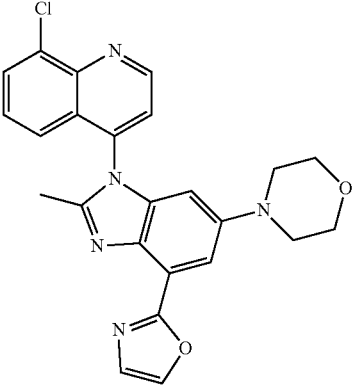 [SMILES: Cc1nc2c(-c3ncco3)cc(N3CCOCC3)cc2n1-c1ccnc2c(Cl)cccc12] |
| 205 | 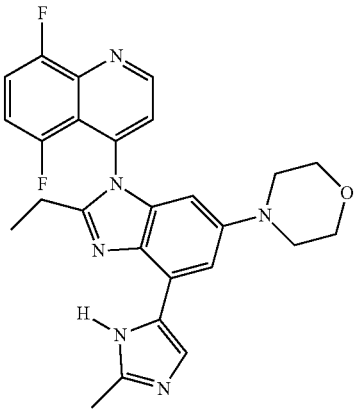 [SMILES: CCc1nc2c(-c3cnc(C)[nH]3)cc(N3CCOCC3)cc2n1-c1ccnc2c(F)ccc(F)c12] |
| 206 | 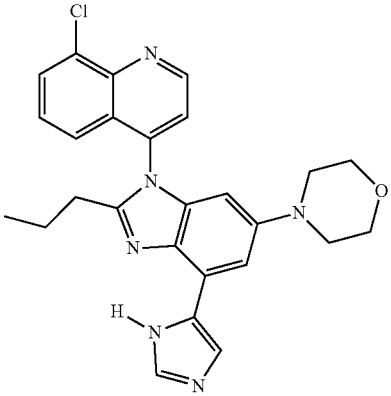 [SMILES: CCCc1nc2c(-c3cnc[nH]3)cc(N3CCOCC3)cc2n1-c1ccnc2c(Cl)cccc12] |
| 207 | 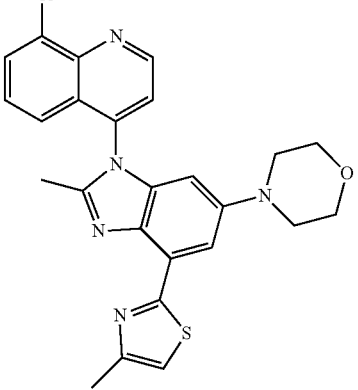 |

TABLE A-continued

| Example | Structure |
|---|---|
| 208 | (8-fluoroquinolin-4-yl, 2-methyl-6-morpholino-benzimidazole, 4-(1H-imidazol-5-yl)) |
| 209 | (8-fluoroquinolin-4-yl, 2-ethyl-6-morpholino-benzimidazole, 4-(1H-imidazol-5-yl)) |
| 210 | (8-fluoro-2-methylquinolin-4-yl, 2-methyl-6-morpholino-benzimidazole, 4-(1H-imidazol-5-yl)) |
| 211 | (8-fluoro-2-methylquinolin-4-yl, 2-ethyl-6-morpholino-benzimidazole, 4-(1H-imidazol-5-yl)) |
| 212 | (8-chloroquinolin-4-yl, 2-propyl-6-morpholino-benzimidazole, 4-(2-methyl-1H-imidazol-5-yl)) |
| 213 | (8-fluoroquinolin-4-yl, 2-ethyl-6-morpholino-benzimidazole, 4-(oxazol-2-yl)) |
| 214 | (8-fluoroquinolin-4-yl, 2-cyclopropyl-6-morpholino-benzimidazole, 4-(oxazol-2-yl)) |

TABLE A-continued

| Example | Structure |
|---------|-----------|
| 215 | |
| 216 | |
| 217 | |
| 218 | 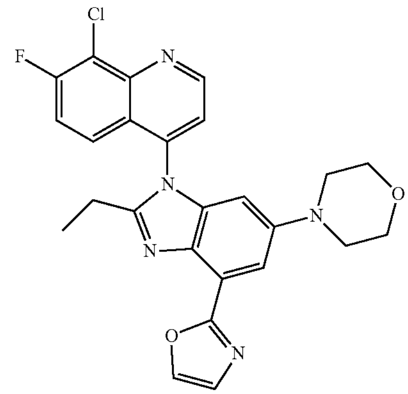 [SMILES: CCc1nc2c(-c3ncco3)cc(N3CCOCC3)cc2n1-c1ccnc2c(Cl)c(F)ccc12] |
| 219 | 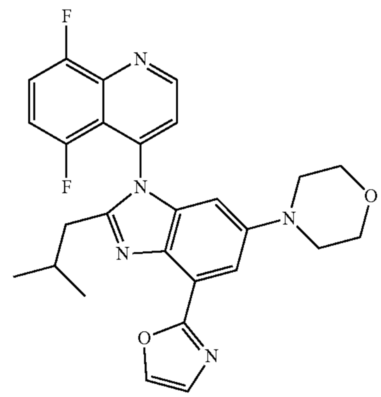 [SMILES: CC(C)Cc1nc2c(-c3ncco3)cc(N3CCOCC3)cc2n1-c1ccnc2c(F)ccc(F)c12] |
| 220 | 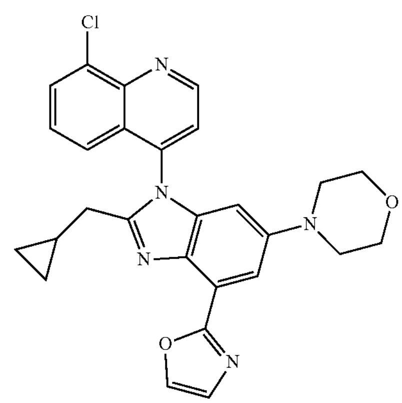 [SMILES: Clc1cccc2c(-n3c(CC4CC4)nc4c(-c5ncco5)cc(N5CCOCC5)cc43)ccnc12] |
| 221 | 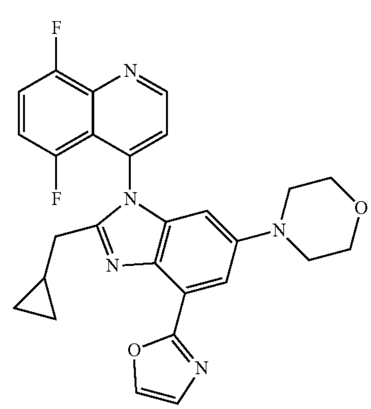 [SMILES: Fc1ccc(F)c2c(-n3c(CC4CC4)nc4c(-c5ncco5)cc(N5CCOCC5)cc43)ccnc12] |

TABLE A-continued
| Example | Structure |
|---------|-----------|
| 222 | 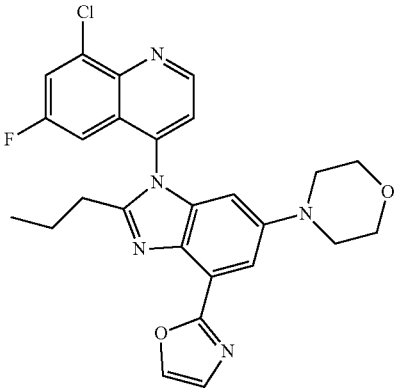 [SMILES: CCCc1nc2c(-c3ncco3)cc(N3CCOCC3)cc2n1-c1ccnc2c(Cl)cc(F)cc12] |
| 223 | 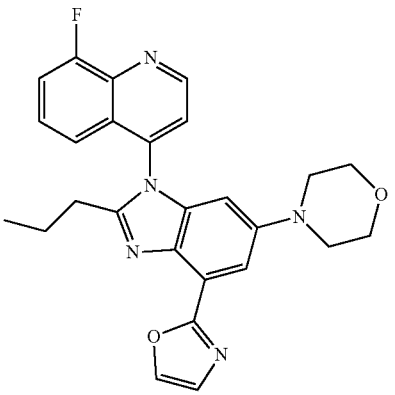 [SMILES: CCCc1nc2c(-c3ncco3)cc(N3CCOCC3)cc2n1-c1ccnc2c(F)cccc12] |
| 224 | 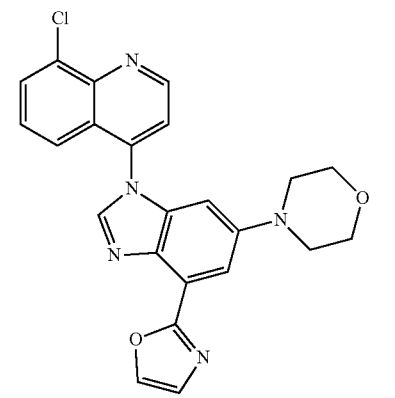 [SMILES: Clc1cccc2c(-n3cnc4c(-c5ncco5)cc(N5CCOCC5)cc43)ccnc12] |
| 225 | 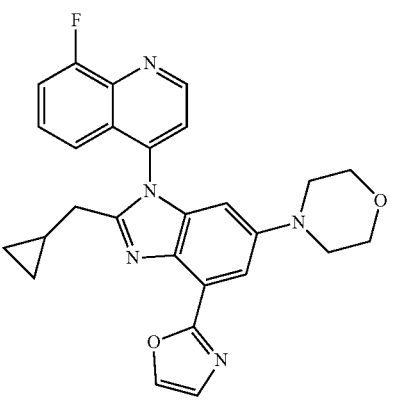 |
TABLE A-continued
| Example | Structure |
|---------|-----------|
| 226 | 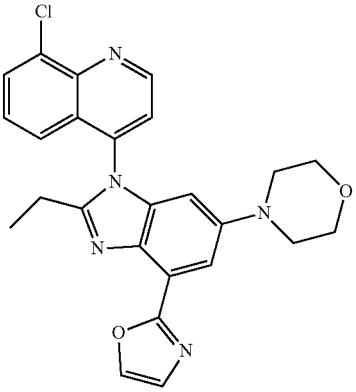 |
| 227 | 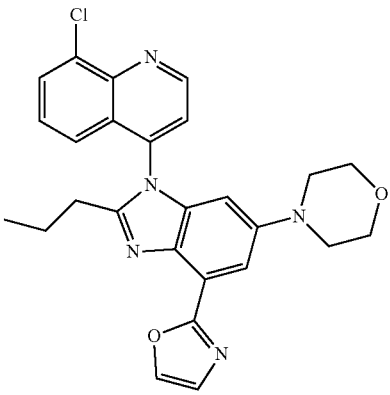 |
| 228 | 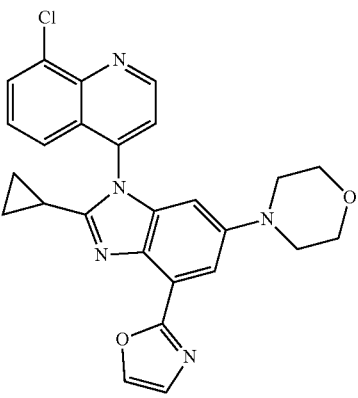 |
| 229 | 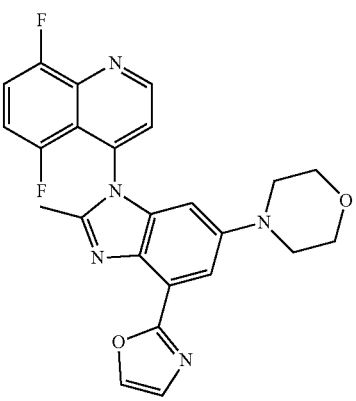 [SMILES: Cc1nc2c(-c3ncco3)cc(N3CCOCC3)cc2n1-c1ccnc2c(F)ccc(F)c12] |

TABLE A-continued

| Example | Structure |
|---------|-----------|
| 230 | 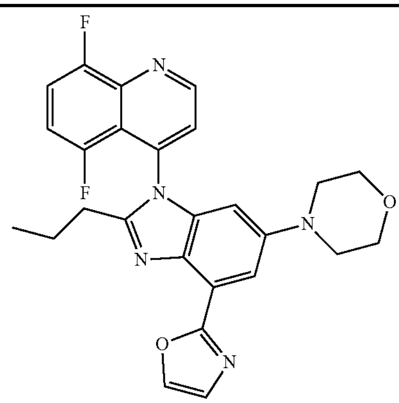 |
| 231 | 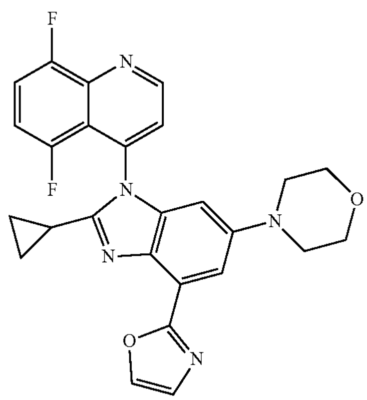 [SMILES: Fc1ccc(F)c2c(-n3c(C4CC4)nc4c(-c5ncco5)cc(N5CCOCC5)cc43)ccnc12] |
| 232 | 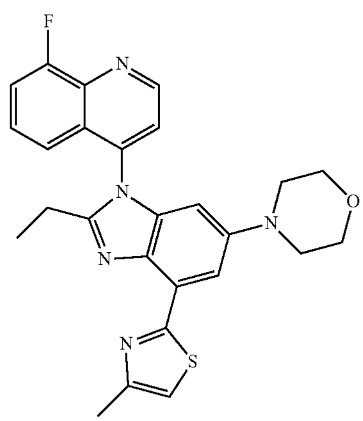 [SMILES: CCc1nc2c(-c3nc(C)cs3)cc(N3CCOCC3)cc2n1-c1ccnc2c(F)cccc12] |
| 233 | 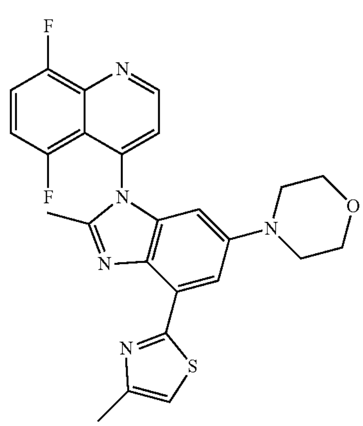 [SMILES: Cc1csc(-c2cc(N3CCOCC3)cc3c2nc(C)n3-c2ccnc3c(F)ccc(F)c23)n1] |
| 234 | |
| 235 | |
| 236 | |

TABLE A-continued
| Example | Structure |
|---------|-----------|
| 237 | 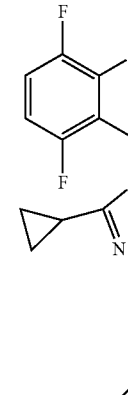 |
| 238 | 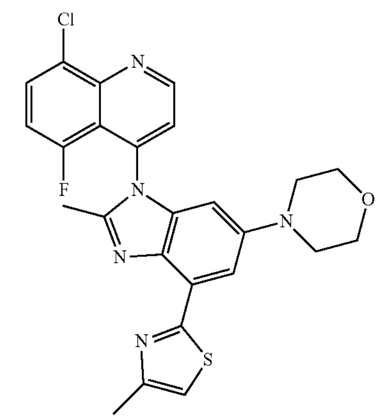 [SMILES: Cc1csc(-c2cc(N3CCOCC3)cc3c2nc(C)n3-c2ccnc3c(Cl)ccc(F)c23)n1] |
| 239 | 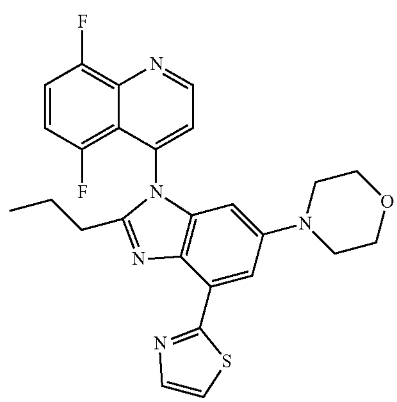 [SMILES: CCCc1nc2c(-c3nccs3)cc(N3CCOCC3)cc2n1-c1ccnc2c(F)ccc(F)c12] |
| 240 | 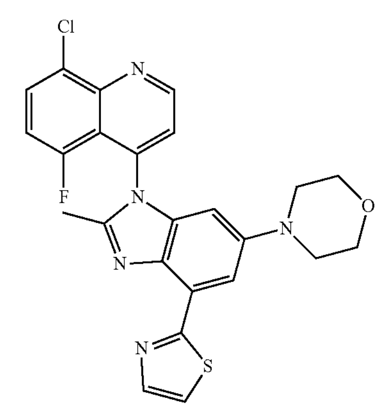 [SMILES: Cc1nc2c(-c3nccs3)cc(N3CCOCC3)cc2n1-c1ccnc2c(Cl)ccc(F)c12] |
TABLE A-continued
| Example | Structure |
|---------|-----------|
| 241 | 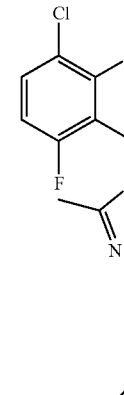 |
| 242 | 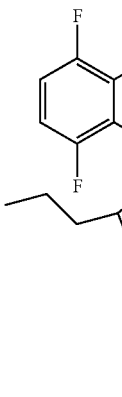 |
| 243 | 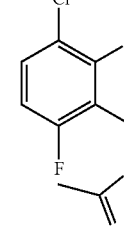 |

TABLE A-continued
| Example | Structure |
|---|---|
| 244 | 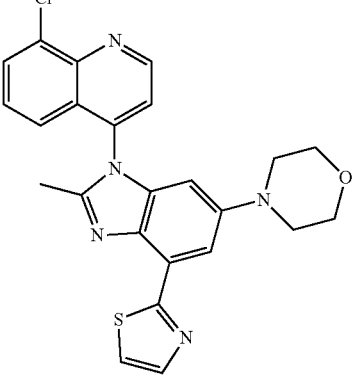 |
| 245 | 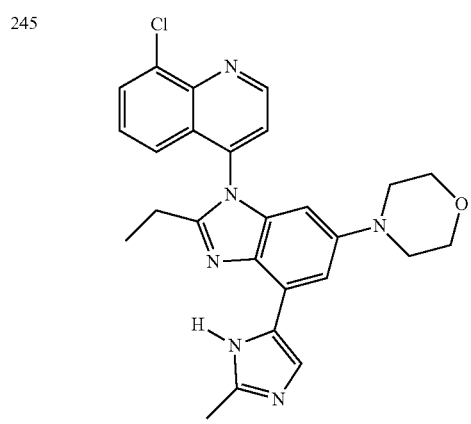 |
| 246 | 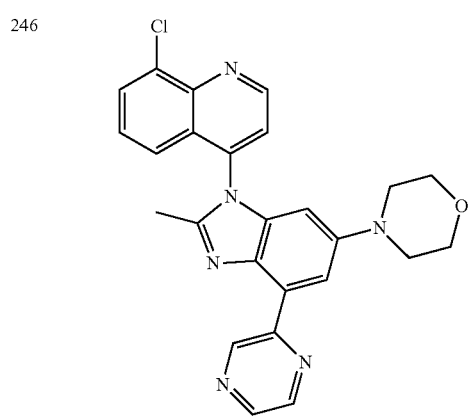 |
| 260 | 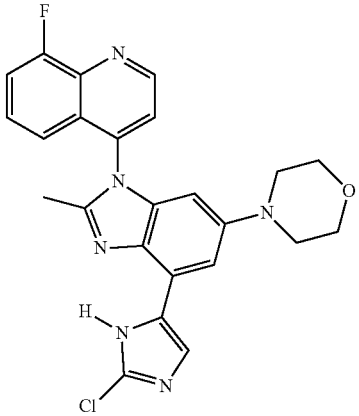 [SMILES: Cc1nc2c(-c3cnc(Cl)[nH]3)cc(N3CCOCC3)cc2n1-c1ccnc2c(F)cccc12] |
| 261 | 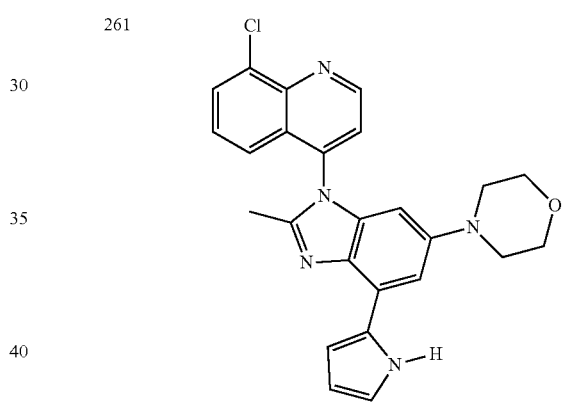 |
| 262 | 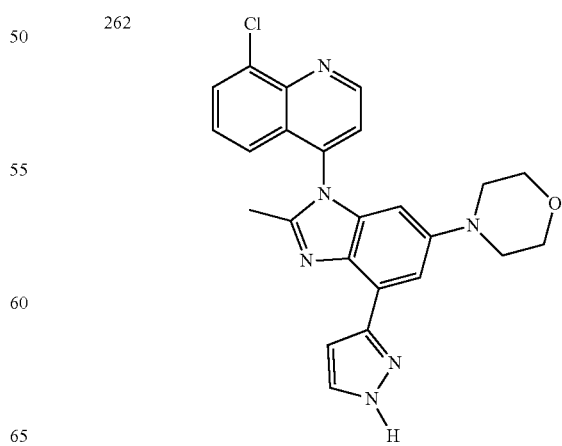 |

TABLE A-continued
| Example | Structure |
|---|---|
| 263 | 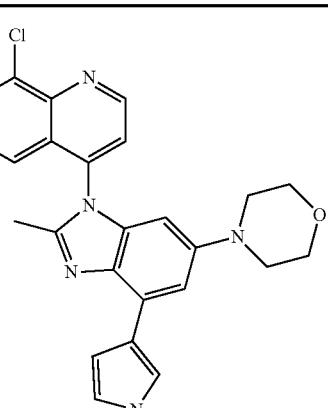 |
| 264 | 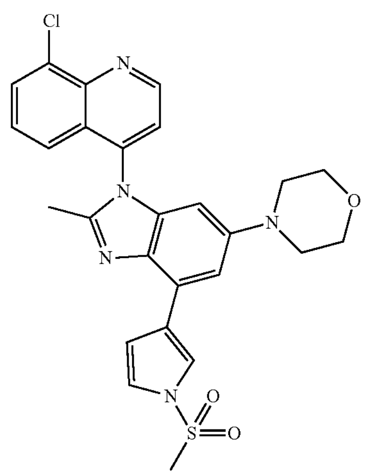 [SMILES: Cc1nc2c(-c3ccn(S(C)(=O)=O)c3)cc(N3CCOCC3)cc2n1-c1ccnc2c(Cl)cccc12] |
| 265 | 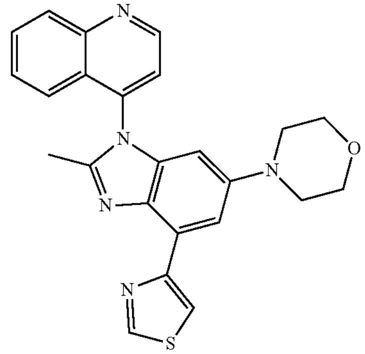 [SMILES: Cc1nc2c(-c3cscn3)cc(N3CCOCC3)cc2n1-c1ccnc2ccccc12] |
| 266 | |
| 267 | |
| 268 | |

TABLE A-continued
| Example | Structure |
|---------|-----------|
| 269 | 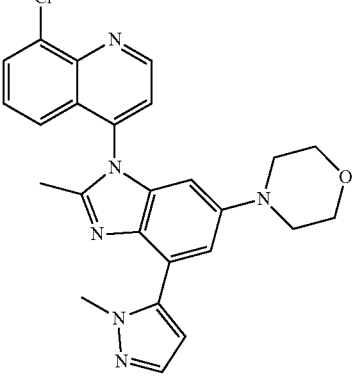 |
| 270 | 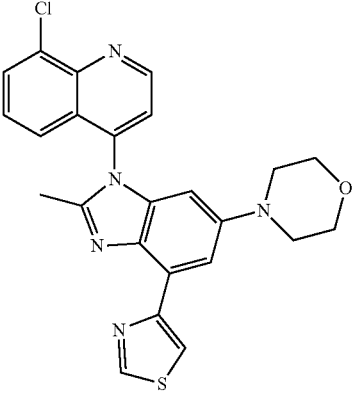 [SMILES: Cc1nc2c(-c3cscn3)cc(N3CCOCC3)cc2n1-c1ccnc2c(Cl)cccc12] |
| 271 | 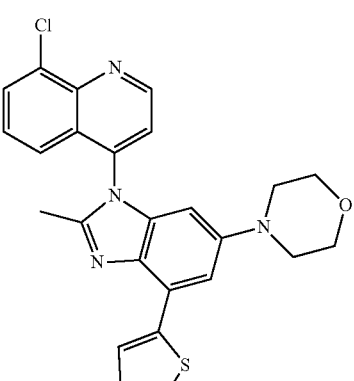 |
| 272 | 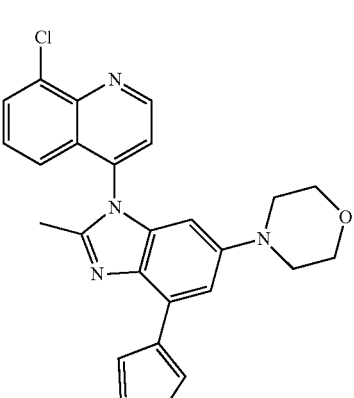 |
| 273 | 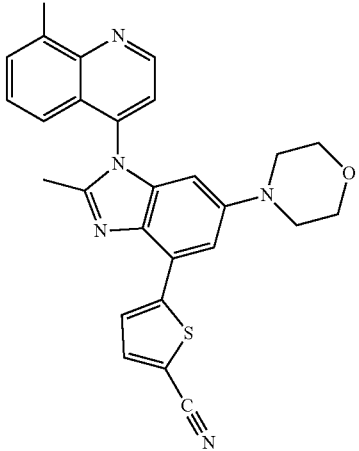 |
| 274 | 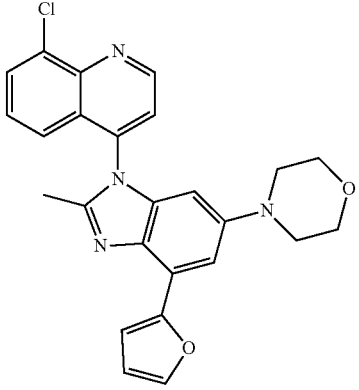 |
| 275 | 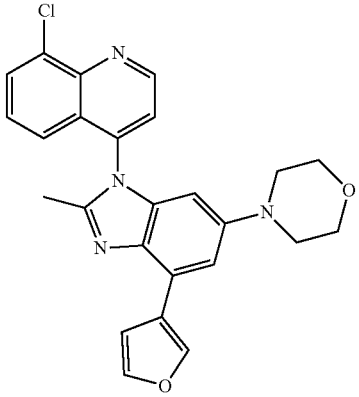 [SMILES: Cc1nc2c(-c3ccsc3)cc(N3CCOCC3)cc2n1-c1ccnc2c(Cl)cccc12] |

TABLE A-continued
| Example | Structure |
|---|---|
| 276 | 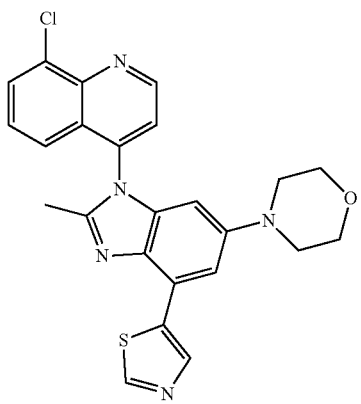 [SMILES: Cc1nc2c(-c3cncs3)cc(N3CCOCC3)cc2n1-c1ccnc2c(Cl)cccc12] |
| 277 | 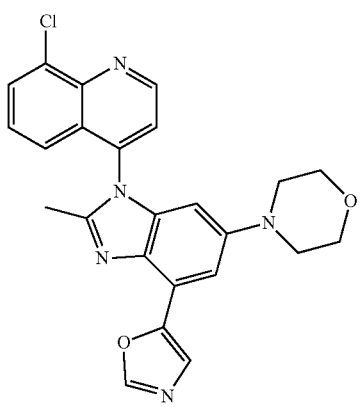 [SMILES: Cc1nc2c(-c3cnco3)cc(N3CCOCC3)cc2n1-c1ccnc2c(Cl)cccc12] |
| 278 | 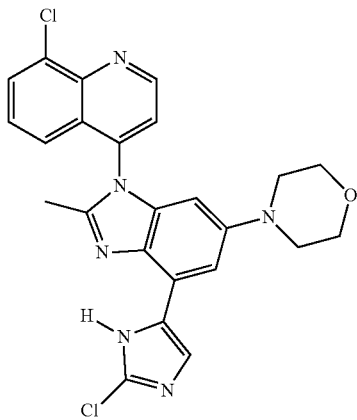 |
| 279 | 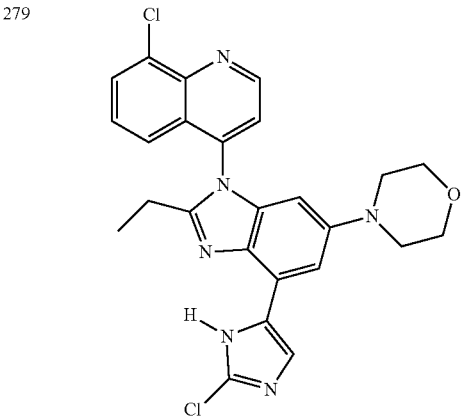 |
| 280 | 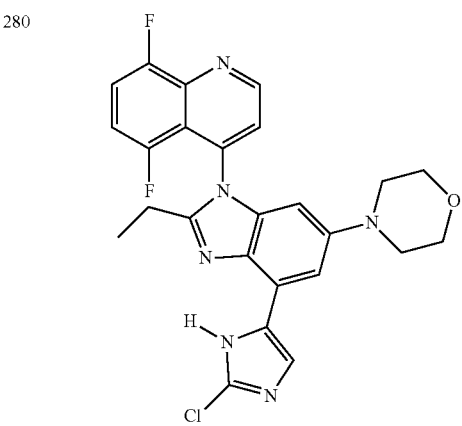 |
| 281 | 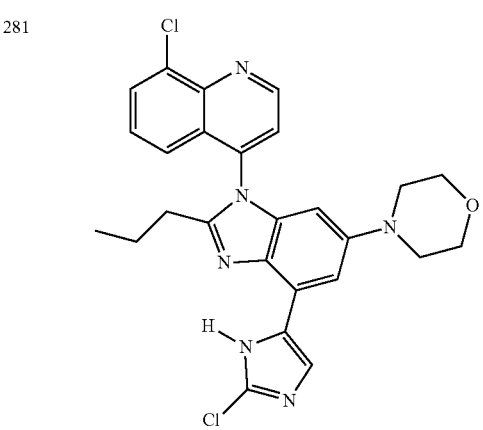 |

TABLE A-continued
| Example | Structure |
|---|---|
| 282 | 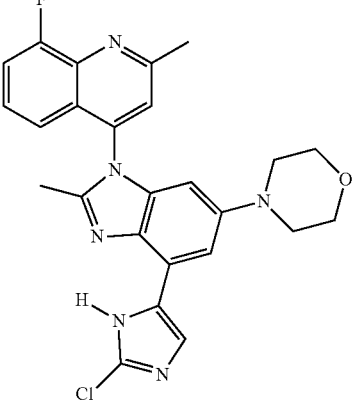 |
| 283 | 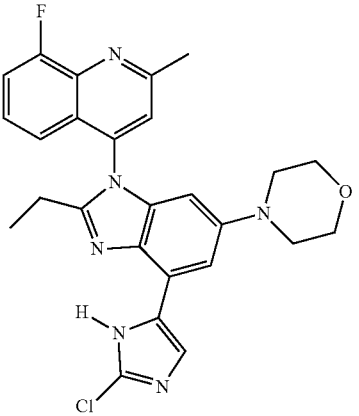 [SMILES: CCc1nc2c(-c3cnc(Cl)[nH]3)cc(N3CCOCC3)cc2n1-c1cc(C)nc2c(F)cccc12] |
| 284 | 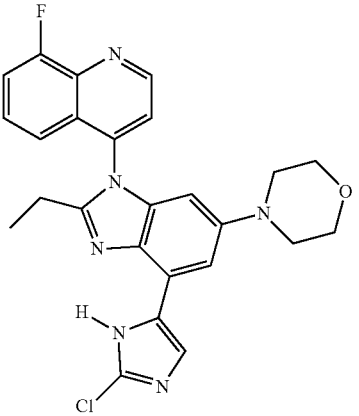 [SMILES: CCc1nc2c(-c3cnc(Cl)[nH]3)cc(N3CCOCC3)cc2n1-c1ccnc2c(F)cccc12] |
TABLE A-continued
| Example | Structure |
|---|---|
| 285 | 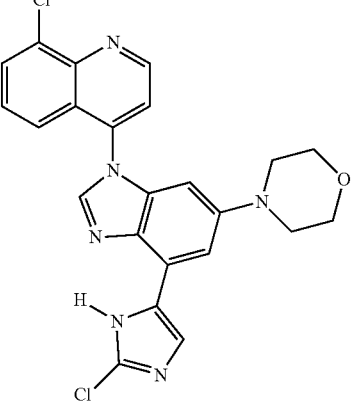 |
| 286 | 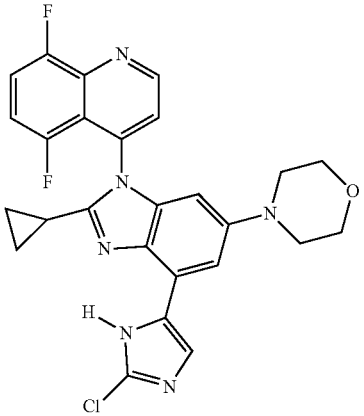 [SMILES: Fc1ccc(F)c2c(-n3c(C4CC4)nc4c(-c5cnc(Cl)[nH]5)cc(N5CCOCC5)cc43)ccnc12] |
| 287 | 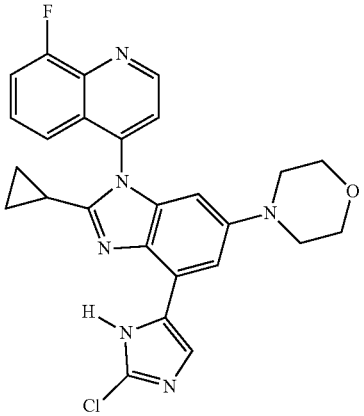 [SMILES: Fc1cccc2c(-n3c(C4CC4)nc4c(-c5cnc(Cl)[nH]5)cc(N5CCOCC5)cc43)ccnc12] |

TABLE A-continued

| Example | Structure |
|---------|-----------|
| 288 | 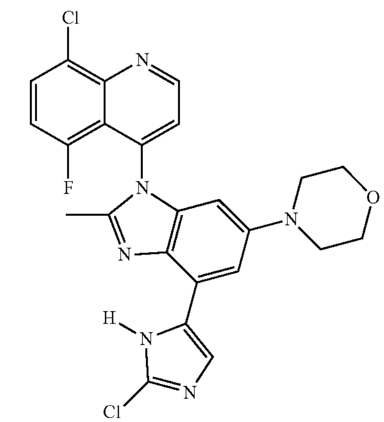 [SMILES: Cc1nc2c(-c3cnc(Cl)[nH]3)cc(N3CCOCC3)cc2n1-c1ccnc2c(Cl)ccc(F)c12] |
| 289 | 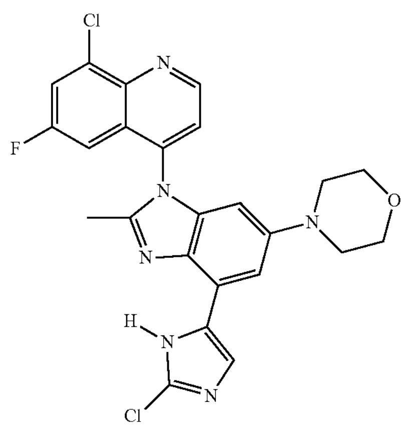 [SMILES: Cc1nc2c(-c3cnc(Cl)[nH]3)cc(N3CCOCC3)cc2n1-c1ccnc2c(Cl)cc(F)cc12] |
| 290 | 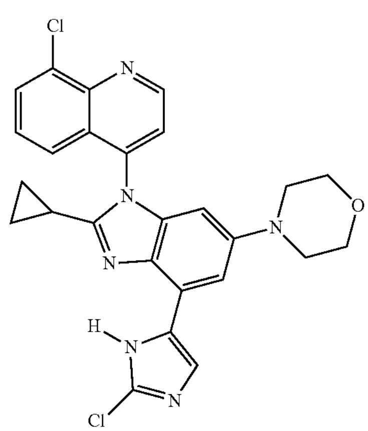 [SMILES: Clc1ncc(-c2cc(N3CCOCC3)cc3c2nc(C2CC2)n3-c2ccnc3c(Cl)cccc23)[nH]1] |
| 291 | 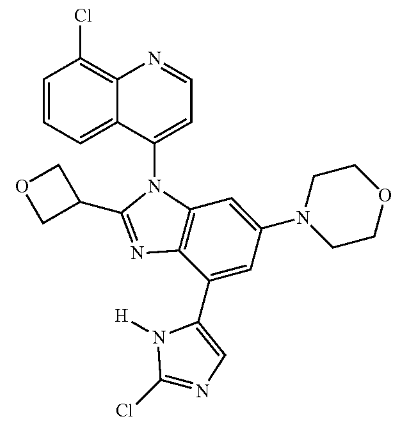 [SMILES: Clc1ncc(-c2cc(N3CCOCC3)cc3c2nc(C2COC2)n3-c2ccnc3c(Cl)cccc23)[nH]1] |
| 292 | 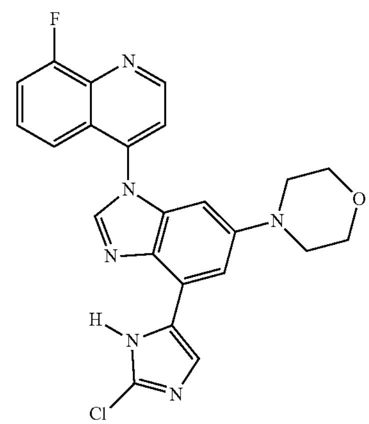 |
| 293 | 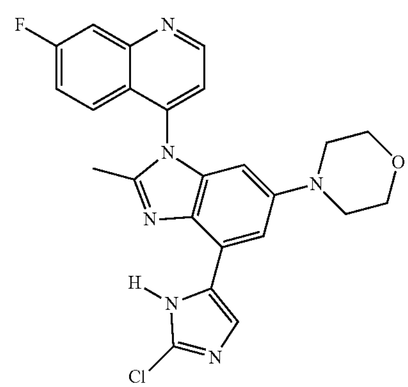 [SMILES: Cc1nc2c(-c3cnc(Cl)[nH]3)cc(N3CCOCC3)cc2n1-c1ccnc2cc(F)ccc12] |

TABLE A-continued

| Example | Structure |
|---------|-----------|
| 294 | 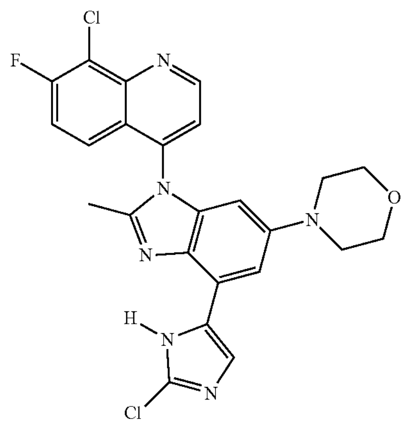 [SMILES: Cc1nc2c(-c3cnc(Cl)[nH]3)cc(N3CCOCC3)cc2n1-c1ccnc2c(Cl)c(F)ccc12] |
| 295 | 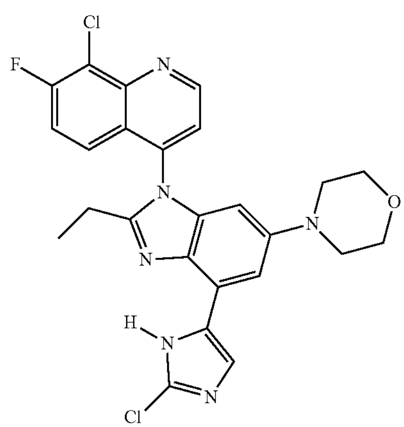 [SMILES: CCc1nc2c(-c3cnc(Cl)[nH]3)cc(N3CCOCC3)cc2n1-c1ccnc2c(Cl)c(F)ccc12] |
| 296 | 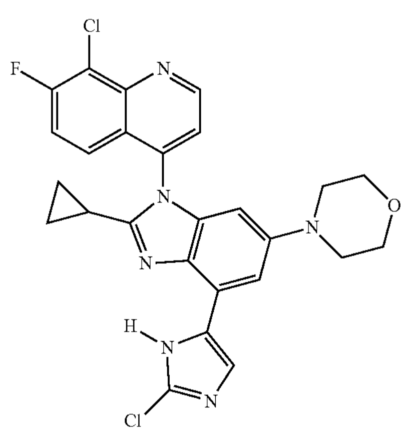 [SMILES: Fc1ccc2c(-n3c(C4CC4)nc4c(-c5cnc(Cl)[nH]5)cc(N5CCOCC5)cc43)ccnc2c1Cl] |
| 297 | |
| 298 | |
| 299 | |

TABLE A-continued
| Example | Structure |
|---|---|
| 300 | 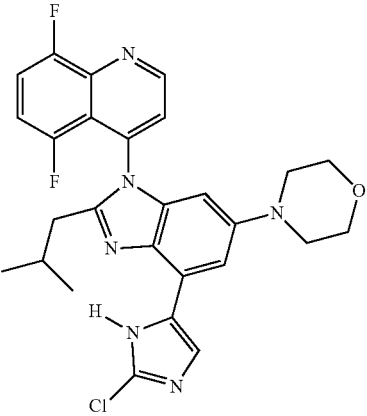 [SMILES: CC(C)Cc1nc2c(-c3cnc(Cl)[nH]3)cc(N3CCOCC3)cc2n1-c1ccnc2c(F)ccc(F)c12] |
| 301 | 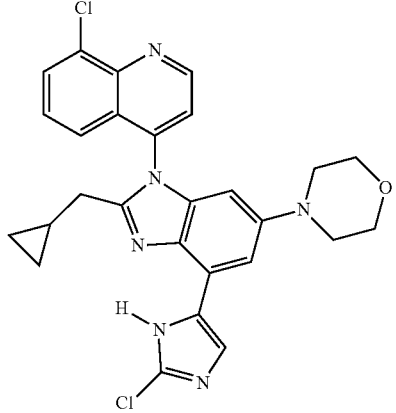 [SMILES: Clc1ncc(-c2cc(N3CCOCC3)cc3c2nc(CC2CC2)n3-c2ccnc3c(Cl)cccc23)[nH]1] |
| 302 | 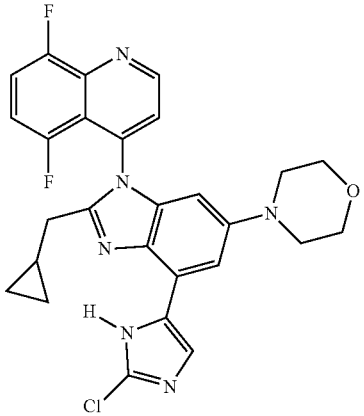 [SMILES: Fc1ccc(F)c2c(-n3c(CC4CC4)nc4c(-c5cnc(Cl)[nH]5)cc(N5CCOCC5)cc43)ccnc12] |
| 303 | 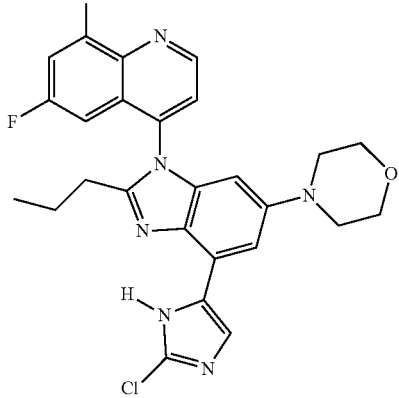 |
| 304 | 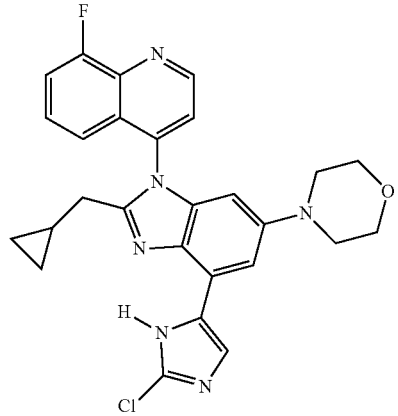 |
| 305 | 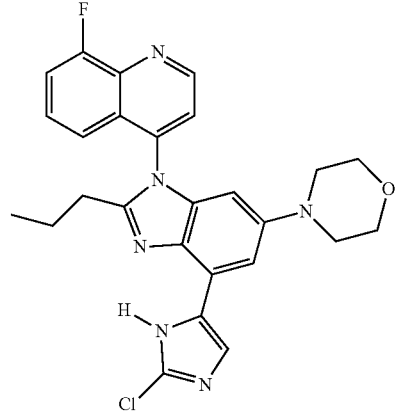 [SMILES: CCCc1nc2c(-c3cnc(Cl)[nH]3)cc(N3CCOCC3)cc2n1-c1ccnc2c(F)cccc12] |

TABLE A-continued

| Example | Structure |
|---------|-----------|
| 306 | 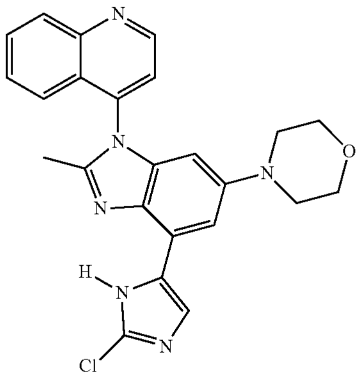 [SMILES: Cc1nc2c(-c3cnc(Cl)[nH]3)cc(N3CCOCC3)cc2n1-c1ccnc2ccccc12] |
| 307 | 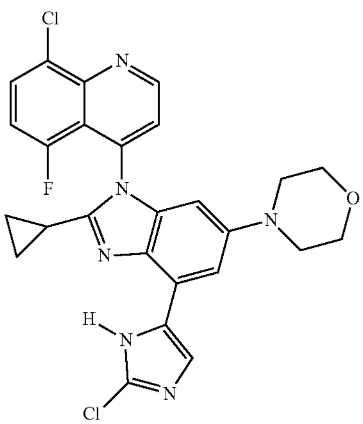 [SMILES: Fc1ccc(Cl)c2nccc(-n3c(C4CC4)nc4c(-c5cnc(Cl)[nH]5)cc(N5CCOCC5)cc43)c12] |
| 308 | 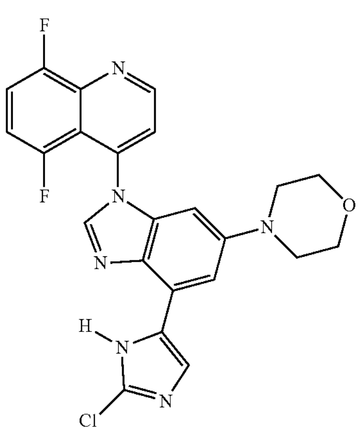 [SMILES: Fc1ccc(F)c2c(-n3cnc4c(-c5cnc(Cl)[nH]5)cc(N5CCOCC5)cc43)ccnc12] |
| 309 | |
| 310 | |
| 311 | |

TABLE A-continued
| Example | Structure |
|---|---|
| 312 | 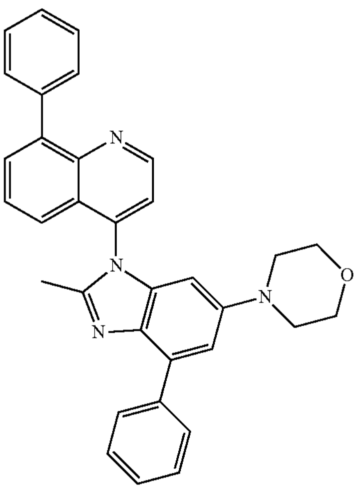 [SMILES: Cc1nc2c(-c3ccccc3)cc(N3CCOCC3)cc2n1-c1ccnc2c(-c3ccccc3)cccc12] |
| 313 | 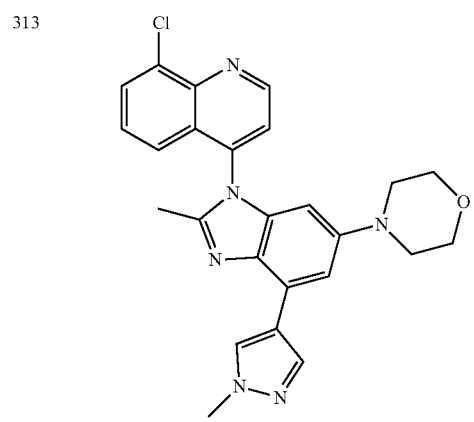 |
| 314 | 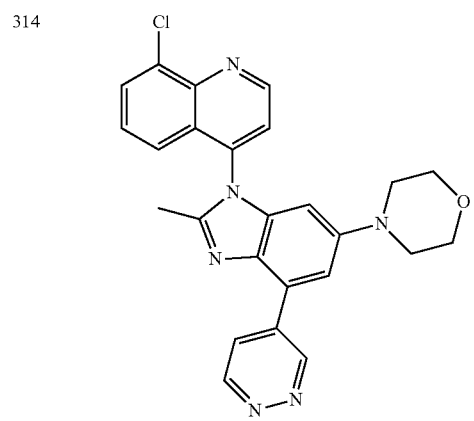 |
TABLE A-continued
| Example | Structure |
|---|---|
| 315 | 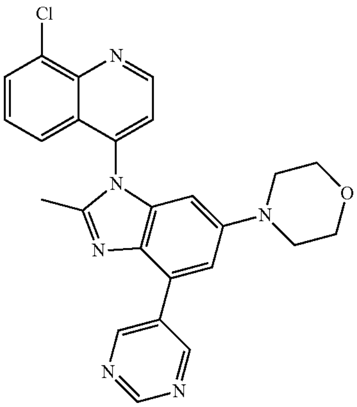 [SMILES: Cc1nc2c(-c3cncnc3)cc(N3CCOCC3)cc2n1-c1ccnc2c(Cl)cccc12] |
| 316 | 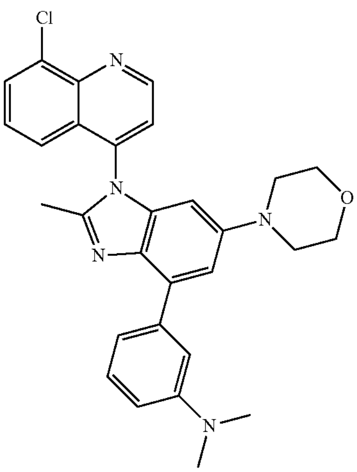 [SMILES: Cc1nc2c(-c3cccc(N(C)C)c3)cc(N3CCOCC3)cc2n1-c1ccnc2c(Cl)cccc12] |
| 317 | 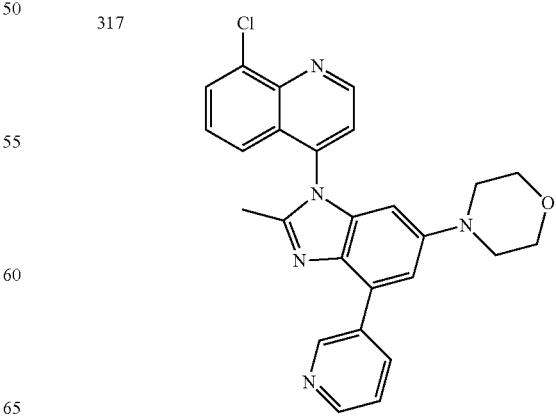 |

TABLE A-continued

| Example | Structure |
|---|---|
| 318 | (structure) |
| 319 | (structure) |
| 320 | (structure) |
| 321 | (structure) |
| 322 | (structure) |
| 323 | (structure) |

TABLE A-continued

| Example | Structure |
|---------|-----------|
| 329 | 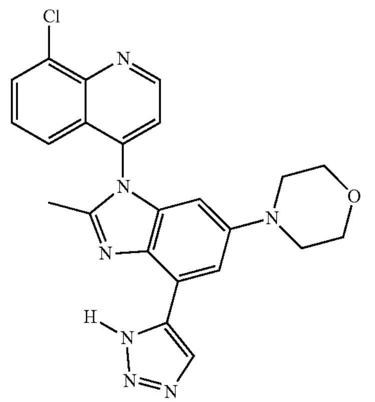 [SMILES: Cc1nc2c(-c3cnn[nH]3)cc(N3CCOCC3)cc2n1-c1ccnc2c(Cl)cccc12] |
| 330 | 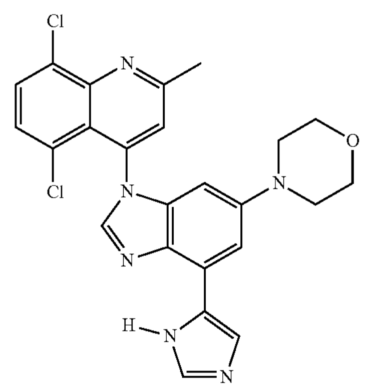 [SMILES: Cc1cc(-n2cnc3c(-c4cnc[nH]4)cc(N4CCOCC4)cc32)c2c(Cl)ccc(Cl)c2n1] |
| 331 | 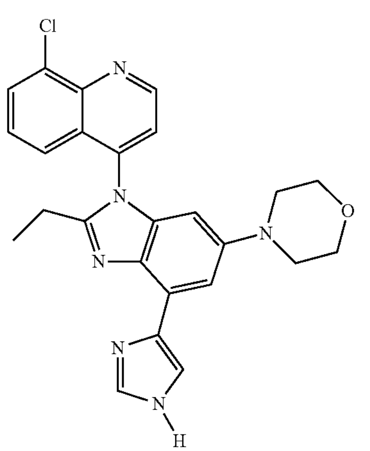 [SMILES: CCc1nc2c(-c3c[nH]cn3)cc(N3CCOCC3)cc2n1-c1ccnc2c(Cl)cccc12] |
| 332 | 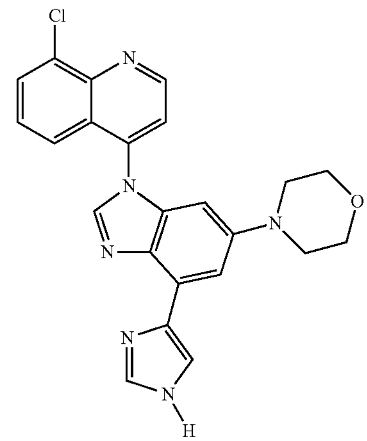 [SMILES: Clc1cccc2c(-n3cnc4c(-c5c[nH]cn5)cc(N5CCOCC5)cc43)ccnc12] |
| 333 | 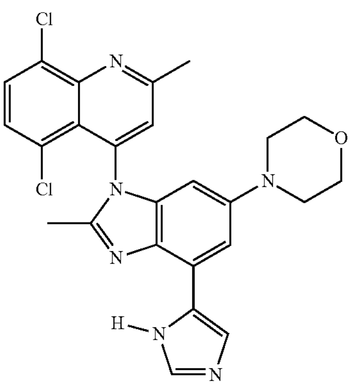 [SMILES: Cc1cc(-n2c(C)nc3c(-c4cnc[nH]4)cc(N4CCOCC4)cc32)c2c(Cl)ccc(Cl)c2n1] |
| 334 | 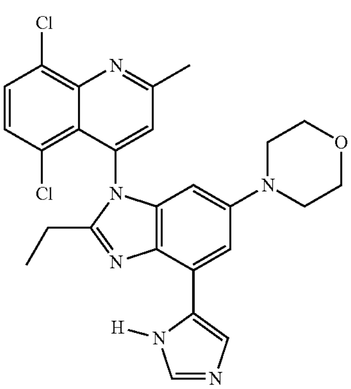 [SMILES: CCc1nc2c(-c3cnc[nH]3)cc(N3CCOCC3)cc2n1-c1cc(C)nc2c(Cl)ccc(Cl)c12] |
| 335 | 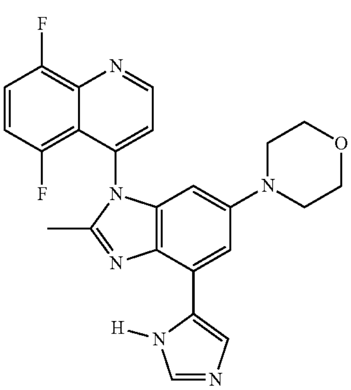 [SMILES: Cc1nc2c(-c3cnc[nH]3)cc(N3CCOCC3)cc2n1-c1ccnc2c(F)ccc(F)c12] |

TABLE A-continued

| Example | Structure |
|---------|-----------|
| 336 | 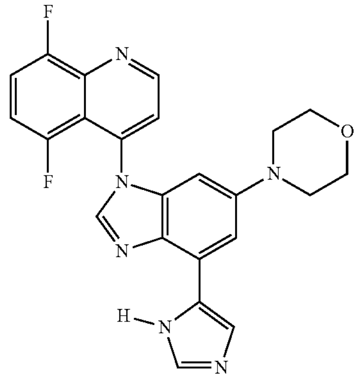 [SMILES: Fc1ccc(F)c2c(-n3cnc4c(-c5cnc[nH]5)cc(N5CCOCC5)cc43)ccnc12] |
| 337 | 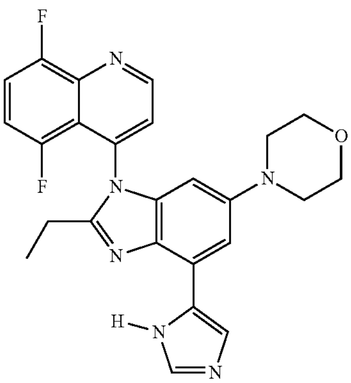 [SMILES: CCc1nc2c(-c3cnc[nH]3)cc(N3CCOCC3)cc2n1-c1ccnc2c(F)ccc(F)c12] |
| 340 | 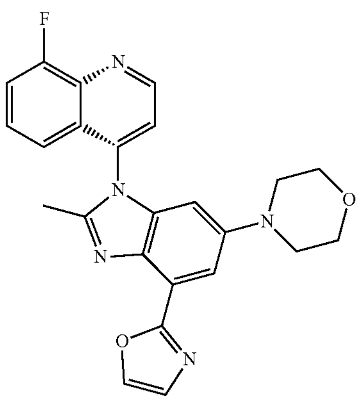 |
| 341 | 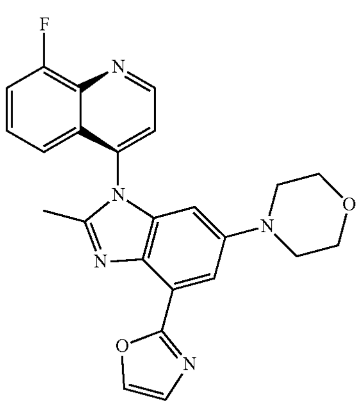 |
| 342 | |
| 343 | |
| 344 | |

TABLE A-continued
| Example | Structure |
|---|---|
| 345 | 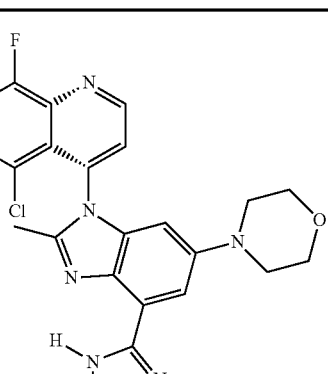 |
| 346 | 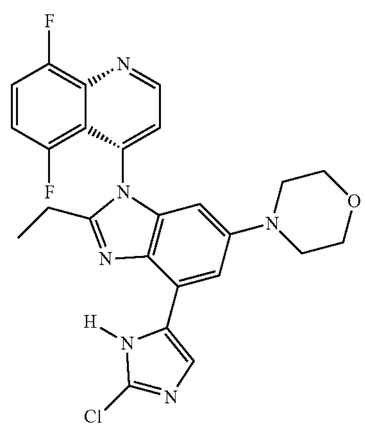 |
| 347 | 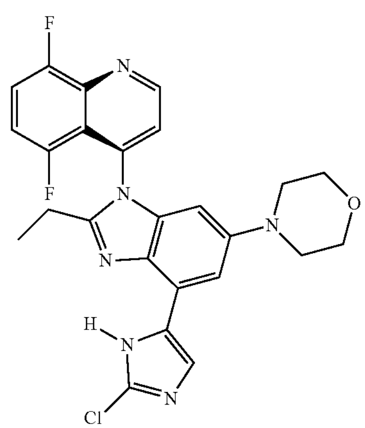 |
| 348 | |
| 349 | |
| 350 | |

TABLE A-continued

| Example | Structure |
|---------|-----------|
| 351 | 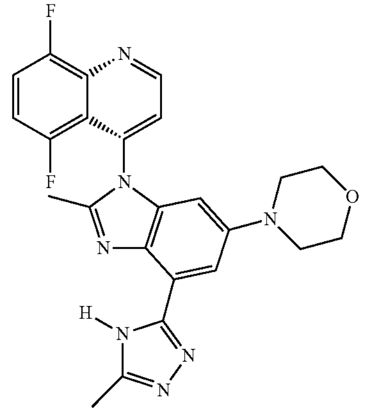 |
| 352 | 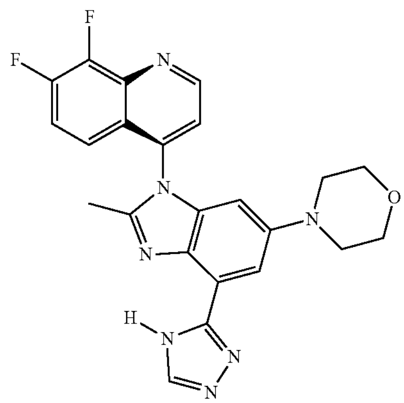 |
| 353 | 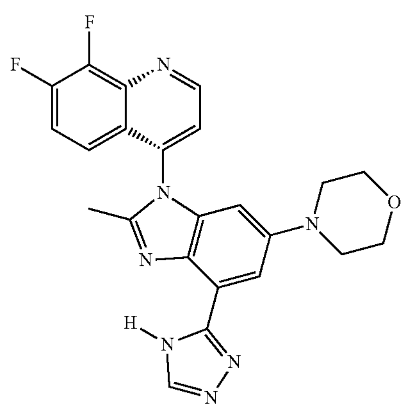 |
| 354 | 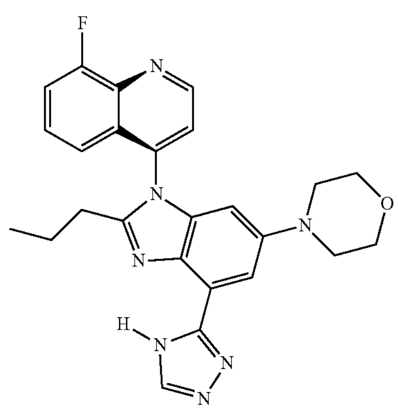 |
| 355 | |
| 356 | |
| 357 | |

TABLE A-continued
| Example | Structure |
|---|---|
| 358 | 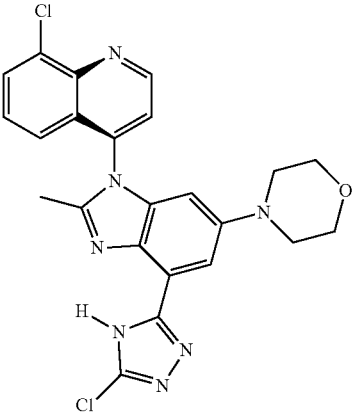 |
| 359 | 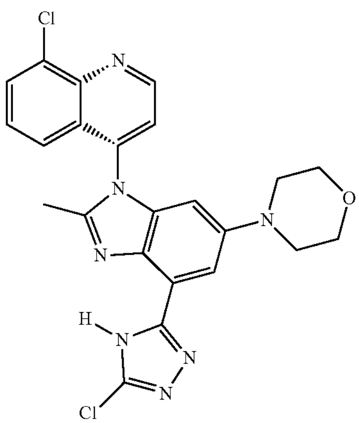 |
| 360 | 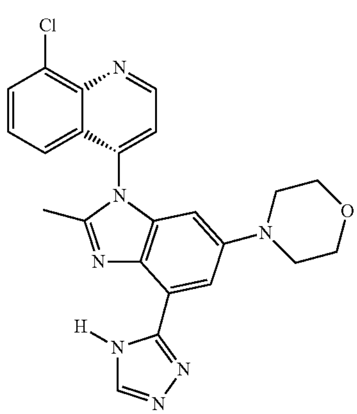 |
| 361 | |
| 362 | |
| 363 | |
In certain embodiments, provided is a compound selected from Table B, or a pharmaceutically acceptable salt, isomer, or a mixture thereof:

TABLE B
| Example | Image |
|---|---|
| 149 | 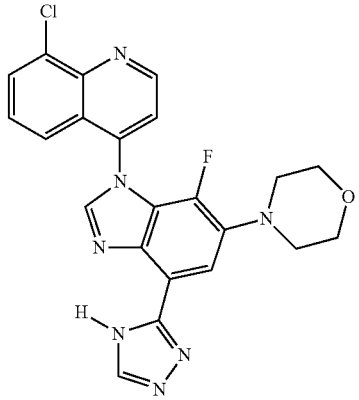 [SMILES: Fc1c(N2CCOCC2)cc(-c2nnc[nH]2)c2ncn(-c3ccnc4c(Cl)cccc34)c12] |
| 150 | 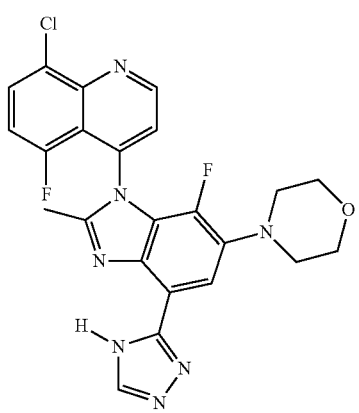 [SMILES: Cc1nc2c(-c3nnc[nH]3)cc(N3CCOCC3)c(F)c2n1-c1ccnc2c(Cl)ccc(F)c12] |
| 151 | 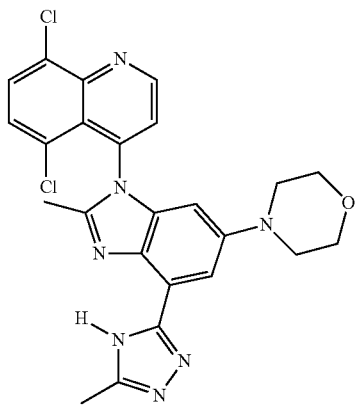 [SMILES: Cc1nnc(-c2cc(N3CCOCC3)cc3c2nc(C)n3-c2ccnc3c(Cl)ccc(Cl)c23)[nH]1] |
TABLE B-continued
| Example | Image |
|---|---|
| 152 | 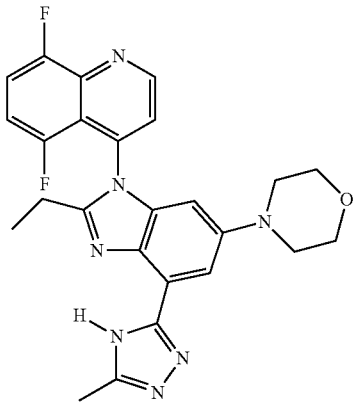 [SMILES: CCc1nc2c(-c3nnc(C)[nH]3)cc(N3CCOCC3)cc2n1-c1ccnc2c(F)ccc(F)c12] |
| 153 | 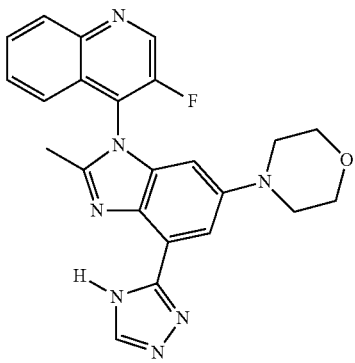 [SMILES: Cc1nc2c(-c3nnc[nH]3)cc(N3CCOCC3)cc2n1-c1c(F)cnc2ccccc12] |
| 154 | 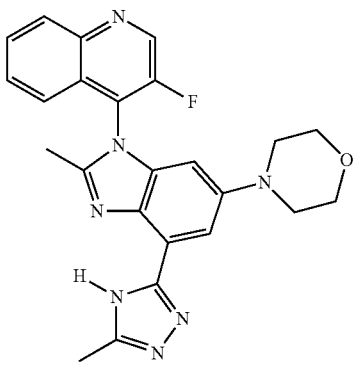 [SMILES: Cc1nnc(-c2cc(N3CCOCC3)cc3c2nc(C)n3-c2c(F)cnc3ccccc23)[nH]1] |
| 155 | 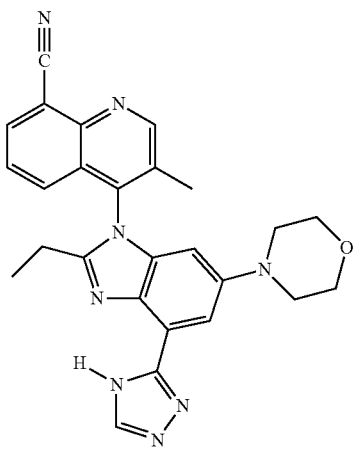 [SMILES: CCc1nc2c(-c3nnc[nH]3)cc(N3CCOCC3)cc2n1-c1c(C)cnc2c(C#N)cccc12] |

TABLE B-continued
| Example | Image |
|---------|-------|
| 156 | 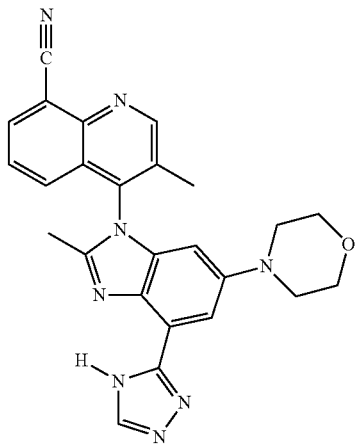 [SMILES: Cc1cnc2c(C#N)cccc2c1-n1c(C)nc2c(-c3nnc[nH]3)cc(N3CCOCC3)cc21] |
| 157 | 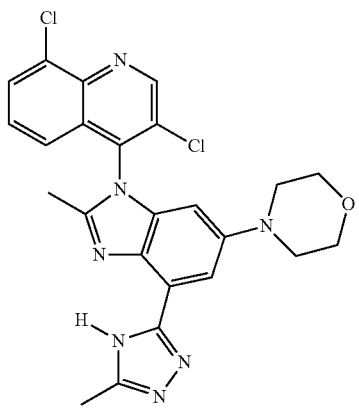 [SMILES: Cc1nnc(-c2cc(N3CCOCC3)cc3c2nc(C)n3-c2c(Cl)cnc3c(Cl)cccc23)[nH]1] |
| 247 | 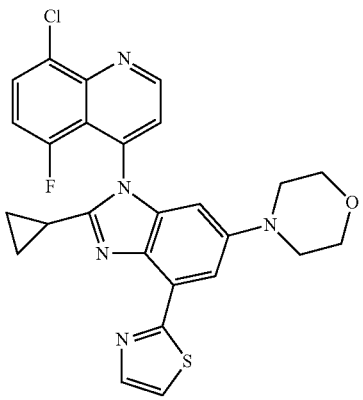 [SMILES: Fc1ccc(Cl)c2nccc(-n3c(C4CC4)nc4c(-c5nccs5)cc(N5CCOCC5)cc43)c12] |
TABLE B-continued
| Example | Image |
|---------|-------|
| 364 | 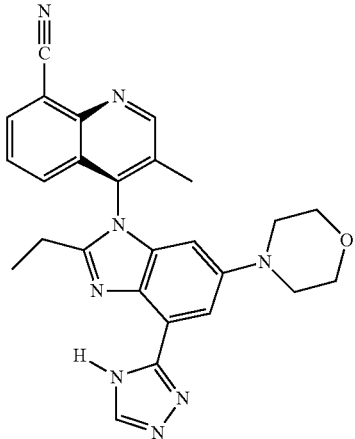 |
| 365 | 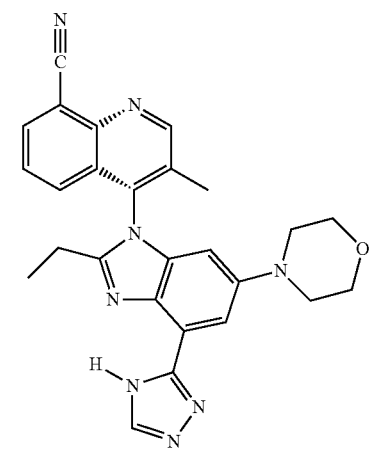 |
| 366 | 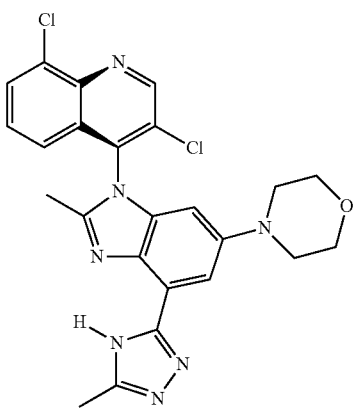 |

TABLE B-continued
| Example | Image |
|---------|-------|
| 367 | 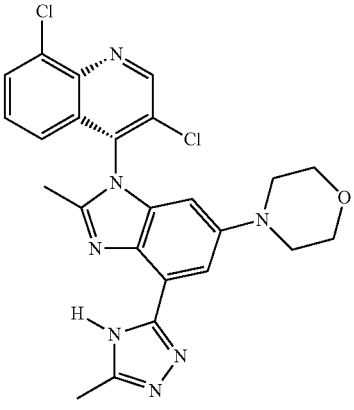 |
| 368 | 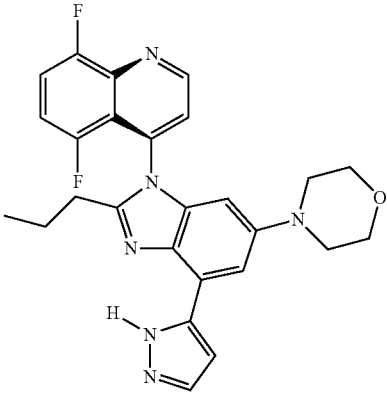 |
| 369 | 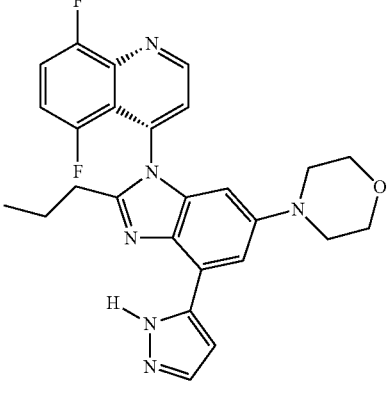 |
| 370 | 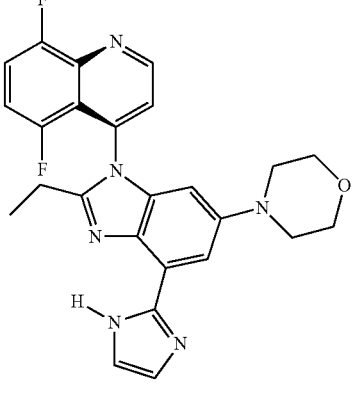 |
| 371 | |
| 372 | |
| 373 | |
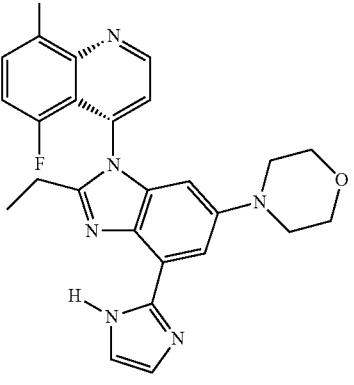

TABLE B-continued

| Example | Image |
|---------|-------|
| 374 | |
| 375 | |
| 376 | |
| 377 | |
| 378 | |
| 379 | |

123
TABLE B-continued
| Example | Image |
|---|---|
| 380 | 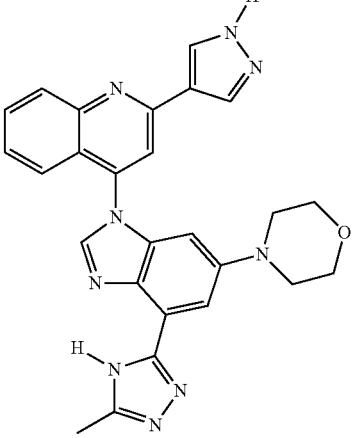 |
| 381 | 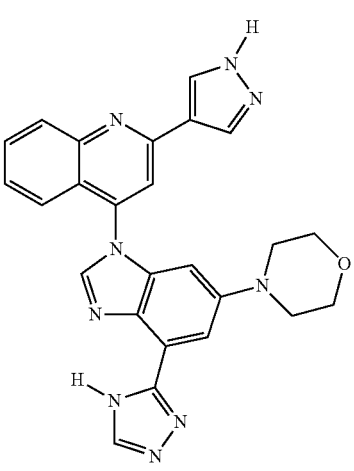 [SMILES: c1ccc2c(-n3cnc4c(-c5nnc[nH]5)cc(N5CCOCC5)cc43)cc(-c3cn[nH]c3)nc2c1] |
| 382 | 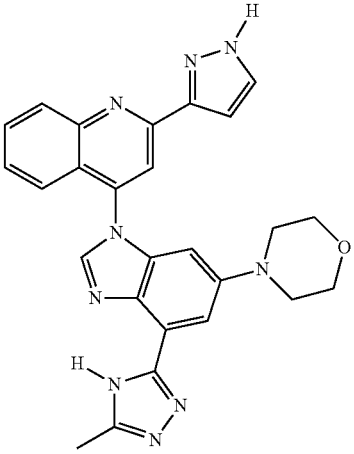 [SMILES: Cc1nnc(-c2cc(N3CCOCC3)cc3c2ncn3-c2cc(-c3cc[nH]n3)nc3ccccc23)[nH]1] |
124
TABLE B-continued
| Example | Image |
|---|---|
| 383 | 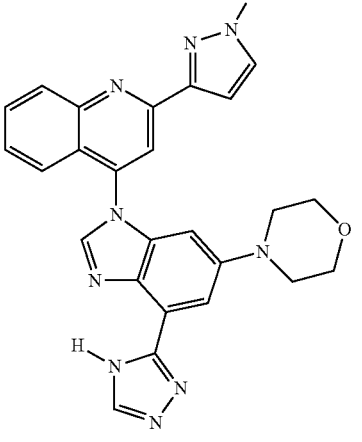 |
| 387 | 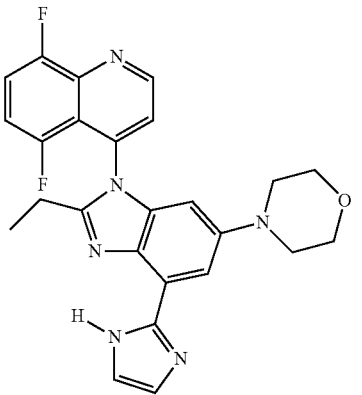 [SMILES: CCc1nc2c(-c3ncc[nH]3)cc(N3CCOCC3)cc2n1-c1ccnc2c(F)ccc(F)c12] |
| 388 | 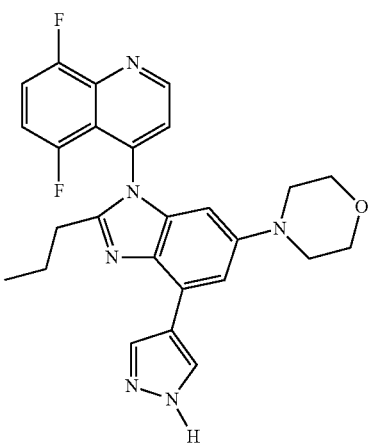 [SMILES: CCCc1nc2c(-c3cn[nH]c3)cc(N3CCOCC3)cc2n1-c1ccnc2c(F)ccc(F)c12] |

TABLE B-continued

| Example | Image |
|---|---|
| 389 | (structure) |
| 390 | (structure) |
| 391 | (structure) |
| 392 | (structure) |
| 393 | (structure) |
| 394 | (structure) |

The present application provides pharmaceutically acceptable salts, hydrates, solvates, isomers, tautomers, stereoisomers, enantiomers, racemates, atropisomers, polymorphs, prodrugs, or a mixture thereof, of the compounds described herein. The terms "a compound of the present application," "a compound described herein," "a compound of any of the formulae described herein," or variant thereof refer to a compound having the structure of any of the formulae, I, IA, IB, IC, ID, IE, IF, IG, IH, IJ, IK, IL and IM.). In some embodiments, compounds of the present application are Compounds 1-363 as described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" refer to salts of pharmaceutical compounds that retain the biological effectiveness and properties of the underlying compound, and which are not biologically or otherwise undesirable. There are acid addition salts and base addition salts. Pharmaceutically acceptable acid addition salts may be prepared from inorganic and organic acids. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources. If the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Salts derived from mineral acids include, hydrochloride, hydrobromide, hydroiodide, nitrate, phosphate, and sulfate. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

"Isomers" refers to compounds that have the same molecular formula. As used herein, the term isomers include double bond isomers, racemates, stereoisomers, enantiomers, diastereomers, and atropisomers. Single isomers, such as enantiomers or diastereomers, can be obtained by asymmetric synthesis or by resolution of a mixture of isomers. Resolution of a mixture of isomers (e.g. racemates) maybe accomplished, for example, by conventional methods such as crystallization in the presence of a resolving agent, or chromatography, using, for example a chiral high pressure liquid chromatography (HPLC) column. "Double bond isomers" refer to Z- and E-forms (or cis- and trans-forms) of the compounds with carbon-carbon double bonds.

"Atropisomers" refers to conformational stereoisomers which occur when rotation about a single bond in the molecule is prevented, or greatly hindered, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers may be separated by the methods well known in the art. Unless otherwise indicated, the description is intended to include individual atropisomers as well as mixtures. Also, as understood by those skilled in the art, the atropisomers may be represented by the same chemical name with different atropisomer designations. By way of example, the below structures are atropisomers of compound 230 (4-(1-(5,8-difluoroquinolin-4-yl)-4-(oxazol-2-yl)-2-propyl-1H-benzo[d]imidazol-6-yl)morpholine).

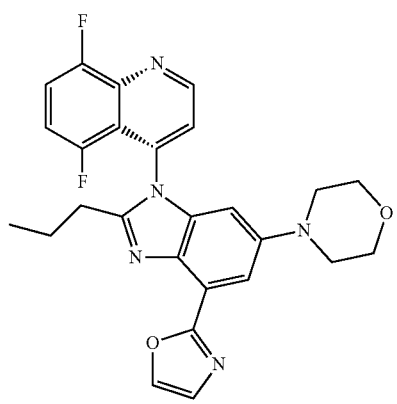

Compound-356

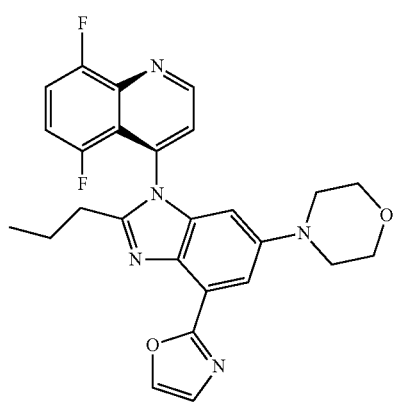

Compound-357

Compounds of the invention are named using Chembiodraw Ultra (version 14).

"Racemates" refers to a mixture of enantiomers.

"Stereoisomers" or "stereoisomeric forms" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomers" or "tautomeric forms" refer to alternate forms of a compound that differ in the position of a proton, such as enol-keto and imine-enamine tautomers, or heteroaryls such as pyrazoles, imidazoles, benzimidazoles, triazoles, and tetrazoles.

A "solvate" is formed by the interaction of a solvent and a compound. Solvates of salts of the compounds of any of the formulae described herein are also provided. Hydrates of the compounds of any of the formulae are also provided.

A "prodrug" is defined in the pharmaceutical field as a biologically inactive derivative of a drug that upon administration to the human body is converted to the biologically active parent drug according to some chemical or enzymatic pathway. A prodrug is thus a covalently modified analog or latent form of a therapeutically active compound. Non-limiting examples of prodrugs include ester moieties, quaternary ammonium moieties, glycol moieties, and the like.

In any one of the foregoing embodiments, the compound described herein or a pharmaceutically acceptable salt thereof is an (S)-enantiomer. In any one of the foregoing embodiments, the compound described herein or a pharmaceutically acceptable salt thereof is an (R)-enantiomer. In any one of the foregoing embodiments, the compound described herein or a pharmaceutically acceptable salt thereof is an atropisomer.

The application also provides a composition containing a mixture of enantiomers of the compound or a pharmaceutically acceptable salt thereof. In one embodiment, the mixture is a racemic mixture. In other embodiments, the composition comprises the (S)-enantiomer of a compound in excess of the corresponding (R)-enantiomer of the compound. In some embodiments, the composition contains the (S)-enantiomer of the compound and is substantially free of its corresponding (R)-enantiomer. In certain embodiments, a composition substantially free of the (R)-enantiomer has less than or about 40%, 35%, 30%, 25%, 20%, 15%, 10%, 5%, 1%, 0.05%, or 0.01% of the (R)-enantiomer. In other embodiments, the composition containing the (S)-enantiomer of a compound or a pharmaceutically acceptable salt thereof, predominates over its corresponding (R)-enantiomer by a molar ratio of at least or about 9:1, at least or about 19:1, at least or about 40:1, at least or about 80:1, at least or about 160:1, or at least or about 320:1.

The composition containing a compound according to any of the formulae described herein or a pharmaceutically acceptable salt thereof, may also contain the compound in enantiomeric excess (e.e.). By way of example, a compound with 95% (S)-isomer and 5% (R)-isomer will have an e.e. of 90%. In some embodiments, the compound has an e.e. of at least or about 60%, 75%, 80%, 85%, 90%, 95%, 98% or 99%.

In any one of the foregoing embodiments, the compound or a pharmaceutically acceptable salt thereof, is an atropisomer. Another embodiment provides the composition containing a mixture of atropisomers of the compound or a pharmaceutically acceptable salt thereof. By way of example, a compound with 95% of one atropisomer and 5% of the other atropisomers. In some embodiments, a compound with about 90, 80, 70, 60, 50, 40, 30, 20, or 10% of one atropisomer and 10, 20, 30, 40, 50, 60, 70, 80, or 90%, respectively, of the other atropisomers.

The application also provides the free base forms of the compounds described herein. In certain embodiments, provided herein are the enantiomers, (R) or (S), of the compounds of the formulae described herein. In other embodiments, provided herein are the atropisomers of the compounds of the formulae described herein.

The application further provides compositions comprising the compounds described herein or a pharmaceutically acceptable salt, isomer, prodrug, or solvate thereof. The composition may include racemic mixtures, mixtures containing an enantiomeric excess of one enantiomer or single diastereomers or diastereomeric mixtures. All such isomeric forms of these compounds are expressly included herein, the same as if each and every isomeric form were specifically and individually listed.

In certain embodiments, provided herein are also polymorphs, such as crystalline and amorphous forms, of the compounds described herein. In some embodiments, provided are also chelates, non-covalent complexes, and mixtures thereof, of the compounds of the formula described herein or pharmaceutically acceptable salts, prodrugs, or solvates thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

In certain embodiments, provided are also chelates, non-covalent complexes, and mixtures thereof, of the compounds described herein or a pharmaceutically acceptable salt, tautomer, stereoisomer, mixture of stereoisomers, prodrug, or deuterated analog thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Therapeutic Uses of the Compounds

The compounds of the formulae described herein or a pharmaceutically acceptable salt, isomer, prodrug, or solvate thereof may be used for the treatment of diseases and/or conditions mediated by PI3K isoforms. In addition, the application provides the compounds for use in therapy. Also, provided herein are methods for inhibiting one or more PI3K isoforms. In one embodiment, provided are methods for inhibiting PI3Kβ activity using the compound described herein or a pharmaceutically acceptable salt, isomer, prodrug, or solvate thereof. In other embodiment, provided are methods for inhibiting PI3Kβ activity using the compound or a pharmaceutically acceptable salt, isomer, prodrug, or solvate thereof. The application further provides methods for use in such methods. The PI3K isoforms may be selectively or specifically inhibited. Additionally, the compounds may be used to inhibit PI3K activity therapeutically or prophylactically, such as PI3Kβ.

The compounds according to the present application may be used in combination with one or more additional therapeutic agents. The therapeutic agents may be in the forms of compounds, antibodies, polypeptides, or polynucleotides. The therapeutic agent includes, but is not limited to, a chemotherapeutic agent, an immunotherapeutic agent, a radiotherapeutic agent, an anti-neoplastic agent, an anticancer agent, an anti-proliferation agent, an anti-fibrotic agent, an anti-angiogenic agent, a therapeutic antibody, or any combination thereof. In one embodiment, the application provides a product comprising a compound described herein and an additional therapeutic agent as a combined preparation for simultaneous, separate or sequential use in therapy, e.g. a method of treating a disease, disorder, or condition that is mediated by PI3K isoforms. The compounds of the invention can be used in combination with compounds that inhibit or modulate the activities of poly (ADP-ribose) polymerases (PARP), such as PARP-1, PARP-2, PARP-3 and Vault-PARP; Tankyrases (TANKs), such as, TANK-1, TANK-2 and TANK-3; matrix metalloproteinases such as MMP-2 and MMP-9; and the androgen receptor.

Therapeutic agents that can be used in combination with compounds of the invention include enzalutamide, abiraterone, abiraterone acetate, apalutamide, galeterone, olaparib, niraparib, veliparib, rucaparib, flutamide, nilutamide, bicalutamide, ketonazole, orteronel, finasteride, dutasteride, bexlosteride, izonsteride, turosteride, episteride, dexamethasone, prednisone, leuprolide, goserelin, triptorelin, histrelin, estrogen, cyproterone acetate, spironolactone, flutamide, hydroxyflutamide, docetaxel, cabazitaxel, sipuleucel-T, ODM-201, VT-464, EPI-506, and combinations thereof.

Also, the therapeutic agents may be those that inhibit or modulate the activities of Bruton's tyrosine kinase, spleen tyrosine kinase, apoptosis signal-regulating kinase, Janus kinase, lysyl oxidase, lysyl oxidase-like proteins, matrix metallopeptidase, bromodomain-containing protein, adenosine A2B receptor, isocitrate dehydrogenase, serine/threonine kinase TPL2, discoidin domain receptor, serine/threonine-protein kinases, IKK, MEK, EGFR, histone deacetylase, protein kinase C, or any combination thereof. In certain embodiments, the therapeutic agent may be selected from a PI3K (including PI3Kγ, PI3Kδ, PI3Kβ, PI3Kα, and/or pan-PI3K) inhibitor, a JAK (Janus kinase, including JAK1, JAK2, and/or JAK3) inhibitor, a SYK (spleen tyrosine kinase) inhibitor, a BTK (Bruton's tyrosine kinase) inhibitor, an A2B (adenosine A2B receptor) inhibitor, an ACK (activated CDC kinase, including ACK1) inhibitor, an ASK (apoptosis signal-regulating kinase, including ASK1) inhibitor, Aurora kinase, a BRD (bromodomain-containing protein, including BRD4) inhibitor, a Bcl (B-cell CLL/lymphoma, including Bcl-1 and/or Bcl-2) inhibitor, a CAK (CDK-activating kinase) inhibitor, a CaMK (calmodulin-dependent protein kinases) inhibitor, a CDK (cyclin-dependent kinases, including CDK1, 2, 3, 4, and/or 6) inhibitor, a CK (casein kinase, including CK1 and/or CK2) inhibitor, a DDR (discoidin domain receptor, including DDR1 and/or DDR2) inhibitor, a EGFR inhibitor, a FXR (farnesoid× receptor) inhibitor, a FAK (focal adhesion kinase) inhibitor, a GSK (glycogen synthase kinase) inhibitor, a HDAC (histone deacetylase) inhibitor, an IDO (indoleamine 2,3-dioxygenase) inhibitor, an IDH (isocitrate dehydrogenase, including IDH1) inhibitor, an IKK (1-Kappa-B kinase) inhibitor, a KDM5 (lysine demethylase) inhibitor, a LCK (lymphocyte-specific protein tyrosine kinase) inhibitor, a LOX (lysyl oxidase) inhibitor, a LOXL (lysyl oxidase like protein, including LOXL1, LOXL2, LOXL3, LOXL4, and/or LOXL5) inhibitor, a MTH (mut T homolog) inhibitor, a MEK (mitogen-activated protein kinase kinase) inhibitor, a matrix metalloprotease (MMP, including MMP2 and/or MMP9) inhibitor, a mitogen-activated protein kinases (MAPK) inhibitor, a PD-1 (programmed cell death protein 1) inhibitor, a PD-L (programmed death-ligand 1) inhibitor, a PDGF (platelet-derived growth factor) inhibitor, a phosphorylase kinase (PK) inhibitor, a PLK (polo-like kinase, including PLK1, 2, 3) inhibitor, a protein kinase (PK, including protein kinase A, B, C) inhibitor, a STK (serine/threonine kinase) inhibitor, a STAT (signal transduction and transcription) inhibitor, a serine/threonine-protein kinase inhibitor, a TBK (tank-binding kinase) inhibitor, a TLR (toll-like receptor modulators, including TLR-1, TLR-2, TLR-3, TLR-4, TLR-5, TLR-6, TLR-7, TLR-8, TLR-9, TLR-10, TLR-11, TLR-12, and/or TLR-13) inhibitor, a TK (tyrosine kinase) inhibitor, a TPL2 (serine/threonine kinase) inhibitor, a NEK9 inhibitor, an Abl inhibitor, a p38 kinase inhibitor, a PYK inhibitor, a PYK inhibitor, a c-Kit inhibitor, a NPM-ALK inhibitor, a Flt-3 inhibitor, a c-Met inhibitor, a KDR inhibitor, a TIE-2 inhibitor, a VEGFR inhibitor, a SRC inhibitor, a HCK inhibitor, a LYN inhibitor, a FYN inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiments, the JAK inhibitor is N-(cyanomethyl)-4-[2-(4-morpholinoanilino)pyrimidin-4-yl]benzamide as named by ChemDraw (may also be referred to as CYT0387 or momelotinib) and may be synthesized by the methods described in U.S. Pat. No. 8,486,941. In certain embodiment, the SyK inhibitor is 6-(1H-indazol-6-yl)-N-(4-morpholinophenyl) imidazo[1,2-a]pyrazin-8-amine as named by ChemDraw (may also be referred to as 6-(1H-indazol-6-yl)-N-[4-(morpholin-4-yl)phenyl]imidazo[1,2-a]pyrazin-8-amine) and may be synthesized by the methods described in U.S. Pat. No. 8,450,321. In other embodiments, the BTK inhibitor is (S)-6-amino-9-(1-(but-2-ynoyl)pyrrolidin-3-yl)-7-(4-phenoxyphenyl)-7H-purin-8(9H)-one as named by ChemDraw (may also be 6-amino-9-[(3R)-1-(2-butynoyl)-3-pyrrolidinyl]-7-(4-phenoxyphenyl)-7,9-dihydro-8H-purin-8-one) and may be synthesized by the methods in U.S. Pat. No. 8,557,803.

Chemotherapeutic agents may be categorized by their mechanism of action into, for example, the following groups: anti-metabolites/anti-cancer agents, such as pyrimidine analogs (floxuridine, capecitabine, and cytarabine); purine analogs, folate antagonists and related inhibitors, antiproliferative/antimitotic agents including natural products such as vinca alkaloid (vinblastine, vincristine) and microtubule such as taxane (paclitaxel, docetaxel), vinblastin, nocodazole, epothilones and navelbine, epidipodophyllotoxins (etoposide, teniposide); DNA damaging agents (actinomycin, amsacrine, busulfan, carboplatin, chlorambucil, cisplatin, cyclophosphamide, Cytoxan, dactinomycin, daunorubicin, doxorubicin, epirubicin, iphosphamide, melphalan, merchlorehtamine, mitomycin, mitoxantrone, nitrosourea, procarbazine, taxol, taxotere, teniposide, etoposide, triethylenethiophosphoramide); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards cyclophosphamide and analogs, melphalan, chlorambucil), and (hexamethylmelamine and thiotepa), alkyl nitrosoureas (BCNU) and analogs, streptozocin), trazenes-dacarbazinine (DTIC); antiproliferative/antimitotic antimetabolites such as folic acid analogs (methotrexate); platinum coordination complexes (cisplatin, oxiloplatinim, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel; antimigratory agents; antisecretory agents (breveldin); immunosuppressives (tacrolimus, sirolimus azathioprine, mycophenolate); phytoestrogens (daidzein, glycitein, genisteinand growth factor inhibitors (vascular endothelial growth factor inhibitors, fibroblast growth factor inhibitors); angiotensin receptor blocker, nitric oxide donors; anti-sense oligonucleotides; antibodies (trastuzumab, rituximab); cell cycle inhibitors and differentiation inducers (tretinoin); inhibitors, topoisomerase inhibitors (doxorubicin (adriamycin), daunorubicin, dactinomycin, eniposide, epirubicin, etoposide, idarubicin, irinotecan and mitoxantrone, topotecan, irinotecan, camptothesin), corticosteroids (cortisone, dexamethasone, hydrocortisone, methylprednisolone, prednisone, and prednisolone); growth factor signal transduction kinase inhibitors; dysfunction inducers, toxins such as Cholera toxin, ricin, *Pseudomonas* exotoxin, *Bordetella pertussis* adenylate cyclase toxin, or diphtheria toxin, and caspase activators; and chromatin.

As used herein the term "chemotherapeutic agent" or "chemotherapeutic" (or "chemotherapy," in the case of treatment with a chemotherapeutic agent) is meant to encompass any non-proteinaceous (i.e, non-peptidic) chemical compound useful in the treatment of cancer. Examples of chemotherapeutic agents include alkylating agents such as thiotepa and cyclophosphamide (CYTOXAN); alkyl sulfonates such as busulfan, improsulfan and piposulfan; aziridines such as benzodopa, carboquone, meturedopa, and uredopa; emylerumines and memylamelamines including alfretamine, triemylenemelamine, triethylenephosphoramide, triethylenethiophosphoramide and trimemylolomelamine; acetogenins (especially bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g., calicheamicin, especially calicheamicin gammaII and calicheamicin phiI1, see, e.g., Agnew, Chem. Intl. Ed. Engl, 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; PSK®; razoxane; rhizoxin; sizofiran; spirogermanium; tenuazonic acid; triaziquone; 2,2',2"-triUorotriemylamine; trichothecenes (especially T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiopeta; taxoids, e.g., paclitaxel (TAXOL® and docetaxel (TAXOTERE®); chlorambucil; gemcitabine (Gemzar®); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine®); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; FOLFIRI (fluorouracil, leucovorin, and irinotecan) and pharmaceutically acceptable salts, acids or derivatives of any of the above. One or more chemotherapeutic agent are used or included in the present application.

Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston®); inhibitors of the enzyme aromatase, which regulates estrogen production in the adrenal glands, such as, for example, 4(5)-imidazoles, aminoglutethimide, megestrol acetate (Megace®), exemestane, formestane, fadrozole, vorozole (Rivisor®), letrozole (Femara®), and anastrozole (Arimidex®); and anti-androgens such as flutamide, nilutamide, bicalutamide, leuprohde, and goserelin; and pharmaceutically acceptable salts, acids or derivatives of any of the above.

The anti-angiogenic agents include, but are not limited to, retinoid acid and derivatives thereof, 2-methoxyestradiol, ANGIOSTATIN®, ENDOSTATIN®, suramin, squalamine, tissue inhibitor of metalloproteinase-1, tissue inhibitor of metalloproternase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,I-3,4-dehydroproline, thiaproline, .alpha.-dipyridyl, beta-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpba-2-antiplasmin, bisantrene, lobenzarit disodium, n-2-carboxyphenyl-4-chloroanthronilic acid disodium or "CCA", thalidomide; angiostatic steroid, cargboxynaminolmidazole; metalloproteinase inhibitors such as BB94. Other anti-angiogenesis agents include antibodies, preferably monoclonal antibodies against these angiogenic growth factors: beta-FGF, alpha-FGF, FGF-5, VEGF isoforms, VEGF-C, HGF/SF and Ang-1/Ang-2. See Ferrara N. and Alitalo, K. "Clinical application of angiogenic growth factors and their inhibitors" (1999) Nature Medicine 5:1359-1364.

The anti-fibrotic agents include, but are not limited to, the compounds such as beta-aminoproprionitrile (BAPN), as well as the compounds disclosed in U.S. Pat. No. 4,965,288 to Palfreyman, et al., issued Oct. 23, 1990, entitled "Inhibitors of lysyl oxidase," relating to inhibitors of lysyl oxidase and their use in the treatment of diseases and conditions associated with the abnormal deposition of collagen; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. Nos. 5,021,456; 5,5059,714; 5,120,764; 5,182,297; 5,252,608 (relating to 2-(1-naphthyloxymemyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives, semicarbazide, and urea derivatives, aminonitriles, such as beta-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. Also, the anti-fibrotic agents are copper chelating agents, penetrating or not penetrating the cells. Exemplary compounds include indirect inhibitors such compounds blocking the aldehyde derivatives originating from the oxidative deamination of the lysyl and hydroxylysyl residues by the lysyl oxidases, such as the thiolamines, in particular D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, sodium-4-mercaptobutanesulphinate trihydrate.

The immunotherapeutic agents include and are not limited to therapeutic antibodies suitable for treating patients; such as abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, obinutuzumab, CC49 and 3F8. The exemplified therapeutic antibodies may be further labeled or combined with a radioisotope particle, such as indium In 111, yttrium Y 90, iodine I-131.

The application also provides method for treating a subject who is undergoing one or more standard therapies, such as chemotherapy, radiotherapy, immunotherapy, surgery, or combination thereof. Accordingly, one or more therapeutic agent or inhibitors may be administered before, during, or after administration of chemotherapy, radiotherapy, immunotherapy, surgery or combination thereof.

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States are profiled in Morton, L. M., et al. "Lymphoma Incidence Patterns by WHO Subtype in the United States, 1992-2001" *Blood* 2006, 107(1), p. 265-276.

Examples of immunotherapeutic agents include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO 131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents include aldesleukin, alvocidib, antineoplaston AS2-1, antineoplaston A10, antithymocyte globulin, amifostine trihydrate, aminocamptothecin, arsenic trioxide, beta alethine, Bcl-2 family protein inhibitor ABT-263, ABT-199, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCl-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hypezCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (R-MCP).

The therapeutic treatments can be supplemented or combined with any of the abovementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the methods include administering a compound of the formula described herein or a pharmaceutically acceptable salt, isomer, prodrug, or solvate thereof, in a therapeutically effective amount to a human in need thereof. The method can be employed to treat a patient who has or is believed to have a disease or condition whose symptoms or pathology is mediated by expression or activity of PI3Kβ. The patient may be a mammal or a human. In certain embodiment, the patient may be a human.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing the effect of another medication, delaying the progression of the disease, increasing the quality of life, and/or prolonging survival.

"Prevention" or "preventing" mean any treatment of a disease or condition that causes the clinical symptoms of the disease or condition not to develop. Compounds may, in some embodiments, be administered to a subject (including a human) who is at risk or has a family history of the disease or condition.

"Subject" or "patient" refer to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human. "Human in need thereof" refers to a human who may have or is suspect to have diseases, or disorders, or conditions that would benefit from certain treatment; for example, being treated with the PI3K inhibitor of the compounds according to the present application. In certain embodiments, the subject may be a human who (i) has not received any treatment including chemotherapy treatment, (ii) is substantially refractory to at least one chemotherapy treatment, (iii) is in relapse after treatment with chemotherapy, or both (i) and (ii). In some of embodiments, the subject is refractory to at least one, at least two, at least three, or at least four chemotherapy treatments (including standard or experimental chemotherapies).

The terms "therapeutically effective amount" or "effective amount" of a compound of the present application or a pharmaceutically acceptable salt, isomers, prodrug, or solvate thereof, mean an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of PI3Kδ and PI3Kβ activity. The therapeutically effective amount may vary depending on the subject, and disease or condition being treated, the weight and age of the subject, the severity of the disease or condition, and the manner of administering, which can readily be determined by one or ordinary skill in the art.

In addition to the therapeutic uses, the compounds described herein have the selectivity or selective inhibition to certain PI3K isoforms. In one embodiment, the compounds have selectivity to PI3Kβ. The selectivity to PI3K isoforms may be determined by measuring the compound's activity in inhibiting certain PI3K isoforms using the assay described in the example below or the methods commonly used. It is understood that the conditions (e.g. the reagent concentration or the incubation temperature) may be varied and the results of the assay may vary. In some instances, the value may vary within a range of one to three-fold.

The term "inhibition" indicates a decrease in the baseline activity of a biological activity or process. The term "inhibition of activity of PI3K isoforms" or variants thereof refer to a decrease in activity in any PI3K isoform (e.g., alpha, beta, gamma, or delta) as a direct or indirect response to the presence of a compound of any of the formula described herein relative to the activity of PI3K isoform in the absence of such compound. "Inhibition of PI3Kδ and/or PI3Kβ activities" or variants thereof refer to a decrease in PI3Kδ and/or PI3Kβ activities as a direct or indirect response to the presence of the compounds described herein, relative to the activities of PI3Kδ and/or PI3Kβ in the absence of such compound. In some embodiments, the inhibition of PI3K isoform activities may be compared in the same subject prior to treatment, or other subjects not receiving the treatment.

Without being bound to any theory, the decrease in the activity of PI3K may be due to the direct interaction of the compound with PI3K, or due to the interaction of the compounds described herein with one or more other factors that affect PI3K activity. For example, the presence of the compounds may decrease the activities of PI3Kδ and/or PI3Kβ by directly binding to PI3Kδ and/or PI3Kβ, by causing (directly or indirectly) another factor to decrease PI3Kδ and/or PI3Kβ activities, or by (directly or indirectly) decreasing the amount of PI3Kδ and/or PI3Kβ present in the cell or organism.

The term "PI3K inhibitor" or variant thereof refers to a compound that inhibits the activity of PI3K. The term "PI3K isoform selective inhibitor" or variant thereof refers to a compound that inhibits the activity of one or more PI3K isoforms more effectively than the other remaining PI3K isoforms. By way of example, the term "PI3Kβ selective inhibitor" generally refers to a compound that inhibits the activity of the PI3Kβ isoform more effectively than other isoforms of the PI3K family, and the term "PI3Kδ selective inhibitor" generally refers to a compound that inhibits the activity of the PI3Kδ isoform more effectively than other isoforms of the PI3K family. The term "dual PI3Kδ/β selective inhibitor" generally refers to a compound that inhibits the activity of both PI3Kδ and PI3Kβ isoforms more effectively than other isoforms of the PI3K family (e.g., PI3K α or γ).

The relative efficacies of compounds as inhibitors of an enzyme activity (or other biological activity) can be established by determining the concentrations at which each compound inhibits the activity to a predefined extent and then comparing the results. In one embodiment, the efficacy of a compound as an inhibitor of one or more PI3K isoforms can be measured by the compound concentration that inhibits 50% of the activity in a biochemical assay, i.e., the 50% inhibitory concentration or "$IC_{50}$". The determination of $IC_{50}$ values can be accomplished using conventional techniques known in the art, including the techniques described in the Examples below. In general, an $IC_{50}$ can be determined by measuring the activity of a given enzyme in the presence of a range of concentrations of the compound under the study. The experimentally obtained values of enzyme activity may then be plotted against the compound concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it may be desirable to establish a 90% inhibitory concentration, i.e., $IC_{90}$.

According to the present application, a PI3Kβ selective inhibitor is a compound that exhibits a 50% inhibitory concentration ($IC_{50}$) with respect to PI3Kβ that is at least 10-fold, at least 20-fold, at least 30-fold, at least 50-fold, at least 100-fold, at least 200-fold, or at least 500-fold lower than the $IC_{50}$ with respect to either PI3Kα or PI3Kγ or both PI3Kα and PI3Kγ. In addition, a PI3Kδ/β selective inhibitor is a compound that exhibits a 50% inhibitory concentration ($IC_{50}$) with respect to PI3Kβ and PI3Kδ that is at least 10-fold, at least 20-fold, at least 30-fold, at least 50-fold, at least 75-fold, at least 100-fold, at least 200-fold, and at least 500-fold lower than the $IC_{50}$ with respect to either PI3Kα or PI3Kγ. The dual PI3Kδ/β selective inhibitor may have the same or similar $IC_{50}$ to both PI3Kδ and PI3Kβ or may have different $IC_{50}$ to either PI3Kδ or PI3Kβ. As used herein, the term "potency," "potent," or variants thereof refer to the compound exhibiting an $IC_{50}$ value that is less than 100 nM. When comparing two compounds, the compound that exhibits a lower $IC_{50}$ value is referred to as a more potent inhibitor.

The compounds of the present application exhibit unexpected selectivity to PI3Kβ. As shown in the example, certain compounds in Table 1 exhibit low $IC_{50}$ values (e.g. 1 to 100 nM) against PI3Kβ. Certain compounds in Table 1a also exhibited such selectivity to PI3K isoforms. Also, certain compounds of formula (I) exhibited at least between 10-fold to 400-fold lower $IC_{50}$ values for PI3Kβ than PI3Kγ, suggesting the compounds exhibit more selectivity to PI3Kβ compared to PI3Kγ (i.e., inhibits the activity of the PI3Kβ isoform more effectively than the PI3Kγ isoform as shown by the PI3Kγ/PI3Kβ ratio).

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds may be used for a variety of purposes, including therapeutic and experimental purposes. For example, it may be used ex vivo to determine the optimal schedule and/or dosing of administration of a PI3K selective inhibitor for a given indication, cell type, individual, and other parameters. Information gleaned from such use may be used for experimental purposes or in the clinic to set protocols for in vivo treatment. Other ex vivo uses for which the compound described herein may be suited are described below or will become apparent to those skilled in the art. The compounds of the formula described herein or a pharmaceutically acceptable salt, prodrug, or solvate thereof, may be further characterized to examine the safety or tolerance dosage in human or non-human subjects. Such properties may be examined using commonly known methods to those skilled in the art.

Compared to other PI3K isoforms, PI3Kβ is generally mis-regulated in certain cancer cells. Aberrant proliferation of cells often interferes with normal tissue function, which may result in abnormal cellular response such as immunity, inflammation, and/or apoptosis. The selective inhibitors to PI3Kβ are useful in treating, inhibiting, or preventing aberrant proliferation of cancerous and/or hematopoietic cells and ameliorating the symptoms and secondary conditions.

The compounds described herein may be used to treat subjects having various disease states, disorders, and conditions (also collectively referred to as "indications") associated with PI3K isoforms or their activities. As used herein, the terms "diseases," "disorders," "conditions" are used interchangeably. Such indications may include, for example, cancer, including hematologic malignancies (e.g. leukemias and lymphomas, myeloproliferative disorders, myelodysplastic syndromes, plasma cell neoplasms) and solid tumors, inflammation, fibrosis, allergic conditions (including hypersensitivity), cardiovascular diseases, neurodegenerative diseases, renal disorders, viral infections, obesity, and autoimmune diseases.

In other embodiments, the compounds described herein may be used to treat cancers that are mediated by, dependent on, or associated with PI3K activity. In certain embodiments, the disease or condition is an autoimmune disease, an inflammatory disease, or a cancer. In some embodiments, the disease or condition is chosen from rheumatoid arthritis, osteoarthritis, atherosclerosis, psoriasis, systemic lupus erythematosus, multiple sclerosis, inflammatory bowel disease, asthma, chronic obstructive airways disease, pneumonitis, dermatitis, alopecia, nephritis, vasculitis, atherosclerosis, Alzheimer's disease, hepatitis, primary biliary cirrhosis, sclerosing cholangitis, diabetes (including type I diabetes), acute rejection of transplanted organs, lymphomas, multiple myelomas, leukemias, neoplasms and solid tumors.

In other embodiments, the disease is a solid tumor. By way of examples, the solid tumor includes but is not limited to prostate cancer, pancreatic cancer, bladder cancer, colorectal cancer, breast cancer, renal cancer, hepatocellular cancer, lung cancer, ovarian cancer, cervical cancer, rectum cancer, liver cancer, kidney cancer, stomach cancer, skin cancer, gastric cancer, esophageal cancer, head and neck cancer, melanoma, neuroendocrine cancers, CNS cancers (e.g., neuroblastoma), brain tumors (e.g., glioma, anaplastic oligodendroglioma, adult glioblastoma multiforme, and adult anaplastic astrocytoma), bone cancer, or soft tissue sarcoma. In some embodiments, the solid tumor is non-small cell lung cancer, small-cell lung cancer, colon cancer, CNS cancer, melanoma, ovarian cancer, renal cancer, pancreatic cancer, prostate cancer, or breast cancer.

The present application also provides a method for treating a human in need thereof, who has or is suspected of having a disease or condition responsive or believed to be responsive to the inhibition PI3Kβ activity by administering to the subject a compound of the formulae described herein or a pharmaceutically acceptable salt, enantiomer, atropisomer, tautomer, prodrug, or solvate thereof.

Additionally, the application provides a method of inhibiting kinase activity of a PI3Kβ polypeptides by contacting the polypeptides with a compound of the formulae described herein or a pharmaceutically acceptable salt, isomer, prodrug, solvate, or a mixture thereof.

Moreover, the application provides a method of decreasing cell viability, increasing cell death or apoptosis, increasing interference with PI3K signaling pathways (including AKT, S6RP, ERK phosphorylation), and/or reduction in chemokine production with an effective amount of a compound of any of the formulae described herein or a pharmaceutically acceptable salt, isomer, prodrug, solvate, or a mixture thereof.

The application further provides a method of disrupting leukocyte function comprising contacting the leukocytes with an effective amount of a compound of any of the formulae described herein or a pharmaceutically acceptable salt, isomer, prodrug, solvate, or a mixture thereof, in a human in need thereof.

Provided is also a method of inhibiting growth or proliferation of cancer cells comprising contacting the cancer cells with an effective amount of a compound of the formulae described herein or a pharmaceutically acceptable salt, isomer, prodrug, solvate, or a mixture thereof.

Kits

Provided herein are also kits that include a compound of the formulae of the present application or a pharmaceutically acceptable salt, isomer, prodrug, or solvate thereof, and suitable packaging. In one embodiment, a kit further includes instructions for use. In one aspect, a kit includes a compound of the formulae described herein or a pharmaceutically acceptable salt, isomer, prodrug, or solvate thereof, and a label and/or instructions for use of the compounds in the treatment of the indications, including the diseases or conditions, described herein.

Provided herein are also articles of manufacture that include a compound of any of the formulae described herein or a pharmaceutically acceptable salt, isomer, prodrug, or solvate thereof, in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provides herein are also pharmaceutical compositions that contain one or more of the compounds of any of the formulae disclosed herein or a pharmaceutically acceptable salt, isomers, prodrug, or solvate thereof, and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant. In some embodiments, the pharmaceutical composition is administered orally.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound of any of the formulae described herein or a pharmaceutically acceptable salt, prodrug, or solvate thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders. In certain embodiments, the pharmaceutical composition is in the form of tablets.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of any of the formulae described herein or a pharmaceutically acceptable salt, isomer, prodrug, or solvate thereof, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound of any of the above formulae or a pharmaceutically acceptable salt, prodrug, or solvate thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the formulae described herein for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound of the formula per kilogram of the subject's body weight (mg/kg). Dosages of between about 0.01 and 200 mg/kg may be appropriate. In some embodiments, about 0.01 and 150 mg/kg may be appropriate. In other embodiments a dosage of between 0.05 and 100 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound of the formulae administered per dose or per day. Daily dosage of a compound may be between about 1 mg and 2,000 mg, between about 1,000 to 2,000 mg/day, between about 1 to 1,000 mg/day, between about 1 to 500 mg/day, between about 100 to 150 mg/day, between about 1 to 100 mg/day, between about between about 1 to 50 mg/day, between about 50 to 100 mg/day, between about 100 to 125 mg/day, between about 100 to 150 mg/day, between about 100 to 175 mg/day, between about 100 to 200 mg/day, between about 100 to 225 mg/day, between about 100 to 250 mg/day, between about 100 to 350 mg/day, between about 100 to 400 mg/day, between about 100 to 450 mg/day, or between about 100 to 500 mg/day.

When administered orally, the total daily dosage for a human subject may be between 1 mg and 1,000 mg/day, between about 1 to 100 mg/day, between about 1 to 50 mg/day, between about 50 to 100 mg/day, between 50 to 300 mg/day, between 50 to 200 mg/day, between 75 to 200 mg/day, between 75 to 150 mg/day, between 100 to 200 mg/day, between about 200 to 300 mg/day, between about 300 to 400 mg/day, between about 400 to 500 mg/day, between about 100 to 150 mg/day, between about 150 to 200 mg/day, between about 200 to 250 mg/day, between about 75 to 150 mg/day, or between about 150 to 300 mg/day.

The compounds of the present application or the compositions thereof may be administered once, twice, three, or four times daily, using any suitable mode described above. Also, administration or treatment with the compounds according to any of the formulae described herein may be continued for a number of days; for example, commonly treatment would continue for at least 7 days, 14 days, or 28 days, for one cycle of treatment. In some treatment, the compound or the composition thereof is administered continuously, i.e. every day. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 500 mg of a compound of the above formula and increasing the dose by increments until clinical efficacy is achieved. Increments of about 1, 5, 10, 25, 50, 75, or 100 mg can be used to increase the dose. The dosage can be increased daily, every other day, twice per week, or once per week.

Synthesis of the Compounds

The compounds of the present application may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present invention are inert organic solvents, and the reactions are carried out under an inert gas, preferably nitrogen or argon.

The compounds of formula (I) may be prepared using the method similar to the Reaction Scheme I shown below:

Reaction Scheme I

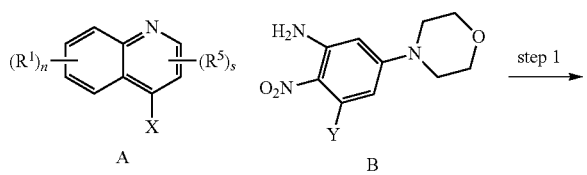

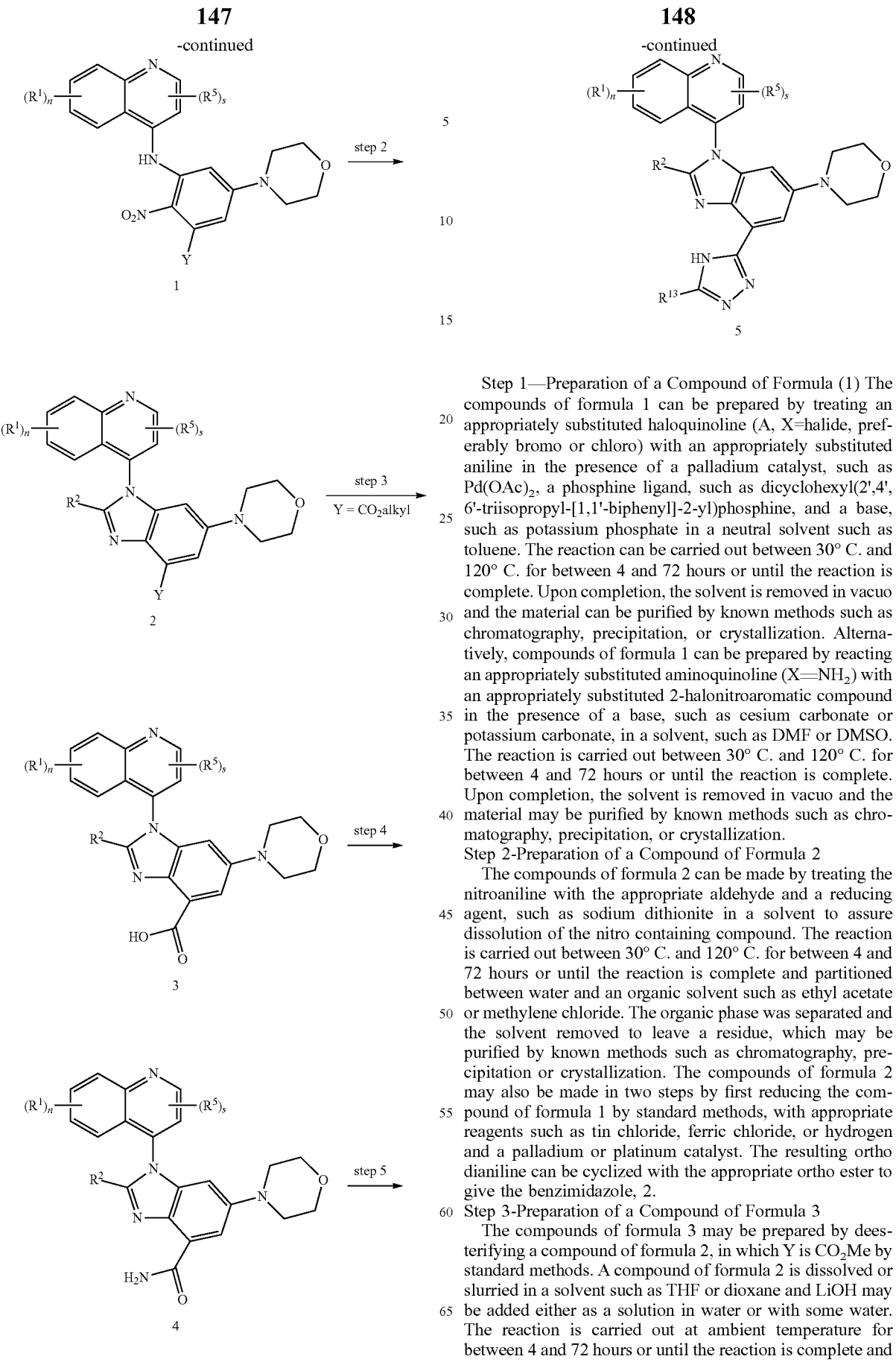

Step 1—Preparation of a Compound of Formula (1) The compounds of formula 1 can be prepared by treating an appropriately substituted haloquinoline (A, X=halide, preferably bromo or chloro) with an appropriately substituted aniline in the presence of a palladium catalyst, such as Pd(OAc)$_2$, a phosphine ligand, such as dicyclohexyl(2',4',6'-triisopropyl-[1,1'-biphenyl]-2-yl)phosphine, and a base, such as potassium phosphate in a neutral solvent such as toluene. The reaction can be carried out between 30° C. and 120° C. for between 4 and 72 hours or until the reaction is complete. Upon completion, the solvent is removed in vacuo and the material can be purified by known methods such as chromatography, precipitation, or crystallization. Alternatively, compounds of formula 1 can be prepared by reacting an appropriately substituted aminoquinoline (X=NH$_2$) with an appropriately substituted 2-halonitroaromatic compound in the presence of a base, such as cesium carbonate or potassium carbonate, in a solvent, such as DMF or DMSO. The reaction is carried out between 30° C. and 120° C. for between 4 and 72 hours or until the reaction is complete. Upon completion, the solvent is removed in vacuo and the material may be purified by known methods such as chromatography, precipitation, or crystallization.

Step 2-Preparation of a Compound of Formula 2

The compounds of formula 2 can be made by treating the nitroaniline with the appropriate aldehyde and a reducing agent, such as sodium dithionite in a solvent to assure dissolution of the nitro containing compound. The reaction is carried out between 30° C. and 120° C. for between 4 and 72 hours or until the reaction is complete and partitioned between water and an organic solvent such as ethyl acetate or methylene chloride. The organic phase was separated and the solvent removed to leave a residue, which may be purified by known methods such as chromatography, precipitation or crystallization. The compounds of formula 2 may also be made in two steps by first reducing the compound of formula 1 by standard methods, with appropriate reagents such as tin chloride, ferric chloride, or hydrogen and a palladium or platinum catalyst. The resulting ortho dianiline can be cyclized with the appropriate ortho ester to give the benzimidazole, 2.

Step 3-Preparation of a Compound of Formula 3

The compounds of formula 3 may be prepared by deesterifying a compound of formula 2, in which Y is CO$_2$Me by standard methods. A compound of formula 2 is dissolved or slurried in a solvent such as THF or dioxane and LiOH may be added either as a solution in water or with some water. The reaction is carried out at ambient temperature for between 4 and 72 hours or until the reaction is complete and acidified with an acid such as HCl. The solvent is removed in vacuo to give a compound of formula 3. Alternatively, t-butyl esters (Y is CO$_2$t-butyl) can be converted to the corresponding acid by treatment with an acid, such as TFA or aqueous HCl, in a solvent such as dichloromethane. The reaction is carried out between 0° C. and 60° C. for between 4 and 72 hours or until the reaction is complete at which time the solvent is removed in vacuo.

Step 4-Preparation of a Compound of Formula 4

The compound of formula 4 may be prepared by amidation of a compound of formula 3 by standard coupling conditions. For example, the acid, 3, may be reacted with ammonium chloride in the presence of HOBT or HATU, a base such as triethylamine, diisopropylethylamine, or methylmorpholine, and diethyldiazodicarboxylate or N1-((ethylimino)methylene)-N3,N3-dimethylpropane-1,3-diamine hydrochloride in a solvent such as DMF. The reaction is carried out at ambient temperature for between 12 and 96 hours or until the reaction is complete. The amide may precipitate with the addition of water or can be isolated by standard extractive methods.

Step 5-Preparation of a Compound of Formula 5

Compounds of formula 5 may be prepared from a compound of formula 4 by first reacting a compound of formula 4 with the appropriate reagent such as 1,1-dimethoxy-N,N-dimethylethanamine to prepare methyltriazoles or 1,1-dimethoxy-N,N-dimethylmethanamine to make unsubstituted triazoles between 80° C. and 150° C. for between 0.5 and 5 hours or until the reaction is complete. Alternatively substituted triazoles may be prepared by using alternative reagents. The solvent is removed in vacuo and the residue is dissolved in acetic acid and hydrazine hydrate and stirred for between 80° C. and 150° C. for between 0.5 and 5 hours or until the reaction is complete. The solvent was removed in vacuo and the residue was purified by standard methods. If protecting groups are present on the compound at this point, they may be removed by appropriate methods. For example, trityl or Boc groups may be removed by treatment with an acid, such as HCl or trifluoroacetic acid in a solvent such as methylene chloride. If the compound is a mixture of atropisomers, the isomers may be separated using a chiral chromatography method. The solvents and chromatography column used will depend on the specific compound being separated, but normal phase, reverse phase or supercritical fluid chromatography may be used. Alternatively, a compound of formula 5 may be prepared by reacting a compound of formula 2 with ammonium chloride and trimethylaluminum in a solvent such as DCE between −20° C. and 100° C. for between 3 hours and 3 days or until the reaction is complete. Work-up and purification gives the nitrile which can be further reacted with sodium azide and ammonium chloride in a solvent such as DMF between 80° C. and 150° C. for between 2 and 24 hours or until the reaction is complete. Alternatively a compound of formula 5 may be prepared by reacting a compound of formula 2 where Y=CO$_2$Me with a diamine, such as ethylenediamine, in the presence of trimethylaluminum in a solvent such as toluene between 10° C. and 150° C. for between 1 and 24 hours or until the reaction is complete. Alternatively a compound of formula 5 may be prepared by reacting a compound of formula 2 where Y=CO$_2$Me with hydrazine hydrate in an appropriate solvent such as ethanol between 40° C. and reflux for between 2 and 24 hours or until the reaction is complete. Work-up and purification gives the hydrazide which can be further reacted with an orthoester, such as trimethylorthoformate, triethylorthoacetate, and the like, to give an 1,3,4-oxadiazole, cyanogen bromide to give a 2-amino-1,3,4-oxadiazole, carbon disulfide to give an 1,3,4-oxadiazole-2-thione, trimethylisocyante to give an 2-amino-1,3,4-thiadiazole, or phosgene or an equivalent, such as carbonyldiimidazole to give an 1,3,4-oxadiazol-2 (3H)-one.

Reaction Scheme 2

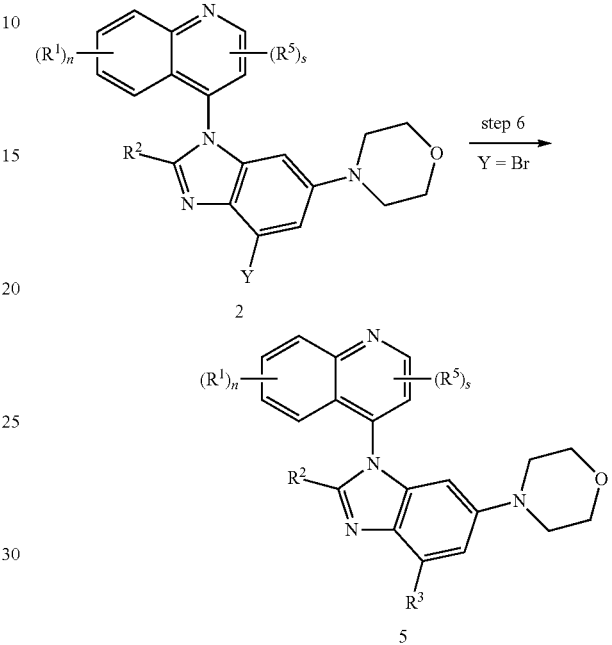

Step 6-Preparation of a Compound of Formula 5

Compounds of formula 5 may also be prepared by reacting a compound of formula 2, Y is a halogen, preferably bromide, with an appropriately substituted tributylstannyl substituted reagent in the presence of catalysts, such as copper iodide and palladium in a solvent, such as dioxane between 50° C. and 150° C. for between 12 hours and 7 days, or until the reaction is complete under an inert atmosphere such as Argon. The reaction may be worked up by standard means and purified by standard methods, such as chromatography. Alternatively, a compound of formula 5 may be prepared by reacting a compound of formula 2, where Y is a halogen, preferably bromide, with an appropriately substituted boronic acid, a MIDA ester of a boronic acid, or pinacol ester of a boronic acid in the presence of cesium fluoride in the presence of catalysts, such as copper iodide and palladium in a solvent, such as dioxane between 50° C. and 150° C. for between 12 hours and 7 days, or until the reaction is complete under an inert atmosphere such as Argon. The reaction may be worked up by standard means and purified by standard methods, such as chromatography. In some cases the product may have had a protecting group and deprotection would proceed by methods known to those skilled in the art. For example, a THP or Boc group would be removed by treatment with an acid such as TFA or aqueous HCl. Alternatively a compound of formula 5 may be prepared by reacting a compound of formula 2 (Y=Br) with ethynyltributylstannane in the presence of Pd(dppf)Cl$_2$ and copper iodide in a solvent such as dioxane between 50° C. and 150° C. for between 12 hours and 7 days, or until the reaction is complete under an inert atmosphere such as Argon. The resulting acetylene containing compound is subsequently reacted with azidotrimethylsilane in the presence of a catalyst such as copper iodide or a solvent such as a mixture of DMF and MeOH between 50° C. and 150° C. for between 8 and 24 hours or until the reaction is complete to give a 1,2,3-triazole after purification by standard means.

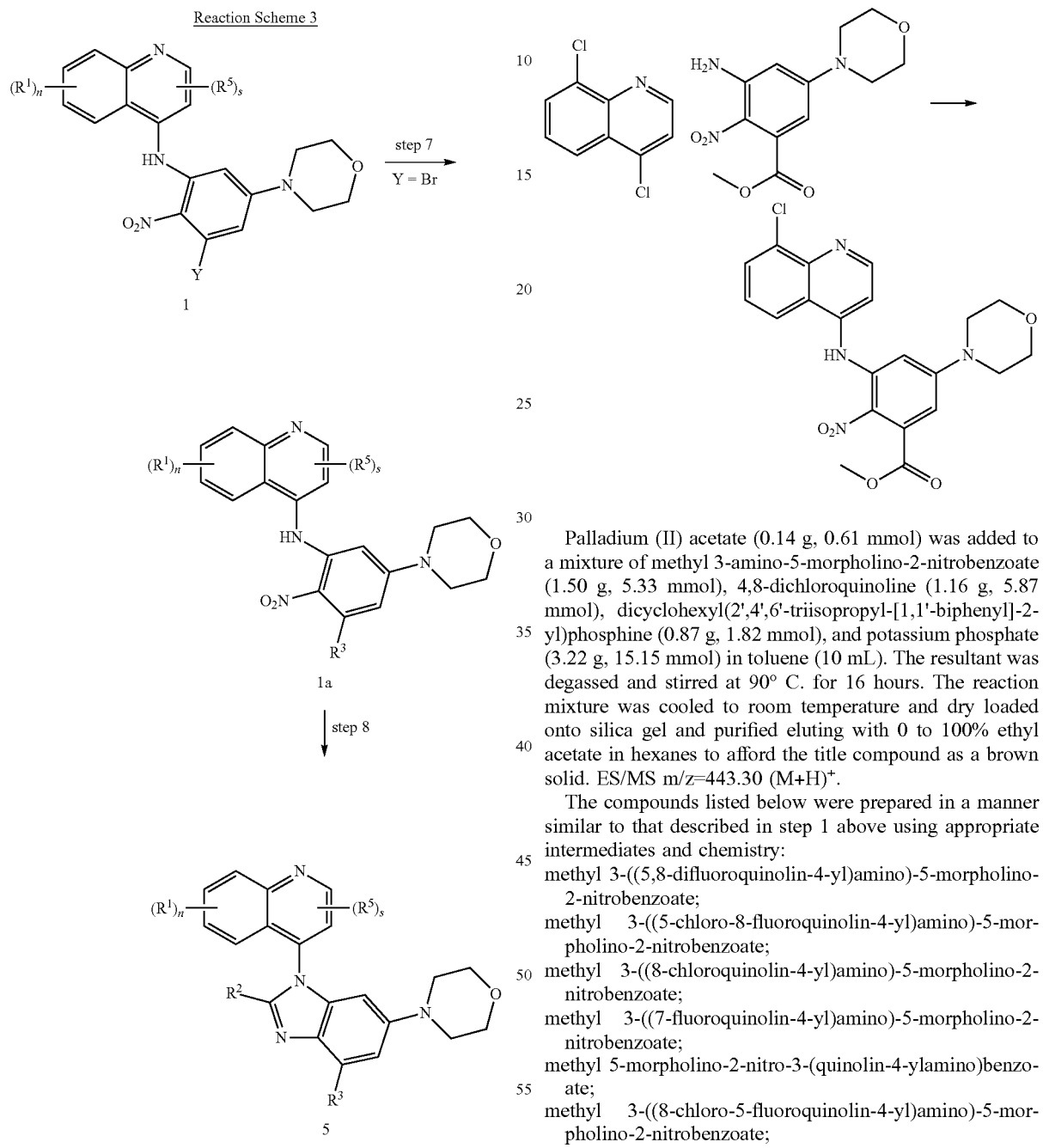

Step 7-Preparation of a Compound of Formula 1a

Compounds of formula 1a may be prepared by methods similar to that described in step 6 from compounds of formula 1 (Y=Br).

Step 8-Preparation of Compounds of Formula 5

Compounds of formula 5 may be prepared by methods similar to that described in step 2.

EXAMPLES

Step 1. Methyl 3-((8-chloroquinolin-4-yl)amino)-5-morpholino-2-nitrobenzoate

Palladium (II) acetate (0.14 g, 0.61 mmol) was added to a mixture of methyl 3-amino-5-morpholino-2-nitrobenzoate (1.50 g, 5.33 mmol), 4,8-dichloroquinoline (1.16 g, 5.87 mmol), dicyclohexyl(2',4',6'-triisopropyl-[1,1'-biphenyl]-2-yl)phosphine (0.87 g, 1.82 mmol), and potassium phosphate (3.22 g, 15.15 mmol) in toluene (10 mL). The resultant was degassed and stirred at 90° C. for 16 hours. The reaction mixture was cooled to room temperature and dry loaded onto silica gel and purified eluting with 0 to 100% ethyl acetate in hexanes to afford the title compound as a brown solid. ES/MS m/z=443.30 (M+H)$^+$.

The compounds listed below were prepared in a manner similar to that described in step 1 above using appropriate intermediates and chemistry:
methyl 3-((5,8-difluoroquinolin-4-yl)amino)-5-morpholino-2-nitrobenzoate;
methyl 3-((5-chloro-8-fluoroquinolin-4-yl)amino)-5-morpholino-2-nitrobenzoate;
methyl 3-((8-chloroquinolin-4-yl)amino)-5-morpholino-2-nitrobenzoate;
methyl 3-((7-fluoroquinolin-4-yl)amino)-5-morpholino-2-nitrobenzoate;
methyl 5-morpholino-2-nitro-3-(quinolin-4-ylamino)benzoate;
methyl 3-((8-chloro-5-fluoroquinolin-4-yl)amino)-5-morpholino-2-nitrobenzoate;
methyl 3-((8-chloro-6-fluoroquinolin-4-yl)amino)-5-morpholino-2-nitrobenzoate;
methyl 3-((8-chloro-7-fluoroquinolin-4-yl)amino)-5-morpholino-2-nitrobenzoate;
methyl 3-((5-fluoro-8-methylquinolin-4-yl)amino)-5-morpholino-2-nitrobenzoate;
methyl 3-((7,8-difluoroquinolin-4-yl)amino)-5-morpholino-2-nitrobenzoate;
methyl 3-((8-fluoroquinolin-4-yl)amino)-5-morpholino-2-nitrobenzoate;

methyl 3-((2-cyclopropyl-3-methylquinolin-4-yl)amino)-5-morpholino-2-nitrobenzoate;
methyl 3-((2-ethyl-3-methylquinolin-4-yl)amino)-5-morpholino-2-nitrobenzoate;
methyl 3-((8-chloro-2-(trifluoromethyl)quinolin-4-yl)amino)-5-morpholino-2-nitrobenzoate;
methyl 5-morpholino-2-nitro-3-((2-phenylquinolin-4-yl)amino)benzoate;
methyl 3-((2-methyl-8-(trifluoromethyl)quinolin-4-yl)amino)-5-morpholino-2-nitrobenzoate;
methyl 3-((3-ethyl-2-methylquinolin-4-yl)amino)-5-morpholino-2-nitrobenzoate;
methyl 3-((7-fluoro-2-methylquinolin-4-yl)amino)-5-morpholino-2-nitrobenzoate;
methyl 3-((8-fluoro-2,3-dimethylquinolin-4-yl)amino)-5-morpholino-2-nitrobenzoate;
methyl 3-((2-cyanoquinolin-4-yl)amino)-5-morpholino-2-nitrobenzoate;
methyl 3-((3-cyclopropylquinolin-4-yl)amino)-5-morpholino-2-nitrobenzoate;
methyl 3-((3-methylquinolin-4-yl)amino)-5-morpholino-2-nitrobenzoate;
methyl 3-((8-chloro-2-methylquinolin-4-yl)amino)-5-morpholino-2-nitrobenzoate;
methyl 3-((2-methylquinolin-4-yl)amino)-5-morpholino-2-nitrobenzoate;
methyl 3-((8-chloro-2,3-dimethylquinolin-4-yl)amino)-5-morpholino-2-nitrobenzoate;
methyl 3-((8-chloro-3-methylquinolin-4-yl)amino)-5-morpholino-2-nitrobenzoate;
methyl 3-((2-ethyl-8-fluoro-3-methylquinolin-4-yl)amino)-5-morpholino-2-nitrobenzoate;
methyl 3-((5-(difluoromethyl)quinolin-4-yl)amino)-5-morpholino-2-nitrobenzoate;
methyl 3-((5-chloroquinolin-4-yl)amino)-5-morpholino-2-nitrobenzoate;
methyl 3-((5-fluoroquinolin-4-yl)amino)-5-morpholino-2-nitrobenzoate;
methyl 3-((5-methylquinolin-4-yl)amino)-5-morpholino-2-nitrobenzoate;
methyl 3-((8-(difluoromethyl)quinolin-4-yl)amino)-5-morpholino-2-nitrobenzoate;
methyl 3-((7-fluoroquinolin-4-yl)amino)-5-morpholino-2-nitrobenzoate;
methyl 3-((8-chloro-2-(difluoromethyl)quinolin-4-yl)amino)-5-morpholino-2-nitrobenzoate;
methyl 3-((8-chloro-5-fluoroquinolin-4-yl)amino)-5-morpholino-2-nitrobenzoate;
methyl 3-((8-cyanoquinolin-4-yl)amino)-5-morpholino-2-nitrobenzoate;
methyl 3-((5,8-dichloroquinolin-4-yl)amino)-5-morpholino-2-nitrobenzoate;
methyl 5-morpholino-2-nitro-3-((2-(thiazol-4-yl)quinolin-4-yl)amino)benzoate;
methyl 3-((3-chloroquinolin-4-yl)amino)-5-morpholino-2-nitrobenzoate;
methyl 3-((5,7-difluoroquinolin-4-yl)amino)-5-morpholino-2-nitrobenzoate;
methyl 3-((6,8-difluoroquinolin-4-yl)amino)-5-morpholino-2-nitrobenzoate;
methyl 3-((3,8-dichloroquinolin-4-yl)amino)-5-morpholino-2-nitrobenzoate;
methyl 3-((3-chloro-8-fluoroquinolin-4-yl)amino)-5-morpholino-2-nitrobenzoate;
methyl 3-((8-methylquinolin-4-yl)amino)-5-morpholino-2-nitrobenzoate;
methyl 5-morpholino-2-nitro-3-((8-(trifluoromethyl)quinolin-4-yl)amino)benzoate;
tert-butyl 3-((8-chloroquinolin-4-yl)amino)-4-fluoro-5-morpholino-2-nitrobenzoate;
methyl (S)-3-((8-chloroquinolin-4-yl)amino)-5-(3-methylmorpholino)-2-nitrobenzoate;
methyl (R)-3-((8-chloroquinolin-4-yl)amino)-5-(3-methylmorpholino)-2-nitrobenzoate;
tert-butyl 3-((8-chloroquinolin-4-yl)amino)-6-fluoro-5-morpholino-2-nitrobenzoate;
8-chloro-N-(5-morpholino-2-nitro-3-(pyridin-3-yl)phenyl)quinolin-4-amine;
8-chloro-N-(5-morpholino-2-nitro-[1,1'-biphenyl]-3-yl)quinolin-4-amine;
methyl 5-morpholino-2-nitro-3-((2-(1-trityl-1H-pyrazol-4-yl)quinolin-4-yl)amino)benzoate;
tert-butyl 4-(4-((3-(methoxycarbonyl)-5-morpholino-2-nitrophenyl)amino)quinolin-2-yl)piperazine-1-carboxylate;
methyl 3-((3-fluoroquinolin-4-yl)amino)-5-morpholino-2-nitrobenzoate;
methyl 3-((8-chloro-5-fluoroquinolin-4-yl)amino)-4-fluoro-5-morpholino-2-nitrobenzoate;
methyl 3-((8-chloroquinolin-4-yl)amino)-4-fluoro-5-morpholino-2-nitrobenzoate;
methyl 3-((8-cyano-3-methylquinolin-4-yl)amino)-5-morpholino-2-nitrobenzoate;
tert-butyl 4-(4-((3-(methoxycarbonyl)-5-morpholino-2-nitrophenyl)amino)quinolin-2-yl)piperazine-1-carboxylate;
methyl 5-morpholino-2-nitro-3-((2-(1-trityl-1H-pyrazol-3-yl)quinolin-4-yl)amino)benzoate;
methyl 5-morpholino-2-nitro-3-((2-(1-trityl-1H-pyrazol-4-yl)quinolin-4-yl)amino)benzoate;
methyl 3-((3-cyanoquinolin-4-yl)amino)-5-morpholino-2-nitrobenzoate.

Step 1a: N-(3-bromo-5-morpholino-2-nitrophenyl)-8-fluoroquinolin-4-amine

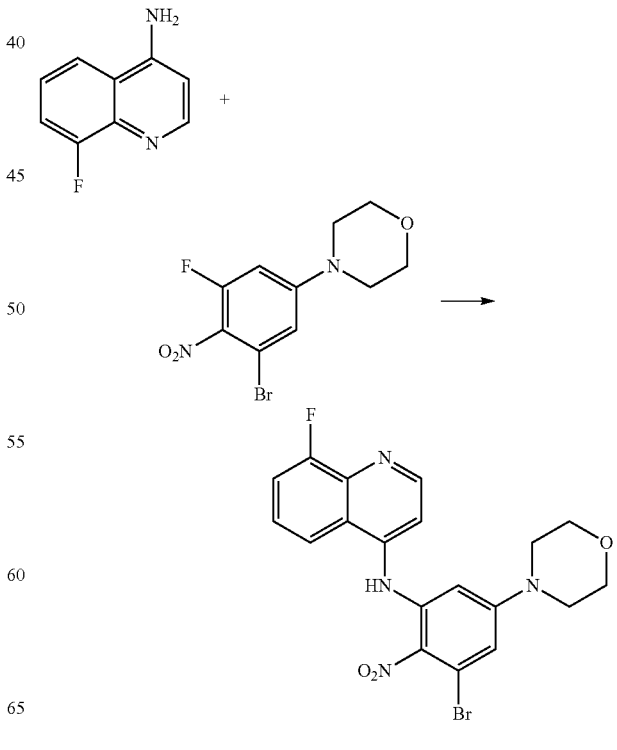

4-amino-8-fluoroquinoline (500 mg, 3.1 mmol), 4-(3-bromo-5-fluoro-4-nitrophenyl)morpholine (941 mg, 3.1 mmol), and cesium carbonate (2.2 g, 6.8 mmol) were combined in DMF (4 mL). The resulting mixture was heated to 90° C. After 18 hours the reaction was allowed to cool and poured into water. The resulting precipitate was washed with water, then methanol, and dried to afford N-(3-bromo-5-morpholino-2-nitrophenyl)-8-fluoroquinolin-4-amine. ES/MS m/z 447.07.

The compounds listed below were prepared in a manner similar to that described above using appropriate intermediates:
N-(3-bromo-5-morpholino-2-nitrophenyl)-5,8-difluoroquinolin-4-amine;
N-(3-bromo-5-morpholino-2-nitrophenyl)-8-chloroquinolin-4-amine;
N-(3-bromo-5-morpholino-2-nitrophenyl)-8-fluoro-2-methylquinolin-4-amine;
N-(3-bromo-5-morpholino-2-nitrophenyl)-8-chloro-6-fluoroquinolin-4-amine;
N-(3-bromo-5-morpholino-2-nitrophenyl)-8-chloro-7-fluoroquinolin-4-amine;
N-(3-bromo-5-morpholino-2-nitrophenyl)-8-chloro-5-fluoroquinolin-4-amine;
N-(3-bromo-5-morpholino-2-nitrophenyl)-7-fluoroquinolin-4-amine;
N-(3-bromo-5-morpholino-2-nitrophenyl)quinolin-4-amine;
N-(3-bromo-5-morpholino-2-nitrophenyl)-5-chloro-8-fluoroquinolin-4-amine.

Step 2. Methyl 1-(8-chloroquinolin-4-yl)-6-morpholino-2-propyl-1H-benzo[d]imidazole-4-carboxylate

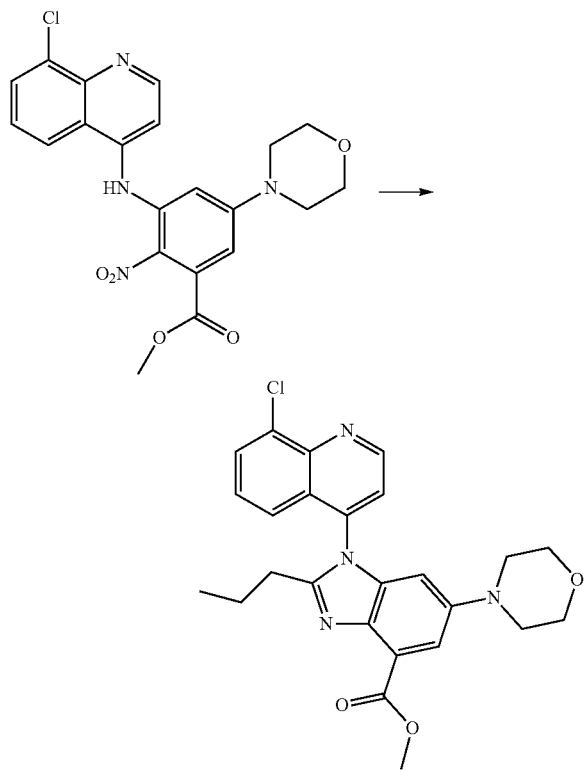 [SMILES: COC(=O)c1cc(N2CCOCC2)cc(Nc2ccnc3c(Cl)cccc23)c1[N+](=O)[O-] ; CCCc1nc2c(C(=O)OC)cc(N3CCOCC3)cc2n1-c1ccnc2c(Cl)cccc12]

Butyraldehyde (0.9 mL, 10.44 mmol) was added to a solution of methyl 3-((8-chloroquinolin-4-yl)amino)-5-morpholino-2-nitrobenzoate (600 mg, 1.36 mmol) and sodium dithionite (833 mg, 4.07 mmol) in ethanol (3 mL) and DMSO (3 mL). The reagents were stirred at 80° C. for 16 hours, after which time the reaction mixture was cooled to ambient temperature and partitioned between ethyl acetate (50 mL) and water (50 mL). The aqueous layer was extracted 3 times with ethyl acetate. The combined organic phases were dried with sodium sulfate and filtered. The resultant residue was purified on silica gel with 0 to 15% methanol in ethyl acetate to afford the title compound as an orange solid. ES/MS m/z=465.235 (M+H)$^+$.

The compounds listed below were prepared in a manner similar to that described above using appropriate intermediates:
methyl 1-(5,8-difluoroquinolin-4-yl)-6-morpholino-2-propyl-1H-benzo[d]imidazole-4-carboxylate;
methyl 1-(5-chloro-8-fluoroquinolin-4-yl)-2-ethyl-6-morpholino-1H-benzo[d]imidazole-4-carboxylate;
methyl 1-(8-chloroquinolin-4-yl)-2-(1-methylcyclopropyl)-6-morpholino-1H-benzo[d]imidazole-4-carboxylate;
methyl 1-(8-chloroquinolin-4-yl)-2-isobutyl-6-morpholino-1H-benzo[d]imidazole-4-carboxylate;
methyl 1-(7-fluoroquinolin-4-yl)-6-morpholino-2-propyl-1H-benzo[d]imidazole-4-carboxylate;
methyl 1-(8-chloroquinolin-4-yl)-2-(cyclopropylmethyl)-6-morpholino-1H-benzo[d]imidazole-4-carboxylate;
methyl 1-(8-chloroquinolin-4-yl)-6-morpholino-2-(tetrahydrofuran-3-yl)-1H-benzo[d]imidazole-4-carboxylate;
methyl 6-morpholino-2-(pyridin-2-yl)-1-(quinolin-4-yl)-1H-benzo[d]imidazole-4-carboxylate;
methyl 1-(8-chloro-5-fluoroquinolin-4-yl)-6-morpholino-2-propyl-1H-benzo[d]imidazole-4-carboxylate;
methyl 1-(8-chloroquinolin-4-yl)-2-(1-methoxyethyl)-6-morpholino-1H-benzo[d]imidazole-4-carboxylate;
methyl 1-(8-chloroquinolin-4-yl)-2-cyclobutyl-6-morpholino-1H-benzo[d]imidazole-4-carboxylate;
methyl 1-(8-chloroquinolin-4-yl)-6-morpholino-2-(pyridin-3-yl)-1H-benzo[d]imidazole-4-carboxylate;
methyl 1-(8-chloroquinolin-4-yl)-2-isopropyl-6-morpholino-1H-benzo[d]imidazole-4-carboxylate;
methyl 1-(8-chloroquinolin-4-yl)-6-morpholino-2-(pyridin-4-yl)-1H-benzo[d]imidazole-4-carboxylate;
methyl 1-(8-chloroquinolin-4-yl)-6-morpholino-2-(tetrahydrofuran-2-yl)-1H-benzo[d]imidazole-4-carboxylate;
methyl 2-cyclopropyl-6-morpholino-1-(quinolin-4-yl)-1H-benzo[d]imidazole-4-carboxylate;
methyl 1-(7-fluoroquinolin-4-yl)-6-morpholino-1H-benzo[d]imidazole-4-carboxylate;
methyl 1-(8-chloro-6-fluoroquinolin-4-yl)-2-methyl-6-morpholino-1H-benzo[d]imidazole-4-carboxylate;
methyl 2-(tert-butyl)-1-(8-chloroquinolin-4-yl)-6-morpholino-1H-benzo[d]imidazole-4-carboxylate;
methyl 2-methyl-6-morpholino-1-(quinolin-4-yl)-1H-benzo[d]imidazole-4-carboxylate;
methyl (S)-1-(5,8-difluoroquinolin-4-yl)-2-methyl-6-morpholino-1H-benzo[d]imidazole-4-carboxylate;
methyl 1-(5,8-difluoroquinolin-4-yl)-6-morpholino-1H-benzo[d]imidazole-4-carboxylate;
methyl 1-(8-chloro-7-fluoroquinolin-4-yl)-6-morpholino-1H-benzo[d]imidazole-4-carboxylate;
methyl 6-morpholino-2-(oxetan-3-yl)-1-(quinolin-4-yl)-1H-benzo[d]imidazole-4-carboxylate;
methyl 1-(5-fluoro-8-methylquinolin-4-yl)-6-morpholino-2-propyl-1H-benzo[d]imidazole-4-carboxylate;

methyl 1-(8-chloro-6-fluoroquinolin-4-yl)-6-morpholino-2-propyl-1H-benzo[d]imidazole-4-carboxylate;
methyl 1-(8-chloro-7-fluoroquinolin-4-yl)-2-(cyclopropylmethyl)-6-morpholino-1H-benzo[d]imidazole-4-carboxylate;
methyl 1-(8-chloro-7-fluoroquinolin-4-yl)-6-morpholino-2-propyl-1H-benzo[d]imidazole-4-carboxylate;
methyl 1-(8-chloro-7-fluoroquinolin-4-yl)-2-cyclopropyl-6-morpholino-1H-benzo[d]imidazole-4-carboxylate;
methyl 1-(8-chloro-7-fluoroquinolin-4-yl)-2-methyl-6-morpholino-1H-benzo[d]imidazole-4-carboxylate;
methyl 1-(8-chloro-7-fluoroquinolin-4-yl)-6-morpholino-1H-benzo[d]imidazole-4-carboxylate;
methyl 6-morpholino-2-propyl-1-(quinolin-4-yl)-1H-benzo[d]imidazole-4-carboxylate;
methyl 1-(5,8-difluoroquinolin-4-yl)-6-morpholino-1H-benzo[d]imidazole-4-carboxylate;
methyl 1-(7,8-difluoroquinolin-4-yl)-6-morpholino-2-propyl-1H-benzo[d]imidazole-4-carboxylate;
methyl 1-(8-chloroquinolin-4-yl)-2-cyclopropyl-6-morpholino-1H-benzo[d]imidazole-4-carboxylate;
methyl 1-(8-fluoroquinolin-4-yl)-2-(2-methoxyethyl)-6-morpholino-1H-benzo[d]imidazole-4-carboxylate;
methyl 1-(7,8-difluoroquinolin-4-yl)-6-morpholino-2-propyl-1H-benzo[d]imidazole-4-carboxylate;
methyl 1-(7-fluoroquinolin-4-yl)-6-morpholino-1H-benzo[d]imidazole-4-carboxylate;
methyl 1-(8-chloroquinolin-4-yl)-2-(1-fluorocyclopropyl)-6-morpholino-1H-benzo[d]imidazole-4-carboxylate;
methyl 1-(2-cyclopropyl-3-methylquinolin-4-yl)-2-methyl-6-morpholino-1H-benzo[d]imidazole-4-carboxylate;
methyl 1-(2-ethyl-3-methylquinolin-4-yl)-2-methyl-6-morpholino-1H-benzo[d]imidazole-4-carboxylate;
methyl 1-(8-chloro-2-(trifluoromethyl)quinolin-4-yl)-2-methyl-6-morpholino-1H-benzo[d]imidazole-4-carboxylate;
methyl 2-methyl-6-morpholino-1-(2-phenylquinolin-4-yl)-1H-benzo[d]imidazole-4-carboxylate;
methyl 1-(3-ethyl-2-methylquinolin-4-yl)-2-methyl-6-morpholino-1H-benzo[d]imidazole-4-carboxylate;
methyl 1-(7-fluoro-2-methylquinolin-4-yl)-2-methyl-6-morpholino-1H-benzo[d]imidazole-4-carboxylate;
methyl 1-(8-fluoro-2,3-dimethylquinolin-4-yl)-2-methyl-6-morpholino-1H-benzo[d]imidazole-4-carboxylate;
methyl 2-methyl-1-(2-methyl-8-(trifluoromethyl)quinolin-4-yl)-6-morpholino-1H-benzo[d]imidazole-4-carboxylate;
methyl 1-(2-cyanoquinolin-4-yl)-2-methyl-6-morpholino-1H-benzo[d]imidazole-4-carboxylate;
methyl 1-(3-cyclopropylquinolin-4-yl)-2-methyl-6-morpholino-1H-benzo[d]imidazole-4-carboxylate;
methyl 1-(8-chloro-2-methylquinolin-4-yl)-2-methyl-6-morpholino-1H-benzo[d]imidazole-4-carboxylate;
methyl 2-methyl-1-(3-methylquinolin-4-yl)-6-morpholino-1H-benzo[d]imidazole-4-carboxylate;
methyl 1-(2-ethyl-3-methylquinolin-4-yl)-6-morpholino-1H-benzo[d]imidazole-4-carboxylate;
methyl 1-(3-ethyl-2-methylquinolin-4-yl)-6-morpholino-1H-benzo[d]imidazole-4-carboxylate;
methyl 1-(8-chloro-2,3-dimethylquinolin-4-yl)-2-methyl-6-morpholino-1H-benzo[d]imidazole-4-carboxylate;
methyl 1-(8-chloro-3-methylquinolin-4-yl)-2-methyl-6-morpholino-1H-benzo[d]imidazole-4-carboxylate;
methyl 2-methyl-1-(2-methylquinolin-4-yl)-6-morpholino-1H-benzo[d]imidazole-4-carboxylate;
methyl 1-(2-ethyl-8-fluoro-3-methylquinolin-4-yl)-2-methyl-6-morpholino-1H-benzo[d]imidazole-4-carboxylate;
methyl 1-(5-(difluoromethyl)quinolin-4-yl)-2-methyl-6-morpholino-1H-benzo[d]imidazole-4-carboxylate;
methyl 1-(5-chloroquinolin-4-yl)-2-methyl-6-morpholino-1H-benzo[d]imidazole-4-carboxylate;
methyl 1-(5-fluoroquinolin-4-yl)-2-methyl-6-morpholino-1H-benzo[d]imidazole-4-carboxylate;
methyl 1-(8-(difluoromethyl)quinolin-4-yl)-2-methyl-6-morpholino-1H-benzo[d]imidazole-4-carboxylate;
methyl 2-methyl-1-(5-methylquinolin-4-yl)-6-morpholino-1H-benzo[d]imidazole-4-carboxylate;
methyl 1-(7-fluoroquinolin-4-yl)-2-methyl-6-morpholino-1H-benzo[d]imidazole-4-carboxylate;
methyl 1-(8-chloro-2-(difluoromethyl)quinolin-4-yl)-6-morpholino-1H-benzo[d]imidazole-4-carboxylate;
methyl 1-(8-chloro-5-fluoroquinolin-4-yl)-2-methyl-6-morpholino-1H-benzo[d]imidazole-4-carboxylate;
methyl 1-(8-cyanoquinolin-4-yl)-2-methyl-6-morpholino-1H-benzo[d]imidazole-4-carboxylate;
methyl 1-(5,8-dichloroquinolin-4-yl)-2-methyl-6-morpholino-1H-benzo[d]imidazole-4-carboxylate;
methyl 1-(5,8-difluoroquinolin-4-yl)-2-ethyl-6-morpholino-1H-benzo[d]imidazole-4-carboxylate;
methyl 1-(5,8-difluoroquinolin-4-yl)-6-morpholino-2-(oxetan-3-yl)-1H-benzo[d]imidazole-4-carboxylate;
methyl 1-(5-chloro-8-fluoroquinolin-4-yl)-2-methyl-6-morpholino-1H-benzo[d]imidazole-4-carboxylate;
methyl 1-(5-fluoro-8-methylquinolin-4-yl)-2-methyl-6-morpholino-1H-benzo[d]imidazole-4-carboxylate;
methyl 2-methyl-6-morpholino-1-(2-(thiazol-4-yl)quinolin-4-yl)-1H-benzo[d]imidazole-4-carboxylate;
methyl 1-(3-chloroquinolin-4-yl)-2-methyl-6-morpholino-1H-benzo[d]imidazole-4-carboxylate;
methyl 1-(5,7-difluoroquinolin-4-yl)-2-methyl-6-morpholino-1H-benzo[d]imidazole-4-carboxylate;
methyl 1-(5-methylquinolin-4-yl)-6-morpholino-1H-benzo[d]imidazole-4-carboxylate;
methyl 1-(8-chloroquinolin-4-yl)-2-ethyl-6-morpholino-1H-benzo[d]imidazole-4-carboxylate;
methyl 1-(8-chloroquinolin-4-yl)-6-morpholino-1H-benzo[d]imidazole-4-carboxylate;
methyl 1-(8-fluoroquinolin-4-yl)-2-methyl-6-morpholino-1H-benzo[d]imidazole-4-carboxylate;
methyl 1-(6,8-difluoroquinolin-4-yl)-2-methyl-6-morpholino-1H-benzo[d]imidazole-4-carboxylate;
methyl 1-(7,8-difluoroquinolin-4-yl)-2-methyl-6-morpholino-1H-benzo[d]imidazole-4-carboxylate;
methyl 1-(8-fluoroquinolin-4-yl)-6-morpholino-2-propyl-1H-benzo[d]imidazole-4-carboxylate;
methyl 2-cyclopropyl-1-(7,8-difluoroquinolin-4-yl)-6-morpholino-1H-benzo[d]imidazole-4-carboxylate;
methyl 2-cyclopropyl-1-(8-fluoroquinolin-4-yl)-6-morpholino-1H-benzo[d]imidazole-4-carboxylate;
methyl 2-ethyl-1-(8-fluoroquinolin-4-yl)-6-morpholino-1H-benzo[d]imidazole-4-carboxylate;
methyl 1-(3,8-dichloroquinolin-4-yl)-2-ethyl-6-morpholino-1H-benzo[d]imidazole-4-carboxylate;
methyl 1-(3,8-dichloroquinolin-4-yl)-2-methyl-6-morpholino-1H-benzo[d]imidazole-4-carboxylate;
methyl 1-(3-chloro-8-fluoroquinolin-4-yl)-2-methyl-6-morpholino-1H-benzo[d]imidazole-4-carboxylate;
methyl 1-(5-chloro-8-fluoroquinolin-4-yl)-6-morpholino-1H-benzo[d]imidazole-4-carboxylate;
methyl 1-(6,8-difluoroquinolin-4-yl)-6-morpholino-2-propyl-1H-benzo[d]imidazole-4-carboxylate;

methyl 1-(8-fluoroquinolin-4-yl)-6-morpholino-1H-benzo[d]imidazole-4-carboxylate;
methyl 1-(8-chloroquinolin-4-yl)-2-cyclopropyl-6-morpholino-1H-benzo[d]imidazole-4-carboxylate;
methyl 1-(8-chloroquinolin-4-yl)-6-morpholino-1H-benzo[d]imidazole-4-carboxylate;
methyl 2-ethyl-6-morpholino-1-(quinolin-4-yl)-1H-benzo[d]imidazole-4-carboxylate;
methyl 2-methyl-1-(8-methylquinolin-4-yl)-6-morpholino-1H-benzo[d]imidazole-4-carboxylate;
methyl 2-methyl-6-morpholino-1-(8-(trifluoromethyl)quinolin-4-yl)-1H-benzo[d]imidazole-4-carboxylate;
methyl 2-methyl-6-morpholino-1-(quinolin-4-yl)-1H-benzo[d]imidazole-4-carboxylate;
methyl 1-(5,8-difluoroquinolin-4-yl)-2-methyl-6-morpholino-1H-benzo[d]imidazole-4-carboxylate;
methyl 1-(8-chloroquinolin-4-yl)-2-(2-methoxyethyl)-6-morpholino-1H-benzo[d]imidazole-4-carboxylate;
methyl 1-(8-chloroquinolin-4-yl)-6-morpholino-2-(oxazol-5-yl)-1H-benzo[d]imidazole-4-carboxylate;
methyl 1-(8-chloroquinolin-4-yl)-6-morpholino-2-(pyridin-2-yl)-1H-benzo[d]imidazole-4-carboxylate;
methyl 1-(8-chloroquinolin-4-yl)-6-morpholino-2-(thiazol-5-yl)-1H-benzo[d]imidazole-4-carboxylate;
methyl 1-(8-chloroquinolin-4-yl)-6-morpholino-2-(oxetan-3-yl)-1H-benzo[d]imidazole-4-carboxylate;
4-(4-bromo-1-(8-fluoroquinolin-4-yl)-2-methyl-1H-benzo[d]imidazol-6-yl)morpholine (ES/MS m/z 443.1);
4-(4-bromo-1-(5,8-difluoroquinolin-4-yl)-2-ethyl-1H-benzo[d]imidazol-6-yl)morpholine;
4-(4-bromo-1-(8-chloroquinolin-4-yl)-2-methyl-1H-benzo[d]imidazol-6-yl)morpholine;
4-(4-bromo-1-(8-chloroquinolin-4-yl)-2-propyl-1H-benzo[d]imidazol-6-yl)morpholine;
4-(4-bromo-1-(8-fluoro-2-methylquinolin-4-yl)-2-methyl-1H-benzo[d]imidazol-6-yl)morpholine;
4-(4-bromo-2-ethyl-1-(8-fluoro-2-methylquinolin-4-yl)-1H-benzo[d]imidazol-6-yl)morpholine;
4-(4-bromo-2-ethyl-1-(8-fluoroquinolin-4-yl)-1H-benzo[d]imidazol-6-yl)morpholine;
4-(4-bromo-1-(5,8-difluoroquinolin-4-yl)-2-isobutyl-1H-benzo[d]imidazol-6-yl)morpholine;
4-(4-bromo-1-(8-chloro-6-fluoroquinolin-4-yl)-2-propyl-1H-benzo[d]imidazol-6-yl)morpholine;
4-(4-bromo-1-(8-chloro-7-fluoroquinolin-4-yl)-2-ethyl-1H-benzo[d]imidazol-6-yl)morpholine;
4-(4-bromo-1-(8-chloroquinolin-4-yl)-2-(cyclopropylmethyl)-1H-benzo[d]imidazol-6-yl)morpholine;
4-(4-bromo-2-(cyclopropylmethyl)-1-(5,8-difluoroquinolin-4-yl)-1H-benzo[d]imidazol-6-yl)morpholine;
4-(4-bromo-2-cyclopropyl-1-(8-fluoroquinolin-4-yl)-1H-benzo[d]imidazol-6-yl)morpholine;
4-(4-bromo-1-(5,8-difluoroquinolin-4-yl)-2-methyl-1H-benzo[d]imidazol-6-yl)morpholine;
4-(4-bromo-1-(5,8-difluoroquinolin-4-yl)-2-propyl-1H-benzo[d]imidazol-6-yl)morpholine;
4-(4-bromo-1-(8-chloroquinolin-4-yl)-1H-benzo[d]imidazol-6-yl)morpholine;
4-(4-bromo-1-(8-chloroquinolin-4-yl)-2-cyclopropyl-1H-benzo[d]imidazol-6-yl)morpholine;
4-(4-bromo-1-(8-chloroquinolin-4-yl)-2-ethyl-1H-benzo[d]imidazol-6-yl)morpholine;
4-(4-bromo-1-(8-fluoroquinolin-4-yl)-2-propyl-1H-benzo[d]imidazol-6-yl)morpholine;
4-(4-bromo-1-(8-chloro-5-fluoroquinolin-4-yl)-2-cyclopropyl-1H-benzo[d]imidazol-6-yl)morpholine;
4-(4-bromo-1-(8-chloro-5-fluoroquinolin-4-yl)-2-methyl-1H-benzo[d]imidazol-6-yl)morpholine;
4-(4-bromo-2-cyclopropyl-1-(5,8-difluoroquinolin-4-yl)-1H-benzo[d]imidazol-6-yl)morpholine;
4-(4-bromo-1-(7-fluoroquinolin-4-yl)-2-methyl-1H-benzo[d]imidazol-6-yl)morpholine;
4-(4-bromo-1-(8-chloro-6-fluoroquinolin-4-yl)-2-propyl-1H-benzo[d]imidazol-6-yl)morpholine;
4-(4-bromo-1-(8-chloroquinolin-4-yl)-2-(oxetan-3-yl)-1H-benzo[d]imidazol-6-yl)morpholine;
4-(4-bromo-1-(8-fluoroquinolin-4-yl)-1H-benzo[d]imidazol-6-yl)morpholine;
4-(4-bromo-2-(cyclopropylmethyl)-1-(8-fluoroquinolin-4-yl)-1H-benzo[d]imidazol-6-yl)morpholine;
4-(4-bromo-2-methyl-1-(quinolin-4-yl)-1H-benzo[d]imidazol-6-yl)morpholine;
4-(4-bromo-1-(5,8-difluoroquinolin-4-yl)-1H-benzo[d]imidazol-6-yl)morpholine;
4-(4-bromo-1-(5-chloro-8-fluoroquinolin-4-yl)-2-ethyl-1H-benzo[d]imidazol-6-yl)morpholine;
4-(4-bromo-1-(5-chloro-8-fluoroquinolin-4-yl)-2-methyl-1H-benzo[d]imidazol-6-yl)morpholine;
4-(4-bromo-1-(8-chloro-7-fluoroquinolin-4-yl)-2-cyclopropyl-1H-benzo[d]imidazol-6-yl)morpholine;
4-(4-bromo-1-(8-chloro-7-fluoroquinolin-4-yl)-2-methyl-1H-benzo[d]imidazol-6-yl)morpholine;
tert-butyl 1-(8-chloroquinolin-4-yl)-7-fluoro-2-methyl-6-morpholino-1H-benzo[d]imidazole-4-carboxylate;
methyl (S)-1-(8-chloroquinolin-4-yl)-2-methyl-6-(3-methylmorpholino)-1H-benzo[d]imidazole-4-carboxylate;
methyl (R)-1-(8-chloroquinolin-4-yl)-2-methyl-6-(3-methylmorpholino)-1H-benzo[d]imidazole-4-carboxylate;
methyl 1-(8-chloroquinolin-4-yl)-6-morpholino-2-(1H-pyrazol-5-yl)-1H-benzo[d]imidazole-4-carboxylate;
methyl 1-(8-chloroquinolin-4-yl)-2-(isothiazol-4-yl)-6-morpholino-1H-benzo[d]imidazole-4-carboxylate;
methyl 1-(8-chloroquinolin-4-yl)-6-morpholino-2-(1H-pyrazol-4-yl)-1H-benzo[d]imidazole-4-carboxylate;
tert-butyl 1-(8-chloroquinolin-4-yl)-5-fluoro-2-methyl-6-morpholino-1H-benzo[d]imidazole-4-carboxylate;
methyl 2-methyl-6-morpholino-1-(2-(1-trityl-1H-pyrazol-4-yl)quinolin-4-yl)-1H-benzo[d]imidazole-4-carboxylate;
methyl 1-(2-(4-(tert-butoxycarbonyl)piperazin-1-yl)quinolin-4-yl)-2-methyl-6-morpholino-1H-benzo[d]imidazole-4-carboxylate;
methyl 1-(3-fluoroquinolin-4-yl)-2-methyl-6-morpholino-1H-benzo[d]imidazole-4-carboxylate;
methyl 1-(8-chloro-5-fluoroquinolin-4-yl)-7-fluoro-2-methyl-6-morpholino-1H-benzo[d]imidazole-4-carboxylate;
methyl 1-(8-chloroquinolin-4-yl)-7-fluoro-6-morpholino-1H-benzo[d]imidazole-4-carboxylate;
methyl 1-(8-cyano-3-methylquinolin-4-yl)-2-ethyl-6-morpholino-1H-benzo[d]imidazole-4-carboxylate;
methyl 1-(8-cyano-3-methylquinolin-4-yl)-2-methyl-6-morpholino-1H-benzo[d]imidazole-4-carboxylate
methyl 1-(2-(4-(tert-butoxycarbonyl)piperazin-1-yl)quinolin-4-yl)-6-morpholino-1H-benzo[d]imidazole-4-carboxylate;
methyl 6-morpholino-1-(2-(1-trityl-1H-pyrazol-4-yl)quinolin-4-yl)-1H-benzo[d]imidazole-4-carboxylate;
methyl 6-morpholino-1-(2-(1-trityl-1H-pyrazol-3-yl)quinolin-4-yl)-1H-benzo[d]imidazole-4-carboxylate;
methyl 1-(3-cyanoquinolin-4-yl)-2-ethyl-6-morpholino-1H-benzo[d]imidazole-4-carboxylate;
methyl 1-(3-cyanoquinolin-4-yl)-2-methyl-6-morpholino-1H-benzo[d]imidazole-4-carboxylate;

Step 3: 1-(8-Chloroquinolin-4-yl)-6-morpholino-2-propyl-1H-benzo[d]imidazole-4-carboxylic acid

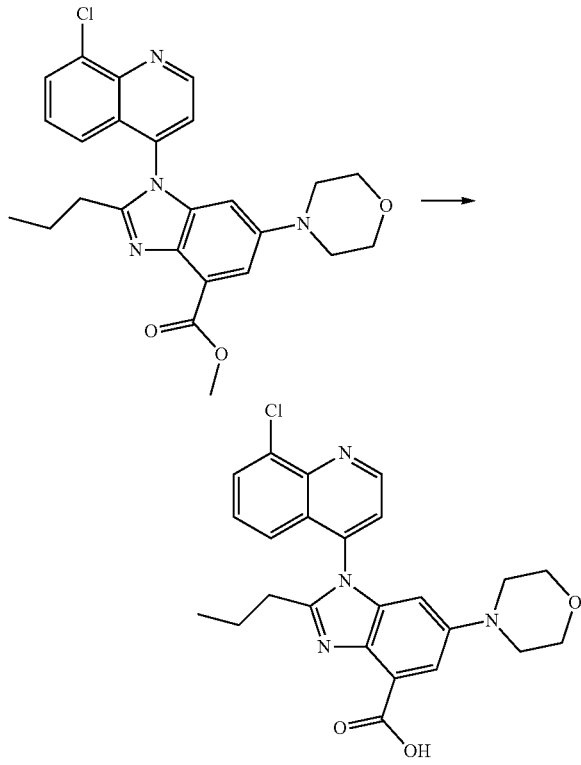

Aqueous lithium hydroxide (1M, 3.8 mL) was added to methyl 1-(8-chloroquinolin-4-yl)-6-morpholino-2-propyl-1H-benzo[d]imidazole-4-carboxylate (443 mg, 0.95 mmol) in THF (2 mL). The reaction was stirred at ambient temperature for 16 hours. The reaction mixture was acidified to pH 6 with the addition of 6M HCl. The resultant solution was concentrated in vacuuo to afford the title compound. ES/MS m/z 451.40 (M+H)+.

The compounds listed below were prepared in a manner similar to that described above using appropriate intermediates:

1-(5,8-difluoroquinolin-4-yl)-6-morpholino-2-propyl-1H-benzo[d]imidazole-4-carboxylic acid;
1-(5-chloro-8-fluoroquinolin-4-yl)-2-ethyl-6-morpholino-1H-benzo[d]imidazole-4-carboxylic acid;
1-(8-chloroquinolin-4-yl)-2-(1-methylcyclopropyl)-6-morpholino-1H-benzo[d]imidazole-4-carboxylic acid;
1-(8-chloroquinolin-4-yl)-2-isobutyl-6-morpholino-1H-benzo[d]imidazole-4-carboxylic acid;
1-(7-fluoroquinolin-4-yl)-6-morpholino-2-propyl-1H-benzo[d]imidazole-4-carboxylic acid;
1-(8-chloroquinolin-4-yl)-2-(cyclopropylmethyl)-6-morpholino-1H-benzo[d]imidazole-4-carboxylic acid;
1-(8-chloroquinolin-4-yl)-6-morpholino-2-(tetrahydrofuran-3-yl)-1H-benzo[d]imidazole-4-carboxylic acid;
6-morpholino-2-(pyridin-2-yl)-1-(quinolin-4-yl)-1H-benzo[d]imidazole-4-carboxylic acid;
1-(8-chloro-5-fluoroquinolin-4-yl)-6-morpholino-2-propyl-1H-benzo[d]imidazole-4-carboxylic acid;
1-(8-chloroquinolin-4-yl)-2-(1-methoxyethyl)-6-morpholino-1H-benzo[d]imidazole-4-carboxylic acid;
1-(8-chloroquinolin-4-yl)-2-cyclobutyl-6-morpholino-1H-benzo[d]imidazole-4-carboxylic acid;
1-(8-chloroquinolin-4-yl)-6-morpholino-2-(pyridin-3-yl)-1H-benzo[d]imidazole-4-carboxylic acid;
1-(8-chloroquinolin-4-yl)-2-isopropyl-6-morpholino-1H-benzo[d]imidazole-4-carboxylic acid;
1-(8-chloroquinolin-4-yl)-6-morpholino-2-(pyridin-4-yl)-1H-benzo[d]imidazole-4-carboxylic acid;
1-(8-chloroquinolin-4-yl)-6-morpholino-2-(tetrahydrofuran-2-yl)-1H-benzo[d]imidazole-4-carboxylic acid;
2-cyclopropyl-6-morpholino-1-(quinolin-4-yl)-1H-benzo[d]imidazole-4-carboxylic acid;
1-(7-fluoroquinolin-4-yl)-6-morpholino-1H-benzo[d]imidazole-4-carboxylic acid;
1-(8-chloro-6-fluoroquinolin-4-yl)-2-methyl-6-morpholino-1H-benzo[d]imidazole-4-carboxylic acid;
2-(tert-butyl)-1-(8-chloroquinolin-4-yl)-6-morpholino-1H-benzo[d]imidazole-4-carboxylic acid;
2-methyl-6-morpholino-1-(quinolin-4-yl)-1H-benzo[d]imidazole-4-carboxylic acid;
(S)-1-(5,8-difluoroquinolin-4-yl)-2-methyl-6-morpholino-1H-benzo[d]imidazole-4-carboxylic acid;
1-(5,8-difluoroquinolin-4-yl)-6-morpholino-1H-benzo[d]imidazole-4-carboxylic acid;
1-(8-chloro-7-fluoroquinolin-4-yl)-6-morpholino-1H-benzo[d]imidazole-4-carboxylic acid;
6-morpholino-2-(oxetan-3-yl)-1-(quinolin-4-yl)-1H-benzo[d]imidazole-4-carboxylic acid;
1-(5-fluoro-8-methylquinolin-4-yl)-6-morpholino-2-propyl-1H-benzo[d]imidazole-4-carboxylic acid;
1-(8-chloro-6-fluoroquinolin-4-yl)-6-morpholino-2-propyl-1H-benzo[d]imidazole-4-carboxylic acid;
1-(8-chloro-7-fluoroquinolin-4-yl)-2-(cyclopropylmethyl)-6-morpholino-1H-benzo[d]imidazole-4-carboxylic acid;
1-(8-chloro-7-fluoroquinolin-4-yl)-6-morpholino-2-propyl-1H-benzo[d]imidazole-4-carboxylic acid;
1-(8-chloro-7-fluoroquinolin-4-yl)-2-cyclopropyl-6-morpholino-1H-benzo[d]imidazole-4-carboxylic acid;
1-(8-chloro-7-fluoroquinolin-4-yl)-2-methyl-6-morpholino-1H-benzo[d]imidazole-4-carboxylic acid;
1-(8-chloro-7-fluoroquinolin-4-yl)-6-morpholino-1H-benzo[d]imidazole-4-carboxylic acid;
6-morpholino-2-propyl-1-(quinolin-4-yl)-1H-benzo[d]imidazole-4-carboxylic acid;
1-(5,8-difluoroquinolin-4-yl)-6-morpholino-1H-benzo[d]imidazole-4-carboxylic acid;
1-(7,8-difluoroquinolin-4-yl)-6-morpholino-2-propyl-1H-benzo[d]imidazole-4-carboxylic acid;
1-(8-chloroquinolin-4-yl)-2-cyclopropyl-6-morpholino-1H-benzo[d]imidazole-4-carboxylic acid;
1-(8-fluoroquinolin-4-yl)-2-(2-methoxyethyl)-6-morpholino-1H-benzo[d]imidazole-4-carboxylic acid;
1-(7,8-difluoroquinolin-4-yl)-6-morpholino-2-propyl-1H-benzo[d]imidazole-4-carboxylic acid;
1-(7-fluoroquinolin-4-yl)-6-morpholino-1H-benzo[d]imidazole-4-carboxylic acid;
1-(8-chloroquinolin-4-yl)-2-(1-fluorocyclopropyl)-6-morpholino-1H-benzo[d]imidazole-4-carboxylic acid;
1-(2-cyclopropyl-3-methylquinolin-4-yl)-2-methyl-6-morpholino-1H-benzo[d]imidazole-4-carboxylic acid;
1-(2-ethyl-3-methylquinolin-4-yl)-2-methyl-6-morpholino-1H-benzo[d]imidazole-4-carboxylic acid;
1-(8-chloro-2-(trifluoromethyl)quinolin-4-yl)-2-methyl-6-morpholino-1H-benzo[d]imidazole-4-carboxylic acid;
2-methyl-6-morpholino-1-(2-phenylquinolin-4-yl)-1H-benzo[d]imidazole-4-carboxylic acid;

1-(3-ethyl-2-methylquinolin-4-yl)-2-methyl-6-morpholino-1H-benzo[d]imidazole-4-carboxylic acid;
1-(7-fluoro-2-methylquinolin-4-yl)-2-methyl-6-morpholino-1H-benzo[d]imidazole-4-carboxylic acid;
1-(8-fluoro-2,3-dimethylquinolin-4-yl)-2-methyl-6-morpholino-1H-benzo[d]imidazole-4-carboxylic acid;
2-methyl-1-(2-methyl-8-(trifluoromethyl)quinolin-4-yl)-6-morpholino-1H-benzo[d]imidazole-4-carboxylic acid;
1-(2-cyanoquinolin-4-yl)-2-methyl-6-morpholino-1H-benzo[d]imidazole-4-carboxylic acid;
1-(3-cyclopropylquinolin-4-yl)-2-methyl-6-morpholino-1H-benzo[d]imidazole-4-carboxylic acid;
1-(8-chloro-2-methylquinolin-4-yl)-2-methyl-6-morpholino-1H-benzo[d]imidazole-4-carboxylic acid;
2-methyl-1-(3-methylquinolin-4-yl)-6-morpholino-1H-benzo[d]imidazole-4-carboxylic acid;
1-(2-ethyl-3-methylquinolin-4-yl)-6-morpholino-1H-benzo[d]imidazole-4-carboxylic acid;
1-(3-ethyl-2-methylquinolin-4-yl)-6-morpholino-1H-benzo[d]imidazole-4-carboxylic acid;
1-(8-chloro-2,3-dimethylquinolin-4-yl)-2-methyl-6-morpholino-1H-benzo[d]imidazole-4-carboxylic acid;
1-(8-chloro-3-methylquinolin-4-yl)-2-methyl-6-morpholino-1H-benzo[d]imidazole-4-carboxylic acid;
2-methyl-1-(2-methylquinolin-4-yl)-6-morpholino-1H-benzo[d]imidazole-4-carboxylic acid;
1-(2-ethyl-8-fluoro-3-methylquinolin-4-yl)-2-methyl-6-morpholino-1H-benzo[d]imidazole-4-carboxylic acid;
1-(5-(difluoromethyl)quinolin-4-yl)-2-methyl-6-morpholino-1H-benzo[d]imidazole-4-carboxylic acid;
1-(5-chloroquinolin-4-yl)-2-methyl-6-morpholino-1H-benzo[d]imidazole-4-carboxylic acid;
1-(5-fluoroquinolin-4-yl)-2-methyl-6-morpholino-1H-benzo[d]imidazole-4-carboxylic acid;
1-(8-(difluoromethyl)quinolin-4-yl)-2-methyl-6-morpholino-1H-benzo[d]imidazole-4-carboxylic acid;
2-methyl-1-(5-methylquinolin-4-yl)-6-morpholino-1H-benzo[d]imidazole-4-carboxylic acid;
1-(7-fluoroquinolin-4-yl)-2-methyl-6-morpholino-1H-benzo[d]imidazole-4-carboxylic acid;
1-(8-chloro-2-(difluoromethyl)quinolin-4-yl)-6-morpholino-1H-benzo[d]imidazole-4-carboxylic acid;
1-(8-chloro-5-fluoroquinolin-4-yl)-2-methyl-6-morpholino-1H-benzo[d]imidazole-4-carboxylic acid;
1-(8-cyanoquinolin-4-yl)-2-methyl-6-morpholino-1H-benzo[d]imidazole-4-carboxylic acid;
1-(5,8-dichloroquinolin-4-yl)-2-methyl-6-morpholino-1H-benzo[d]imidazole-4-carboxylic acid;
1-(5,8-difluoroquinolin-4-yl)-2-ethyl-6-morpholino-1H-benzo[d]imidazole-4-carboxylic acid;
1-(5,8-difluoroquinolin-4-yl)-6-morpholino-2-(oxetan-3-yl)-1H-benzo[d]imidazole-4-carboxylic acid;
1-(5-chloro-8-fluoroquinolin-4-yl)-2-methyl-6-morpholino-1H-benzo[d]imidazole-4-carboxylic acid;
1-(5-fluoro-8-methylquinolin-4-yl)-2-methyl-6-morpholino-1H-benzo[d]imidazole-4-carboxylic acid;
2-methyl-6-morpholino-1-(2-(thiazol-4-yl)quinolin-4-yl)-1H-benzo[d]imidazole-4-carboxylic acid;
1-(3-chloroquinolin-4-yl)-2-methyl-6-morpholino-1H-benzo[d]imidazole-4-carboxylic acid;
1-(5,7-difluoroquinolin-4-yl)-2-methyl-6-morpholino-1H-benzo[d]imidazole-4-carboxylic acid;
1-(5-methylquinolin-4-yl)-6-morpholino-1H-benzo[d]imidazole-4-carboxylic acid;
1-(8-chloroquinolin-4-yl)-2-ethyl-6-morpholino-1H-benzo[d]imidazole-4-carboxylic acid;
1-(8-chloroquinolin-4-yl)-6-morpholino-1H-benzo[d]imidazole-4-carboxylic acid;
1-(8-fluoroquinolin-4-yl)-2-methyl-6-morpholino-1H-benzo[d]imidazole-4-carboxylic acid;
1-(6,8-difluoroquinolin-4-yl)-2-methyl-6-morpholino-1H-benzo[d]imidazole-4-carboxylic acid;
1-(7,8-difluoroquinolin-4-yl)-2-methyl-6-morpholino-1H-benzo[d]imidazole-4-carboxylic acid;
1-(8-fluoroquinolin-4-yl)-6-morpholino-2-propyl-1H-benzo[d]imidazole-4-carboxylic acid;
2-cyclopropyl-1-(7,8-difluoroquinolin-4-yl)-6-morpholino-1H-benzo[d]imidazole-4-carboxylic acid;
2-cyclopropyl-1-(8-fluoroquinolin-4-yl)-6-morpholino-1H-benzo[d]imidazole-4-carboxylic acid;
2-ethyl-1-(8-fluoroquinolin-4-yl)-6-morpholino-1H-benzo[d]imidazole-4-carboxylic acid;
1-(3,8-dichloroquinolin-4-yl)-2-ethyl-6-morpholino-1H-benzo[d]imidazole-4-carboxylic acid;
1-(3,8-dichloroquinolin-4-yl)-2-methyl-6-morpholino-1H-benzo[d]imidazole-4-carboxylic acid;
1-(3-chloro-8-fluoroquinolin-4-yl)-2-methyl-6-morpholino-1H-benzo[d]imidazole-4-carboxylic acid;
1-(5-chloro-8-fluoroquinolin-4-yl)-6-morpholino-1H-benzo[d]imidazole-4-carboxylic acid;
1-(6,8-difluoroquinolin-4-yl)-6-morpholino-2-propyl-1H-benzo[d]imidazole-4-carboxylic acid;
1-(8-fluoroquinolin-4-yl)-6-morpholino-1H-benzo[d]imidazole-4-carboxylic acid;
1-(8-chloroquinolin-4-yl)-2-cyclopropyl-6-morpholino-1H-benzo[d]imidazole-4-carboxylic acid;
1-(8-chloroquinolin-4-yl)-6-morpholino-1H-benzo[d]imidazole-4-carboxylic acid;
2-ethyl-6-morpholino-1-(quinolin-4-yl)-1H-benzo[d]imidazole-4-carboxylic acid;
2-methyl-1-(8-methylquinolin-4-yl)-6-morpholino-1H-benzo[d]imidazole-4-carboxylic acid;
2-methyl-6-morpholino-1-(8-(trifluoromethyl)quinolin-4-yl)-1H-benzo[d]imidazole-4-carboxylic acid;
2-methyl-6-morpholino-1-(quinolin-4-yl)-1H-benzo[d]imidazole-4-carboxylic acid;
1-(5,8-difluoroquinolin-4-yl)-2-methyl-6-morpholino-1H-benzo[d]imidazole-4-carboxylic acid;
1-(8-chloroquinolin-4-yl)-2-(2-methoxyethyl)-6-morpholino-1H-benzo[d]imidazole-4-carboxylic acid;
1-(8-chloroquinolin-4-yl)-6-morpholino-2-(oxazol-5-yl)-1H-benzo[d]imidazole-4-carboxylic acid;
1-(8-chloroquinolin-4-yl)-6-morpholino-2-(pyridin-2-yl)-1H-benzo[d]imidazole-4-carboxylic acid;
1-(8-chloroquinolin-4-yl)-6-morpholino-2-(thiazol-5-yl)-1H-benzo[d]imidazole-4-carboxylic acid;
1-(8-chloroquinolin-4-yl)-6-morpholino-2-(oxetan-3-yl)-1H-benzo[d]imidazole-4-carboxylic acid;
(S)-1-(8-chloroquinolin-4-yl)-2-methyl-6-(3-methylmorpholino)-1H-benzo[d]imidazole-4-carboxylic acid;
(R)-1-(8-chloroquinolin-4-yl)-2-methyl-6-(3-methylmorpholino)-1H-benzo[d]imidazole-4-carboxylic acid;
1-(8-chloroquinolin-4-yl)-6-morpholino-2-(1H-pyrazol-5-yl)-1H-benzo[d]imidazole-4-carboxylic acid;
1-(8-chloroquinolin-4-yl)-2-(isothiazol-4-yl)-6-morpholino-1H-benzo[d]imidazole-4-carboxylic acid;
1-(8-chloroquinolin-4-yl)-6-morpholino-2-(1H-pyrazol-4-yl)-1H-benzo[d]imidazole-4-carboxylic acid;
2-methyl-6-morpholino-1-(2-(1-trityl-1H-pyrazol-4-yl)quinolin-4-yl)-1H-benzo[d]imidazole-4-carboxylic acid;
1-(2-(4-(tert-butoxycarbonyl)piperazin-1-yl)quinolin-4-yl)-2-methyl-6-morpholino-1H-benzo[d]imidazole-4-carboxylic acid;

1-(3-fluoroquinolin-4-yl)-2-methyl-6-morpholino-1H-benzo[d]imidazole-4-carboxylic acid;
1-(8-chloro-5-fluoroquinolin-4-yl)-7-fluoro-2-methyl-6-morpholino-1H-benzo[d]imidazole-4-carboxylic acid;
1-(8-chloroquinolin-4-yl)-7-fluoro-6-morpholino-1H-benzo[d]imidazole-4-carboxylic acid;
1-(8-cyano-3-methylquinolin-4-yl)-2-ethyl-6-morpholino-1H-benzo[d]imidazole-4-carboxylic acid;
1-(8-cyano-3-methylquinolin-4-yl)-2-methyl-6-morpholino-1H-benzo[d]imidazole-4-carboxylic acid;
1-(3-carbamoylquinolin-4-yl)-2-ethyl-6-morpholino-1H-benzo[d]imidazole-4-carboxylic acid;
1-(3-carbamoylquinolin-4-yl)-2-methyl-6-morpholino-1H-benzo[d]imidazole-4-carboxylic acid;
1-(2-(4-(tert-butoxycarbonyl)piperazin-1-yl)quinolin-4-yl)-6-morpholino-1H-benzo[d]imidazole-4-carboxylic acid;
6-morpholino-1-(2-(1-trityl-1H-pyrazol-3-yl)quinolin-4-yl)-1H-benzo[d]imidazole-4-carboxylic acid;
6-morpholino-1-(2-(1-trityl-1H-pyrazol-4-yl)quinolin-4-yl)-1H-benzo[d]imidazole-4-carboxylic acid;

Step 3a: 1-(8-chloroquinolin-4-yl)-5-fluoro-2-methyl-6-morpholino-1H-benzo[d]imidazole-4-carboxylic acid

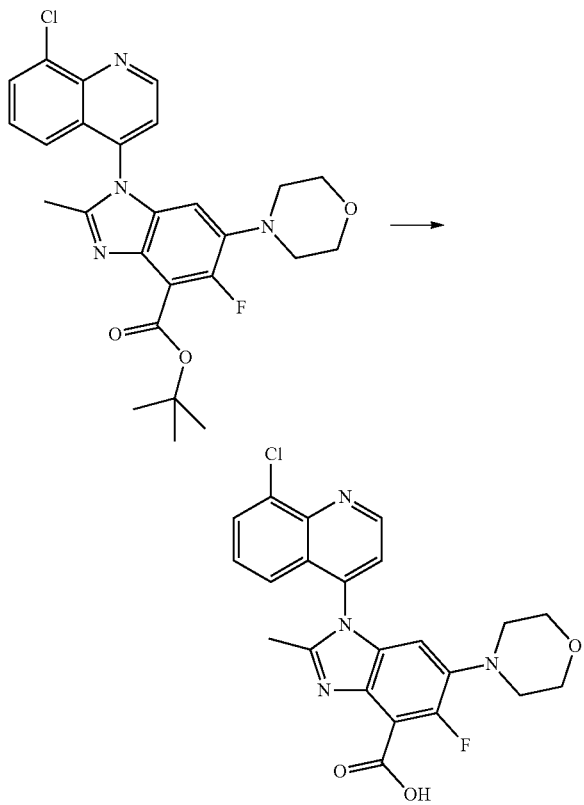

To a solution of tert-butyl 1-(8-chloroquinolin-4-yl)-5-fluoro-2-methyl-6-morpholino-1H-benzo[d]imidazole-4-carboxylate (170 mg, 0.34 mmol) in DCM (3.0 mL) was added TFA (0.4 mL). The mixture was stirred at room temperature for 20 hours and concentrated in vacuuo to afford 1-(8-chloroquinolin-4-yl)-5-fluoro-2-methyl-6-morpholino-1H-benzo[d]imidazole-4-carboxylic acid which was used without further purification in the next step.

The following compound was prepared in a manner similar to that described above using appropriate intermediates:
1-(8-chloroquinolin-4-yl)-7-fluoro-2-methyl-6-morpholino-1H-benzo[d]imidazole-4-carboxylic acid.

Step: 1-(8-Chloroquinolin-4-yl)-6-morpholino-2-propyl-1H-benzo[d]imidazole-4-carboxamide

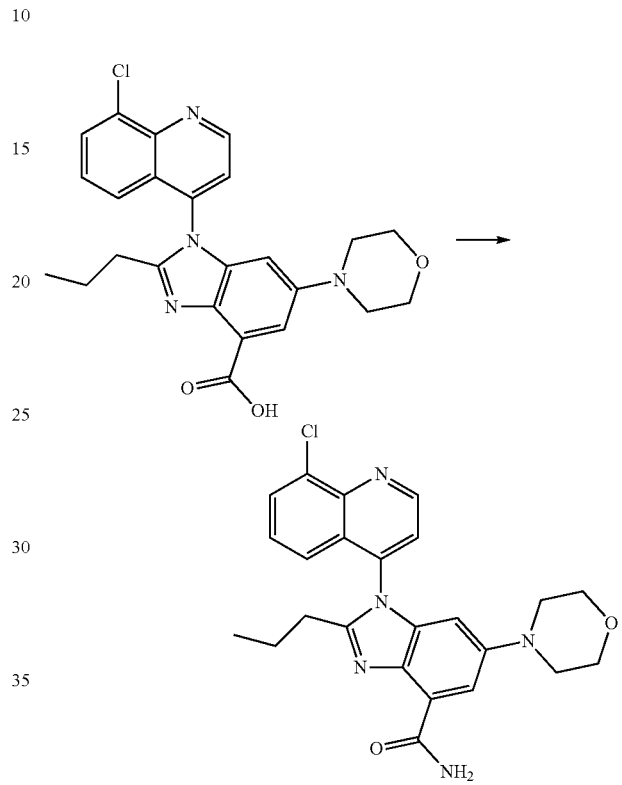

Hünig's base (1.35 mL, 7.74 mmol) was added to 1-(8-chloroquinolin-4-yl)-6-morpholino-2-propyl-1H-benzo[d]imidazole-4-carboxylic acid (349 mg, 0.77 mmol), ammonium hydrochloride (248 mg, 4.64 mmol), 1H-benzo[d][1,2,3]triazol-1-ol hydrate (356 mg, 2.32 mmol), and N1-((ethylimino)methylene)-N3,N3-dimethylpropane-1,3-diamine hydrochloride (445 mg, 2.32 mmol) in DMF (3 mL). The reagents were stirred at ambient temperature for 72 hours. Material precipitated with the addition of water. The resulting solid was filtered, washed with water, and dried under high vacuum to afford the title compound as a white solid. $^1$H NMR (400 MHz, DMSO-$d_6$) δ 9.30 (d, 1H), 9.20 (d, 1H), 8.10 (d, 1H), 7.98 (d, 1H), 7.89 (d, 1H), 7.65-7.55 (m, 2H), 7.20 (d, 1H), 6.64 (d, 1H), 3.64 (t, J=4.7 Hz, 4H), 3.03-2.92 (m, 4H), 2.66-2.52 (m, 2H), 1.72-1.58 (m, 2H), 0.82 (t, J=7.4, 0.6 Hz, 3H). ES/MS m/z 450.20 (M+H)$^+$.

The compounds listed below were prepared in a manner similar to that described above using appropriate intermediates and chemistry:
1-(5,8-difluoroquinolin-4-yl)-6-morpholino-2-propyl-1H-benzo[d]imidazole-4-carboxamide;
1-(5-chloro-8-fluoroquinolin-4-yl)-2-ethyl-6-morpholino-1H-benzo[d]imidazole-4-carboxamide;
1-(8-chloroquinolin-4-yl)-2-(1-methylcyclopropyl)-6-morpholino-1H-benzo[d]imidazole-4-carboxamide;

1-(8-chloroquinolin-4-yl)-2-isobutyl-6-morpholino-1H-benzo[d]imidazole-4-carboxamide;
1-(7-fluoroquinolin-4-yl)-6-morpholino-2-propyl-1H-benzo[d]imidazole-4-carboxamide;
1-(8-chloroquinolin-4-yl)-2-(cyclopropylmethyl)-6-morpholino-1H-benzo[d]imidazole-4-carboxamide;
1-(8-chloroquinolin-4-yl)-6-morpholino-2-(tetrahydrofuran-3-yl)-1H-benzo[d]imidazole-4-carboxamide;
6-morpholino-2-(pyridin-2-yl)-1-(quinolin-4-yl)-1H-benzo[d]imidazole-4-carboxamide;
1-(8-chloro-5-fluoroquinolin-4-yl)-6-morpholino-2-propyl-1H-benzo[d]imidazole-4-carboxamide;
1-(8-chloroquinolin-4-yl)-2-(1-methoxyethyl)-6-morpholino-1H-benzo[d]imidazole-4-carboxamide;
1-(8-chloroquinolin-4-yl)-2-cyclobutyl-6-morpholino-1H-benzo[d]imidazole-4-carboxamide;
1-(8-chloroquinolin-4-yl)-6-morpholino-2-(pyridin-3-yl)-1H-benzo[d]imidazole-4-carboxamide;
1-(8-chloroquinolin-4-yl)-2-isopropyl-6-morpholino-1H-benzo[d]imidazole-4-carboxamide;
1-(8-chloroquinolin-4-yl)-6-morpholino-2-(pyridin-4-yl)-1H-benzo[d]imidazole-4-carboxamide;
1-(8-chloroquinolin-4-yl)-6-morpholino-2-(tetrahydrofuran-2-yl)-1H-benzo[d]imidazole-4-carboxamide;
2-cyclopropyl-6-morpholino-1-(quinolin-4-yl)-1H-benzo[d]imidazole-4-carboxamide;
1-(7-fluoroquinolin-4-yl)-6-morpholino-1H-benzo[d]imidazole-4-carboxamide;
1-(8-chloro-6-fluoroquinolin-4-yl)-2-methyl-6-morpholino-1H-benzo[d]imidazole-4-carboxamide;
2-(tert-butyl)-1-(8-chloroquinolin-4-yl)-6-morpholino-1H-benzo[d]imidazole-4-carboxamide;
2-methyl-6-morpholino-1-(quinolin-4-yl)-1H-benzo[d]imidazole-4-carboxamide;
(S)-1-(5,8-difluoroquinolin-4-yl)-2-methyl-6-morpholino-1H-benzo[d]imidazole-4-carboxamide;
1-(5,8-difluoroquinolin-4-yl)-6-morpholino-1H-benzo[d]imidazole-4-carboxamide;
1-(8-chloro-7-fluoroquinolin-4-yl)-6-morpholino-1H-benzo[d]imidazole-4-carboxamide;
6-morpholino-2-(oxetan-3-yl)-1-(quinolin-4-yl)-1H-benzo[d]imidazole-4-carboxamide;
1-(5-fluoro-8-methylquinolin-4-yl)-6-morpholino-2-propyl-1H-benzo[d]imidazole-4-carboxamide;
1-(8-chloro-6-fluoroquinolin-4-yl)-6-morpholino-2-propyl-1H-benzo[d]imidazole-4-carboxamide;
1-(8-chloro-7-fluoroquinolin-4-yl)-2-(cyclopropylmethyl)-6-morpholino-1H-benzo[d]imidazole-4-carboxamide;
1-(8-chloro-7-fluoroquinolin-4-yl)-6-morpholino-2-propyl-1H-benzo[d]imidazole-4-carboxamide;
1-(8-chloro-7-fluoroquinolin-4-yl)-2-cyclopropyl-6-morpholino-1H-benzo[d]imidazole-4-carboxamide;
1-(8-chloro-7-fluoroquinolin-4-yl)-2-methyl-6-morpholino-1H-benzo[d]imidazole-4-carboxamide;
1-(8-chloro-7-fluoroquinolin-4-yl)-6-morpholino-1H-benzo[d]imidazole-4-carboxamide;
6-morpholino-2-propyl-1-(quinolin-4-yl)-1H-benzo[d]imidazole-4-carboxamide;
1-(5,8-difluoroquinolin-4-yl)-6-morpholino-1H-benzo[d]imidazole-4-carboxamide;
1-(7,8-difluoroquinolin-4-yl)-6-morpholino-2-propyl-1H-benzo[d]imidazole-4-carboxamide;
1-(8-chloroquinolin-4-yl)-2-cyclopropyl-6-morpholino-1H-benzo[d]imidazole-4-carboxamide;
1-(8-fluoroquinolin-4-yl)-2-(2-methoxyethyl)-6-morpholino-1H-benzo[d]imidazole-4-carboxamide;
1-(7,8-difluoroquinolin-4-yl)-6-morpholino-2-propyl-1H-benzo[d]imidazole-4-carboxamide;
1-(7-fluoroquinolin-4-yl)-6-morpholino-1H-benzo[d]imidazole-4-carboxamide;
1-(8-chloroquinolin-4-yl)-2-(1-fluorocyclopropyl)-6-morpholino-1H-benzo[d]imidazole-4-carboxamide;
1-(2-cyclopropyl-3-methylquinolin-4-yl)-2-methyl-6-morpholino-1H-benzo[d]imidazole-4-carboxamide;
1-(2-ethyl-3-methylquinolin-4-yl)-2-methyl-6-morpholino-1H-benzo[d]imidazole-4-carboxamide;
1-(8-chloro-2-(trifluoromethyl)quinolin-4-yl)-2-methyl-6-morpholino-1H-benzo[d]imidazole-4-carboxamide;
2-methyl-6-morpholino-1-(2-phenylquinolin-4-yl)-1H-benzo[d]imidazole-4-carboxamide;
1-(3-ethyl-2-methylquinolin-4-yl)-2-methyl-6-morpholino-1H-benzo[d]imidazole-4-carboxamide;
1-(7-fluoro-2-methylquinolin-4-yl)-2-methyl-6-morpholino-1H-benzo[d]imidazole-4-carboxamide;
1-(8-fluoro-2,3-dimethylquinolin-4-yl)-2-methyl-6-morpholino-1H-benzo[d]imidazole-4-carboxamide;
2-methyl-1-(2-methyl-8-(trifluoromethyl)quinolin-4-yl)-6-morpholino-1H-benzo[d]imidazole-4-carboxamide;
1-(2-cyanoquinolin-4-yl)-2-methyl-6-morpholino-1H-benzo[d]imidazole-4-carboxamide;
1-(3-cyclopropylquinolin-4-yl)-2-methyl-6-morpholino-1H-benzo[d]imidazole-4-carboxamide;
1-(8-chloro-2-methylquinolin-4-yl)-2-methyl-6-morpholino-1H-benzo[d]imidazole-4-carboxamide;
2-methyl-1-(3-methylquinolin-4-yl)-6-morpholino-1H-benzo[d]imidazole-4-carboxamide;
1-(2-ethyl-3-methylquinolin-4-yl)-6-morpholino-1H-benzo[d]imidazole-4-carboxamide;
1-(3-ethyl-2-methylquinolin-4-yl)-6-morpholino-1H-benzo[d]imidazole-4-carboxamide;
1-(8-chloro-2,3-dimethylquinolin-4-yl)-2-methyl-6-morpholino-1H-benzo[d]imidazole-4-carboxamide;
1-(8-chloro-3-methylquinolin-4-yl)-2-methyl-6-morpholino-1H-benzo[d]imidazole-4-carboxamide;
2-methyl-1-(2-methylquinolin-4-yl)-6-morpholino-1H-benzo[d]imidazole-4-carboxamide;
1-(2-ethyl-8-fluoro-3-methylquinolin-4-yl)-2-methyl-6-morpholino-1H-benzo[d]imidazole-4-carboxamide;
1-(5-(difluoromethyl)quinolin-4-yl)-2-methyl-6-morpholino-1H-benzo[d]imidazole-4-carboxamide;
1-(5-chloroquinolin-4-yl)-2-methyl-6-morpholino-1H-benzo[d]imidazole-4-carboxamide;
1-(5-fluoroquinolin-4-yl)-2-methyl-6-morpholino-1H-benzo[d]imidazole-4-carboxamide;
1-(8-(difluoromethyl)quinolin-4-yl)-2-methyl-6-morpholino-1H-benzo[d]imidazole-4-carboxamide;
2-methyl-1-(5-methylquinolin-4-yl)-6-morpholino-1H-benzo[d]imidazole-4-carboxamide;
1-(7-fluoroquinolin-4-yl)-2-methyl-6-morpholino-1H-benzo[d]imidazole-4-carboxamide;
1-(8-chloro-2-(difluoromethyl)quinolin-4-yl)-6-morpholino-1H-benzo[d]imidazole-4-carboxamide;
1-(8-chloro-5-fluoroquinolin-4-yl)-2-methyl-6-morpholino-1H-benzo[d]imidazole-4-carboxamide;
1-(8-cyanoquinolin-4-yl)-2-methyl-6-morpholino-1H-benzo[d]imidazole-4-carboxamide;
1-(5,8-dichloroquinolin-4-yl)-2-methyl-6-morpholino-1H-benzo[d]imidazole-4-carboxamide;
1-(5,8-difluoroquinolin-4-yl)-2-ethyl-6-morpholino-1H-benzo[d]imidazole-4-carboxamide;
1-(5,8-difluoroquinolin-4-yl)-6-morpholino-2-(oxetan-3-yl)-1H-benzo[d]imidazole-4-carboxamide;

1-(5-chloro-8-fluoroquinolin-4-yl)-2-methyl-6-morpholino-1H-benzo[d]imidazole-4-carboxamide;
1-(5-fluoro-8-methylquinolin-4-yl)-2-methyl-6-morpholino-1H-benzo[d]imidazole-4-carboxamide;
2-methyl-6-morpholino-1-(2-(thiazol-4-yl)quinolin-4-yl)-1H-benzo[d]imidazole-4-carboxamide;
1-(3-chloroquinolin-4-yl)-2-methyl-6-morpholino-1H-benzo[d]imidazole-4-carboxamide;
1-(5,7-difluoroquinolin-4-yl)-2-methyl-6-morpholino-1H-benzo[d]imidazole-4-carboxamide;
1-(5-methylquinolin-4-yl)-6-morpholino-1H-benzo[d]imidazole-4-carboxamide;
1-(8-chloroquinolin-4-yl)-2-ethyl-6-morpholino-1H-benzo[d]imidazole-4-carboxamide;
1-(8-chloroquinolin-4-yl)-6-morpholino-1H-benzo[d]imidazole-4-carboxamide;
1-(8-fluoroquinolin-4-yl)-2-methyl-6-morpholino-1H-benzo[d]imidazole-4-carboxamide;
1-(6,8-difluoroquinolin-4-yl)-2-methyl-6-morpholino-1H-benzo[d]imidazole-4-carboxamide;
1-(7,8-difluoroquinolin-4-yl)-2-methyl-6-morpholino-1H-benzo[d]imidazole-4-carboxamide;
1-(8-fluoroquinolin-4-yl)-6-morpholino-2-propyl-1H-benzo[d]imidazole-4-carboxamide;
2-cyclopropyl-1-(7,8-difluoroquinolin-4-yl)-6-morpholino-1H-benzo[d]imidazole-4-carboxamide;
2-cyclopropyl-1-(8-fluoroquinolin-4-yl)-6-morpholino-1H-benzo[d]imidazole-4-carboxamide;
2-ethyl-1-(8-fluoroquinolin-4-yl)-6-morpholino-1H-benzo[d]imidazole-4-carboxamide;
1-(3,8-dichloroquinolin-4-yl)-2-ethyl-6-morpholino-1H-benzo[d]imidazole-4-carboxamide;
1-(3,8-dichloroquinolin-4-yl)-2-methyl-6-morpholino-1H-benzo[d]imidazole-4-carboxamide;
1-(3-chloro-8-fluoroquinolin-4-yl)-2-methyl-6-morpholino-1H-benzo[d]imidazole-4-carboxamide;
1-(5-chloro-8-fluoroquinolin-4-yl)-6-morpholino-1H-benzo[d]imidazole-4-carboxamide;
1-(6,8-difluoroquinolin-4-yl)-6-morpholino-2-propyl-1H-benzo[d]imidazole-4-carboxamide;
1-(8-fluoroquinolin-4-yl)-6-morpholino-1H-benzo[d]imidazole-4-carboxamide;
1-(8-chloroquinolin-4-yl)-2-cyclopropyl-6-morpholino-1H-benzo[d]imidazole-4-carboxamide;
1-(8-chloroquinolin-4-yl)-6-morpholino-1H-benzo[d]imidazole-4-carboxamide;
2-ethyl-6-morpholino-1-(quinolin-4-yl)-1H-benzo[d]imidazole-4-carboxamide;
2-methyl-1-(8-methylquinolin-4-yl)-6-morpholino-1H-benzo[d]imidazole-4-carboxamide;
2-methyl-6-morpholino-1-(8-(trifluoromethyl)quinolin-4-yl)-1H-benzo[d]imidazole-4-carboxamide;
2-methyl-6-morpholino-1-(quinolin-4-yl)-1H-benzo[d]imidazole-4-carboxamide;
1-(5,8-difluoroquinolin-4-yl)-2-methyl-6-morpholino-1H-benzo[d]imidazole-4-carboxamide;
1-(8-chloroquinolin-4-yl)-2-(2-methoxyethyl)-6-morpholino-1H-benzo[d]imidazole-4-carboxamide;
1-(8-chloroquinolin-4-yl)-6-morpholino-2-(oxazol-5-yl)-1H-benzo[d]imidazole-4-carboxamide;
1-(8-chloroquinolin-4-yl)-6-morpholino-2-(pyridin-2-yl)-1H-benzo[d]imidazole-4-carboxamide;
1-(8-chloroquinolin-4-yl)-6-morpholino-2-(thiazol-5-yl)-1H-benzo[d]imidazole-4-carboxamide;
1-(8-chloroquinolin-4-yl)-6-morpholino-2-(oxetan-3-yl)-1H-benzo[d]imidazole-4-carboxamide;
1-(8-chloroquinolin-4-yl)-7-fluoro-2-methyl-6-morpholino-1H-benzo[d]imidazole-4-carboxamide;
(S)-1-(8-chloroquinolin-4-yl)-2-methyl-6-(3-methylmorpholino)-1H-benzo[d]imidazole-4-carboxamide;
(R)-1-(8-chloroquinolin-4-yl)-2-methyl-6-(3-methylmorpholino)-1H-benzo[d]imidazole-4-carboxamide;
1-(8-chloroquinolin-4-yl)-6-morpholino-2-(1H-pyrazol-5-yl)-1H-benzo[d]imidazole-4-carboxamide;
1-(8-chloroquinolin-4-yl)-2-(isothiazol-4-yl)-6-morpholino-1H-benzo[d]imidazole-4-carboxamide;
1-(8-chloroquinolin-4-yl)-6-morpholino-2-(1H-pyrazol-4-yl)-1H-benzo[d]imidazole-4-carboxamide;
1-(8-chloroquinolin-4-yl)-5-fluoro-2-methyl-6-morpholino-1H-benzo[d]imidazole-4-carboxamide;
2-methyl-6-morpholino-1-(2-(1-trityl-1H-pyrazol-4-yl)quinolin-4-yl)-1H-benzo[d]imidazole-4-carboxamide;
tert-butyl 4-(4-(4-carbamoyl-2-methyl-6-morpholino-1H-benzo[d]imidazol-1-yl)quinolin-2-yl)piperazine-1-carboxylate;
tert-butyl 4-(4-(4-carbamoyl-2-methyl-6-morpholino-1H-benzo[d]imidazol-1-yl)quinolin-2-yl)piperazine-1-carboxylate;
1-(3-fluoroquinolin-4-yl)-2-methyl-6-morpholino-1H-benzo[d]imidazole-4-carboxamide;
1-(8-chloro-5-fluoroquinolin-4-yl)-7-fluoro-2-methyl-6-morpholino-1H-benzo[d]imidazole-4-carboxamide;
1-(8-chloroquinolin-4-yl)-7-fluoro-6-morpholino-1H-benzo[d]imidazole-4-carboxamide;
1-(8-cyano-3-methylquinolin-4-yl)-2-ethyl-6-morpholino-1H-benzo[d]imidazole-4-carboxamide;
1-(8-cyano-3-methylquinolin-4-yl)-2-methyl-6-morpholino-1H-benzo[d]imidazole-4-carboxamide;
tert-butyl 4-(4-(4-carbamoyl-6-morpholino-1H-benzo[d]imidazol-1-yl)quinolin-2-yl)piperazine-1-carboxylate;
6-morpholino-1-(2-(1-trityl-1H-pyrazol-4-yl)quinolin-4-yl)-1H-benzo[d]imidazole-4-carboxamide;
6-morpholino-1-(2-(1-trityl-1H-pyrazol-3-yl)quinolin-4-yl)-1H-benzo[d]imidazole-4-carboxamide;
4-(4-carbamoyl-2-ethyl-6-morpholino-1H-benzo[d]imidazol-1-yl)quinoline-3-carboxamide;
4-(4-carbamoyl-2-methyl-6-morpholino-1H-benzo[d]imidazol-1-yl)quinoline-3-carboxamide;

Step 5: 4-(1-(8-Chloroquinolin-4-yl)-2-propyl-4-(4H-1,2,4-triazol-3-yl)-1H-benzo[d]imidazol-6-yl)morpholine 2,2,2-trifluoroacetate

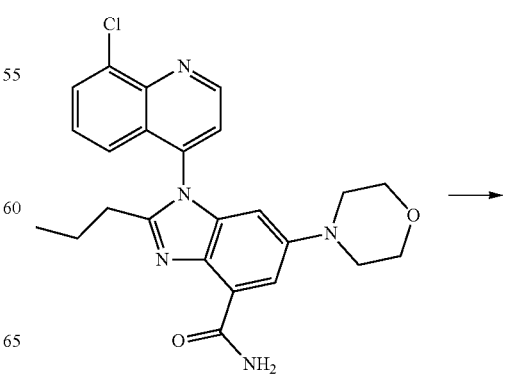

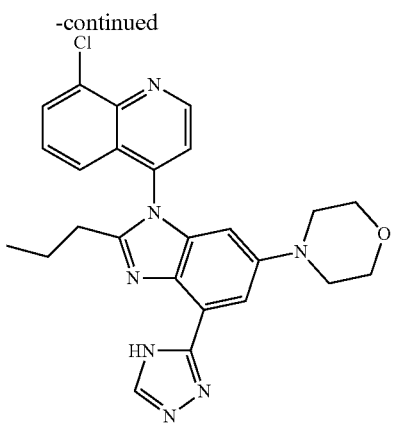

1-(8-chloroquinolin-4-yl)-6-morpholino-2-propyl-1H-benzo[d]imidazole-4-carboxamide (60 mg, 0.13 mmol) was suspended in 1,1-dimethoxy-N,N-dimethylmethanamine (2.3 mL, 17 mmol) and stirred at 120° C. for 1 hour. The solution was cooled to ambient temperature and concentrated in vacuuo. The residue was dissolved in acetic acid (1 mL) and hydrazine hydrate (8 µL, 0.17 mmol) was added. The reaction mixture was stirred at 90° C. for 1 hour, after which the reaction was cooled to ambient temperature. The resultant was purified by HPLC eluting with 5-95% water/acetonitrile (0.1% v/v trifluoroacetic acid). The appropriate fractions were pooled and lyophilized to afford 4-(1-(8-chloroquinolin-4-yl)-2-propyl-4-(4H-1,2,4-triazol-3-yl)-1H-benzo[d]imidazol-6-yl)morpholine 2,2,2-trifluoroacetate (Compound 1). $^1$H NMR (400 MHz, DMSO-d6) δ 9.37 (d, J=4.5 Hz, 1H), 8.68 (s, 1H), 8.16-8.10 (m, 2H), 7.79 (d, J=1.6 Hz, 1H), 7.66-7.59 (m, 1H), 7.47 (d, J=8.8 Hz, 1H), 6.68 (d, J=2.2 Hz, 1H), 3.66 (t, J=4.7 Hz, 4H), 3.09-3.02 (m, 4H), 2.88-2.80 (m, 2H), 1.62-1.45 (m, 2H), 0.78 (t, J=7.4 Hz, 3H). ES/MS m/z 474.20 (M+H)$^+$.

The compounds listed in the table below were prepared in a manner similar to that described above using appropriate intermediates and chemistry:

| Compound | Compound Name | MS | NMR |
| --- | --- | --- | --- |
| 2 | 4-(1-(8-chloroquinolin-4-yl)-2-isobutyl-4-(5-methyl-4H-1,2,4-triazol-3-yl)-1H-benzo[d]imidazol-6-yl)morpholine | 502.3 | 1H NMR (400 MHz, DMSO-d6) δ 9.36 (d, J = 4.5 Hz, 1H), 8.13 (dd, J = 7.6, 1.2 Hz, 1H), 8.10 (d, J = 4.5 Hz, 1H), 7.73 (d, J = 2.1 Hz, 1H), 7.63 (dd, J = 8.5, 7.5 Hz, 1H), 7.42 (d, J = 8.4 Hz, 1H), 6.64 (d, J = 2.2 Hz, 1H), 3.65 (t, J = 4.7 Hz, 4H), 3.04 (d, J = 3.8 Hz, 4H), 2.81 (s, 1H), 2.76-2.66 (m, 1H), 2.58-2.51 (m, 3H), 2.32 (s, 1H), 0.78 (d, J = 6.6 Hz, 3H), 0.73 (d, J = 6.6 Hz, 3H). |
| 3 | 4-(1-(5,8-difluoroquinolin-4-yl)-4-(5-methyl-4H-1,2,4-triazol-3-yl)-2-propyl-1H-benzo[d]imidazol-6-yl)morpholine | 490.33 | 1H NMR (400 MHz, DMSO-d6) δ 9.37 (dd, J = 4.5, 2.0 Hz, 1H), 8.17 (dd, J = 4.5, 1.5 Hz, 1H), 7.83 (td, J = 9.8, 3.6 Hz, 1H), 7.74 (t, J = 1.8 Hz, 1H), 7.57-7.48 (m, 1H), 6.81 (d, J = 2.2 Hz, 1H), 3.67 (q, J = 3.7, 2.2 Hz, 4H), 3.10 (d, J = 5.1 Hz, 4H), 2.90 (t, J = 8.1 Hz, 2H), 2.53 (d, J = 1.9 Hz, 3H), 1.57 (d, J = 8.3 Hz, 2H), 0.81 (td, J = 7.3, 2.4 Hz, 3H). |
| 4 | 4-(1-(8-chloroquinolin-4-yl)-2-(1-methylcyclopropyl)-4-(4H-1,2,4-triazol-3-yl)-1H-benzo[d]imidazol-6-yl)morpholine | 486.2 | 1H NMR (400 MHz, DMSO-d6) δ 9.36 (d, J = 4.5 Hz, 1H), 8.52 (s, 1H), 8.13 (d, J = 1.4 Hz, 1H), 8.12-8.11 (m, 1H), 7.70 (d, J = 2.3 Hz, 1H), 7.62 (dd, J = 8.5, 7.5 Hz, 1H), 7.41 (dd, J = 8.5, 1.2 Hz, 1H), 6.53 (d, J = 2.3 Hz, 1H), 3.64 (t, J = 4.8 Hz, 4H), 3.06-2.98 (m, 4H), 1.39 (ddd, J = 10.2, 6.3, 4.2 Hz, 1H), 1.26 (d, J = 5.1 Hz, 1H), 1.02 (s, 3H), 0.69 (ddd, J = 8.9, 6.3, 4.1 Hz, 1H), 0.55 (ddd, J = 9.0, 6.3, 4.3 Hz, 1H). |
| 5 | 4-(1-(5-chloro-8-fluoroquinolin-4-yl)-2-ethyl-4-(4H-1,2,4-triazol-3-yl)-1H-benzo[d]imidazol-6-yl)morpholine | 478.22 | 1H NMR (400 MHz, DMSO-d6) δ 9.36 (d, J = 4.4 Hz, 1H), 8.69 (s, 1H), 8.17 (d, J = 4.4 Hz, 1H), 7.84 (d, J = 7.2 Hz, 2H), 7.78 (d, J = 2.3 Hz, 1H), 6.79 (d, J = 1.7 Hz, 1H), 3.68 (t, J = 4.8 Hz, 4H), 3.11 (t, J = 4.9 Hz, 4H), 2.87 (p, J = 7.6, 7.1 Hz, 2H), 1.18 (t, J = 7.5 Hz, 3H). |
| 6 | 4-(2-(pyridin-2-yl)-1-(quinolin-4-yl)-4-(4H-1,2,4-triazol-3-yl)-1H-benzo[d]imidazol-6-yl)morpholine | 475.19 | 1H NMR (400 MHz, DMSO-d6) δ 9.14 (dd, J = 4.6, 2.2 Hz, 1H), 8.88 (d, J = 7.9 Hz, 1H), 8.31 (s, 1H), 8.20 (d, J = 8.5 Hz, 1H), 7.95-7.88 (m, 2H), 7.82-7.74 (m, 3H), 7.49-7.43 (m, 1H), 7.23 (dd, J = 7.9, 4.9 Hz, 2H), 6.48 (s, 1H), 3.65 (t, J = 4.8 Hz, 4H), 3.04 (q, J = 4.5 Hz, 4H). |
| 7 | 4-(1-(7-fluoroquinolin-4-yl)-2-propyl-4-(4H-1,2,4-triazol-3-yl)-1H-benzo[d]imidazol-6-yl)morpholine | 458.4 | 1H NMR (400 MHz, DMSO-d6) δ 9.26 (dd, J = 4.7, 2.5 Hz, 1H), 8.70 (s, 1H), 8.10-8.04 (m, 1H), 7.98 (dd, J = 4.7, 2.5 Hz, 1H), 7.80 (t, J = 2.5 Hz, 1H), 7.68-7.55 (m, 2H), 6.62 (d, J = 2.4 Hz, 1H), 3.71-3.58 (m, 4H), 3.12-2.99 (m, 4H), 2.90-2.77 (m, 2H), 1.59-1.41 (m, 2H), 0.79-0.70 (m, 3H). |

-continued

| Compound | Compound Name | MS | NMR |
|---|---|---|---|
| 8 | 4-(1-(8-chloroquinolin-4-yl)-2-(cyclopropylmethyl)-4-(5-methyl-4H-1,2,4-triazol-3-yl)-1H-benzo[d]imidazol-6-yl)morpholine | 500.3 | 1H NMR (400 MHz, DMSO-d6) δ 9.36 (d, J = 4.5 Hz, 1H), 8.16-8.11 (m, 2H), 7.76 (d, J = 2.2 Hz, 1H), 7.62 (dd, J = 8.5, 7.5 Hz, 1H), 7.45 (d, J = 8.4 Hz, 1H), 6.67 (d, J = 2.3 Hz, 1H), 3.65 (t, J = 4.8 Hz, 4H), 3.06 (s, 4H), 2.88 (dt, J = 15.2, 7.4 Hz, 2H), 2.53 (d, J = 5.9 Hz, 3H), 0.78 (s, 1H), 0.27 (dd, J = 9.6, 4.3 Hz, 2H), 0.08 (ddd, J = 17.4, 8.9, 4.4 Hz, 2H). |
| 9 | 4-(1-(8-chloroquinolin-4-yl)-2-(tetrahydrofuran-3-yl)-4-(4H-1,2,4-triazol-3-yl)-1H-benzo[d]imidazol-6-yl)morpholine | 502.37 | 1H NMR (400 MHz, DMSO-d6) δ 9.35-9.28 (m, 1H), 8.34 (s, 1H), 8.15-8.07 (m, 1H), 8.06-7.99 (m, 1H), 7.68-7.63 (m, 1H), 7.65-7.55 (m, 1H), 7.27-7.18 (m, 1H), 6.63-6.56 (m, 1H), 4.22-3.98 (m, 1H), 3.95-3.82 (m, 2H), 3.70-3.56 (m, 5H), 3.35-3.24 (m, 1H), 3.06-2.97 (m, 4H), 2.56-2.44 (m, 0.5H), 2.39-2.28 (m, 0.5H), 2.13-2.03 (m, 0.5H), 1.85-1.75 (m, 0.5H). |
| 10 | 4-(1-(8-chloroquinolin-4-yl)-2-(pyridin-3-yl)-4-(4H-1,2,4-triazol-3-yl)-1H-benzo[d]imidazol-6-yl)morpholine | 509.38 | 1H NMR (400 MHz, DMSO-d6) δ 9.29 (dd, J = 4.5, 1.7 Hz, 1H), 8.96 (d, J = 1.6 Hz, 1H), 8.55 (dd, J = 4.9, 1.6 Hz, 1H), 8.36 (s, 1H), 8.08 (dd, J = 7.5, 1.2 Hz, 1H), 8.03 (dd, J = 4.5, 1.6 Hz, 1H), 7.92 (dt, J = 8.1, 1.9 Hz, 1H), 7.77 (d, J = 2.2 Hz, 1H), 7.56 (ddd, J = 9.2, 7.6, 1.7 Hz, 1H), 7.40-7.32 (m, 2H), 6.66 (d, J = 2.2 Hz, 1H), 3.68 (t, J = 4.6 Hz, 4H), 3.14-3.02 (m, 4H). |
| 11 | 4-(1-(8-chloro-5-fluoroquinolin-4-yl)-4-(5-methyl-4H-1,2,4-triazol-3-yl)-2-propyl-1H-benzo[d]imidazol-6-yl)morpholine | 506.33 | 1H NMR (400 MHz, DMSO-d6) δ 9.44 (t, J = 4.2 Hz, 1H), 8.18 (dt, J = 8.5, 4.4 Hz, 2H), 7.75 (d, J = 2.5 Hz, 1H), 7.54 (ddd, J = 12.3, 8.5, 3.9 Hz, 1H), 6.85-6.80 (m, 1H), 3.67 (q, J = 4.2 Hz, 4H), 3.14-3.06 (m, 4H), 2.91 (s, 2H), 2.55 (d, J = 4.0 Hz, 3H), 1.57 (dd, J = 7.9, 3.8 Hz, 2H), 0.81 (td, J = 7.3, 3.6 Hz, 3H). |
| 12 | 4-(1-(8-chloroquinolin-4-yl)-2-(1-methoxyethyl)-4-(4H-1,2,4-triazol-3-yl)-1H-benzo[d]imidazol-6-yl)morpholine | 490.2 | 1H NMR (400 MHz, DMSO-d6) δ 9.33-9.27 (m, 1H), 8.43-8.30 (m, 1H), 8.13-8.05 (m, 1H), 7.99-7.95 (m, 1H), 7.68-7.63 (m, 1H), 7.61-7.54 (m, 1H), 7.26-7.18 (m, 1H), 6.61-6.48 (m, 1H), 4.67-4.35 (m, 1H), 3.70-3.61 (m, 4H), 3.07-2.96 (m, 4H), 2.95-2.78 (m, 3H), 1.57-1.47 (m, 3H). |
| 13 | 4-(1-(8-chloroquinolin-4-yl)-2-cyclobutyl-4-(5-methyl-4H-1,2,4-triazol-3-yl)-1H-benzo[d]imidazol-6-yl)morpholine | 500.37 | 1H NMR (400 MHz, DMSO-d6) δ 9.32 (d, J = 8.3 Hz, 1H), 8.12 (d, J = 4.7 Hz, 1H), 7.96 (d, J = 4.4 Hz, 1H), 7.71-7.57 (m, 2H), 7.27 (d, J = 7.6 Hz, 1H), 6.64 (s, 1H), 3.65 (s, 4H), 3.48 (s, 1H), 3.04 (s, 4H), 2.65 (d, J = 8.2 Hz, 2H), 2.50 (s, 3H), 2.08 (s, 2H), 1.82 (s, 3H). |
| 14 | 4-(1-(8-chloroquinolin-4-yl)-2-isopropyl-4-(5-methyl-4H-1,2,4-triazol-3-yl)-1H-benzo[d]imidazol-6-yl)morpholine | 488.2 | 1H NMR (400 MHz, DMSO-d6) δ 9.33 (dd, J = 4.5, 1.9 Hz, 1H), 8.14-8.09 (m, 1H), 8.09-8.04 (m, 1H), 7.65-7.58 (m, 2H), 7.27 (d, J = 8.5 Hz, 1H), 6.58 (s, 1H), 3.65 (t, J = 4.5 Hz, 4H), 3.01 (s, 4H), 2.67 (s, 1H), 2.47 (d, J = 1.8 Hz, 3H), 1.31 (dd, J = 6.8, 1.8 Hz, 3H), 1.19 (dd, J = 6.9, 1.8 Hz, 3H). |
| 15 | 4-(1-(8-chloroquinolin-4-yl)-2-(pyridin-4-yl)-4-(4H-1,2,4-triazol-3-yl)-1H-benzo[d]imidazol-6-yl)morpholine | 509.26 | 1H NMR (400 MHz, DMSO-d6) δ 9.30 (d, J = 4.5 Hz, 1H), 8.50 (d, J = 5.9 Hz, 2H), 8.19 (s, 1H), 8.08 (d, J = 7.6 Hz, 1H), 8.02 (d, J = 4.6 Hz, 1H), 7.77 (s, 1H), 7.62 (s, 2H), 7.59-7.52 (m, 1H), 7.31 (d, J = 8.5 Hz, 1H), 6.60 (s, 1H), 3.67 (t, J = 4.6 Hz, 4H), 3.13-3.01 (m, 4H). |
| 16 | 4-(1-(8-chloroquinolin-4-yl)-4-(5-methyl-4H-1,2,4-triazol-3-yl)-2-(tetrahydrofuran-2-yl)-1H-benzo[d]imidazol-6-yl)morpholine | 516.4 | 1H NMR (400 MHz, DMSO-d6) δ 9.29 (dd, J = 6.4, 4.5 Hz, 1H), 8.08 (ddd, J = 7.5, 2.6, 1.2 Hz, 1H), 7.98 (d, J = 4.5 Hz, 1H), 7.64 (dd, J = 9.0, 2.2 Hz, 1H), 7.58 (ddd, J = 8.5, 7.4, 1.3 Hz, 1H), 7.23 (td, J = 8.4, 7.9, 1.2 Hz, 1H), 6.52 (d, J = 2.3 Hz, 1H), 5.07 (dd, J = 7.6, 5.8 Hz, 1H), 4.92 (t, J = 7.1 Hz, 1H), 3.65 (q, J = 4.3 |

| Compound | Compound Name | MS | NMR |
|---|---|---|---|
| | | | Hz, 4H), 3.59-3.29 (m, 3H), 3.02 (dd, J = 10.6, 3.9 Hz, 4H), 2.72 (ddd, J = 22.0, 11.7, 5.6 Hz, 2H), 2.20-2.08 (m, 1H), 1.99-1.72 (m, 2H). |
| 17 | 4-(2-cyclopropyl-1-(quinolin-4-yl)-4-(4H-1,2,4-triazol-3-yl)-1H-benzo[d]imidazol-6-yl)morpholine | 438.26 | 1H NMR (400 MHz, DMSO-d6) δ 9.24 (d, J = 4.5 Hz, 1H), 8.39 (s, 1H), 8.30-8.26 (m, 1H), 7.96-7.90 (m, 2H), 7.71-7.64 (m, 2H), 7.45-7.40 (m, 1H), 6.61 (d, J = 2.2 Hz, 1H), 3.66 (t, J = 4.7 Hz, 4H), 3.03 (q, J = 4.0 Hz, 4H), 1.63 (td, J = 8.4, 4.3 Hz, 1H), 1.39 (dt, J = 23.4, 4.8 Hz, 2H), 1.00-0.81 (m, 2H). |
| 18 | 4-(1-(8-chloro-6-fluoroquinolin-4-yl)-2-methyl-4-(5-methyl-4H-1,2,4-triazol-3-yl)-1H-benzo[d]imidazol-6-yl)morpholine | 478.3 | 1H NMR (400 MHz, DMSO-d6) δ 9.34 (d, J = 4.5 Hz, 1H), 8.30-8.24 (m, 1H), 8.13 (d, J = 4.5 Hz, 1H), 7.82-7.78 (m, 1H), 7.59 (d, J = 9.1 Hz, 1H), 6.75-6.72 (m, 1H), 3.72-3.63 (m, 4H), 3.14-3.04 (m, 4H), 2.60 (s, 3H), 2.54 (dd, J = 1.5, 0.8 Hz, 3H). |
| 19 | 4-(2-methyl-4-(5-methyl-4H-1,2,4-triazol-3-yl)-1-(quinolin-4-yl)-1H-benzo[d]imidazol-6-yl)morpholine | 426.1 | 1H NMR (400 MHz, DMSO-d6) δ 9.27 (d, J = 4.5 Hz, 1H), 8.31 (d, J = 8.5 Hz, 1H), 7.99 (d, J = 4.6 Hz, 1H), 7.97-7.93 (m, 1H), 7.81 (d, J = 2.2 Hz, 1H), 7.71-7.66 (m, 1H), 7.60 (d, J = 8.4 Hz, 1H), 6.65-6.62 (m, 1H), 3.65 (t, J = 4.7 Hz, 4H), 3.11-2.99 (m, 4H), 2.59 (s, 3H), 2.55 (s, 3H). |
| 20 | 4-(2-(tert-butyl)-1-(8-chloroquinolin-4-yl)-4-(4H-1,2,4-triazol-3-yl)-1H-benzo[d]imidazol-6-yl)morpholine | 488.2 | 1H NMR (400 MHz, DMSO-d6) δ 9.32 (d, J = 4.5 Hz, 1H), 8.40-8.34 (m, 1H), 8.11-8.06 (m, 2H), 7.62 (d, J = 2.3 Hz, 1H), 7.58 (dd, J = 8.5, 7.5 Hz, 1H), 7.12 (dd, J = 8.5, 1.3 Hz, 1H), 6.33 (d, J = 2.3 Hz, 1H), 3.63 (t, J = 4.8 Hz, 4H), 3.00-2.94 (m, 4H), 1.24 (s, 9H). |
| 21 | 4-(1-(7-fluoroquinolin-4-yl)-4-(5-methyl-4H-1,2,4-triazol-3-yl)-2-propyl-1H-benzo[d]imidazol-6-yl)morpholine | 472.3 | 1H NMR (400 MHz, DMSO-d6) δ 9.29 (dd, J = 4.5, 2.0 Hz, 1H), 8.09 (dt, J = 10.1, 2.3 Hz, 1H), 8.02 (dd, J = 4.6, 2.0 Hz, 1H), 7.80 (d, J = 2.2 Hz, 1H), 7.72-7.58 (m, 2H), 6.63 (t, J = 2.1 Hz, 1H), 3.66 (q, J = 3.3, 1.9 Hz, 4H), 3.14-3.03 (m, 4H), 2.96-2.84 (m, 2H), 2.55 (dt, J = 2.0, 1.1 Hz, 3H), 1.50 (dd, J = 18.3, 8.3 Hz, 2H), 0.76 (td, J = 7.4, 2.2 Hz, 3H). |
| 22 | 4-(1-(7-fluoroquinolin-4-yl)-4-(5-methyl-4H-1,2,4-triazol-3-yl)-1H-benzo[d]imidazol-6-yl)morpholine | 430.34 | 1H NMR (400 MHz, DMSO-d6) δ 11.27 (s, 0.5H), 9.31-9.30 (m, 0.5H), 9.22 (dd, J = 4.6, 1.6 Hz, 0.5H), 8.93 (dd, J = 9.5, 5.5 Hz, 0.5H), 8.44 (d, J = 7.0 Hz, 0.5H), 8.07 (d, J = 2.5 Hz, 0.5H), 8.04 (d, J = 2.5 Hz, 0.5H), 7.95-7.92 (m, 0.5H), 7.87 (d, J = 8.7 Hz, 0.5H), 7.83 (d, J = 2.8 Hz, 0.5H), 7.78 (dt, J = 7.4, 3.4 Hz, 1.5H), 7.76-7.72 (m, 1H), 7.65 (td, J = 8.9, 2.5 Hz, 0.5H), 6.85 (d, J = 2.1 Hz, 0.5H), 6.46 (dd, J = 7.4, 1.4 Hz, 0.5H), 3.80 (d, J = 5.0 Hz, 2H), 3.69 (t, J = 4.9 Hz, 2H), 3.44 (d, J = 5.2 Hz, 2H), 3.11 (s, 2H), 2.59 (t, J = 1.0 Hz, 1.5H), 2.54 (d, J = 0.7 Hz, 1.5H). |
| 23 | 4-(1-(8-chloroquinolin-4-yl)-4-(5-methyl-4H-1,2,4-triazol-3-yl)-2-(pyridin-3-yl)-1H-benzo[d]imidazol-6-yl)morpholine | 523.4 | 1H NMR (400 MHz, DMSO-d6) δ 9.28 (d, J = 4.5 Hz, 1H), 8.92 (s, 1H), 8.54 (d, J = 4.9 Hz, 1H), 8.07 (d, J = 7.5 Hz, 1H), 8.02 (d, J = 4.5 Hz, 1H), 7.89 (d, J = 8.0 Hz, 1H), 7.72 (d, J = 2.2 Hz, 1H), 7.60-7.53 (m, 1H), 7.42-7.31 (m, 2H), 6.66 (s, 1H), 3.68 (s, 4H), 3.08 (s, 4H), 2.50 (s, 3H). |
| 24 | 4-(2-(oxetan-3-yl)-1-(quinolin-4-yl)-4-(4H-1,2,4-triazol-3-yl)-1H-benzo[d]imidazol-6-yl)morpholine | 454.23 | 1H NMR (400 MHz, DMSO-d6) δ 9.19 (d, J = 4.5 Hz, 1H), 8.40 (s, 1H), 8.29-8.24 (m, 1H), 7.92 (ddd, J = 8.5, 6.9, 1.4 Hz, 1H), 7.79 (d, J = 4.5 Hz, 1H), 7.71 (d, J = 2.2 Hz, 1H), 7.64 (ddd, J = 8.1, 6.9, 1.2 Hz, 1H), 7.28-7.24 (m, 1H), 6.58 (d, J = 2.3 Hz, 1H), 5.14 (dd, J = 6.9, 5.6 Hz, 1H), 5.07 (dd, J = 6.9, 5.6 Hz, 1H), 4.64 (dd, J = 8.7, 5.5 Hz, 1H), 4.46 (dd, J = 8.6, 5.5 Hz, 1H), 4.25- |

| Compound | Compound Name | MS | NMR |
|---|---|---|---|
| 25 | 4-(1-(8-chloroquinolin-4-yl)-4-(5-methyl-4H-1,2,4-triazol-3-yl)-2-(pyridin-4-yl)-1H-benzo[d]imidazol-6-yl)morpholine | 523.25 | 4.13 (m, 1H), 3.66 (t, J = 4.7 Hz, 4H), 3.03 (q, J = 4.3 Hz, 4H). 1H NMR (400 MHz, DMSO-d6) δ 9.32 (d, J = 4.5 Hz, 1H), 8.64 (d, J = 6.5 Hz, 2H), 8.10 (d, J = 3.4 Hz, 1H), 8.04 (d, J = 4.6 Hz, 1H), 7.84 (t, J = 4.9 Hz, 2H), 7.81-7.76 (m, 1H), 7.57 (s, 1H), 7.35 (d, J = 1.5 Hz, 1H), 6.62 (s, 1H), 3.68 (s, 4H), 3.11 (s, 4H) 2.50 (s, 3H). |
| 26 | 4-[3-(3,8-dichloroquinolin-4-yl)-2-ethyl-7-(5-methyl-4H-1,2,4-triazol-3-yl)benzimidazol-5-yl]morpholine | 508.2 | 1H NMR (400 MHz, DMSO-d6) δ 9.40 (s, 1H), 8.13 (dd, J = 7.5, 1.2 Hz, 1H), 7.70-7.57 (m, 2H), 7.29 (d, J = 8.4 Hz, 1H), 6.73 (d, J = 2.2 Hz, 1H), 3.64 (t, J = 4.8 Hz, 4H), 3.03 (t, J = 4.9 Hz, 4H), 2.73-2.50 (m, 2H), 1.15 (t, J = 7.5 Hz, 3H). |
| 27 | 4-[3-(3-chloro-8-fluoroquinolin-4-yl)-2-methyl-7-(4H-1,2,4-triazol-3-yl)benzimidazol-5-yl]morpholine | 464.2 | 1H NMR (400 MHz, DMSO-d6) δ 9.36 (s, 1H), 8.59 (s, 1H), 7.80 (ddd, J = 10.7, 7.8, 1.2 Hz, 1H), 7.77-7.60 (m, 1H), 7.34-7.18 (m, 1H), 6.80 (d, J = 2.2 Hz, 1H), 3.65 (dd, J = 5.8, 3.9 Hz, 4H), 3.07 (dd, J = 6.2, 3.7 Hz, 4H), 2.48 (s, 3H). |
| 28 | 4-(1-(5,8-difluoroquinolin-4-yl)-4-(4H-1,2,4-triazol-3-yl)-1H-benzo[d]imidazol-6-yl)morpholine | 434.2 | 1H NMR (400 MHz, DMSO-d6) δ 9.29 (d, J = 4.5 Hz, 1H), 9.13 (s, 1H), 8.51 (s, 1H), 8.06 (s, 1H), 7.82 (dt, J = 9.5, 4.6 Hz, 1H), 7.78 (d, J = 2.2 Hz, 1H), 7.52 (ddd, J = 12.4, 8.9, 3.9 Hz, 1H), 6.98 (d, J = 2.0 Hz, 1H), 3.70 (t, J = 4.6 Hz, 4H), 3.15-3.11 (m, 4H). |
| 29 | 4-(1-(8-chloro-7-fluoroquinolin-4-yl)-4-(4H-1,2,4-triazol-3-yl)-1H-benzo[d]imidazol-6-yl)morpholine | 450.2 | 1H NMR (400 MHz, DMSO-d6) δ 9.33 (dd, J = 4.6, 0.6 Hz, 1H), 9.03 (s, 1H), 8.45 (s, 1H), 8.02 (d, J = 4.6 Hz, 1H), 7.83-7.76 (m, 2H), 7.68 (dd, J = 9.4, 5.7 Hz, 1H), 6.88 (d, J = 2.2 Hz, 1H), 3.69 (t, J = 4.8 Hz, 4H), 3.10 (s, 4H). |
| 30 | 4-(1-(8-chloroquinolin-4-yl)-2-cyclobutyl-4-(4H-1,2,4-triazol-3-yl)-1H-benzo[d]imidazol-6-yl)morpholine | 486.27 | 1H NMR (400 MHz, DMSO-d6) δ 9.31 (d, J = 4.5 Hz, 1H), 8.47 (s, 1H), 8.11 (dd, J = 7.5, 1.2 Hz, 1H), 7.96 (d, J = 4.5 Hz, 1H), 7.68 (d, J = 2.2 Hz, 1H), 7.63-7.56 (m, 1H), 7.27 (d, J = 8.5 Hz, 1H), 6.63 (d, J = 2.3 Hz, 1H), 3.69-3.58 (m, 4H), 3.53-3.36 (m, 2H), 3.08-2.96 (m, 4H), 2.12-2.01 (m, 1H), 1.90-1.67 (m, 4H). |
| 31 | 4-(1-(8-chloro-7-fluoroquinolin-4-yl)-2-(cyclopropylmethyl)-4-(4H-1,2,4-triazol-3-yl)-1H-benzo[d]imidazol-6-yl)morpholine | 504.2 | 1H NMR (400 MHz, DMSO-d6) δ 9.38 (d, J = 4.5 Hz, 1H), 8.57 (s, 1H), 8.08 (d, J = 4.6 Hz, 1H), 7.79-7.71 (m, 2H), 7.52 (s, 1H), 6.66 (d, 1H), 3.66 (t, J = 4.8 Hz, 4H), 3.09-3.02 (m, 4H), 2.91-2.74 (m, 2H), 0.92-0.76 (m, 1H), 0.35-0.23 (m, 1H), 0.19-0.11 (m, 1H), 0.10-0.02 (m, 1H), −0.12−−0.24 (m, 1H). |
| 32 | 4-(1-(8-chloroquinolin-4-yl)-2-(cyclopropylmethyl)-4-(4H-1,2,4-triazol-3-yl)-1H-benzo[d]imidazol-6-yl)morpholine | 486.2 | 1H NMR (400 MHz, DMSO-d6) δ 9.36 (d, J = 4.5 Hz, 1H), 8.68 (s, 1H), 8.16-8.10 (m, 2H), 7.80 (d, J = 2.2 Hz, 1H), 7.67-7.58 (m, 1H), 7.45 (d, J = 8.5 Hz, 1H), 6.69 (d, J = 2.2 Hz, 1H), 3.66 (t, J = 4.7 Hz, 4H), 3.10-3.04 (m, 4H), 2.96-2.78 (m, 2H), 0.87-0.74 (m, 1H), 0.34-0.22 (m, 1H), 0.18-0.01 (m, 2H), −0.14−−0.25 (m, 1H). |
| 33 | 4-(1-(8-chloro-6-fluoroquinolin-4-yl)-2-propyl-4-(4H-1,2,4-triazol-3-yl)-1H-benzo[d]imidazol-6-yl)morpholine | 492.2 | 1H NMR (400 MHz, DMSO-d6) δ 9.31 (d, J = 4.5 Hz, 1H), 8.64 (s, 1H), 8.27-8.19 (m, 1H), 8.15-8.09 (m, 1H), 7.79-7.74 (m, 1H), 7.39 (s, 1H), 6.70-6.65 (m, 1H), 3.65 (t, J = 4.8 Hz, 4H), 3.09-3.01 (m, 4H), 2.93-2.72 (m, 2H), 1.64-1.47 (m, 2H), 0.77 (t, J = 7.3 Hz, 3H). |
| 34 | 4-(1-(8-chloro-7-fluoroquinolin-4-yl)-2-propyl-4-(4H-1,2,4-triazol-3-yl)-1H-benzo[d]imidazol-6-yl)morpholine | 492.2 | 1H NMR (400 MHz, DMSO-d6) δ 9.39 (d, J = 4.6 Hz, 1H), 8.60 (s, 1H), 8.08 (d, J = 4.5 Hz, 1H), 7.80-7.74 (m, 1H), 7.58-7.52 (m, 1H), 6.66 (d, J = 2.3 Hz, 1H), 3.66 (t, J = 4.8 Hz, 4H), 3.05 (dd, J = 6.4, 3.8 Hz, 4H), 2.81 (t, J = 7.7 Hz, 2H), 1.57 (dq, J = 13.9, 7.0 Hz, 2H), 0.79 (t, J = 7.4 Hz, 3H). |

| Compound | Compound Name | MS | NMR |
|---|---|---|---|
| 35 | 4-(1-(8-chloro-6-fluoroquinolin-4-yl)-2-methyl-4-(4H-1,2,4-triazol-3-yl)-1H-benzo[d]imidazol-6-yl)morpholine | 464.24 | 1H NMR (400 MHz, DMSO-d6) δ 9.34 (d, J = 4.5 Hz, 1H), 8.80 (s, 1H), 8.27 (ddd, J = 8.5, 2.7, 0.8 Hz, 1H), 8.13 (d, J = 4.5 Hz, 1H), 7.84 (d, J = 2.2 Hz, 1H), 7.58 (d, J = 9.1 Hz, 1H), 6.76 (d, J = 2.2 Hz, 1H), 3.67 (t, J = 4.8 Hz, 4H), 3.14-3.07 (m, 4H), 2.60 (s, 3H). |
| 36 | 4-(1-(8-chloroquinolin-4-yl)-2-isopropyl-4-(4H-1,2,4-triazol-3-yl)-1H-benzo[d]imidazol-6-yl)morpholine | 474.2 | 1H NMR (400 MHz, DMSO-d6) δ 9.32 (dd, J = 4.5, 0.8 Hz, 1H), 8.33 (s, 1H), 8.11 (dd, J = 7.5, 1.1 Hz, 1H), 8.04 (d, J = 4.5 Hz, 1H), 7.64 (d, J = 2.7 Hz, 1H), 7.60 (d, J = 8.0 Hz, 1H), 7.23 (d, J = 8.4 Hz, 1H), 6.58 (s, 1H), 3.65 (t, J = 4.7 Hz, 4H), 3.01 (s, 4H), 2.85-2.78 (m, 1H), 1.33 (d, J = 6.8 Hz, 3H), 1.19 (d, J = 6.8 Hz, 3H). |
| 37 | 4-(1-(5-fluoro-8-methylquinolin-4-yl)-2-propyl-4-(4H-1,2,4-triazol-3-yl)-1H-benzo[d]imidazol-6-yl)morpholine | 472.25 | 1H NMR (400 MHz, DMSO-d6) δ 9.34 (d, J = 4.5 Hz, 1H), 8.72 (s, 1H), 8.08 (d, J = 4.5 Hz, 1H), 7.84-7.77 (m, 2H), 7.42 (dd, J = 12.5, 8.1 Hz, 1H), 6.76 (d, J = 2.3 Hz, 1H), 3.67 (t, J = 4.8 Hz, 4H), 3.10 (t, J = 4.9 Hz, 4H), 2.88 (q, J = 6.8 Hz, 2H), 2.82 (s, 3H), 1.55 (d, J = 8.2 Hz, 2H), 0.80 (t, J = 7.3 Hz, 3H). |
| 38 | 4-(1-(8-chloro-7-fluoroquinolin-4-yl)-2-cyclopropyl-4-(4H-1,2,4-triazol-3-yl)-1H-benzo[d]imidazol-6-yl)morpholine | 490.28 | 1H NMR (400 MHz, DMSO-d6) δ 9.36 (dd, J = 4.6, 3.3 Hz, 1H), 8.31 (s, 1H), 8.02 (d, J = 4.6 Hz, 1H), 7.79-7.72 (m, 1H), 7.63 (d, J = 2.3 Hz, 1H), 7.46 (dd, J = 9.4, 5.6 Hz, 1H), 6.66 (d, J = 2.2 Hz, 1H), 3.69-3.64 (m, 4H), 3.03 (dd, J = 6.2, 3.6 Hz, 4H), 1.64 (tt, J = 8.5, 4.8 Hz, 1H), 1.48-1.30 (m, 2H), 1.00-0.80 (m, 2H). |
| 39 | 4-(1-(8-chloro-7-fluoroquinolin-4-yl)-2-methyl-4-(4H-1,2,4-triazol-3-yl)-1H-benzo[d]imidazol-6-yl)morpholine | 464.2 | 1H NMR (400 MHz, DMSO-d6) δ 9.41 (t, J = 4.2 Hz, 1H), 8.73 (s, 1H), 8.09 (t, J = 4.2 Hz, 1H), 7.84-7.77 (m, 2H), 7.70 (s, 1H), 6.73 (d, J = 2.4 Hz, 1H), 3.67 (d, J = 4.6 Hz, 4H), 3.08 (s, 4H), 2.58 (d, J = 3.6 Hz, 3H). |
| 40 | 4-(1-(8-chloro-7-fluoroquinolin-4-yl)-4-(5-methyl-4H-1,2,4-triazol-3-yl)-1H-benzo[d]imidazol-6-yl)morpholine | 464.2 | 1H NMR (400 MHz, DMSO-d6) δ 9.33 (d, J = 4.6 Hz, 1H), 9.05 (s, 1H), 8.02 (d, J = 4.6 Hz, 1H), 7.80 (t, J = 9.1 Hz, 1H), 7.74 (d, J = 2.1 Hz, 1H), 7.68 (dd, J = 9.4, 5.6 Hz, 1H), 6.86 (d, J = 2.3 Hz, 1H), 3.69 (t, J = 4.8 Hz, 4H), 3.09 (s, 4H), 2.48 (s, 3H). |
| 41 | 4-(2-propyl-1-(quinolin-4-yl)-4-(4H-1,2,4-triazol-3-yl)-1H-benzo[d]imidazol-6-yl)morpholine | 440.3 | 1H NMR (400 MHz, DMSO-d6) δ 9.25 (d, J = 4.5 Hz, 1H), 8.64 (s, 1H), 8.30 (ddd, J = 8.5, 1.2, 0.6 Hz, 1H), 7.99 (d, J = 4.5 Hz, 1H), 7.95 (ddd, J = 8.5, 6.9, 1.4 Hz, 1H), 7.79 (d, J = 2.2 Hz, 1H), 7.67 (ddd, J = 8.2, 6.9, 1.2 Hz, 1H), 7.46 (d, J = 8.3 Hz, 1H), 6.59 (d, J = 2.3 Hz, 1H), 3.66 (t, J = 4.8 Hz, 4H), 3.05 (q, J = 4.3 Hz, 4H), 2.81 (tq, J = 14.9, 7.4 Hz, 2H), 1.55 (dt, J = 16.7, 7.5 Hz, 2H), 0.77 (t, J = 7.4 Hz, 3H). |
| 42 | 4-(1-(8-fluoroquinolin-4-yl)-2-(2-methoxyethyl)-4-(4H-1,2,4-triazol-3-yl)-1H-benzo[d]imidazol-6-yl)morpholine | 474.2 | 1H NMR (400 MHz, DMSO-d6) δ 9.28 (d, J = 4.5 Hz, 1H), 8.58 (s, 1H), 8.03 (d, J = 4.5 Hz, 1H), 7.82-7.72 (m, 2H), 7.64 (td, J = 8.2, 5.0 Hz, 1H), 7.20 (d, J = 8.5 Hz, 1H), 6.64 (d, J = 2.3 Hz, 1H), 3.66 (t, J = 4.8 Hz, 4H), 3.57 (ddd, J = 16.0, 10.4, 6.4 Hz, 2H), 3.09 (d, J = 5.3 Hz, 2H), 3.05 (q, J = 4.4 Hz, 4H), 2.98 (s, 3H). |
| 43 | 4-(1-(5-fluoro-8-methylquinolin-4-yl)-4-(5-methyl-4H-1,2,4-triazol-3-yl)-2-propyl-1H-benzo[d]imidazol-6-yl)morpholine | 486.31 | 1H NMR (400 MHz, DMSO-d6) δ 9.35 (dd, J = 4.4, 0.9 Hz, 1H), 8.11 (dd, J = 4.5, 0.9 Hz, 1H), 7.84-7.76 (m, 1H), 7.46-7.39 (m, 1H), 6.76 (dd, J = 2.3, 0.9 Hz, 1H), 3.66 (t, J = 4.8 Hz, 4H), 3.09 (t, J = 5.0 Hz, 4H), 2.92 (q, J = 8.1 Hz, 2H), 2.85-2.79 (m, 3H), 2.55 (d, J = 0.9 Hz, 3H), 1.52 (dt, J = 13.7, 6.9 Hz, 2H), 0.85-0.75 (m, 3H). |

-continued

| Compound | Compound Name | MS | NMR |
|---|---|---|---|
| 44 | 4-(1-(5,8-difluoroquinolin-4-yl)-4-(5-methyl-4H-1,2,4-triazol-3-yl)-1H-benzo[d]imidazol-6-yl)morpholine | 448.2 | 1H NMR (400 MHz, DMSO-d6) δ 9.27 (d, J = 4.7 Hz, 1H), 8.05 (d, J = 5.4 Hz, 1H), 7.85-7.77 (m, 2H), 7.71 (d, J = 2.6 Hz, 1H), 7.56-7.46 (m, 1H), 6.95 (d, J = 2.8 Hz, 1H), 3.72-3.68 (m, 4H), 3.11 (s, 4H), 2.47 (s, 3H). |
| 45 | 4-(1-(5,8-difluoroquinolin-4-yl)-2-propyl-4-(4H-1,2,4-triazol-3-yl)-1H-benzo[d]imidazol-6-yl)morpholine | 476.3 | 1H NMR (400 MHz, DMSO-d6) δ 9.37 (t, J = 4.0 Hz, 1H), 8.70 (s, 1H), 8.17 (t, J = 4.0 Hz, 1H), 7.88-7.77 (m, 2H), 7.58-7.48 (m, 1H), 6.85-6.82 (m, 1H), 3.73-3.63 (m, 4H), 3.10 (d, J = 3.9 Hz, 4H), 2.90 (s, 2H), 1.64-1.52 (m, 2H), 0.82 (td, J = 7.3, 3.4 Hz, 3H). |
| 46 | 4-(1-(8-chloroquinolin-4-yl)-4-(5-methyl-4H-1,2,4-triazol-3-yl)-2-propyl-1H-benzo[d]imidazol-6-yl)morpholine | 488.2 | 1H NMR (400 MHz, DMSO-d6) δ 9.37 (dd, J = 4.6, 0.8 Hz, 1H), 8.16-8.11 (m, 2H), 7.77 (d, J = 2.4 Hz, 1H), 7.63 (ddd, J = 8.3, 7.4, 0.7 Hz, 1H), 7.49 (d, J = 8.4 Hz, 1H), 6.69-6.64 (m, 1H), 3.65 (t, J = 4.8 Hz, 4H), 3.05 (d, J = 3.0 Hz, 4H), 2.93-2.81 (m, 2H), 2.54 (s, 3H), 1.60-1.43 (m, 2H), 0.80-0.73 (m, 3H). |
| 47 | 4-(1-(8-chloroquinolin-4-yl)-2-cyclopropyl-4-(5-methyl-4H-1,2,4-triazol-3-yl)-1H-benzo[d]imidazol-6-yl)morpholine | 486.2 | 1H NMR (400 MHz, DMSO-d6) δ 9.34 (dd, J = 7.9, 4.5 Hz, 1H), 8.13 (s, 1H), 8.04 (s, 1H), 7.69-7.57 (m, 2H), 7.37 (d, J = 9.0 Hz, 1H), 6.67 (s, 1H), 3.67 (d, J = 7.7 Hz, 4H), 3.04 (s, 4H), 2.47 (s, 3H), 1.66 (s, 1H), 1.37 (d, J = 33.2 Hz, 2H), 0.91 (d, J = 42.9 Hz, 2H). |
| 48 | 4-(1-(8-chloro-5-fluoroquinolin-4-yl)-2-propyl-4-(4H-1,2,4-triazol-3-yl)-1H-benzo[d]imidazol-6-yl)morpholine | 492.2 | 1H NMR (400 MHz, DMSO-d6) δ 9.42 (d, J = 4.5 Hz, 1H), 8.63 (s, 1H), 8.15 (td, J = 5.5, 3.8 Hz, 2H), 7.75 (s, 1H), 7.53 (dd, J = 11.9, 8.5 Hz, 1H), 6.82 (d, J = 2.2 Hz, 1H), 3.67 (t, J = 4.9 Hz, 4H), 3.09 (t, J = 4.9 Hz, 4H), 2.84 (d, J = 10.0 Hz, 2H), 1.64-1.53 (m, 2H), 0.81 (t, J = 7.3 Hz, 3H). |
| 49 | 4-(1-(7,8-difluoroquinolin-4-yl)-2-propyl-4-(4H-1,2,4-triazol-3-yl)-1H-benzo[d]imidazol-6-yl)morpholine | 476.2 | 1H NMR (400 MHz, DMSO-d6) δ 9.33 (d, J = 4.5 Hz, 1H), 8.62 (s, 1H), 8.08 (d, J = 4.5 Hz, 1H), 7.85-7.73 (m, 2H), 7.44-7.36 (m, 1H), 6.65 (d, J = 2.3 Hz, 1H), 3.66 (t, J = 4.8 Hz, 4H), 3.10-3.02 (m, 4H), 2.83 (t, J = 7.7 Hz, 2H), 1.65-1.48 (m, 2H), 0.79 (t, J = 7.4 Hz, 3H). |
| 50 | 4-(1-(8-chloroquinolin-4-yl)-2-isobutyl-4-(4H-1,2,4-triazol-3-yl)-1H-benzo[d]imidazol-6-yl)morpholine | 488.2 | 1H NMR (400 MHz, DMSO-d6) δ 9.35 (d, J = 4.5 Hz, 1H), 8.55 (s, 1H), 8.13 (dd, J = 7.5, 1.3 Hz, 1H), 8.07 (d, J = 4.5 Hz, 1H), 7.74 (s, 1H), 7.62 (dd, J = 8.5, 7.5 Hz, 1H), 7.38 (d, J = 8.0 Hz, 1H), 6.64 (s, 1H), 3.65 (t, J = 4.7 Hz, 4H), 3.04 (d, J = 5.7 Hz, 4H), 2.67 (s, 2H), 2.54 (s, 1H), 0.79 (d, J = 6.6 Hz, 3H), 0.75 (d, J = 6.6 Hz, 3H). |
| 51 | 4-(1-(5,8-difluoroquinolin-4-yl)-2-methyl-4-(5-methyl-4H-1,2,4-triazol-3-yl)-1H-benzo[d]imidazol-6-yl)morpholine | 462.2 | 1H NMR (400 MHz, DMSO-d6) δ 9.38 (d, J = 4.5 Hz, 1H), 8.14 (d, J = 4.5 Hz, 1H), 7.90-7.74 (m, 2H), 7.62-7.49 (m, 1H), 6.87-6.83 (m, 1H), 3.70-3.64 (m, 4H), 3.11 (t, J = 4.9 Hz, 4H), 2.63 (s, 3H), 2.55-2.53 (m, 3H). |
| 52 | 4-(1-(8-chloro-7-fluoroquinolin-4-yl)-2-methyl-4-(5-methyl-4H-1,2,4-triazol-3-yl)-1H-benzo[d]imidazol-6-yl)morpholine | 478.2 | 1H NMR (400 MHz, DMSO-d6) δ 9.40 (d, J = 4.5 Hz, 1H), 8.08 (d, J = 4.6 Hz, 1H), 7.83-7.75 (m, 2H), 7.70 (d, J = 6.7 Hz, 1H), 6.70 (d, J = 2.2 Hz, 1H), 3.65 (d, J = 4.8 Hz, 4H), 3.06 (s, 4H), 2.58 (s, 3H), 2.53 (s, 3H). |
| 53 | 4-(1-(7-fluoroquinolin-4-yl)-4-(4H-1,2,4-triazol-3-yl)-1H-benzo[d]imidazol-6-yl)morpholine | 416.32 | 1H NMR (400 MHz, DMSO-d6) δ 9.22 (dd, J = 4.6, 1.6 Hz, 1H), 9.17 (s, 1H), 8.53 (s, 1H), 8.05 (dd, J = 10.1, 2.4 Hz, 1H), 7.92 (dd, J = 4.6, 1.6 Hz, 1H), 7.82 (d, J = 2.2 Hz, 1H), 7.74 (dd, J = 9.3, 6.0 Hz, 1H), 7.69-7.62 (m, 1H), 6.85 (s, 1H), 3.70 (t, J = 4.9 Hz, 4H), 3.11 (s, 4H). |

-continued

| Compound | Compound Name | MS | NMR |
|---|---|---|---|
| 54 | 4-(1-(8-chloroquinolin-4-yl)-2-(1-fluorocyclopropyl)-4-(4H-1,2,4-triazol-3-yl)-1H-benzo[d]imidazol-6-yl)morpholine | 490.2 | 1H NMR (400 MHz, DMSO-d6) δ 9.30 (d, J = 4.5 Hz, 1H), 8.36 (s, 1H), 8.09 (dd, J = 7.5, 1.2 Hz, 1H), 8.04 (d, J = 4.5 Hz, 1H), 7.70 (d, J = 2.3 Hz, 1H), 7.60 (dd, J = 8.5, 7.5 Hz, 1H), 7.32 (dd, J = 8.5, 1.3 Hz, 1H), 6.61 (d, J = 2.3 Hz, 1H), 3.66 (t, J = 4.7 Hz, 4H), 3.04 (td, J = 4.3, 2.2 Hz, 4H), 1.70 (dddd, J = 14.5, 11.2, 8.5, 3.3 Hz, 2H), 1.43-1.17 (m, 2H). |
| 55 | 4-[3-(2-ethyl-3-methylquinolin-4-yl)-2-methyl-7-(4H-1,2,4-triazol-3-yl)benzimidazol-5-yl]morpholine | 454.2 | 1H NMR (400 MHz, DMSO-d6) δ 8.77 (s, 1H), 8.14 (dt, J = 8.2, 0.9 Hz, 1H), 7.83 (d, J = 2.2 Hz, 1H), 7.79 (ddd, J = 8.4, 7.0, 1.4 Hz, 1H), 7.51 (ddd, J = 8.3, 6.9, 1.2 Hz, 1H), 7.25-7.18 (m, 1H), 6.62 (d, J = 2.2 Hz, 1H), 3.63 (t, J = 4.8 Hz, 4H), 3.17-3.00 (m, 6H), 2.48 (s, 3H), 2.10 (s, 3H), 1.41 (t, J = 7.4 Hz, 3H). |
| 56 | 4-[3-(2-cyclopropyl-3-methylquinolin-4-yl)-2-methyl-7-(4H-1,2,4-triazol-3-yl)benzimidazol-5-yl]morpholine | 466.2 | 1H NMR (400 MHz, DMSO-d6) δ 8.81 (s, 1H), 8.01 (dt, J = 8.4, 0.9 Hz, 1H), 7.85 (d, J = 2.2 Hz, 1H), 7.74 (ddd, J = 8.4, 6.9, 1.4 Hz, 1H), 7.45 (ddd, J = 8.2, 6.9, 1.2 Hz, 1H), 7.22-7.15 (m, 1H), 6.67 (d, J = 2.2 Hz, 1H), 3.64 (t, J = 4.8 Hz, 4H), 3.09 (td, J = 4.2, 2.0 Hz, 4H), 2.55-2.49 (m, 1H), 2.51 (s, 3H), 2.23 (s, 3H), 1.40-1.06 (m, 4H). |
| 57 | 4-[2-methyl-7-(4H-1,2,4-triazol-3-yl)-3-[2-(4H-1,2,4-triazol-3-yl)quinolin-4-yl]benzimidazol-5-yl]morpholine | 479.2 | 1H NMR (400 MHz, DMSO-d6) δ 8.80 (br s, 1H), 8.65 (s, 1H), 8.57 (br s, 2H), 8.33 (dt, J = 8.5, 0.9 Hz, 1H), 7.97 (ddd, J = 8.4, 6.8, 1.5 Hz, 1H), 7.83 (d, J = 2.2 Hz, 1H), 7.67 (ddd, J = 8.2, 6.9, 1.2 Hz, 1H), 7.62-7.56 (m, 1H), 6.77 (d, J = 2.2 Hz, 1H), 3.61 (t, J = 4.8 Hz, 4H), 3.05 (q, J = 4.5 Hz, 4H), 2.60 (s, 3H). |
| 58 | 4-[3-[8-chloro-2-(trifluoromethyl)quinolin-4-yl]-2-methyl-7-(4H-1,2,4-triazol-3-yl)benzimidazol-5-yl]morpholine | 514.1 | 1H NMR (400 MHz, DMSO-d6) δ 8.75 (br s, 1H), 8.61 (s, 1H), 8.27 (dd, J = 7.5, 1.2 Hz, 1H), 7.83-7.72 (m, 2H), 7.72-7.63 (m, 1H), 6.82 (d, J = 2.2 Hz, 1H), 3.63 (t, J = 4.8 Hz, 4H), 3.04 (q, J = 4.4 Hz, 4H), 2.59 (s, 3H). |
| 59 | 4-[2-methyl-3-(2-phenylquinolin-4-yl)-7-(4H-1,2,4-triazol-3-yl)benzimidazol-5-yl]morpholine | 488.2 | 1H NMR (400 MHz, DMSO-d6) δ 8.81 (br s, 1H), 8.65 (s, 1H), 8.36-8.27 (m, 3H), 7.93 (ddd, J = 8.4, 6.5, 1.8 Hz, 1H), 7.85 (d, J = 2.2 Hz, 1H), 7.67-7.49 (m, 6H), 6.75 (d, J = 2.2 Hz, 1H), 3.62 (t, J = 4.9 Hz, 4H), 3.13-2.98 (m, 4H), 2.65 (s, 3H). |
| 60 | 4-[2-methyl-3-[2-methyl-8-(trifluoromethyl)quinolin-4-yl]-7-(4H-1,2,4-triazol-3-yl)benzimidazol-5-yl]morpholine | 494.2 | 1H NMR (400 MHz, DMSO-d6) δ 8.68 (s, 1H), 8.30-8.23 (m, 1H), 7.98 (s, 1H), 7.83-7.72 (m, 2H), 7.67 (t, J = 7.9 Hz, 1H), 6.73 (d, J = 2.2 Hz, 1H), 3.63 (t, J = 4.8 Hz, 4H), 3.13-2.96 (m, 4H), 2.82 (s, 3H), 2.54 (s, 3H). |
| 61 | 4-[3-(8-fluoro-2,3-dimethylquinolin-4-yl)-2-methyl-7-(4H-1,2,4-triazol-3-yl)benzimidazol-5-yl]morpholine | 458.2 | 1H NMR (400 MHz, DMSO-d6) δ 8.71 (s, 1H), 7.85-7.77 (m, 1H), 7.70-7.59 (m, 1H), 7.50 (td, J = 8.1, 4.9 Hz, 1H), 7.03 (d, J = 8.2 Hz, 1H), 6.69 (d, J = 2.2 Hz, 1H), 3.67 (t, J = 4.8 Hz, 4H), 3.09 (dt, J = 4.4, 2.5 Hz, 4H), 2.84 (s, 3H), 2.49 (s, 3H), 2.13 (s, 3H). |
| 62 | 4-[3-(3-ethyl-2-methylquinolin-4-yl)-2-methyl-7-(4H-1,2,4-triazol-3-yl)benzimidazol-5-yl]morpholine | 454.26 | 1H NMR (400 MHz, DMSO-d6) δ 8.74 (br s, 1H), 8.18-8.09 (m, 1H), 7.88-7.75 (m, 2H), 7.53 (ddd, J = 8.2, 6.9, 1.2 Hz, 1H), 7.12 (d, J = 8.3 Hz, 1H), 6.70 (d, J = 2.2 Hz, 1H), 3.66 (t, J = 4.8 Hz, 4H), 3.09 (q, J = 4.1 Hz, 4H), 2.88 (s, 3H), 2.63-2.52 (m, 2H), 2.48 (s, 3H), 1.01 (t, J = 7.5 Hz, 3H). |

| Compound | Compound Name | MS | NMR |
|---|---|---|---|
| 63 | 4-[3-(7-fluoro-2-methylquinolin-4-yl)-2-methyl-7-(4H-1,2,4-triazol-3-yl)benzimidazol-5-yl]morpholine | 444.2 | 1H NMR (400 MHz, DMSO-d6) δ 8.75 (br s, 1H), 7.96 (dd, J = 10.2, 2.6 Hz, 1H), 7.88-7.79 (m, 2H), 7.69-7.57 (m, 1H), 7.53 (td, J = 8.8, 2.6 Hz, 1H), 6.67 (d, J = 2.2 Hz, 1H), 3.67 (t, J = 4.8 Hz, 4H), 3.08 (q, J = 4.7 Hz, 4H), 2.80 (s, 3H), 2.58 (s, 3H). |
| 64 | 4-[3-(8-chloro-2-methylquinolin-4-yl)-2-methyl-7-(4H-1,2,4-triazol-3-yl)benzimidazol-5-yl]morpholine | 460.2 | 1H NMR (400 MHz, DMSO-d6) δ 8.78 (s, 1H), 8.11-8.03 (m, 1H), 7.98 (s, 1H), 7.83 (d, J = 2.2 Hz, 1H), 7.55 (dd, J = 8.4, 7.3 Hz, 1H), 7.52-7.44 (m, 1H), 6.74 (d, J = 2.2 Hz, 1H), 3.66 (t, J = 4.8 Hz, 4H), 3.16-3.00 (m, 4H), 2.85 (s, 3H), 2.60 (s, 3H). |
| 65 | 4-[2-methyl-3-(3-methylquinolin-4-yl)-7-(4H-1,2,4-triazol-3-yl)benzimidazol-5-yl]morpholine | 426.2 | 1H NMR (400 MHz, DMSO-d6) δ 9.20 (s, 1H), 8.78 (s, 1H), 8.29-8.21 (m, 1H), 7.92-7.81 (m, 2H), 7.63 (ddd, J = 8.2, 6.9, 1.2 Hz, 1H), 7.43-7.35 (m, 1H), 6.68 (d, J = 2.2 Hz, 1H), 3.67 (t, J = 4.9 Hz, 4H), 3.17-3.05 (m, 4H), 2.52 (s, 3H), 2.23 (s, 3H). |
| 66 | 4-[3-(3-cyclopropylquinolin-4-yl)-2-methyl-7-(4H-1,2,4-triazol-3-yl)benzimidazol-5-yl]morpholine | 452.2 | 1H NMR (400 MHz, DMSO-d6) δ 8.88 (s, 1H), 8.76 (br s, 1H), 8.26-8.19 (m, 1H), 7.89-7.80 (m, 2H), 7.62 (ddd, J = 8.2, 6.9, 1.2 Hz, 1H), 7.35 (d, J = 8.3 Hz, 1H), 6.70 (d, J = 2.2 Hz, 1H), 3.74-3.55 (m, 4H), 3.10 (t, J = 4.8 Hz, 4H), 2.56 (s, 3H), 1.65-1.56 (m, 1H), 1.11-1.03 (m, 2H), 1.00-0.81 (m, 2H). |
| 67 | 4-[2-methyl-6-morpholin-4-yl-4-(4H-1,2,4-triazol-3-yl)benzimidazol-1-yl]quinoline-2-carbonitrile | 437.1 | 1H NMR (400 MHz, DMSO-d6) δ 8.63 (br s, 1H), 8.51 (s, 1H), 8.45-8.38 (m, 1H), 8.10 (ddd, J = 8.5, 6.9, 1.3 Hz, 1H), 7.85 (ddd, J = 8.4, 6.8, 1.1 Hz, 1H), 7.77 (s, 1H), 7.63 (d, J = 8.4 Hz, 1H), 6.76 (d, J = 2.2 Hz, 1H), 3.67 (t, J = 4.9 Hz, 4H), 3.07 (q, J = 5.0 Hz, 4H), 2.53 (d, J = 17.6 Hz, 3H). |
| 68 | 4-[3-(8-chloro-3-methylquinolin-4-yl)-2-methyl-7-(4H-1,2,4-triazol-3-yl)benzimidazol-5-yl]morpholine | 460.1 | 1H NMR (400 MHz, DMSO-d6) δ 9.29 (s, 1H), 8.69 (br s, 1H), 8.05 (dd, J = 7.5, 1.2 Hz, 1H), 7.80 (d, J = 2.2 Hz, 1H), 7.58 (dd, J = 8.4, 7.6 Hz, 1H), 7.32 (d, J = 8.2 Hz, 1H), 6.70 (d, J = 2.2 Hz, 1H), 3.71-3.61 (m, 4H), 3.13-3.06 (m, 4H), 2.49 (s, 3H), 2.23 (s, 3H). |
| 69 | 4-[2-methyl-3-(2-methylquinolin-4-yl)-7-(4H-1,2,4-triazol-3-yl)benzimidazol-5-yl]morpholine | 426.2 | 1H NMR (400 MHz, DMSO-d6) δ 13.94 (s, 1H), 11.95 (s, 1H), 8.18-8.09 (m, 2H), 7.84 (ddd, J = 8.4, 7.0, 1.4 Hz, 1H), 7.78-7.73 (m, 1H), 7.62-7.51 (m, 2H), 7.19 (dd, J = 8.2, 1.3 Hz, 1H), 6.54 (s, 1H), 3.66 (t, J = 4.8 Hz, 4H), 3.07-2.94 (m, 4H), 2.80 (s, 3H), 2.37 (s, 3H), 1.91 (s, 3H). |
| 70 | 4-[3-(8-chloro-2,3-dimethylquinolin-4-yl)-2-methyl-7-(4H-1,2,4-triazol-3-yl)benzimidazol-5-yl]morpholine | 474.16 | 1H NMR (400 MHz, DMSO-d6) δ 8.75 (s, 1H), 7.99 (dd, J = 7.6, 1.2 Hz, 1H), 7.84 (d, J = 2.2 Hz, 1H), 7.49 (dd, J = 8.3, 7.6 Hz, 1H), 7.21 (dd, J = 8.4, 1.2 Hz, 1H), 6.70 (d, J = 2.2 Hz, 1H), 3.67 (t, J = 4.8 Hz, 4H), 3.16-3.04 (m, 4H), 2.86 (s, 3H), 2.51 (s, 3H), 2.13 (s, 3H). |
| 71 | 4-[3-(3-ethyl-2-methylquinolin-4-yl)-7-(4H-1,2,4-triazol-3-yl)benzimidazol-5-yl]morpholine | 440.2 | 1H NMR (400 MHz, DMSO-d6) δ 9.10 (s, 1H), 8.51 (s, 1H), 8.16-8.09 (m, 1H), 7.85-7.76 (m, 2H), 7.52 (ddd, J = 8.2, 6.7, 1.2 Hz, 1H), 7.02 (dd, J = 8.3, 0.9 Hz, 1H), 6.67 (d, J = 2.2 Hz, 1H), 3.67 (dd, J = 6.0, 3.6 Hz, 4H), 3.08 (t, J = 4.8 Hz, 4H), 2.87 (s, 3H), 2.67-2.55 (m, 1H), 2.48-2.34 (m, 1H), 1.04 (t, J = 7.5 Hz, 3H). |
| 72 | 4-[3-(2-ethyl-3-methylquinolin-4-yl)-7-(4H-1,2,4-triazol-3-yl)benzimidazol-5-yl]morpholine | 440.2 | 1H NMR (400 MHz, DMSO-d6) δ 9.36 (s, 1H), 8.67 (s, 1H), 8.20-8.13 (m, 1H), 7.88 (d, J = 2.3 Hz, 1H), 7.81 (ddd, J = 8.4, 6.9, 1.4 Hz, 1H), 7.54 (ddd, J = 8.2, 6.9, 1.2 Hz, 1H), 7.22-7.15 (m, 1H), 6.72 (d, J = 2.2 Hz, 1H), 3.68 (t, J = 4.8 Hz, 4H), 3.22-3.06 (m, 6H), 2.16 (s, 3H), 1.43 (t, J = 7.4 Hz, 3H). |

| Compound | Compound Name | MS | NMR |
|---|---|---|---|
| 73 | 4-[2-methyl-3-(2-methylquinolin-4-yl)-7-(3-methyl-1H-1,2,4-triazol-5-yl)benzimidazol-5-yl]morpholine | 440.2 | 1H NMR (400 MHz, DMSO-d6) δ 8.20 (d, J = 8.5 Hz, 1H), 7.95-7.86 (m, 2H), 7.82 (d, J = 2.0 Hz, 1H), 7.65-7.57 (m, 1H), 7.56-7.50 (m, 1H), 6.69-6.63 (m, 1H), 3.66 (t, J = 4.8 Hz, 4H), 3.15-3.00 (m, 4H), 2.81 (s, 3H), 2.62 (s, 3H), 2.56 (s, 3H). |
| 74 | 4-[2-methyl-3-(3-methylquinolin-4-yl)-7-(3-methyl-1H-1,2,4-triazol-5-yl)benzimidazol-5-yl]morpholine | 440.2 | 1H NMR (400 MHz, DMSO-d6) δ 9.20 (s, 1H), 8.26 (d, J = 8.7 Hz, 1H), 7.92-7.84 (m, 1H), 7.84-7.79 (m, 1H), 7.70-7.58 (m, 1H), 7.44-7.36 (m, 1H), 6.67 (d, J = 2.4 Hz, 1H), 3.66 (t, J = 4.7 Hz, 4H), 3.10 (dd, J = 6.3, 3.7 Hz, 4H), 2.56 (s, 3H), 2.54 (s, 3H), 2.23 (s, 3H). |
| 75 | 4-[3-(3-ethyl-2-methylquinolin-4-yl)-7-(3-methyl-1H-1,2,4-triazol-5-yl)benzimidazol-5-yl]morpholine | 454.29 | 1H NMR (400 MHz, DMSO-d6) δ 9.15 (s, 1H), 8.12 (d, J = 8.0 Hz, 1H), 7.80 (t, J = 7.8 Hz, 1H), 7.76 (d, J = 2.2 Hz, 1H), 7.56-7.47 (m, 1H), 7.02 (d, J = 8.4 Hz, 1H), 6.68 (d, J = 2.2 Hz, 1H), 3.70-3.63 (m, 4H), 3.09-3.03 (m, 4H), 2.87 (s, 3H), 2.65-2.57 (m, 1H), 2.45-2.35 (m, 1H), 1.04 (t, J = 7.5 Hz, 3H). |
| 76 | 4-[3-(2-ethyl-3-methylquinolin-4-yl)-2-methyl-7-(3-methyl-1H-1,2,4-triazol-5-yl)benzimidazol-5-yl]morpholine | 468.3 | 1H NMR (400 MHz, DMSO-d6) δ 8.17 (d, J = 8.4 Hz, 1H), 7.86-7.76 (m, 2H), 7.58-7.49 (m, 1H), 7.21 (d, J = 8.3 Hz, 1H), 6.61 (s, 1H), 3.66 (t, J = 4.8 Hz, 4H), 3.18-3.10 (m, 2H), 3.10-3.03 (m, 4H), 2.54 (s, 3H), 2.13 (s, 3H), 1.45 (t, J = 7.4 Hz, 3H). |
| 77 | 4-[2-methyl-7-(3-methyl-1H-1,2,4-triazol-5-yl)-3-[2-methyl-8-(trifluoromethyl)quinolin-4-yl]benzimidazol-5-yl]morpholine | 508.33 | 1H NMR (400 MHz, DMSO-d6) δ 8.31 (d, J = 7.3 Hz, 1H), 8.02 (s, 1H), 7.82 (d, J = 8.5 Hz, 1H), 7.78 (d, J = 2.2 Hz, 1H), 7.70 (t, J = 7.9 Hz, 1H), 6.75 (d, J = 2.2 Hz, 1H), 3.66 (t, J = 4.8 Hz, 4H), 3.15-3.00 (m, 4H), 2.85 (s, 3H), 2.59 (s, 3H), 2.54 (s, 3H). |
| 78 | 4-[3-(8-chloro-3-methylquinolin-4-yl)-2-methyl-7-(3-methyl-1H-1,2,4-triazol-5-yl)benzimidazol-5-yl]morpholine | 474.25 | 1H NMR (400 MHz, DMSO-d6) δ 9.29 (s, 1H), 8.05 (d, J = 7.6 Hz, 1H), 7.76 (s, 1H), 7.58 (t, J = 8.0 Hz, 1H), 7.32 (d, J = 8.4 Hz, 1H), 6.69 (d, J = 2.2 Hz, 1H), 3.66 (t, J = 4.9 Hz, 4H), 3.08 (t, J = 4.9 Hz, 4H), 2.53 (s, 3H), 2.23 (s, 3H). |
| 79 | 4-[3-(7-fluoro-2-methylquinolin-4-yl)-2-methyl-7-(3-methyl-1H-1,2,4-triazol-5-yl)benzimidazol-5-yl]morpholine | 458.29 | 1H NMR (400 MHz, DMSO-d6) δ 7.97 (dd, J = 10.2, 2.5 Hz, 1H), 7.86 (s, 1H), 7.80 (d, J = 2.3 Hz, 1H), 7.69-7.61 (m, 1H), 7.53 (td, J = 8.8, 2.6 Hz, 1H), 6.66 (d, J = 2.3 Hz, 1H), 3.66 (t, J = 4.8 Hz, 4H), 3.15-2.98 (m, 4H), 2.80 (s, 3H), 2.61 (s, 3H), 2.54 (s, 3H). |
| 80 | 4-[3-(2-ethyl-8-fluoro-3-methylquinolin-4-yl)-2-methyl-7-(3-methyl-1H-1,2,4-triazol-5-yl)benzimidazol-5-yl]morpholine | 486.3 | 1H NMR (400 MHz, DMSO-d6) δ 7.75 (s, 1H), 7.69-7.60 (m, 1H), 7.50 (td, J = 8.0, 4.8 Hz, 1H), 7.00 (d, J = 8.5 Hz, 1H), 6.65 (s, 1H), 3.66 (t, J = 4.8 Hz, 4H), 3.15 (q, J = 15.0, 7.8 Hz, 2H), 3.10-3.04 (m, 4H), 2.52 (s, 3H), 2.47 (s, 3H), 2.13 (s, 3H), 1.45 (t, J = 7.3 Hz, 3H). |
| 81 | 4-[3-(5-fluoroquinolin-4-yl)-2-methyl-7-(4H-1,2,4-triazol-3-yl)benzimidazol-5-yl]morpholine | 430.2 | 1H NMR (400 MHz, DMSO-d6) δ 9.31 (d, J = 4.5 Hz, 1H), 8.20-8.16 (m, 1H), 8.00 (d, J = 4.5 Hz, 1H), 7.94 (td, J = 8.3, 5.8 Hz, 1H), 7.78 (s, 1H), 7.52 (dd, J = 12.4, 7.9 Hz, 1H), 6.80 (d, J = 2.2 Hz, 1H), 3.67 (t, J = 4.8 Hz, 4H), 3.10 (t, J = 5.0 Hz, 4H), 2.57 (s, 3H). |
| 82 | 4-[3-[8-(difluoromethyl)quinolin-4-yl]-2-methyl-7-(4H-1,2,4-triazol-3-yl)benzimidazol-5-yl]morpholine | 462.1 | 1H NMR (400 MHz, DMSO-d6) δ 9.34 (d, J = 4.5 Hz, 1H), 8.20 (d, J = 7.0 Hz, 1H), 8.14-7.82 (m, 2H), 7.82-7.71 (m, 3H), 6.68 (d, J = 2.2 Hz, 1H), 3.64 (t, J = 4.7 Hz, 4H), 3.05 (q, J = 4.2 Hz, 4H), 2.53 (d, J = 6.2 Hz, 3H). |
| 83 | 4-[2-methyl-3-(5-methylquinolin-4-yl)-7-(4H-1,2,4-triazol-3-yl)benzimidazol-5-yl]morpholine | 426.2 | 1H NMR (400 MHz, DMSO-d6) δ 9.21 (d, J = 4.4 Hz, 1H), 8.73 (s, 1H), 8.21-8.15 (m, 1H), 7.90-7.80 (m, 3H), 7.57-7.50 (m, 1H), 6.69 (d, J = 2.2 Hz, 1H), 3.67 (t, J = 4.8 Hz, 4H), 3.15-3.07 (m, 4H), 2.55 (s, 3H), 1.82 (s, 3H). |

-continued

| Compound | Compound Name | MS | NMR |
|---|---|---|---|
| 84 | 4-[3-(5-chloroquinolin-4-yl)-2-methyl-7-(4H-1,2,4-triazol-3-yl)benzimidazol-5-yl]morpholine | 446.1 | 1H NMR (400 MHz, DMSO-d6) δ 9.32 (d, J = 4.5 Hz, 1H), 8.83-8.53 (m, 1H), 8.33 (dd, J = 8.5, 1.2 Hz, 1H), 8.01 (d, J = 4.5 Hz, 1H), 7.96-7.90 (m, 1H), 7.84 (dd, J = 7.7, 1.2 Hz, 1H), 7.81-7.77 (m, 1H), 6.77-6.75 (m, 1H), 3.67 (t, J = 4.9 Hz, 4H), 3.11 (t, J = 4.9 Hz, 4H), 2.54 (s, 3H). |
| 85 | 4-[3-[5-(difluoromethyl)quinolin-4-yl]-2-methyl-7-(4H-1,2,4-triazol-3-yl)benzimidazol-5-yl]morpholine | 462.1 | 1H NMR (400 MHz, DMSO-d6) δ 9.29 (d, J = 4.5 Hz, 1H), 8.64 (s, 1H), 8.54-8.48 (m, 1H), 8.13-8.02 (m, 2H), 7.96 (d, J = 4.5 Hz, 1H), 7.77 (d, J = 2.2 Hz, 1H), 6.71 (d, J = 2.2 Hz, 1H), 6.30 (t, J = 54.8 Hz, 1H), 3.65 (t, J = 4.7 Hz, 4H), 3.07 (q, J = 4.0 Hz, 4H), 2.45 (s, 3H). |
| 86 | 4-[3-(8-chloroquinolin-4-yl)-6-fluoro-2-methyl-7-(4H-1,2,4-triazol-3-yl)benzimidazol-5-yl]morpholine | 464.1 | 1H NMR (400 MHz, DMSO-d6) δ 9.33 (d, J = 4.5 Hz, 1H), 8.63 (s, 1H), 8.11 (dd, J = 7.5, 1.2 Hz, 1H), 8.01 (d, J = 4.5 Hz, 1H), 7.61 (dd, J = 8.5, 7.5 Hz, 1H), 7.40 (d, J = 8.4 Hz, 1H), 6.82 (d, J = 6.9 Hz, 1H), 3.65 (t, J = 4.6 Hz, 4H), 2.93-2.76 (m, 4H), 2.42 (s, 3H). |
| 87 | 4-[3-(8-chloro-5-fluoroquinolin-4-yl)-2-methyl-7-(4H-1,2,4-triazol-3-yl)benzimidazol-5-yl]morpholine | 464.1 | 1H NMR (400 MHz, DMSO-d6) δ 9.42 (d, J = 4.5 Hz, 1H), 8.74 (s, 1H), 8.18-8.10 (m, 2H), 7.80 (d, J = 2.2 Hz, 1H), 7.52 (dd, J = 11.9, 8.6 Hz, 1H), 6.87 (d, J = 2.2 Hz, 1H), 3.65 (dd, J = 5.9, 3.7 Hz, 5H), 3.10 (dd, J = 6.1, 3.7 Hz, 4H), 2.61 (s, 3H). |
| 88 | 4-[3-[8-chloro-2-(difluoromethyl)quinolin-4-yl]-7-(4H-1,2,4-triazol-3-yl)benzimidazol-5-yl]morpholine | 482.1 | 1H NMR (400 MHz, DMSO-d6) δ 8.94 (s, 1H), 8.39 (s, 1H), 8.29 (s, 1H), 8.21 (dt, J = 7.5, 1.0 Hz, 1H), 7.75 (s, 1H), 7.72 (d, J = 7.9 Hz, 1H), 7.57 (d, J = 8.5 Hz, 1H), 7.31 (t, J = 54.0 Hz, 1H), 6.86 (d, J = 2.3 Hz, 1H), 3.70-3.64 (m, 4H), 3.10-3.02 (m, 4H). |
| 89 | 4-[2-methyl-6-morpholin-4-yl-4-(4H-1,2,4-triazol-3-yl)benzimidazol-1-yl]quinoline-8-carbonitrile | 437.2 | 1H NMR (400 MHz, DMSO-d6) δ 9.42 (d, J = 4.6 Hz, 1H), 8.56-8.51 (m, 1H), 8.12 (d, J = 4.5 Hz, 1H), 7.86 (s, 1H), 7.82-7.73 (m, 2H), 6.69 (s, 1H), 3.70-3.60 (m, 4H), 3.08-3.00 (m, 4H), 2.48 (s, 3H). |
| 90 | 4-[3-(7-fluoroquinolin-4-yl)-2-methyl-7-(4H-1,2,4-triazol-3-yl)benzimidazol-5-yl]morpholine | 430.2 | 1H NMR (400 MHz, DMSO-d6) δ 9.27 (d, J = 4.5 Hz, 1H), 8.77 (s, 1H), 8.07 (dd, J = 10.0, 2.5 Hz, 1H), 7.95 (d, J = 4.6 Hz, 1H), 7.83 (d, J = 2.2 Hz, 1H), 7.76-7.69 (m, 1H), 7.61 (td, J = 8.7, 2.5 Hz, 1H), 6.66 (d, J = 2.2 Hz, 1H), 3.65 (t, J = 4.7 Hz, 4H), 3.07 (d, J = 3.5 Hz, 4H), 2.58 (s, 3H). |
| 91 | 4-[3-(8-chloroquinolin-4-yl)-4-fluoro-2-methyl-7-(4H-1,2,4-triazol-3-yl)benzimidazol-5-yl]morpholine | 464.2 | 1H NMR (400 MHz, DMSO-d6) δ 9.29 (dd, J = 4.5, 1.6 Hz, 1H), 8.38 (s, 1H), 8.14-8.07 (m, 2H), 7.70-7.59 (m, 3H), 7.41 (dd, J = 8.4, 1.6 Hz, 1H), 3.63 (t, J = 4.3 Hz, 4H), 3.02-2.84 (m, 4H), 2.45 (s, 3H). |
| 92 | 4-[3-[8-(difluoromethyl)quinolin-4-yl]-2-methyl-7-(5-methyl-4H-1,2,4-triazol-3-yl)benzimidazol-5-yl]morpholine | 476.3 | 1H NMR (400 MHz, DMSO-d6) δ 9.35 (dd, J = 4.5, 1.3 Hz, 1H), 8.22-8.18 (d, J = 4.7 Hz, 1H), 8.14-7.83 (m, 2H), 7.83-7.75 (m, 4H), 6.68 (d, J = 2.1 Hz, 1H), 3.64 (t, J = 4.7 Hz, 4H), 3.09-3.00 (m, 4H), 2.57 (d, J = 1.3 Hz, 3H), 2.52 (d, J = 1.4 Hz, 3H). |
| 93 | 4-[2-methyl-3-(5-methylquinolin-4-yl)-7-(5-methyl-4H-1,2,4-triazol-3-yl)benzimidazol-5-yl]morpholine | 440.5 | 1H NMR (400 MHz, DMSO-d6) δ 9.19 (d, J = 4.4 Hz, 1H), 8.16 (d, J = 8.4 Hz, 1H), 7.84 (d, J = 4.4 Hz, 1H), 7.81 (dd, J = 8.5, 7.1 Hz, 1H), 7.75 (s, 1H), 7.51 (d, J = 7.2 Hz, 1H), 6.65 (d, J = 2.3 Hz, 1H), 3.64 (t, J = 4.8 Hz, 5H), 3.13-3.02 (m, 4H), 2.52 (s, 3H), 2.51 (s, 2H), 1.79 (s, 3H). |
| 94 | 4-[3-(8-chloro-5-fluoroquinolin-4-yl)-2-methyl-7-(5-methyl-4H-1,2,4-triazol-3-yl)benzimidazol-5-yl]morpholine | 478.4 | 1H NMR (400 MHz, DMSO-d6) δ 9.40 (d, J = 4.5 Hz, 1H), 8.17-8.07 (m, 2H), 7.71 (s, 1H), 7.51 (dd, J = 11.9, 8.5 Hz, 1H), 6.81 (s, 1H), 3.70-3.60 (m, 4H), 3.11-3.01 (m, 4H), 2.57 (s, 3H). |

| Compound | Compound Name | MS | NMR |
|---|---|---|---|
| 95 | 4-[3-(8-fluoroquinolin-4-yl)-7-(4H-1,2,4-triazol-3-yl)benzimidazol-5-yl]morpholine | 416.2 | 1H NMR (400 MHz, DMSO-d6) δ 9.21 (d, J = 4.5 Hz, 1H), 9.06 (s, 1H), 8.46 (s, 1H), 8.00 (d, J = 4.6 Hz, 1H), 7.81-7.70 (m, 2H), 7.66 (td, J = 8.1, 5.1 Hz, 1H), 7.42 (dt, J = 8.4, 1.0 Hz, 1H), 6.85 (d, J = 2.3 Hz, 1H), 3.68 (t, J = 4.8 Hz, 4H), 3.09 (d, J = 5.2 Hz, 4H). |
| 96 | 4-[3-(5-chloro-8-fluoroquinolin-4-yl)-7-(4H-1,2,4-triazol-3-yl)benzimidazol-5-yl]morpholine | 450.1 | 1H NMR (400 MHz, DMSO-d6) δ 9.29 (d, J = 4.5 Hz, 1H), 9.19 (s, 1H), 8.54 (d, J = 6.7 Hz, 1H), 8.10-8.00 (m, 1H), 7.85-7.76 (m, 3H), 6.89 (d, J = 2.3 Hz, 1H), 3.67 (t, J = 4.8 Hz, 4H), 3.11 (t, J = 5.0 Hz, 4H). |
| 97 | 4-[3-(3,8-dichloroquinolin-4-yl)-2-methyl-7-(4H-1,2,4-triazol-3-yl)benzimidazol-5-yl]morpholine | 480.1 | 1H NMR (400 MHz, DMSO-d6) δ 9.42 (s, 1H), 8.51 (s, 1H), 8.14 (dd, J = 7.6, 1.2 Hz, 1H), 7.66 (dd, J = 8.5, 7.6 Hz, 2H), 7.38 (d, J = 8.4 Hz, 1H), 6.78 (d, J = 2.2 Hz, 1H), 3.72-3.51 (m, 4H), 3.05 (t, J = 5.0 Hz, 4H), 2.43 (s, 3H). |
| 98 | 4-[3-(3,8-dichloroquinolin-4-yl)-2-ethyl-7-(4H-1,2,4-triazol-3-yl)benzimidazol-5-yl]morpholine | 494.1 | 1H NMR (400 MHz, DMSO-d6) δ 9.40 (s, 1H), 8.45 (s, 1H), 8.13 (dd, J = 7.6, 1.2 Hz, 1H), 7.70-7.61 (m, 2H), 7.30 (d, J = 8.5 Hz, 1H), 6.75 (d, J = 2.3 Hz, 1H), 3.64 (t, J = 4.9 Hz, 4H), 3.17-2.92 (m, 4H), 2.64 (q, J = 7.5 Hz, 2H), 1.17 (t, J = 7.5 Hz, 3H). |
| 99 | (3S)-4-[3-(8-chloroquinolin-4-yl)-2-methyl-7-(4H-1,2,4-triazol-3-yl)benzimidazol-5-yl]-3-methylmorpholine | 460.3 | 1H NMR (400 MHz, DMSO-d6) δ 9.35 (dd, J = 4.5, 1.9 Hz, 0.5H), 8.71 (s, 0.5H), 8.16-8.03 (m, 1H), 7.80-7.70 (m, 1H), 7.67-7.49 (m, 1H), 6.70-6.55 (m, 1H), 3.89-3.75 (m, 2H), 3.62-3.40 (m, 3H), 3.15-2.84 (m, 2H), 2.60-2.51 (mz, 3H), 0.96-0.82 (m, 3H). |
| 100 | (3R)-4-[3-(8-chloroquinolin-4-yl)-2-methyl-7-(4H-1,2,4-triazol-3-yl)benzimidazol-5-yl]-3-methylmorpholine | 460.3 | 1H NMR (400 MHz, DMSO-d6) δ 9.35 (dd, J = 4.5, 1.9 Hz, 0.5H), 8.71 (s, 0.5H), 8.16-8.03 (m, 1H), 7.80-7.70 (m, 1H), 7.67-7.49 (m, 1H), 6.70-6.55 (m, 1H), 3.89-3.75 (m, 2H), 3.62-3.40 (m, 3H), 3.15-2.84 (m, 2H), 2.60-2.51 (mz, 3H), 0.96-0.82 (m, 3H). |
| 101 | 4-[3-(8-chloroquinolin-4-yl)-2-methyl-7-(4H-1,2,4-triazol-3-yl)benzimidazol-5-yl]morpholine | 446.1 | 1H NMR (400 MHz, DMSO-d6) δ 9.37 (dd, J = 4.5, 0.6 Hz, 1H), 8.77 (s, 1H), 8.15 (dd, J = 7.4, 1.3 Hz, 1H), 8.09 (d, J = 4.5 Hz, 1H), 7.83 (d, J = 2.3 Hz, 1H), 7.64 (dd, J = 8.4, 7.5 Hz, 1H), 7.57 (d, J = 8.4 Hz, 1H), 6.73 (d, J = 2.3 Hz, 1H), 3.66 (t, J = 4.8 Hz, 4H), 3.08 (q, J = 3.9 Hz, 4H), 2.59 (s, 3H). |
| 102 | 4-[3-(8-chloroquinolin-4-yl)-2-(oxolan-2-yl)-7-(4H-1,2,4-triazol-3-yl)benzimidazol-5-yl]morpholine | 502.2 | 1H NMR (400 MHz, DMSO-d6) δ 9.30 (d, J = 4.5 Hz, 0.5H), 9.28 (d, J = 4.5 Hz, 0.5H), 8.46 (s, 0.5H), 8.41 (s, 0.5H), 8.09 (dd, J = 3.7, 1.2 Hz, 0.5H), 8.08-8.06 (m, 0.5H), 8.00-7.96 (m, 1H), 7.71-7.67 (m, 1H), 7.60-7.54 (m, 1H), 7.27-7.21 (m, 1H), 6.61 (d, J = 2.3 Hz, 0.5H), 6.52 (d, J = 2.3 Hz, 1H), 5.07 (dd, J = 7.6, 5.7 Hz, 0.5H), 4.90 (t, J = 7.0 Hz, 0.5H), 3.65 (q, J = 4.5 Hz, 4H), 3.55 (td, J = 7.7, 5.2 Hz, 0.5H), 3.52-3.32 (m, 1.5H), 3.03 (dq, J = 12.1, 4.2 Hz, 4H), 2.89-2.68 (m, 1H), 2.20-2.06 (m, 1H), 2.04-1.85 (m, 1H), 1.85-1.70 (m, 1H). |
| 103 | 4-(2-methyl-1-(2-(thiazol-4-yl)quinolin-4-yl)-4-(4H-1,2,4-triazol-3-yl)-1H-benzo[d]imidazol-6-yl)morpholine | 495.20 | 1H NMR (400 MHz, DMSO-d6) δ 9.34-9.32 (m, 1H), 8.74-8.73 (m, 1H), 8.71 (s, 1H), 8.33-8.28 (m, 1H), 7.99-7.92 (m, 1H), 7.86-7.84 (m, 1H), 7.69-7.62 (m, 1H), 7.60-7.53 (m, 1H), 6.79-6.76 (m, 1H), 3.67-3.61 (m, 4H), 3.11-3.04 (m, 4H), 2.62 (s, 3H). |
| 104 | 4-(2-methyl-4-(5-methyl-4H-1,2,4-triazol-3-yl)-1-(2-(thiazol-4-yl)quinolin-4-yl)-1H-benzo[d]imidazol-6-yl)morpholine | 509.2 | 1H NMR (400 MHz, DMSO-d6) δ 9.33 (d, J = 2.0 Hz, 1H), 8.73 (d, J = 2.0 Hz, 1H), 8.69 (s, 1H), 8.33-8.29 (m, 1H), 7.98-7.93 (m, 1H), 7.78 (s, 1H), 7.68-7.62 (m, 1H), 7.53 (s, 1H), 6.74 (s, 1H), 3.64 (t, J = 4.8 Hz, 4H), 3.09-3.03 (m, 4H), 2.60 (s, 3H), 2.53 (s, 3H). |

| Compound | Compound Name | MS | NMR |
|---|---|---|---|
| 105 | 4-[3-(8-chloroquinolin-4-yl)-2-ethyl-7-(4H-1,2,4-triazol-3-yl)benzimidazol-5-yl]morpholine | 460.2 | 1H NMR (400 MHz, DMSO-d6) δ 9.36 (d, J = 4.5 Hz, 1H), 8.70-8.60 (m, 1H), 8.17-8.07 (m, 2H), 7.78 (d, J = 2.2 Hz, 1H), 7.67-7.59 (m, 1H), 7.51-7.41 (m, 1H), 6.68 (d, J = 2.3 Hz, 1H), 3.66 (t, J = 4.8 Hz, 4H), 3.11-3.00 (m, 4H), 2.90-2.80 (m, 2H), 1.11 (t, J = 7.5 Hz, 3H). |
| 106 | 4-[2-methyl-3-quinolin-4-yl-7-(4H-1,2,4-triazol-3-yl)benzimidazol-5-yl]morpholine | 412.2 | 1H NMR (400 MHz, DMSO-d6) δ 9.29-9.24 (m, 1H), 8.79 (s, 1H), 8.34-8.27 (m, 1H), 8.00-7.93 (m, 2H), 7.87-7.84 (m, 1H), 7.71-7.66 (m, 1H), 7.62-7.58 (m, 1H), 6.66 (d, J = 2.2 Hz, 1H), 3.66 (t, J = 4.8 Hz, 4H), 3.12-3.05 (m, 4H), 2.59 (s, 3H). |
| 107 | 4-[2-ethyl-3-quinolin-4-yl-7-(4H-1,2,4-triazol-3-yl)benzimidazol-5-yl]morpholine | 426.2 | 1H NMR (400 MHz, DMSO-d6) δ 9.26 (d, J = 4.5 Hz, 1H), 8.68 (s, 1H), 8.30 (dd, J = 8.4, 1.0 Hz, 1H), 8.01 (d, J = 4.5 Hz, 1H), 7.98-7.91 (m, 1H), 7.80 (d, J = 2.2 Hz, 1H), 7.71-7.64 (m, 1H), 7.50 (d, J = 8.4 Hz, 1H), 6.62 (d, J = 2.2 Hz, 1H), 3.66 (t, J = 4.8 Hz, 4H), 3.12-3.00 (m, 4H), 2.86 (q, J = 7.4 Hz, 2H), 1.10 (t, J = 7.5 Hz, 3H). |
| 108 | 4-[2-methyl-7-(4H-1,2,4-triazol-3-yl)-3-[8-(trifluoromethyl)quinolin-4-yl]benzimidazol-5-yl]morpholine | 480.2 | 1H NMR (400 MHz, DMSO-d6) δ 9.42 (d, J = 4.6 Hz, 1H), 8.82-8.69 (m, 1H), 8.38 (d, J = 7.3 Hz, 1H), 8.14 (d, J = 4.5 Hz, 1H), 7.97-7.87 (m, 1H), 7.87-7.76 (m, 2H), 6.81-6.74 (m, 1H), 3.66 (t, J = 4.8 Hz, 4H), 3.14-3.04 (m, 4H), 2.58 (s, 3H). |
| 109 | 4-[2-methyl-3-(8-methylquinolin-4-yl)-7-(4H-1,2,4-triazol-3-yl)benzimidazol-5-yl]morpholine | 426.2 | 1H NMR (400 MHz, DMSO-d6) δ 9.30-9.26 (m, 1H), 8.86-8.75 (m, 1H), 7.99 (d, J = 4.5 Hz, 1H), 7.86 (d, J = 2.2 Hz, 1H), 7.82 (d, J = 7.1 Hz, 1H), 7.61-7.52 (m, 1H), 7.44-7.38 (m, 1H), 6.65 (d, J = 2.2 Hz, 1H), 3.66 (t, J = 4.8 Hz, 4H), 3.12-3.04 (m, 4H), 2.86 (s, 3H), 2.58 (s, 3H). |
| 110 | 4-[3-(8-chloroquinolin-4-yl)-2-cyclopropyl-7-(4H-1,2,4-triazol-3-yl)benzimidazol-5-yl]morpholine | 472.1 | 1H NMR (400 MHz, DMSO-d6) δ 9.34 (d, J = 4.5 Hz, 1H), 8.40 (s, 1H), 8.15-8.10 (m, 1H), 8.05 (d, J = 4.5 Hz, 1H), 7.67-7.60 (m, 2H), 7.39 (dd, J = 8.4, 1.2 Hz, 1H), 6.67 (d, J = 2.2 Hz, 1H), 3.66 (t, J = 4.8 Hz, 4H), 3.09-2.98 (m, 4H), 1.70-1.61 (m, 1H), 1.49-1.30 (m, 2H), 1.02-0.80 (m, 2H). |
| 111 | 4-[3-(8-chloroquinolin-4-yl)-7-(4H-1,2,4-triazol-3-yl)benzimidazol-5-yl]morpholine | 432.1 | 1H NMR (400 MHz, DMSO-d6) δ 9.30 (d, J = 4.6 Hz, 1H), 9.12 (s, 1H), 8.50 (s, 1H), 8.14 (dd, J = 7.4, 1.3 Hz, 1H), 8.04 (d, J = 4.6 Hz, 1H), 7.81 (d, J = 2.3 Hz, 1H), 7.69-7.62 (m, 1H), 7.61-7.56 (m, 1H), 6.87 (d, J = 2.3 Hz, 1H), 3.69 (t, J = 4.8 Hz, 4H), 3.13-3.07 (m, 4H). |
| 112 | 4-[3-(8-chloroquinolin-4-yl)-2-(1,3-oxazol-5-yl)-7-(4H-1,2,4-triazol-3-yl)benzimidazol-5-yl]morpholine | 499.1 | 1H NMR (400 MHz, DMSO-d6) δ 9.26 (d, J = 4.5 Hz, 1H), 9.07 (s, 1H), 8.30 (s, 1H), 8.20-8.16 (m, 1H), 8.04 (dd, J = 7.5, 1.2 Hz, 1H), 7.93 (d, J = 4.5 Hz, 1H), 7.72 (d, J = 2.3 Hz, 1H), 7.54-7.48 (m, 1H), 7.24 (dd, J = 8.5, 1.2 Hz, 1H), 6.60 (d, J = 2.3 Hz, 1H), 3.67 (t, J = 4.7 Hz, 4H), 3.09-3.02 (m, 4H). |
| 113 | 4-[3-(8-chloroquinolin-4-yl)-2-(oxetan-3-yl)-7-(4H-1,2,4-triazol-3-yl)benzimidazol-5-yl]morpholine | 488.1 | 1H NMR (400 MHz, DMSO-d6) δ 9.28 (d, J = 4.4 Hz, 1H), 8.33 (s, 1H), 8.10 (dd, J = 7.5, 1.2 Hz, 1H), 7.88 (d, J = 4.5 Hz, 1H), 7.68 (d, J = 2.2 Hz, 1H), 7.63-7.55 (m, 1H), 7.20 (dd, J = 8.5, 1.2 Hz, 1H), 6.61 (d, J = 2.3 Hz, 1H), 5.19-5.12 (m, 1H), 5.10-5.03 (m, 1H), 4.66 (dd, J = 8.6, 5.5 Hz, 1H), 4.47 (dd, J = 8.6, 5.5 Hz, 1H), 4.24-4.14 (m, 1H), 3.66 (t, J = 4.7 Hz, 4H), 3.06-3.00 (m, 4H). |
| 114 | 4-[3-(5,8-difluoroquinolin-4-yl)-2-methyl-7-(4H-1,2,4-triazol-3- | 448.1 | 1H NMR (400 MHz, DMSO-d6) δ 9.36 (d, J = 4.5 Hz, 1H), 8.79-8.61 (m, 1H), 8.12 (d, J = 4.5 Hz, 1H), 7.88-7.76 (m, 2H), 7.57-7.48 (m, 1H), 6.85 (d, J = |

| Compound | Compound Name | MS | NMR |
|---|---|---|---|
| | yl)benzimidazol-5-yl]morpholine | | 2.2 Hz, 1H), 3.68 (t, J = 4.8 Hz, 4H), 3.11 (t, J = 4.9 Hz, 4H), 2.60 (s, 3H). |
| 115 | 4-[3-(8-chloroquinolin-4-yl)-2-pyridin-2-yl-7-(4H-1,2,4-triazol-3-yl)benzimidazol-5-yl]morpholine | 509.1 | 1H NMR (400 MHz, DMSO-d6) δ 9.22 (d, J = 4.5 Hz, 1H), 8.95-8.88 (m, 1H), 8.30 (s, 1H), 7.99 (dd, J = 7.5, 1.3 Hz, 1H), 7.97-7.90 (m, 2H), 7.85 (d, J = 4.6 Hz, 1H), 7.77 (d, J = 2.2 Hz, 1H), 7.44 (dd, J = 8.4, 7.5 Hz, 1H), 7.27-7.20 (m, 2H), 6.52 (d, J = 2.3 Hz, 1H), 3.67 (t, J = 4.7 Hz, 4H), 3.10-3.02 (m, 4H). |
| 116 | 4-[3-(8-chloroquinolin-4-yl)-2-(2-methoxyethyl)-7-(4H-1,2,4-triazol-3-yl)benzimidazol-5-yl]morpholine | 490.1 | 1H NMR (400 MHz, DMSO-d6) δ 9.34 (d, J = 4.5 Hz, 1H), 8.66-8.47 (m, 1H), 8.12 (dd, J = 7.5, 1.2 Hz, 1H), 8.04 (d, J = 4.5 Hz, 1H), 7.78-7.73 (m, 1H), 7.62 (dd, J = 8.5, 7.5 Hz, 1H), 7.34 (d, J = 8.4 Hz, 1H), 6.64 (d, J = 2.3 Hz, 1H), 3.69-3.50 (m, 6H), 3.13-3.00 (m, 6H), 2.98 (s, 3H). |
| 117 | 4-[3-(8-chloroquinolin-4-yl)-2-(1H-pyrazol-5-yl)-7-(4H-1,2,4-triazol-3-yl)benzimidazol-5-yl]morpholine | 498.1 | 1H NMR (400 MHz, DMSO-d6) δ 9.29 (d, J = 4.5 Hz, 1H), 8.33 (s, 1H), 8.04 (dd, J = 7.6, 1.3 Hz, 1H), 7.95 (d, J = 4.6 Hz, 1H), 7.73 (d, J = 2.2 Hz, 1H), 7.68-7.62 (m, 1H), 7.53-7.46 (m, 1H), 7.26 (s, 1H), 7.22 (dd, J = 8.4, 1.2 Hz, 1H), 7.13 (s, 1H), 7.00 (s, 1H), 6.61 (d, J = 2.2 Hz, 1H), 3.67 (t, J = 4.8 Hz, 4H), 3.09-3.03 (m, 4H). |
| 118 | 4-[3-(8-chloroquinolin-4-yl)-2-(1,2-thiazol-4-yl)-7-(4H-1,2,4-triazol-3-yl)benzimidazol-5-yl]morpholine | 515.1 | 1H NMR (400 MHz, DMSO-d6) δ 9.40-9.33 (m, 2H), 8.42-8.38 (m, 1H), 8.34-8.27 (m, 1H), 8.11-8.04 (m, 2H), 7.78-7.75 (m, 1H), 7.58-7.52 (m, 1H), 7.28-7.22 (m, 1H), 6.65-6.62 (m, 1H), 3.67 (t, J = 4.7 Hz, 4H), 3.11-3.04 (m, 4H). |
| 119 | 4-[3-(8-chloroquinolin-4-yl)-2-(1,3-thiazol-5-yl)-7-(4H-1,2,4-triazol-3-yl)benzimidazol-5-yl]morpholine | 515.1 | 1H NMR (400 MHz, DMSO-d6) δ 9.38-9.35 (m, 1H), 9.01-8.97 (m, 1H), 8.37-8.30 (m, 1H), 8.29-8.20 (m, 1H), 8.13-8.07 (m, 2H), 7.72 (d, J = 2.3 Hz, 1H), 7.59-7.52 (m, 1H), 7.24-7.18 (m, 1H), 6.65 (d, J = 2.3 Hz, 1H), 3.67 (t, J = 4.8 Hz, 4H), 3.11-3.04 (m, 4H). |
| 120 | 4-[3-(8-chloroquinolin-4-yl)-2-(1H-pyrazol-4-yl)-7-(4H-1,2,4-triazol-3-yl)benzimidazol-5-yl]morpholine | 498.1 | 1H NMR (400 MHz, DMSO-d6) δ 9.35 (d, J = 4.5 Hz, 1H), 8.37 (s, 1H), 8.09 (dd, J = 7.5, 1.2 Hz, 1H), 8.06 (d, J = 4.5 Hz, 1H), 7.70 (d, J = 2.3 Hz, 1H), 7.66 (s, 2H), 7.57-7.51 (m, 1H), 7.25-7.21 (m, 1H), 6.64 (d, J = 2.3 Hz, 1H), 3.67 (t, J = 4.8 Hz, 4H), 3.08-3.03 (m, 4H). |
| 121 | 4-[3-(8-chloroquinolin-4-yl)-2-(1-methylpyrazol-4-yl)-7-(4H-1,2,4-triazol-3-yl)benzimidazol-5-yl]morpholine | 512 | 1H NMR (400 MHz, DMSO-d6) δ 9.35 (d, J = 4.5 Hz, 1H), 8.38 (s, 1H), 8.09 (dd, J = 7.5, 1.2 Hz, 1H), 8.04 (d, J = 4.5 Hz, 1H), 7.84-7.83 (m, 1H), 7.70 (d, J = 2.2 Hz, 1H), 7.57-7.52 (m, 1H), 7.51-7.50 (m, 1H), 7.23 (dd, J = 8.6, 1.2 Hz, 1H), 6.60 (d, J = 2.3 Hz, 1H), 3.73 (s, 3H), 3.66 (t, J = 4.8 Hz, 4H), 3.07-3.01 (m, 4H). |
| 122 | 4-[3-(5,8-dichloroquinolin-4-yl)-2-methyl-7-(4H-1,2,4-triazol-3-yl)benzimidazol-5-yl]morpholine | 481.1 | 1H NMR (400 MHz, DMSO-d6) δ 9.43 (d, J = 4.4 Hz, 1H), 8.77-8.60 (m, 1H), 8.17-8.12 (m, 2H), 7.84-7.76 (m, 2H), 6.83-6.79 (m, 1H), 3.67 (t, J = 4.9 Hz, 4H), 3.11 (t, J = 4.9 Hz, 4H), 2.56 (s, 3H). |
| 123 | 4-[3-(5,8-difluoroquinolin-4-yl)-2-(oxetan-3-yl)-7-(4H-1,2,4-triazol-3-yl)benzimidazol-5-yl]morpholine | 490.1 | 1H NMR (400 MHz, DMSO-d6) δ 9.25 (d, J = 4.5 Hz, 1H), 8.32-8.27 (m, 1H), 7.91 (d, J = 4.6 Hz, 1H), 7.82-7.73 (m, 1H), 7.64 (d, J = 2.3 Hz, 1H), 7.44 (ddd, J = 12.3, 8.8, 3.8 Hz, 1H), 6.72 (d, J = 2.3 Hz, 1H), 5.16-5.09 (m, 2H), 4.59 (ddd, J = 13.5, 8.6, 5.5 Hz, 2H), 4.29-4.19 (m, 1H), 3.71-3.63 (m, 4H), 3.05 (t, J = 4.9 Hz, 4H). |
| 124 | 4-[3-(5-fluoro-8-methylquinolin-4-yl)-2-methyl-7-(4H-1,2,4- | 444.2 | 1H NMR (400 MHz, DMSO-d6) δ 9.35 (d, J = 4.5 Hz, 1H), 8.81-8.69 (m, 1H), 8.03 (d, J = 4.5 Hz, 1H), 7.85-7.77 (m, |

| Compound | Compound Name | MS | NMR |
|---|---|---|---|
| | triazol-3-yl)benzimidazol-5-yl]morpholine | | 2H), 7.42 (dd, J = 12.5, 8.1 Hz, 1H), 6.80 (d, J = 2.2 Hz, 1H), 3.67 (t, J = 4.8 Hz, 4H), 3.11 (t, J = 4.9 Hz, 4H), 2.81 (s, 3H), 2.59 (s, 3H). |
| 125 | 4-[3-(5,8-difluoroquinolin-4-yl)-2-ethyl-7-(4H-1,2,4-triazol-3-yl)benzimidazol-5-yl]morpholine | 462.2 | 1H NMR (400 MHz, DMSO-d6) δ 9.35 (d, J = 4.5 Hz, 1H), 8.67-8.59 (m, 1H), 8.14 (d, J = 4.5 Hz, 1H), 7.86-7.78 (m, 1H), 7.75 (d, J = 2.2 Hz, 1H), 7.52 (ddd, J = 12.3, 8.7, 3.8 Hz, 1H), 6.81 (d, J = 2.2 Hz, 1H), 3.67 (t, J = 4.8 Hz, 4H), 3.10 (t, J = 4.9 Hz, 4H), 2.94-2.81 (m, 2H), 1.16 (t, J = 7.5 Hz, 3H). |
| 126 | 4-[3-(5-chloro-8-fluoroquinolin-4-yl)-2-methyl-7-(4H-1,2,4-triazol-3-yl)benzimidazol-5-yl]morpholine | 464.1 | 1H NMR (400 MHz, DMSO-d6) δ 9.37 (d, J = 4.4 Hz, 1H), 8.78-8.67 (m, 1H), 8.14 (d, J = 4.4 Hz, 1H), 7.87-7.82 (m, 2H), 7.83-7.79 (m, 1H), 6.81 (d, J = 2.2 Hz, 1H), 3.70-3.65 (m, 4H), 3.15-3.09 (m, 4H), 2.58 (s, 3H). |
| 127 | 4-[3-(5-methylquinolin-4-yl)-7-(4H-1,2,4-triazol-3-yl)benzimidazol-5-yl]morpholine | 412.1 | 1H NMR (400 MHz, DMSO-d6) δ 9.15-9.08 (m, 1H), 9.07-8.99 (m, 1H), 8.50-8.45 (m, 1H), 8.17-8.11 (m, 1H), 7.84-7.73 (m, 3H), 7.52-7.46 (m, 1H), 6.75-6.72 (m, 1H), 3.71-3.66 (m, 4H), 3.13-3.08 (m, 4H), 1.84 (s, 3H). |
| 128 | 4-[3-(3-chloroquinolin-4-yl)-2-methyl-7-(4H-1,2,4-triazol-3-yl)benzimidazol-5-yl]morpholine | 446.1 | 1H NMR (400 MHz, DMSO-d6) δ 9.38-9.29 (m, 1H), 8.67-8.56 (m, 1H), 8.38-8.27 (m, 1H), 8.02-7.92 (m, 1H), 7.79-7.68 (m, 2H), 7.54-7.44 (m, 1H), 6.82-6.72 (m, 1H), 3.74-3.61 (m, 4H), 3.14-3.04 (m, 4H), 2.78-2.63 (m, 3H). |
| 129 | 4-[3-(8-chloroquinolin-4-yl)-2-methyl-7-(5-methyl-4H-1,2,4-triazol-3-yl)benzimidazol-5-yl]morpholine | 460.1 | 1H NMR (400 MHz, DMSO-d6) δ 9.35 (dd, J = 4.5, 0.6 Hz, 1H), 8.16-8.10 (m, 1H), 8.07 (d, J = 4.5 Hz, 1H), 7.77 (d, J = 2.2 Hz, 1H), 7.62 (ddd, J = 8.1, 7.4, 0.6 Hz, 1H), 7.58-7.48 (m, 1H), 6.69 (d, J = 2.2 Hz, 1H), 3.64 (t, J = 4.8 Hz, 4H), 3.05 (t, J = 4.1 Hz, 4H), 2.60-2.56 (m, 2H), 2.52 (d, J = 0.6 Hz, 2H). |
| 130 | 4-[3-(8-fluoroquinolin-4-yl)-2-methyl-7-(5-methyl-4H-1,2,4-triazol-3-yl)benzimidazol-5-yl]morpholine | 444.1 | 1H NMR (400 MHz, DMSO-d6) δ 9.32-9.20 (m, 1H), 8.07 (d, J = 4.5 Hz, 1H), 7.83-7.71 (m, 2H), 7.64 (td, J = 8.1, 4.9 Hz, 1H), 7.40 (d, J = 8.5 Hz, 1H), 6.68 (d, J = 2.3 Hz, 1H), 3.64 (t, J = 4.8 Hz, 4H), 3.11-2.96 (m, 4H), 2.58 (s, 3H), 2.52 (d, J = 0.7 Hz, 3H). |
| 131 | 4-[3-(5,7-difluoroquinolin-4-yl)-2-methyl-7-(4H-1,2,4-triazol-3-yl)benzimidazol-5-yl]morpholine | 448.1 | 1H NMR (400 MHz, DMSO-d6) δ 9.25 (d, J = 4.5 Hz, 1H), 8.72 (s, 1H), 8.09 (d, J = 4.5 Hz, 1H), 7.95 (ddd, J = 11.3, 9.0, 2.7 Hz, 1H), 7.80 (d, J = 2.2 Hz, 1H), 7.36 (s, 1H), 6.71 (d, J = 2.2 Hz, 1H), 3.66 (s, 4H), 3.13-3.02 (m, 4H), 2.56 (s, 3H). |
| 132 | 4-[2-(azetidin-3-yl)-3-(8-chloroquinolin-4-yl)-7-(4H-1,2,4-triazol-3-yl)benzimidazol-5-yl]morpholine | 487.2 | 1H NMR (400 MHz, DMSO-d6) δ 9.29 (dd, J = 4.5, 0.7 Hz, 1H), 9.10 (s, 1H), 8.70 (s, 1H), 8.25 (s, 1H), 8.10 (dt, J = 7.5, 1.0 Hz, 1H), 7.89 (dd, J = 4.6, 0.7 Hz, 1H), 7.74-7.69 (m, 1H), 7.62-7.53 (m, 1H), 7.26 (dt, J = 8.5, 1.0 Hz, 1H), 6.67-6.62 (m, 1H), 4.47 (d, J = 8.1 Hz, 1H), 4.21 (s, 4H), 3.76 (p, J = 7.8 Hz, 1H), 3.65 (t, J = 4.8 Hz, 4H), 3.01 (q, J = 3.9 Hz, 4H). |
| 133 | 4-[3-(8-chloroquinolin-4-yl)-2-ethyl-7-(5-methyl-4H-1,2,4-triazol-3-yl)benzimidazol-5-yl]morpholine | 474.2 | 1H NMR (400 MHz, DMSO-d6) δ 9.50-9.25 (m, 1H), 8.11 (s, 2H), 7.73 (s, 1H), 7.61 (s, 1H), 7.54-7.39 (m, 1H), 6.65 (d, J = 3.1 Hz, 1H), 3.63 (d, J = 4.9 Hz, 4H), 3.12-2.95 (m, 4H), 2.86 (d, J = 7.6 Hz, 2H), 2.53-2.49 (m, 3H), 1.06 (s, 3H). |

| Compound | Compound Name | MS | NMR |
|---|---|---|---|
| 134 | 4-[3-(8-chloroquinolin-4-yl)-7-(5-methyl-4H-1,2,4-triazol-3-yl)benzimidazol-5-yl]morpholine | 446.2 | 1H NMR (400 MHz, DMSO-d6) δ 9.32-9.27 (m, 1H), 9.07-8.95 (m, 1H), 8.16-8.11 (m, 1H), 8.05-8.01 (m, 1H), 7.76-7.72 (m, 1H), 7.70-7.63 (m, 1H), 7.59-7.54 (m, 1H), 6.87-6.83 (m, 1H), 3.72-3.66 (m, 4H), 3.14-3.04 (m, 4H), 2.48-2.47 (m, 3H). |
| 135 | 4-[3-(8-chloroquinolin-4-yl)-7-(5-cyclopropyl-4H-1,2,4-triazol-3-yl)-2-methylbenzimidazol-5-yl]morpholine | 486.2 | 1H NMR (400 MHz, DMSO-d6) δ 9.40-9.35 (m, 1H), 8.18-8.13 (m, 1H), 8.11-8.06 (m, 1H), 7.75-7.69 (m, 1H), 7.68-7.61 (m, 1H), 7.59-7.53 (m, 1H), 6.71-6.67 (m, 1H), 3.72-3.59 (m, 4H), 3.11-3.01 (m, 4H), 2.62-2.56 (m, 3H), 2.26-2.16 (m, 1H), 1.17-1.05 (m, 4H). |
| 136 | 4-[3-(8-chloroquinolin-4-yl)-2-methyl-7-[5-(trifluoromethyl)-4H-1,2,4-triazol-3-yl]benzimidazol-5-yl]morpholine | 514.2 | 1H NMR (400 MHz, DMSO-d6) δ 9.33-9.30 (m, 1H), 8.14-8.09 (m, 1H), 8.00 (d, J = 4.5 Hz, 1H), 7.65-7.57 (m, 2H), 7.30-7.25 (m, 1H), 6.71 (d, J = 2.2 Hz, 1H), 3.65 (t, J = 4.7 Hz, 4H), 3.07-3.00 (m, 4H), 2.41 (s, 3H). |
| 137 | 4-[3-(8-chloroquinolin-4-yl)-7-(5-ethyl-4H-1,2,4-triazol-3-yl)-2-methylbenzimidazol-5-yl]morpholine | 474.2 | 1H NMR (400 MHz, DMSO-d6) δ 9.38 (d, J = 4.5 Hz, 1H), 8.17-8.07 (m, 2H), 7.78 (d, J = 2.2 Hz, 1H), 7.68-7.54 (m, 2H), 6.71 (d, J = 2.2 Hz, 1H), 3.66 (t, J = 4.8 Hz, 4H), 3.13-3.03 (m, 4H), 2.91 (q, J = 7.6 Hz, 2H), 2.60 (s, 3H), 1.37 (t, J = 7.6 Hz, 3H). |
| 138 | 4-[3-(8-chloroquinolin-4-yl)-2-methyl-7-(5-propan-2-yl-4H-1,2,4-triazol-3-yl)benzimidazol-5-yl]morpholine | 488.2 | 1H NMR (400 MHz, DMSO-d6) δ 9.36 (d, J = 4.5 Hz, 1H), 8.16-8.12 (m, 1H), 8.08 (d, J = 4.5 Hz, 1H), 7.74 (d, J = 2.2 Hz, 1H), 7.67-7.61 (m, 1H), 7.52 (d, J = 8.5 Hz, 1H), 6.68 (d, J = 2.3 Hz, 1H), 3.66 (t, J = 4.8 Hz, 4H), 3.29-3.19 (m, 1H), 3.12-2.99 (m, 4H), 2.56 (s, 3H), 1.40 (d, J = 7.0 Hz, 6H). |
| 139 | 4-[2-ethyl-3-(8-fluoroquinolin-4-yl)-7-(4H-1,2,4-triazol-3-yl)benzimidazol-5-yl]morpholine | 444.2 | 1H NMR (400 MHz, DMSO-d6) δ 9.30 (d, J = 4.5 Hz, 1H), 8.65 (s, 1H), 8.10 (d, J = 4.5 Hz, 1H), 7.82-7.75 (m, 2H), 7.69-7.61 (m, 1H), 7.32 (d, J = 8.5 Hz, 1H), 6.67 (d, J = 2.3 Hz, 1H), 3.66 (t, J = 4.7 Hz, 4H), 3.11-3.02 (m, 4H), 2.86 (q, J = 7.5 Hz, 2H), 1.12 (t, J = 7.5 Hz, 3H). |
| 140 | 4-[3-(8-fluoroquinolin-4-yl)-2-methyl-7-(4H-1,2,4-triazol-3-yl)benzimidazol-5-yl]morpholine | 430.2 | 1H NMR (400 MHz, DMSO-d6) δ 9.30 (d, J = 4.5 Hz, 1H), 8.79-8.65 (m, 1H), 8.07 (d, J = 4.5 Hz, 1H), 7.84-7.75 (m, 2H), 7.69-7.62 (m, 1H), 7.39 (d, J = 8.4 Hz, 1H), 6.71 (d, J = 2.3 Hz, 1H), 3.66 (t, J = 4.8 Hz, 4H), 3.11-3.03 (m, 4H), 2.58 (s, 3H). |
| 141 | 4-[3-(8-fluoroquinolin-4-yl)-2-propyl-7-(4H-1,2,4-triazol-3-yl)benzimidazol-5-yl]morpholine | 458.2 | 1H NMR (400 MHz, DMSO-d6) δ 9.29 (d, J = 4.4 Hz, 1H), 8.62 (s, 1H), 8.09 (d, J = 4.5 Hz, 1H), 7.83-7.73 (m, 2H), 7.64 (td, J = 8.1, 5.0 Hz, 1H), 7.28 (d, J = 8.5 Hz, 1H), 6.65 (d, J = 2.3 Hz, 1H), 3.66 (t, J = 4.8 Hz, 4H), 3.12-2.98 (m, 4H), 2.91-2.74 (m, 2H), 1.66-1.46 (m, 2H), 0.78 (t, J = 7.4 Hz, 3H). |
| 142 | 4-[3-(7,8-difluoroquinolin-4-yl)-2-methyl-7-(4H-1,2,4-triazol-3-yl)benzimidazol-5-yl]morpholine | 448.2 | 1H NMR (400 MHz, Methanol-d4) δ 9.34 (d, J = 4.5 Hz, 1H), 8.75-8.59 (m, 1H), 8.06 (d, J = 4.5 Hz, 1H), 7.85-7.75 (m, 2H), 7.53-7.44 (m, 1H), 6.69 (d, J = 2.2 Hz, 1H), 3.67 (t, J = 4.8 Hz, 4H), 3.10-3.04 (m, 4H), 2.57 (s, 3H). |
| 143 | 4-[2-cyclopropyl-3-(7,8-difluoroquinolin-4-yl)-7-(4H-1,2,4-triazol-3-yl)benzimidazol-5-yl]morpholine | 474.2 | 1H NMR (400 MHz, Methanol-d4) δ 9.30 (d, J = 4.6 Hz, 1H), 8.38-8.30 (m, 1H), 8.01 (d, J = 4.5 Hz, 1H), 7.85-7.74 (m, 1H), 7.66-7.60 (m, 1H), 7.36-7.26 (m, 1H), 6.68-6.64 (m, 1H), 3.67 (t, J = 4.7 Hz, 4H), 3.10-2.97 (m, 4H), 1.70-1.60 (m, 1H), 1.49-1.30 (m, 2H), 1.02-0.80 (m, 2H). |
| 144 | 4-[2-cyclopropyl-3-(8-fluoroquinolin-4-yl)-7-(4H-1,2,4-triazol-3-yl)benzimidazol-5- | 456.2 | 1H NMR (400 MHz, Methanol-d4) δ 9.27 (d, J = 4.5 Hz, 1H), 8.41 (s, 1H), 8.03 (d, J = 4.5 Hz, 1H), 7.80-7.72 (m, 1H), 7.68-7.61 (m, 2H), 7.27-7.21 |

| Compound | Compound Name | MS | NMR |
|---|---|---|---|
| | yl]morpholine | | (m, 1H), 6.67 (d, J = 2.3 Hz, 1H), 3.67 (t, J = 4.8 Hz, 4H), 3.09-2.99 (m, 4H), 1.71-1.61 (m, 1H), 1.48-1.30 (m, 2H), 1.02-0.82 (m, 2H). |
| 145 | 4-[3-(6,8-difluoroquinolin-4-yl)-2-methyl-7-(4H-1,2,4-triazol-3-yl)benzimidazol-5-yl]morpholine | 448.2 | 1H NMR (400 MHz, DMSO-d6) δ 9.28 (d, J = 4.5 Hz, 1H), 8.79 (s, 1H), 8.12 (d, J = 4.5 Hz, 1H), 7.97 (ddd, J = 10.7, 9.0, 2.7 Hz, 1H), 7.86-7.81 (m, 1H), 7.48-7.37 (m, 1H), 6.74 (d, J = 2.3 Hz, 1H), 3.68 (t, J = 4.8 Hz, 4H), 3.14-3.07 (m, 4H), 2.61 (s, 3H). |
| 146 | 4-[3-(6,8-difluoroquinolin-4-yl)-2-propyl-7-(4H-1,2,4-triazol-3-yl)benzimidazol-5-yl]morpholine | 476.2 | 1H NMR (400 MHz, DMSO-d6) δ 9.26 (d, J = 4.5 Hz, 1H), 8.72-8.61 (m, 1H), 8.17-8.11 (m, 1H), 8.01-7.90 (m, 1H), 7.84-7.76 (m, 1H), 7.34-7.20 (m, 1H), 6.72-6.66 (m, 1H), 3.67 (t, J = 4.8 Hz, 4H), 3.10-3.05 (m, 4H), 2.95-2.74 (m, 2H), 1.68-1.45 (m, 2H), 0.80 (t, J = 7.3 Hz, 3H). |
| 147 | 4-(2-methyl-4-(4H-1,2,4-triazol-3-yl)-1-(2-(1-trityl-1H-pyrazol-4-yl)quinolin-4-yl)-1H-benzo[d]imidazol-6-yl)morpholine | 720.4 | |
| 148 | tert-butyl 4-(4-(2-methyl-6-morpholino-4-(4H-1,2,4-triazol-3-yl)-1H-benzo[d]imidazol-1-yl)quinolin-2-yl)piperazine-1-carboxylate | 596.4 | |
| 149 | 4-(1-(8-chloroquinolin-4-yl)-7-fluoro-4-(4H-1,2,4-triazol-3-yl)-1H-benzo[d]imidazol-6-yl)morpholine | 450.1 | 1H NMR (400 MHz, DMSO-d6) δ 9.26 (d, J = 4.5 Hz, 1H), 8.73 (s, 1H), 8.28 (s, 1H), 8.12 (dd, J = 7.5, 1.2 Hz, 1H), 8.07 (d, J = 4.6 Hz, 1H), 7.75 (d, J = 7.6 Hz, 1H), 7.69-7.63 (m, 1H), 7.57-7.52 (m, 1H), 3.68 (t, J = 4.6 Hz, 4H), 3.08-2.93 (m, 4H). |
| 150 | 4-(1-(8-chloro-5-fluoroquinolin-4-yl)-7-fluoro-2-methyl-4-(4H-1,2,4-triazol-3-yl)-1H-benzo[d]imidazol-6-yl)morpholine | 482.1 | 1H NMR (400 MHz, DMSO-d6) δ 9.35 (d, J = 4.5 Hz, 1H), 8.36 (s, 1H), 8.18-8.13 (m, 2H), 7.64 (d, J = 7.7 Hz, 1H), 7.55 (dd, J = 11.9, 8.5 Hz, 1H), 3.69-3.63 (m, 4H), 3.05-2.90 (m, 4H), 2.43 (s, 3H). |
| 151 | 4-(1-(5,8-dichloroquinolin-4-yl)-2-methyl-4-(5-methyl-4H-1,2,4-triazol-3-yl)-1H-benzo[d]imidazol-6-yl)morpholine | 494.1 | 1H NMR (400 MHz, DMSO-d6) δ 9.42 (d, J = 4.4 Hz, 1H), 8.18-8.08 (m, 2H), 7.81 (d, J = 8.3 Hz, 1H), 7.74 (d, J = 2.2 Hz, 1H), 6.79 (d, J = 2.2 Hz, 1H), 3.70-3.49 (m, 4H), 3.08 (t, J = 4.9 Hz, 4H), 2.56 (s, 3H), 2.51 (s, 3H). |
| 152 | 4-(1-(5,8-difluoroquinolin-4-yl)-2-ethyl-4-(5-methyl-4H-1,2,4-triazol-3-yl)-1H-benzo[d]imidazol-6-yl)morpholine | 476.2 | 1H NMR (400 MHz, DMSO-d6) δ 9.35 (d, J = 4.5 Hz, 1H), 8.15 (d, J = 4.5 Hz, 1H), 7.86-7.75 (m, 1H), 7.71 (d, J = 2.3 Hz, 1H), 7.51 (ddd, J = 12.3, 8.8, 3.7 Hz, 1H), 6.79 (d, J = 2.2 Hz, 1H), 3.65 (t, J = 4.8 Hz, 4H), 3.07 (dd, J = 6.0, 3.8 Hz, 4H), 2.90 (dd, J = 7.5, 3.4 Hz, 2H), 2.51 (s, 3H), 1.11 (t, J = 7.5 Hz, 3H). |
| 153 | 4-(1-(3-fluoroquinolin-4-yl)-2-methyl-4-(4H-1,2,4-triazol-3-yl)-1H-benzo[d]imidazol-6-yl)morpholine | 430.2 | 1H NMR (400 MHz, DMSO-d6) δ 9.35 (d, J = 4.6 Hz, 1H), 8.53 (s, 1H), 8.29 (d, J = 8.4 Hz, 1H), 7.91 (ddd, J = 8.5, 6.9, 1.4 Hz, 1H), 7.71 (t, J = 7.6 Hz, 2H), 7.49 (d, J = 8.2 Hz, 1H), 6.79 (s, 1H), 3.65 (t, J = 4.8 Hz, 4H), 3.06 (d, J = 3.3 Hz, 4H), 2.49 (s, 3H). |
| 154 | 4-(1-(3-fluoroquinolin-4-yl)-2-methyl-4-(5-methyl-4H-1,2,4-triazol-3-yl)-1H-benzo[d]imidazol-6-yl)morpholine | 444.2 | 1H NMR (400 MHz, DMSO-d6) δ 9.35 (d, J = 0.9 Hz, 1H), 8.33-8.26 (m, 1H), 7.91 (ddd, J = 8.5, 6.9, 1.3 Hz, 1H), 7.76-7.65 (m, 2H), 7.50 (d, J = 8.4 Hz, 1H), 6.78 (d, J = 2.2 Hz, 1H), 3.64 (t, J = 4.8 Hz, 4H), 3.05 (q, J = 3.9 Hz, 4H), 2.49 (d, J = 1.9 Hz, 6H). |
| 155 | 4-(2-ethyl-6-morpholino-4-(4H-1,2,4-triazol-3-yl)-1H- | 465.2 | 1H NMR (400 MHz, DMSO-d6) δ 9.34 (d, J = 0.5 Hz, 1H), 8.54 (s, 1H), 8.43 (dd, J = 7.2, 1.3 Hz, 1H), 7.76-7.67 (m, |

| Compound | Compound Name | MS | NMR |
|---|---|---|---|
| | benzo[d]imidazol-1-yl)-3-methylquinoline-8-carbonitrile | | 2H), 7.60 (d, J = 8.4 Hz, 1H), 6.64 (d, J = 2.3 Hz, 1H), 3.64 (t, J = 4.8 Hz, 4H), 3.05 (dd, J = 6.3, 3.8 Hz, 4H), 2.67 (d, J = 8.1 Hz, 2H), 2.21 (s, 3H), 1.11 (t, J = 7.5 Hz, 3H). |
| 156 | 3-methyl-4-(2-methyl-6-morpholino-4-(4H-1,2,4-triazol-3-yl)-1H-benzo[d]imidazol-1-yl)quinoline-8-carbonitrile | 451.2 | 1H NMR (400 MHz, DMSO-d6) δ 9.35 (d, J = 0.5 Hz, 1H), 8.61 (s, 1H), 8.44 (dd, J = 7.1, 1.4 Hz, 1H), 7.87-7.60 (m, 3H), 6.68 (d, J = 2.3 Hz, 1H), 3.64 (t, J = 4.7 Hz, 4H), 3.06 (dd, J = 6.2, 3.7 Hz, 4H), 2.44 (s, 3H), 2.23 (s, 3H). |
| 157 | 4-(1-(3,8-dichloroquinolin-4-yl)-2-methyl-4-(5-methyl-4H-1,2,4-triazol-3-yl)-1H-benzo[d]imidazol-6-yl)morpholine | 494.1 | 1H NMR (400 MHz, DMSO-d6) δ 9.42 (s, 1H), 8.14 (dd, J = 7.6, 1.2 Hz, 1H), 7.71-7.62 (m, 2H), 7.38 (d, J = 8.5 Hz, 1H), 6.76 (d, J = 2.3 Hz, 1H), 3.72-3.58 (m, 4H), 3.04 (dd, J = 6.1, 3.8 Hz, 4H), 2.48 (s, 3H), 2.44 (s, 3H). |
| 158 | tert-butyl 4-(4-(6-morpholino-4-(4H-1,2,4-triazol-3-yl)-1H-benzo[d]imidazol-1-yl)quinolin-2-yl)piperazine-1-carboxylate | | |
| 159 | 4-(4-(5-methyl-4H-1,2,4-triazol-3-yl)-1-(2-(1-trityl-1H-pyrazol-3-yl)quinolin-4-yl)-1H-benzo[d]imidazol-6-yl)morpholine | | |
| 384 | 4-(4-(4H-1,2,4-triazol-3-yl)-1-(2-(1-trityl-1H-pyrazol-3-yl)quinolin-4-yl)-1H-benzo[d]imidazol-6-yl)morpholine | | |
| 385 | 4-(4-(5-methyl-4H-1,2,4-triazol-3-yl)-1-(2-(1-trityl-1H-pyrazol-4-yl)quinolin-4-yl)-1H-benzo[d]imidazol-6-yl)morpholine | | |
| 386 | 4-(4-(4H-1,2,4-triazol-3-yl)-1-(2-(1-trityl-1H-pyrazol-4-yl)quinolin-4-yl)-1H-benzo[d]imidazol-6-yl)morpholine | | |
| 391 | 4-(1-(3-(4H-1,2,4-triazol-3-yl)quinolin-4-yl)-2-ethyl-4-(4H-1,2,4-triazol-3-yl)-1H-benzo[d]imidazol-6-yl)morpholine | 493.2 | 1H NMR (400 MHz, DMSO-d6) δ 9.91 (s, 1H), 8.72 (s, 1H), 8.60 (s, 1H), 8.35-8.28 (m, 1H), 7.96 (ddd, J = 8.4, 6.9, 1.4 Hz, 1H), 7.77-7.65 (m, 2H), 7.57 (s, 1H), 6.57 (d, J = 2.2 Hz, 1H), 3.81-3.43 (m, 4H), 2.98 (t, J = 4.9 Hz, 4H), 2.84-2.57 (m, 2H), 0.95 (t, J = 7.5 Hz, 3H). |
| 392 | 4-(1-(3-(4H-1,2,4-triazol-3-yl)quinolin-4-yl)-2-methyl-4-(4H-1,2,4-triazol-3-yl)-1H-benzo[d]imidazol-6-yl)morpholine | 479.2 | 1H NMR (400 MHz, DMSO-d6) δ 9.91 (s, 1H), 8.83 (s, 1H), 8.60 (s, 1H), 8.32 (dt, J = 8.5, 0.9 Hz, 1H), 7.97 (ddd, J = 8.4, 6.8, 1.5 Hz, 1H), 7.89-7.53 (m, 4H), 6.60 (d, J = 2.2 Hz, 1H), 3.59 (t, J = 4.8 Hz, 4H), 2.99 (t, J = 5.0 Hz, 4H), 2.49 (s, 3H). |

Step 5a: 4-(2-methyl-1-(2-methylquinolin-4-yl)-4-(1H-tetrazol-5-yl)-1H-benzo[d]imidazol-6-yl)morpholine

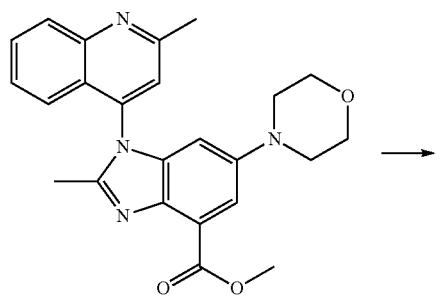

morpholino-1H-benzo[d]imidazole-4-carbonitrile. 2-Methyl-1-(2-methylquinolin-4-yl)-6-morpholino-1H-benzo[d]imidazole-4-carbonitrile (50 mg, 0.13 mmol) was combined with sodium azide (85 mg, 1.3 mmol) and ammonium chloride (70 mg, 1.3 mmol) in DMF (1 mL) and heated in a microwave at 100° C. for 14 hours. The crude reaction was purified by preparatory LC to provide 4-(2-methyl-1-(2-methylquinolin-4-yl)-4-(1H-tetrazol-5-yl)-1H-benzo[d]imidazol-6-yl)morpholine (Compound 160). 1H NMR (400 MHz, DMSO-d6) δ 8.21-8.14 (m, 1H), 7.88 (ddd, J=8.5, 6.9, 1.4 Hz, 1H), 7.83 (s, 1H), 7.71 (d, J=2.2 Hz, 1H), 7.58 (ddd, J=8.2, 6.9, 1.2 Hz, 1H), 7.31 (d, J=8.2 Hz, 1H), 6.71 (d, J=2.2 Hz, 1H), 3.67 (t, J=4.8 Hz, 4H), 3.14-2.99 (m, 4H), 2.82 (s, 3H), 2.45 (s, 3H). ES/MS m/z=427.2 (M+H)+.

The compounds listed in the table below were prepared in a manner similar to that described above using appropriate intermediates and chemistry.

| Compound | Compound Name | MS | NMR |
|---|---|---|---|
| 161 | 4-(1-(8-chloroquinolin-4-yl)-2-methyl-4-(1H-tetrazol-5-yl)-1H-benzo[d]imidazol-6-yl)morpholine | 447.1 | 1H NMR (400 MHz, DMSO-d6) δ 9.34 (d, J = 4.5 Hz, 1H), 8.12 (dd, J = 7.6, 1.2 Hz, 1H), 8.02 (d, J = 4.5 Hz, 1H), 7.70 (d, J = 2.2 Hz, 1H), 7.62 (dd, J = 8.5, 7.5 Hz, 1H), 7.36 (dd, J = 8.5, 1.2 Hz, 1H), 6.76 (d, J = 2.2 Hz, 1H), 3.67 (t, J = 4.7 Hz, 4H), 3.07 (q, J = 4.1 Hz, 4H), 2.45 (s, 3H). |

-continued

Step 5b: 4-(1-(8-chloroquinolin-4-yl)-2-methyl-4-(1,3,4-oxadiazol-2-yl)-1H-benzo[d]imidazol-6-yl)morpholine

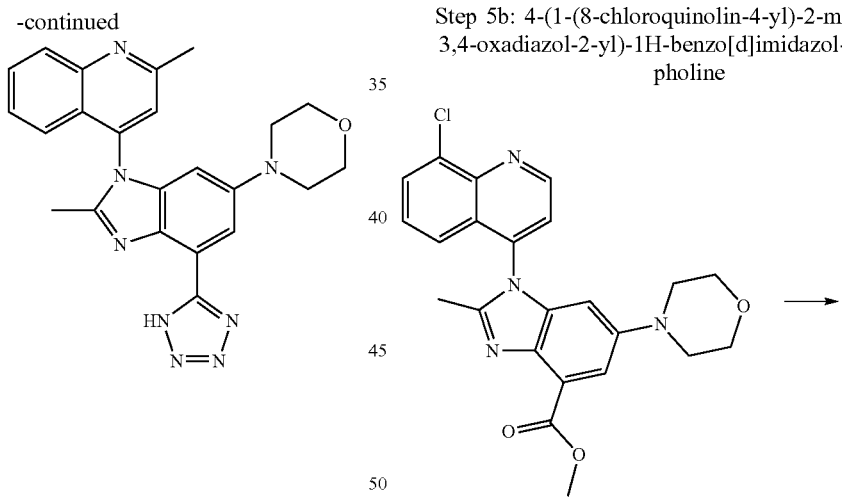

To a suspension of ammonium chloride (193 mg, 3.6 mmol) in dichloroethane (2 mL) at 0° C. under N₂ was added trimethylaluminum (1.8 mL of a 2.0M heptane solution, 3.6 mmol). The mixture was stirred at 0° C. for 5 minutes, then at ambient temperature for 20 minutes. The reaction was cooled back to 0° C., and a suspension of methyl 2-methyl-1-(2-methylquinolin-4-yl)-6-morpholino-1H-benzo[d]imidazole-4-carboxylate (300 mg, 0.72 mmol) in dichloroethane (1 mL) was added. The reaction was allowed to warm to ambient temperature and stir for 3 days. After heating to 60° C. for 3 hours the reaction was allowed to cool, then treated with aq. citric acid. The product was extracted 3× into dichloromethane and was purified on silica (0-100% EtOAc in DCM) to give 2-methyl-1-(2-methylquinolin-4-yl)-6-

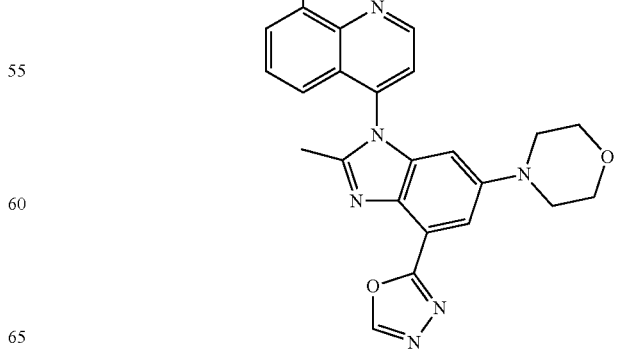

A solution of methyl 1-(8-chloroquinolin-4-yl)-2-methyl-6-morpholino-1H-benzo[d]imidazole-4-carboxylate (210 mg, 0.48 mmol) and hydrazine hydrate (0.46 mL, 9.6 mmol) in ethanol was refluxed for 2 h. Upon cooling, the reaction mixture was concentrated. Ethyl acetate and water were added followed by two extractions of the aqueous phase with ethyl acetate. The combined organic phases were dried over MgSO4, filtrated and concentrated under reduce pressure to afford 1-(8-chloroquinolin-4-yl)-2-methyl-6-morpholino-1H-benzo[d]imidazole-4-carbohydrazide (ES/MS m/z=437.1 (M+H)$^+$) which was dissolved in trimethylorthoformate (2.6 mL) and trifluoroacetic acid (0.5 mL) and heated to 100° C. for 45 minutes. After cooling and concentration under reduced pressure, the resultant was purified by HPLC eluting with 5-95% water/acetonitrile (0.1% v/v trifluoroacetic acid). The appropriate fractions were pooled and lyophilized to afford 4-(1-(8-chloroquinolin-4-yl)-2-methyl-4-(1,3,4-oxadiazol-2-yl)-1H-benzo[d]imidazol-6-yl)morpholine as a 2,2,2-trifluoroacetic acid salt (Compound 162). 1H NMR (400 MHz, DMSO-d6) δ 9.50 (s, 1H), 9.31 (d, J=4.5 Hz, 1H), 8.10 (dd, J=7.5, 1.2 Hz, 1H), 7.98 (d, J=4.5 Hz, 1H), 7.63-7.56 (m, 2H), 7.32 (dd, J=8.5, 1.2 Hz, 1H), 6.77 (d, J=2.2 Hz, 1H), 3.64 (t, J=4.8 Hz, 4H), 3.04 (q, J=4.3 Hz, 4H), 2.39 (s, 3H). ES/MS m/z=447.1 (M+H)$^+$.

Step 5c: 5-(1-(7-fluoroquinolin-4-yl)-2-methyl-6-morpholino-1H-benzo[d]imidazol-4-yl)-1,3,4-oxadiazol-2-amine 1-(7-fluoroquinolin-4-yl)-2-methyl-6-morpholino-1H-benzo[d]imidazole-4-carbohydrazide was prepared in a manner similar to 1-(8-chloroquinolin-4-yl)-2-methyl-6-morpholino-1H-benzo[d]imidazole-4-carbohydrazide. A mixture of 1-(7-fluoroquinolin-4-yl)-2-methyl-6-morpholino-1H-benzo[d]imidazole-4-carbohydrazide (50 mg, 0.119 mmol), sodium bicarbonate (15 mg, 0.178 mmol) and BrCN (14.5 mg, 0.137 mmol) was stirred at room temperature for 4 hours. After concentration under reduced pressure, the resultant was purified by HPLC eluting with 5-95% water/acetonitrile (0.1% v/v trifluoroacetic acid). The appropriate fractions were pooled and lyophilized to afford 5-(1-(7-fluoroquinolin-4-yl)-2-methyl-6-morpholino-1H-benzo[d]imidazol-4-yl)-1,3,4-oxadiazol-2-amine as a 2,2,2-trifluoroacetic acid salt (Compound 163). 1H NMR (400 MHz, DMSO-d6) δ 9.23 (d, J=4.6 Hz, 1H), 8.09-8.00 (m, 1H), 7.88 (d, J=4.6 Hz, 1H), 7.63-7.45 (m, 5H), 7.39 (d, J=2.2 Hz, 1H), 6.66 (s, 1H), 3.63 (t, J=4.8 Hz, 4H), 3.06-2.98 (m, 4H), 2.44 (s, 3H). ES/MS m/z=446.2 (M+H)$^+$.

Step 5d: 5-(1-(7-fluoroquinolin-4-yl)-2-methyl-6-morpholino-1H-benzo[d]imidazol-4-yl)-1,3,4-oxadiazole-2(3H)-thione

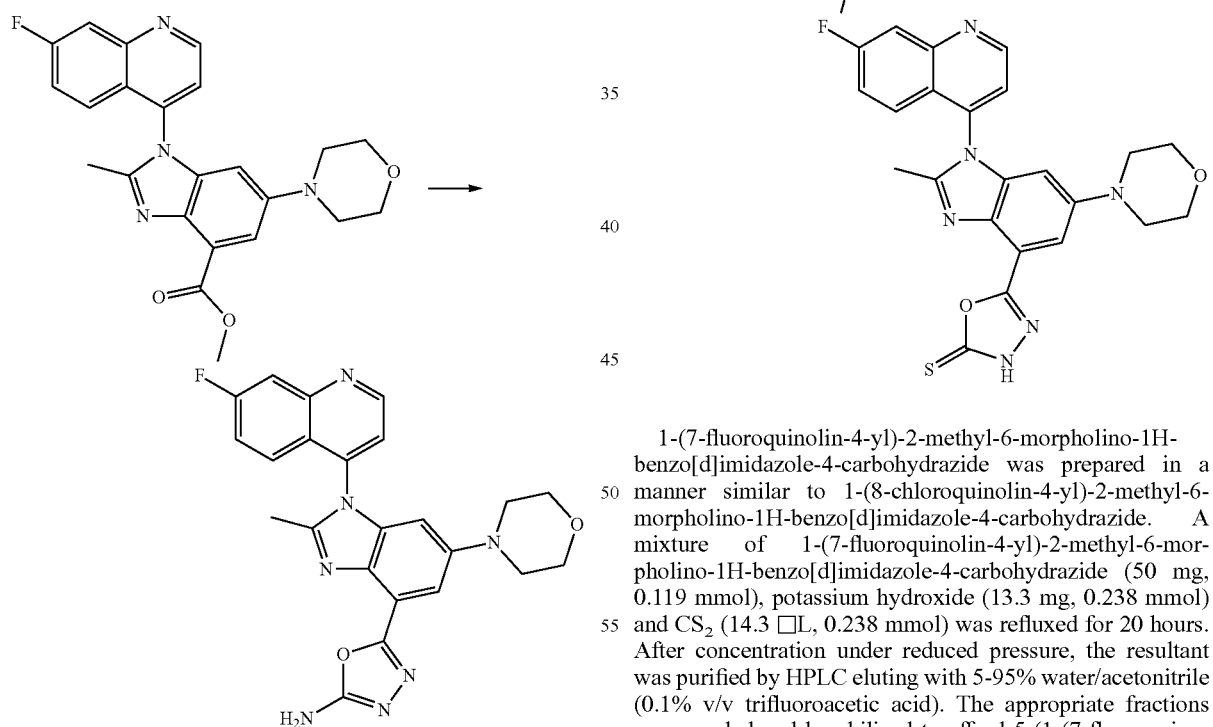

1-(7-fluoroquinolin-4-yl)-2-methyl-6-morpholino-1H-benzo[d]imidazole-4-carbohydrazide was prepared in a manner similar to 1-(8-chloroquinolin-4-yl)-2-methyl-6-morpholino-1H-benzo[d]imidazole-4-carbohydrazide. A mixture of 1-(7-fluoroquinolin-4-yl)-2-methyl-6-morpholino-1H-benzo[d]imidazole-4-carbohydrazide (50 mg, 0.119 mmol), potassium hydroxide (13.3 mg, 0.238 mmol) and CS$_2$ (14.3 □L, 0.238 mmol) was refluxed for 20 hours. After concentration under reduced pressure, the resultant was purified by HPLC eluting with 5-95% water/acetonitrile (0.1% v/v trifluoroacetic acid). The appropriate fractions were pooled and lyophilized to afford 5-(1-(7-fluoroquinolin-4-yl)-2-methyl-6-morpholino-1H-benzo[d]imidazol-4-yl)-1,3,4-oxadiazole-2(3H)-thione as a 2,2,2-trifluoroacetic acid salt (Compound 164). H NMR (400 MHz, DMSO-d6) δ 9.21 (d, J=4.6 Hz, 1H), 8.02 (dd, J=10.1, 2.6 Hz, 1H), 7.83 (d, J=4.7 Hz, 1H), 7.57 (td, J=8.9, 2.7 Hz, 1H), 7.43-7.35 (m, 2H), 6.71 (d, J=2.2 Hz, 1H), 3.63 (t, J=4.7 Hz, 4H), 3.08-2.94 (m, 4H), 2.35 (d, J=1.3 Hz, 3H). ES/MS m/z=463.2 (M+H)$^+$.

209

Step 5e: 5-(1-(7-fluoroquinolin-4-yl)-2-methyl-6-morpholino-1H-benzo[d]imidazol-4-yl)-1,3,4-thiadiazol-2-amine

210

Step 5f: 5-(1-(7-fluoroquinolin-4-yl)-2-methyl-6-morpholino-1H-benzo[d]imidazol-4-yl)-1,3,4-oxadiazol-2(3H)-one

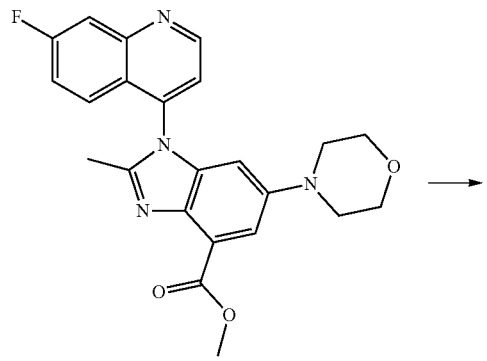

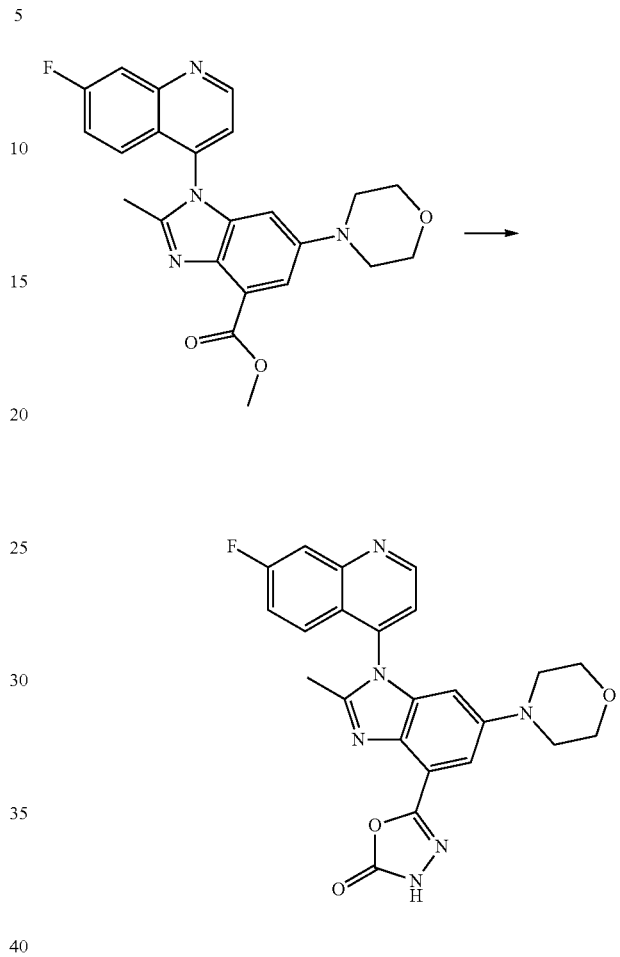

1-(7-fluoroquinolin-4-yl)-2-methyl-6-morpholino-1H-benzo[d]imidazole-4-carbohydrazide was prepared in a manner similar to 1-(8-chloroquinolin-4-yl)-2-methyl-6-morpholino-1H-benzo[d]imidazole-4-carbohydrazide. A mixture of 1-(7-fluoroquinolin-4-yl)-2-methyl-6-morpholino-1H-benzo[d]imidazole-4-carbohydrazide (100 mg, 0.238 mmol) and trimethylsilyl isothiocyanate (33 □L, 0.238 mmol) in ethanol (2.3 mL) was refluxed for 4 h, and then the reaction mixture was concentrated. After adding conc. $H_2SO_4$ (2.3 mL), the solution was stirred at 30° C. for 6 h. The mixture was slowly neutralized by adding potassium carbonate. The aqueous phase was extracted twice with dichloromethane. After concentration under reduced pressure, the resultant was purified by HPLC eluting with 5-95% water/acetonitrile (0.1% v/v trifluoroacetic acid). The appropriate fractions were pooled and lyophilized to 5-(1-(7-fluoroquinolin-4-yl)-2-methyl-6-morpholino-1H-benzo[d]imidazol-4-yl)-1,3,4-thiadiazol-2-amine as a 2,2,2-trifluoroacetic acid salt (Compound 165). 1H NMR (400 MHz, DMSO-d6) δ 9.22-9.19 (m, 1H), 8.03-7.98 (m, 1H), 7.85-7.82 (m, 1H), 7.73-7.51 (m, 4H), 7.48-7.41 (m, 1H), 6.55-6.52 (m, 1H), 3.68-3.60 (m, 4H), 3.05-2.95 (m, 4H), 2.35 (s, 3H). ES/MS m/z=462.2 (M+H)+.

1-(7-fluoroquinolin-4-yl)-2-methyl-6-morpholino-1H-benzo[d]imidazole-4-carbohydrazide was prepared in a manner similar to 1-(8-chloroquinolin-4-yl)-2-methyl-6-morpholino-H-benzo[d]imidazole-4-carbohydrazide. A mixture of 1-(7-fluoroquinolin-4-yl)-2-methyl-6-morpholino-1H-benzo[d]imidazole-4-carbohydrazide (50 mg, 0.119 mmol) and carbonyl diimidazole (21 mg, 0.131 mmol) in THF (2.0 mL) was stirred at room temperature for 16 h. After concentration under reduced pressure, the resultant was purified by HPLC eluting with 5-95% water/acetonitrile (0.1% v/v trifluoroacetic acid). The appropriate fractions were pooled and lyophilized to afford 5-(1-(7-fluoroquinolin-4-yl)-2-methyl-6-morpholino-1H-benzo[d]imidazol-4-yl)-1,3,4-oxadiazol-2(3H)-one as a 2,2,2-trifluoroacetic acid salt (Compound 166). 1H NMR (400 MHz, DMSO-d6) δ 12.75 (s, 1H), 9.20 (d, J=4.6 Hz, 1H), 8.02 (dd, J=10.1, 2.6 Hz, 1H), 7.83 (d, J=4.6 Hz, 1H), 7.57 (td, J=8.8, 2.7 Hz, 1H), 7.42 (dd, J=9.2, 6.0 Hz, 1H), 7.35 (d, J=2.2 Hz, 1H), 6.65 (d, J=2.2 Hz, 1H), 3.62 (t, J=4.8 Hz, 4H), 3.08-2.93 (m, 4H), 2.36 (s, 3H). ES/MS m/z=447.2 (M+H)+.

Step 5g: 4-(1-(2-(1H-pyrazol-4-yl)quinolin-4-yl)-2-methyl-4-(4H-1,2,4-triazol-3-yl)-1H-benzo[d]imidazol-6-yl)morpholine

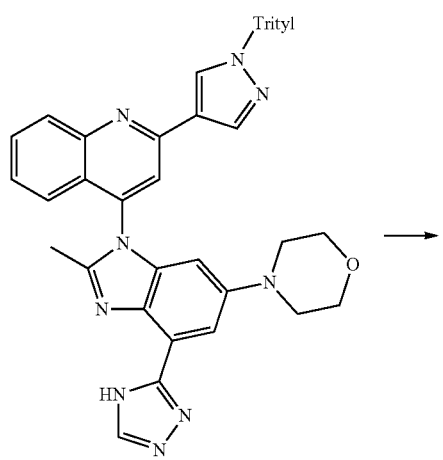

→

-continued

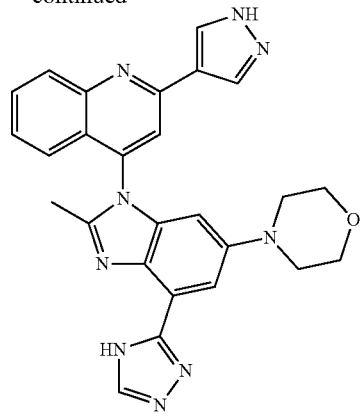

Trifluoroacetic acid (0.50 mL, 6.53 mmol) was added to 4-(2-methyl-4-(4H-1,2,4-triazol-3-yl)-1-(2-(1-trityl-1H-pyrazol-4-yl)quinolin-4-yl)-1H-benzo[d]imidazol-6-yl) morpholine (180 mg, 0.25 mmol) in DCM (6 mL). The reaction mixture was stirred for 2 hours at ambient temperature. The resultant was purified by HPLC eluting with 5-95% water/acetonitrile (0.1% v/v trifluoroacetic acid). The appropriate fractions were pooled and lyophilized to afford 4-(1-(2-(1H-pyrazol-4-yl)quinolin-4-yl)-2-methyl-4-(4H-1,2,4-triazol-3-yl)-1H-benzo[d]imidazol-6-yl)morpholine 2,2,2-trifluoroacetate (Compound 167). $^1$H NMR (400 MHz, DMSO-d6) δ 8.81 (s, 1H), 8.40 (s, 2H), 8.35 (s, 1H), 8.23-8.13 (m, 1H), 7.93-7.83 (m, 2H), 7.60-7.48 (m, 2H), 6.79-6.73 (m, 1H), 3.65 (t, J=4.8 Hz, 4H), 3.13-3.04 (m, 4H), 2.66 (s, 3H). ES/MS m/z=478.20 (M+H)$^+$. The compounds listed in the table below were prepared in a manner similar to that described above using appropriate intermediates and chemistry known to those skilled in the art.

| Compound | name | MS | NMR |
|---|---|---|---|
| 380 | 4-(1-(2-(1H-pyrazol-4-yl)quinolin-4-yl)-4-(5-methyl-4H-1,2,4-triazol-3-yl)-1H-benzo[d]imidazol-6-yl)morpholine | 478.2 | 1H NMR (400 MHz, DMSO-d6) δ 9.23 (s, 1H), 8.44 (s, 2H), 8.30 (s, 1H), 8.18-8.12 (m, 1H), 7.85 (ddd, J = 8.4, 6.8, 1.5 Hz, 1H), 7.77 (d, J = 2.2 Hz, 1H), 7.55 (ddd, J = 8.1, 6.8, 1.2 Hz, 1H), 7.47 (d, J = 8.1 Hz, 1H), 6.84 (d, J = 2.3 Hz, 1H), 3.66 (t, J = 4.8 Hz, 4H), 3.08 (d, J = 5.2 Hz, 5H), 2.49 (s, 3H). |
| 381 | 4-(1-(2-(1H-pyrazol-4-yl)quinolin-4-yl)-4-(4H-1,2,4-triazol-3-yl)-1H-benzo[d]imidazol-6-yl)morpholine | 464.2 | 1H NMR (400 MHz, DMSO-d6) δ 9.19 (s, 1H), 8.50 (s, 1H), 8.45 (s, 2H), 8.30 (s, 1H), 8.15 (ddd, J = 8.5, 1.2, 0.6 Hz, 1H), 7.85 (ddd, J = 8.4, 6.8, 1.4 Hz, 1H), 7.82 (d, J = 2.2 Hz, 1H), 7.55 (ddd, J = 8.1, 6.8, 1.2 Hz, 1H), 7.49-7.44 (m, 1H), 6.85 (d, J = 2.3 Hz, 1H), 3.67 (t, J = 4.8 Hz, 4H), 3.15-3.02 (m, 4H). |
| 382 | 4-(1-(2-(1H-pyrazol-3-yl)quinolin-4-yl)-4-(5-methyl-4H-1,2,4-triazol-3-yl)-1H-benzo[d]imidazol-6-yl)morpholine | 478.2 | 1H NMR (400 MHz, DMSO-d6) δ 8.42 (s, 1H), 8.23 (d, J = 8.6 Hz, 1H), 7.94-7.86 (m, 1H), 7.77 (d, J = 2.2 Hz, 1H), 7.61 (ddd, J = 8.2, 6.9, 1.2 Hz, 1H), 7.51 (d, J = 8.3 Hz, 1H), 7.12 (d, J = 2.3 Hz, 1H), 6.84 (d, J = 2.2 Hz, 1H), 3.66 (t, J = 4.8 Hz, 5H), 3.08 (d, J = 7.2 Hz, 5H), 2.49 (s, 3H). |
| 383 | 4-(1-(2-(1H-pyrazol-3-yl)quinolin-4-yl)-4-(4H-1,2,4-triazol-3-yl)-1H-benzo[d]imidazol-6-yl)morpholine | 464.2 | 1H NMR (400 MHz, DMSO-d6) δ 9.20 (s, 1H), 8.50 (s, 1H), 8.42 (s, 1H), 8.23 (ddd, J = 8.5, 1.1, 0.6 Hz, 1H), 7.90 (ddd, J = 8.4, 6.9, 1.4 Hz, 2H), 7.81 (d, J = 2.2 Hz, |

| Compound name | MS | NMR |
|---|---|---|
| | | 1H), 7.61 (ddd, J = 8.2, 6.8, 1.2 Hz, 1H), 7.51 (ddd, J = 8.4, 1.5, 0.7 Hz, 1H), 7.12 (d, J = 2.3 Hz, 1H), 6.85 (d, J = 2.3 Hz, 1H), 3.66 (t, J = 4.8 Hz, 4H), 3.08 (d, J = 5.1 Hz, 4H). |

Step 5h: 4-(2-methyl-1-(2-(piperazin-1-yl)quinolin-4-yl)-4-(4H-1,2,4-triazol-3-yl)-1H-benzo[d]imidazol-6-yl)morpholine 2,2,2-trifluoroacetate

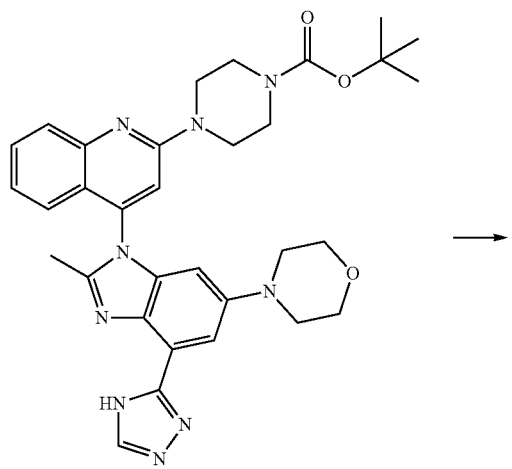

→

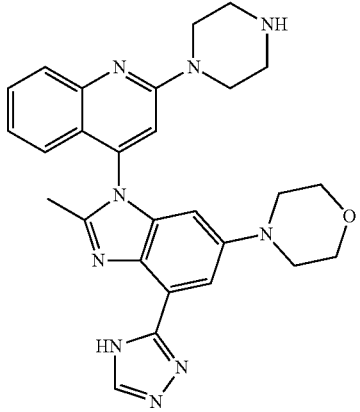

To a solution of tert-butyl 4-(4-(2-methyl-6-morpholino-4-(4H-1,2,4-triazol-3-yl)-1H-benzo[d]imidazol-1-yl)quinolin-2-yl)piperazine-1-carboxylate (319 mg, 0.54 mmol) in DCM (3.0 mL) was added TFA (0.8 mL). After concentration under reduced pressure, the resultant was purified by HPLC eluting with 5-95% water/acetonitrile (0.1% v/v trifluoroacetic acid). The appropriate fractions were pooled and lyophilized to afford the parent compound as a 2,2,2-trifluoroacetic acid salt. ES/MS m/z=482.2 (M+H)$^+$. (Compound 168). $^1$H NMR (400 MHz, DMSO-d6) δ 8.96 (s, 2H), 8.71 (s, 1H), 7.87-7.67 (m, 4H), 7.34-7.21 (m, 2H), 6.71-6.64 (m, 1H), 4.03-3.90 (m, 4H), 3.72-3.64 (m, 4H), 3.31-3.26 (m, 4H), 3.14-3.04 (m, 4H), 2.59 (s, 3H). ES/MS m/z 496.30 (M+H)$^+$.

The compounds listed in the table below were prepared in a manner similar to that described above using appropriate intermediates and chemistry known to those skilled in the art.

| Compound | name | MS | NMR |
|---|---|---|---|
| 169 | 4-(2-methyl-4-(5-methyl-4H-1,2,4-triazol-3-yl)-1-(2-(piperazin-1-yl)quinolin-4-yl)-1H-benzo[d]imidazol-6-yl)morpholine | 510.3 | 1H NMR (400 MHz, DMSO-d6) δ 8.87 (s, 1H), 7.82 (dt, J = 8.6, 0.9 Hz, 1H), 7.76 (s, 1H), 7.73 (dddd, J = 8.4, 6.7, 1.4, 0.0 Hz, 1H), 7.30 (ddd, J = 8.1, 6.8, 1.2 Hz, 1H), 7.25-7.19 (m, 1H), 6.63 (d, J = 1.9 Hz, 1H), 3.96 (dd, J = 6.2, 4.0 Hz, 4H), 3.67 (t, J = 4.8 Hz, 4H), 3.33-3.24 (m, 4H), 3.07 (q, J = 4.6 Hz, 4H), 2.56 (s, 3H), 2.51 (s, 3H). |
| 379 | 4-(1-(2-(piperazin-1-yl)quinolin-4-yl)-4-(4H-1,2,4-triazol-3-yl)-1H-benzo[d]imidazol-6-yl)morpholine | 482.3 | 1H NMR (400 MHz, DMSO-d6) δ 8.89 (s, 3H), 8.40 (s, 1H), 7.82-7.75 (m, 2H), 7.74-7.67 (m, 2H), 7.34-7.25 (m, 2H), 6.79 (d, J = 2.3 Hz, 1H), 3.97 (s, 4H), 3.69 (t, J = 4.8 Hz, 4H), 3.25 (s, 4H), 3.08 (d, J = 5.1 Hz, 4H). |

Step 5i: 5-(1-(5,8-difluoroquinolin-4-yl)-2-methyl-6-morpholino-1H-benzo[d]imidazol-4-yl)-4H-1,2,4-triazol-3-amine

Step 6: 4-(4-(5-chloro-4H-1,2,4-triazol-3-yl)-1-(8-chloro-5-fluoroquinolin-4-yl)-2-methyl-1H-benzo[d]imidazol-6-yl)morpholine

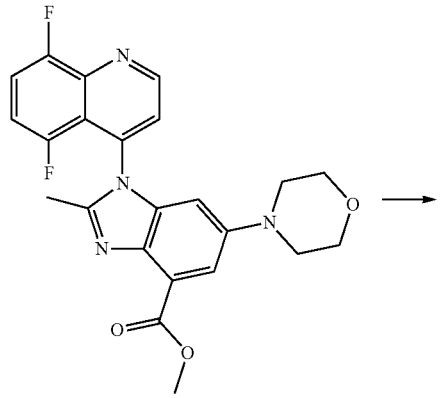

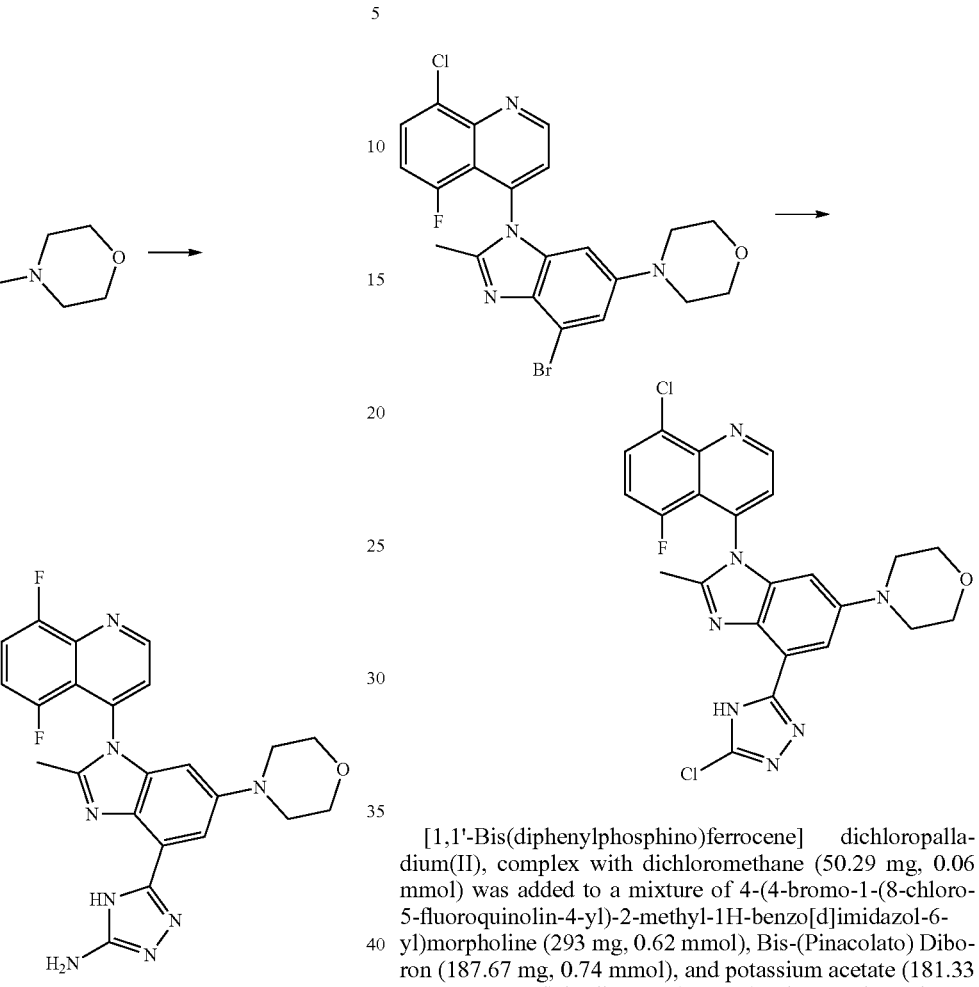

Anhydrous hydrazine (0.36 mL, 11.4 mmol) was added to a suspension of methyl 1-(5,8-difluoroquinolin-4-yl)-2-methyl-6-morpholino-1H-benzo[d]imidazole-4-carboxylate (500 mg, 1.14 mmol) in MeOH (4 mL) and heated to 65 C. After several hours, the reaction was cooled and filtered. The yellow solid was washed with MeOH and dried to give 1-(5,8-difluoroquinolin-4-yl)-2-methyl-6-morpholino-1H-benzo[d]imidazole-4-carbohydrazide. 1-(5,8-difluoroquinolin-4-yl)-2-methyl-6-morpholino-1H-benzo[d]imidazole-4-carbohydrazide (99 mg, 0.226 mmol) and cyanamide (80 mg, 1.90 mmol) were combined in DMF (0.5 mL) and heated to 120° C. for 4 days. The mixture was purified by HPLC eluting with 5-95% water/acetonitrile (0.1% v/v trifluoroacetic acid) to give the title compound (Compound 393). 1H NMR (400 MHz, DMSO-d6) δ 9.33 (d, J=4.5 Hz, 1H), 8.05 (d, J=4.5 Hz, 1H), 7.81 (ddd, J=10.0, 9.0, 4.2 Hz, 1H), 7.53 (d, J=2.3 Hz, 1H), 7.54-7.44 (m, 1H), 6.83 (d, J=2.3 Hz, 1H), 3.70-3.63 (m, 4H), 3.09-3.02 (m, 4H), 2.48 (s, 3H). ES/MS m/z=463.2 (M+H)+.

[1,1'-Bis(diphenylphosphino)ferrocene] dichloropalladium(II), complex with dichloromethane (50.29 mg, 0.06 mmol) was added to a mixture of 4-(4-bromo-1-(8-chloro-5-fluoroquinolin-4-yl)-2-methyl-1H-benzo[d]imidazol-6-yl)morpholine (293 mg, 0.62 mmol), Bis-(Pinacolato) Diboron (187.67 mg, 0.74 mmol), and potassium acetate (181.33 mg, 1.85 mmol) in dioxane (1.2 mL). The reaction mixture was degassed and stirred at 125° C. for 5 hours. The resultant was filtered through a pad of celite and washed with ethyl acetate (25 mL). The filtrate was concentrated to afford 4-(1-(8-chloro-5-fluoroquinolin-4-yl)-2-methyl-4-(4,4,5,5-tetramethyl-1,3,2-dioxaborolan-2-yl)-1H-benzo[d]imidazol-6-yl)morpholine, which was dissolved in THF (10 mL) and water (2 mL) with 3,5-dichloro-4-(tetrahydro-2H-pyran-2-yl)-4H-1,2,4-triazole (205.16 mg, 0.92 mmol) and tripotassium phosphate (39 mg, 2 mmol).

Tetrakis(triphenylphosphine)palladium(0) (71 mg, 0.06 mmol) was added and the reagents were stirred at 90° C. for 16 hours, after which time the reaction mixture was cooled to ambient temperature and partitioned between ethyl acetate (50 mL) and water (50 mL). The aqueous layer was extracted 3 times with ethyl acetate. The combined organic phases were dried with sodium sulfate and filtered. The resultant residue was purified on silica gel with 0 to 100% ethyl acetate in hexanes to afford 4-(4-(5-chloro-4-(tetrahydro-2H-pyran-2-yl)-4H-1,2,4-triazol-3-yl)-1-(8-chloro-5-fluoroquinolin-4-yl)-2-methyl-1H-benzo[d]imidazol-6-yl)morpholine which was dissolved in DCM (2 mL). Trifluoroacetic acid (2 mL) was added and the reaction mixture was stirred at 40° C. for 2 hour, after which the reaction was cooled to ambient temperature. The resultant was purified by HPLC eluting with 5-95% water/acetonitrile (0.1% v/v trifluoroacetic acid). The appropriate fractions were pooled and lyophilized to afford 4-(4-(5-chloro-4H-1,2,4-triazol-3-yl)-1-(8-chloro-5-fluoroquinolin-4-yl)-2-methyl-1H-benzo[d]imidazol-6-yl)morpholine (Compound 170). ¹H NMR (400 MHz, DMSO-d6) δ 9.35 (d, J=4.5 Hz, 1H), 8.15-8.07 (m, 1H), 8.00 (d, J=4.5 Hz, 1H), 7.53-7.43 (m, 2H), 6.79 (d, J=2.2 Hz, 1H), 3.67-3.61 (m, 4H), 3.04 (t, J=4.9 Hz, 4H), 2.39 (s, 3H). ES/MS m/z=498.1 (M+H)⁺.

The compounds listed in the table below were prepared in a manner similar to that described above using appropriate intermediates and chemistry known to those skilled in the art.

| Compound | name | MS | NMR |
|---|---|---|---|
| 171 | 4-(4-(5-chloro-4H-1,2,4-triazol-3-yl)-1-(8-chloro-7-fluoroquinolin-4-yl)-2-methyl-1H-benzo[d]imidazol-6-yl)morpholine | 498.1 | 1H NMR (400 MHz, DMSO-d6) δ 9.36 (d, J = 4.5 Hz, 1H), 7.99 (d, J = 4.6 Hz, 1H), 7.75 (t, J = 9.1 Hz, 1H), 7.59-7.54 (m, 1H), 7.44-7.36 (m, 1H), 6.73-6.65 (m, 1H), 3.66 (t, J = 4.8 Hz, 4H), 3.05-3.01 (m, 4H), 2.43 (s, 3H). |
| 172 | 4-(4-(5-chloro-4H-1,2,4-triazol-3-yl)-1-(8-chloro-7-fluoroquinolin-4-yl)-2-ethyl-1H-benzo[d]imidazol-6-yl)morpholine | 512.1 | 1H NMR (400 MHz, DMSO-d6) δ 9.35 (d, J = 4.5 Hz, 1H), 8.00 (d, J = 4.6 Hz, 1H), 7.74 (t, J = 9.1 Hz, 1H), 7.57-7.52 (m, 1H), 7.38-7.30 (m, 1H), 6.69-6.65 (m, 1H), 3.65 (t, J = 4.8 Hz, 4H), 3.06-2.98 (m, 4H), 2.77-2.57 (m, 2H), 1.21 (t, J = 7.5 Hz, 3H). |
| 173 | 4-(4-(5-chloro-4H-1,2,4-triazol-3-yl)-1-(8-chloro-7-fluoroquinolin-4-yl)-2-cyclopropyl-1H-benzo[d]imidazol-6-yl)morpholine | 524.1 | 1H NMR (400 MHz, DMSO-d6) δ 9.35 (d, J = 4.6 Hz, 1H), 8.00 (d, J = 4.6 Hz, 1H), 7.79-7.72 (m, 1H), 7.53-7.51 (m, 1H), 7.45-7.37 (m, 1H), 6.71-6.68 (m, 1H), 3.65 (t, J = 4.8 Hz, 4H), 3.05-2.97 (m, 4H), 1.63-1.53 (m, 1H), 1.52-1.42 (m, 1H), 1.43-1.33 (m, 1H), 0.98-0.89 (m, 1H), 0.87-0.77 (m, 1H),. |
| 174 | 4-(4-(5-chloro-4H-1,2,4-triazol-3-yl)-1-(8-chloro-5-fluoroquinolin-4-yl)-2-cyclopropyl-1H-benzo[d]imidazol-6-yl)morpholine | 524.1 | 1H NMR (400 MHz, DMSO-d6) δ 9.36 (d, J = 4.5 Hz, 1H), 8.15-8.09 (m, 1H), 8.03 (d, J = 4.5 Hz, 1H), 7.53-7.45 (m, 2H), 6.81-6.78 (m, 1H), 3.66 (t, J = 4.8 Hz, 4H), 3.04 (t, J = 4.8 Hz, 4H), 1.66-1.55 (m, 1H), 1.48-1.38 (m, 1H), 1.33-1.25 (m, 1H), 0.93-0.78 (m, 2H). |
| 175 | 4-[3-(8-chloroquinolin-4-yl)-7-(1H-imidazol-2-yl)-2-methylbenzimidazol-5-yl]morpholine | 445.1 | 1H NMR (400 MHz, DMSO-d6) δ 9.33 (d, J = 4.6 Hz, 1H), 8.16-8.09 (m, 1H), 7.99 (d, J = 4.5 Hz, 1H), 7.87 (d, J = 0.6 Hz, 2H), 7.72 (d, J = 2.1 Hz, 1H), 7.62 (dd, J = 8.4, 7.6 Hz, 1H), 7.26-7.18 (m, 1H), 6.78 (d, J = 2.1 Hz, 1H), 3.70-3.60 (m, 4H), 3.06 (dd, J = 6.6, 3.7 Hz, 4H), 2.44-2.39 (m, 3H). |
| 176 | 4-[3-(8-chloroquinolin-4-yl)-2-methyl-7-(4-methyl-1H-imidazol-2-yl)benzimidazol-5-yl]morpholine | 459.1 | 1H NMR (400 MHz, DMSO-d6) δ 9.31 (d, J = 4.5 Hz, 1H), 9.16 (s, 1H), 8.12 (dd, J = 7.6, 1.2 Hz, 1H), 7.95 (d, J = 4.5 Hz, 1H), 7.67-7.59 (m, 1H), 7.21 (dd, J = 8.4, 1.2 Hz, 1H), 7.10 (d, J = 2.2 Hz, 1H), 6.57 (d, J = 2.2 Hz, 1H), 3.65 (t, J = 4.7 Hz, 4H), 3.07-2.95 (m, 4H), 2.54 (s, 3H), 2.32 (s, 3H). |
| 177 | 4-[3-(8-chloroquinolin-4-yl)-2-methyl-7-(4-methyl-1H-imidazol-5-yl)benzimidazol-5-yl]morpholine | 459.1 | 1H NMR (400 MHz, DMSO-d6) δ 9.32 (d, J = 4.5, 0.7 Hz, 1H), 9.16 (s, 1H), 8.12 (d, J = 7.5, 1.0 Hz, 1H), 7.95 (d, J = 4.6, 0.7 Hz, 1H), 7.63 (dd, J = 8.3, 7.5 Hz, 1H), 7.21 (d, J = 8.5 Hz, 1H), 7.10 (d, J = 2.2 Hz, 1H), 6.60-6.54 (m, 1H), 3.65 (t, J = 4.7 Hz, 4H), 3.01 (q, J = 4.1 Hz, 4H), 2.53 (s, 3H), 2.33 (s, 3H). |

-continued

| Compound | name | MS | NMR |
|---|---|---|---|
| 178 | 4-[3-(8-chloroquinolin-4-yl)-7-(5-chloro-4H-1,2,4-triazol-3-yl)-2-methylbenzimidazol-5-yl]morpholine | 480.1 | 1H NMR (400 MHz, DMSO-d6) δ 9.30 (d, J = 4.5 Hz, 1H), 8.10 (d, J = 7.5 Hz, 1H), 7.99 (d, J = 4.5 Hz, 1H), 7.59 (m, 2H), 7.30 (s, 1H), 6.67 (s, 1H), 3.63 (m, 4H), 3.02 (bs, 4H), 2.41 (s, 3H). |
| 179 | 4-[7-(5-chloro-4H-1,2,4-triazol-3-yl)-3-(5,8-difluoroquinolin-4-yl)-2-ethylbenzimidazol-5-yl]morpholine | 496.2 | 1H NMR (400 MHz, DMSO-d6) δ 9.27 (d, J = 4.6 Hz, 1H), 8.00 (d, J = 4.5 Hz, 1H), 7.82-7.71 (m, 1H), 7.54-7.40 (m, 2H), 6.76 (d, J = 2.0 Hz, 1H), 3.70-3.58 (m, 4H), 3.09-3.00 (m, 4H), 2.73-2.61 (m, 2H), 1.20 (t, J = 7.9, 7.1 Hz, 3H). |
| 180 | 4-[7-(5-chloro-4H-1,2,4-triazol-3-yl)-3-(5,8-difluoroquinolin-4-yl)-2-methylbenzimidazol-5-yl]morpholine | 482.2 | 1H NMR (400 MHz, DMSO-d6) δ 9.29 (d, J = 4.5 Hz, 1H), 8.00 (d, J = 4.4 Hz, 1H), 7.78 (td, J = 9.4, 4.2 Hz, 1H), 7.57-7.41 (m, 2H), 6.80 (d, J = 2.1 Hz, 1H), 3.75-3.55 (m, 4H), 3.05 (t, J = 4.8 Hz, 4H), 2.42 (s, 3H). |
| 181 | 4-[7-(5-chloro-4H-1,2,4-triazol-3-yl)-2-cyclopropyl-3-(5,8-difluoroquinolin-4-yl)benzimidazol-5-yl]morpholine | 508.2 | 1H NMR (400 MHz, DMSO-d6) δ 9.27 (d, J = 4.5 Hz, 1H), 8.00 (d, J = 4.5 Hz, 1H), 7.76 (ddd, J = 10.1, 8.7, 4.1 Hz, 1H), 7.49-7.41 (m, 2H), 6.77 (d, J = 2.2 Hz, 1H), 3.65 (dd, J = 6.0, 3.5 Hz, 4H), 3.11-2.90 (m, 4H), 1.59 (td, J = 8.2, 4.1 Hz, 1H), 1.47-1.18 (m, 2H), 0.85 (dddd, J = 12.2, 8.5, 6.3, 3.1 Hz, 2H). |
| 182 | 4-[7-(5-chloro-4H-1,2,4-triazol-3-yl)-3-(5,8-difluoroquinolin-4-yl)-2-propylbenzimidazol-5-yl]morpholine | 510.2 | 1H NMR (400 MHz, DMSO-d6) δ 9.28 (d, J = 4.5 Hz, 1H), 8.00 (d, J = 4.5 Hz, 1H), 7.77 (ddd, J = 9.9, 8.7, 4.2 Hz, 1H), 7.56-7.40 (m, 2H), 6.77 (d, J = 2.2 Hz, 1H), 3.64 (dd, J = 5.9, 3.7 Hz, 4H), 3.13-2.92 (m, 4H), 2.65 (td, J = 7.3, 2.8 Hz, 2H), 1.68 (h, J = 7.4 Hz, 2H), 0.80 (t, J = 7.4 Hz, 3H). |
| 183 | 4-(1-(8-chloroquinolin-4-yl)-2-methyl-4-(1H-pyrazol-4-yl)-1H-benzo[d]imidazol-6-yl)morpholine | 445.2 | 1H NMR (400 MHz, DMSO-d6) δ 9.32 (d, J = 4.5 Hz, 1H), 8.48 (s, 2H), 8.12 (dd, J = 7.5, 1.2 Hz, 1H), 7.98 (d, J = 4.5 Hz, 1H), 7.62 (dd, J = 8., 7.6 Hz, 1H), 7.41-7.28 (m, 2H), 6.33 (s, 1H), 3.66 (m, 4H), 3.04 (m, 4H), 2.39 (s, 3H). |

Step 6a: 4-(1-(8-fluoroquinolin-4-yl)-2-methyl-4-(oxazol-2-yl)-1H-benzo[d]imidazol-6-yl)morpholine

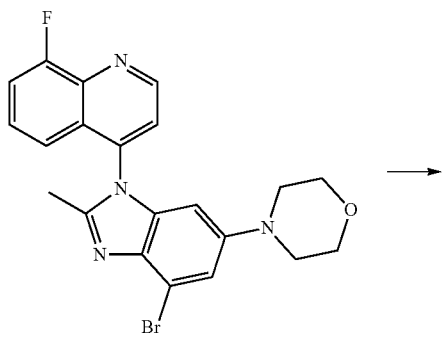

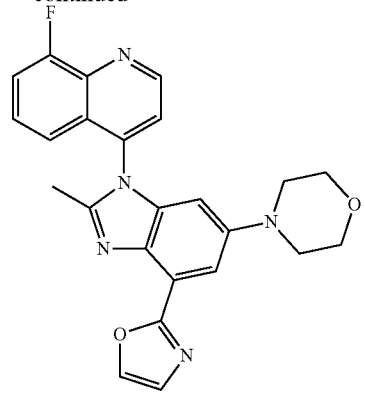

-continued

To a solution of 4-(4-bromo-1-(8-fluoroquinolin-4-yl)-2-methyl-1H-benzo[d]imidazol-6-yl)morpholine (290 mg, 0.66 mmol) in dioxane (3.5 mL) were added 2-(tri-n-butylstannyl)oxazole (0.21 mL, 0.99 mmol), copper iodide (13 mg, 0.07 mmol), and Pd(II)Cl$_2$dppf (42 mg, 0.07 mmol). The resulting mixture was degassed under Argon and heated to 80° C. for 6 days. The reaction was purified directly on silica (0-30% MeOH/DCM), then by prep LC to give 4-(1-(8-fluoroquinolin-4-yl)-2-methyl-4-(oxazol-2-yl)-1H-benzo[d]imidazol-6-yl)morpholine (Compound 200). 1H NMR (400 MHz, DMSO-d6) δ 9.29 (d, J=4.5 Hz, 1H), 8.45 (d, J=0.8 Hz, 1H), 8.04 (d, J=4.5 Hz, 1H), 7.78 (ddd, J=10.8, 7.8, 1.2 Hz, 1H), 7.69 (d, J=2.3 Hz, 1H), 7.68-7.62 (m, 1H), 7.61 (d, J=0.8 Hz, 1H), 7.34 (d, J=8.4 Hz, 1H), 6.76 (d, J=2.2 Hz, 1H), 3.66 (t, J=4.8 Hz, 4H), 3.08 (td, J=4.5, 2.8 Hz, 4H), 2.52 (s, 3H). ES/MS m/z 430.2 (M+H)⁺.

The compounds listed in the table below were prepared in a manner similar to that described above using appropriate intermediates and chemistry.

| Compound | Name | MS | NMR |
|---|---|---|---|
| 201 | 4-[3-(8-chloroquinolin-4-yl)-2-methyl-7-(2-methyl-1H-imidazol-5-yl)benzimidazol-5-yl]morpholine | 459.15 | 1H NMR (400 MHz, DMSO-d6) δ 9.31 (d, J = 4.5 Hz, 1H), 8.40 (s, 1H), 8.11 (dd, J = 7.5, 1.2 Hz, 1H), 7.95 (d, J = 4.5 Hz, 1H), 7.61 (dd, J = 8.5, 7.5 Hz, 1H), 7.43 (d, J = 2.1 Hz, 1H), 7.21 (dd, J = 8.4, 1.2 Hz, 1H), 6.49 (d, J = 2.1 Hz, 1H), 3.68 (t, J = 4.8 Hz, 4H), 3.10-2.95 (m, 4H), 2.72 (s, 3H), 2.35 (s, 3H). |
| 202 | 4-[3-(8-chloroquinolin-4-yl)-2-methyl-7-(3-methylimidazol-4-yl)benzimidazol-5-yl]morpholine | 459.1 | 1H NMR (400 MHz, DMSO-d6) δ 9.32 (d, J = 4.5 Hz, 1H), 9.29 (s, 1H), 8.12 (dd, J = 7.5, 1.2 Hz, 1H), 7.99 (s, 1H), 7.96 (d, J = 4.5 Hz, 1H), 7.63 (dd, J = 8.5, 7.5 Hz, 1H), 7.25 (dd, J = 8.5, 1.2 Hz, 1H), 7.14 (d, J = 2.2 Hz, 1H), 6.64 (d, J = 2.2 Hz, 1H), 3.97 (s, 3H), 3.65 (t, J = 4.8 Hz, 4H), 3.09-2.95 (m, 4H), 2.31 (s, 3H). |
| 203 | 4-[3-(8-chloroquinolin-4-yl)-2-methyl-7-(1-methylimidazol-4-yl)benzimidazol-5-yl]morpholine | 459.1 | 1H NMR (400 MHz, DMSO-d6) δ 9.31 (d, J = 4.5 Hz, 1H), 9.22 (s, 1H), 8.55 (d, J = 1.5 Hz, 1H), 8.11 (dd, J = 7.6, 1.2 Hz, 1H), 7.96 (d, J = 4.5 Hz, 1H), 7.65-7.56 (m, 1H), 7.50 (d, J = 2.1 Hz, 1H), 7.21 (dd, J = 8.4, 1.2 Hz, 1H), 6.51 (d, J = 2.1 Hz, 1H), 4.01 (s, 3H), 3.67 (t, J = 4.7 Hz, 4H), 3.10-2.96 (m, 4H), 2.37 (s, 3H). |
| 204 | 4-[3-(8-chloroquinolin-4-yl)-2-methyl-7-(1,3-oxazol-2-yl)benzimidazol-5-yl]morpholine | 446.1 | 1H NMR (400 MHz, DMSO-d6) δ 9.34 (d, J = 4.5 Hz, 1H), 8.43 (s, 1H), 8.13 (dd, J = 7.5, 1.2 Hz, 1H), 8.03 (d, J = 4.5 Hz, 1H), 7.66 (d, J = 2.3 Hz, 1H), 7.65-7.56 (m, 2H), 7.44 (d, J = 8.5 Hz, 1H), 6.74 (d, J = 2.3 Hz, 1H), 3.65 (t, J = 4.8 Hz, 4H), 3.13-3.00 (m, 4H), 2.48 (s, 3H). |
| 205 | 4-[3-(8-chloroquinolin-4-yl)-2-methyl-7-(4-methyl-1,3-thiazol-2-yl)benzimidazol-5-yl]morpholine | 476.1 | 1H NMR (400 MHz, DMSO-d6) δ 9.32 (d, J = 4.5 Hz, 1H), 8.11 (dd, J = 7.5, 1.2 Hz, 1H), 7.99 (d, J = 4.5 Hz, 1H), 7.78 (d, J = 2.2 Hz, 1H), 7.61 (dd, J = 8.4, 7.6 Hz, 1H), 7.49-7.43 (m, 1H), 7.34 (dd, J = 8.5, 1.2 Hz, 1H), 6.63 (d, J = 2.2 Hz, 1H), 3.67 (t, J = 4.7 Hz, 4H), 3.10-2.99 (m, 4H), 2.51 (s, 3H), 2.40 (s, 3H). |
| 206 | 4-[3-(5,8-difluoroquinolin-4-yl)-2-ethyl-7-(2-methyl-1H-imidazol-5-yl)benzimidazol-5-yl]morpholine | 475.2 | 1H NMR (400 MHz, DMSO-d6) δ 9.28 (d, J = 4.5 Hz, 1H), 8.40 (s, 1H), 7.97 (d, J = 4.5 Hz, 1H), 7.84-7.72 (m, 1H), 7.51-7.39 (m, 2H), 6.61-6.55 (m, 1H), 3.69 (t, J = 4.7 Hz, 4H), 3.12-2.99 (m, 4H), 2.73 (s, 3H), 2.70-2.54 (m, 2H), 1.22 (t, J = 7.5 Hz, 3H). |
| 207 | 4-[3-(8-chloroquinolin-4-yl)-7-(1H-imidazol-5-yl)-2-propylbenzimidazol-5-yl]morpholine | 473.21 | 1H NMR (400 MHz, DMSO-d6) δ 9.31 (d, J = 4.5 Hz, 1H), 9.30 (s, 1H), 8.56 (s, 1H), 8.11 (dd, J = 7.5, 1.1 Hz, 1H), 7.97 (d, J = 4.5 Hz, 1H), 7.60 (t, J = 8.0 Hz, 1H), 7.56 (d, J = 2.1 Hz, 1H), 7.18 (dd, J = 8.4, 1.2 Hz, 1H), 6.49 (d, J = 2.0 Hz, 1H), 3.67 (t, J = 4.8 Hz, 4H), 3.10-2.96 (m, 4H), 2.59 (td, J = 7.4, 2.4 Hz, 2H), 1.75-1.59 (m, 2H), 0.83 (t, J = 7.4 Hz, 3H). |
| 208 | 4-[3-(8-fluoroquinolin-4-yl)-7-(1H-imidazol-5-yl)-2-methylbenzimidazol-5- | 429.2 | 1H NMR (400 MHz, DMSO-d6) δ 9.28 (s, 1H), 9.25 (d, J = 4.5 Hz, 1H), 8.54 (s, 1H), 7.96 (d, J = 4.5 Hz, 1H), 7.76 (dd, J = 10.8, 7.7 Hz, |

| Compound | Name | MS | NMR |
|---|---|---|---|
| | yl]morpholine | | 1H), 7.63 (td, J = 8.1, 4.9 Hz, 1H), 7.55 (d, J = 2.0 Hz, 1H), 7.09 (d, J = 8.4 Hz, 1H), 6.51 (d, J = 2.0 Hz, 1H), 3.68 (t, J = 4.8 Hz, 4H), 3.11-2.97 (m, 4H), 2.37 (s, 3H). |
| 209 | 4-[2-ethyl-3-(8-fluoroquinolin-4-yl)-7-(1H-imidazol-5-yl)benzimidazol-5-yl]morpholine | 443.2 | 1H NMR (400 MHz, DMSO-d6) δ 9.31 (s, 1H), 9.25 (d, J = 4.5 Hz, 1H), 8.57 (s, 1H), 7.97 (d, J = 4.5 Hz, 1H), 7.75 (dd, J = 10.8, 7.7 Hz, 1H), 7.62 (td, J = 8.1, 4.9 Hz, 1H), 7.57 (d, J = 2.1 Hz, 1H), 7.05 (d, J = 8.4 Hz, 1H), 6.50 (d, J = 2.0 Hz, 1H), 3.68 (t, J = 4.8 Hz, 4H), 3.11-2.97 (m, 4H), 2.64 (ddt, J = 28.6, 16.0, 7.9 Hz, 2H), 1.22 (t, J = 7.4 Hz, 3H). |
| 210 | 4-[3-(8-fluoro-2-methylquinolin-4-yl)-7-(1H-imidazol-5-yl)-2-methylbenzimidazol-5-yl]morpholine | 443.2 | 1H NMR (400 MHz, DMSO-d6) δ 9.28 (d, J = 1.4 Hz, 1H), 8.54 (d, J = 1.3 Hz, 1H), 7.85 (s, 1H), 7.74-7.64 (m, 1H), 7.56 (d, J = 2.2 Hz, 1H), 7.52 (dt, J = 7.9, 4.0 Hz, 1H), 7.00 (d, J = 8.4 Hz, 1H), 6.52 (d, J = 2.1 Hz, 1H), 3.68 (t, J = 4.8 Hz, 4H), 3.12-2.97 (m, 4H), 2.82 (s, 3H), 2.38 (s, 3H). |
| 211 | 4-[2-ethyl-3-(8-fluoro-2-methylquinolin-4-yl)-7-(1H-imidazol-5-yl)benzimidazol-5-yl]morpholine | 457.27 | 1H NMR (400 MHz, DMSO-d6) δ 9.30 (s, 1H), 8.57 (s, 1H), 7.86 (s, 1H), 7.68 (m, 1H), 7.57 (d, J = 2.1 Hz, 1H), 7.52 (m, 1H), 6.95 (d, J = 8.4 Hz, 1H), 6.50 (d, J = 2.1 Hz, 1H), 3.68 (t, J = 4.8 Hz, 4H), 3.12-2.93 (m, 4H), 2.82 (s, 3H), 2.64 (m, 2H), 1.22 (t, J = 7.4 Hz, 3H). |
| 212 | 4-[3-(8-chloroquinolin-4-yl)-7-(2-methyl-1H-imidazol-5-yl)-2-propylbenzimidazol-5-yl]morpholine | 487.2 | 1H NMR (400 MHz, DMSO-d6) δ 9.31 (d, J = 4.5 Hz, 1H), 8.41 (s, 1H), 8.11 (d, J = 7.6 Hz, 1H), 7.95 (d, J = 4.6 Hz, 1H), 7.60 (app. t, 1H), 7.44 (d, J = 2.1 Hz, 1H), 7.16 (d, J = 8.4 Hz, 1H), 6.46 (d, J = 2.0 Hz, 1H), 3.67 (t, J = 4.8 Hz, 4H), 3.08-2.95 (m, 4H), 2.72 (s, 3H), 2.58 (t, J = 7.5 Hz, 2H), 1.71-1.59 (m, 2H), 0.82 (t, J = 7.3 Hz, 3H). |
| 213 | 4-[2-ethyl-3-(8-fluoroquinolin-4-yl)-7-(1,3-oxazol-2-yl)benzimidazol-5-yl]morpholine | 444.2 | 1H NMR (400 MHz, DMSO-d6) δ 9.28 (d, J = 4.5 Hz, 1H), 8.43 (d, J = 0.8 Hz, 1H), 8.05 (d, J = 4.5 Hz, 1H), 7.77 (ddd, J = 10.8, 7.8, 1.2 Hz, 1H), 7.66 (d, J = 2.3 Hz, 1H), 7.65-7.59 (m, 1H), 7.57 (d, J = 0.8 Hz, 1H), 7.23 (d, J = 8.4 Hz, 1H), 6.70 (d, J = 2.3 Hz, 1H), 3.65 (t, J = 4.8 Hz, 4H), 3.05 (td, J = 4.3, 2.3 Hz, 4H), 2.78 (q, J = 7.5 Hz, 2H), 1.10 (t, J = 7.5 Hz, 3H). |
| 214 | 4-[2-cyclopropyl-3-(8-fluoroquinolin-4-yl)-7-(1,3-oxazol-2-yl)benzimidazol-5-yl]morpholine | 456.2 | 1H NMR (400 MHz, DMSO-d6) δ 9.26 (d, J = 4.5 Hz, 1H), 8.36 (d, J = 0.8 Hz, 1H), 8.00 (d, J = 4.5 Hz, 1H), 7.75 (ddd, J = 10.8, 7.8, 1.2 Hz, 1H), 7.64 (td, J = 8.1, 5.1 Hz, 1H), 7.57 (d, J = 2.3 Hz, 1H), 7.47 (d, J = 0.8 Hz, 1H), 7.24-7.17 (m, 1H), 6.66 (d, J = 2.3 Hz, 1H), 3.66 (t, J = 4.7 Hz, 4H), 3.03 (td, J = 4.3, 1.9 Hz, 4H), 1.70-1.58 (m, 1H), 1.26-1.08 (m, 2H), 0.95 (tdd, J = 8.9, 6.2, 3.2 Hz, 1H), 0.89-0.78 (m, 1H). |
| 215 | 4-[3-(8-chloroquinolin-4-yl)-2-methyl-7-(5-methyl-1,3-thiazol-2-yl)benzimidazol-5-yl]morpholine | 476.19 | 1H NMR (400 MHz, DMSO-d6) δ 9.32 (d, J = 4.5 Hz, 1H), 8.12 (dd, J = 7.5, 1.2 Hz, 1H), 8.00 (d, J = 4.5 Hz, 1H), 7.76-7.70 (m, 2H), 7.61 (dd, J = 8.5, 7.5 Hz, 1H), 7.36 (dd, J = 8.5, 1.2 Hz, 1H), 6.62 (d, J = 2.2 Hz, 1H), 3.66 (t, J = 4.7 Hz, 4H), 3.10-2.98 (m, 4H), 2.58 (d, J = 1.2 Hz, 3H), 2.42 (s, 3H). |

| Compound | Name | MS | NMR |
|---|---|---|---|
| 216 | 4-[3-(8-chloroquinolin-4-yl)-7-(4,5-dimethyl-1,3-thiazol-2-yl)-2-methylbenzimidazol-5-yl]morpholine | 490.2 | 1H NMR (400 MHz, DMSO-d6) δ 9.31 (d, J = 4.5 Hz, 1H), 8.11 (dd, J = 7.5, 1.2 Hz, 1H), 7.98 (d, J = 4.5 Hz, 1H), 7.72 (d, J = 2.3 Hz, 1H), 7.61 (dd, J = 8.5, 7.5 Hz, 1H), 7.33 (dd, J = 8.5, 1.2 Hz, 1H), 6.59 (d, J = 2.2 Hz, 1H), 3.66 (t, J = 4.7 Hz, 4H), 3.09-2.97 (m, 4H), 2.46 (d, J = 0.9 Hz, 3H), 2.40 (d, J = 0.9 Hz, 3H), 2.39 (s, 3H). |
| 217 | 4-[3-(5,8-difluoroquinolin-4-yl)-2-ethyl-7-(1,3-oxazol-2-yl)benzimidazol-5-yl]morpholine | 462.2 | 1H NMR (400 MHz, DMSO-d6) δ 9.33 (d, J = 4.5 Hz, 1H), 8.42 (d, J = 0.8 Hz, 1H), 8.09 (d, J = 4.5 Hz, 1H), 7.81 (ddd, J = 10.1, 8.8, 4.2 Hz, 1H), 7.63 (d, J = 2.3 Hz, 1H), 7.56 (d, J = 0.8 Hz, 1H), 7.54-7.45 (m, 1H), 6.83 (d, J = 2.2 Hz, 1H), 3.70-3.56 (m, 4H), 3.12-3.05 (m, 4H), 2.79 (q, J = 7.6 Hz, 2H), 1.13 (t, J = 7.5 Hz, 3H). |
| 218 | 4-[3-(8-chloro-7-fluoroquinolin-4-yl)-2-ethyl-7-(1,3-oxazol-2-yl)benzimidazol-5-yl]morpholine | 478.2 | 1H NMR (400 MHz, DMSO-d6) δ 9.37 (d, J = 4.6 Hz, 1H), 8.43 (d, J = 0.8 Hz, 1H), 8.05 (d, J = 4.6 Hz, 1H), 7.76 (t, J = 9.1 Hz, 1H), 7.64 (d, J = 2.3 Hz, 1H), 7.56 (d, J = 0.9 Hz, 1H), 7.49 (dd, J = 9.3, 5.6 Hz, 1H), 6.70 (d, J = 2.3 Hz, 1H), 3.65 (t, J = 4.8 Hz, 4H), 3.11-2.99 (m, 4H), 2.77 (q, J = 7.6 Hz, 2H), 1.10 (t, J = 7.5 Hz, 3H). |
| 219 | 4-[3-(5,8-difluoroquinolin-4-yl)-2-(2-methylpropyl)-7-(1,3-oxazol-2-yl)benzimidazol-5-yl]morpholine | 490.2 | 1H NMR (400 MHz, DMSO-d6) δ 9.33 (d, J = 4.5 Hz, 1H), 8.42 (d, J = 0.8 Hz, 1H), 8.09 (d, J = 4.5 Hz, 1H), 7.81 (ddd, J = 10.0, 8.8, 4.2 Hz, 1H), 7.64 (d, J = 2.3 Hz, 1H), 7.56 (d, J = 0.8 Hz, 1H), 7.55-7.45 (m, 1H), 6.83 (d, J = 2.3 Hz, 1H), 3.67 (t, J = 4.8 Hz, 4H), 3.12-3.05 (m, 4H), 2.77 (dd, J = 14.6, 6.8 Hz, 1H), 2.66 (dd, J = 14.5, 7.9 Hz, 1H), 1.99-1.84 (m, 1H), 0.80 (dd, J = 6.6, 3.3 Hz, 6H). |
| 220 | 4-[3-(8-chloroquinolin-4-yl)-2-(cyclopropylmethyl)-7-(1,3-oxazol-2-yl)benzimidazol-5-yl]morpholine | 486.2 | 1H NMR (400 MHz, DMSO-d6) δ 9.35 (d, J = 4.5 Hz, 1H), 8.44 (d, J = 0.8 Hz, 1H), 8.12 (dd, J = 7.5, 1.2 Hz, 1H), 8.08 (d, J = 4.5 Hz, 1H), 7.68 (d, J = 2.3 Hz, 1H), 7.66-7.57 (m, 2H), 7.38 (dd, J = 8.6, 1.2 Hz, 1H), 6.72 (d, J = 2.3 Hz, 1H), 3.65 (t, J = 4.8 Hz, 4H), 3.06 (td, J = 4.3, 1.9 Hz, 4H), 2.80 (d, J = 6.9 Hz, 2H), 0.83-0.68 (m, 1H), 0.33-0.21 (m, 1H), 0.18-0.08 (m, 1H), 0.08--0.03 (m, 1H), -0.16--0.27 (m, 1H). |
| 221 | 4-[2-(cyclopropylmethyl)-3-(5,8-difluoroquinolin-4-yl)-7-(1,3-oxazol-2-yl)benzimidazol-5-yl]morpholine | 488.2 | 1H NMR (400 MHz, DMSO-d6) δ 9.34 (d, J = 4.5 Hz, 1H), 8.44 (d, J = 0.8 Hz, 1H), 8.12 (d, J = 4.5 Hz, 1H), 7.81 (ddd, J = 10.0, 8.8, 4.2 Hz, 1H), 7.67 (d, J = 2.3 Hz, 1H), 7.59 (d, J = 0.8 Hz, 1H), 7.49 (ddd, J = 12.3, 8.8, 3.8 Hz, 1H), 6.86 (d, J = 2.3 Hz, 1H), 3.71-3.63 (m, 4H), 3.16-3.06 (m, 4H), 2.84 (qd, J = 15.2, 7.0 Hz, 2H), 0.88-0.73 (m, 1H), 0.36-0.24 (m, 1H), 0.19 (dddd, J = 9.2, 7.9, 5.7, 4.1 Hz, 1H), 0.06 (dq, J = 9.6, 5.0 Hz, 1H), -0.12--0.23 (m, 1H). |
| 222 | 4-[3-(8-chloro-6-fluoroquinolin-4-yl)-7-(1,3-oxazol-2-yl)-2-propylbenzimidazol-5-yl]morpholine | 492.2 | 1H NMR (400 MHz, DMSO-d6) δ 9.31 (d, J = 4.5 Hz, 1H), 8.44 (d, J = 0.8 Hz, 1H), 8.24 (dd, J = 8.5, 2.7 Hz, 1H), 8.10 (d, J = 4.5 Hz, 1H), 7.67 (d, J = 2.3 Hz, 1H), 7.58 (d, J = 0.8 Hz, 1H), 7.29 (d, J = 8.9 Hz, 1H), 6.73 (d, J = 2.3 Hz, 1H), 3.66 (t, J = 4.8 Hz, 4H), 3.13-3.00 (m, |

| Compound | Name | MS | NMR |
|---|---|---|---|
| | | | 4H), 2.87-2.66 (m, 2H), 1.67-1.43 (m, 2H), 0.79 (t, J = 7.4 Hz, 3H). |
| 223 | 4-[3-(8-fluoroquinolin-4-yl)-7-(1,3-oxazol-2-yl)-2-propylbenzimidazol-5-yl]morpholine | 458.2 | 1H NMR (400 MHz, DMSO-d6) δ 9.28 (d, J = 4.5 Hz, 1H), 8.43 (d, J = 0.8 Hz, 1H), 8.05 (d, J = 4.5 Hz, 1H), 7.77 (ddd, J = 10.8, 7.8, 1.2 Hz, 1H), 7.66 (d, J = 2.1 Hz, 1H), 7.63 (dd, J = 7.8, 5.0 Hz, 1H), 7.57 (d, J = 0.8 Hz, 1H), 7.22 (d, J = 8.5 Hz, 1H), 6.69 (d, J = 2.3 Hz, 1H), 3.65 (t, J = 4.7 Hz, 4H), 3.05 (td, J = 4.3, 2.2 Hz, 4H), 2.86-2.66 (m, 2H), 1.63-1.43 (m, 2H), 0.77 (t, J = 7.4 Hz, 3H). |
| 224 | 4-[3-(8-chloroquinolin-4-yl)-7-(1,3-oxazol-2-yl)benzimidazol-5-yl]morpholine | 432.2 | 1H NMR (400 MHz, DMSO-d6) δ 9.28 (d, J = 4.6 Hz, 1H), 8.89 (s, 1H), 8.40 (d, J = 0.8 Hz, 1H), 8.13 (dd, J = 7.5, 1.3 Hz, 1H), 8.00 (d, J = 4.5 Hz, 1H), 7.71 (d, J = 2.3 Hz, 1H), 7.65 (dd, J = 8.5, 7.5 Hz, 1H), 7.55 (dd, J = 8.5, 1.3 Hz, 1H), 7.53 (d, J = 0.8 Hz, 1H), 6.91 (d, J = 2.3 Hz, 1H), 3.69 (t, J = 4.8 Hz, 4H), 3.10 (br s, 4H). |
| 225 | 4-[2-(cyclopropylmethyl)-3-(8-fluoroquinolin-4-yl)-7-(1,3-oxazol-2-yl)benzimidazol-5-yl]morpholine | 470.2 | 1H NMR (400 MHz, DMSO-d6) δ 9.28 (d, J = 4.5 Hz, 1H), 8.44 (d, J = 0.9 Hz, 1H), 8.06 (d, J = 4.5 Hz, 1H), 7.77 (ddd, J = 10.8, 7.8, 1.2 Hz, 1H), 7.68 (d, J = 2.3 Hz, 1H), 7.63 (td, J = 8.2, 5.0 Hz, 1H), 7.58 (d, J = 0.8 Hz, 1H), 7.22 (d, J = 8.4 Hz, 1H), 6.70 (d, J = 2.3 Hz, 1H), 3.66 (t, J = 4.7 Hz, 4H), 3.06 (td, J = 4.4, 2.4 Hz, 4H), 2.79 (d, J = 6.9 Hz, 2H), 0.84-0.69 (m, 1H), 0.33-0.21 (m, 1H), 0.13 (dddd, J = 9.0, 7.9, 5.7, 4.2 Hz, 1H), 0.02 (ddt, J = 9.2, 5.6, 4.6 Hz, 1H), −0.21 (ddt, J = 9.1, 5.5, 4.4 Hz, 1H). |
| 226 | 4-[3-(8-chloroquinolin-4-yl)-2-ethyl-7-(1,3-oxazol-2-yl)benzimidazol-5-yl]morpholine | 460.2 | 1H NMR (400 MHz, DMSO-d6) δ 9.34 (d, J = 4.5 Hz, 1H), 8.43 (s, 1H), 8.12 (d, J = 7.5 Hz, 1H), 8.06 (d, J = 4.5 Hz, 1H), 7.68-7.64 (m, 1H), 7.64-7.58 (m, 1H), 7.57 (s, 1H), 7.38 (d, J = 8.4 Hz, 1H), 6.70 (d, J = 2.2 Hz, 1H), 3.65 (t, J = 4.7 Hz, 4H), 3.12-2.98 (m, 4H), 2.76 (q, J = 7.5 Hz, 2H), 1.10 (td, J = 7.5, 0.7 Hz, 3H). |
| 227 | 4-[3-(8-chloroquinolin-4-yl)-7-(1,3-oxazol-2-yl)-2-propylbenzimidazol-5-yl]morpholine | 474.2 | 1H NMR (400 MHz, DMSO-d6) δ 9.34 (d, J = 4.5 Hz, 1H), 8.42 (s, 1H), 8.12 (d, J = 7.5 Hz, 1H), 8.05 (d, J = 4.5 Hz, 1H), 7.64 (d, J = 2.2 Hz, 1H), 7.61 (dd, J = 7.9, 7.4 Hz, 1H), 7.56 (s, 1H), 7.35 (d, J = 8.4 Hz, 1H), 6.68 (d, J = 2.2 Hz, 1H), 3.65 (t, J = 4.8 Hz, 4H), 3.10-2.98 (m, 4H), 2.82-2.63 (m, 2H), 1.63-1.43 (m, 2H), 0.77 (t, J = 7.3 Hz, 3H). |
| 228 | 4-[3-(8-chloroquinolin-4-yl)-2-cyclopropyl-7-(1,3-oxazol-2-yl)benzimidazol-5-yl]morpholine | 472.2 | 1H NMR (400 MHz, DMSO-d6) δ 9.32 (d, J = 4.5 Hz, 1H), 8.36 (s, 1H), 8.11 (d, J = 7.5 Hz, 1H), 8.01 (d, J = 4.5 Hz, 1H), 7.62 (dd, J = 8.4, 7.5 Hz, 1H), 7.56 (d, J = 2.1 Hz, 1H), 7.47 (s, 1H), 7.34 (d, J = 8.5 Hz, 1H), 6.66 (d, J = 2.0 Hz, 1H), 3.65 (t, J = 4.7 Hz, 4H), 3.09-2.95 (m, 3H), 1.68-1.56 (m, 1H), 1.26-1.07 (m, 2H), 1.00-0.88 (m, 1H), 0.88-0.76 (m, 1H). |
| 229 | 4-[3-(5,8-difluoroquinolin-4-yl)-2-methyl-7-(1,3-oxazol-2-yl)benzimidazol-5-yl]morpholine | 448.2 | 1H NMR (400 MHz, DMSO-d6) δ 9.35 (d, J = 4.5 Hz, 1H), 8.44 (d, J = 0.8 Hz, 1H), 8.09 (d, J = 4.5 Hz, 1H), 7.82 (ddd, J = 10.1, 8.8, 4.3 Hz, 1H), 7.67 (d, J = 2.3 Hz, 1H), |

| Compound | Name | MS | NMR |
|---|---|---|---|
| | | | 7.60 (d, J = 0.8 Hz, 1H), 7.52 (ddd, J = 12.4, 8.8, 3.8 Hz, 1H), 6.91 (d, J = 2.3 Hz, 1H), 3.75-3.58 (m, 4H), 3.15-3.07 (m, 4H), 2.55 (s, 3H). |
| 230 | 4-[3-(5,8-difluoroquinolin-4-yl)-7-(1,3-oxazol-2-yl)-2-propylbenzimidazol-5-yl]morpholine | 476.2 | 1H NMR (400 MHz, DMSO-d6) δ 9.34 (d, J = 4.5 Hz, 1H), 8.43 (d, J = 0.8 Hz, 1H), 8.10 (d, J = 4.5 Hz, 1H), 7.81 (ddd, J = 10.0, 8.8, 4.2 Hz, 1H), 7.65 (d, J = 2.2 Hz, 1H), 7.57 (d, J = 0.8 Hz, 1H), 7.51 (ddd, J = 12.4, 8.8, 3.8 Hz, 1H), 6.84 (d, J = 2.3 Hz, 1H), 3.73-3.58 (m, 4H), 3.13-3.05 (m, 4H), 2.89-2.71 (m, 2H), 1.56 (qd, J = 7.4, 1.2 Hz, 2H), 0.81 (t, J = 7.4 Hz, 3H). |
| 231 | 4-[2-cyclopropyl-3-(5,8-difluoroquinolin-4-yl)-7-(1,3-oxazol-2-yl)benzimidazol-5-yl]morpholine | 474.2 | 1H NMR (400 MHz, DMSO-d6) δ 9.31 (d, J = 4.5 Hz, 1H), 8.35 (d, J = 0.8 Hz, 1H), 8.04 (d, J = 4.5 Hz, 1H), 7.78 (ddd, J = 10.1, 8.7, 4.2 Hz, 1H), 7.54 (d, J = 2.3 Hz, 1H), 7.52-7.45 (m, 1H), 7.47 (d, J = 0.8 Hz, 1H), 6.79 (d, J = 2.3 Hz, 1H), 3.73-3.58 (m, 4H), 3.10-3.02 (m, 4H), 1.75-1.63 (m, 1H), 1.25-1.14 (m, 1H), 1.17-1.04 (m, 1H), 0.98-0.81 (m, 2H). |
| 232 | 4-[2-ethyl-3-(8-fluoroquinolin-4-yl)-7-(4-methyl-1,3-thiazol-2-yl)benzimidazol-5-yl]morpholine | 474.2 | 1H NMR (400 MHz, DMSO-d6) δ 9.25 (d, J = 4.5 Hz, 1H), 8.00 (d, J = 4.5 Hz, 1H), 7.82 (d, J = 2.3 Hz, 1H), 7.75 (ddd, J = 10.8, 7.8, 1.2 Hz, 1H), 7.62 (ddd, J = 8.5, 7.7, 5.0 Hz, 1H), 7.47 (q, J = 0.8 Hz, 1H), 7.15 (dt, J = 8.4, 0.9 Hz, 1H), 6.65 (d, J = 2.3 Hz, 1H), 3.68 (t, J = 4.7 Hz, 4H), 3.12-2.99 (m, 4H), 2.79-2.55 (m, 2H), 2.51 (s, 3H), 1.22 (t, J = 7.5 Hz, 3H). |
| 233 | 4-[3-(5,8-difluoroquinolin-4-yl)-2-methyl-7-(4-methyl-1,3-thiazol-2-yl)benzimidazol-5-yl]morpholine | 478.1 | 1H NMR (400 MHz, DMSO-d6) δ 9.30 (d, J = 4.5 Hz, 1H), 8.01 (d, J = 4.5 Hz, 1H), 7.79 (ddd, J = 10.1, 8.8, 4.4 Hz, 1H), 7.76 (d, J = 2.2 Hz, 1H), 7.53-7.42 (m, 2H), 6.77 (d, J = 2.2 Hz, 1H), 3.72-3.65 (m, 4H), 3.12-3.05 (m, 4H), 2.51 (s, 3H), 2.41 (s, 3H). |
| 234 | 4-[3-(8-chloroquinolin-4-yl)-2-cyclopropyl-7-(4-methyl-1,3-thiazol-2-yl)benzimidazol-5-yl]morpholine | 502.1 | 1H NMR (400 MHz, DMSO-d6) δ 9.32 (d, J = 4.5 Hz, 1H), 8.11 (dd, J = 7.5, 1.2 Hz, 1H), 8.02 (d, J = 4.5 Hz, 1H), 7.80 (d, J = 2.3 Hz, 1H), 7.63 (dd, J = 8.5, 7.5 Hz, 1H), 7.43 (q, J = 0.8 Hz, 1H), 7.36 (dd, J = 8.5, 1.3 Hz, 1H), 6.66 (d, J = 2.3 Hz, 1H), 3.68 (t, J = 4.8 Hz, 4H), 3.05 (dd, J = 6.4, 3.6 Hz, 4H), 2.48 (d, J = 1.0 Hz, 3H), 1.68-1.57 (m, 1H), 1.28-1.12 (m, 1H), 1.04-0.93 (m, 1H), 0.93-0.81 (m, 1H). |
| 235 | 4-[3-(5,8-difluoroquinolin-4-yl)-7-(4-methyl-1,3-thiazol-2-yl)-2-propylbenzimidazol-5-yl]morpholine | 506.2 | 1H NMR (400 MHz, DMSO-d6) δ 9.28 (d, J = 4.5 Hz, 1H), 7.98 (d, J = 4.5 Hz, 1H), 7.83-7.72 (m, 1H), 7.75 (d, J = 2.4 Hz, 1H), 7.46 (ddd, J = 12.4, 8.7, 3.8 Hz, 1H), 7.42 (m, 1H), 6.67 (d, J = 2.3 Hz, 1H), 3.71-3.64 (m, 4H), 3.08-3.00 (m, 4H), 2.63-2.55 (m, 2H), 2.49-2.48 (m, 3H), 1.71 (h, J = 7.5 Hz, 2H), 0.89 (t, J = 7.4 Hz, 3H). |
| 236 | 4-[3-(5,8-difluoroquinolin-4-yl)-7-(1,3-oxazol-2-yl)benzimidazol-5-yl]morpholine | 434.1 | 1H NMR (400 MHz, DMSO-d6) δ 9.25 (d, J = 4.6 Hz, 1H), 8.73 (s, 1H), 8.37 (d, J = 0.8 Hz, 1H), 7.99 (d, J = 4.6 Hz, 1H), 7.79 (ddd, J = 10.0, 8.7, 4.2 Hz, 1H), 7.65 (d, J = 2.3 Hz, 1H), 7.50 (d, J = 0.8 Hz, 1H), 7.55-7.44 (m, 1H), 6.98 (d, J = 2.3 Hz, 1H), 3.69 (t, J = 4.7 Hz, 4H), 3.16-3.04 (m, 4H). |

| Compound | Name | MS | NMR |
|---|---|---|---|
| 237 | 4-[2-cyclopropyl-3-(5,8-difluoroquinolin-4-yl)-7-(4-methyl-1,3-thiazol-2-yl)benzimidazol-5-yl]morpholine | 504.2 | 1H NMR (400 MHz, DMSO-d6) δ 9.36-9.29 (m, 1H), 8.20-8.10 (m, 1H), 7.84-7.72 (m, 1H), 7.60 (dd, J = 5.1, 1.1 Hz, 1H), 7.57-7.39 (m, 2H), 6.93-6.84 (m, 1H), 3.73-3.65 (m, 4H), 3.17-3.10 (m, 4H), 1.98-1.91 (m, 3H), 1.66-1.56 (m, 1H), 1.54-1.21 (m, 1H), 1.04-0.69 (m, 1H), 0.59-0.42 (m, 2H). |
| 238 | 4-[3-(8-chloro-5-fluoroquinolin-4-yl)-2-methyl-7-(4-methyl-1,3-thiazol-2-yl)benzimidazol-5-yl]morpholine | 494.1 | 1H NMR (400 MHz, DMSO-d6) δ 9.36 (d, J = 4.5 Hz, 1H), 8.13 (dd, J = 8.6, 5.0 Hz, 1H), 8.00 (d, J = 4.5 Hz, 1H), 7.75 (d, J = 2.3 Hz, 1H), 7.48 (dd, J = 11.9, 8.5 Hz, 1H), 7.43 (d, J = 1.0 Hz, 1H), 6.73 (d, J = 2.3 Hz, 1H), 3.71-3.64 (m, 4H), 3.10-3.02 (m, 4H), 2.50 (s, 3H), 2.38 (s, 3H). |
| 239 | 4-[3-(5,8-difluoroquinolin-4-yl)-2-propyl-7-(1,3-thiazol-2-yl)benzimidazol-5-yl]morpholine | 492.2 | 1H NMR (400 MHz, DMSO-d6) δ 9.29 (d, J = 4.5 Hz, 1H), 8.05-7.99 (m, 2H), 7.90 (d, J = 3.3 Hz, 1H), 7.81 (d, J = 2.3 Hz, 1H), 7.78 (ddd, J = 10.1, 8.8, 4.2 Hz, 1H), 7.47 (ddd, J = 12.3, 8.8, 3.8 Hz, 1H), 6.74 (d, J = 2.2 Hz, 1H), 3.72-3.65 (m, 4H), 3.11-3.04 (m, 4H), 2.64 (dd, J = 7.8, 6.9 Hz, 2H), 1.71 (h, J = 7.4 Hz, 2H), 0.89 (t, J = 7.4 Hz, 3H). |
| 240 | 4-[3-(8-chloro-5-fluoroquinolin-4-yl)-2-methyl-7-(1,3-thiazol-2-yl)benzimidazol-5-yl]morpholine | 480.1 | 1H NMR (400 MHz, DMSO-d6) δ 9.37 (d, J = 4.5 Hz, 1H), 8.13 (dd, J = 8.5, 5.0 Hz, 1H), 8.03 (d, J = 3.3 Hz, 1H), 8.02 (d, J = 4.6 Hz, 1H), 7.91 (d, J = 3.2 Hz, 1H), 7.79 (d, J = 2.3 Hz, 1H), 7.49 (dd, J = 11.9, 8.5 Hz, 1H), 6.76 (d, J = 2.3 Hz, 1H), 3.71-3.64 (m, 4H), 3.07 (t, J = 4.9 Hz, 4H), 2.41 (s, 3H). |
| 241 | 4-[2-cyclopropyl-3-(5,8-difluoroquinolin-4-yl)-7-(1,3-thiazol-2-yl)benzimidazol-5-yl]morpholine | 490.2 | 1H NMR (400 MHz, DMSO-d6) δ 9.30 (d, J = 4.5 Hz, 1H), 8.04 (d, J = 4.5 Hz, 1H), 7.98 (d, J = 3.3 Hz, 1H), 7.87 (d, J = 3.3 Hz, 1H), 7.81 (d, J = 2.2 Hz, 1H), 7.78 (ddq, J = 10.0, 8.8, 4.1 Hz, 1H), 7.48 (ddd, J = 11.8, 8.8, 3.8 Hz, 1H), 6.77 (d, J = 2.2 Hz, 1H), 3.73-3.65 (m, 4H), 3.11-3.04 (m, 4H), 1.73-1.62 (m, 1H), 1.27-1.16 (m, 1H), 1.16-1.06 (m, 1H), 1.01-0.84 (m, 2H). |
| 242 | 4-[3-(8-chloro-5-fluoroquinolin-4-yl)-2-cyclopropyl-7-(1,3-oxazol-2-yl)benzimidazol-5-yl]morpholine | 490.15 | 1H NMR (400 MHz, DMSO-d6) δ 9.39 (d, J = 4.6 Hz, 1H), 8.48 (s, 1H), 8.17-8.09 (m, 2H), 7.64 (d, J = 2.2 Hz, 1H), 7.53-7.29 (m, 2H), 6.96 (s, 1H), 3.69 (t, J = 4.8 Hz, 4H), 3.13 (t, J = 4.9 Hz, 4H), 1.75-1.43 (m, 2H), 1.40-1.06 (m, 1H), 0.72-0.38 (m, 2H). |
| 243 | 4-[3-(8-chloro-5-fluoroquinolin-4-yl)-2-cyclopropyl-7-(4-methyl-1,3-thiazol-2-yl)benzimidazol-5-yl]morpholine | 520.19 | 1H NMR (400 MHz, DMSO-d6) δ 9.42-9.35 (m, 1H), 8.21-8.02 (m, 2H), 7.63-7.37 (m, 3H), 6.94-6.85 (m, 1H), 3.68 (t, J = 4.5 Hz, 4H), 3.18-3.01 (m, 4H), 1.98-1.91 (m, 3H), 1.68-1.40 (m, 2H), 1.34-1.17 (m, 1H), 1.06-0.67 (m, 1H), 0.60-0.39 (m, 1H). |

| Compound | Name | MS | NMR |
|---|---|---|---|
| 244 | 4-[3-(8-chloroquinolin-4-yl)-2-methyl-7-(1,3-thiazol-2-yl)benzimidazol-5-yl]morpholine | 462.1 | 1H NMR (400 MHz, DMSO-d6) δ 9.30 (d, J = 4.5 Hz, 1H), 8.10 (dd, J = 7.5, 1.2 Hz, 1H), 7.99 (dd, J = 3.2, 0.4 Hz, 1H), 7.97 (d, J = 4.5 Hz, 1H), 7.89 (dd, J = 3.3, 0.4 Hz, 1H), 7.84 (d, J = 2.3 Hz, 1H), 7.61 (dd, J = 8.4, 7.5 Hz, 1H), 7.28 (dd, J = 8.4, 1.2 Hz, 1H), 6.57 (d, J = 2.3 Hz, 1H), 3.66 (t, J = 4.8 Hz, 4H), 3.05-2.96 (m, 4H), 2.37 (s, 3H). |
| 245 | 4-[3-(8-chloroquinolin-4-yl)-2-ethyl-7-(2-methyl-1H-imidazol-5-yl)benzimidazol-5-yl]morpholine | 473.2 | 1H NMR (400 MHz, DMSO-d6) δ 9.31 (d, J = 4.5 Hz, 1H), 8.43 (s, 1H), 8.11 (dd, J = 7.5, 1.3 Hz, 1H), 7.97 (d, J = 4.5 Hz, 1H), 7.61 (dd, J = 8.5, 7.5 Hz, 1H), 7.48 (d, J = 2.2 Hz, 1H), 7.19 (dd, J = 8.4, 1.3 Hz, 1H), 6.48 (d, J = 2.1 Hz, 1H), 3.67 (t, J = 4.8 Hz, 4H), 3.10-2.96 (m, 4H), 2.74 (s, 3H), 2.70-2.52 (m, 2H), 1.20 (t, J = 7.5 Hz, 3H). |
| 246 | 4-[3-(8-chloroquinolin-4-yl)-2-methyl-7-pyrazin-2-ylbenzimidazol-5-yl]morpholine | 457.1 | 1H NMR (400 MHz, DMSO-d6) δ 10.28 (d, J = 1.5 Hz, 1H), 9.31 (d, J = 4.5 Hz, 1H), 8.83-8.77 (m, 1H), 8.65 (d, J = 2.6 Hz, 1H), 8.11 (dd, J = 7.6, 1.2 Hz, 1H), 7.98 (d, J = 4.5 Hz, 1H), 7.86 (d, J = 2.2 Hz, 1H), 7.66-7.57 (m, 1H), 7.27 (dd, J = 8.5, 1.2 Hz, 1H), 6.60 (d, J = 2.3 Hz, 1H), 3.66 (t, J = 4.7 Hz, 4H), 3.08-2.96 (m, 4H), 2.37 (s, 3H). |
| 247 | 4-(1-(8-chloro-5-fluoroquinolin-4-yl)-2-cyclopropyl-4-(thiazol-2-yl)-1H-benzo[d]imidazol-6-yl)morpholine | 506.1 | 1H NMR (400 MHz, DMSO-d6) δ 9.36 (d, J = 4.5 Hz, 1H), 8.12 (dd, J = 8.5, 4.9 Hz, 1H), 8.04 (d, J = 4.5 Hz, 1H), 7.96 (d, J = 3.2 Hz, 1H), 7.85 (d, J = 3.2 Hz, 1H), 7.77 (d, J = 2.3 Hz, 1H), 7.49 (dd, J = 11.8, 8.5 Hz, 1H), 6.72 (d, J = 2.3 Hz, 1H), 3.75-3.57 (m, 4H), 3.07-3.00 (m, 4H), 1.71-1.60 (m, 1H), 1.26-1.03 (m, 2H), 0.99-0.82 (m, 2H). |

Step 6b: 4-(4-(2-chloro-1H-imidazol-5-yl)-1-(8-fluoroquinolin-4-yl)-2-methyl-1H-benzo[d]imidazol-6-yl)morpholine

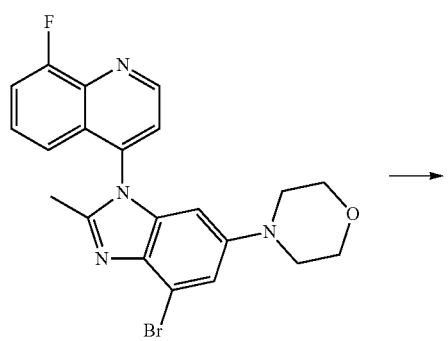

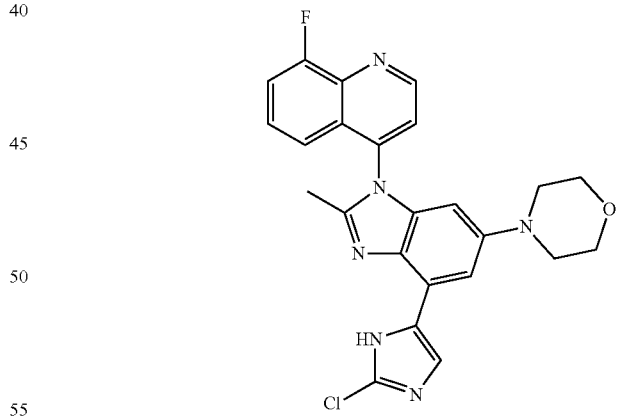

To a solution of 4-(4-bromo-1-(8-fluoroquinolin-4-yl)-2-methyl-1H-benzo[d]imidazol-6-yl)morpholine (100 mg, 0.23 mmol) in dioxane (1 mL) was added 2-chloro-1-THP-1H-imidazole-5-boronic acid pinacol ester (106 mg, 0.34 mmol), cesium fluoride (100 mg, 0.66 mmol), copper iodide (4 mg, 0.023 mmol), and Pd(II)Cl₂dppf (13 mg, 0.023 mmol). The resulting mixture was degassed under Argon and heated to 80° C. for 5 days. The reaction was purified directly on silica (0-30% MeOH/DCM), then by prep LC to give 4-(4-(2-chloro-1H-imidazol-5-yl)-1-(8-fluoroquinolin- 4-yl)-2-methyl-1H-benzo[d]imidazol-6-yl)morpholine as an off-white solid (Compound 260). 1H NMR (400 MHz, DMSO-d6) δ 9.25 (d, J=4.5 Hz, 1H), 8.17 (s, 1H), 7.96 (d, J=4.5 Hz, 1H), 7.82-7.70 (m, 1H), 7.68-7.56 (m, 1H), 7.49 (s, 1H), 7.19 (d, J=8.8 Hz, 1H), 6.35 (s, 1H), 3.66 (t, J=4.8 Hz, 4H), 3.09-2.92 (m, 4H), 2.40 (s, 3H). ES/MS m/z 463.2 (M+H)⁺.

The compounds listed in the table below were prepared in a manner similar to that described above using appropriate intermediates and chemistry.

| Compound | Name | MS | NMR |
|---|---|---|---|
| 261 | 4-[3-(8-chloroquinolin-4-yl)-2-methyl-7-(1H-pyrrol-2-yl)benzimidazol-5-yl]morpholine | 444.15 | 1H NMR (400 MHz, DMSO-d6) δ 11.52 (s, 1H), 9.28 (d, J = 4.5 Hz, 1H), 8.08 (dd, J = 7.5, 1.2 Hz, 1H), 7.95 (d, J = 4.5 Hz, 1H), 7.58 (dd, J = 8.5, 7.5 Hz, 1H), 7.33-7.24 (m, 2H), 7.01 (ddt, J = 13.3, 2.6, 1.7 Hz, 2H), 6.27-6.14 (m, 2H), 3.63 (t, J = 4.8 Hz, 4H), 2.99 (q, J = 4.7 Hz, 4H), 2.36 (s, 3H). |
| 262 | 4-[3-(8-chloroquinolin-4-yl)-2-methyl-7-(1H-pyrazol-3-yl)benzimidazol-5-yl]morpholine | 445.12 | 1H NMR (400 MHz, DMSO-d6) δ 9.32 (d, J = 4.5 Hz, 1H), 8.10 (dd, J = 7.5, 1.2 Hz, 1H), 8.03 (d, J = 4.5 Hz, 1H), 7.90 (d, J = 2.3 Hz, 1H), 7.65-7.56 (m, 2H), 7.47 (dd, J = 8.2, 1.2 Hz, 1H), 7.22 (d, J = 2.3 Hz, 1H), 6.47 (d, J = 2.1 Hz, 1H), 3.63 (t, J = 4.8 Hz, 4H), 3.11-2.95 (m, 4H), 2.49 (s, 3H). |
| 263 | 4-[3-(8-chloroquinolin-4-yl)-2-methyl-7-(1H-pyrrol-3-yl)benzimidazol-5-yl]morpholine | 444.17 | 1H NMR (400 MHz, DMSO-d6) δ 11.18 (d, J = 23.0 Hz, 1H), 9.34 (d, J = 4.5 Hz, 1H), 8.13 (dd, J = 7.5, 1.3 Hz, 1H), 8.01 (d, J = 4.5 Hz, 1H), 7.72 (br s, 1H), 7.63 (dd, J = 8.5, 7.5 Hz, 1H), 7.49-7.37 (m, 1H), 7.26 (s, 1H), 6.95 (s, 1H), 6.78 (s, 1H), 6.32 (s, 1H), 3.65 (t, J = 4.7 Hz, 4H), 3.11-2.96 (m, 4H), 2.44 (s, 3H). |
| 264 | 4-[3-(8-chloroquinolin-4-yl)-2-methyl-7-(1-methylsulfonylpyrrol-3-yl)benzimidazol-5-yl]morpholine | 522.2 | 1H NMR (400 MHz, DMSO-d6) δ 9.31 (d, J = 4.5 Hz, 1H), 8.34 (t, J = 2.0 Hz, 1H), 8.11 (dd, J = 7.5, 1.2 Hz, 1H), 7.97 (d, J = 4.5 Hz, 1H), 7.61 (dd, J = 8.5, 7.5 Hz, 1H), 7.43-7.38 (m, 1H), 7.35 (d, J = 2.2 Hz, 1H), 7.32-7.25 (m, 2H), 6.36 (s, 1H), 3.66 (t, J = 4.8 Hz, 4H), 3.56 (s, 3H), 3.04 (q, J = 5.0 Hz, 4H), 2.37 (s, 3H). |
| 265 | 4-[2-methyl-3-quinolin-4-yl-7-(1,3-thiazol-4-yl)benzimidazol-5-yl]morpholine | 428.1 | 1H NMR (400 MHz, DMSO-d6) δ 9.33 (d, J = 2.0 Hz, 1H), 9.23 (d, J = 4.5 Hz, 1H), 8.93 (d, J = 2.0 Hz, 1H), 8.28 (dd, J = 8.4, 1.0 Hz, 1H), 7.98-7.83 (m, 3H), 7.71-7.62 (m, 1H), 7.41 (d, J = 8.4 Hz, 1H), 6.46 (s, 1H), 3.67 (t, J = 4.8 Hz, 4H), 3.04 (q, J = 4.6 Hz, 4H), 2.44 (s, 3H). |
| 266 | 4-[3-(8-chloroquinolin-4-yl)-7-(1H-imidazol-5-yl)-2-methylbenzimidazol-5-yl]morpholine | 445.1 | 1H NMR (400 MHz, DMSO-d6) δ 9.31 (d, J = 4.6 Hz, 1H), 9.27 (d, J = 1.4 Hz, 1H), 8.53 (d, J = 1.4 Hz, 1H), 8.11 (dd, J = 7.6, 1.2 Hz, 1H), 7.96 (d, J = 4.6 Hz, 1H), 7.61 (dd, J = 8.5, 7.6 Hz, 1H), 7.53 (d, J = 2.1 Hz, 1H), 7.22 (dd, J = 8.5, 1.2 Hz, 1H), 6.51 (d, J = 2.1 Hz, 1H), 3.67 (t, J = 4.8 Hz, 4H), 3.03 (q, J = 4.3 Hz, 4H), 2.36 (s, 3H). |
| 267 | 4-[3-(8-chloroquinolin-4-yl)-7-(5-chlorothiophen-2-yl)-2-methylbenzimidazol-5-yl]morpholine | 495.03 | 1H NMR (400 MHz, DMSO-d6) δ 9.29 (d, J = 4.4 Hz, 1H), 8.10 (dd, J = 7.6, 1.2 Hz, 1H), 7.98-7.90 (m, 2H), 7.65-7.56 (m, 1H), 7.32 (d, J = 2.1 Hz, 1H), 7.26 (dd, J = 8.5, 1.2 Hz, 1H), 7.22 (dd, J = 4.0, 0.5 Hz, 1H), 6.39 (d, J = 2.1 Hz, 1H), 3.65 (t, J = 4.7 Hz, 4H), 3.01 (q, J = 4.4 Hz, 4H), 2.33 (s, 3H). |
| 268 | 4-[3-(8-chloroquinolin-4-yl)-2-methyl-7-(5-methyl-1H-pyrazol-3-yl)benzimidazol-5-yl]morpholine | 459.1 | 1H NMR (400 MHz, DMSO-d6) δ 9.37 (d, J = 4.6 Hz, 1H), 8.15 (dd, J = 7.5, 1.2 Hz, 1H), 8.09 (d, J = 4.5 Hz, 1H), 7.77 (d, J = 1.0 Hz, 1H), 7.65 (dd, J = 8.4, 7.5 Hz, 1H), |

| Compound | Name | MS | NMR |
|---|---|---|---|
| | | | 7.54 (dd, J = 8.6, 1.3 Hz, 1H), 7.30 (d, J = 2.1 Hz, 1H), 6.58 (d, J = 2.2 Hz, 1H), 3.65 (t, J = 4.8 Hz, 4H), 3.12-2.99 (m, 4H), 2.53 (s, 3H), 2.31 (s, 3H). |
| 269 | 4-[3-(8-chloroquinolin-4-yl)-2-methyl-7-(2-methylpyrazol-3-yl)benzimidazol-5-yl]morpholine | 459.1 | 1H NMR (400 MHz, DMSO-d6) δ 9.32 (d, J = 4.5 Hz, 1H), 8.12 (dd, J = 7.5, 1.2 Hz, 1H), 7.99 (d, J = 4.5 Hz, 1H), 7.68-7.60 (m, 1H), 7.59 (d, J = 1.8 Hz, 1H), 7.41-7.33 (m, 1H), 7.08 (d, J = 2.2 Hz, 1H), 6.57 (d, J = 2.2 Hz, 1H), 6.56 (d, J = 1.8 Hz, 1H), 3.91 (s, 3H), 3.64 (t, J = 4.8 Hz, 4H), 3.02 (q, J = 4.4 Hz, 4H), 2.35 (s, 3H). |
| 270 | 4-[3-(8-chloroquinolin-4-yl)-2-methyl-7-(1,3-thiazol-4-yl)benzimidazol-5-yl]morpholine | 462.1 | 1H NMR (400 MHz, DMSO-d6) δ 9.37 (d, J = 1.9 Hz, 1H), 9.35 (d, J = 4.5 Hz, 1H), 8.88 (d, J = 2.0 Hz, 1H), 8.13 (dd, J = 7.5, 1.2 Hz, 1H), 8.04 (d, J = 4.5 Hz, 1H), 7.85 (d, J = 2.2 Hz, 1H), 7.63 (dd, J = 8.5, 7.5 Hz, 1H), 7.44 (dd, J = 8.7, 1.3 Hz, 1H), 6.57 (d, J = 2.2 Hz, 1H), 3.67 (t, J = 4.8 Hz, 4H), 3.08 (q, J = 4.2 Hz, 4H), 2.49 (s, 3H). |
| 271 | 4-[3-(8-chloroquinolin-4-yl)-2-methyl-7-thiophen-2-ylbenzimidazol-5-yl]morpholine | 461.1 | 1H NMR (400 MHz, DMSO-d6) δ 9.31 (d, J = 4.5 Hz, 1H), 8.11 (dd, J = 7.5, 1.2 Hz, 1H), 8.08 (dd, J = 3.6, 1.2 Hz, 1H), 7.97 (d, J = 4.5 Hz, 1H), 7.67 (dd, J = 5.1, 1.1 Hz, 1H), 7.61 (dd, J = 8.5, 7.5 Hz, 1H), 7.35-7.28 (m, 2H), 7.25 (dd, J = 5.1, 3.6 Hz, 1H), 6.45 (d, J = 2.1 Hz, 1H), 3.66 (t, J = 4.7 Hz, 4H), 3.11-2.97 (m, 4H), 2.36 (s, 3H). |
| 272 | 4-[3-(8-chloroquinolin-4-yl)-2-methyl-7-thiophen-3-ylbenzimidazol-5-yl]morpholine | 461.1 | 1H NMR (400 MHz, DMSO-d6) δ 9.32 (d, J = 4.5 Hz, 1H), 8.48 (d, J = 2.4 Hz, 1H), 8.11 (dd, J = 7.5, 1.2 Hz, 1H), 8.02-7.94 (m, 2H), 7.71 (dd, J = 5.0, 3.0 Hz, 1H), 7.62 (dd, J = 8.5, 7.5 Hz, 1H), 7.37 (d, J = 2.2 Hz, 1H), 7.32 (dd, J = 8.5, 1.2 Hz, 1H), 6.41 (d, J = 2.1 Hz, 1H), 3.66 (t, J = 4.8 Hz, 4H), 3.11-2.97 (m, 4H), 2.37 (s, 3H). |
| 273 | 5-[1-(8-chloroquinolin-4-yl)-2-methyl-6-morpholin-4-ylbenzimidazol-4-yl]thiophene-2-carbonitrile | 486.1 | 1H NMR (400 MHz, DMSO-d6) δ 9.30 (d, J = 4.5 Hz, 1H), 8.19 (d, J = 4.1 Hz, 1H), 8.10 (dd, J = 7.5, 1.2 Hz, 1H), 8.04 (d, J = 4.0 Hz, 1H), 7.96 (d, J = 4.5 Hz, 1H), 7.60 (dd, J = 8.5, 7.5 Hz, 1H), 7.51 (d, J = 2.1 Hz, 1H), 7.27 (dd, J = 8.5, 1.2 Hz, 1H), 6.51 (d, J = 2.1 Hz, 1H), 3.66 (t, J = 4.8 Hz, 4H), 3.12-2.97 (m, 4H), 2.35 (s, 3H). |
| 274 | 4-[3-(8-chloroquinolin-4-yl)-7-(furan-2-yl)-2-methylbenzimidazol-5-yl]morpholine | 445.1 | 1H NMR (400 MHz, DMSO-d6) δ 9.31 (d, J = 4.5 Hz, 1H), 8.11 (dd, J = 7.6, 1.2 Hz, 1H), 7.97 (d, J = 4.5 Hz, 1H), 7.89-7.83 (m, 1H), 7.66-7.55 (m, 2H), 7.36 (d, J = 2.2 Hz, 1H), 7.32 (d, J = 8.4 Hz, 1H), 6.73 (dd, J = 3.4, 1.9 Hz, 1H), 6.42 (d, J = 2.2 Hz, 1H), 3.65 (t, J = 4.7 Hz, 4H), 3.01 (q, J = 4.3 Hz, 4H), 2.38 (s, 3H). |
| 275 | 4-[3-(8-chloroquinolin-4-yl)-7-(furan-3-yl)-2-methylbenzimidazol-5-yl]morpholine | 445.1 | 1H NMR (400 MHz, DMSO-d6) δ 9.32 (d, J = 4.5 Hz, 1H), 8.65 (dd, J = 1.6, 0.7 Hz, 1H), 8.11 (dd, J = 7.5, 1.2 Hz, 1H), 7.97 (d, J = 4.5 Hz, 1H), 7.85 (t, J = 1.7 Hz, 1H), 7.62 (dd, J = 8.4, 7.5 Hz, 1H), 7.37-7.28 (m, 3H), 6.41 (d, J = 2.1 Hz, 1H), 3.67 (t, J = 4.8 Hz, 4H), 3.13-2.98 (m, 4H), 2.39 (s, 3H). |
| 276 | 4-[3-(8-chloroquinolin-4-yl)-2-methyl-7-(1,3-thiazol-5- | 462.1 | 1H NMR (400 MHz, DMSO-d6) δ 9.30 (d, J = 4.4 Hz, 1H), 9.15 (d, J = 0.6 Hz, 1H), 8.84 (t, J = 0.6 Hz, |

| Compound | Name | MS | NMR |
|---|---|---|---|
| | yl)benzimidazol-5-yl]morpholine | | 1H), 8.10 (dd, J = 7.4, 1.2 Hz, 1H), 7.95 (d, J = 4.5 Hz, 1H), 7.64-7.55 (m, 1H), 7.37 (d, J = 2.2 Hz, 1H), 7.26 (dd, J = 8.4, 1.2 Hz, 1H), 6.41 (d, J = 2.2 Hz, 1H), 3.65 (t, J = 4.8 Hz, 4H), 3.07-2.94 (m, 4H), 2.33 (s, 3H). |
| 277 | 4-[3-(8-chloroquinolin-4-yl)-2-methyl-7-(1,3-oxazol-5-yl)benzimidazol-5-yl]morpholine | 446.1 | 1H NMR (400 MHz, DMSO-d6) δ 9.31 (d, J = 4.5 Hz, 1H), 8.57 (s, 1H), 8.11 (dd, J = 7.5, 1.2 Hz, 1H), 8.11 (s, 1H), 7.97 (d, J = 4.5 Hz, 1H), 7.61 (dd, J = 8.5, 7.5 Hz, 1H), 7.34 (d, J = 2.2 Hz, 1H), 7.30 (dd, J = 8.5, 1.3 Hz, 1H), 6.52 (d, J = 2.2 Hz, 1H), 3.66 (t, J = 4.7 Hz, 4H), 3.08-2.96 (m, 4H), 2.38 (s, 3H). |
| 278 | 4-[7-(2-chloro-1H-imidazol-5-yl)-3-(8-chloroquinolin-4-yl)-2-methylbenzimidazol-5-yl]morpholine | 479.11 | 1H NMR (400 MHz, DMSO-d6) δ 13.61 (s, 1H), 9.32 (s, 1H), 8.34-8.14 (m, 1H), 8.12 (d, J = 7.4 Hz, 1H), 8.06-7.96 (m, 1H), 7.70-7.56 (m, 1H), 7.50 (s, 1H), 7.41-7.05 (m, 1H), 6.46-6.35 (m, 1H), 3.66 (t, J = 4.8 Hz, 4H), 3.11-2.95 (m, 4H), 2.46-2.05 (m, 3H). |
| 279 | 4-[7-(2-chloro-1H-imidazol-5-yl)-3-(8-chloroquinolin-4-yl)-2-ethylbenzimidazol-5-yl]morpholine | 493.2 | 1H NMR (400 MHz, DMSO-d6) δ 9.32 (d, J = 4.5 Hz, 1H), 8.21 (s, 1H), 8.11 (d, J = 7.5 Hz, 1H), 8.01 (d, J = 4.5 Hz, 1H), 7.61 (dd, J = 8.5, 7.5 Hz, 1H), 7.52 (d, J = 2.2 Hz, 1H), 7.32 (d, J = 8.4 Hz, 1H), 6.39 (d, J = 2.1 Hz, 1H), 3.66 (t, J = 4.7 Hz, 4H), 3.09-2.97 (m, 4H), 2.81-2.60 (m, 2H), 1.15 (t, J = 7.5 Hz, 3H). |
| 280 | 4-[7-(2-chloro-1H-imidazol-5-yl)-3-(5,8-difluoroquinolin-4-yl)-2-ethylbenzimidazol-5-yl]morpholine | 495.2 | 1H NMR (400 MHz, DMSO-d6) δ 9.31 (d, J = 4.5 Hz, 1H), 8.19 (s, 1H), 8.05 (d, J = 4.5 Hz, 1H), 7.79 (ddd, J = 10.0, 8.8, 4.2 Hz, 1H), 7.54-7.43 (m, 2H), 6.54 (d, J = 2.1 Hz, 1H), 3.78-3.54 (m, 4H), 3.14-3.03 (m, 4H), 2.75 (qd, J = 7.7, 3.2 Hz, 2H), 1.17 (t, J = 7.5 Hz, 3H). |
| 281 | 4-[7-(2-chloro-1H-imidazol-5-yl)-3-(8-chloroquinolin-4-yl)-2-propylbenzimidazol-5-yl]morpholine | 507.2 | 1H NMR (400 MHz, DMSO-d6) δ 9.33 (d, J = 4.5 Hz, 1H), 8.20 (s, 1H), 8.12 (dd, J = 7.6, 1.2 Hz, 1H), 8.02 (d, J = 4.5 Hz, 1H), 7.61 (dd, J = 8.5, 7.5 Hz, 1H), 7.54 (d, J = 2.2 Hz, 2H), 7.32 (dd, J = 8.5, 1.2 Hz, 1H), 6.41 (d, J = 2.2 Hz, 1H), 3.66 (t, J = 4.8 Hz, 4H), 3.11-2.97 (m, 4H), 2.70 (t, J = 7.6 Hz, 2H), 1.69-1.47 (m, 2H), 0.81 (t, J = 7.3 Hz, 3H). |
| 282 | 4-[7-(2-chloro-1H-imidazol-5-yl)-3-(8-fluoro-2-methylquinolin-4-yl)-2-methylbenzimidazol-5-yl]morpholine | 477.2 | 1H NMR (400 MHz, DMSO-d6) δ 8.18 (s, 1H), 7.91 (s, 1H), 7.71 (m, 1H), 7.60-7.50 (m, 2H), 7.20 (d, J = 8.4 Hz, 1H), 6.45 (d, J = 2.2 Hz, 1H), 3.67 (t, J = 4.8 Hz, 4H), 3.10-2.98 (m, 4H), 2.83 (s, 3H), 2.50 (s, 3H). |
| 283 | 4-[7-(2-chloro-1H-imidazol-5-yl)-2-ethyl-3-(8-fluoro-2-methylquinolin-4-yl)benzimidazol-5-yl]morpholine | 491.2 | 1H NMR (400 MHz, DMSO-d6) δ 8.21 (s, 1H), 7.91 (s, 1H), 7.70 (ddd, J = 10.9, 7.8, 1.1 Hz, 1H), 7.58-7.48 (m, 2H), 7.10 (d, J = 8.4 Hz, 1H), 6.45-6.39 (m, 1H), 3.67 (t, J = 4.8 Hz, 4H), 3.12-2.98 (m, 4H), 2.82 (s, 3H), 2.81-2.65 (m, 2H), 1.15 (t, J = 7.5 Hz, 3H). |

-continued

| Compound | Name | MS | NMR |
|---|---|---|---|
| 284 | 4-[7-(2-chloro-1H-imidazol-5-yl)-2-ethyl-3-(8-fluoroquinolin-4-yl)benzimidazol-5-yl]morpholine | 477.2 | 1H NMR (400 MHz, DMSO-d6) δ 9.25 (d, J = 4.5 Hz, 1H), 8.21 (s, 1H), 8.00 (d, J = 4.5 Hz, 1H), 7.75 (ddd, J = 10.8, 7.8, 1.2 Hz, 1H), 7.63 (ddd, J = 8.5, 7.8, 5.0 Hz, 1H), 7.53 (d, J = 2.3 Hz, 1H), 7.17 (dd, J = 8.5, 1.0 Hz, 1H), 6.39 (d, J = 2.1 Hz, 1H), 3.67 (t, J = 4.7 Hz, 4H), 3.11-2.96 (m, 4H), 2.81-2.61 (m, 2H), 1.16 (t, J = 7.5 Hz, 3H). |
| 285 | 4-[7-(2-chloro-1H-imidazol-5-yl)-3-(8-chloroquinolin-4-yl)benzimidazol-5-yl]morpholine | 465.1 | 1H NMR (400 MHz, DMSO-d6) δ 9.26 (d, J = 4.6 Hz, 1H), 8.66 (s, 1H), 8.20 (s, 1H), 8.12 (dd, J = 7.5, 1.3 Hz, 1H), 7.95 (d, J = 4.6 Hz, 1H), 7.64 (dd, J = 8.5, 7.4 Hz, 1H), 7.61-7.52 (m, 2H), 6.60 (d, J = 2.2 Hz, 1H), 3.70 (t, J = 4.8 Hz, 4H), 3.12-2.97 (m, 4H). |
| 286 | 4-[7-(2-chloro-1H-imidazol-5-yl)-2-cyclopropyl-3-(5,8-difluoroquinolin-4-yl)benzimidazol-5-yl]morpholine | 507.2 | 1H NMR (400 MHz, DMSO-d6) δ 9.30 (d, J = 4.5 Hz, 1H), 8.13 (s, 1H), 8.02 (d, J = 4.5 Hz, 1H), 7.78 (ddd, J = 10.0, 8.7, 4.1 Hz, 1H), 7.56 (d, J = 2.2 Hz, 1H), 7.47 (ddd, J = 11.7, 8.8, 3.8 Hz, 1H), 6.68 (s, 1H), 3.79-3.68 (m, 4H), 3.19-3.12 (m, 4H), 1.74-1.63 (m, 1H), 1.27-1.07 (m, 2H), 0.99-0.82 (m, 2H). |
| 287 | 4-[7-(2-chloro-1H-imidazol-5-yl)-2-cyclopropyl-3-(8-fluoroquinolin-4-yl)benzimidazol-5-yl]morpholine | 489.2 | 1H NMR (400 MHz, DMSO-d6) δ 9.25 (d, J = 4.5 Hz, 1H), 8.14 (s, 1H), 7.98 (d, J = 4.5 Hz, 1H), 7.75 (ddd, J = 10.8, 7.8, 1.2 Hz, 1H), 7.64 (ddd, J = 8.6, 7.8, 5.0 Hz, 1H), 7.55 (d, J = 2.2 Hz, 1H), 7.20 (d, J = 8.2 Hz, 1H), 6.52 (s, 1H), 3.74-3.67 (m, 4H), 3.15-3.03 (m, 4H), 1.69-1.57 (m, 1H), 1.28-1.13 (m, 2H), 1.02-0.80 (m, 2H). |
| 288 | 4-[3-(8-chloro-5-fluoroquinolin-4-yl)-7-(2-chloro-1H-imidazol-5-yl)-2-methylbenzimidazol-5-yl]morpholine | 497.2 | 1H NMR (400 MHz, DMSO-d6) δ 9.40 (d, J = 4.5 Hz, 1H), 8.16 (s, 1H), 8.14 (dd, J = 8.6, 5.0 Hz, 1H), 8.06 (d, J = 4.5 Hz, 1H), 7.56-7.46 (m, 2H), 6.58 (d, J = 2.2 Hz, 1H), 3.77-3.54 (m, 4H), 3.12-3.04 (m, 4H), 2.50 (s, 3H). |
| 289 | 4-[3-(8-chloro-6-fluoroquinolin-4-yl)-7-(2-chloro-1H-imidazol-5-yl)-2-methylbenzimidazol-5-yl]morpholine | 497.18 | 1H NMR (400 MHz, DMSO-d6) δ 9.31 (d, J = 4.5 Hz, 1H), 8.24 (dd, J = 8.5, 2.7 Hz, 1H), 8.17 (s, 1H), 8.06 (d, J = 4.6 Hz, 1H), 7.54 (d, J = 2.2 Hz, 1H), 7.36 (dd, J = 9.1, 2.7 Hz, 1H), 6.48 (d, J = 2.2 Hz, 1H), 3.67 (t, J = 4.7 Hz, 4H), 3.14-3.00 (m, 4H), 2.51 (s, 3H). |
| 290 | 4-[7-(2-chloro-1H-imidazol-5-yl)-3-(8-chloroquinolin-4-yl)-2-cyclopropylbenzimidazol-5-yl]morpholine | 505.2 | 1H NMR (400 MHz, DMSO-d6) δ 9.32 (d, J = 4.5 Hz, 1H), 8.14 (s, 1H), 8.11 (dd, J = 7.5, 1.2 Hz, 1H), 7.99 (d, J = 4.5 Hz, 1H), 7.62 (dd, J = 8.5, 7.5 Hz, 1H), 7.53 (d, J = 2.2 Hz, 1H), 7.34 (dd, J = 8.5, 1.3 Hz, 1H), 6.49 (s, 1H), 3.69 (t, J = 4.7 Hz, 4H), 3.11-3.04 (m, 4H), 1.62 (tt, J = 8.2, 4.8 Hz, 1H), 1.28-1.10 (m, 2H), 1.01-0.89 (m, 1H), 0.90-0.78 (m, 1H). |
| 291 | 4-[7-(2-chloro-1H-imidazol-5-yl)-3-(8-chloroquinolin-4-yl)-2-(oxetan-3-yl)benzimidazol-5-yl]morpholine | 521.2 | 1H NMR (400 MHz, DMSO-d6) δ 9.27 (d, J = 4.5 Hz, 1H), 8.32 (s, 1H), 8.09 (dd, J = 7.5, 1.2 Hz, 1H), 7.84 (d, J = 4.5 Hz, 1H), 7.63-7.53 (m, 2H), 7.19 (dd, J = 8.5, 1.3 Hz, 1H), 6.39 (d, J = 2.1 Hz, 1H), 5.02 (dd, J = 6.8, 5.5 Hz, 1H), 4.93 (dd, J = 6.8, 5.5 Hz, 1H), 4.68 (dd, J = 8.6, 5.5 Hz, 1H), 4.51 (dd, J = 8.5, 5.5 Hz, 1H), 4.15 (tt, J = 8.5, 6.8 Hz, 1H), 3.67 (t, J = 4.7 Hz, 4H), 3.11-2.92 (m, 4H). |

| Compound | Name | MS | NMR |
|---|---|---|---|
| 292 | 4-[7-(2-chloro-1H-imidazol-5-yl)-3-(8-fluoroquinolin-4-yl)benzimidazol-5-yl]morpholine | 449.18 | 1H NMR (400 MHz, DMSO-d6) δ 9.20 (d, J = 4.6 Hz, 1H), 8.72 (s, 1H), 8.20 (s, 1H), 7.95 (d, J = 4.6 Hz, 1H), 7.76 (dd, J = 10.6, 7.7 Hz, 1H), 7.66 (td, J = 8.1, 5.0 Hz, 1H), 7.60 (d, J = 2.2 Hz, 1H), 7.42 (d, J = 8.5 Hz, 1H), 6.63 (d, J = 2.0 Hz, 1H), 3.71 (t, J = 4.8 Hz, 4H), 3.09 (t, J = 4.8 Hz, 4H). |
| 293 | 4-[7-(2-chloro-1H-imidazol-5-yl)-3-(7-fluoroquinolin-4-yl)-2-methylbenzimidazol-5-yl]morpholine | 463.2 | 1H NMR (400 MHz, DMSO-d6) δ 9.25 (d, J = 4.6 Hz, 1H), 8.17 (s, 1H), 8.06 (ddd, J = 10.1, 2.4, 0.7 Hz, 1H), 7.90 (d, J = 4.6 Hz, 1H), 7.66-7.51 (m, 3H), 6.39 (d, J = 2.2 Hz, 1H), 3.66 (t, J = 4.7 Hz, 4H), 3.12-2.98 (m, 4H), 2.49 (s, 3H). |
| 294 | 4-[3-(8-chloro-7-fluoroquinolin-4-yl)-7-(2-chloro-1H-imidazol-5-yl)-2-methylbenzimidazol-5-yl]morpholine | 497.17 | 1H NMR (400 MHz, DMSO-d6) δ 9.37 (d, J = 4.5 Hz, 1H), 8.18 (s, 1H), 8.01 (d, J = 4.6 Hz, 1H), 7.77 (t, J = 9.1 Hz, 1H), 7.58-7.49 (m, 2H), 6.44 (d, J = 2.2 Hz, 1H), 3.66 (t, J = 4.7 Hz, 4H), 3.11-2.98 (m, 4H), 2.48 (s, 3H). |
| 295 | 4-[3-(8-chloro-7-fluoroquinolin-4-yl)-7-(2-chloro-1H-imidazol-5-yl)-2-ethylbenzimidazol-5-yl]morpholine | 511.2 | 1H NMR (400 MHz, DMSO-d6) δ 9.36 (d, J = 4.5 Hz, 1H), 8.21 (s, 1H), 8.01 (d, J = 4.6 Hz, 1H), 7.75 (t, J = 9.1 Hz, 1H), 7.53 (d, J = 2.2 Hz, 1H), 7.44 (dd, J = 9.4, 5.7 Hz, 1H), 6.42 (d, J = 2.2 Hz, 1H), 3.67 (t, J = 4.7 Hz, 4H), 3.04 (td, J = 4.2, 2.1 Hz, 4H), 2.84-2.48 (m, 2H), 1.15 (t, J = 7.5 Hz, 3H). |
| 296 | 4-[3-(8-chloro-7-fluoroquinolin-4-yl)-7-(2-chloro-1H-imidazol-5-yl)-2-cyclopropylbenzimidazol-5-yl]morpholine | 523.2 | 1H NMR (400 MHz, DMSO-d6) δ 9.35 (d, J = 4.6 Hz, 1H), 8.14 (s, 1H), 7.99 (d, J = 4.6 Hz, 1H), 7.75 (t, J = 9.1 Hz, 1H), 7.54 (d, J = 2.2 Hz, 1H), 7.44 (dd, J = 9.4, 5.7 Hz, 1H), 6.53 (s, 1H), 3.70 (dd, J = 5.5, 4.0 Hz, 4H), 3.09 (dd, J = 6.5, 3.6 Hz, 4H), 1.64 (tt, J = 8.3, 4.8 Hz, 1H), 1.29-1.11 (m, 2H), 1.02-0.92 (m, 1H), 0.89-0.79 (m, 1H). |
| 297 | 4-[3-(8-chloroquinolin-4-yl)-2-methyl-7-(2-methyl-1,3-thiazol-5-yl)benzimidazol-5-yl]morpholine | 476.19 | 1H NMR (400 MHz, DMSO-d6) δ 9.30 (d, J = 4.5 Hz, 1H), 8.56 (s, 1H), 8.10 (dd, J = 7.5, 1.2 Hz, 1H), 7.95 (d, J = 4.5 Hz, 1H), 7.60 (dd, J = 8.5, 7.5 Hz, 1H), 7.32 (d, J = 2.2 Hz, 1H), 7.27 (dd, J = 8.5, 1.2 Hz, 1H), 6.42 (d, J = 2.1 Hz, 1H), 3.65 (t, J = 4.7 Hz, 4H), 3.09-2.95 (m, 4H), 2.74 (s, 3H), 2.33 (s, 3H). |
| 298 | 4-[7-(2-chloro-1H-imidazol-5-yl)-3-(5,8-difluoroquinolin-4-yl)-2-methylbenzimidazol-5-yl]morpholin | 481.2 | 1H NMR (400 MHz, DMSO-d6) δ 9.33 (d, J = 4.5 Hz, 1H), 8.16 (s, 1H), 8.06 (d, J = 4.5 Hz, 1H), 7.81 (ddd, J = 10.1, 8.8, 4.3 Hz, 1H), 7.56-7.45 (m, 2H), 6.58 (d, J = 2.2 Hz, 1H), 3.68 (t, J = 4.8 Hz, 4H), 3.16-2.94 (m, 4H), 2.51 (s, 3H). |
| 299 | 4-[7-(2-chloro-1H-imidazol-5-yl)-3-(5,8-difluoroquinolin-4-yl)-2-propylbenzimidazol-5-yl]morpholine | 509.2 | 1H NMR (400 MHz, DMSO-d6) δ 9.30 (d, J = 4.5 Hz, 1H), 8.17 (s, 1H), 8.02 (d, J = 4.5 Hz, 1H), 7.79 (ddd, J = 10.1, 8.8, 4.2 Hz, 1H), 7.53-7.42 (m, 2H), 6.49 (s, 1H), 3.67 (t, J = 4.7 Hz, 4H), 3.06 (dt, J = 5.6, 2.1 Hz, 4H), 2.74-2.61 (m, 2H), 1.71-1.56 (m, 2H), 0.84 (t, J = 7.3 Hz, 3H). |
| 300 | 4-[7-(2-chloro-1H-imidazol-5-yl)-3-(5,8-difluoroquinolin-4-yl)-2-(2-methylpropyl)benzimidazol-5-yl]morpholine | 523.2 | 1H NMR (400 MHz, DMSO-d6) δ 9.30 (d, J = 4.5 Hz, 1H), 8.18 (s, 1H), 8.02 (d, J = 4.5 Hz, 1H), 7.79 (ddd, J = 10.1, 8.8, 4.2 Hz, 1H), 7.54-7.43 (m, 2H), 6.53 (s, 1H), 3.68 (t, J = 4.8 Hz, 4H), 3.17-2.97 (m, 4H), 2.66 (dd, J = 14.9, 6.9 Hz, 1H), 2.57 (dd, J = 14.9, 7.5 Hz, 1H), 2.02 (hept, J = 6.8 Hz, 1H), 0.84 (d, J = 6.6 Hz, 6H). |

| Compound | Name | MS | NMR |
|---|---|---|---|
| 301 | 4-[7-(2-chloro-1H-imidazol-5-yl)-3-(8-chloroquinolin-4-yl)-2-(cyclopropylmethyl)benzimidazol-5-yl]morpholine | 519.2 | 1H NMR (400 MHz, DMSO-d6) δ 9.33 (d, J = 4.5 Hz, 1H), 8.22 (s, 1H), 8.11 (dd, J = 7.5, 1.2 Hz, 1H), 8.04 (d, J = 4.5 Hz, 1H), 7.61 (dd, J = 8.5, 7.5 Hz, 1H), 7.57 (d, J = 2.2 Hz, 1H), 7.35 (dd, J = 8.5, 1.3 Hz, 1H), 6.45 (d, J = 2.2 Hz, 1H), 3.67 (t, J = 4.7 Hz, 4H), 3.13-2.99 (m, 4H), 2.83-2.67 (m, 2H), 0.92-0.77 (m, 1H), 0.31 (dddd, J = 9.1, 8.1, 5.7, 4.2 Hz, 1H), 0.18 (dddd, J = 9.1, 7.9, 5.7, 4.2 Hz, 1H), −0.11−−0.22 (m, 1H). |
| 302 | 4-[7-(2-chloro-1H-imidazol-5-yl)-2-(cyclopropylmethyl)-3-(5,8-difluoroquinolin-4-yl)benzimidazol-5-yl]morpholine | 521.2 | 1H NMR (400 MHz, DMSO-d6) δ 9.31 (d, J = 4.5 Hz, 1H), 8.19 (s, 1H), 8.05 (d, J = 4.5 Hz, 1H), 7.79 (ddd, J = 10.0, 8.8, 4.2 Hz, 1H), 7.53 (s, 0H), 7.47 (ddd, J = 12.3, 8.8, 3.8 Hz, 1H), 6.58-6.52 (m, 1H), 3.68 (t, J = 4.7 Hz, 4H), 3.12-3.03 (m, 4H), 2.76 (qd, J = 15.5, 6.8 Hz, 2H), 0.96-0.81 (m, 1H), 0.33 (dddd, J = 9.7, 8.2, 5.6, 4.1 Hz, 1H), 0.23 (dddd, J = 9.2, 7.9, 5.6, 4.1 Hz, 1H), 0.09-0.01 (m, 1H), −0.14 (dq, J = 9.6, 4.9 Hz, 1H). |
| 303 | 4-[3-(8-chloro-6-fluoroquinolin-4-yl)-7-(2-chloro-1H-imidazol-5-yl)-2-propylbenzimidazol-5-yl]morpholine | 525.2 | 1H NMR (400 MHz, DMSO-d6) δ 9.29 (d, J = 4.5 Hz, 1H), 8.23 (dd, J = 8.5, 2.7 Hz, 1H), 8.19 (s, 1H), 8.05 (d, J = 4.5 Hz, 1H), 7.53 (d, J = 2.2 Hz, 1H), 7.16 (dd, J = 9.3, 2.6 Hz, 1H), 6.42 (d, J = 2.2 Hz, 1H), 3.67 (t, J = 4.7 Hz, 4H), 3.10-2.97 (m, 4H), 2.77-2.61 (m, 2H), 1.72-1.51 (m, 2H), 0.83 (t, J = 7.4 Hz, 3H). |
| 304 | 4-[7-(2-chloro-1H-imidazol-5-yl)-2-(cyclopropylmethyl)-3-(8-fluoroquinolin-4-yl)benzimidazol-5-yl]morpholine | 503.2 | 1H NMR (400 MHz, DMSO-d6) δ 9.25 (d, J = 4.5 Hz, 1H), 8.23 (s, 1H), 8.01 (d, J = 4.5 Hz, 1H), 7.75 (ddd, J = 10.8, 7.8, 1.2 Hz, 1H), 7.62 (td, J = 8.2, 5.0 Hz, 1H), 7.55 (d, J = 2.2 Hz, 1H), 7.16 (d, J = 8.5 Hz, 1H), 6.41 (s, 1H), 3.67 (t, J = 4.7 Hz, 4H), 3.13-2.97 (m, 4H), 2.79-2.64 (m, 2H), 0.93-0.78 (m, 1H), 0.32 (dddd, J = 9.1, 8.1, 5.7, 4.1 Hz, 1H), 0.25-0.13 (m, 1H), 0.10−−0.04 (m, 1H), −0.10−−0.21 (m, 1H) |
| 305 | 4-[7-(2-chloro-1H-imidazol-5-yl)-3-(8-fluoroquinolin-4-yl)-2-propylbenzimidazol-5-yl]morpholine | 491.2 | 1H NMR (400 MHz, DMSO-d6) δ 9.26 (d, J = 4.5 Hz, 1H), 8.21 (s, 1H), 8.01 (d, J = 4.5 Hz, 1H), 7.76 (ddd, J = 10.8, 7.8, 1.2 Hz, 1H), 7.63 (td, J = 8.1, 5.0 Hz, 1H), 7.55 (d, J = 2.2 Hz, 1H), 7.17 (d, J = 8.5 Hz, 1H), 6.42 (s, 1H), 3.67 (t, J = 4.7 Hz, 4H), 3.12-2.98 (m, 4H), 2.70 (t, J = 7.5 Hz, 2H), 1.60 (qq, J = 13.8, 7.3 Hz, 2H), 0.81 (t, J = 7.4 Hz, 3H). |
| 306 | 4-[7-(2-chloro-1H-imidazol-5-yl)-2-methyl-3-quinolin-4-ylbenzimidazol-5-yl]morpholine | 445.2 | 1H NMR (400 MHz, DMSO-d6) δ 9.24 (d, J = 4.5 Hz, 1H), 8.29 (ddd, J = 8.5, 1.3, 0.7 Hz, 1H), 8.18 (s, 1H), 7.99-7.90 (m, 1H), 7.92 (d, J = 4.5 Hz, 1H), 7.67 (ddd, J = 8.2, 6.9, 1.2 Hz, 1H), 7.55 (d, J = 2.2 Hz, 1H), 7.47 (d, J = 8.4 Hz, 1H), 6.38 (d, J = 2.1 Hz, 1H), 3.66 (t, J = 4.8 Hz, 4H), 3.11-2.97 (m, 4H), 2.48 (s, 3H). |
| 307 | 4-[3-(8-chloro-5-fluoroquinolin-4-yl)-7-(2-chloro-1H-imidazol-5-yl)-2-cyclopropylbenzimidazol-5-yl]morpholine | 523.1 | 1H NMR (400 MHz, DMSO-d6) δ 9.36 (d, J = 4.5 Hz, 1H), 8.12 (dd, J = 8.5, 4.9 Hz, 1H), 8.11 (s, 1H), 8.01 (d, J = 4.5 Hz, 1H), 7.54-7.40 (m, 2H), 6.59 (s, 1H), 3.70 (t, J = 4.8 Hz, 4H), 3.12-3.07 (m, 4H), 1.64 (td, J = 8.2, 4.2 Hz, 1H), |

| Compound | Name | MS | NMR |
|---|---|---|---|
| | | | 1.24-1.15 (m, 1H), 1.14-1.03 (m, 1H), 0.96-0.79 (m, 2H). |
| 308 | 4-[7-(2-chloro-1H-imidazol-5-yl)-3-(5,8-difluoroquinolin-4-yl)benzimidazol-5-yl]morpholine | 467.1 | 1H NMR (400 MHz, DMSO-d6) δ 9.65 (s, 1H), 9.21 (s, 1H), 8.74-8.00 (m, 1H), 8.00-7.68 (m, 2H), 7.63-7.26 (m, 2H), 6.80-6.38 (m, 1H), 4.11-3.72 (m, 4H), 3.24-2.95 (m, 4H). |
| 309 | 4-[3-(5-chloro-8-fluoroquinolin-4-yl)-7-(2-chloro-1H-imidazol-5-yl)-2-methylbenzimidazol-5-yl]morpholine | 497.1 | 1H NMR (400 MHz, DMSO-d6) δ 9.35 (d, J = 4.4 Hz, 1H), 8.17 (s, 1H), 8.08 (d, J = 4.4 Hz, 1H), 7.84 (s, 1H), 7.82 (d, J = 1.5 Hz, 1H), 7.54 (d, J = 2.2 Hz, 1H), 6.56 (d, J = 2.2 Hz, 1H), 3.68 (t, J = 4.8 Hz, 4H), 3.14-3.06 (m, 4H), 2.51 (s, 3H). |
| 310 | 4-[3-(5-chloro-8-fluoroquinolin-4-yl)-7-(2-chloro-1H-imidazol-5-yl)-2-ethylbenzimidazol-5-yl]morpholine | 511.1 | 1H NMR (400 MHz, DMSO-d6) δ 9.33 (d, J = 4.4 Hz, 1H), 8.21 (s, 1H), 8.09 (d, J = 4.5 Hz, 1H), 7.85-7.76 (m, 2H), 7.55 (d, J = 2.2 Hz, 1H), 6.56 (d, J = 2.2 Hz, 1H), 3.69 (dd, J = 5.6, 4.0 Hz, 4H), 3.17-3.06 (m, 4H), 2.85-2.68 (m, 2H), 1.20 (t, J = 7.5 Hz, 3H). |
| 311 | 4-(1-(8-chloroquinolin-4-yl)-2-methyl-4-phenyl-1H-benzo[d]imidazol-6-yl)morpholine | 455.2 | 1H NMR (400 MHz, DMSO-d6) δ 9.36 (d, J = 4.5 Hz, 1H), 8.14 (dd, J = 7.5, 1.2 Hz, 1H), 8.04 (d, J = 4.5 Hz, 1H), 7.97-7.89 (m, 2H), 7.70-7.55 (m, 3H), 7.56-7.43 (m, 2H), 7.25 (d, J = 2.2 Hz, 1H), 6.58 (d, J = 2.2 Hz, 1H), 3.65 (t, J = 4.8 Hz, 4H), 3.08 (q, J = 4.2 Hz, 4H), 2.43 (s, 3H). |
| 312 | 4-(2-methyl-4-phenyl-1-(8-phenylquinolin-4-yl)-1H-benzo[d]imidazol-6-yl)morpholine | 497.3 | 1H NMR (400 MHz, DMSO-d6) δ 9.24 (d, J = 4.4 Hz, 1H), 7.99-7.90 (m, 4H), 7.79-7.71 (m, 3H), 7.65-7.57 (m, 2H), 7.57-7.43 (m, 5H), 7.28 (d, J = 2.2 Hz, 1H), 6.60 (d, J = 2.1 Hz, 1H), 3.66 (t, J = 4.8 Hz, 4H), 3.10 (q, J = 4.0 Hz, 4H), 2.46 (s, 3H). |
| 313 | 4-(1-(8-chloroquinolin-4-yl)-2-methyl-4-(1-methyl-1H-pyrazol-4-yl)-1H-benzo[d]imidazol-6-yl)morpholine | 459.1 | 1H NMR (400 MHz, DMSO-d6) δ 9.33 (d, J = 4.6 Hz, 1H), 8.56 (s, 1H), 8.25 (d, J = 0.7 Hz, 1H), 8.13 (dd, J = 7.5, 1.2 Hz, 1H), 8.00 (d, J = 4.5 Hz, 1H), 7.63 (dd, J = 8.5, 7.6 Hz, 1H), 7.43-7.30 (m, 2H), 6.41 (d, J = 2.3 Hz, 1H), 3.97 (s, 3H), 3.67 (t, J = 4.7 Hz, 4H), 3.14-2.99 (m, 4H), 2.42 (s, 3H). |
| 314 | 4-(1-(8-chloroquinolin-4-yl)-2-methyl-4-(pyridazin-4-yl)-1H-benzo[d]imidazol-6-yl)morpholine | 457.1 | 1H NMR (400 MHz, DMSO-d6) δ 10.15 (dd, J = 2.5, 1.2 Hz, 1H), 9.44-9.37 (m, 1H), 9.31 (d, J = 4.6 Hz, 1H), 8.62 (dd, J = 5.5, 2.4 Hz, 1H), 8.11 (dd, J = 7.5, 1.2 Hz, 1H), 7.97 (d, J = 4.5 Hz, 1H), 7.61 (dd, J = 8.5, 7.5 Hz, 1H), 7.52 (d, J = 2.2 Hz, 1H), 7.26 (dd, J = 8.5, 1.2 Hz, 1H), 6.61 (d, J = 2.2 Hz, 1H), 3.66 (t, J = 4.8 Hz, 4H), 3.07 (q, J = 4.5 Hz, 4H), 2.35 (s, 3H). |
| 315 | 4-(1-(8-chloroquinolin-4-yl)-2-methyl-4-(pyrimidin-5-yl)-1H-benzo[d]imidazol-6-yl)morpholine | 457.1 | 1H NMR (400 MHz, DMSO-d6) δ 9.55 (s, 2H), 9.31 (d, J = 4.5 Hz, 1H), 9.23 (s, 1H), 8.11 (dd, J = 7.5, 1.2 Hz, 1H), 7.96 (d, J = 4.5 Hz, 1H), 7.61 (dd, J = 8.5, 7.5 Hz, 1H), 7.38 (d, J = 2.2 Hz, 1H), 7.27 (dd, J = 8.5, 1.2 Hz, 1H), 6.52 (d, J = 2.2 Hz, 1H), 3.65 (t, J = 4.8 Hz, 4H), 3.05 (q, J = 4.5 Hz, 4H), 2.34 (s, 3H). |
| 316 | 3-(1-(8-chloroquinolin-4-yl)-2-methyl-6-morpholino-1H-benzo[d]imidazol-4-yl)-N,N-dimethylaniline | 498.2 | 1H NMR (400 MHz, DMSO-d6) δ 9.35 (d, J = 4.7 Hz, 1H), 8.14 (d, J = 7.5 Hz, 1H), 8.02 (d, J = 3.9 Hz, 1H), 7.65 (t, J = 8.0 Hz, 1H), 7.46 (br s, 1H), 7.45-7.36 (m, 1H), 7.29-7.12 (m, 2H), 6.92 (br s, 1H), |

| Compound | Name | MS | NMR |
|---|---|---|---|
| | | | 6.53 (s, 2H), 3.65 (t, J = 4.8 Hz, 4H), 3.08-3.05 (m, 4H), 3.03 (s, 6H), 2.42 (s, 3H). |
| 317 | 4-[3-(8-chloroquinolin-4-yl)-2-methyl-7-pyridin-3-ylbenzimidazol-5-yl]morpholine | 456.1 | 1H NMR (400 MHz, DMSO-d6) δ 9.55 (s, 1H), 9.32 (d, J = 4.5 Hz, 1H), 8.98 (br d, J = 8.1 Hz, 1H), 8.82 (dd, J = 5.3, 1.5 Hz, 1H), 8.12 (dd, J = 7.5, 1.2 Hz, 1H), 7.97 (d, J = 4.5 Hz, 1H), 7.96-7.90 (m, 1H), 7.62 (dd, J = 8.5, 7.5 Hz, 1H), 7.39 (d, J = 2.2 Hz, 1H), 7.27 (dd, J = 8.5, 1.3 Hz, 1H), 6.57 (d, J = 2.2 Hz, 1H), 3.66 (t, J = 4.8 Hz, 4H), 3.13-2.99 (m, 4H), 2.35 (s, 3H). |
| 318 | 4-[2-methyl-7-pyridin-3-yl-3-(8-pyridin-3-ylquinolin-4-yl)benzimidazol-5-yl]morpholine | 499.2 | 1H NMR (400 MHz, DMSO-d6) δ 9.68-9.62 (m, 1H), 9.26 (d, J = 4.5 Hz, 1H), 9.25-9.22 (m, 1H), 9.14 (dt, J = 8.2, 1.8 Hz, 1H), 8.92 (td, J = 5.5, 1.5 Hz, 2H), 8.73 (dt, J = 8.1, 1.8 Hz, 1H), 8.15 (dd, J = 7.2, 1.4 Hz, 1H), 8.11-8.01 (m, 2H), 7.98 (d, J = 4.5 Hz, 1H), 7.82 (dd, J = 8.5, 7.2 Hz, 1H), 7.48 (d, J = 2.2 Hz, 1H), 7.46 (dd, J = 8.5, 1.3 Hz, 1H), 6.61 (d, J = 2.1 Hz, 1H), 3.69 (t, J = 4.8 Hz, 4H), 3.17-3.01 (m, 4H), 2.39 (s, 3H). |
| 319 | 4-[3-(8-chloroquinolin-4-yl)-2-methyl-7-pyridin-4-ylbenzimidazol-5-yl]morpholine | 456.2 | 1H NMR (400 MHz, DMSO-d6) δ 9.32 (d, J = 4.5 Hz, 1H), 8.95 (d, J = 6.6 Hz, 2H), 8.85 (br d, J = 5.9 Hz, 2H), 8.11 (dd, J = 7.5, 1.2 Hz, 1H), 7.97 (d, J = 4.6 Hz, 1H), 7.61 (dd, J = 8.5, 7.6 Hz, 1H), 7.53 (d, J = 2.2 Hz, 1H), 7.24 (dd, J = 8.5, 1.3 Hz, 1H), 6.68 (d, J = 2.1 Hz, 1H), 3.67 (t, J = 4.8 Hz, 4H), 3.07 (q, J = 4.5 Hz, 4H), 2.35 (s, 3H). |
| 320 | 4-[2-methyl-7-pyridin-4-yl-3-(8-pyridin-4-ylquinolin-4-yl)benzimidazol-5-yl]morpholine | 499.2 | 1H NMR (400 MHz, DMSO-d6) δ 9.27 (d, J = 4.5 Hz, 1H), 9.09-8.97 (m, 6H), 8.42-8.34 (m, 2H), 8.19 (dd, J = 7.2, 1.3 Hz, 1H), 8.01 (d, J = 4.5 Hz, 1H), 7.84 (dd, J = 8.5, 7.2 Hz, 1H), 7.62 (d, J = 2.2 Hz, 1H), 7.50 (dd, J = 8.4, 1.3 Hz, 1H), 6.74 (d, J = 2.1 Hz, 1H), 3.70 (t, J = 4.8 Hz, 4H), 3.18-3.02 (m, 4H), 2.40 (s, 3H). |
| 321 | 3-[1-(8-chloroquinolin-4-yl)-2-methyl-6-morpholin-4-ylbenzimidazol-4-yl]benzamide | 498.1 | 1H NMR (400 MHz, DMSO-d6) δ 9.34 (d, J = 4.5 Hz, 1H), 8.35 (t, J = 1.8 Hz, 1H), 8.22-8.16 (m, 1H), 8.15-8.07 (m, 2H), 8.00 (d, J = 4.5 Hz, 1H), 7.95 (dt, J = 7.8, 1.4 Hz, 1H), 7.70-7.59 (m, 2H), 7.50 (s, 1H), 7.39 (d, J = 8.5 Hz, 1H), 7.27 (d, J = 2.2 Hz, 1H), 6.54 (d, J = 2.1 Hz, 1H), 3.66 (t, J = 4.8 Hz, 4H), 3.14-2.99 (m, 4H), 2.39 (s, 3H). |
| 322 | 3-[4-[4-(3-carbamoylphenyl)-2-methyl-6-morpholin-4-ylbenzimidazol-1-yl]quinolin-8-yl]benzamide | 583.2 | 1H NMR (400 MHz, DMSO-d6) δ 9.24 (d, J = 4.5 Hz, 1H), 8.35 (t, J = 1.8 Hz, 1H), 8.22 (t, J = 1.8 Hz, 1H), 8.17 (d, J = 7.8 Hz, 1H), 8.12 (s, 1H), 8.07 (s, 1H), 8.03-7.93 (m, 4H), 7.90 (dt, J = 7.7, 1.3 Hz, 1H), 7.77 (dd, J = 8.4, 7.2 Hz, 1H), 7.68 (t, J = 7.7 Hz, 1H), 7.61 (t, J = 7.7 Hz, 1H), 7.52 (s, 1H), 7.50-7.45 (m, 1H), 7.43 (s, 1H), 7.31 (d, J = 2.2 Hz, 1H), 6.57 (d, J = 2.1 Hz, 1H), 3.68 (t, J = 4.8 Hz, 4H), 3.17-3.03 (m, 4H), 2.44 (s, 3H). |
| 323 | 4-[3-(8-chloroquinolin-4-yl)-2-methyl-7-pyridin-2-ylbenzimidazol-5-yl]morpholine | 456.1 | 1H NMR (400 MHz, DMSO-d6) δ 9.37 (d, J = 4.5 Hz, 1H), 8.92-8.86 (m, 1H), 8.70 (d, J = 8.1 Hz, 1H), 8.20-8.11 (m, 2H), 8.07 (d, J = 4.5 Hz, 1H), 7.89 (d, J = 2.2 Hz, 1H), 7.69-7.56 (m, 2H), 7.49 (dd, J = 8.5, 1.2 Hz, 1H), 6.70 (d, J = 2.1 Hz, |

| Compound | Name | MS | NMR |
|---|---|---|---|
| | | | 1H), 3.68 (t, J = 4.8 Hz, 4H), 3.19-3.04 (m, 4H), 2.54 (s, 3H). |

Step 6c: 4-(1-(8-chloroquinolin-4-yl)-2-methyl-4-(1H-1,2,3-triazol-5-yl)-1H-benzo[d]imidazol-6-yl)morpholine

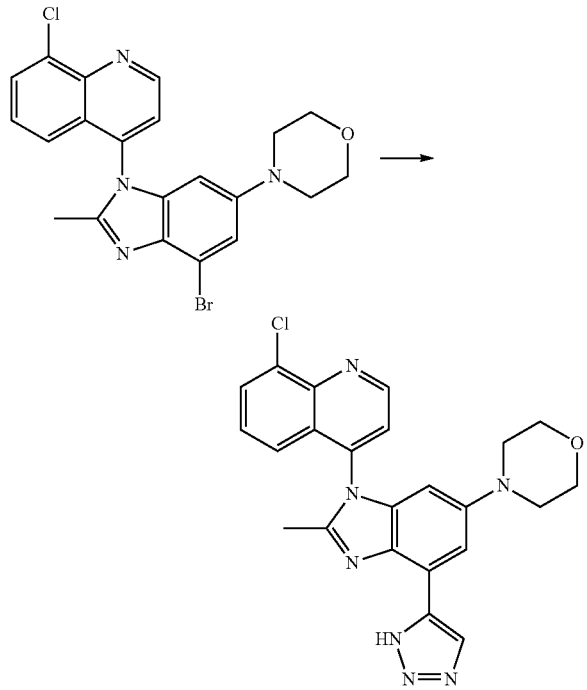

4-(4-Bromo-1-(8-chloroquinolin-4-yl)-2-methyl-1H-benzo[d]imidazol-6-yl)morpholine (220 mg, 0.48 mmol), ethynyltributylstannane (0.181 mL, 0.63 mmol), Pd(dppf)Cl2 (31 mg, 0.048 mmol), and copper iodide (9 mg, 0.048 mmol) were combined in dioxane (2 mL), degassed under $Ar_2$, and heated to 70° C. After 5 days the reaction was purified directly on silica to give 4-(1-(8-chloroquinolin-4-yl)-4-ethynyl-2-methyl-1H-benzo[d]imidazol-6-yl)morpholine. 4-(1-(8-Chloroquinolin-4-yl)-4-ethynyl-2-methyl-1H-benzo[d]imidazol-6-yl)morpholine (39 mg, 0.097 mmol) was combined with copper iodide (2 mg, 0.01 mmol) in a mixture of DMF (0.5 mL) and MeOH (0.1 mL) under $N_2$. Azidotrimethylsilane (0.019 mL, 0.145 mmol) was added, and the resulting mixture was heated to 80° C. overnight. Purification on silica (0-30% MeOH/DCM), followed by preparatory LC, provided 4-(1-(8-chloroquinolin-4-yl)-2-methyl-4-(1H-1,2,3-triazol-5-yl)-1H-benzo[d]imidazol-6-yl)morpholine (Compound 329). 1H NMR (400 MHz, DMSO-d6) δ 9.32 (d, J=4.5 Hz, 1H), 8.81 (s, 1H), 8.11 (d, J=7.5 Hz, 1H), 7.99 (d, J=4.5 Hz, 1H), 7.68-7.48 (m, 2H), 7.34 (s, 1H), 6.49 (s, 1H), 3.68-3.64 (m, 4H), 3.10-2.95 (m, 4H), 2.41 (s, 3H). ES/MS m/z 446.2 (M+H)+.

The compounds listed in the table below were prepared in a manner similar to that described above using appropriate intermediates and chemistry.

| Compound | Name | MS | NMR |
|---|---|---|---|
| 376 | 4-(1-(5,8-difluoroquinolin-4-yl)-2-ethyl-4-(1H-1,2,3-triazol-5-yl)-1H-benzo[d]imidazol-6-yl)morpholine | 462.2 | 1H NMR (400 MHz, DMSO-d6) δ 9.31 (d, J = 28.5 Hz, 1H), 8.89-8.72 (m, 1H), 8.11-7.91 (m, 1H), 7.83-7.70 (m, 1H), 7.69-7.55 (m, 1H), 7.55-7.36 (m, 1H), 6.67-6.50 (m, 1H), 3.68 (t, J = 4.7 Hz, 4H), 3.15-2.95 (m, 4H), 1.26-1.09 (m, 3H), 0.72-0.55 (m, 2H). |
| 377 | 4-(1-(5,8-difluoroquinolin-4-yl)-2-methyl-4-(1H-1,2,3-triazol-5-yl)-1H-benzo[d]imidazol-6-yl)morpholine | 448.2 | 1H NMR (400 MHz, DMSO-d6) δ 9.32 (d, J = 4.5 Hz, 1H), 8.86-8.76 (m, 1H), 8.04 (d, J = 4.5 Hz, 1H), 7.80 (td, J = 9.4, 4.1 Hz, 1H), 7.64 (s, 1H), 7.50 (ddd, J = 12.3, 8.8, 3.8 Hz, 1H), 6.65 (s, 1H), 3.68 (t, J = 4.8 Hz, 4H), 3.09 (s, 4H), 2.48 (s, 3H). |
| 378 | 4-(1-(8-chloroquinolin-4-yl)-2-cyclopropyl-4-(1H-1,2,3-triazol-5-yl)-1H-benzo[d]imidazol-6-yl)morpholine | 472.2 | 1H NMR (400 MHz, DMSO-d6) δ 9.32 (d, J = 4.4 Hz, 1H), 8.80-8.67 (m, 1H), 8.10 (d, J = 7.5 Hz, 1H), 8.03-7.95 (m, 1H), 7.66-7.56 (m, 2H), 7.37-7.27 (m, 1H), 6.53-6.44 (m, 1H), 3.67 (t, J = 4.7 Hz, 4H), 3.11-2.95 (m, 4H), 1.65-1.52 (m, 1H), 1.30-1.11 (m, 2H), 1.01-0.75 (m, 2H). |

253

Step 6d: 4-(1-(5,8-difluoroquinolin-4-yl)-2-ethyl-4-(1H-imidazol-2-yl)-1H-benzo[d]imidazol-6-yl)morpholine

254

Step 6e: 4-(1-(5,8-difluoroquinolin-4-yl)-2-propyl-4-(1H-pyrazol-4-yl)-1H-benzo[d]imidazol-6-yl)morpholine

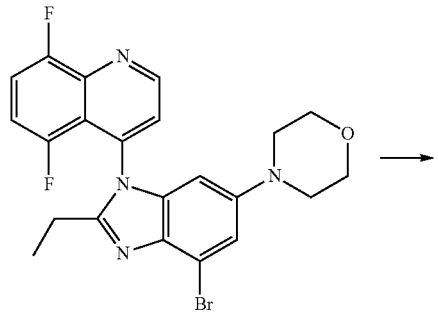

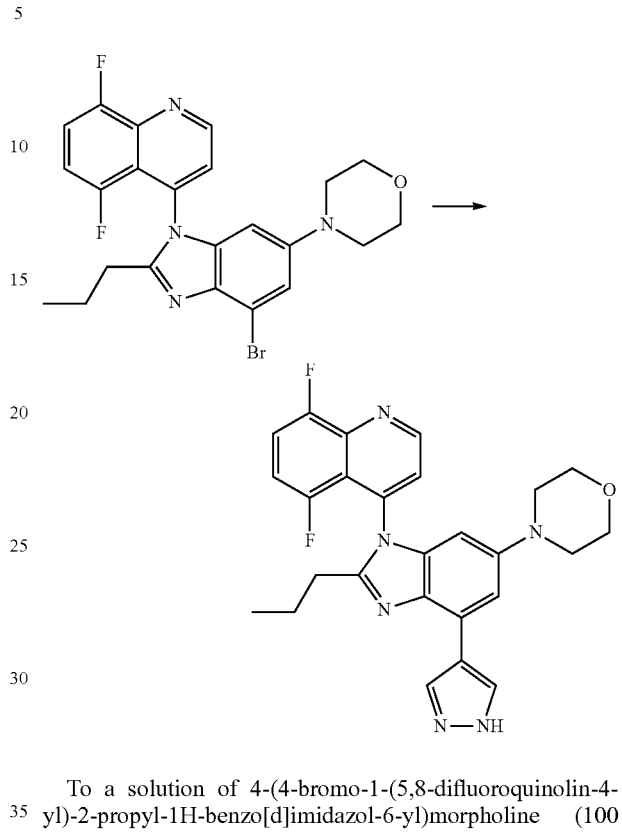

4-(4-bromo-1-(5,8-difluoroquinolin-4-yl)-2-ethyl-1H-benzo[d]imidazol-6-yl)morpholine (200 mg, 0.42 mmol) was combined with N,N-dimethyl imidazole-1-sulfonamide (81 mg, 0.47 mmol), PdOAc (7 mg, 0.07 mmol), and CuI (210 mg, 1.1 mmol) in DMF (2 mL). The mixture was degassed under $Ar_2$ and heated to 140° C. under microwave irradiation for 10 hours. The reaction was filtered and the filtrate concentrated, then precipitated from water to give the protected product as a brown solid. Treatment with TFA in DCM, followed by reverse phase prep LC purification, provided the title compound (Compound 387). 1H NMR (400 MHz, DMSO-d6) δ 9.30 (d, J=4.5 Hz, 1H), 8.01 (d, J=4.5 Hz, 1H), 7.87 (s, 2H), 7.79 (ddd, J=10.0, 8.7, 4.2 Hz, 1H), 7.71 (d, J=2.1 Hz, 1H), 7.52-7.41 (m, 1H), 6.89 (d, J=2.1 Hz, 1H), 3.78-3.62 (m, 4H), 3.12-3.05 (m, 4H), 2.75-2.60 (m, 2H), 1.25 (t, J=7.5 Hz, 3H). ES/MS m/z=461.2 (M+H)+.

To a solution of 4-(4-bromo-1-(5,8-difluoroquinolin-4-yl)-2-propyl-1H-benzo[d]imidazol-6-yl)morpholine (100 mg, 0.21 mmol) in dioxane (1 mL) was added 1-Boc-pyrazole-4-boronic acid pinacol ester (91 mg, 0.31 mmol), cesium fluoride (78 mg, 0.51 mmol), and BrettPhos Pd G3 (17 mg, 0.021 mmol). The resulting mixture was degassed under Argon and heated to 80° C. for 3 days. The reaction was purified directly on silica (0-100% EtOAc/DCM), then treated with TFA in DCM to remove the Boc group. Final purification by prep HPLC eluting with 5-95% water/acetonitrile (0.1% v/v trifluoroacetic acid) afforded the title compound (Compound 388). 1H NMR (400 MHz, DMSO-d6) δ 9.30 (d, J=4.5 Hz, 1H), 8.50 (s, 2H), 8.00 (d, J=4.5 Hz, 1H), 7.79 (ddd, J=10.1, 8.8, 4.2 Hz, 1H), 7.48 (ddd, J=12.3, 8.8, 3.8 Hz, 1H), 7.35 (d, J=2.2 Hz, 1H), 6.47 (s, 1H), 3.74-3.52 (m, 4H), 3.15-3.03 (m, 4H), 2.72-2.56 (m, 2H), 1.66 (h, J=7.4 Hz, 2H), 0.86 (t, J=7.4 Hz, 3H). ES/MS m/z 475.2 (M+H)+.

The compound listed in the table below was prepared in a manner similar to that described above using appropriate intermediates and chemistry.

| Compound | Name | MS | NMR |
|---|---|---|---|
| 389 | 4-(1-(5,8-difluoroquinolin-4-yl)-2-propyl-4-(1H-pyrazol-5-yl)-1H-benzo[d]imidazol-6-yl)morpholine | 475.20 | 1H NMR (400 MHz, DMSO-d6) δ 9.34 (d, J = 4.5 Hz, 1H), 8.11 (d, J = 4.5 Hz, 1H), 7.89 (d, J = 2.2 Hz, 1H), 7.81 (ddd, J = 10.1, 8.8, 4.2 Hz, 1H), 7.59 (d, J = 2.2 Hz, 1H), 7.51 (ddd, J = 12.3, 8.8, 3.8 Hz, 1H), 7.29 (d, J = 2.2 Hz, 1H), |

| Compound Name | MS | NMR |
|---|---|---|
| | | 6.60 (d, J = 2.2 Hz, 1H), 3.68 (t, J = 4.7 Hz, 4H), 3.15-3.02 (m, 4H), 2.87-2.74 (m, 2H), 1.59 (h, J = 7.6 Hz, 2H), 0.83 (t, J = 7.3 Hz, 3H). |

Step 6f: 4-(1-(5,8-difluoroquinolin-4-yl)-4-(2-(trifluoromethyl)-1H-imidazol-5-yl)-1H-benzo[d]imidazol-6-yl)morpholine as a yellow solid

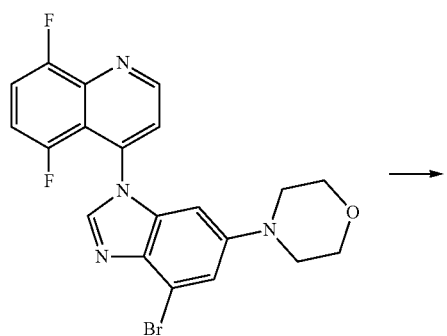

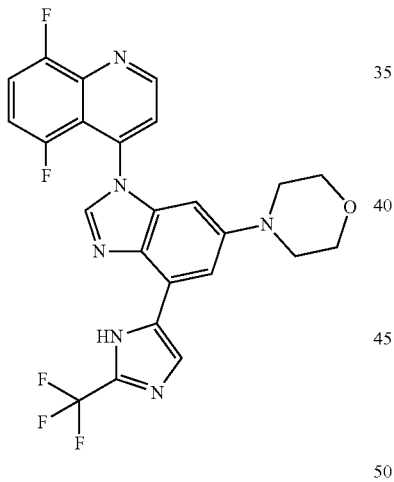

4-(4-bromo-1-(5,8-difluoroquinolin-4-yl)-1H-benzo[d]imidazol-6-yl)morpholine (150 mg, 0.337 mmol), 2-(trifluoromethyl)-1-((2-(trimethylsilyl)ethoxy)methyl)-1H-imidazole (117 mg, 0.438 mmol), butyl di-1-adamantylphosphine tretrafluoroborate salt (45 mg, 0.101 mmol), K$_2$CO$_3$ (116 mg, 0.842 mmol), Pd(OAc)$_2$ (11 mg, 0.051 mmol), and pivalic acid (10 mg, 0.101 mmol) were combined in toluene (0.5 mL). The mixture was purged with N$_2$ and heated to 100° C. overnight. Purification on silica gel (12 g column, 0-100% EtOAc/DCM) gave 4-(1-(5,8-difluoroquinolin-4-yl)-4-(2-(trifluoromethyl)-1-((2-(trimethylsilyl)ethoxy)methyl)-1H-imidazol-5-yl)-1H-benzo[d]imidazol-6-yl)morpholine, ES/MS m/z=631.2 (M+H)$^+$. Treatment with TFA in DCM afforded the title compound (Compound 390). 1H NMR (400 MHz, DMSO-d6) δ 9.17 (d, J=4.5 Hz, 1H), 8.55 (s, 1H), 8.34 (s, 1H), 7.90 (d, J=4.6 Hz, 1H), 7.72 (ddd, J=10.1, 8.8, 4.2 Hz, 1H), 7.58 (d, J=2.1 Hz, 1H), 7.42 (ddd, J=12.5, 8.8, 3.9 Hz, 1H), 6.68 (s, 1H), 3.65 (t, J=4.7 Hz, 4H), 3.13-2.90 (m, 4H). ES/MS m/z=501.1 (M+H)$^+$.

Step 7: 8-chloro-N-(5-morpholino-2-nitro-3-(1-trityl-1H-imidazol-4-yl)phenyl)quinolin-4-amine

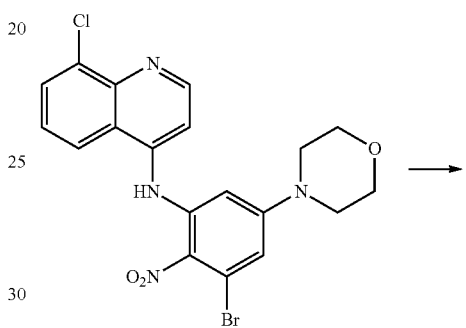

To a solution of N-(3-bromo-5-morpholino-2-nitrophenyl)-8-chloroquinolin-4-amine (250 mg, 0.54 mmol) in dioxane (3 mL) was added 4-(tri-n-butylstannyl)-1-tritylimidazole (355 mg, 0.59 mmol), copper iodide (10 mg, 0.05 mmol), and Pd(II)Cl$_2$dppf (35 mg, 0.05 mmol). The resulting mixture was degassed under Argon and heated to 80° C. After 18 hours the reaction was allowed to cool and was purified directly on silica (0-100% EtOAc/DCM) to give 8-chloro-N-(5-morpholino-2-nitro-3-(1-trityl-1H-imidazol-4-yl)phenyl)quinolin-4-amine. ES/MS m/z 693.2. (M+H)$^+$.

Step 8: 4-(1-(8-chloroquinolin-4-yl)-4-(1H-imidazol-4-yl)-1H-benzo[d]imidazol-6-yl)morpholine

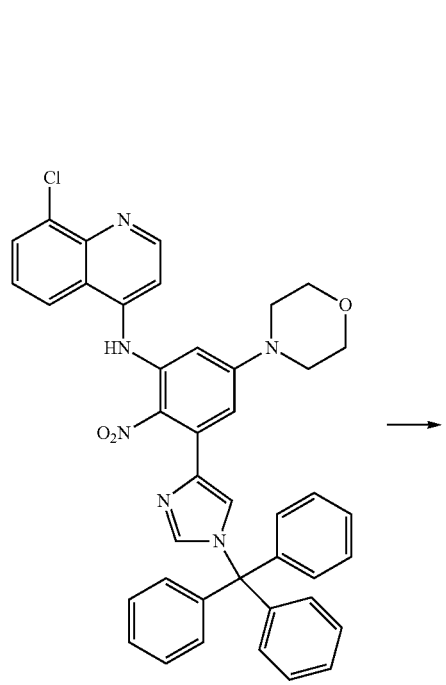

→

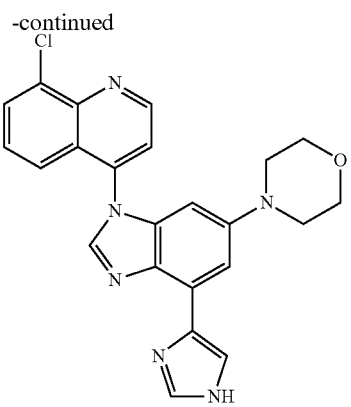

Formaldehyde (0.11 mL, 1.3 mmol) was added to a suspension of 8-chloro-N-(5-morpholino-2-nitro-3-(1-trityl-1H-imidazol-4-yl)phenyl)quinolin-4-amine (150 mg, 0.22 mmol) and sodium thiosulfite (113 mg, 0.65 mmol) in a mixture of EtOH (1 mL) and DMSO (1 mL). The vessel was sealed and heated to 80° C. for 18 hours. After cooling, the mixture was poured into EtOAc and washed with water, then aq. NaHCO$_3$. The organic phase was purified on silica (0-30% MeOH/DCM), then by prep LC, to give 4-(1-(8-chloroquinolin-4-yl)-4-(1H-imidazol-4-yl)-1H-benzo[d]imidazol-6-yl)morpholine (Compound 332). 1H NMR (400 MHz, DMSO-d6) δ 9.29 (s, 1H), 9.27 (d, J=4.5 Hz, 1H), 8.68 (m, 1H), 8.57 (m, 1H), 8.13 (d, J=7.5 Hz, 1H), 7.96 (d, J=4.6, 1H), 7.69-7.60 (m, 2H), 7.50 (d, J=8.5 Hz, 1H), 6.76 (d, J=2.0 Hz, 1H), 3.71 (t, J=4.8 Hz, 4H), 3.13-3.08 (m, 4H). ES/MS m/z 431.1 (M+H)$^+$.

The compounds listed in the table below were prepared in a manner similar to that described above using appropriate intermediates and chemistry.

| Compound | Name | MS | NMR |
|---|---|---|---|
| 331 | 4-[3-(8-chloroquinolin-4-yl)-2-ethyl-7-(1H-imidazol-4-yl)benzimidazol-5-yl]morpholine | 459.11 | 1H NMR (400 MHz, DMSO-d6) δ 9.34-9.27 (m, 2H), 8.57 (d, J = 1.5, 1H), 8.11 (d, J = 7.5 Hz, 1H), 7.97 (d, J = 4.6 Hz, 1H), 7.65-7.57 (m, 1H), 7.55 (d, J = 2.4 Hz, 1H), 7.18 (d, J = 8.4 Hz, 1H), 6.53-6.47 (m, 1H), 3.67 (t, J = 4.8 Hz, 4H), 3.10-2.96 (m, 4H), 2.75-2.52 (m, 2H), 1.21 (t, J = 7.5 Hz, 3H). |
| 332 | 4-[3-(8-chloroquinolin-4-yl)-7-(1H-imidazol-4-yl)benzimidazol-5-yl]morpholine | 431.1 | 1H NMR (400 MHz, DMSO-d6) δ 9.29 (s, 1H), 9.27 (d, J = 4.5 Hz, 1H), 8.68 (m, 1H), 8.57 (m, 1H), 8.13 (d, J = 7.5 Hz, 1H), 7.96 (d, J = 4.6, 1H), 7.69-7.60 (m, 2H), 7.50 (d, J = 8.5 Hz, 1H), 6.76 (d, J = 2.0 Hz, 1H), 3.71 (t, J = 4.8 Hz, 4H), 3.13-3.08 (m, 4H). |
| 333 | 4-[3-(5,8-dichloro-2-methylquinolin-4-yl)-7-(1H-imidazol-5-yl)-2-methylbenzimidazol-5-yl]morpholine | 493.17 | 1H NMR (400 MHz, DMSO-d6) δ 9.25 (s, 1H), 8.51 (s, 1H), 8.05 (d, J = 8.3 Hz, 1H), 7.84 (s, 1H), 7.66 (d, J = 8.3 Hz, 1H), 7.48 (d, J = 2.1 Hz, 1H), 6.57 (d, J = 1.8 Hz, 1H), 3.69 (t, J = 4.7 Hz, 4H), 3.12-3.00 (m, 4H), 2.83 (s, 3H), 2.31 (s, 3H). |
| 334 | 4-[3-(5,8-dichloro-2-methylquinolin-4-yl)-2-ethyl-7-(1H-imidazol-5-yl)benzimidazol-5-yl]morpholine | 507.2 | 1H NMR (400 MHz, DMSO-d6) δ 9.27 (d, J = 1.3 Hz, 1H), 8.54 (d, J = 1.3 Hz, 1H), 8.04 (d, J = 8.3 Hz, 1H), 7.84 (s, 1H), 7.65 (d, J = 8.3 Hz, 1H), 7.49 (d, J = 2.1 Hz, 1H), 6.57 (d, J = 2.0 Hz, 1H), 3.69 (t, J = 4.7 Hz, 4H), 3.12-2.99 (m, 4H), 2.82 (s, 3H), 2.64-2.51 (m, 2H), 1.26 (t, J = 7.4 Hz, 3H). |

-continued

| Compound | Name | MS | NMR |
|---|---|---|---|
| 335 | 4-[3-(5,8-difluoroquinolin-4-yl)-7-(1H-imidazol-5-yl)-2-methylbenzimidazol-5-yl]morpholine | 447.26 | 1H NMR (400 MHz, DMSO-d6) δ 9.29 (d, J = 4.5 Hz, 1H), 9.26 (d, J = 1.4 Hz, 1H), 8.51 (d, J = 1.3 Hz, 1H), 7.96 (d, J = 4.5 Hz, 1H), 7.78 (ddd, J = 10.2, 8.8, 4.2 Hz, 1H), 7.52-7.40 (m, 2H), 6.62 (d, J = 2.1 Hz, 1H), 3.69 (t, J = 4.8 Hz, 4H), 3.12-3.02 (m, 4H), 2.35 (s, 3H). |
| 336 | 4-[3-(5,8-difluoroquinolin-4-yl)-7-(1H-imidazol-5-yl)benzimidazol-5-yl]morpholine | 433.24 | 1H NMR (400 MHz, DMSO-d6) δ 9.28 (d, J = 1.4 Hz, 2H), 9.24 (d, J = 4.5 Hz, 1H), 8.61 (d, J = 2.6 Hz, 1H), 8.55 (d, J = 1.4 Hz, 1H), 7.96 (d, J = 4.6 Hz, 1H), 7.79 (ddd, J = 10.1, 8.7, 4.1 Hz, 1H), 7.61 (d, J = 2.1 Hz, 1H), 7.49 (ddt, J = 12.4, 8.8, 4.5 Hz, 1H), 6.84 (d, J = 2.1 Hz, 1H), 3.72 (t, J = 4.7 Hz, 4H), 3.19-3.05 (m, 4H). |
| 337 | 4-[3-(5,8-difluoroquinolin-4-yl)-2-ethyl-7-(1H-imidazol-5-yl)benzimidazol-5-yl]morpholine | 461.19 | 1H NMR (400 MHz, DMSO-d6) δ 9.31-9.25 (m, 2H), 8.56-8.51 (m, 1H), 7.97 (d, J = 4.6 Hz, 1H), 7.78 (td, J = 9.3, 8.9, 4.0 Hz, 1H), 7.51 (d, J = 2.0 Hz, 1H), 7.45 (ddd, J = 12.2, 8.7, 3.7 Hz, 1H), 6.61 (d, J = 1.9 Hz, 1H), 3.69 (t, J = 4.8 Hz, 4H), 3.10-3.02 (m, 4H), 2.72-2.52 (m, 2H), 1.23 (t, J = 7.5 Hz, 3H). |

Separation of atropisomers: The atropisomers of compound 200 were separated on OD-H SFC 5 uM 21×250 mm column in 30% EtOH/CO2 at 60 mL/min to give the atropisomers of 4-[3-(8-fluoroquinolin-4-yl)-2-methyl-7-(1,3-oxazol-2-yl)benzimidazol-5-yl]morpholine, Compound 340 and Compound 341. 1H NMR (400 MHz, DMSO-d6) δ 9.27 (d, J=4.5 Hz, 1H), 8.42 (d, J=0.8 Hz, 1H), 8.01 (d, J=4.5 Hz, 1H), 7.77 (ddd, J=10.9, 7.8, 1.2 Hz, 1H), 7.69-7.59 (m, 2H), 7.56 (d, J=0.8 Hz, 1H), 7.24 (d, J=8.4 Hz, 1H), 6.71 (d, J=2.3 Hz, 1H), 3.68 (t, J=4.7 Hz, 4H), 3.12-2.95 (m, 4H), 2.45 (s, 3H). ES/MS m/z 430.1 (M+H)+.

The compounds listed in the table below were prepared in a manner similar to that described above using appropriate intermediates and chemistry.

| Compound | Name | MS | NMR |
|---|---|---|---|
| 342 | 4-[7-(2-chloro-1H-imidazol-5-yl)-2-cyclopropyl-3-(5,8-difluoroquinolin-4-yl)benzimidazol-5-yl]morpholine | 507.2 | 1H NMR (400 MHz, DMSO-d6) δ 12.89 (s, 1H), 9.27 (d, J = 4.5 Hz, 1H), 8.09 (s, 1H), 7.97 (d, J = 4.5 Hz, 1H), 7.76 (td, J = 9.3, 4.1 Hz, 1H), 7.46 (ddd, J = 12.3, 8.7, 3.8 Hz, 1H), 7.39 (s, 1H), 6.40 (d, J = 2.2 Hz, 1H), 3.67 (t, J = 4.7 Hz, 4H), 3.04-2.96 (m, 4H), 1.59 (td, J = 8.3, 4.2 Hz, 1H), 1.22-0.99 (m, 2H), 0.94-0.74 (m, 2H). |
| 343 | 4-[7-(2-chloro-1H-imidazol-5-yl)-2-cyclopropyl-3-(5,8-difluoroquinolin-4-yl)benzimidazol-5-yl]morpholine | 507.2 | 1H NMR (400 MHz, DMSO-d6) δ 13.19-12.81 (m, 1H), 9.27 (d, J = 4.5 Hz, 1H), 8.13 (s, 1H), 7.97 (d, J = 4.5 Hz, 1H), 7.76 (ddd, J = 10.0, 8.7, 4.1 Hz, 1H), 7.46 (ddd, J = 12.3, 8.7, 3.8 Hz, 1H), 6.39 (d, J = 2.1 Hz, 1H), 3.67 (t, J = 4.7 Hz, 4H), 3.03-2.97 (m, 4H), 1.59 (td, J = 8.2, 4.2 Hz, 1H), 1.20-1.12 (m, 1H), 1.11-1.03 (m, 1H), 0.95-0.75 (m, 2H). |
| 344 | 4-[3-(5-chloro-8-fluoroquinolin-4-yl)-2-methyl-7-(4H-1,2,4-triazol-3-yl)benzimidazol-5-yl]morpholine | 464.1 | 1H NMR (400 MHz, DMSO-d6) δ 9.30 (d, J = 4.4 Hz, 1H), 8.00 (d, J = 4.4 Hz, 1H), 7.79 (d, J = 7.2 Hz, 2H), 7.63 (s, 1H), 6.68 (s, 1H), 3.65 (dd, J = 6.0, 3.6 Hz, 4H), 3.11-2.97 (m, 4H), 2.39 (s, 3H). |
| 345 | 4-[3-(5-chloro-8-fluoroquinolin-4-yl)-2-methyl-7-(4H-1,2,4-triazol-3-yl)benzimidazol-5-yl]morpholine | 464.1 | 1H NMR (400 MHz, DMSO-d6) δ 9.29 (d, J = 4.4 Hz, 1H), 7.99 (d, J = 4.5 Hz, 1H), 7.79 (d, J = 7.1 Hz, 2H), 7.61 (s, 1H), 6.67 (s, 1H), 3.68-3.49 (m, 4H), 3.13-2.95 (m, 4H), 2.38 (s, 3H). |

| Compound | Name | MS | NMR |
|---|---|---|---|
| 346 | 4-[7-(2-chloro-1H-imidazol-5-yl)-3-(5,8-difluoroquinolin-4-yl)-2-ethylbenzimidazol-5-yl]morpholine | 495.2 | 1H NMR (400 MHz, DMSO-d6) δ 12.91 (s, 1H), 9.26 (d, J = 4.5 Hz, 1H), 8.24 (d, J = 1.7 Hz, 1H), 7.93 (d, J = 4.5 Hz, 1H), 7.76 (ddd, J = 9.9, 8.8, 4.1 Hz, 1H), 7.50-7.38 (m, 2H), 6.35 (d, J = 2.3 Hz, 1H), 3.71-3.62 (m, 4H), 3.06-2.95 (m, 4H), 2.65-2.51 (m, 2H), 1.20 (t, J = 7.5 Hz, 3H). |
| 347 | 4-[7-(2-chloro-1H-imidazol-5-yl)-3-(5,8-difluoroquinolin-4-yl)-2-ethylbenzimidazol-5-yl]morpholine | 495.2 | 1H NMR (400 MHz, DMSO-d6) δ 12.91 (s, 1H), 9.26 (d, J = 4.5 Hz, 1H), 8.24 (s, 1H), 7.93 (d, J = 4.5 Hz, 1H), 7.76 (td, J = 9.3, 4.1 Hz, 1H), 7.48-7.38 (m, 2H), 6.39-6.32 (m, 1H), 3.68-3.63 (m, 4H), 3.01-2.96 (m, 4H), 2.61-2.51 (m, 2H), 1.20 (t, J = 7.5 Hz, 3H). |
| 348 | 4-[3-(3,8-dichloroquinolin-4-yl)-2-ethyl-7-(5-methyl-4H-1,2,4-triazol-3-yl)benzimidazol-5-yl]morpholine | 508.2 | 1H NMR (400 MHz, DMSO-d6) δ 9.37 (s, 1H), 8.11 (dd, J = 7.6, 1.2 Hz, 1H), 7.64 (dd, J = 8.5, 7.6 Hz, 1H), 7.52 (s, 1H), 7.15 (d, J = 8.4 Hz, 1H), 6.67 (s, 1H), 3.63 (t, J = 4.8 Hz, 4H), 3.00 (s, 4H), 2.97-2.74 (m, 2H), 2.37 (s, 3H), 1.30-1.16 (m, 3H). |
| 349 | 4-[3-(3,8-dichloroquinolin-4-yl)-2-ethyl-7-(5-methyl-4H-1,2,4-triazol-3-yl)benzimidazol-5-yl]morpholine | 508.1 | 1H NMR (400 MHz, DMSO-d6) δ 9.38 (s, 1H), 8.11 (dd, J = 7.6, 1.2 Hz, 1H), 7.64 (dd, J = 8.5, 7.6 Hz, 1H), 7.53 (d, J = 2.3 Hz, 1H), 7.18 (dd, J = 8.5, 1.2 Hz, 1H), 6.65 (s, 1H), 3.63 (s, 4H), 3.00 (s, 4H), 2.54 (dp, J = 7.6, 4.1 Hz, 2H), 2.40 (s, 3H), 1.18 (t, J = 7.5 Hz, 3H). |
| 350 | (S)-4-(1-(5,8-difluoroquinolin-4-yl)-2-methyl-4-(5-methyl-4H-1,2,4-triazol-3-yl)-1H-benzo[d]imidazol-6-yl)morpholine | 462.2 | 1H NMR (400 MHz, DMSO-d6) δ 9.28 (d, J = 4.5 Hz, 1H), 7.97 (d, J = 4.5 Hz, 1H), 7.81-7.74 (m, 1H), 7.52 (s, 1H), 7.47 (ddd, J = 12.3, 8.8, 3.8 Hz, 1H), 6.69 (s, 1H), 3.70-3.63 (m, 4H), 3.06-2.99 (m, 4H), 2.36 (s, 6H). |
| 351 | (R)-4-(1-(5,8-difluoroquinolin-4-yl)-2-methyl-4-(5-methyl-4H-1,2,4-triazol-3-yl)-1H-benzo[d]imidazol-6-yl)morpholine | 462.2 | 1H NMR (400 MHz, DMSO-d6) δ 9.32 (d, J = 4.5 Hz, 1H), 8.04 (d, J = 4.5 Hz, 1H), 7.84-7.75 (m, 1H), 7.62 (s, 1H), 7.49 (ddd, J = 12.2, 8.8, 3.7 Hz, 1H), 6.74 (s, 1H), 3.70-3.63 (m, 4H), 3.06 (t, J = 4.9 Hz, 4H), 2.48-2.42 (m, 6H). |
| 352 | 4-[3-(7,8-difluoroquinolin-4-yl)-2-methyl-7-(4H-1,2,4-triazol-3-yl)benzimidazol-5-yl]morpholine | 448.2 | 1H NMR (400 MHz, DMSO-d6) δ 9.29 (d, J = 4.5 Hz, 1H), 7.99 (d, J = 4.5 Hz, 1H), 7.87-7.72 (m, 1H), 7.67 (s, 1H), 7.32 (s, 1H), 6.62 (d, J = 2.2 Hz, 1H), 3.64 (t, J = 4.7 Hz, 5H), 3.01 (d, J = 4.1 Hz, 2H), 2.46 (s, 3H). |
| 353 | 4-[3-(7,8-difluoroquinolin-4-yl)-2-methyl-7-(4H-1,2,4-triazol-3-yl)benzimidazol-5-yl]morpholine | 448.2 | 1H NMR (400 MHz, DMSO-d6) δ 9.29 (d, J = 4.5 Hz, 1H), 7.98 (d, J = 4.5 Hz, 1H), 7.77 (td, J = 9.8, 7.2 Hz, 1H), 7.66 (s, 1H), 7.30 (s, 1H), 6.62 (d, J = 2.2 Hz, 1H), 3.64 (t, J = 4.7 Hz, 4H), 3.09-2.95 (m, 4H), 2.44 (s, 3H). |
| 354 | 4-[3-(8-fluoroquinolin-4-yl)-2-propyl-7-(4H-1,2,4-triazol-3-yl)benzimidazol-5-yl]morpholine | 458.2 | 1H NMR (400 MHz, DMSO-d6) δ 9.24 (d, J = 4.5 Hz, 1H), 8.00 (d, J = 4.5 Hz, 1H), 7.63 (dd, J = 13.3, 5.0 Hz, 2H), 6.58 (s, 1H), 3.64 (t, J = 4.7 Hz, 4H), 3.00 (d, J = 3.8 Hz, 4H), 2.66 (d, J = 6.6 Hz, 2H), 1.63 (s, 2H), 0.78 (t, J = 7.4 Hz, 3H). |
| 355 | 4-[3-(8-fluoroquinolin-4-yl)-2-propyl-7-(4H-1,2,4-triazol-3-yl)benzimidazol-5-yl]morpholine | 458.2 | 1H NMR (400 MHz, DMSO-d6) δ 9.26 (d, J = 4.5 Hz, 1H), 8.48 (s, 1H), 8.03 (d, J = 4.5 Hz, 1H), 7.85-7.45 (m, 3H), 7.19 (s, 1H), 6.60 (d, J = 2.2 Hz, 1H), 3.64 (t, J = 4.8 Hz, 4H), 3.02 (q, J = 3.9 Hz, 4H), 2.84-2.52 (m, 2H), 1.72-1.30 (m, 2H), 0.77 (t, J = 7.4 Hz, 3H). |

| Compound | Name | MS | NMR |
|---|---|---|---|
| 356 | 4-[3-(5,8-difluoroquinolin-4-yl)-7-(1,3-oxazol-2-yl)-2-propylbenzimidazol-5-yl]morpholine | 476.2 | 1H NMR (400 MHz, DMSO-d6) δ 9.27 (d, J = 4.5 Hz, 1H), 8.35 (d, J = 0.8 Hz, 1H), 7.97 (d, J = 4.5 Hz, 1H), 7.77 (ddd, J = 10.0, 8.8, 4.2 Hz, 1H), 7.52 (d, J = 2.3 Hz, 1H), 7.51-7.40 (m, 2H), 6.69 (d, J = 2.3 Hz, 1H), 3.69-3.62 (m, 4H), 3.06-2.98 (m, 4H), 2.68-2.51 (m, 2H), 1.67-1.53 (m, 2H), 0.81 (t, J = 7.4 Hz, 3H). |
| 357 | 4-[3-(5,8-difluoroquinolin-4-yl)-7(1,3-oxazol-2-yl)-2-propylbenzimidazol-5-yl]morpholine | 476.2 | 1H NMR (400 MHz, DMSO-d6) δ 9.27 (d, J = 4.5 Hz, 1H), 8.35 (d, J = 0.8 Hz, 1H), 7.97 (d, J = 4.5 Hz, 1H), 7.77 (ddd, J = 10.0, 8.8, 4.2 Hz, 1H), 7.52 (d, J = 2.3 Hz, 1H), 7.49-7.41 (m, 2H), 6.69 (d, J = 2.3 Hz, 1H), 3.69-3.62 (m, 4H), 3.06-2.98 (m, 4H), 2.69-2.51 (m, 2H), 1.65-1.54 (m, 2H), 0.81 (t, J = 7.4 Hz, 3H). |
| 358 | 4-[3-(8-chloroquinolin-4-yl)-7-(5-chloro-4H-1,2,4-triazol-3-yl)-2-methylbenzimidazol-5-yl]morpholine | 480.1 | 1H NMR (400 MHz, DMSO-d6) δ 9.29 (d, J = 4.5 Hz, 1H), 8.09 (dd, J = 7.5, 1.2 Hz, 1H), 7.96 (d, J = 4.5 Hz, 1H), 7.59 (dd, J = 8.5, 7.5 Hz, 1H), 7.50 (d, J = 2.2 Hz, 1H), 7.22 (dd, J = 8.5, 1.2 Hz, 1H), 6.63 (d, J = 2.3 Hz, 1H), 3.63 (t, J = 4.7 Hz, 4H), 3.07-2.93 (m, 4H), 2.36 (s, 3H). |
| 359 | 4-[3-(8-chloroquinolin-4-yl)-7-(5-chloro-4H-1,2,4-triazol-3-yl)-2-methylbenzimidazol-5-yl]morpholine | 480.1 | 1H NMR (400 MHz, DMSO-d6) δ 9.29 (d, J = 4.5 Hz, 1H), 8.09 (dd, J = 7.5, 1.2 Hz, 1H), 7.96 (d, J = 4.5 Hz, 1H), 7.59 (dd, J = 8.5, 7.6 Hz, 1H), 7.50 (d, J = 2.2 Hz, 1H), 7.22 (dd, J = 8.5, 1.2 Hz, 1H), 6.63 (d, J = 2.2 Hz, 1H), 3.63 (t, J = 4.7 Hz, 4H), 3.00 (q, J = 4.0 Hz, 4H), 2.36 (s, 3H). |
| 360 | 4-[3-(8-chloroquinolin-4-yl)-2-methyl-7-(4H-1,2,4-triazol-3-yl)benzimidazol-5-yl]morpholine | 446.2 | 1H NMR (400 MHz, DMSO-d6) δ 9.37 (dd, J = 4.5, 0.6 Hz, 1H), 8.77 (s, 1H), 8.15 (dd, J = 7.4, 1.3 Hz, 1H), 8.09 (d, J = 4.5 Hz, 1H), 7.83 (d, J = 2.3 Hz, 1H), 7.64 (dd, J = 8.4, 7.5 Hz, 1H), 7.57 (d, J = 8.4 Hz, 1H), 6.73 (d, J = 2.3 Hz, 1H), 3.66 (t, J = 4.8 Hz, 4H), 3.08 (q, J = 3.9 Hz, 4H), 2.59 (s, 3H). |
| 361 | 4-[3-(8-chloroquinolin-4-yl)-2-methyl-7-(4H-1,2,4-triazol-3-yl)benzimidazol-5-yl]morpholine | 446.2 | 1H NMR (400 MHz, DMSO-d6) δ 9.37 (dd, J = 4.5, 0.6 Hz, 1H), 8.77 (s, 1H), 8.15 (dd, J = 7.4, 1.3 Hz, 1H), 8.09 (d, J = 4.5 Hz, 1H), 7.83 (d, J = 2.3 Hz, 1H), 7.64 (dd, J = 8.4, 7.5 Hz, 1H), 7.57 (d, J = 8.4 Hz, 1H), 6.73 (d, J = 2.3 Hz, 1H), 3.66 (t, J = 4.8 Hz, 4H), 3.08 (q, J = 3.9 Hz, 4H), 2.59 (s, 3H). |
| 362 | 4-[2-methyl-3-(5-methylquinolin-4-yl)-7-(4H-1,2,4-triazol-3-yl)benzimidazol-5-yl]morpholine | 426.2 | 1H NMR (400 MHz, DMSO-d6) δ 9.21 (d, J = 4.4 Hz, 1H), 8.73 (s, 1H), 8.21-8.15 (m, 1H), 7.90-7.80 (m, 3H), 7.57-7.50 (m, 1H), 6.69 (d, J = 2.2 Hz, 1H), 3.67 (t, J = 4.8 Hz, 4H), 3.15-3.07 (m, 4H), 2.55 (s, 3H), 1.82 (s, 3H). |
| 363 | 4-[2-methyl-3-(5-methylquinolin-4-yl)-7-(4H-1,2,4-triazol-3-yl)benzimidazol-5-yl]morpholine | 426.2 | 1H NMR (400 MHz, DMSO-d6) δ 9.21 (d, J = 4.4 Hz, 1H), 8.73 (s, 1H), 8.21-8.15 (m, 1H), 7.90-7.80 (m, 3H), 7.57-7.50 (m, 1H), 6.69 (d, J = 2.2 Hz, 1H), 3.67 (t, J = 4.8 Hz, 4H), 3.15-3.07 (m, 4H), 2.55 (s, 3H), 1.82 (s, 3H). |

| Compound | Name | MS | NMR |
|---|---|---|---|
| 364 | 4-(2-ethyl-6-morpholino-4-(4H-1,2,4-triazol-3-yl)-1H-benzo[d]imidazol-1-yl)-3-methylquinoline-8-carbonitrile | 465.2 | 1H NMR (400 MHz, DMSO-d6) δ 9.34 (d, J = 0.5 Hz, 1H), 8.54 (s, 1H), 8.43 (dd, J = 7.2, 1.3 Hz, 1H), 7.76-7.67 (m, 2H), 7.60 (d, J = 8.4 Hz, 1H), 6.64 (d, J = 2.3 Hz, 1H), 3.64 (t, J = 4.8 Hz, 4H), 3.05 (dd, J = 6.3, 3.8 Hz, 4H), 2.67 (d, J = 8.1 Hz, 2H), 2.21 (s, 3H), 1.11 (t, J = 7.5 Hz, 3H). |
| 365 | 4-(2-ethyl-6-morpholino-4-(4H-1,2,4-triazol-3-yl)-1H-benzo[d]imidazol-1-yl)-3-methylquinoline-8-carbonitrile | 465.2 | 1H NMR (400 MHz, DMSO-d6) δ 9.34 (d, J = 0.5 Hz, 1H), 8.54 (s, 1H), 8.43 (dd, J = 7.2, 1.3 Hz, 1H), 7.76-7.67 (m, 2H), 7.60 (d, J = 8.4 Hz, 1H), 6.64 (d, J = 2.3 Hz, 1H), 3.64 (t, J = 4.8 Hz, 4H), 3.05 (dd, J = 6.3, 3.8 Hz, 4H), 2.67 (d, J = 8.1 Hz, 2H), 2.21 (s, 3H), 1.11 (t, J = 7.5 Hz, 3H). |
| 366 | 4-(1-(3,8-dichloroquinolin-4-yl)-2-methyl-4-(5-methyl-4H-1,2,4-triazol-3-yl)-1H-benzo[d]imidazol-6-yl)morpholine | 494.1 | 1H NMR (400 MHz, DMSO-d6) δ 9.42 (s, 1H), 8.14 (dd, J = 7.6, 1.2 Hz, 1H), 7.71-7.62 (m, 2H), 7.38 (d, J = 8.5 Hz, 1H), 6.76 (d, J = 2.3 Hz, 1H), 3.72-3.58 (m, 4H), 3.04 (dd, J = 6.1, 3.8 Hz, 4H), 2.48 (s, 3H), 2.44 (s, 3H). |
| 367 | 4-(1-(3,8-dichloroquinolin-4-yl)-2-methyl-4-(5-methyl-4H-1,2,4-triazol-3-yl)-1H-benzo[d]imidazol-6-yl)morpholine | 494.1 | 1H NMR (400 MHz, DMSO-d6) δ 9.42 (s, 1H), 8.14 (dd, J = 7.6, 1.2 Hz, 1H), 7.71-7.62 (m, 2H), 7.38 (d, J = 8.5 Hz, 1H), 6.76 (d, J = 2.3 Hz, 1H), 3.72-3.58 (m, 4H), 3.04 (dd, J = 6.1, 3.8 Hz, 4H), 2.48 (s, 3H), 2.44 (s, 3H). |
| 368 | 4-(1-(5,8-difluoroquinolin-4-yl)-2-propyl-4-(1H-pyrazol-5-yl)-1H-benzo[d]imidazol-6-yl)morpholine | 475.2 | 1H NMR (400 MHz, DMSO-d6) δ 9.26 (d, J = 4.5 Hz, 1H), 7.94 (d, J = 4.5 Hz, 1H), 7.76 (ddd, J = 10.0, 8.8, 4.2 Hz, 1H), 7.71 (br s, 1H), 7.45 (ddd, J = 12.5, 8.8, 3.8 Hz, 1H), 7.39 (br s, 2H), 6.44 (d, J = 2.1 Hz, 1H), 3.67 (t, J = 4.7 Hz, 4H), 3.05-2.98 (m, 4H), 2.60-2.51 (m, 2H), 1.69 (h, J = 7.4 Hz, 2H), 0.86 (t, J = 7.4 Hz, 3H). |
| 369 | 4-(1-(5,8-difluoroquinolin-4-yl)-2-propyl-4-(1H-pyrazol-5-yl)-1H-benzo[d]imidazol-6-yl)morpholine | 475.2 | 1H NMR (400 MHz, DMSO-d6) δ 13.27-12.80 (m, 1H), 9.26 (d, J = 4.5 Hz, 1H), 7.94 (d, J = 4.5 Hz, 1H), 7.76 (ddd, J = 10.1, 8.9, 4.2 Hz, 1H), 7.85-7.59 (m, 1H), 7.49-7.41 (m, 1H), 7.58-7.24 (m, 1H), 6.44 (s, 1H), 3.67 (t, J = 4.7 Hz, 4H), 3.04-2.97 (m, 4H), 2.56 (t, J = 7.4 Hz, 2H), 1.69 (q, J = 7.4 Hz, 2H), 0.86 (t, J = 7.4 Hz, 3H) |
| 370 | 4-(1-(5,8-difluoroquinolin-4-yl)-2-ethyl-4-(1H-imidazol-2-yl)-1H-benzo[d]imidazol-6-yl)morpholine | 461.2 | 1H NMR (400 MHz, DMSO-d6) δ 12.21 (s, 1H), 9.28 (d, J = 4.5 Hz, 1H), 7.99 (d, J = 4.5 Hz, 1H), 7.77 (ddd, J = 10.0, 8.8, 4.2 Hz, 1H), 7.60 (d, J = 2.3 Hz, 1H), 7.46 (ddd, J = 12.4, 8.8, 3.8 Hz, 1H), 7.37 (dd, J = 2.1, 1.2 Hz, 1H), 7.09 (t, J = 1.4 Hz, 1H), 6.53 (d, J = 2.3 Hz, 1H), 3.70-3.63 (m, 4H), 3.05-2.98 (m, 4H), 2.71-2.53 (m, 2H), 1.26 (t, J = 7.5 Hz, 3H). |
| 371 | 4-(1-(5,8-difluoroquinolin-4-yl)-2-ethyl-4-(1H-imidazol-2-yl)-1H-benzo[d]imidazol-6-yl)morpholine | 461.2 | 1H NMR (400 MHz, DMSO-d6) δ 12.28 (s, 1H), 9.28 (d, J = 4.5 Hz, 1H), 7.99 (d, J = 4.5 Hz, 1H), 7.77 (ddd, J = 10.0, 8.8, 4.2 Hz, 1H), 7.61 (d, J = 2.3 Hz, 1H), 7.46 (ddd, J = 12.4, 8.8, 3.8 Hz, 1H), 7.26 (br s, 2H), 6.53 (d, J = 2.3 Hz, 1H), 3.70-3.63 (m, 4H), 3.06-2.98 (m, 4H), 2.68-2.57 (m, 2H), 1.25 (t, J = 7.5 Hz, 3H). |
| 372 | 4-(4-(2-chloro-1H-imidazol-5-yl)-1-(5,8-difluoroquinolin-4-yl)-2-methyl-1H- | 481.18 | 1H NMR (400 MHz, DMSO-d6) δ 9.29 (d, J = 4.5 Hz, 1H), 8.15 (s, 1H), 7.97 (d, J = 4.5 Hz, 1H), 7.78 (ddd, J = 10.0, 8.9, 4.2 Hz, 1H), |

-continued

| Compound | Name | MS | NMR |
|---|---|---|---|
| | benzo[d]imidazol-6-yl)morpholine | | 7.53-7.44 (m, 1H), 7.44 (s, 1H), 6.45 (s, 1H), 3.67 (t, J = 4.7 Hz, 4H), 3.07-2.99 (m, 4H), 2.38 (s, 3H). |
| 373 | 4-(4-(2-chloro-1H-imidazol-5-yl)-1-(5,8-difluoroquinolin-4-yl)-2-methyl-1H-benzo[d]imidazol-6-yl)morpholine | 481.2 | 1H NMR (400 MHz, DMSO-d6) δ 9.29 (d, J = 4.5 Hz, 1H), 8.15 (s, 1H), 7.97 (d, J = 4.5 Hz, 1H), 7.78 (ddd, J = 10.0, 8.8, 4.2 Hz, 1H), 7.53-7.44 (m, 1H), 7.44 (s, 1H), 6.45 (s, 1H), 3.67 (t, J = 4.7 Hz, 4H), 3.13-2.91 (m, 4H), 2.38 (s, 3H). |
| 374 | 3-methyl-4-(2-methyl-6-morpholino-4-(4H-1,2,4-triazol-3-yl)-1H-benzo[d]imidazol-1-yl)quinoline-8-carbonitrile | 451.2 | 1H NMR (400 MHz, DMSO-d6) δ 9.35 (d, J = 0.5 Hz, 1H), 8.61 (s, 1H), 8.44 (dd, J = 7.1, 1.4 Hz, 1H), 7.87-7.60 (m, 3H), 6.68 (d, J = 2.3 Hz, 1H), 3.64 (t, J = 4.7 Hz, 4H), 3.06 (dd, J = 6.2, 3.7 Hz, 4H), 2.44 (s, 3H), 2.23 (s, 3H). |
| 375 | 3-methyl-4-(2-methyl-6-morpholino-4-(4H-1,2,4-triazol-3-yl)-1H-benzo[d]imidazol-1-yl)quinoline-8-carbonitrile | 451.2 | 1H NMR (400 MHz, DMSO-d6) δ 9.35 (d, J = 0.5 Hz, 1H), 8.61 (s, 1H), 8.44 (dd, J = 7.1, 1.4 Hz, 1H), 7.87-7.60 (m, 3H), 6.68 (d, J = 2.3 Hz, 1H), 3.64 (t, J = 4.7 Hz, 4H), 3.06 (dd, J = 6.2, 3.7 Hz, 4H), 2.44 (s, 3H), 2.23 (s, 3H). |

5-(1-(5,8-Difluoroquinolin-4-yl)-6-morpholino-1H-benzo[d]imidazol-4-yl)-1H-imidazole-2-carbonitrile

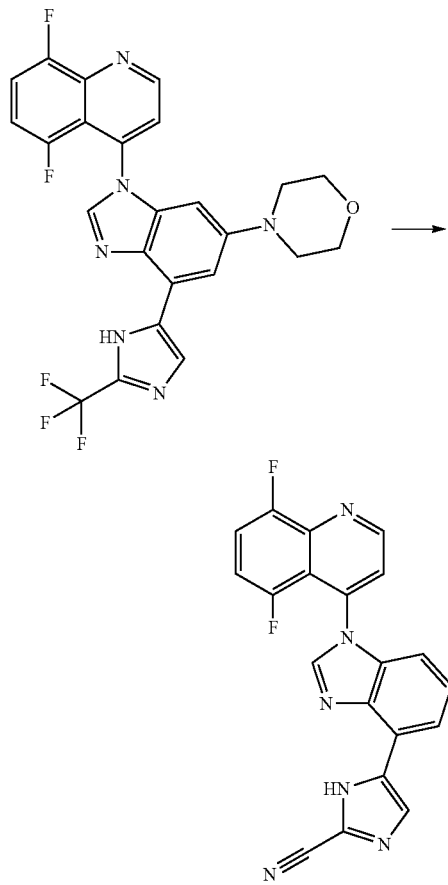

4-(1-(5,8-difluoroquinolin-4-yl)-4-(2-(trifluoromethyl)-1H-imidazol-5-yl)-1H-benzo[d]imidazol-6-yl)morpholine (26 mg, 0.042 mmol) was combined with NH₄OH (5% aqueous solution) and stirred at 50° C. for 12 days. The reaction was poured into water and extracted 3 times with DCM. The combined extracts were purified by HPLC eluting with 5-95% water/acetonitrile (0.1% v/v trifluoroacetic acid) to give the title compound (Compound 394). 1H NMR (400 MHz, DMSO-d6) δ 9.23 (d, J=4.5 Hz, 1H), 8.60 (s, 1H), 8.46 (s, 1H), 7.96 (d, J=4.6 Hz, 1H), 7.78 (ddd, J=10.0, 8.7, 4.1 Hz, 1H), 7.65-7.59 (m, 1H), 7.48 (ddd, J=12.4, 8.8, 3.9 Hz, 1H), 6.76 (d, J=2.2 Hz, 1H), 3.71 (t, J=4.7 Hz, 4H), 3.17-3.04 (m, 4H). ES/MS m/z=458.2 (M+H)⁺.

tert-Butyl 4-(4-chloroquinolin-2-yl)piperazine-1-carboxylate

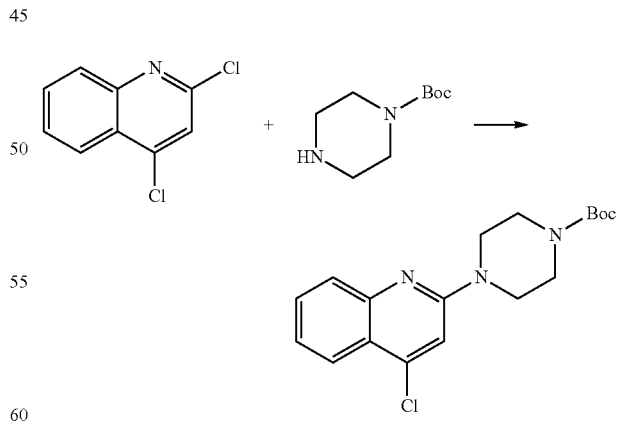

A suspension of 2,4-dichloroquinoline (6.4 g, 32.2 mmol), tert-butyl piperazine-1-carboxylate (5.0 g, 26.8 mmol) and diethylisopropylamine (6.5 mL, 38.0 mmol) was stirred in a sealed tube at 100° C. for 2 days. Upon cooling, the reaction mixture was concentrated in vacuuo to afford material which was purified by column chromatography on SiO₂ eluting with EtOAc in hexanes (0-15%) to afford the title compound. ES/MS m/z=348.1 (M+H)+.

4-Chloro-2-(1-trityl-1H-pyrazol-3-yl)quinoline

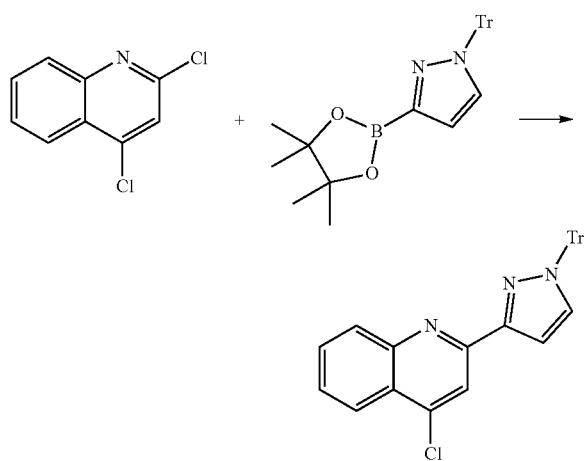

A sealed tube was charged with 2,4-dichloroquinoline (1.0 g, 5.05 mmol), 3-(4,4,5,5-tetramethyl-1,3,2-dioxaborolan-2-yl)-1-trityl-1H-pyrazole (2.2 g, 5.05 mmol), K$_3$PO$_4$ (3.2 g, 15.1 mmol) and Pd(PPh$_3$)$_4$(0.58 g, 0.50 mmol) followed by dioxane (50 mL) and water (12 mL). The reaction mixture was stirred at 90° C. for 3 h. Upon cooling, the reaction mixture was absorbed on SiO$_2$ followed by purification on column chromatography on SiO$_2$ eluting with EtOAc in hexanes (0-100%) to afford the title compound. ES/MS m/z=472.2 (M+H)+.

The compound listed below was prepared in a similar manner using appropriate intermediates:
4-chloro-2-(1-trityl-1H-pyrazol-4-yl)quinoline 2-(Trifluoromethyl)-1-((2-(trimethylsilyl)ethoxy methyl)-1H-imidazole

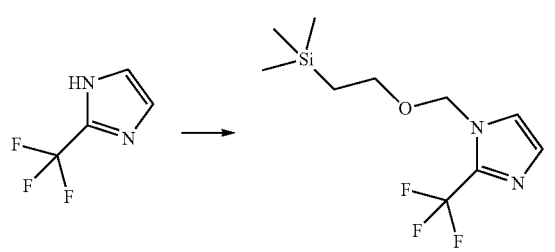 [SMILES: FC(F)(F)c1ncc[nH]1 ; C[Si](C)(C)CCOCn1ccnc1C(F)(F)F]

Sodium hydride (60% in mineral oil, 764 mg, 19.1 mmol) was slowly added to a solution of 2-(trifluoromethyl)imidazole (650 mg, 4.78 mmol) in THF (25 mL) at 0° C. under N2. The mixture was stirred at 0° C. for 2 hours, then 2-(trimethylsilyl)ethoxymethyl chloride (1.0 mL, 5.73 mmol) was added. The reaction was allowed to gradually attain ambient temperature and stir overnight. The reaction was quenched slowly with water, then poured into EtOAc. The organic phase was washed with water, brine, then purified on silica gel (40 g column, 0-100% EtOAc/hexanes) to give the title compound. ES/MS m/z=267.1 (M+H)+.

Biological Examples

The compounds of formula (I) were characterized for their enzymatic activity against the PI3K isoforms. The activities were measured using a time-resolved fluorescence resonance energy transfer (TR-FRET) assay. TR-FRET monitored the formation of 3,4,5-inositol triphosphate molecule that competed with fluorescently labeled PIP3 for binding to the GRP-1 pleckstrin homology domain protein. An increase in phosphatidylinositide 3-phosphate product resulted in a decrease in TR-FRET signal as the labeled fluorophore was displaced from the GRP-1 protein binding site.

Class I PI3K isoforms were expressed and purified as heterodimeric recombinant proteins. All assay reagents and buffers for the TR-FRET assay were purchased from Millipore. PI3K isoforms were assayed under initial rate conditions in the presence of 25 mM Hepes (pH 7.4), and 2× Km ATP (75-500 μM), 2 μM PIP2, 5% glycerol, 5 mM MgCl$_2$, 50 mM NaCl, 0.05% (v/v) Chaps, 1 mM dithiothreitol, and 1% (v/v) DMSO at the following concentrations for each isoform: PI3Kα, PI3Kβ, and PI3Kδ between 25 and 50 μM, and PI3Kγ at 2 nM. The compounds were added to the assay solution and incubated for 30 minutes at 25° C. The reactions were terminated with a final concentration of 10 mM EDTA, 10 nM labeled-PIP3, and 35 nM Europium labeled GRP-1 detector protein before reading TR-FRET on an Envision plate reader (Ex: 340 nm; Em: 615/665 nm; 100 μs delay and 500 μs read window).

The results were normalized based on positive (1 μM wortmanin) and negative (DMSO) controls, and the IC$_{50}$ values for PI3K α, β, δ, and γ were calculated from the fit of the dose-response curves to a four-parameter equation. These assays generally produced results within 3-fold of the reported mean. As shown in Table 1, the compounds provided herein are inhibitors of PI3Kβ.

The compounds of formula (I) were also characterized for their metabolic stability in human hepatocytes by incubating the test articles (TA) in cryopreserved human hepatocytes and monitoring parent drug disappearance via LC/MC. The TA was incubated with 1 million hepatocytes/mL at 2 μM substrate in duplicate. The incubation was carried out at 37° C. with 5% CO$_2$ and saturating humidity. Samples were taken at 0, 1, 2, and 4 hours to monitor the disappearance of TA and a half-life (t$_{1/2}$) was determined.

TABLE 1

| example | IC$_{50}$-PIP-β (nM) |
|---|---|
| 1 | 4 |
| 2 | 24 |
| 3 | 24 |
| 4 | 28 |
| 5 | 29 |
| 6 | 31 |
| 7 | 31 |
| 8 | 32 |
| 9 | 33 |
| 10 | 41 |
| 11 | 42 |
| 12 | 43 |
| 13 | 45 |
| 14 | 49 |
| 15 | 49 |
| 16 | 53 |
| 17 | 60 |
| 18 | 63 |
| 19 | 110 |
| 20 | 120 |
| 21 | 130 |
| 22 | 280 |
| 23 | 390 |

TABLE 1-continued

| example | IC$_{50}$-PIP-β (nM) |
|---|---|
| 24 | 1500 |
| 25 | 2200 |
| 26 | 22 |
| 27 | 56 |
| 28 | 3 |
| 29 | 7 |
| 30 | 8 |
| 31 | 9 |
| 32 | 9 |
| 33 | 10 |
| 34 | 10 |
| 35 | 11 |
| 36 | 11 |
| 37 | 11 |
| 38 | 11 |
| 39 | 11 |
| 40 | 22 |
| 41 | 21 |
| 42 | 20 |
| 43 | 20 |
| 44 | 19 |
| 45 | 19 |
| 46 | 19 |
| 47 | 18 |
| 48 | 18 |
| 49 | 18 |
| 50 | 16 |
| 51 | 15 |
| 52 | 15 |
| 53 | 15 |
| 54 | 14 |
| 55 | 27 |
| 56 | 72 |
| 57 | 55 |
| 58 | 62 |
| 59 | 130 |
| 60 | 30 |
| 61 | 27 |
| 62 | 23 |
| 63 | 28 |
| 64 | 21 |
| 65 | 24 |
| 66 | 16 |
| 67 | 99 |
| 68 | 8 |
| 69 | 17 |
| 70 | 36 |
| 71 | 23 |
| 72 | 25 |
| 73 | 78 |
| 74 | 62 |
| 75 | 29 |
| 76 | 29 |
| 77 | 97 |
| 78 | 27 |
| 79 | 110 |
| 80 | 61 |
| 81 | 11 |
| 82 | 9 |
| 83 | 19 |
| 84 | 17 |
| 85 | 280 |
| 86 | 16 |
| 87 | 14 |
| 88 | 4 |
| 89 | 12 |
| 90 | 11 |
| 91 | 19 |
| 92 | 46 |
| 93 | 290 |
| 94 | 26 |
| 95 | 6 |
| 96 | 24 |
| 97 | 12 |
| 98 | 13 |
| 99 | 33 |
| 100 | 43 |
| 101 | 7 |
| 102 | 21 |
| 103 | 9 |
| 104 | 84 |
| 105 | 10 |
| 106 | 17 |
| 107 | 29 |
| 108 | 26 |
| 109 | 13 |
| 110 | 19 |
| 111 | 3 |
| 112 | 17 |
| 113 | 17 |
| 114 | 12 |
| 115 | 14 |
| 116 | 21 |
| 117 | 15 |
| 118 | 52 |
| 119 | 24 |
| 120 | 27 |
| 121 | 44 |
| 122 | 13 |
| 123 | 110 |
| 124 | 9 |
| 125 | 16 |
| 126 | 21 |
| 127 | 23 |
| 128 | 51 |
| 129 | 23 |
| 130 | 87 |
| 131 | 46 |
| 132 | 380 |
| 133 | 21 |
| 134 | 16 |
| 135 | 43 |
| 136 | 48 |
| 137 | 17 |
| 138 | 140 |
| 139 | 14 |
| 140 | 13 |
| 141 | 10 |
| 142 | 15 |
| 143 | 84 |
| 144 | 65 |
| 145 | 56 |
| 146 | 101 |
| 149 | 100 |
| 150 | 27 |
| 151 | 44 |
| 152 | 59 |
| 153 | 120 |
| 154 | 2200 |
| 155 | 20 |
| 156 | 20 |
| 157 | 47 |
| 160 | 470 |
| 161 | 23 |
| 162 | 77 |
| 163 | 630 |
| 164 | 130 |
| 165 | 720 |
| 166 | 480 |
| 167 | 12 |
| 168 | 9 |
| 169 | 16 |
| 170 | 7 |
| 171 | 100 |
| 172 | 100 |
| 173 | 140 |
| 174 | 13 |
| 175 | 10 |
| 176 | 510 |
| 177 | 230 |
| 178 | 12 |
| 179 | 44 |
| 180 | 42 |
| 181 | 210 |
| 182 | 34 |
| 183 | 170 |

TABLE 1-continued

| example | IC$_{50}$-PIP-β (nM) |
|---|---|
| 198 | 120 |
| 199 | 610 |
| 200 | 9 |
| 201 | 19 |
| 202 | >10000 |
| 203 | 120 |
| 204 | 8 |
| 205 | 12 |
| 206 | 40 |
| 207 | 13 |
| 208 | 14 |
| 209 | 15 |
| 210 | 27 |
| 211 | 22 |
| 212 | 34 |
| 213 | 16 |
| 214 | 56 |
| 215 | 630 |
| 216 | 380 |
| 217 | 9 |
| 218 | 11 |
| 219 | 8 |
| 220 | 7 |
| 221 | 11 |
| 222 | 12 |
| 223 | 9 |
| 224 | 3 |
| 225 | 18 |
| 226 | 5 |
| 227 | 10 |
| 228 | 10 |
| 229 | 5 |
| 230 | 7 |
| 231 | 16 |
| 232 | 56 |
| 233 | 8 |
| 234 | 100 |
| 235 | 17 |
| 236 | 5 |
| 237 | 50 |
| 238 | 4 |
| 239 | 12 |
| 240 | 2 |
| 241 | 27 |
| 242 | 6 |
| 243 | 26 |
| 244 | 9 |
| 245 | 21 |
| 246 | 1100 |
| 247 | 12 |
| 260 | 22 |
| 261 | 24 |
| 262 | 27 |
| 263 | 13 |
| 264 | 770 |
| 265 | 460 |
| 266 | 11 |
| 267 | 2100 |
| 268 | 317 |
| 269 | 7000 |
| 270 | 36 |
| 271 | 46 |
| 272 | 65 |
| 273 | 2600 |
| 274 | 27 |
| 275 | 88 |
| 276 | 420 |
| 277 | 620 |
| 278 | 4 |
| 279 | 10 |
| 280 | 13 |
| 281 | 15 |
| 282 | 25 |
| 283 | 71 |
| 284 | 13 |
| 285 | 4 |
| 286 | 14 |
| 287 | 56 |
| 288 | 5 |
| 289 | 24 |
| 290 | 68 |
| 291 | 27 |
| 292 | 42 |
| 293 | 38 |
| 294 | 6 |
| 295 | 12 |
| 296 | 17 |
| 297 | 3800 |
| 298 | 10 |
| 299 | 17 |
| 300 | 14 |
| 301 | 20 |
| 302 | 24 |
| 303 | 21 |
| 304 | 81 |
| 305 | 13 |
| 306 | 370 |
| 307 | 8 |
| 308 | 6 |
| 309 | 50 |
| 310 | 36 |
| 311 | 47 |
| 312 | 967 |
| 313 | 9800 |
| 314 | 7800 |
| 315 | 490 |
| 316 | 2500 |
| 317 | 690 |
| 318 | 5200 |
| 319 | 8600 |
| 320 | >10000 |
| 321 | 4400 |
| 322 | >10000 |
| 323 | 417 |
| 329 | 7 |
| 330 | 5 |
| 331 | 7 |
| 332 | 2 |
| 333 | 9 |
| 334 | 24 |
| 335 | 15 |
| 336 | 5 |
| 337 | 20 |
| 340 | 1900 |
| 341 | 6 |
| 342 | >10000 |
| 343 | 5 |
| 344 | 5 |
| 345 | 4462 |
| 346 | 10000 |
| 347 | 7 |
| 348 | 13 |
| 349 | 439 |
| 350 | 10 |
| 351 | 460 |
| 352 | 7 |
| 353 | 270 |
| 354 | 8 |
| 355 | 2500 |
| 356 | >10000 |
| 357 | 5 |
| 358 | 10 |
| 359 | 1200 |
| 360 | 2800 |
| 361 | 2 |
| 362 | 28 |
| 363 | 8000 |
| 364 | 25 |
| 365 | 9100 |
| 366 | 17 |
| 367 | 5600 |
| 368 | 18 |
| 369 | >10000 |
| 370 | 13 |
| 371 | 6800 |
| 372 | 6 |

TABLE 1-continued

| example | IC$_{50}$-PIP-β (nM) |
|---|---|
| 373 | 1000 |
| 374 | 22 |
| 375 | 7100 |
| 376 | 70 |
| 377 | 35 |
| 378 | 27 |
| 379 | 8 |
| 380 | 240 |
| 381 | 24 |
| 382 | 130 |
| 383 | 11 |
| 387 | 13 |
| 388 | 1100 |
| 389 | 16 |
| 390 | 840 |
| 391 | 10 |
| 392 | 9 |
| 393 | 21 |
| 394 | 860 |

From the foregoing it will be appreciated that, although specific embodiments have been described herein for purposes of illustration, various modifications may be made without deviating from the spirit and scope of the present application.

What is claimed:
1. A compound having the structure of formula (I):

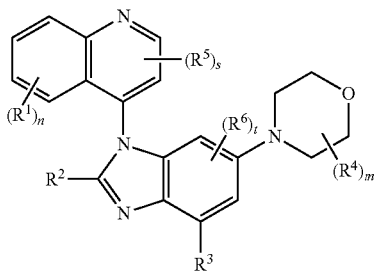

Formula I wherein n is 1, 2, 3 or 4;
m is 1, 2, 3 or 4;
s is 1 or 2;
t is 1 or 2;
each $R^1$ is independently selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{100}$;
$R^2$ is selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{101}$;
$R^3$ is selected from $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{6-10}$ aryl, 5-10 membered heteroaryl and 4-10 membered heterocyclyl is optionally substituted with one to four $R^{102}$;
$R^4$ is selected from hydrogen, $C_{1-6}$ alkyl, $C_{2-6}$ alkenyl, $C_{2-6}$ alkynyl, acyl, $C_{3-8}$ cycloalkyl and $C_{1-6}$ alkyl sulfonyl;
each $R^5$ is independently selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{103}$;
each $R^6$ is independently selected from hydrogen, halo, cyano, hydroxy, amino, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl or $C_{2-6}$ alkynyl;
each $R^a$ and $R^b$ is independently selected from hydrogen, $C_{1-6}$ alkyl, $C_{2-6}$ alkenyl and $C_{2-6}$ alkynyl;
wherein each $C_{1-6}$ alkyl, $C_{2-6}$ alkenyl, and $C_{2-6}$ alkynyl, is optionally substituted with one to four $R^{200}$;
each $R^{100}$, $R^{101}$, $R^{102}$, and $R^{103}$ is independently selected from hydrogen, halo, cyano, hydroxy, amino, oxo, thioxo, vinyl, —C(O)$R^a$, —C(O)O$R^b$, —C(O)N$R^a R^b$, —N($R^a$)C(O)$R^b$, —S(O)N$R^a R^b$, —S(O)$_2$N$R^a R^b$, —S(O)$R^a$, —S(O)$_2 R^a$, —N$R^a R^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl;
wherein each $C_{1-6}$ alkyl, $C_{2-6}$ alkenyl, and $C_{2-6}$ alkynyl, is optionally substituted with one to four $R^{201}$; and,
each $R^{200}$ and $R^{201}$ is independently selected from hydrogen, halo, cyano, hydroxy, amino, oxo, thioxo, vinyl, —C(O)$R^c$, —C(O)O$R^d$, —C(O)N$R^c R^d$, —N($R^c$)C(O)$R^d$, —S(O)N$R^c R^d$, —S(O)$_2$N$R^c R^d$, —S(O)$R^c$, —S(O)$_2 R^c$, —N$R^c R^d$, —O$R^c$, —S$R^c$, $C_{1-6}$ alkyl, $C_{2-6}$ alkenyl and $C_{2-6}$ alkynyl;
each $R^c$ and $R^d$ is independently selected from hydrogen, $C_{1-6}$ alkyl, $C_{2-6}$ alkenyl and $C_{2-6}$ alkynyl;
or a pharmaceutically acceptable salt, isomer, or a mixture thereof.

2. The compound of claim 1 having the structure of formula IB:

Formula IB

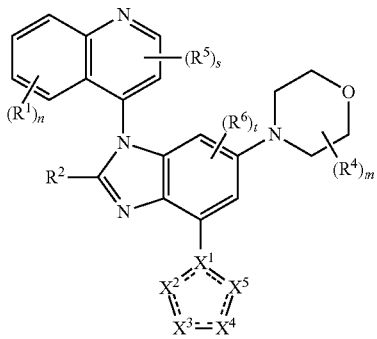

wherein ------ is a single or double bond;
$X^1$ is N or C;
each $X^2$, $X^3$, $X^4$ and $X^5$ is independently selected from S, O, $CR^{10}$ and $NR^{11}$;
wherein each $R^{10}$ is independently selected from hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{104}$;
wherein each $R^{11}$ is independently selected from absent, hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
alternatively, one $R^{10}$ and one $R^{11}$ group, together with the atoms to which they are attached form a five, six or seven membered fused or bridged ring;
each $R^{104}$ is independently selected from hydrogen, halo, cyano, hydroxy, amino, oxo, thioxo, vinyl, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl;
wherein each $C_{1-6}$ alkyl, $C_{2-6}$ alkenyl, $C_{2-6}$ alkynyl, is optionally substituted with one to four $R^{201}$; and
each $R^{201}$ is independently selected from hydrogen, halo, cyano, hydroxy, amino, oxo, thioxo, vinyl, —C(O)$R^c$, —C(O)O$R^d$, —C(O)N$R^cR^d$, —N($R^c$)C(O)$R^d$, —S(O)N$R^cR^d$, —S(O)$_2$N$R^cR^d$, —S(O)$R^c$, —S(O)$_2$R, —N$R^cR^d$, —O$R^c$, —S$R^c$, $C_{1-6}$ alkyl, $C_{2-6}$ alkenyl and $C_{2-6}$ alkynyl;
each $R^c$ and $R^d$ is independently selected from hydrogen, $C_{1-6}$ alkyl, $C_{2-6}$ alkenyl and $C_{2-6}$ alkynyl;
or a pharmaceutically acceptable salt, isomer, or a mixture thereof.

3. The compound of claim 1, wherein $R^3$ is selected from:

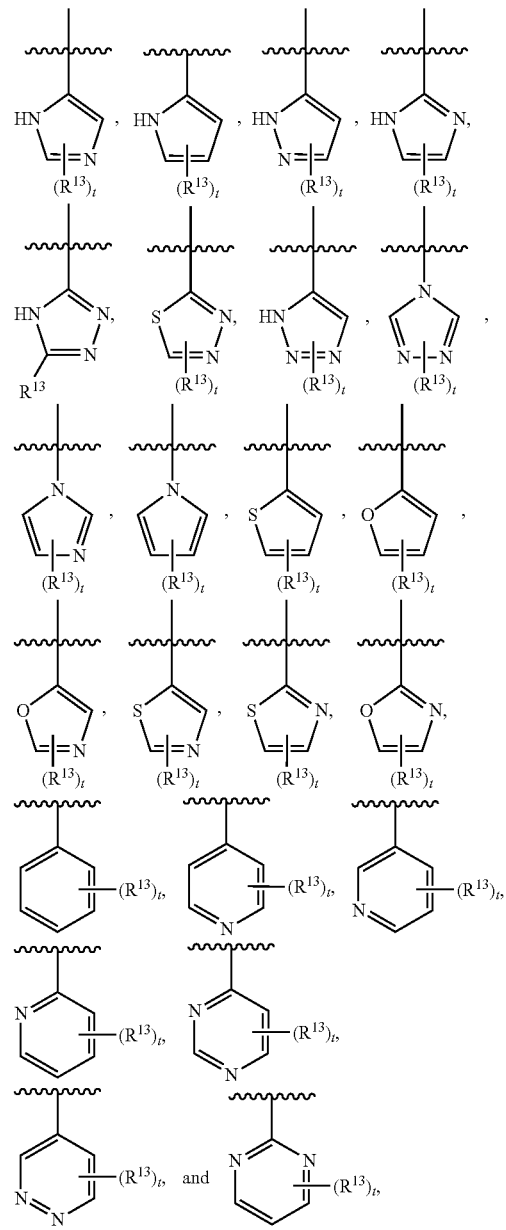

wherein t is 1 or 2;
wherein each $R^{13}$ is independently selected from hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;
or a pharmaceutically acceptable salt, isomer, or a mixture thereof.

4. The compound of claim 3 having the structure of formula IC:

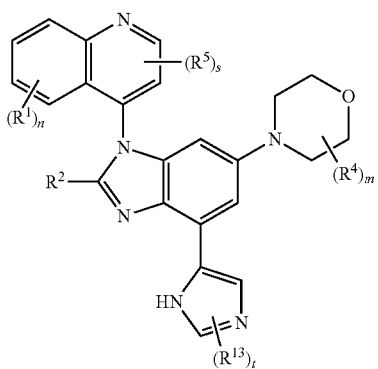

Formula IC or a pharmaceutically acceptable salt, isomer, or a mixture thereof.

5. The compound of claim 3 having the structure of formula ID:

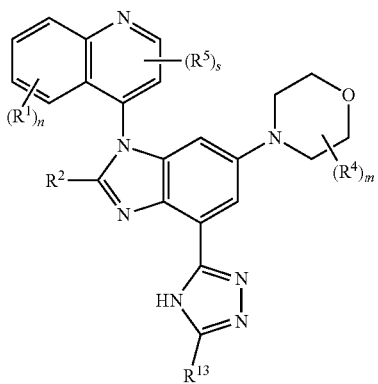

Formula ID or a pharmaceutically acceptable salt, isomer, or a mixture thereof.

6. The compound of claim 2 having the structure of formula IE:

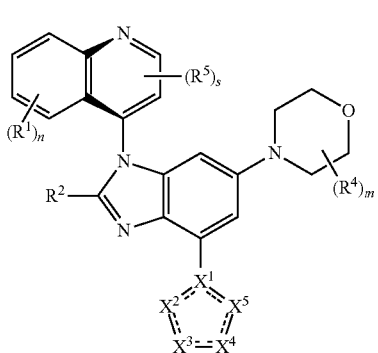

Formula IE or a pharmaceutically acceptable salt, isomer, or a mixture thereof.

7. The compound of claim 3 having the structure of formula IF:

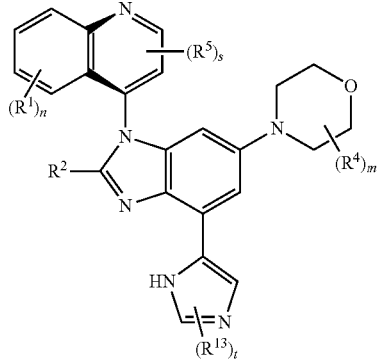

Formula IF or a pharmaceutically acceptable salt, isomer, or a mixture thereof.

8. The compound of claim 3 having the structure of formula IG:

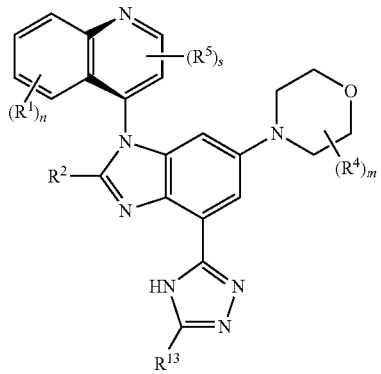

Formula IG or a pharmaceutically acceptable salt, isomer, or a mixture thereof.

9. A composition comprising an atropisomer of formula IE:

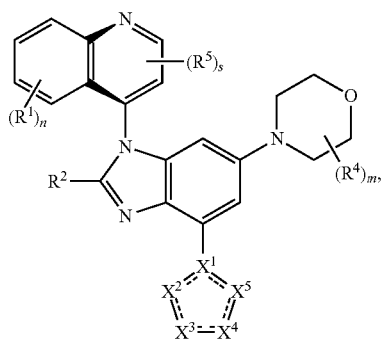

Formula IE wherein n is 1, 2, 3 or 4;
m is 1, 2, 3 or 4;
s is 1 or 2;
------ is a single or double bond;
$X^1$ is N or C;
each $X^2$, $X^3$, $X^4$ and $X^5$ is independently selected from S, O, $CR^{10}$ and $NR^{11}$;

wherein each $R^{10}$ is independently selected from hydrogen, halo, cyano, hydroxy, amino, —C(O)$R^a$, —C(O)O$R^b$, —C(O)N$R^aR^b$, —N($R^a$)C(O)$R^b$—S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{104}$;

wherein each $R^{11}$ is independently selected from absent, hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

alternatively, one $R^{10}$ and one $R^{11}$ group, together with the atoms to which they are attached form a five, six or seven membered fused or bridged ring;

each $R^1$ is independently selected from hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{100}$;

$R^2$ is selected from hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{101}$;

$R^4$ is selected from hydrogen, $C_{1-6}$ alkyl, $C_{2-6}$ alkenyl, $C_{2-6}$ alkynyl, acyl, $C_{3-8}$ cycloalkyl and $C_{1-6}$ alkyl sulfonyl;

each $R^5$ is independently selected from hydrogen, halo, cyano, hydroxy, amino, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl containing 1 to 4 heteroatoms selected from the group consisting of N, O, and S, and 4-10 membered heterocyclyl containing 1 to 4 heteroatoms selected from the group consisting of N, O, and S;

wherein each $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl is optionally substituted with one to four $R^{103}$;

each $R^a$ and $R^b$ is independently selected from hydrogen, $C_{1-6}$ alkyl, $C_{2-6}$ alkenyl and $C_{2-6}$ alkynyl;

wherein each $C_{1-6}$ alkyl, $C_{2-6}$ alkenyl, and $C_{2-6}$ alkynyl is optionally substituted with one to four $R^{200}$;

each $R^{100}$, $R^{101}$, R103, and $R^{104}$ is independently selected from hydrogen, halo, cyano, hydroxy, amino, oxo, thioxo, vinyl, —C(O)$R^a$, —C(O)O$R^b$, —C(O)N$R^aR^b$, —N($R^a$)C(O)$R^b$, —S(O)N$R^aR^b$, —S(O)$_2$N$R^aR^b$, —S(O)$R^a$, —S(O)$_2R^a$, —N$R^aR^b$, —O$R^a$, —S$R^b$, $C_{1-6}$ alkyl, $C_{2-6}$ alkenyl, $C_{2-6}$ alkynyl, $C_{3-8}$ cycloalkyl, $C_{6-10}$ aryl, 5-10 membered heteroaryl and 4-10 membered heterocyclyl;

wherein each $C_{1-6}$ alkyl, $C_{2-6}$ alkenyl, and $C_{2-6}$ alkynyl is optionally substituted with one to four $R^{201}$; and each $R^{200}$ and $R^{201}$ is independently selected from hydrogen, halo, cyano, hydroxy, amino, oxo, thioxo, vinyl, —C(O)$R^c$, —C(O)O$R^d$, —C(O)N$R^cR^d$, —N($R^c$)C(O)$R^d$, —S(O)N$R^dR^d$, —S(O)$_2$N$R^cR^d$, —S(O)$R^c$, —S(O)$_2R^c$, —N$R^cR^d$, —O$R^c$, —S$R^c$, $C_{1-6}$ alkyl, $C_{2-6}$ alkenyl and $C_{2-6}$ alkynyl;

each $R^c$ and $R^d$ is independently selected from hydrogen, $C_{1-6}$ alkyl, $C_{2-6}$ alkenyl and $C_{2-6}$ alkynyl;

or a pharmaceutically acceptable salt thereof, and a carrier; wherein the atropisomer of formula IE or a pharmaceutically acceptable salt thereof, is present in excess of its corresponding enantiomer or a pharmaceutically acceptable salt thereof.

10. The compound of claim 2 having the structure of formula IH:

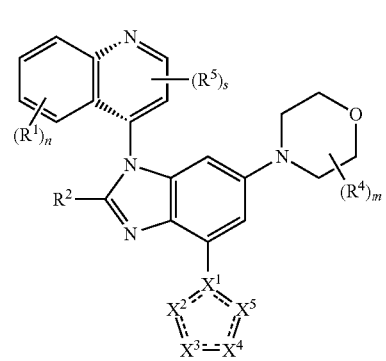

Formula IH or a pharmaceutically acceptable salt, isomer, or a mixture thereof.

11. The compound of claim 3, having the structure of formula IJ:

Formula IJ

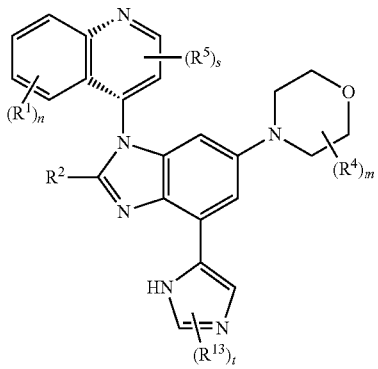

or a pharmaceutically acceptable salt, isomer, or a mixture thereof.

12. The compound of claim 3, having the structure of formula IK:

Formula IK

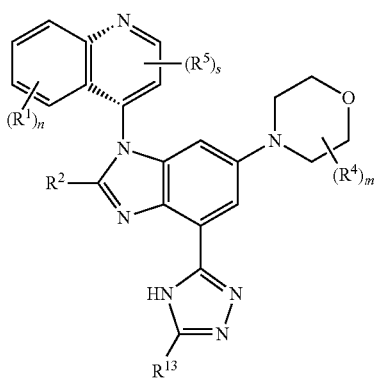

or a pharmaceutically acceptable salt, isomer, or a mixture thereof.

13. The compound of claim 1, wherein $R^1$ is independently selected from hydrogen, fluoro, chloro, bromo, iodo, methyl, ethyl, propyl, butyl, fluoromethyl, difluoromethyl, trifluoromethyl, fluoroethyl, difluoroethyl and trifluoroethyl; or a pharmaceutically acceptable salt, isomer, or a mixture thereof.

14. The compound of claim 1, wherein $R^2$ is $C_{1-6}$ alkyl, $C_{3-8}$ cycloalkyl, 5-6 membered heteroaryl containing 1 to 3 heteroatoms selected from the group consisting of N, O, and S, and 4-6 membered heterocyclyl containing 1 to 4 heteroatoms selected from the group consisting of N, O, and S; wherein each $C_{1-6}$ alkyl, $C_{3-8}$ cycloalkyl, 5-6 membered heteroaryl and 4-6 membered heterocyclyl is optionally substituted with one to four $R^{101}$;

or a pharmaceutically acceptable salt, isomer, or a mixture thereof.

15. The compound of claim 1, wherein $R^4$ is selected from hydrogen and methyl; or a pharmaceutically acceptable salt, isomer, or a mixture thereof.

16. The compound of claim 1, wherein $R^5$ is selected from hydrogen, methyl, ethyl, trifluoromethyl, carboxamide, cyano, piperazinyl, cyclopropyl, phenyl and triazolyl; or a pharmaceutically acceptable salt, isomer, or a mixture thereof.

17. The compound of claim 1, wherein the compound is selected from:

| Example | Structure |
|---|---|
| 1 | 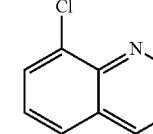 |
| 2 | 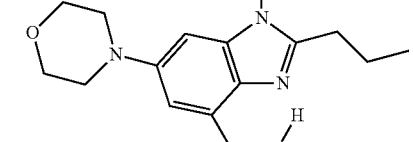 |
| 3 | 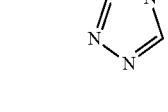 |
| 4 | 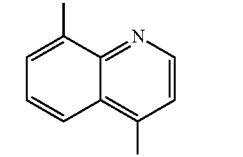 |

-continued
| Example | Structure |
|---|---|
| 5 | 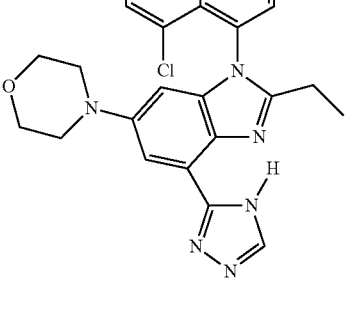 |
| 6 | 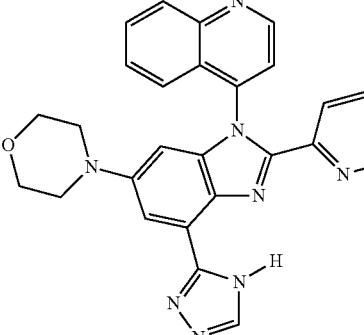 |
| 7 | 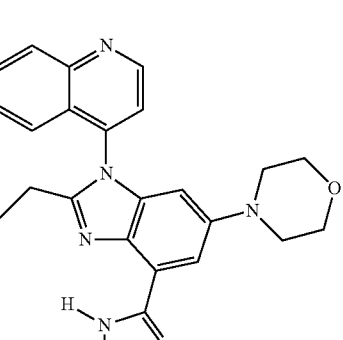 |
| 8 | 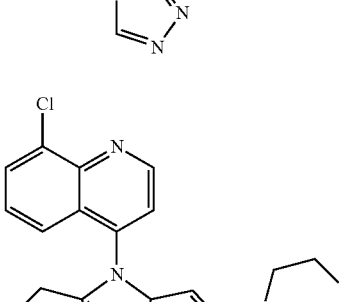 |
| 9 | 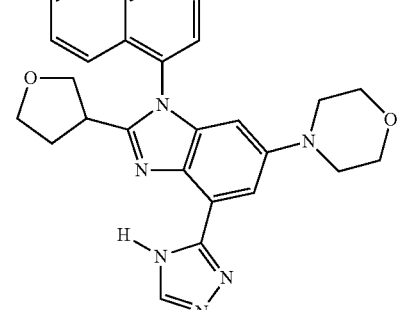 |
| 10 | 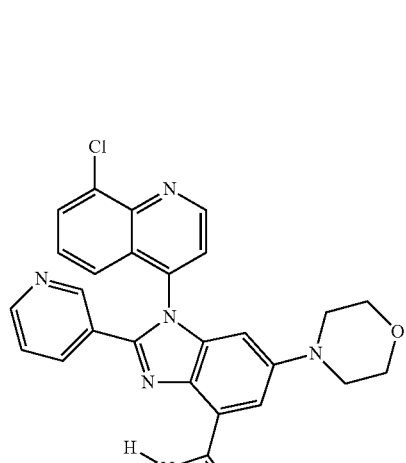 |
| 11 | 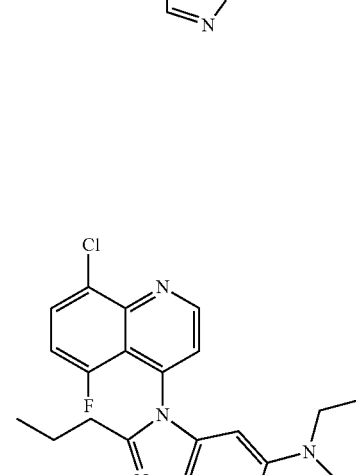 |

-continued

| Example | Structure |
|---|---|
| 12 | |
| 13 | |
| 14 | |
| 15 | 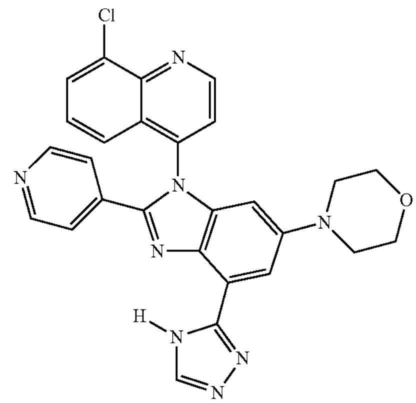 [SMILES: Clc1cccc2c(-n3c(-c4ccncc4)nc4c(-c5nnc[nH]5)cc(N5CCOCC5)cc43)ccnc12] |
| 16 | 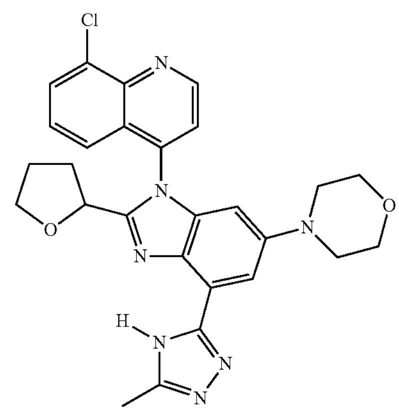 [SMILES: Cc1nnc(-c2cc(N3CCOCC3)cc3c2nc(C2CCCO2)n3-c2ccnc3c(Cl)cccc23)[nH]1] |
| 17 | 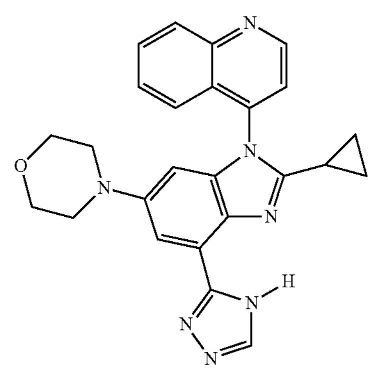 [SMILES: c1ccc2c(-n3c(C4CC4)nc4c(-c5nnc[nH]5)cc(N5CCOCC5)cc43)ccnc2c1] |
| 18 | 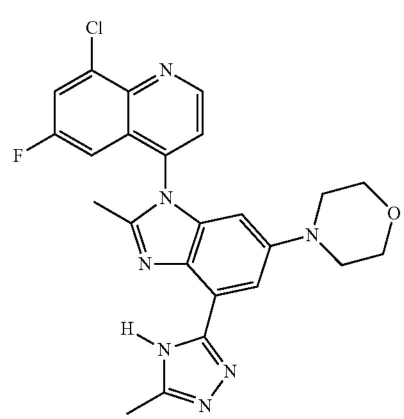 [SMILES: Cc1nnc(-c2cc(N3CCOCC3)cc3c2nc(C)n3-c2ccnc3c(Cl)cc(F)cc23)[nH]1] |

-continued

| Example | Structure |
|---|---|
| 19 | 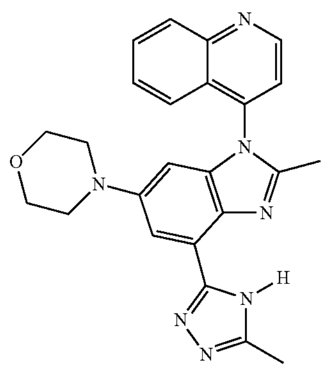 [SMILES: Cc1nnc(-c2cc(N3CCOCC3)cc3c2nc(C)n3-c2ccnc3ccccc23)[nH]1] |
| 20 | 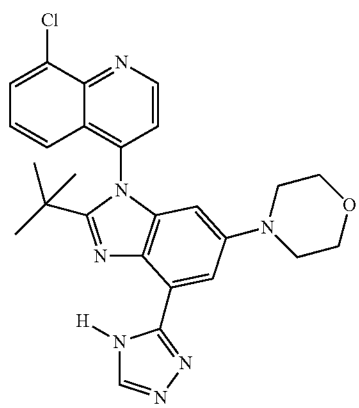 [SMILES: CC(C)(C)c1nc2c(-c3nnc[nH]3)cc(N3CCOCC3)cc2n1-c1ccnc2c(Cl)cccc12] |
| 21 | 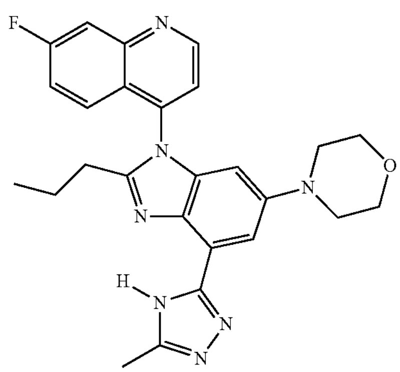 [SMILES: CCCc1nc2c(-c3nnc(C)[nH]3)cc(N3CCOCC3)cc2n1-c1ccnc2cc(F)ccc12] |
| 22 | 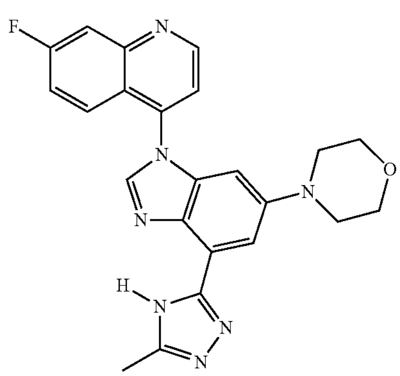 [SMILES: Cc1nnc(-c2cc(N3CCOCC3)cc3c2ncn3-c2ccnc3cc(F)ccc23)[nH]1] |
| 23 | |
| 24 | |
| 25 | |
| 26 | |

-continued

| Example | Structure |
|---------|-----------|
| 27 | 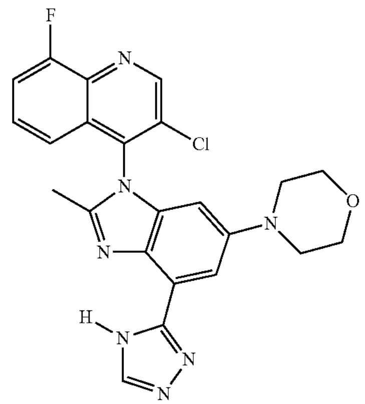 |
| 28 | 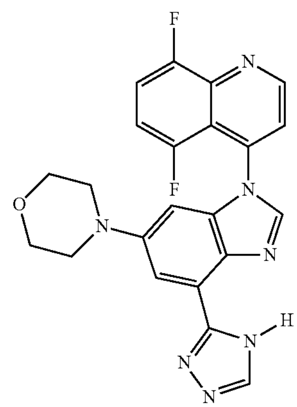 [SMILES: Fc1ccc(F)c2c(-n3cnc4c(-c5nnc[nH]5)cc(N5CCOCC5)cc43)ccnc12] |
| 29 | 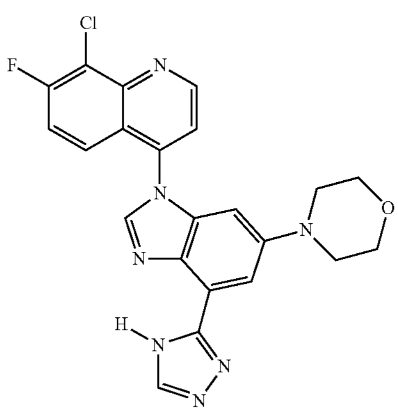 [SMILES: Fc1ccc2c(-n3cnc4c(-c5nnc[nH]5)cc(N5CCOCC5)cc43)ccnc2c1Cl] |
| 30 | 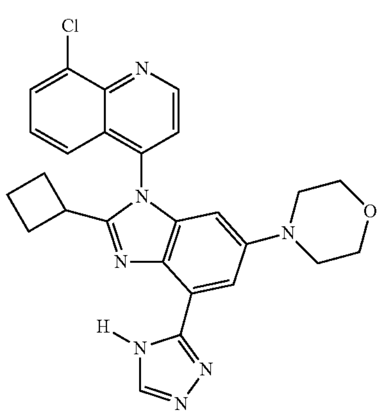 [SMILES: Clc1cccc2c(-n3c(C4CCC4)nc4c(-c5nnc[nH]5)cc(N5CCOCC5)cc43)ccnc12] |
| 31 | |
| 32 | |
| 33 | |

| Example | Structure |
|---|---|
| 34 | 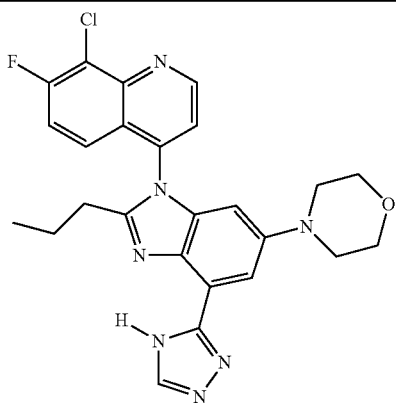 |
| 35 | 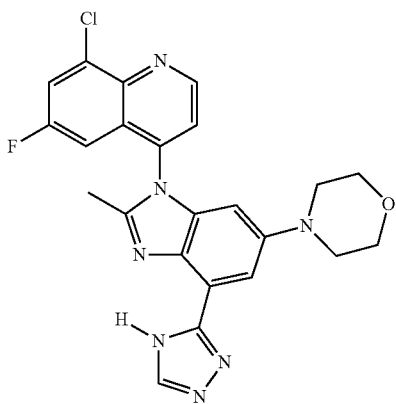 |
| 36 | 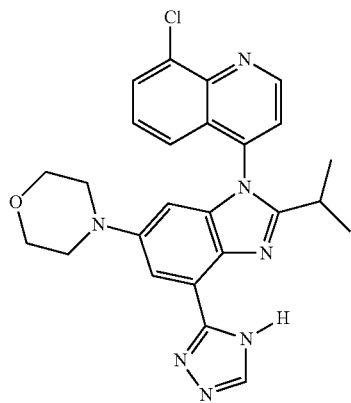 [SMILES: CC(C)c1nc2c(-c3nnc[nH]3)cc(N3CCOCC3)cc2n1-c1ccnc2c(Cl)cccc12] |
| 37 | 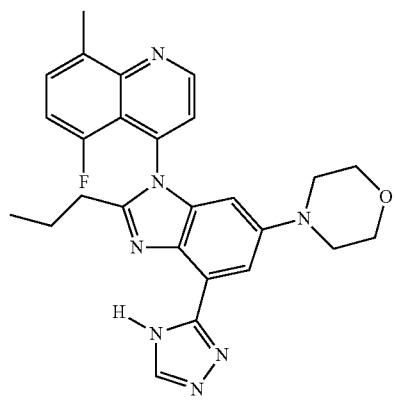 [SMILES: CCCc1nc2c(-c3nnc[nH]3)cc(N3CCOCC3)cc2n1-c1ccnc2c(C)ccc(F)c12] |
| Example | Structure |
|---|---|
| 38 | 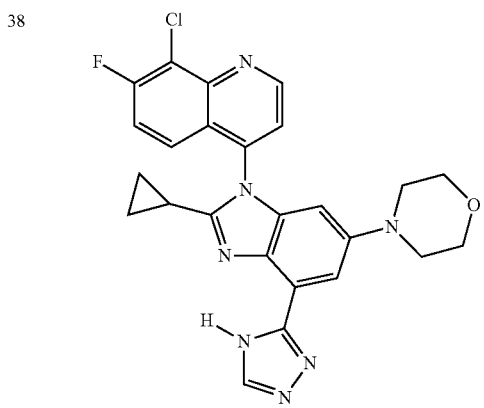 |
| 39 | 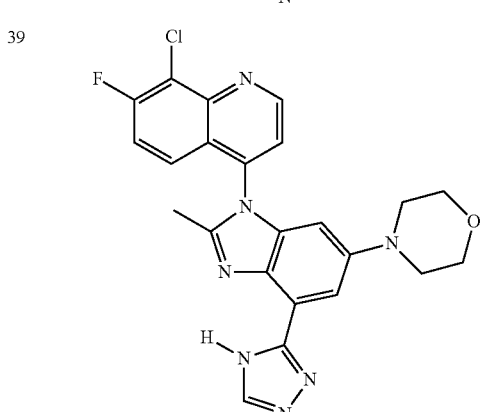 |
| 40 | 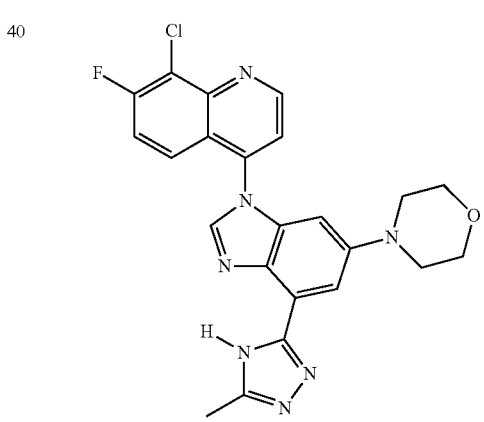 |
| 41 | 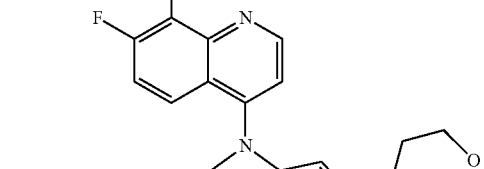 |

-continued
| Example | Structure |
|---|---|
| 42 | 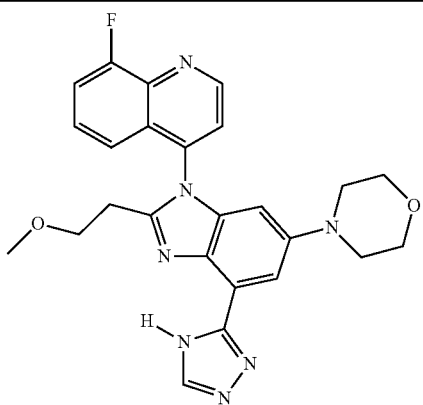 |
| 43 | 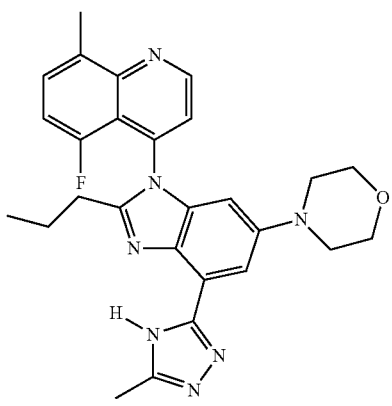 [SMILES: CCCc1nc2c(-c3nnc(C)[nH]3)cc(N3CCOCC3)cc2n1-c1ccnc2c(C)ccc(F)c12] |
| 44 | 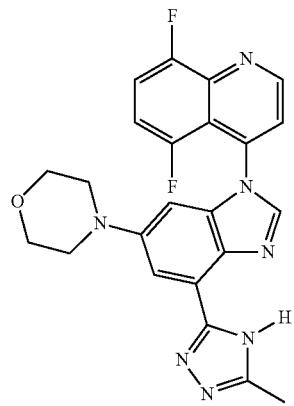 [SMILES: Cc1nnc(-c2cc(N3CCOCC3)cc3c2ncn3-c2ccnc3c(F)ccc(F)c23)[nH]1] |
| 45 | 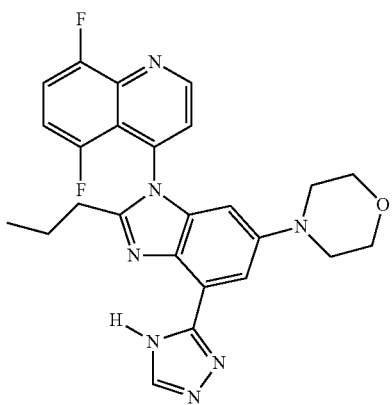 |
-continued
| Example | Structure |
|---|---|
| 46 | 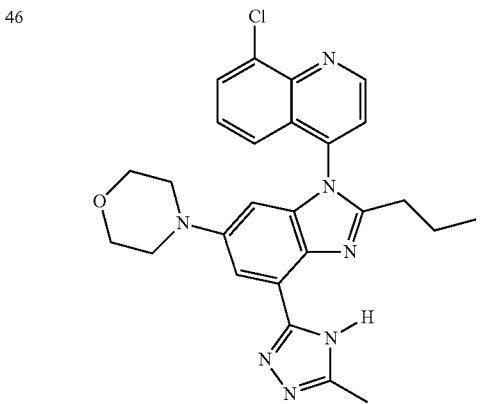 |
| 47 | 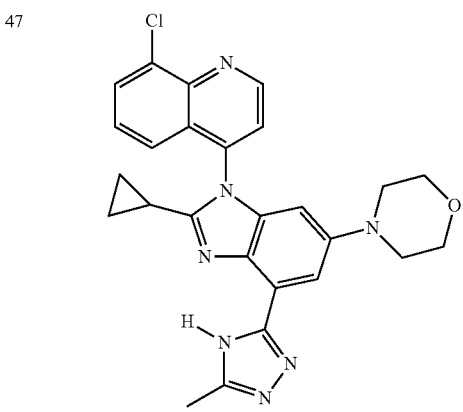 |
| 48 | 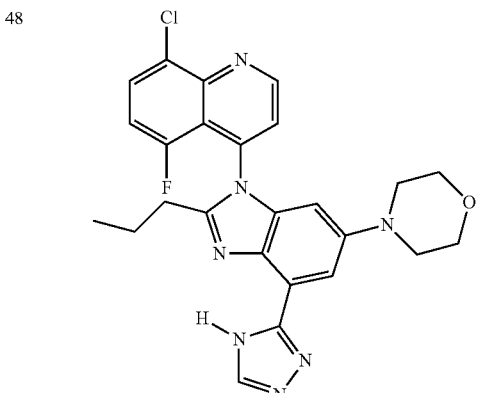 |

| Example | Structure |
|---|---|
| 49 | |
| 50 | |
| 51 | |
| 52 | 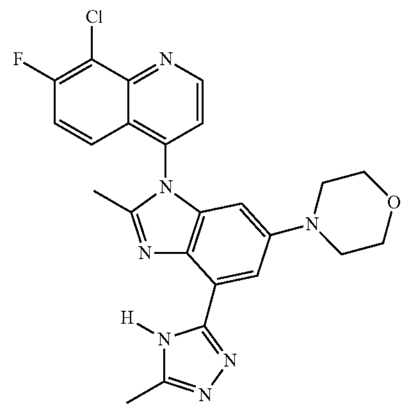 [SMILES: Cc1nnc(-c2cc(N3CCOCC3)cc3c2nc(C)n3-c2ccnc3c(Cl)c(F)ccc23)[nH]1] |
| 53 | 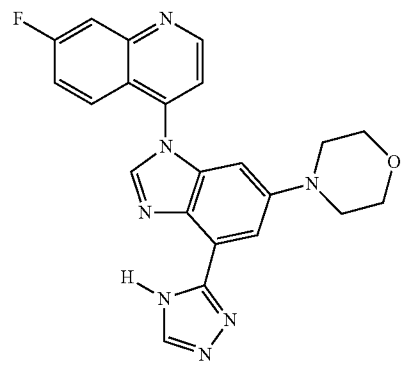 [SMILES: Fc1ccc2c(-n3cnc4c(-c5nnc[nH]5)cc(N5CCOCC5)cc43)ccnc2c1] |
| 54 | 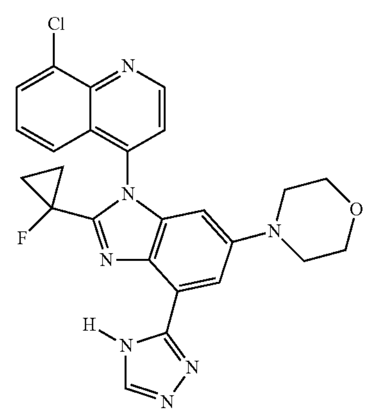 |
| 55 | 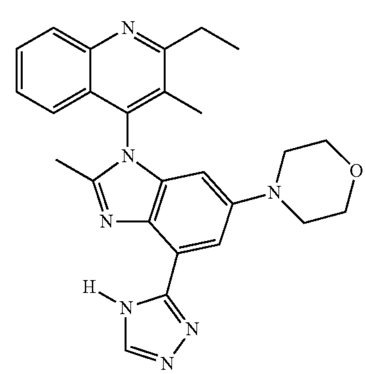 [SMILES: CCc1nc2ccccc2c(-n2c(C)nc3c(-c4nnc[nH]4)cc(N4CCOCC4)cc32)c1C] |

299
-continued
| Example | Structure |
|---|---|
| 56 | 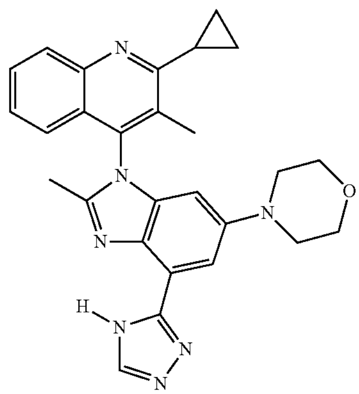 [SMILES: Cc1c(C2CC2)nc2ccccc2c1-n1c(C)nc2c(-c3nnc[nH]3)cc(N3CCOCC3)cc21] |
| 57 | 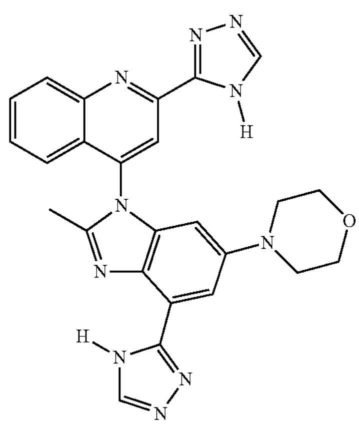 [SMILES: Cc1nc2c(-c3nnc[nH]3)cc(N3CCOCC3)cc2n1-c1cc(-c2nnc[nH]2)nc2ccccc12] |
| 58 | 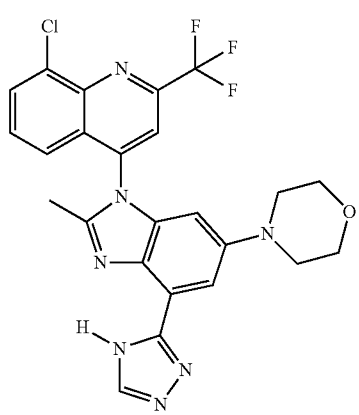 [SMILES: Cc1nc2c(-c3nnc[nH]3)cc(N3CCOCC3)cc2n1-c1cc(C(F)(F)F)nc2c(Cl)cccc12] |
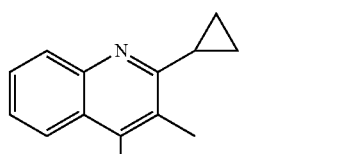
300
-continued
| Example | Structure |
|---|---|
| 59 | 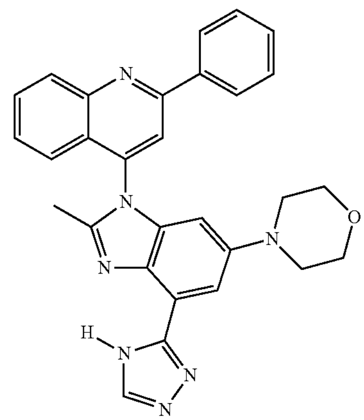 [SMILES: Cc1nc2c(-c3nnc[nH]3)cc(N3CCOCC3)cc2n1-c1cc(-c2ccccc2)nc2ccccc12] |
| 60 | 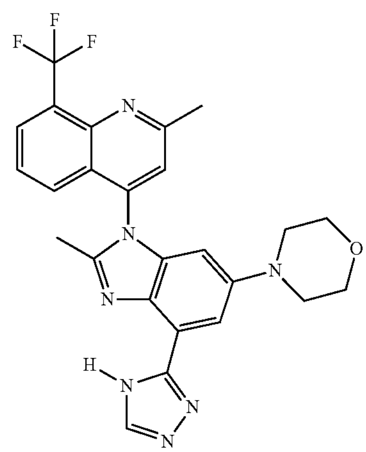 [SMILES: Cc1cc(-n2c(C)nc3c(-c4nnc[nH]4)cc(N4CCOCC4)cc32)c2cccc(C(F)(F)F)c2n1] |
| 61 | 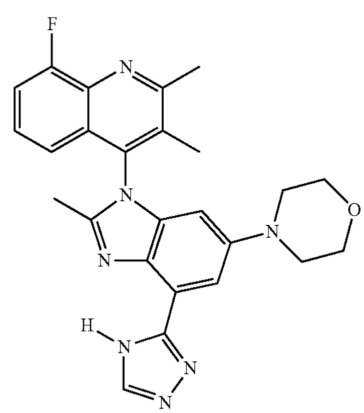 [SMILES: Cc1nc2c(F)cccc2c(-n2c(C)nc3c(-c4nnc[nH]4)cc(N4CCOCC4)cc32)c1C] |
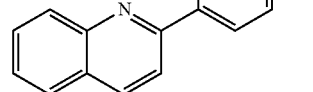

301
-continued

| Example | Structure |
|---------|-----------|
| 62 | 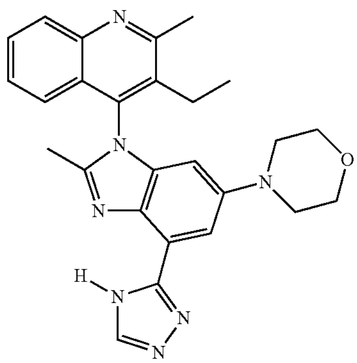 [SMILES: CCc1c(C)nc2ccccc2c1-n1c(C)nc2c(-c3nnc[nH]3)cc(N3CCOCC3)cc21] |
| 63 | 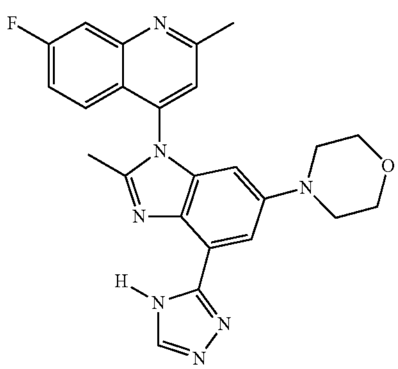 [SMILES: Cc1cc(-n2c(C)nc3c(-c4nnc[nH]4)cc(N4CCOCC4)cc32)c2ccc(F)cc2n1] |
| 64 | 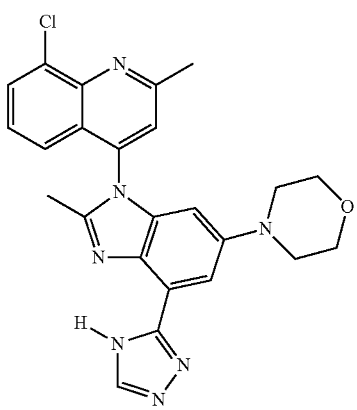 [SMILES: Cc1cc(-n2c(C)nc3c(-c4nnc[nH]4)cc(N4CCOCC4)cc32)c2cccc(Cl)c2n1] |
| 65 | 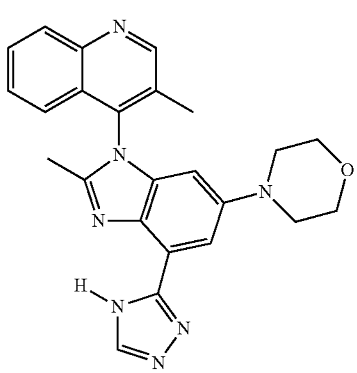 [SMILES: Cc1cnc2ccccc2c1-n1c(C)nc2c(-c3nnc[nH]3)cc(N3CCOCC3)cc21] |

302
-continued

| Example | Structure |
|---------|-----------|
| 66 | 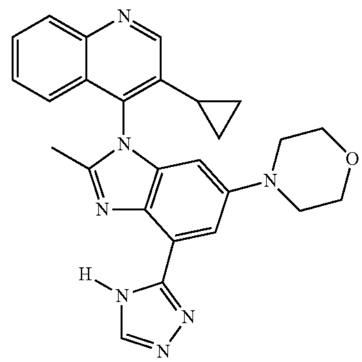 [SMILES: Cc1nc2c(-c3nnc[nH]3)cc(N3CCOCC3)cc2n1-c1c(C2CC2)cnc2ccccc12] |
| 67 | 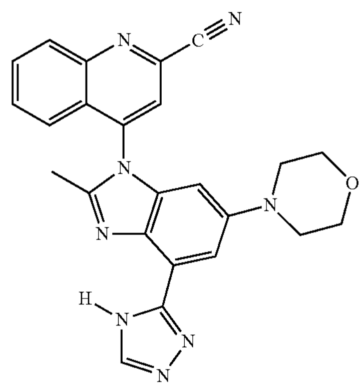 [SMILES: Cc1nc2c(-c3nnc[nH]3)cc(N3CCOCC3)cc2n1-c1cc(C#N)nc2ccccc12] |
| 68 | 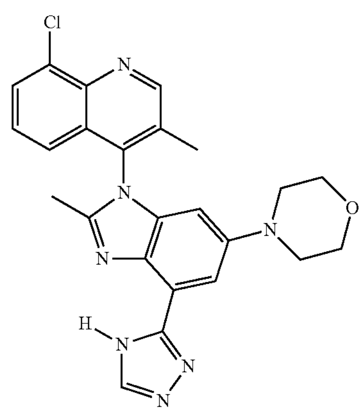 [SMILES: Cc1cnc2c(Cl)cccc2c1-n1c(C)nc2c(-c3nnc[nH]3)cc(N3CCOCC3)cc21] |
| 69 | 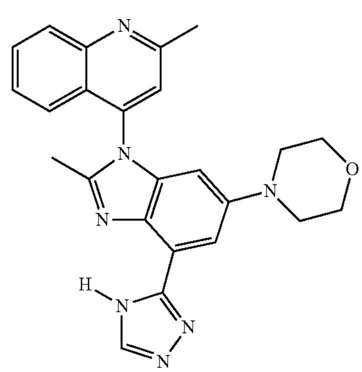 [SMILES: Cc1cc(-n2c(C)nc3c(-c4nnc[nH]4)cc(N4CCOCC4)cc32)c2ccccc2n1] |

-continued

| Example | Structure |
|---------|-----------|
| 70 | 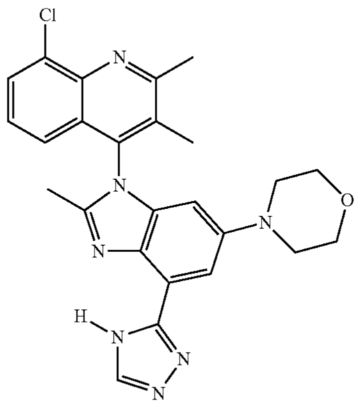 |
| 71 | 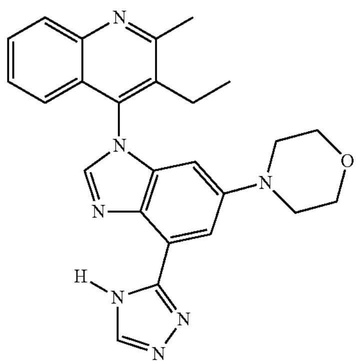 [SMILES: CCc1c(C)nc2ccccc2c1-n1cnc2c(-c3nnc[nH]3)cc(N3CCOCC3)cc21] |
| 72 | 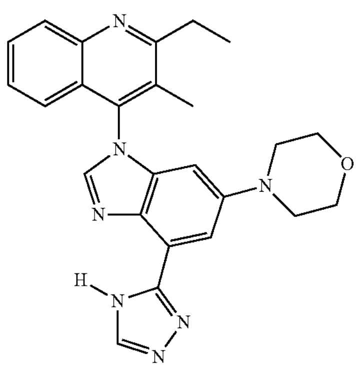 [SMILES: CCc1nc2ccccc2c(-n2cnc3c(-c4nnc[nH]4)cc(N4CCOCC4)cc32)c1C] |
| 73 | 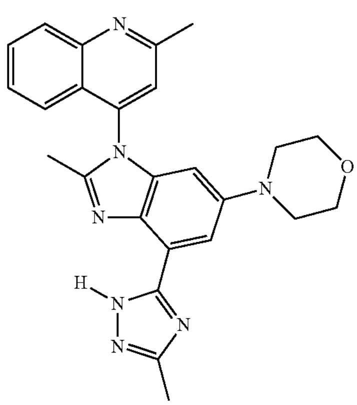 [SMILES: Cc1cc(-n2c(C)nc3c(-c4nc(C)n[nH]4)cc(N4CCOCC4)cc32)c2ccccc2n1] |
| 74 | |
| 75 | |
| 76 | |

-continued

| Example | Structure |
|---------|-----------|
| 77 | 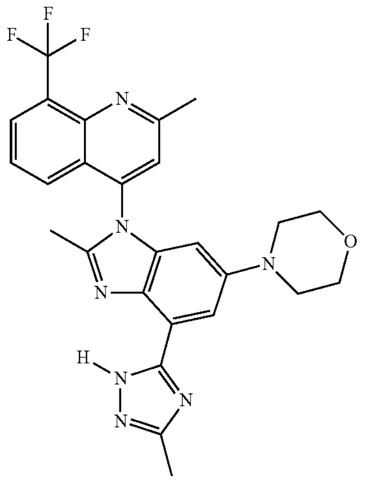 [SMILES: Cc1cc(-n2c(C)nc3c(-c4nc(C)n[nH]4)cc(N4CCOCC4)cc32)c2cccc(C(F)(F)F)c2n1] |
| 78 | 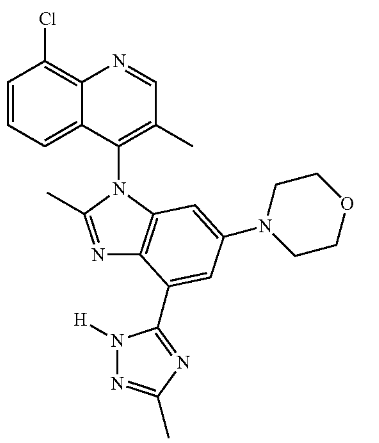 [SMILES: Cc1n[nH]c(-c2cc(N3CCOCC3)cc3c2nc(C)n3-c2c(C)cnc3c(Cl)cccc23)n1] |
| 79 | 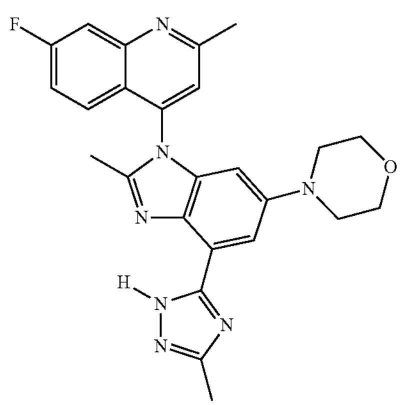 [SMILES: Cc1cc(-n2c(C)nc3c(-c4nc(C)n[nH]4)cc(N4CCOCC4)cc32)c2ccc(F)cc2n1] |
| 80 | 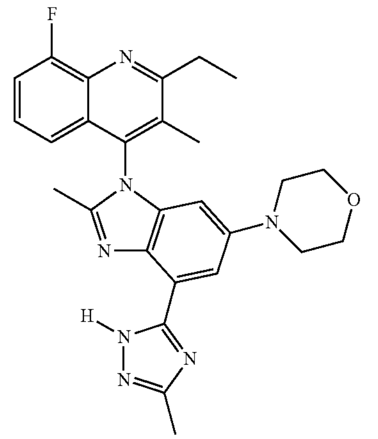 [SMILES: CCc1nc2c(F)cccc2c(-n2c(C)nc3c(-c4nc(C)n[nH]4)cc(N4CCOCC4)cc32)c1C] |
| 81 | 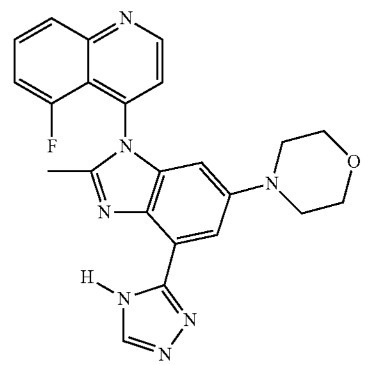 [SMILES: Cc1nc2c(-c3nnc[nH]3)cc(N3CCOCC3)cc2n1-c1ccnc2cccc(F)c12] |
| 82 | 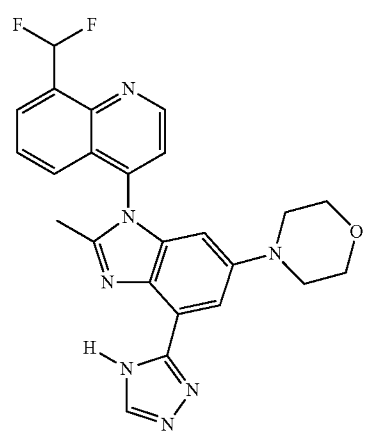 [SMILES: Cc1nc2c(-c3nnc[nH]3)cc(N3CCOCC3)cc2n1-c1ccnc2c(C(F)F)cccc12] |
| 83 | 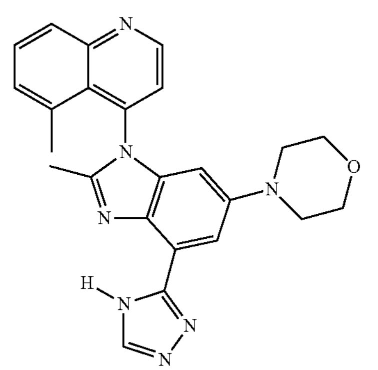 [SMILES: Cc1cccc2nccc(-n3c(C)nc4c(-c5nnc[nH]5)cc(N5CCOCC5)cc43)c12] |

307
-continued

| Example | Structure |
|---------|-----------|
| 84 | 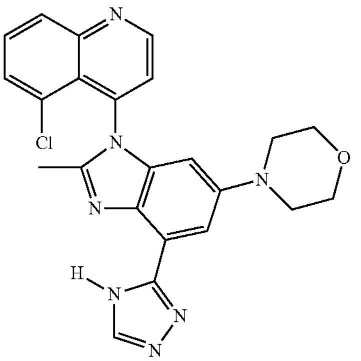 [SMILES: Cc1nc2c(-c3nnc[nH]3)cc(N3CCOCC3)cc2n1-c1ccnc2cccc(Cl)c12] |
| 85 | 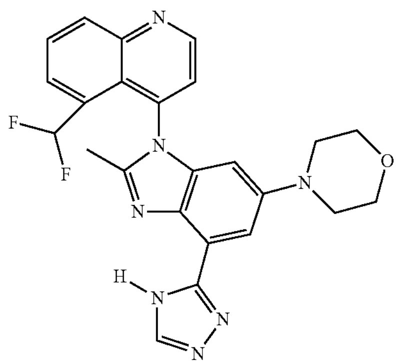 [SMILES: Cc1nc2c(-c3nnc[nH]3)cc(N3CCOCC3)cc2n1-c1ccnc2cccc(C(F)F)c12] |
| 86 | 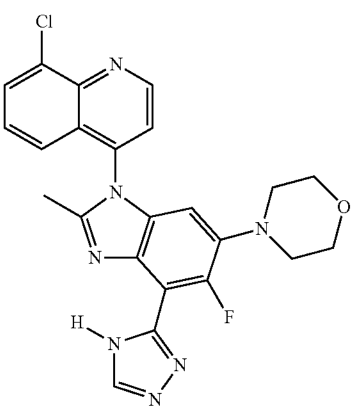 [SMILES: Cc1nc2c(-c3nnc[nH]3)c(F)c(N3CCOCC3)cc2n1-c1ccnc2c(Cl)cccc12] |
| 87 | 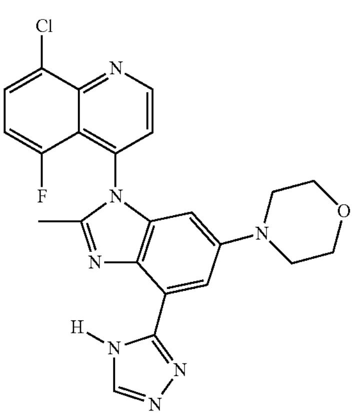 [SMILES: Cc1nc2c(-c3nnc[nH]3)cc(N3CCOCC3)cc2n1-c1ccnc2c(Cl)ccc(F)c12] |

308
-continued

| Example | Structure |
|---------|-----------|
| 88 | 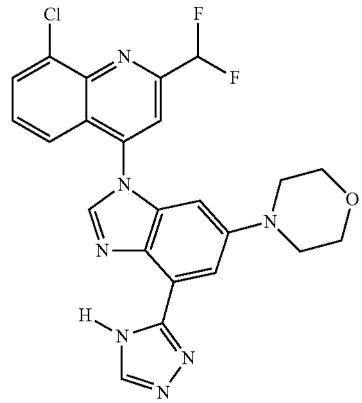 [SMILES: FC(F)c1cc(-n2cnc3c(-c4nnc[nH]4)cc(N4CCOCC4)cc32)c2cccc(Cl)c2n1] |
| 89 | 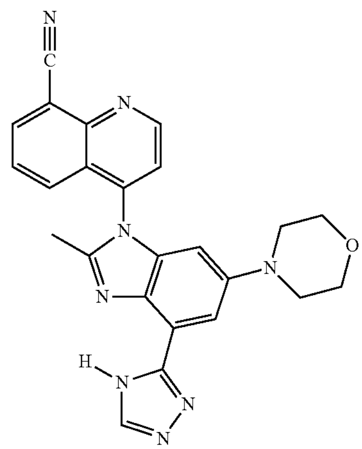 [SMILES: Cc1nc2c(-c3nnc[nH]3)cc(N3CCOCC3)cc2n1-c1ccnc2c(C#N)cccc12] |
| 90 | 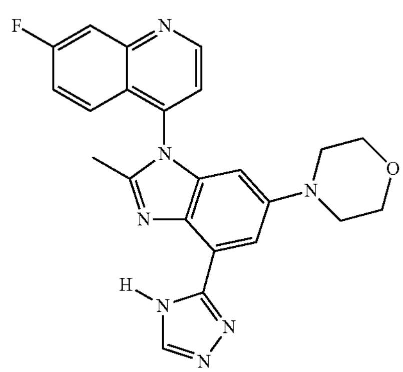 [SMILES: Cc1nc2c(-c3nnc[nH]3)cc(N3CCOCC3)cc2n1-c1ccnc2cc(F)ccc12] |

| Example | Structure |
|---|---|
| 91 | 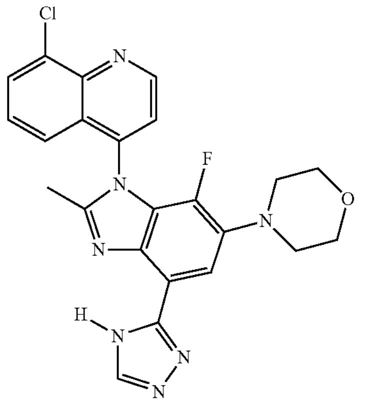 [SMILES: Cc1nc2c(-c3nnc[nH]3)cc(N3CCOCC3)c(F)c2n1-c1ccnc2c(Cl)cccc12] |
| 92 | 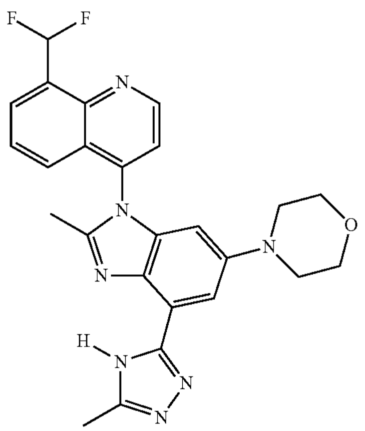 [SMILES: Cc1nnc(-c2cc(N3CCOCC3)cc3c2nc(C)n3-c2ccnc3c(C(F)F)cccc23)[nH]1] |
| 93 | 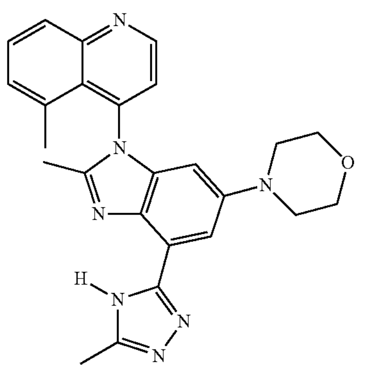 [SMILES: Cc1nnc(-c2cc(N3CCOCC3)cc3c2nc(C)n3-c2ccnc3cccc(C)c23)[nH]1] |
| 94 | 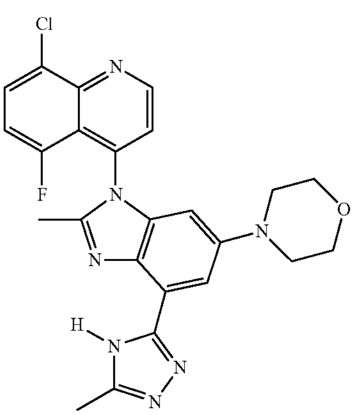 [SMILES: Cc1nnc(-c2cc(N3CCOCC3)cc3c2nc(C)n3-c2ccnc3c(Cl)ccc(F)c23)[nH]1] |
| 95 | |
| 96 | |
| 97 | |

-continued
| Example | Structure |
|---|---|
| 98 | 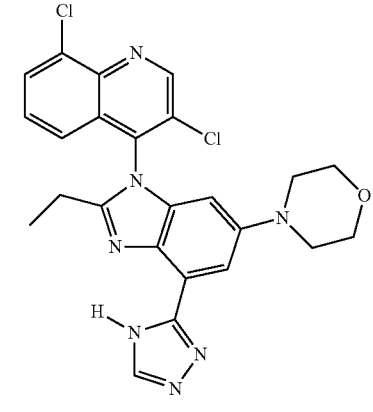 [SMILES: CCc1nc2c(-c3nnc[nH]3)cc(N3CCOCC3)cc2n1-c1c(Cl)cnc2c(Cl)cccc12] |
| 99 | 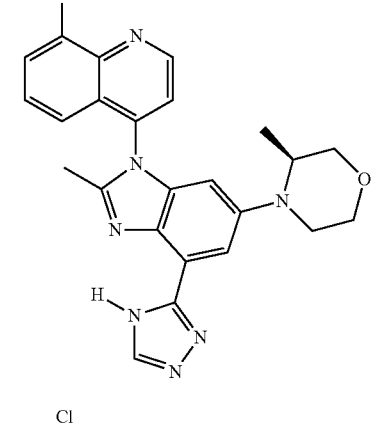 |
| 100 | 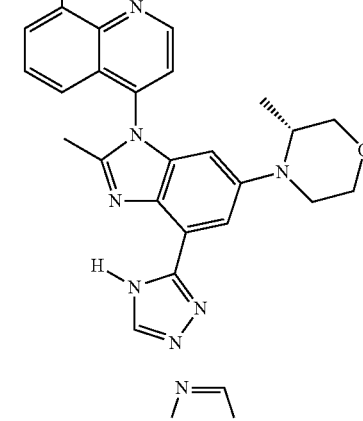 |
| 101 | 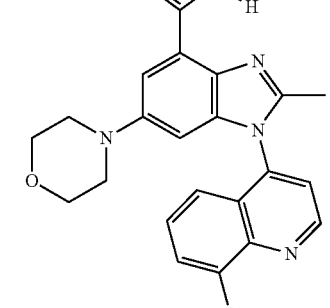 |
-continued
| Example | Structure |
|---|---|
| 102 | 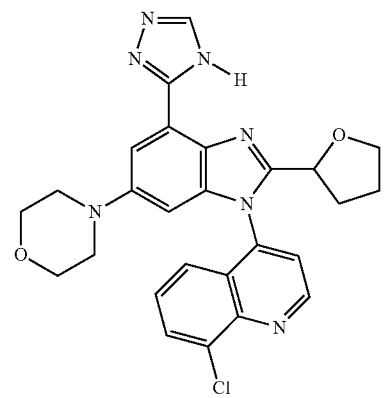 [SMILES: Clc1cccc2c(-n3c(C4CCCO4)nc4c(-c5nnc[nH]5)cc(N5CCOCC5)cc43)ccnc12] |
| 103 | 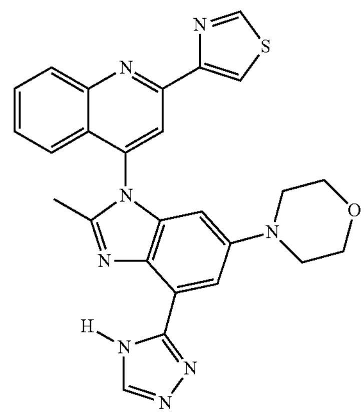 [SMILES: Cc1nc2c(-c3nnc[nH]3)cc(N3CCOCC3)cc2n1-c1cc(-c2cscn2)nc2ccccc12] |
| 104 | 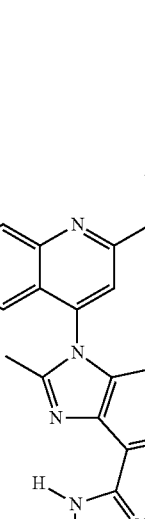 |

-continued

| Example | Structure |
|---|---|
| 105 | (structure) |
| 106 | (structure) |
| 107 | (structure) |
| 108 | (structure) |
| 109 | (structure) |
| 110 | (structure) |
| 111 | (structure) |
| 112 | (structure) |

-continued

| Example | Structure |
|---------|-----------|
| 113 | |
| 114 | |
| 115 | |
| 116 | 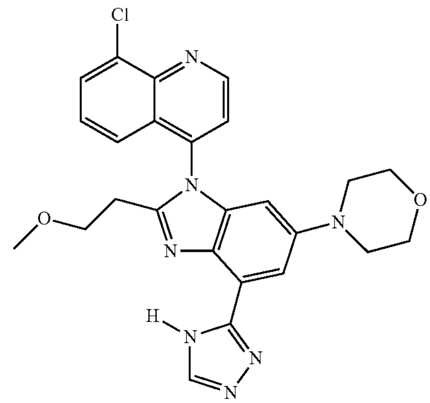 [SMILES: COCCc1nc2c(-c3nnc[nH]3)cc(N3CCOCC3)cc2n1-c1ccnc2c(Cl)cccc12] |
| 117 | 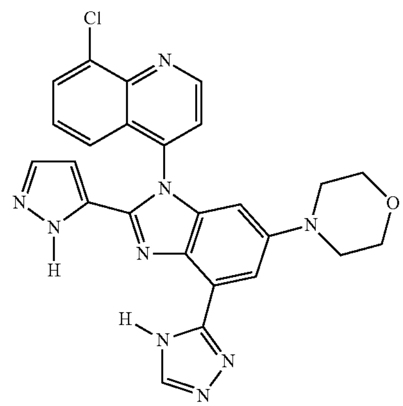 [SMILES: Clc1cccc2c(-n3c(-c4ccn[nH]4)nc4c(-c5nnc[nH]5)cc(N5CCOCC5)cc43)ccnc12] |
| 118 | 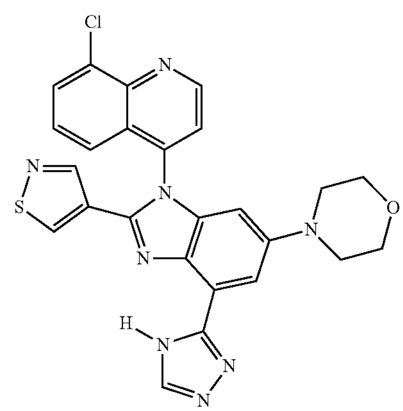 [SMILES: Clc1cccc2c(-n3c(-c4cnsc4)nc4c(-c5nnc[nH]5)cc(N5CCOCC5)cc43)ccnc12] |
| 119 | 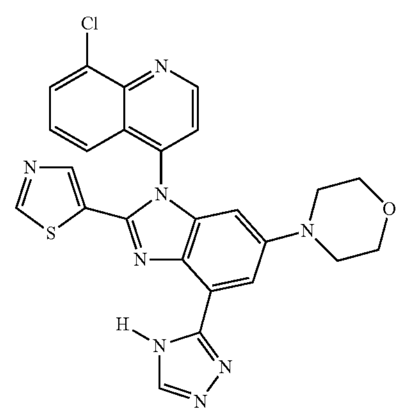 [SMILES: Clc1cccc2c(-n3c(-c4cncs4)nc4c(-c5nnc[nH]5)cc(N5CCOCC5)cc43)ccnc12] |

-continued

| Example | Structure |
|---------|-----------|
| 120 | 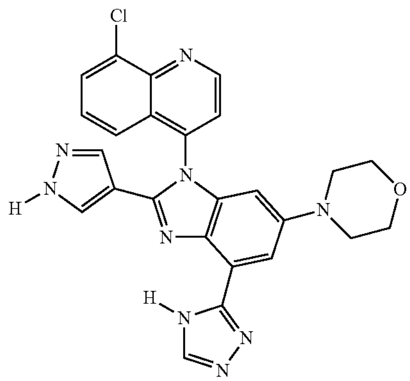 [SMILES: Clc1cccc2c(-n3c(-c4cn[nH]c4)nc4c(-c5nnc[nH]5)cc(N5CCOCC5)cc43)ccnc12] |
| 121 | 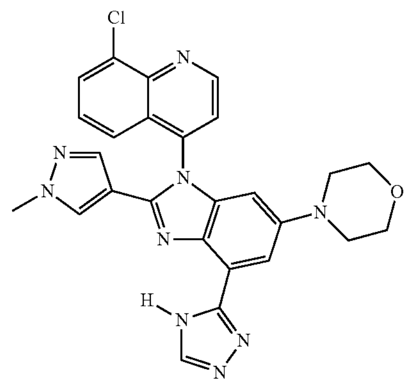 [SMILES: Cn1cc(-c2nc3c(-c4nnc[nH]4)cc(N4CCOCC4)cc3n2-c2ccnc3c(Cl)cccc23)cn1] |
| 122 | 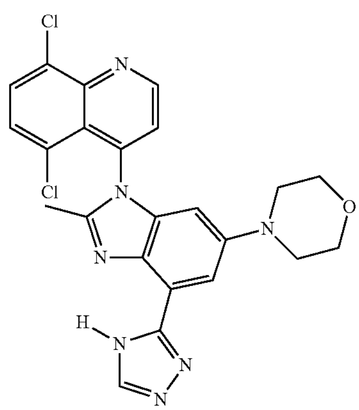 [SMILES: Cc1nc2c(-c3nnc[nH]3)cc(N3CCOCC3)cc2n1-c1ccnc2c(Cl)ccc(Cl)c12] |
| 123 | 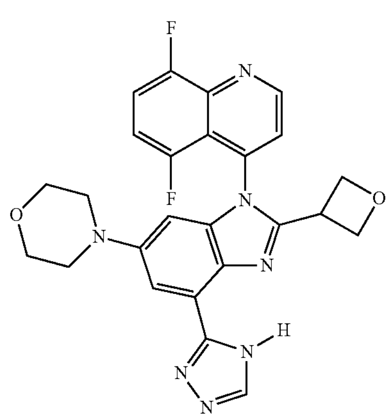 [SMILES: Fc1ccc(F)c2c(-n3c(C4COC4)nc4c(-c5nnc[nH]5)cc(N5CCOCC5)cc43)ccnc12] |
| 124 | |
| 125 | |
| 126 | |
| 127 | |

TABLE-continued
| Example | Structure |
|---------|-----------|
| 128 | 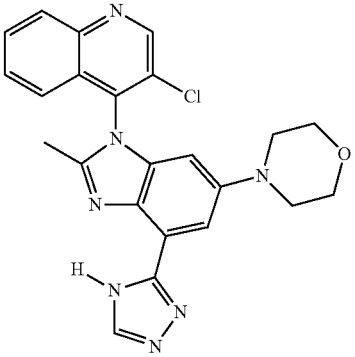 [SMILES: Cc1nc2c(-c3nnc[nH]3)cc(N3CCOCC3)cc2n1-c1c(Cl)cnc2ccccc12] |
| 129 | 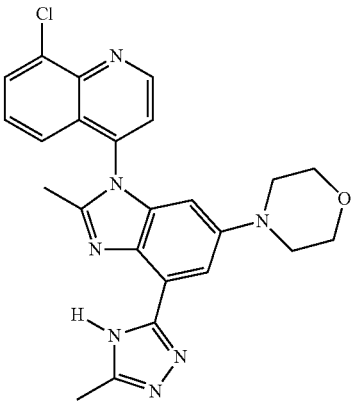 [SMILES: Cc1nnc(-c2cc(N3CCOCC3)cc3c2nc(C)n3-c2ccnc3c(F)cccc23)[nH]1] |
| 130 | 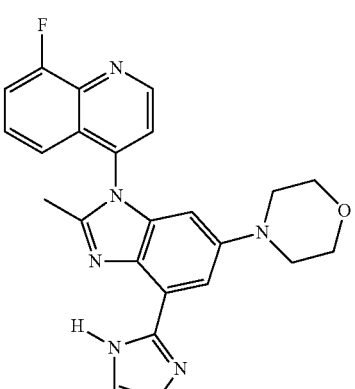 |
| 131 | 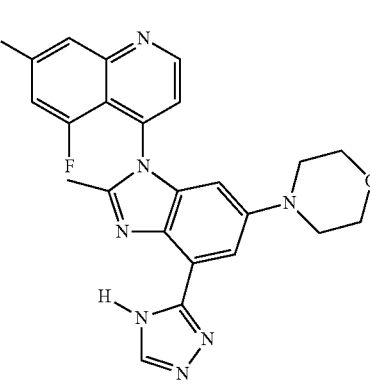 |
| 132 | 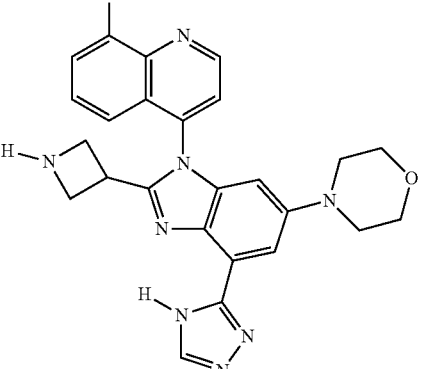 |
| 133 | 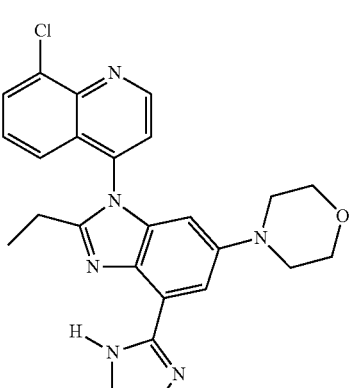 |
| 134 | 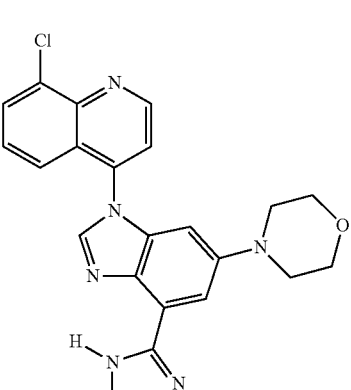 |

-continued
| Example | Structure |
|---------|-----------|
| 135 | 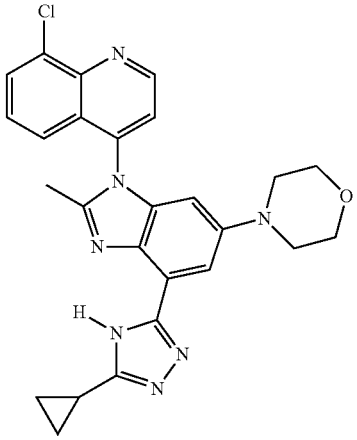 [SMILES: Cc1nc2c(-c3nnc(C4CC4)[nH]3)cc(N3CCOCC3)cc2n1-c1ccnc2c(Cl)cccc12] |
| 136 | 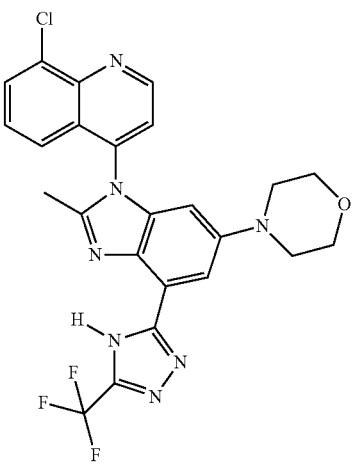 [SMILES: Cc1nc2c(-c3nnc(C(F)(F)F)[nH]3)cc(N3CCOCC3)cc2n1-c1ccnc2c(Cl)cccc12] |
| 137 | 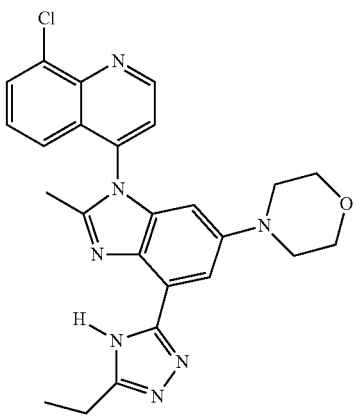 [SMILES: CCc1nnc(-c2cc(N3CCOCC3)cc3c2nc(C)n3-c2ccnc3c(Cl)cccc23)[nH]1] |
-continued
| Example | Structure |
|---------|-----------|
| 138 | 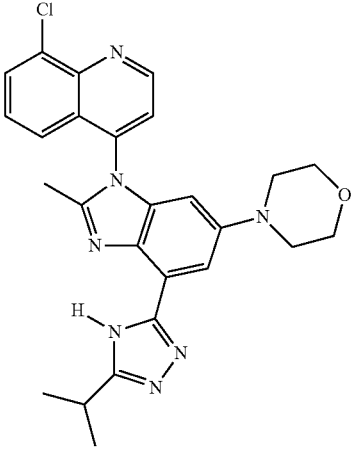 [SMILES: Cc1nc2c(-c3nnc(C(C)C)[nH]3)cc(N3CCOCC3)cc2n1-c1ccnc2c(Cl)cccc12] |
| 139 | 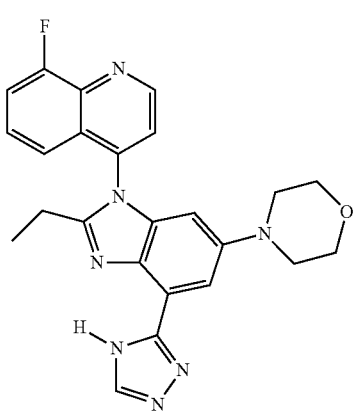 [SMILES: CCc1nc2c(-c3nnc[nH]3)cc(N3CCOCC3)cc2n1-c1ccnc2c(F)cccc12] |
| 140 | 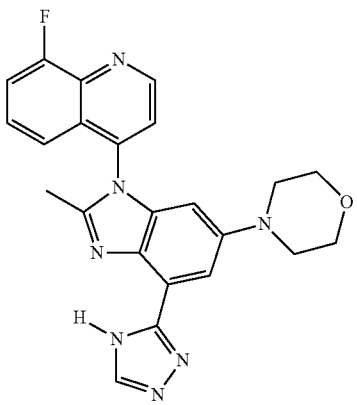 [SMILES: Cc1nc2c(-c3nnc[nH]3)cc(N3CCOCC3)cc2n1-c1ccnc2c(F)cccc12] |

-continued
| Example | Structure |
|---|---|
| 141 | 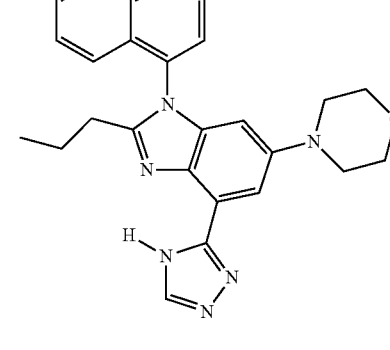 |
| 142 | 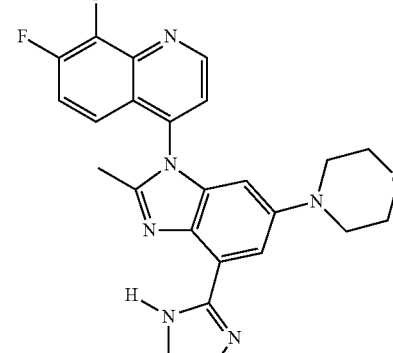 |
| 143 | 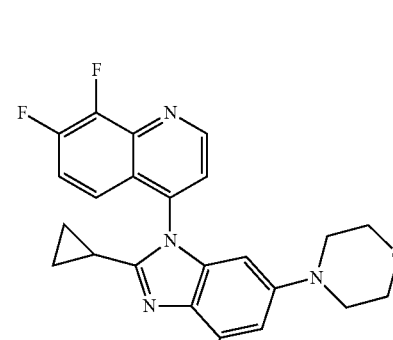 |
-continued
| Example | Structure |
|---|---|
| 144 | 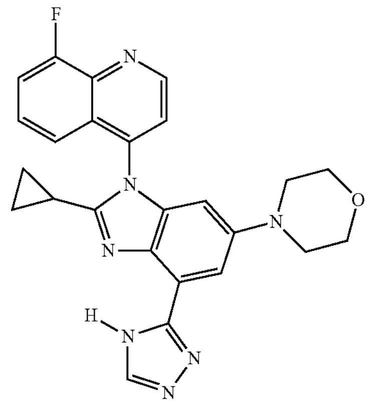 [SMILES: Fc1cccc2c(-n3c(C4CC4)nc4c(-c5nnc[nH]5)cc(N5CCOCC5)cc43)ccnc12] |
| 145 | 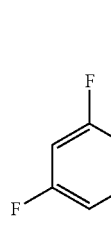 |
| 146 | 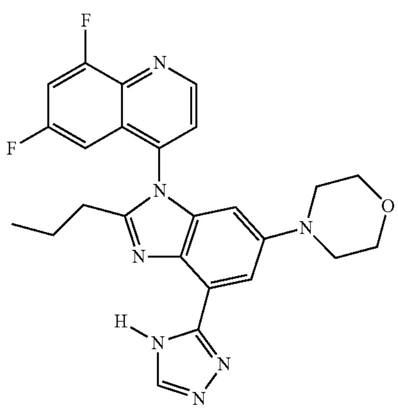 [SMILES: CCCc1nc2c(-c3nnc[nH]3)cc(N3CCOCC3)cc2n1-c1ccnc2c(F)cc(F)cc12] |
| 160 | 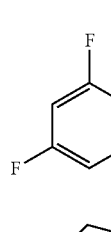 |

| Example | Structure |
|---|---|
| 161 | 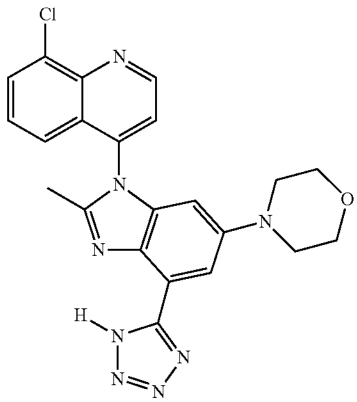 [SMILES: Cc1nc2c(-c3nnn[nH]3)cc(N3CCOCC3)cc2n1-c1ccnc2c(Cl)cccc12] |
| 162 | 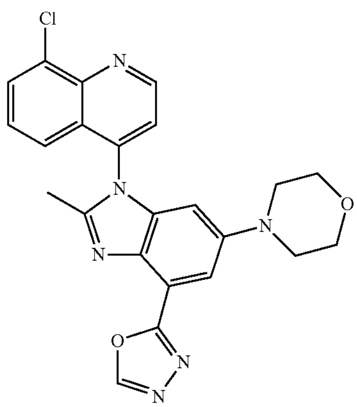 [SMILES: Cc1nc2c(-c3nnco3)cc(N3CCOCC3)cc2n1-c1ccnc2c(Cl)cccc12] |
| 163 | 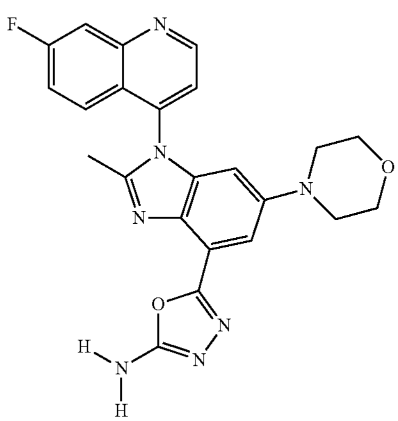 [SMILES: Cc1nc2c(-c3nnc(N)o3)cc(N3CCOCC3)cc2n1-c1ccnc2cc(F)ccc12] |
| 164 | |
| 165 | |
| 166 | |
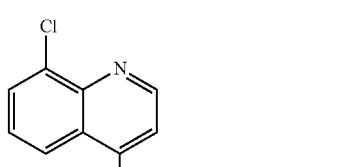
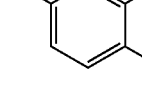

327
-continued
| Example | Structure |
|---|---|
| 167 | 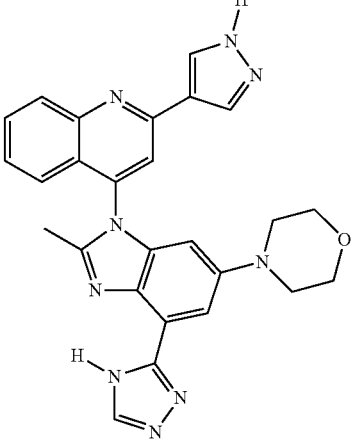 |
| 168 | 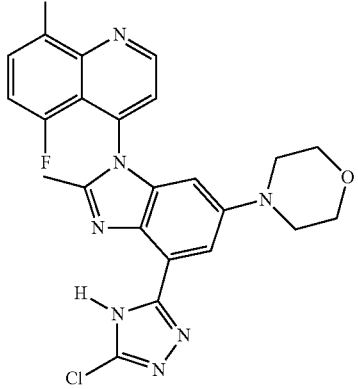 |
| 169 | 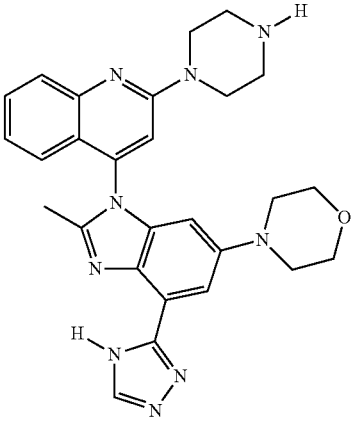 [SMILES: Cc1nc2c(-c3nnc[nH]3)cc(N3CCOCC3)cc2n1-c1cc(N2CCNCC2)nc2ccccc12] |
328
-continued
| Example | Structure |
|---|---|
| 170 | 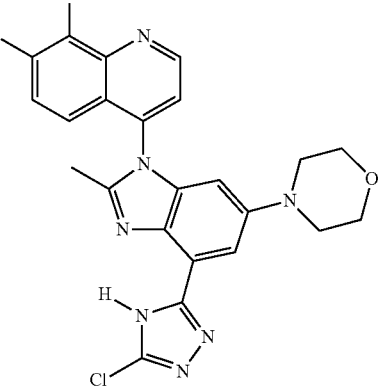 |
| 171 | 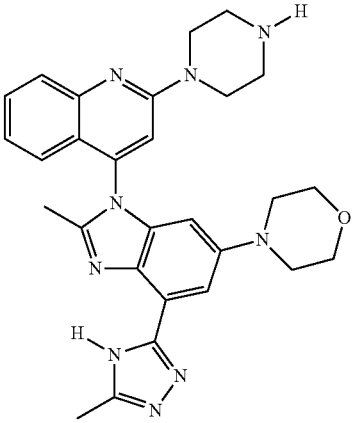 [SMILES: Cc1nnc(-c2cc(N3CCOCC3)cc3c2nc(C)n3-c2cc(N3CCNCC3)nc3ccccc23)[nH]1] |
| 172 | 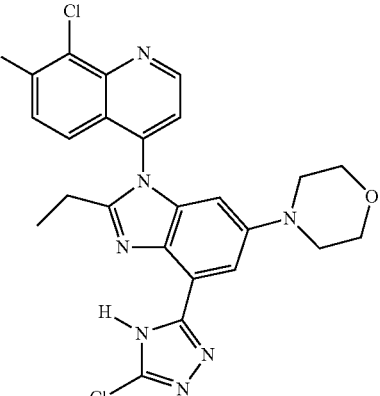 |

329
-continued
| Example | Structure |
|---------|-----------|
| 173 | 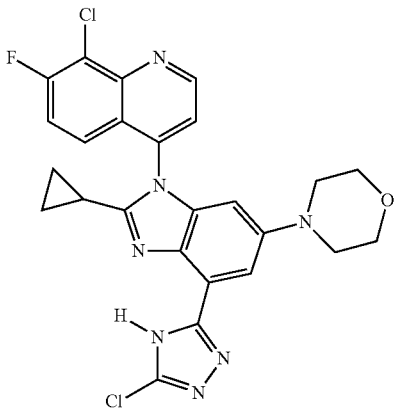 [SMILES: Fc1ccc2c(-n3c(C4CC4)nc4c(-c5nnc(Cl)[nH]5)cc(N5CCOCC5)cc43)ccnc2c1Cl] |
| 174 | 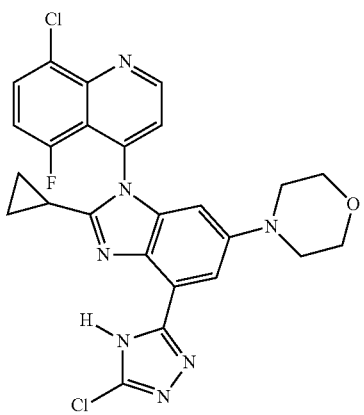 |
| 175 | 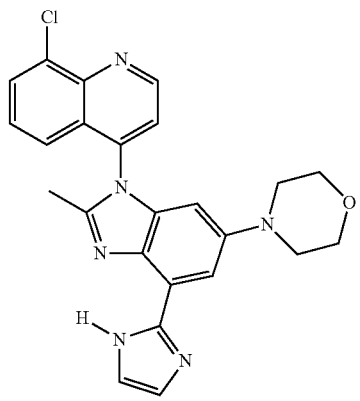 [SMILES: Cc1nc2c(-c3ncc[nH]3)cc(N3CCOCC3)cc2n1-c1ccnc2c(Cl)cccc12] |
330
-continued
| Example | Structure |
|---------|-----------|
| 176 | 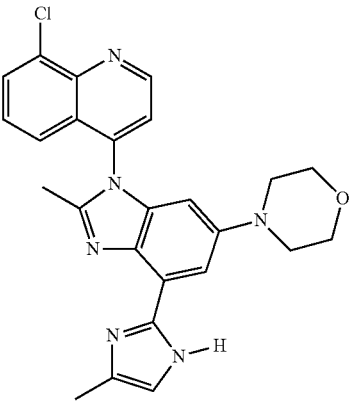 [SMILES: Cc1c[nH]c(-c2cc(N3CCOCC3)cc3c2nc(C)n3-c2ccnc3c(Cl)cccc23)n1] |
| 177 | 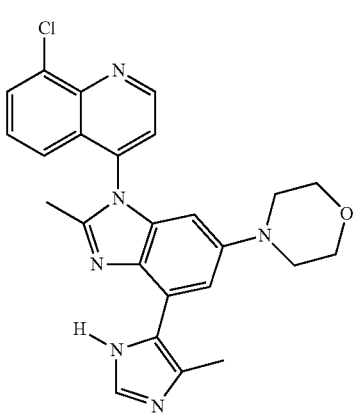 [SMILES: Cc1nc[nH]c1-c1cc(N2CCOCC2)cc2c1nc(C)n2-c1ccnc2c(Cl)cccc12] |
| 178 | 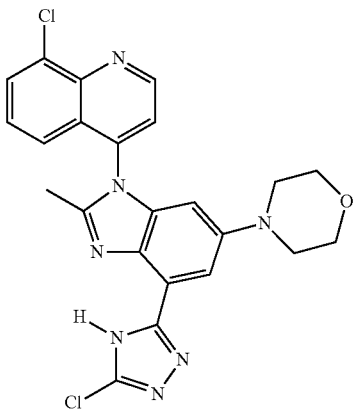 [SMILES: Cc1nc2c(-c3nnc(Cl)[nH]3)cc(N3CCOCC3)cc2n1-c1ccnc2c(Cl)cccc12] |

-continued

| Example | Structure |
|---------|-----------|
| 179 | 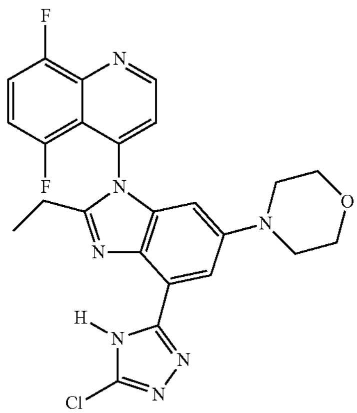 [SMILES: CCc1nc2c(-c3nnc(Cl)[nH]3)cc(N3CCOCC3)cc2n1-c1ccnc2c(F)ccc(F)c12] |
| 180 | 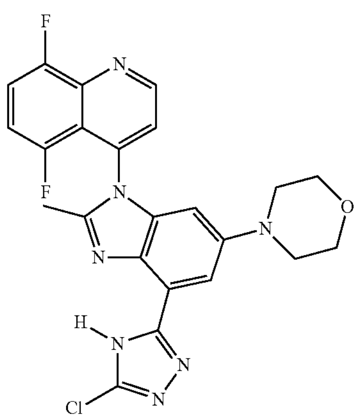 [SMILES: Cc1nc2c(-c3nnc(Cl)[nH]3)cc(N3CCOCC3)cc2n1-c1ccnc2c(F)ccc(F)c12] |
| 181 | 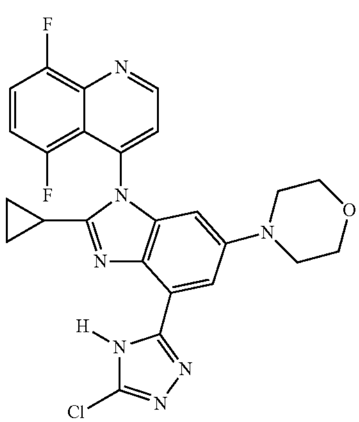 [SMILES: Fc1ccc(F)c2c(-n3c(C4CC4)nc4c(-c5nnc(Cl)[nH]5)cc(N5CCOCC5)cc43)ccnc12] |

-continued

| Example | Structure |
|---------|-----------|
| 182 | 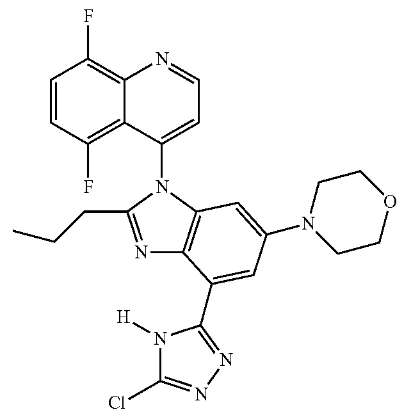 [SMILES: CCCc1nc2c(-c3nnc(Cl)[nH]3)cc(N3CCOCC3)cc2n1-c1ccnc2c(F)ccc(F)c12] |
| 183 | 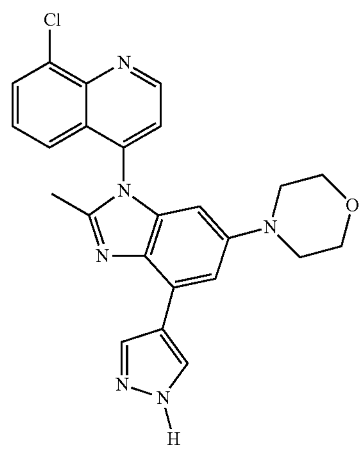 [SMILES: Cc1nc2c(-c3cn[nH]c3)cc(N3CCOCC3)cc2n1-c1ccnc2c(Cl)cccc12] |
| 198 | 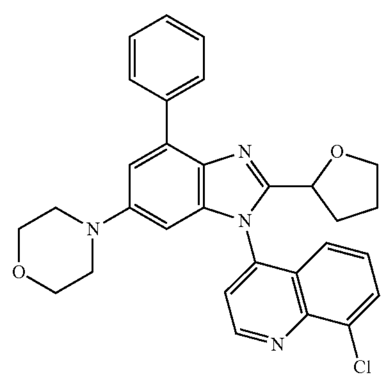 [SMILES: Clc1cccc2c(-n3c(C4CCCO4)nc4c(-c5ccccc5)cc(N5CCOCC5)cc43)ccnc12] |
| 199 | 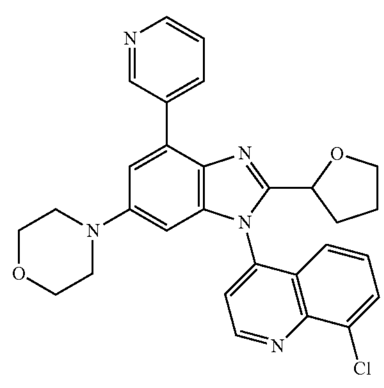 [SMILES: Clc1cccc2c(-n3c(C4CCCO4)nc4c(-c5cccnc5)cc(N5CCOCC5)cc43)ccnc12] |

| Example | Structure |
|---------|-----------|
| 200 | 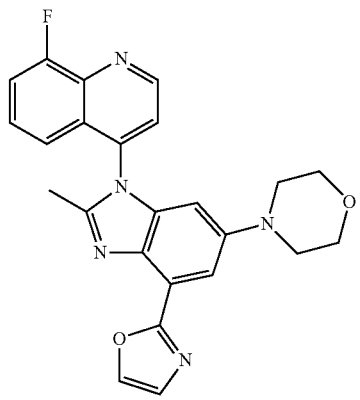 [SMILES: Cc1nc2c(-c3ncco3)cc(N3CCOCC3)cc2n1-c1ccnc2c(F)cccc12] |
| 201 | 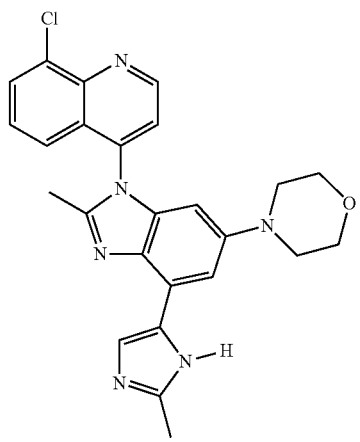 [SMILES: Cc1ncc(-c2cc(N3CCOCC3)cc3c2nc(C)n3-c2ccnc3c(Cl)cccc23)[nH]1] |
| 202 | 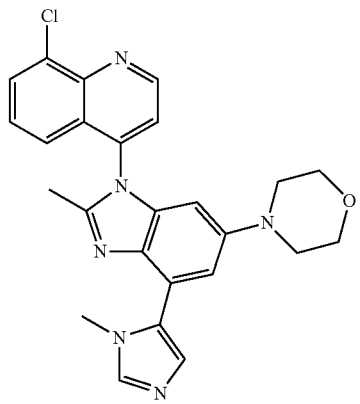 [SMILES: Cc1nc2c(-c3cncn3C)cc(N3CCOCC3)cc2n1-c1ccnc2c(Cl)cccc12] |
| Example | Structure |
|---------|-----------|
| 203 | 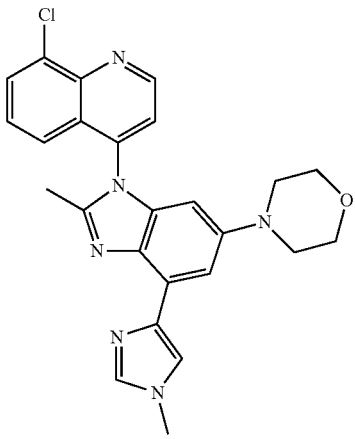 [SMILES: Cc1nc2c(-c3cn(C)cn3)cc(N3CCOCC3)cc2n1-c1ccnc2c(Cl)cccc12] |
| 204 | 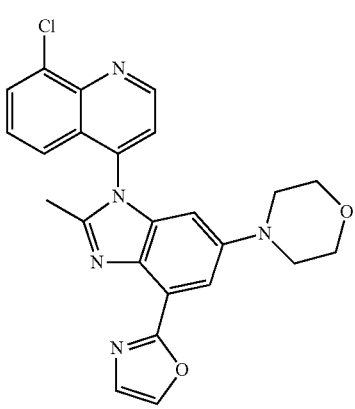 [SMILES: Cc1nc2c(-c3ncco3)cc(N3CCOCC3)cc2n1-c1ccnc2c(Cl)cccc12] |
| 205 | 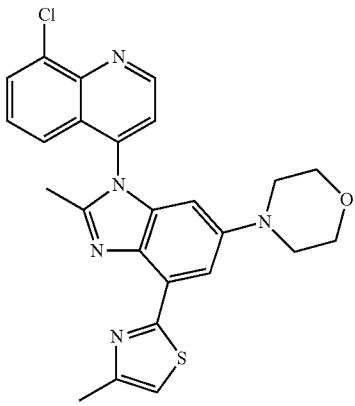 [SMILES: Cc1csc(-c2cc(N3CCOCC3)cc3c2nc(C)n3-c2ccnc3c(Cl)cccc23)n1] |

| Example | Structure |
|---|---|
| 206 | (8-fluoroquinolin-4-yl on N1, 2-ethyl, 6-morpholino benzimidazole, 4-(2-methyl-1H-imidazol-5-yl); 5-F on quinoline) |
| 207 | (8-chloroquinolin-4-yl, 2-propyl, 6-morpholino, 4-(1H-imidazol-5-yl) benzimidazole) |
| 208 | (8-fluoroquinolin-4-yl, 2-methyl, 6-morpholino, 4-(1H-imidazol-5-yl) benzimidazole) |
| 209 | (8-fluoroquinolin-4-yl, 2-ethyl, 6-morpholino, 4-(1H-imidazol-5-yl) benzimidazole) |
| 210 | (8-fluoro-2-methylquinolin-4-yl, 2-methyl, 6-morpholino, 4-(1H-imidazol-5-yl) benzimidazole) |
| 211 | (8-fluoro-2-methylquinolin-4-yl, 2-ethyl, 6-morpholino, 4-(1H-imidazol-5-yl) benzimidazole) |
| 212 | (8-chloroquinolin-4-yl, 2-propyl, 6-morpholino, 4-(2-methyl-1H-imidazol-5-yl) benzimidazole) |

| Example | Structure |
|---|---|
| 213 | 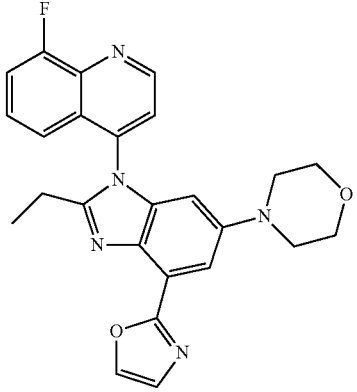 [SMILES: CCc1nc2c(-c3ncco3)cc(N3CCOCC3)cc2n1-c1ccnc2c(F)cccc12] |
| 214 | 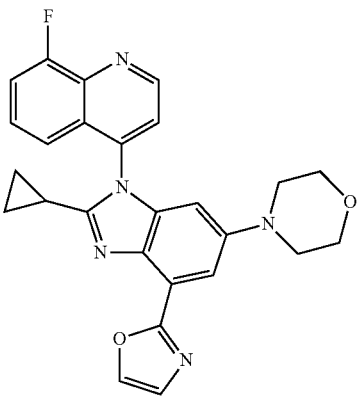 [SMILES: Fc1cccc2c(-n3c(C4CC4)nc4c(-c5ncco5)cc(N5CCOCC5)cc43)ccnc12] |
| 215 | 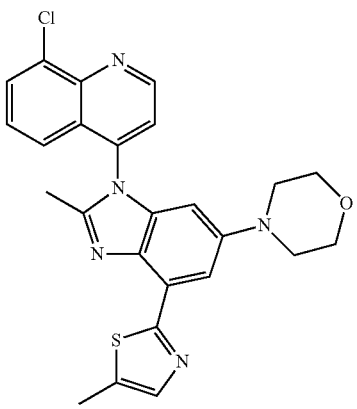 [SMILES: Cc1cnc(-c2cc(N3CCOCC3)cc3c2nc(C)n3-c2ccnc3c(Cl)cccc23)s1] |
| Example | Structure |
|---|---|
| 216 | 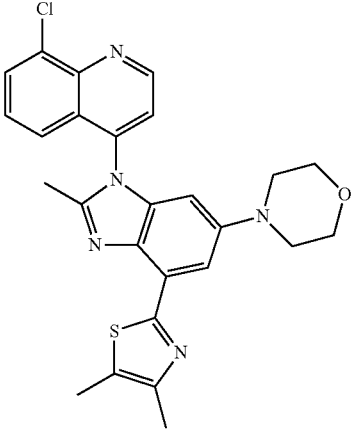 [SMILES: Cc1nc(-c2cc(N3CCOCC3)cc3c2nc(C)n3-c2ccnc3c(Cl)cccc23)sc1C] |
| 217 | 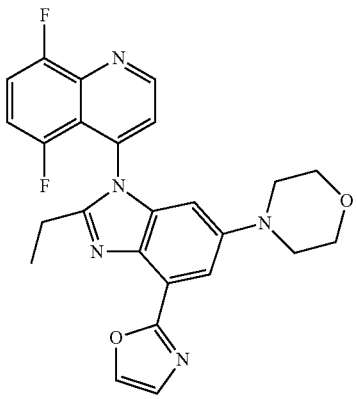 [SMILES: CCc1nc2c(-c3ncco3)cc(N3CCOCC3)cc2n1-c1ccnc2c(F)ccc(F)c12] |
| 218 | 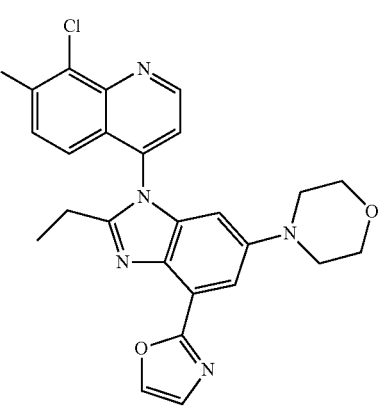 |

| Example | Structure |
|---|---|
| 219 | 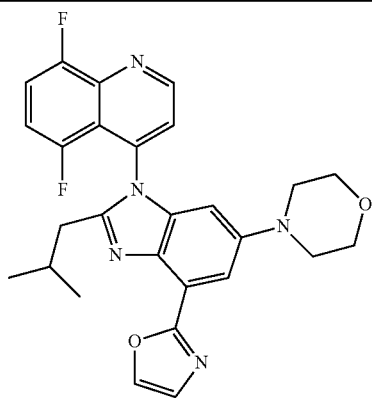 |
| 220 | 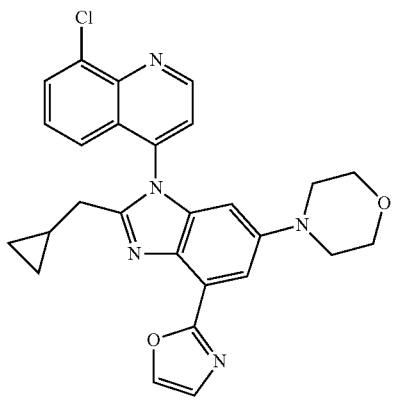 |
| 221 | 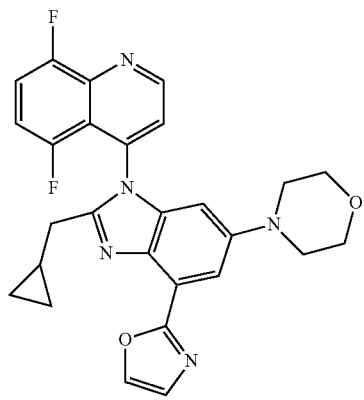 [SMILES: Fc1ccc(F)c2c(-n3c(CC4CC4)nc4c(-c5ncco5)cc(N5CCOCC5)cc43)ccnc12] |
| 222 | 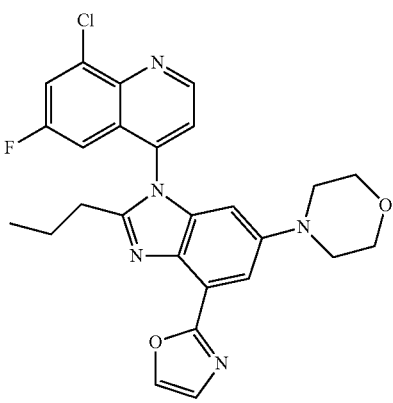 [SMILES: CCCc1nc2c(-c3ncco3)cc(N3CCOCC3)cc2n1-c1ccnc2c(Cl)cc(F)cc12] |
| 223 | 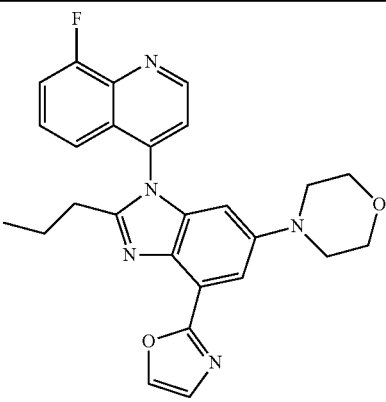 |
| 224 | 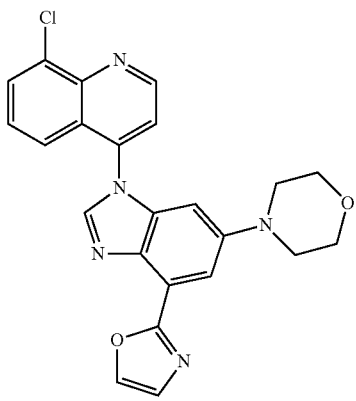 [SMILES: Clc1cccc2c(-n3cnc4c(-c5ncco5)cc(N5CCOCC5)cc43)ccnc12] |
| 225 | 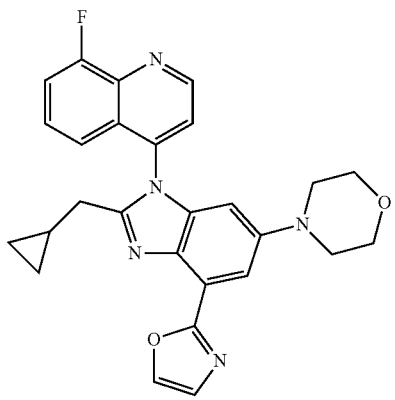 [SMILES: Fc1cccc2c(-n3c(CC4CC4)nc4c(-c5ncco5)cc(N5CCOCC5)cc43)ccnc12] |
| 226 | 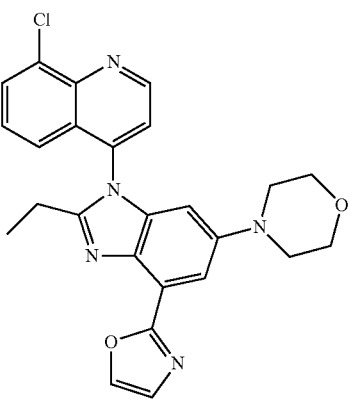 |

-continued

| Example | Structure |
|---|---|
| 227 | (8-chloroquinolin-4-yl, 2-propyl benzimidazole, 6-morpholino, 4-oxazol-2-yl) |
| 228 | (8-chloroquinolin-4-yl, 2-cyclopropyl benzimidazole, 6-morpholino, 4-oxazol-2-yl) |
| 229 | (5,8-difluoroquinolin-4-yl, 2-methyl benzimidazole, 6-morpholino, 4-oxazol-2-yl) |
| 230 | (5,8-difluoroquinolin-4-yl, 2-propyl benzimidazole, 6-morpholino, 4-oxazol-2-yl) |
| 231 | (5,8-difluoroquinolin-4-yl, 2-cyclopropyl benzimidazole, 6-morpholino, 4-oxazol-2-yl) |
| 232 | (8-fluoroquinolin-4-yl, 2-ethyl benzimidazole, 6-morpholino, 4-(4-methylthiazol-2-yl)) |
| 233 | (5,8-difluoroquinolin-4-yl, 2-methyl benzimidazole, 6-morpholino, 4-(4-methylthiazol-2-yl)) |
| 234 | (8-chloroquinolin-4-yl, 2-cyclopropyl benzimidazole, 6-morpholino, 4-(4-methylthiazol-2-yl)) |

| Example | Structure |
|---|---|
| 235 | 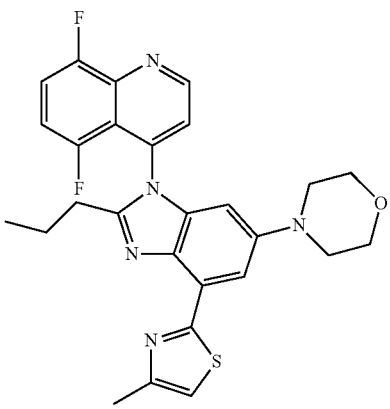 [SMILES: CCCc1nc2c(-c3nc(C)cs3)cc(N3CCOCC3)cc2n1-c1ccnc2c(F)ccc(F)c12] |
| 236 | 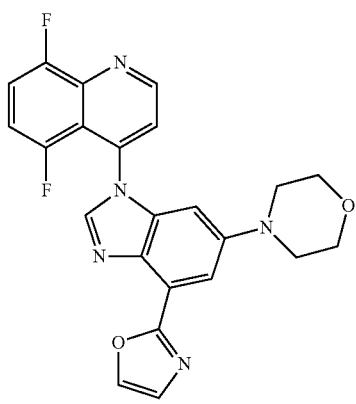 [SMILES: Fc1ccc(F)c2c(-n3cnc4c(-c5ncco5)cc(N5CCOCC5)cc43)ccnc12] |
| 237 | 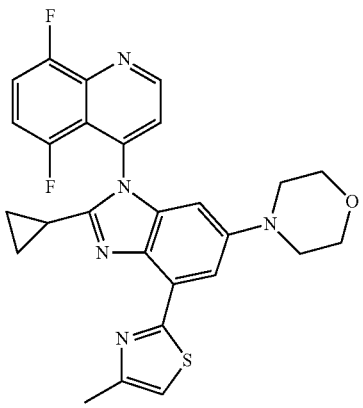 [SMILES: Cc1csc(-c2cc(N3CCOCC3)cc3c2nc(C2CC2)n3-c2ccnc3c(F)ccc(F)c23)n1] |
| Example | Structure |
|---|---|
| 238 | 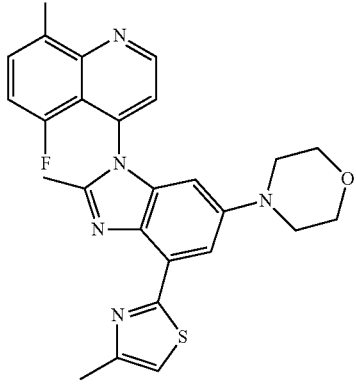 |
| 239 | 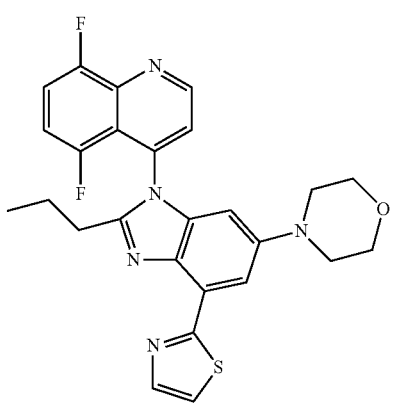 [SMILES: CCCc1nc2c(-c3nccs3)cc(N3CCOCC3)cc2n1-c1ccnc2c(F)ccc(F)c12] |
| 240 | 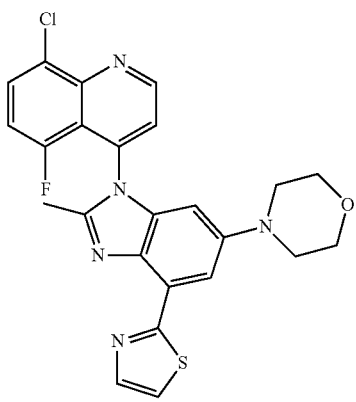 [SMILES: Cc1nc2c(-c3nccs3)cc(N3CCOCC3)cc2n1-c1ccnc2c(Cl)ccc(F)c12] |
| 241 | 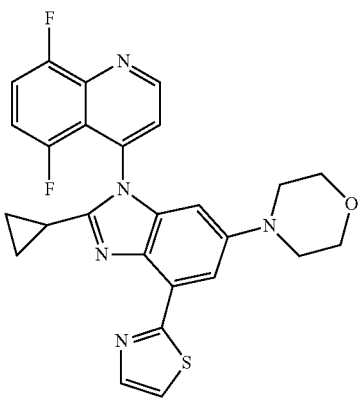 [SMILES: Fc1ccc(F)c2c(-n3c(C4CC4)nc4c(-c5nccs5)cc(N5CCOCC5)cc43)ccnc12] |

345
-continued
| Example | Structure |
|---|---|
| 242 | 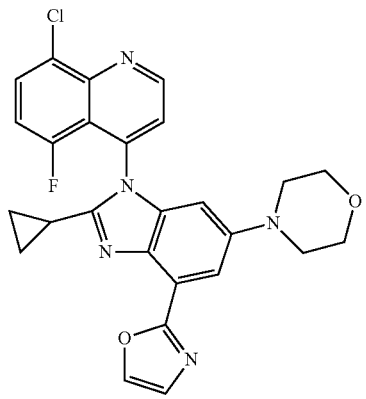 |
| 243 | 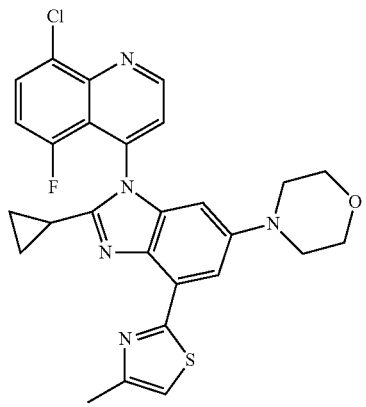 [SMILES: Cc1csc(-c2cc(N3CCOCC3)cc3c2nc(C2CC2)n3-c2ccnc3c(Cl)ccc(F)c23)n1] |
| 244 | 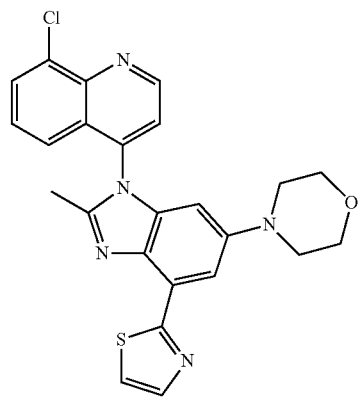 |
346
-continued
| Example | Structure |
|---|---|
| 245 | 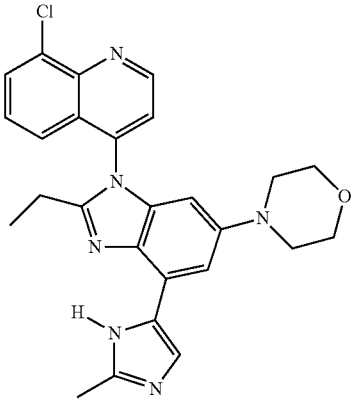 [SMILES: CCc1nc2c(-c3cnc(C)[nH]3)cc(N3CCOCC3)cc2n1-c1ccnc2c(Cl)cccc12] |
| 246 | 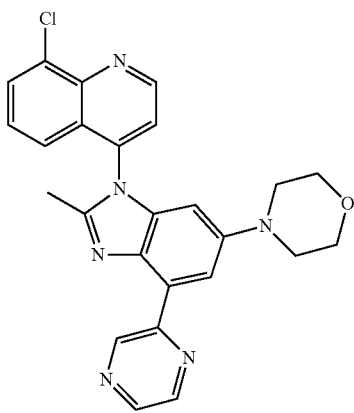 [SMILES: Cc1nc2c(-c3cnccn3)cc(N3CCOCC3)cc2n1-c1ccnc2c(Cl)cccc12] |
| 260 | 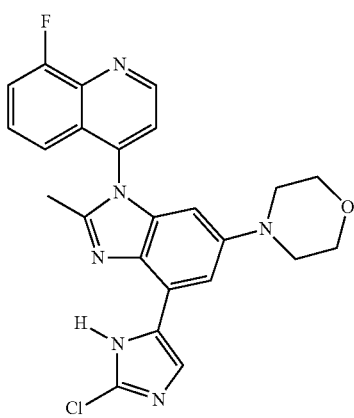 [SMILES: Cc1nc2c(-c3cnc(Cl)[nH]3)cc(N3CCOCC3)cc2n1-c1ccnc2c(F)cccc12] |

-continued
| Example | Structure |
|---------|-----------|
| 261 | 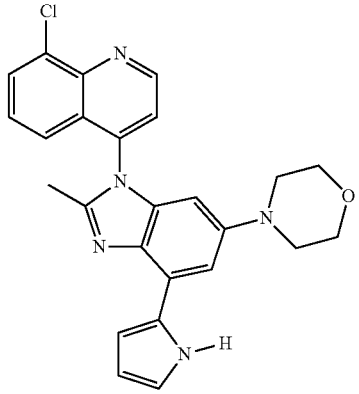 [SMILES: Cc1nc2c(-c3ccc[nH]3)cc(N3CCOCC3)cc2n1-c1ccnc2c(Cl)cccc12] |
| 262 | 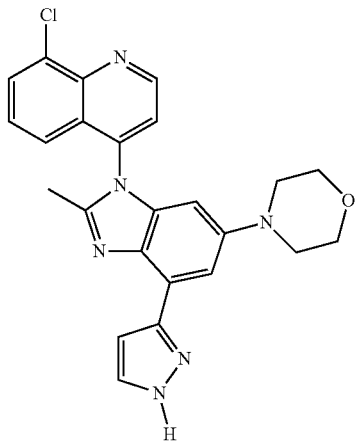 [SMILES: Cc1nc2c(-c3cc[nH]n3)cc(N3CCOCC3)cc2n1-c1ccnc2c(Cl)cccc12] |
| 263 | 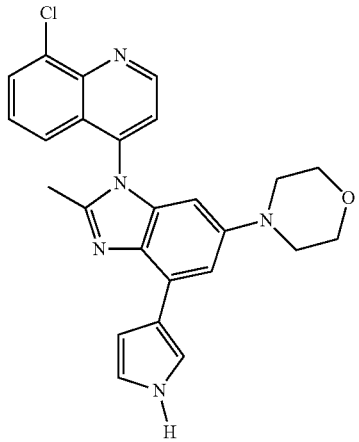 [SMILES: Cc1nc2c(-c3cc[nH]c3)cc(N3CCOCC3)cc2n1-c1ccnc2c(Cl)cccc12] |
-continued
| Example | Structure |
|---------|-----------|
| 264 | 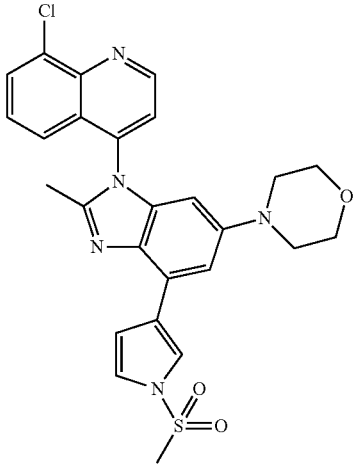 [SMILES: Cc1nc2c(-c3ccn(S(C)(=O)=O)c3)cc(N3CCOCC3)cc2n1-c1ccnc2c(Cl)cccc12] |
| 265 | 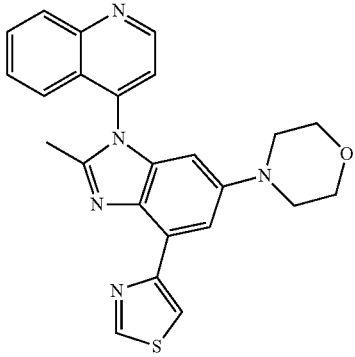 [SMILES: Cc1nc2c(-c3cscn3)cc(N3CCOCC3)cc2n1-c1ccnc2ccccc12] |
| 266 | 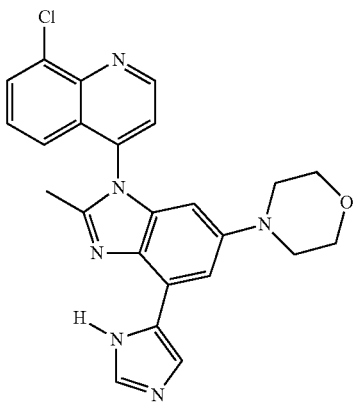 [SMILES: Cc1nc2c(-c3cnc[nH]3)cc(N3CCOCC3)cc2n1-c1ccnc2c(Cl)cccc12] |

-continued
| Example | Structure |
|---|---|
| 267 | 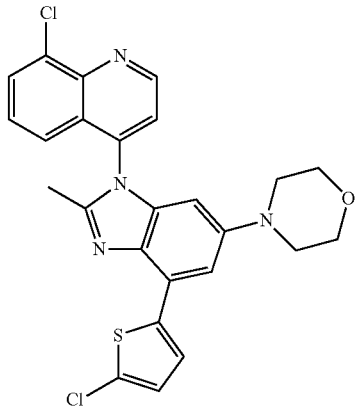 [SMILES: Cc1nc2c(-c3ccc(Cl)s3)cc(N3CCOCC3)cc2n1-c1ccnc2c(Cl)cccc12] |
| 268 | 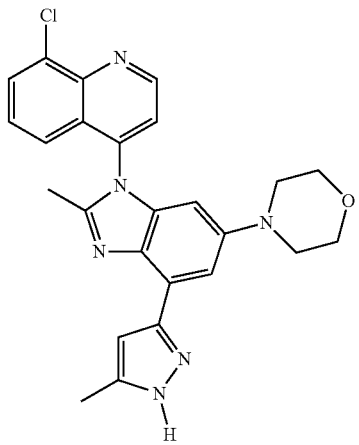 [SMILES: Cc1cc(-c2cc(N3CCOCC3)cc3c2nc(C)n3-c2ccnc3c(Cl)cccc23)n[nH]1] |
| 269 | 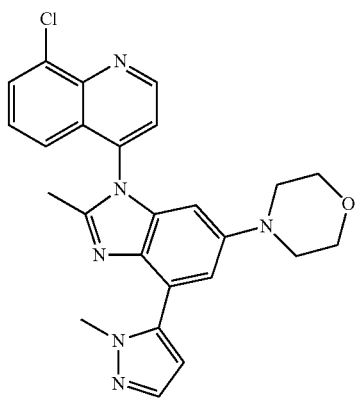 [SMILES: Cc1nc2c(-c3ccnn3C)cc(N3CCOCC3)cc2n1-c1ccnc2c(Cl)cccc12] |
-continued
| Example | Structure |
|---|---|
| 270 | 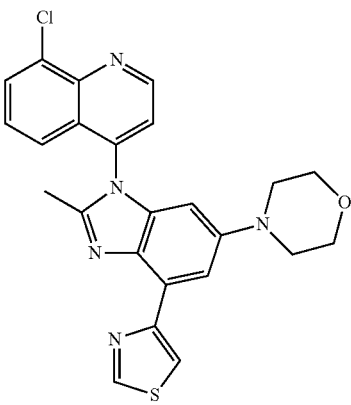 [SMILES: Cc1nc2c(-c3cscn3)cc(N3CCOCC3)cc2n1-c1ccnc2c(Cl)cccc12] |
| 271 | 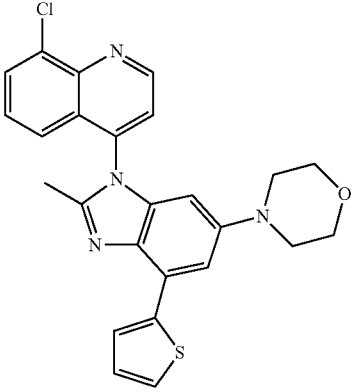 [SMILES: Cc1nc2c(-c3cccs3)cc(N3CCOCC3)cc2n1-c1ccnc2c(Cl)cccc12] |
| 272 | 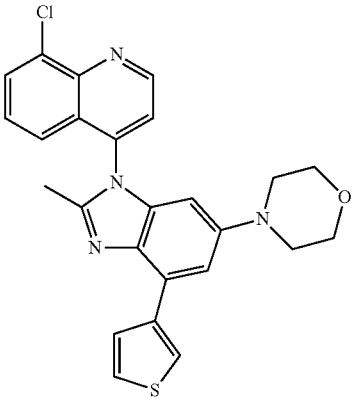 [SMILES: Cc1nc2c(-c3ccsc3)cc(N3CCOCC3)cc2n1-c1ccnc2c(Cl)cccc12] |

| Example | Structure |
|---|---|
| 273 | 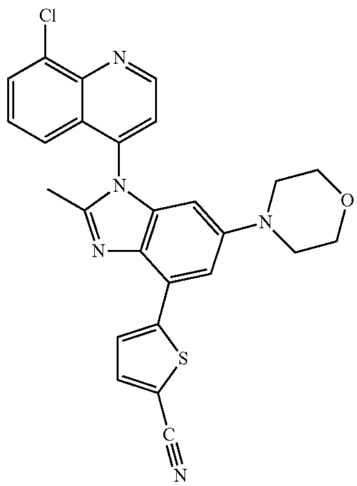 [SMILES: Cc1nc2c(-c3ccc(C#N)s3)cc(N3CCOCC3)cc2n1-c1ccnc2c(Cl)cccc12] |
| 274 | 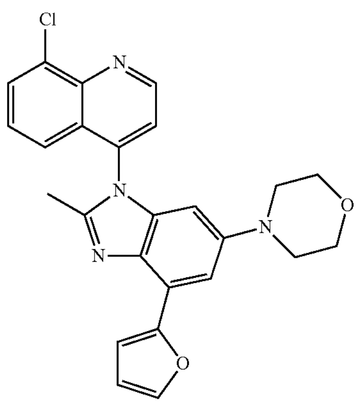 [SMILES: Cc1nc2c(-c3ccco3)cc(N3CCOCC3)cc2n1-c1ccnc2c(Cl)cccc12] |
| 275 | 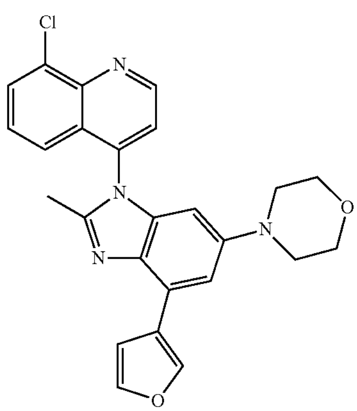 [SMILES: Cc1nc2c(-c3ccoc3)cc(N3CCOCC3)cc2n1-c1ccnc2c(Cl)cccc12] |
| 276 | |
| 277 | |
| 278 | |
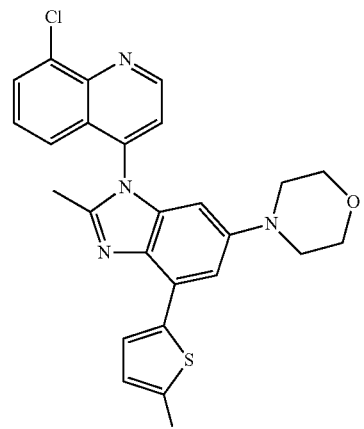

353
-continued
| Example | Structure |
|---------|-----------|
| 279 | 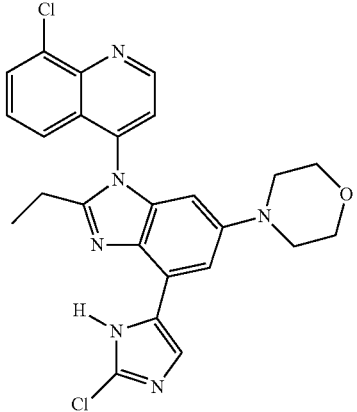 [SMILES: CCc1nc2c(-c3cnc(Cl)[nH]3)cc(N3CCOCC3)cc2n1-c1ccnc2c(Cl)cccc12] |
| 280 | 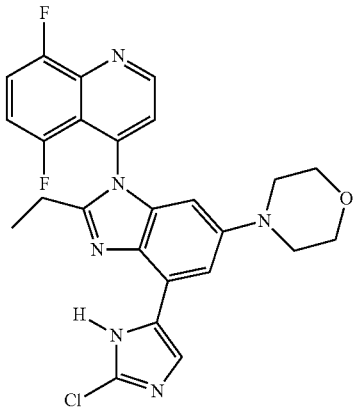 [SMILES: CCc1nc2c(-c3cnc(Cl)[nH]3)cc(N3CCOCC3)cc2n1-c1ccnc2c(F)ccc(F)c12] |
| 281 | 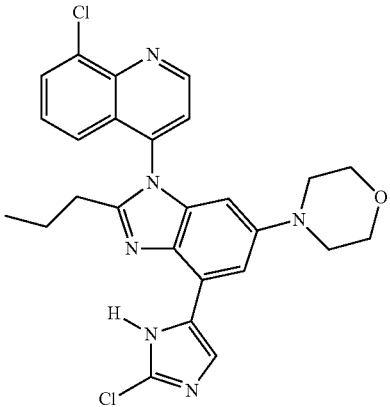 |
354
-continued
| Example | Structure |
|---------|-----------|
| 282 | 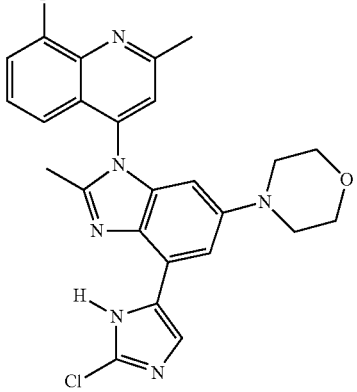 |
| 283 | 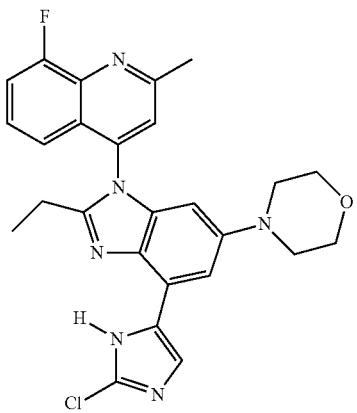 [SMILES: CCc1nc2c(-c3cnc(Cl)[nH]3)cc(N3CCOCC3)cc2n1-c1cc(C)nc2c(F)cccc12] |
| 284 | 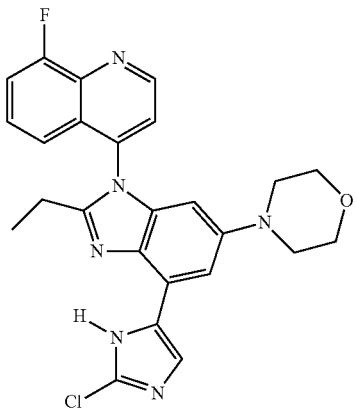 [SMILES: CCc1nc2c(-c3cnc(Cl)[nH]3)cc(N3CCOCC3)cc2n1-c1ccnc2c(F)cccc12] |

355
-continued
| Example | Structure |
|---|---|
| 285 | 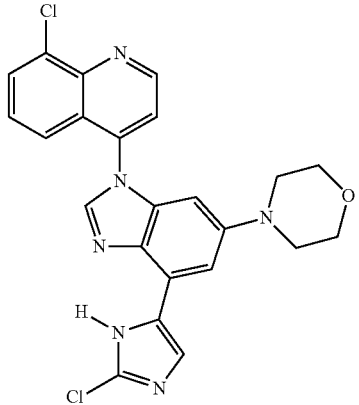 |
| 286 | 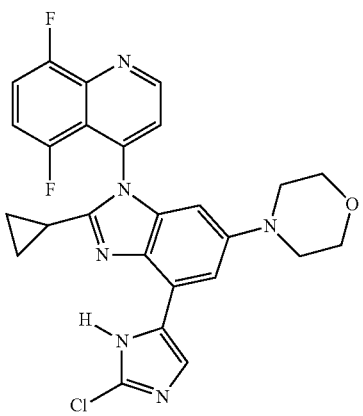 [SMILES: Fc1ccc(F)c2c(-n3c(C4CC4)nc4c(-c5cnc(Cl)[nH]5)cc(N5CCOCC5)cc43)ccnc12] |
| 287 | 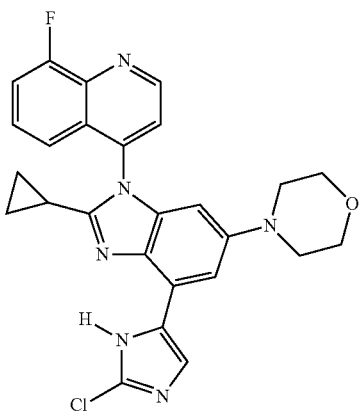 [SMILES: Fc1cccc2c(-n3c(C4CC4)nc4c(-c5cnc(Cl)[nH]5)cc(N5CCOCC5)cc43)ccnc12] |
356
-continued
| Example | Structure |
|---|---|
| 288 | 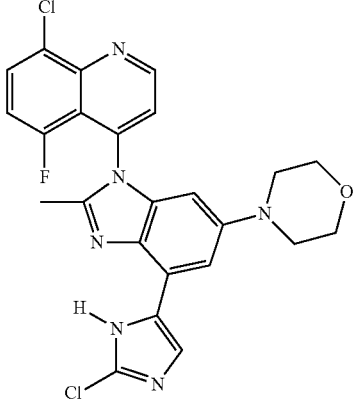 [SMILES: Cc1nc2c(-c3cnc(Cl)[nH]3)cc(N3CCOCC3)cc2n1-c1ccnc2c(Cl)ccc(F)c12] |
| 289 | 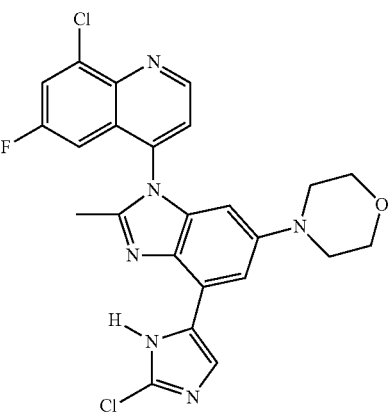 [SMILES: Cc1nc2c(-c3cnc(Cl)[nH]3)cc(N3CCOCC3)cc2n1-c1ccnc2c(Cl)cc(F)cc12] |
| 290 | 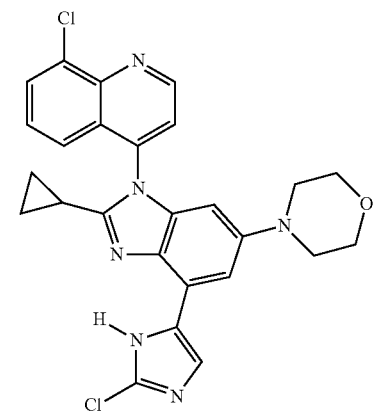 [SMILES: Clc1ncc(-c2cc(N3CCOCC3)cc3c2nc(C2CC2)n3-c2ccnc3c(Cl)cccc23)[nH]1] |

-continued

| Example | Structure |
|---------|-----------|
| 291 | 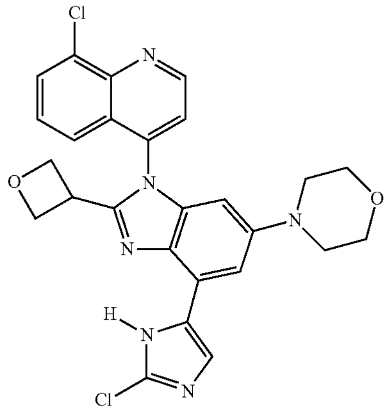 [SMILES: Clc1ncc(-c2cc(N3CCOCC3)cc3c2nc(C2COC2)n3-c2ccnc3c(Cl)cccc23)[nH]1] |
| 292 | 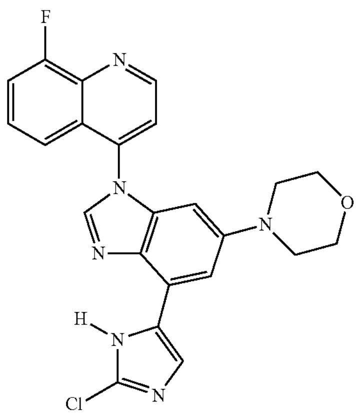 [SMILES: Fc1cccc2c(-n3cnc4c(-c5cnc(Cl)[nH]5)cc(N5CCOCC5)cc43)ccnc12] |
| 293 | 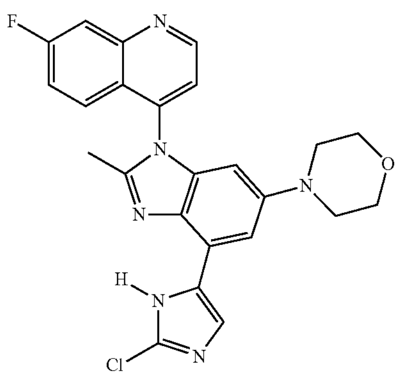 [SMILES: Cc1nc2c(-c3cnc(Cl)[nH]3)cc(N3CCOCC3)cc2n1-c1ccnc2cc(F)ccc12] |
| 294 | 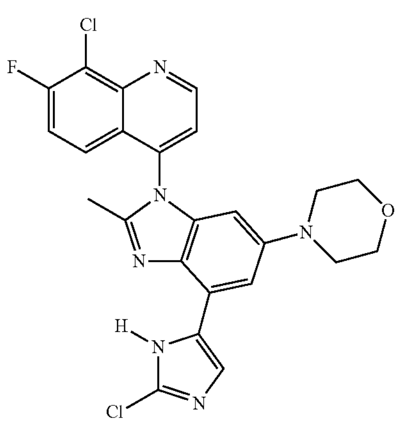 [SMILES: Cc1nc2c(-c3cnc(Cl)[nH]3)cc(N3CCOCC3)cc2n1-c1ccnc2c(Cl)c(F)ccc12] |
| 295 | |
| 296 | |
| 297 | |

TABLE-continued
| Example | Structure |
|---|---|
| 298 | 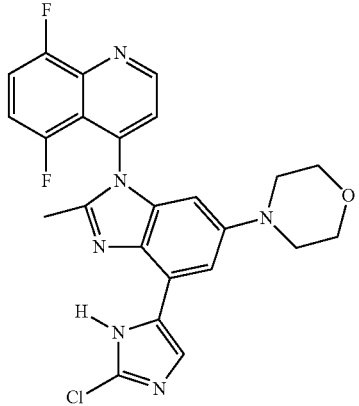 [SMILES: Cc1nc2c(-c3cnc(Cl)[nH]3)cc(N3CCOCC3)cc2n1-c1ccnc2c(F)ccc(F)c12] |
| 299 | 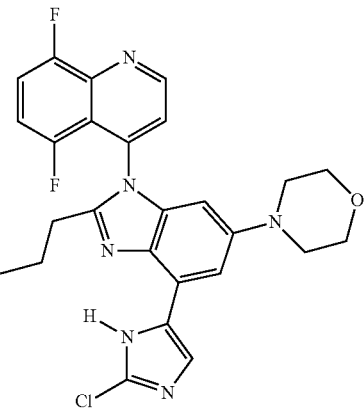 [SMILES: CCCc1nc2c(-c3cnc(Cl)[nH]3)cc(N3CCOCC3)cc2n1-c1ccnc2c(F)ccc(F)c12] |
| 300 | 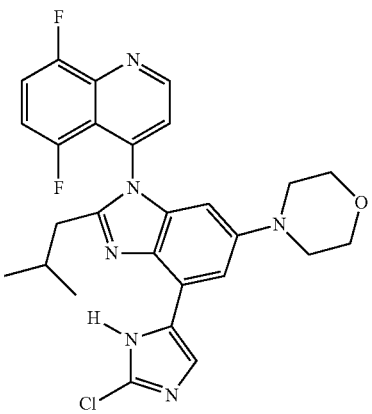 [SMILES: CC(C)Cc1nc2c(-c3cnc(Cl)[nH]3)cc(N3CCOCC3)cc2n1-c1ccnc2c(F)ccc(F)c12] |
TABLE-continued
| Example | Structure |
|---|---|
| 301 | 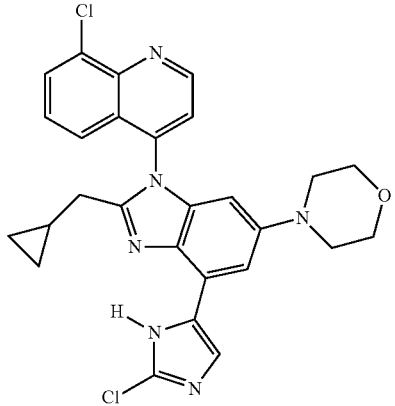 [SMILES: Clc1ncc(-c2cc(N3CCOCC3)cc3c2nc(CC2CC2)n3-c2ccnc3c(Cl)cccc23)[nH]1] |
| 302 | 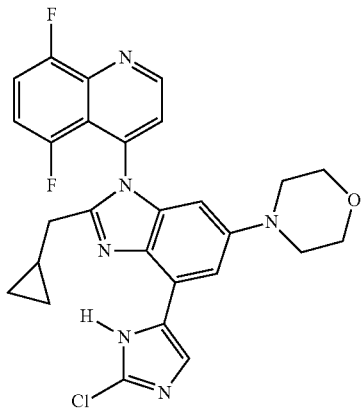 [SMILES: Fc1ccc(F)c2c(-n3c(CC4CC4)nc4c(-c5cnc(Cl)[nH]5)cc(N5CCOCC5)cc43)ccnc12] |
| 303 | 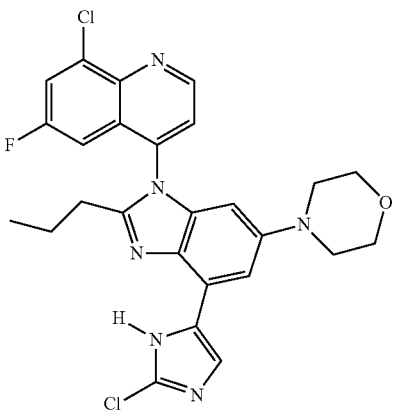 [SMILES: CCCc1nc2c(-c3cnc(Cl)[nH]3)cc(N3CCOCC3)cc2n1-c1ccnc2c(Cl)cc(F)cc12] |

| Example | Structure |
|---|---|
| 304 | 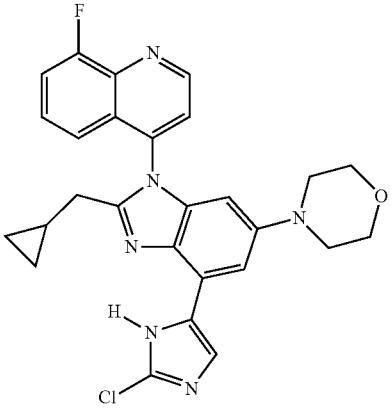 [SMILES: Fc1cccc2c(-n3c(CC4CC4)nc4c(-c5cnc(Cl)[nH]5)cc(N5CCOCC5)cc43)ccnc12] |
| 305 | 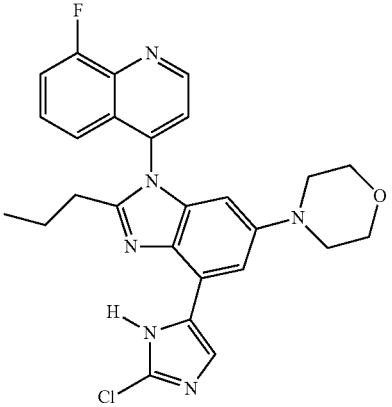 [SMILES: CCCc1nc2c(-c3cnc(Cl)[nH]3)cc(N3CCOCC3)cc2n1-c1ccnc2c(F)cccc12] |
| 306 | 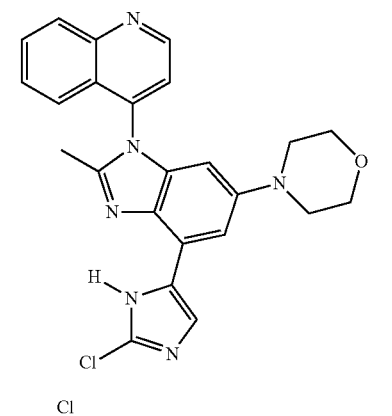 |
| 307 | 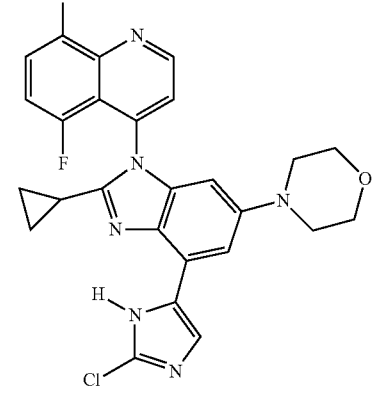 |
| 308 | 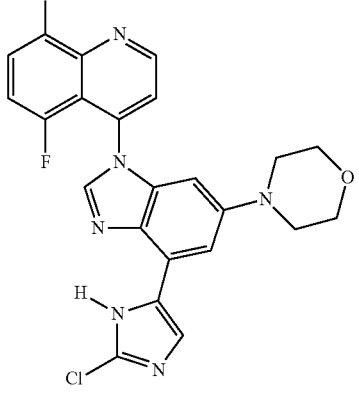 |
| 309 | 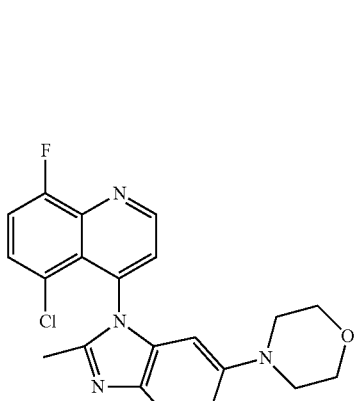 |
| 310 | 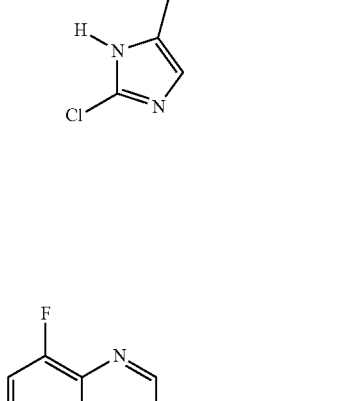 |

US 10,214,519 B2
| Example | Structure |
|---|---|
| 311 | 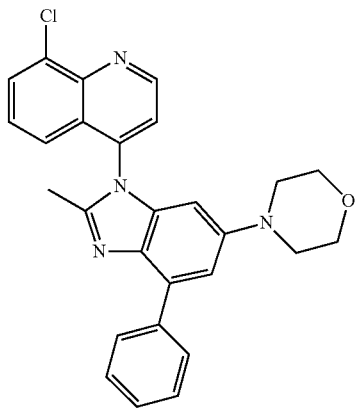 [SMILES: Cc1nc2c(-c3ccccc3)cc(N3CCOCC3)cc2n1-c1ccnc2c(Cl)cccc12] |
| 312 | 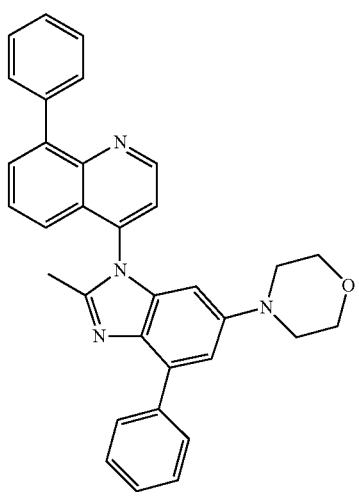 [SMILES: Cc1nc2c(-c3ccccc3)cc(N3CCOCC3)cc2n1-c1ccnc2c(-c3ccccc3)cccc12] |
| 313 | 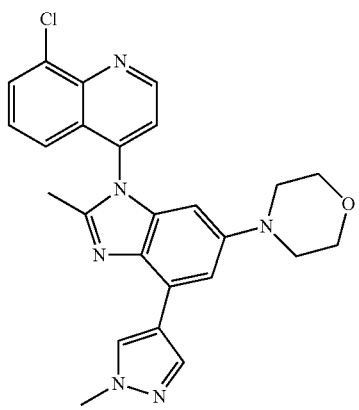 [SMILES: Cc1nc2c(-c3cnn(C)c3)cc(N3CCOCC3)cc2n1-c1ccnc2c(Cl)cccc12] |
| Example | Structure |
|---|---|
| 314 | 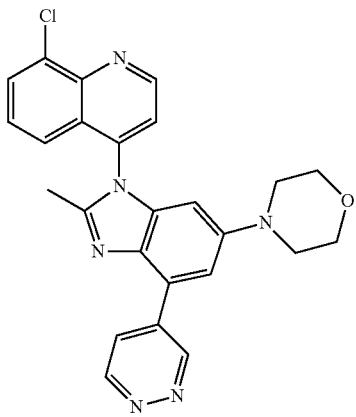 [SMILES: Cc1nc2c(-c3ccnnc3)cc(N3CCOCC3)cc2n1-c1ccnc2c(Cl)cccc12] |
| 315 | 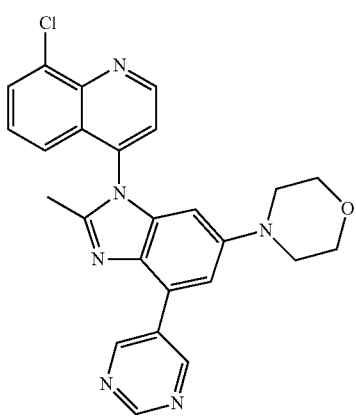 [SMILES: Cc1nc2c(-c3cncnc3)cc(N3CCOCC3)cc2n1-c1ccnc2c(Cl)cccc12] |
| 316 | 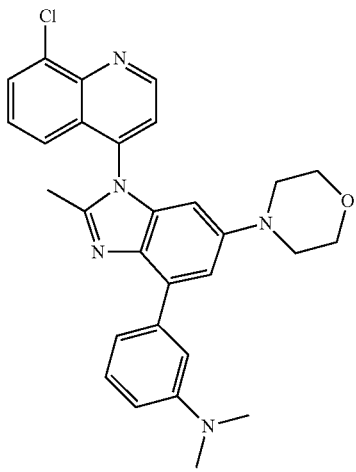 [SMILES: Cc1nc2c(-c3cccc(N(C)C)c3)cc(N3CCOCC3)cc2n1-c1ccnc2c(Cl)cccc12] |

| Example | Structure |
|---|---|
| 317 | 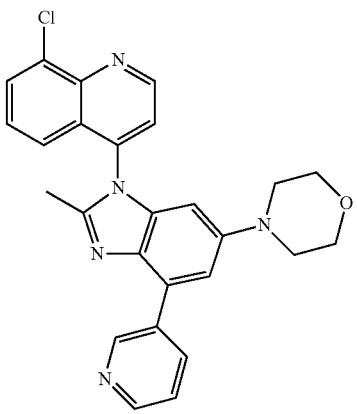 [SMILES: Cc1nc2c(-c3cccnc3)cc(N3CCOCC3)cc2n1-c1ccnc2c(Cl)cccc12] |
| 318 | 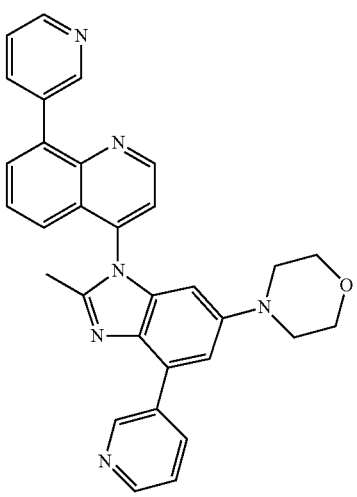 [SMILES: Cc1nc2c(-c3cccnc3)cc(N3CCOCC3)cc2n1-c1ccnc2c(-c3cccnc3)cccc12] |
| 319 | 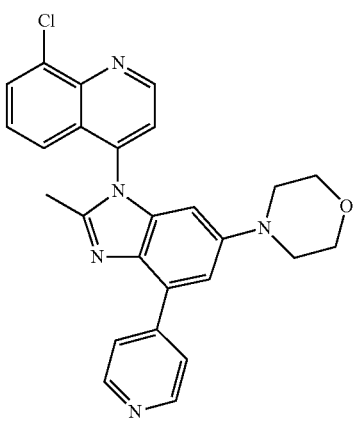 [SMILES: Cc1nc2c(-c3ccncc3)cc(N3CCOCC3)cc2n1-c1ccnc2c(Cl)cccc12] |
| 320 | 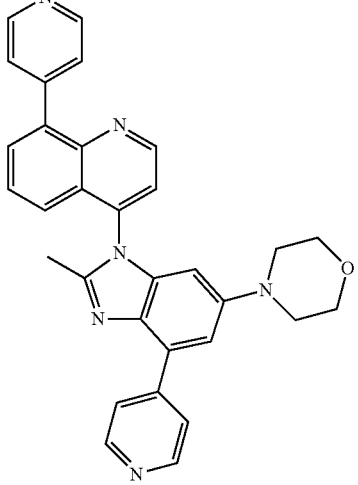 |
| 321 | 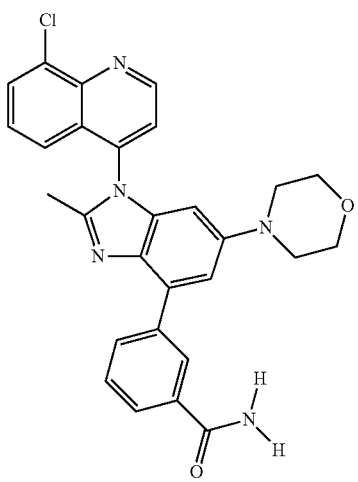 [SMILES: Cc1nc2c(-c3cccc(C(N)=O)c3)cc(N3CCOCC3)cc2n1-c1ccnc2c(Cl)cccc12] |
| 322 | 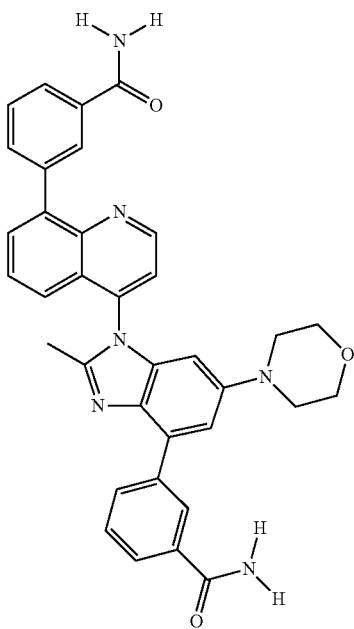 [SMILES: Cc1nc2c(-c3cccc(C(N)=O)c3)cc(N3CCOCC3)cc2n1-c1ccnc2c(-c3cccc(C(N)=O)c3)cccc12] |

-continued
| Example | Structure |
|---------|-----------|
| 323 | 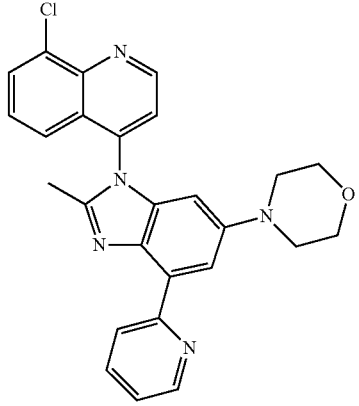 [SMILES: Cc1nc2c(-c3ccccn3)cc(N3CCOCC3)cc2n1-c1ccnc2c(Cl)cccc12] |
| 329 | 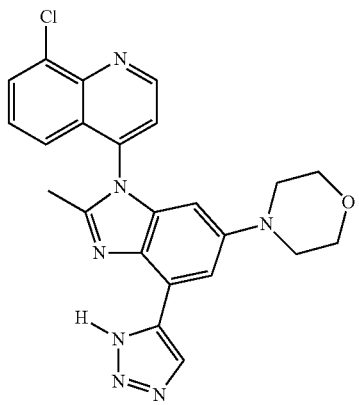 |
| 330 | 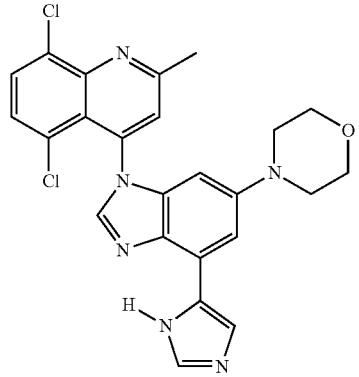 [SMILES: Cc1cc(-n2cnc3c(-c4cnc[nH]4)cc(N4CCOCC4)cc32)c2c(Cl)ccc(Cl)c2n1] |
-continued
| Example | Structure |
|---------|-----------|
| 331 | 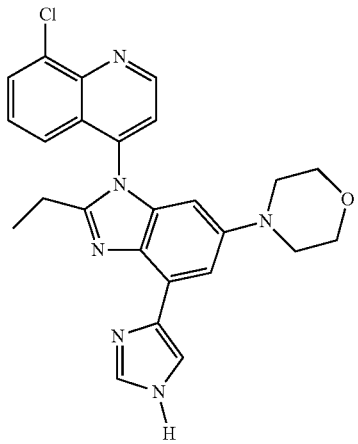 [SMILES: CCc1nc2c(-c3c[nH]cn3)cc(N3CCOCC3)cc2n1-c1ccnc2c(Cl)cccc12] |
| 332 | 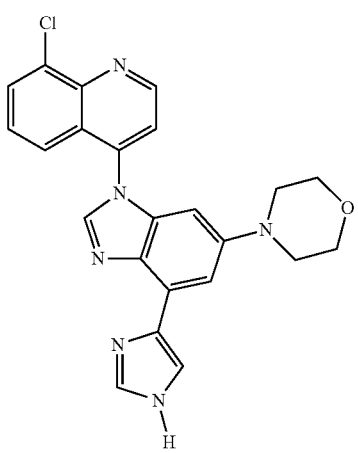 [SMILES: Clc1cccc2c(-n3cnc4c(-c5c[nH]cn5)cc(N5CCOCC5)cc43)ccnc12] |
| 333 | 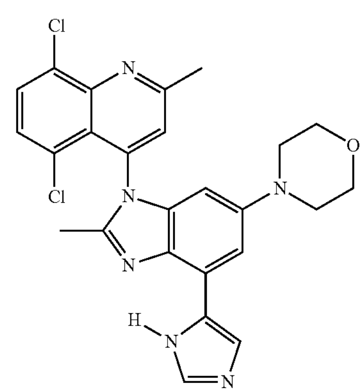 [SMILES: Cc1cc(-n2c(C)nc3c(-c4cnc[nH]4)cc(N4CCOCC4)cc32)c2c(Cl)ccc(Cl)c2n1] |

-continued

| Example | Structure |
|---------|-----------|
| 334 | 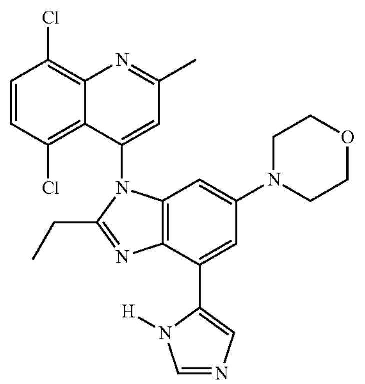 [SMILES: CCc1nc2c(-c3cnc[nH]3)cc(N3CCOCC3)cc2n1-c1cc(C)nc2c(Cl)ccc(Cl)c12] |
| 335 | 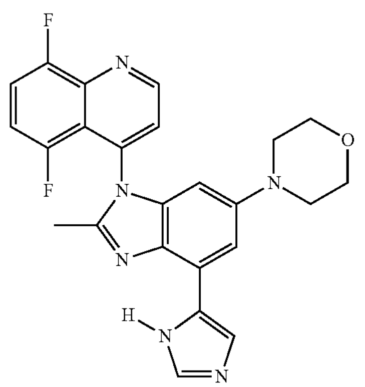 [SMILES: Cc1nc2c(-c3cnc[nH]3)cc(N3CCOCC3)cc2n1-c1ccnc2c(F)ccc(F)c12] |
| 336 | 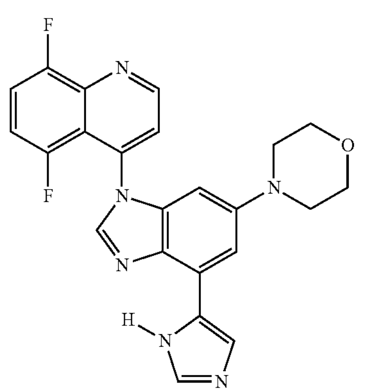 [SMILES: Fc1ccc(F)c2c(-n3cnc4c(-c5cnc[nH]5)cc(N5CCOCC5)cc43)ccnc12] |
| 337 | 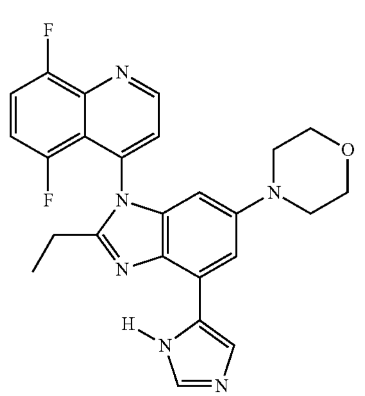 [SMILES: CCc1nc2c(-c3cnc[nH]3)cc(N3CCOCC3)cc2n1-c1ccnc2c(F)ccc(F)c12] |

-continued

| Example | Structure |
|---------|-----------|
| 340 | 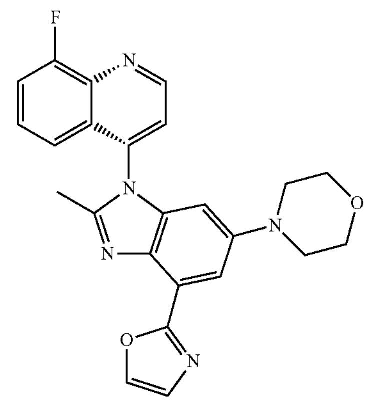 |
| 341 | 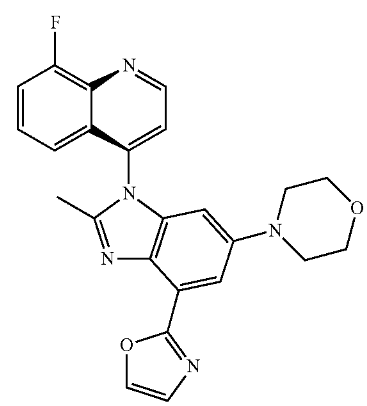 |
| 342 | 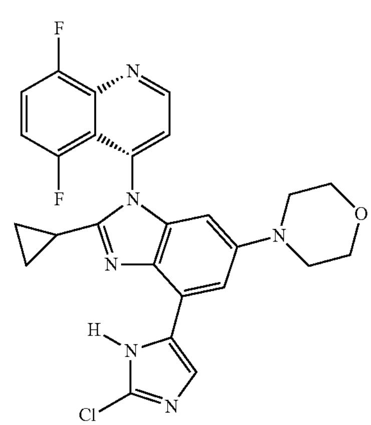 |

TABLE -continued
| Example | Structure |
|---|---|
| 343 | 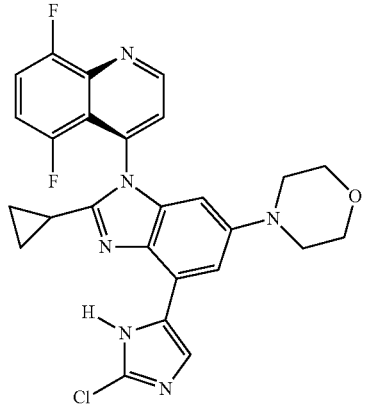 |
| 344 | 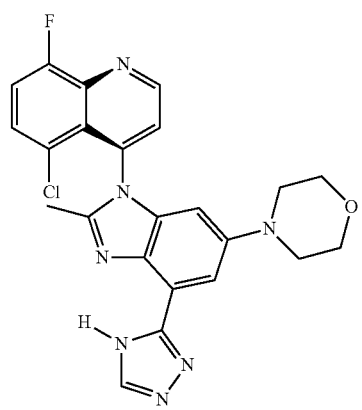 |
| 345 | 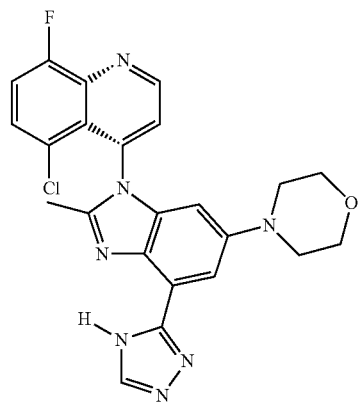 |
| 346 | 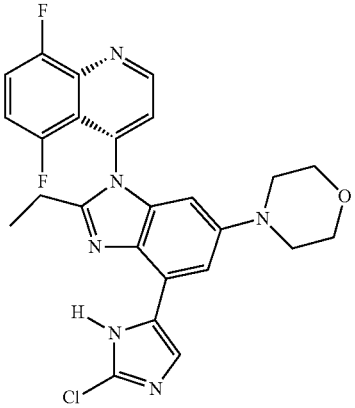 |
| 347 | 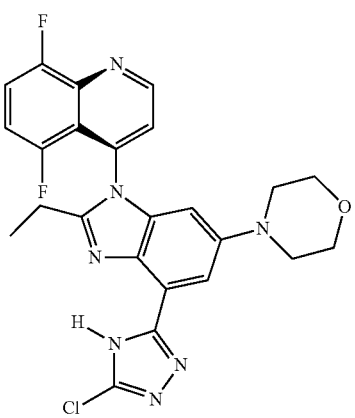 |
| 348 | 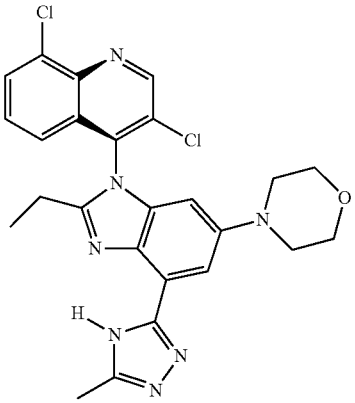 |

-continued
| Example | Structure |
|---------|-----------|
| 349 | 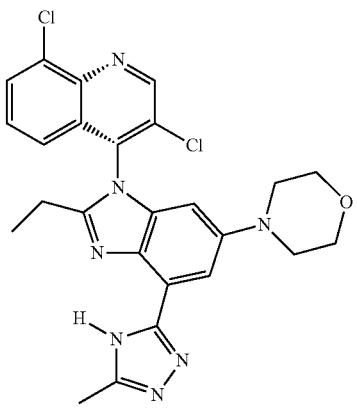 |
| 350 | 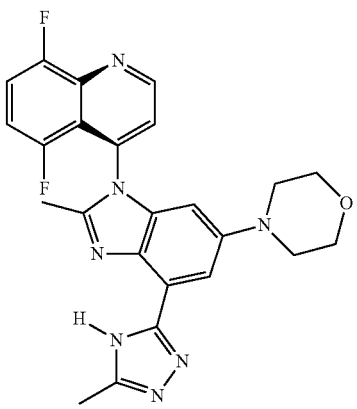 |
| 351 | 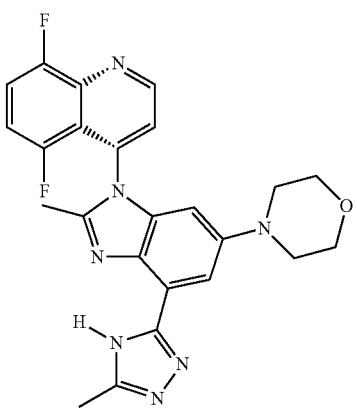 |
-continued
| Example | Structure |
|---------|-----------|
| 352 | 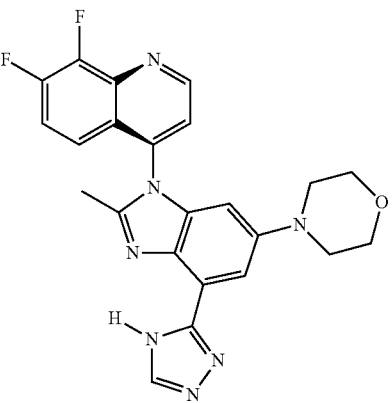 |
| 353 | 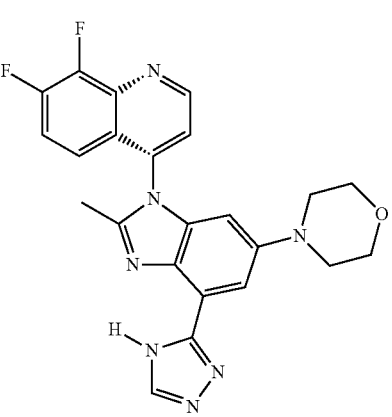 |
| 354 | 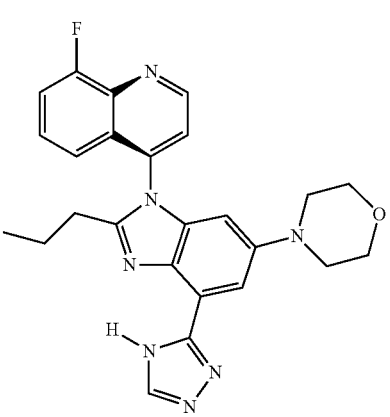 |

375
-continued
| Example | Structure |
|---|---|
| 355 | 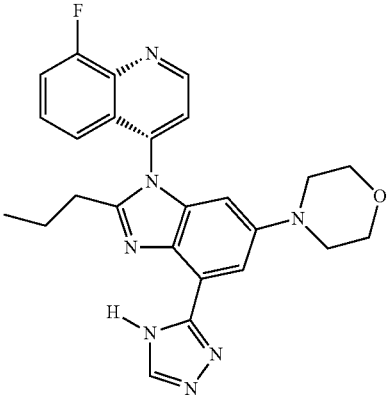 |
| 356 | 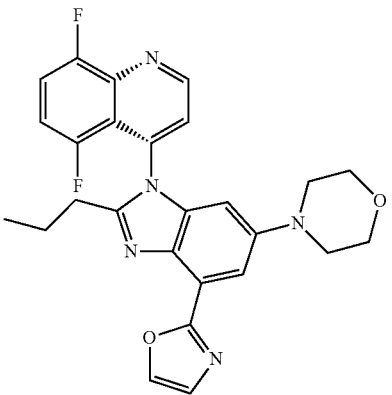 |
| 357 | 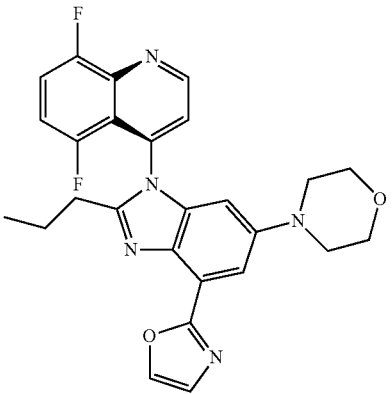 |
| 358 | 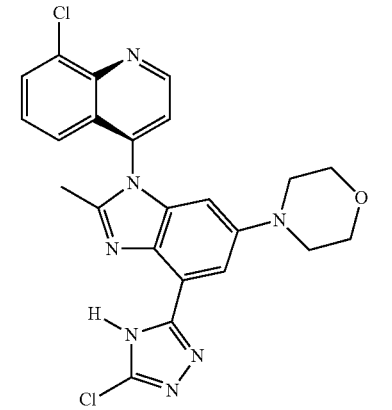 |
376
-continued
| Example | Structure |
|---|---|
| 359 | 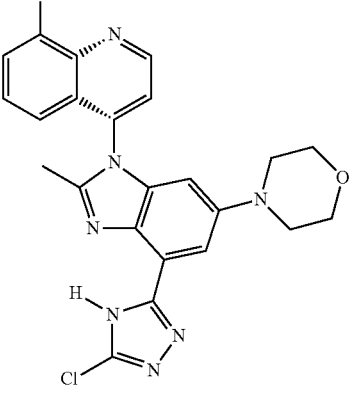 |
| 360 | 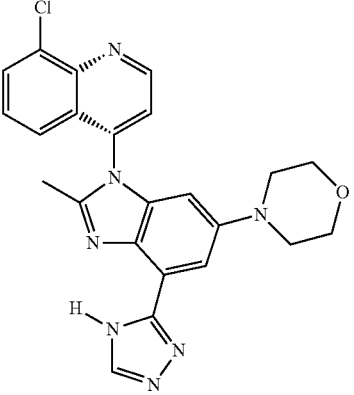 |
| 361 | 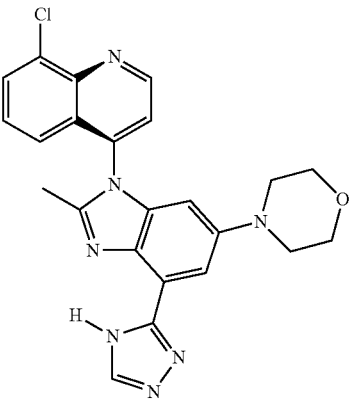 |
| 362 | 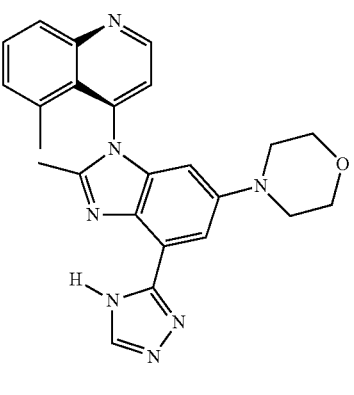 |

| Example | Structure |
|---------|-----------|
| 363 | 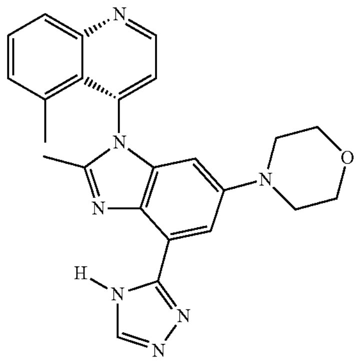 |
or a pharmaceutically acceptable salt, isomer, or a mixture thereof.
18. The compound of claim 1, wherein the compound is selected from the group consisting of:
| Compound No. | Structure |
|--------------|-----------|
| 341 | 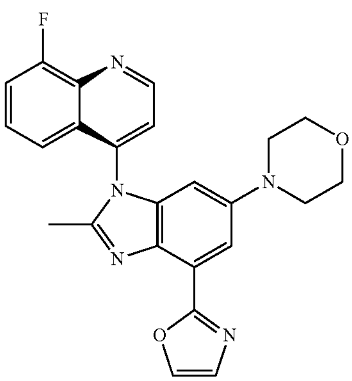 |
| 344 | 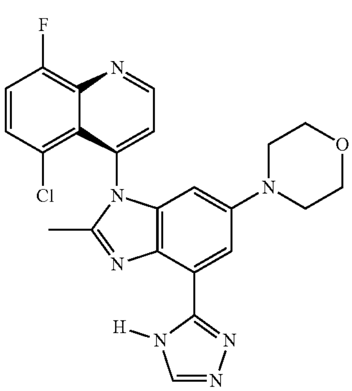 |
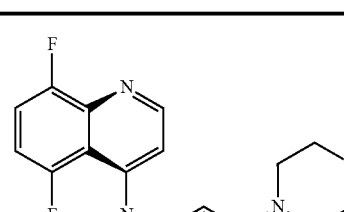
| Compound No. | Structure |
|--------------|-----------|
| 347 | 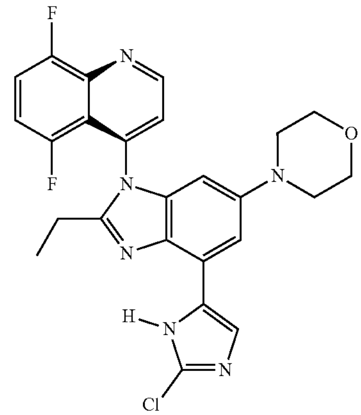 |
| 348 | 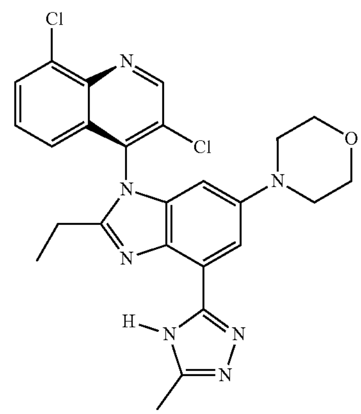 |
| 350 | 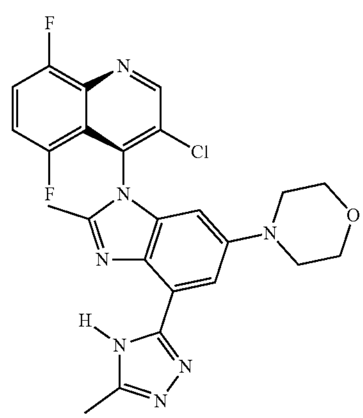 |
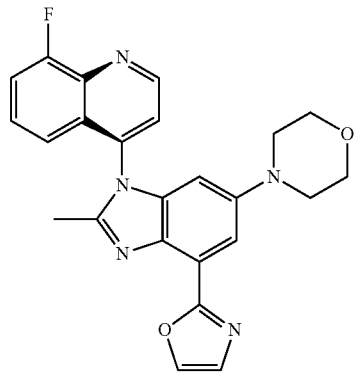

379
-continued
| Compound No. | Structure |
|---|---|
| 352 | 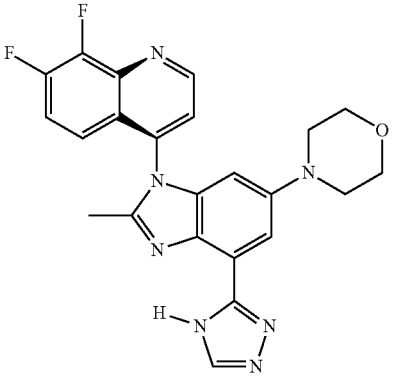 |
| 354 | 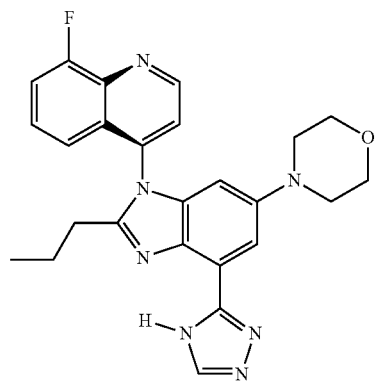 |
| 357 | 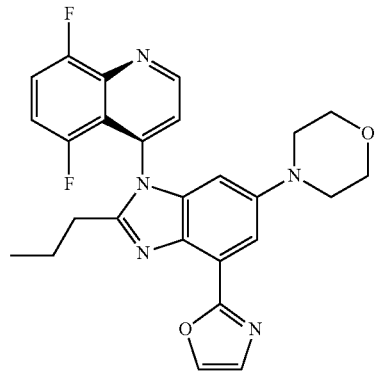 |
| 361 | 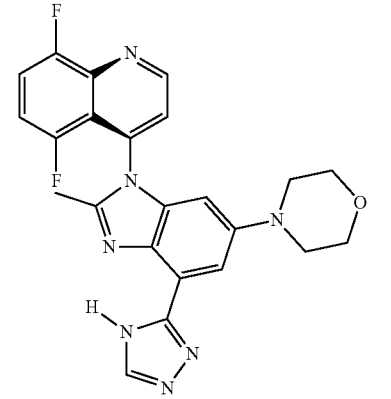 |
or a pharmaceutically acceptable salt, isomer, or a mixture thereof.
380
19. The compound of claim 1, wherein the compound is selected from the group consisting of:
| Example | Image |
|---|---|
| 149 | 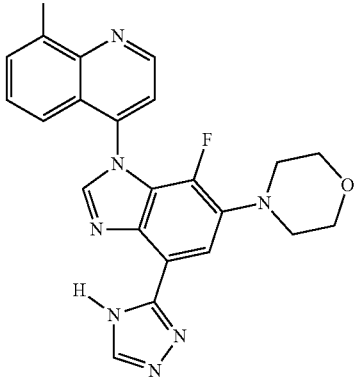 |
| 150 | 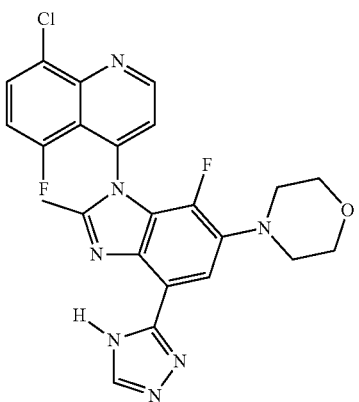 [SMILES: Cc1nc2c(-c3nnc[nH]3)cc(N3CCOCC3)c(F)c2n1-c1ccnc2c(Cl)ccc(F)c12] |
| 151 | 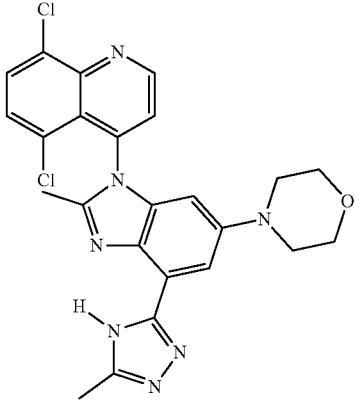 [SMILES: Cc1nnc(-c2cc(N3CCOCC3)cc3c2nc(C)n3-c2ccnc3c(Cl)ccc(Cl)c23)[nH]1] |

381
-continued
| Example | Image |
| --- | --- |
| 152 | 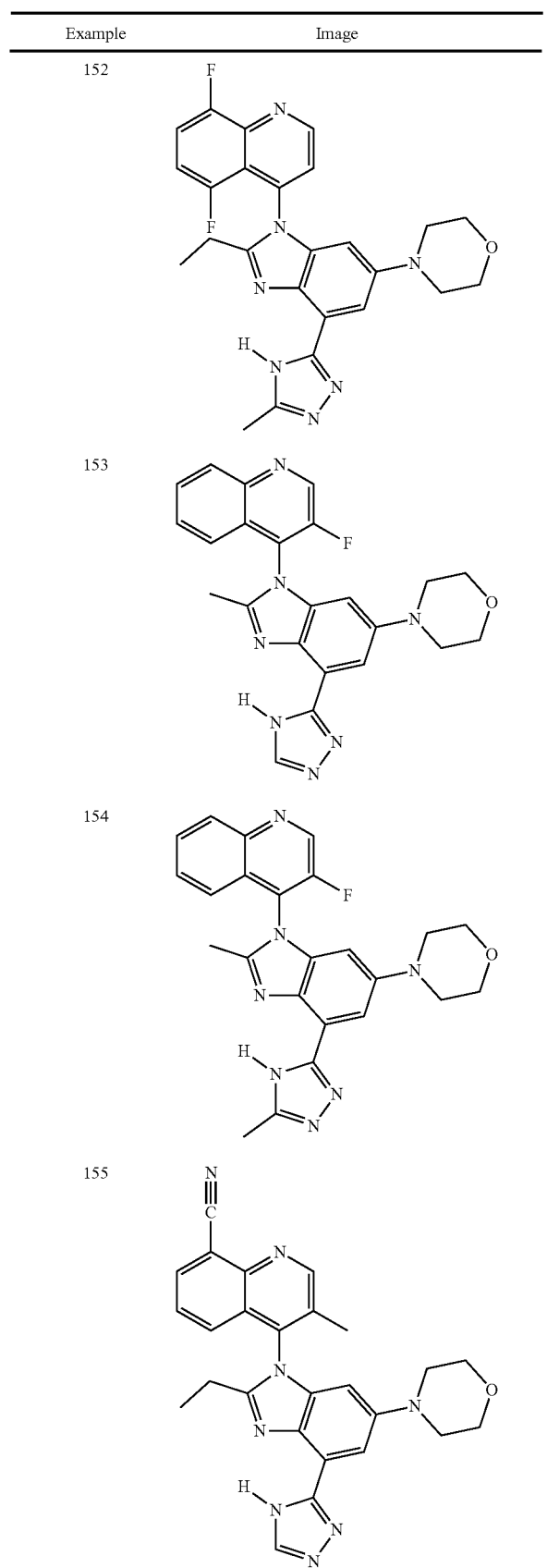 |
| 153 | |
| 154 | |
| 155 | |
382
-continued
| Example | Image |
| --- | --- |
| 156 | 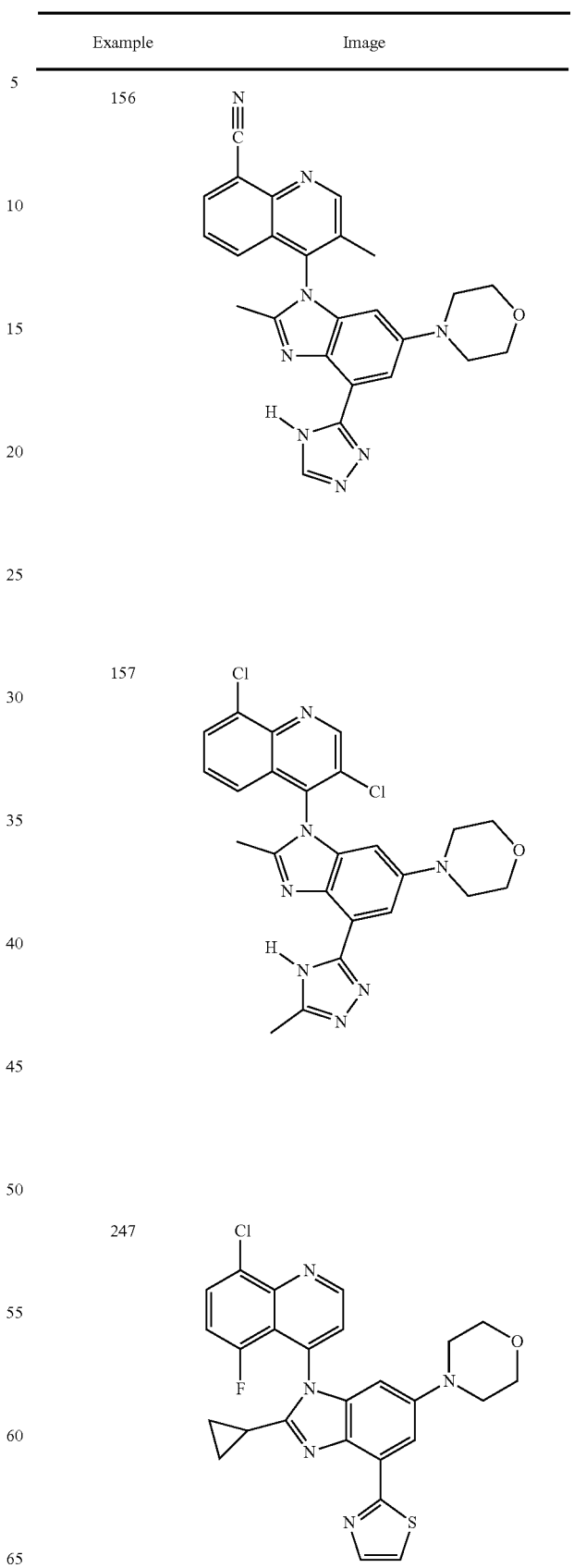 |
| 157 | |
| 247 | |

| Example | Image |
|---------|-------|
| 364 | |
| 365 | |
| 366 | |
| 367 | |
| 368 | |
| 369 | |
| 370 | |

385
-continued
| Example | Image |
|---------|-------|
| 371 | 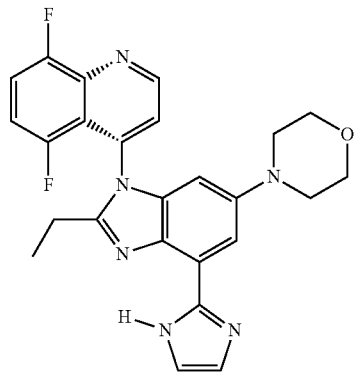 |
| 372 | 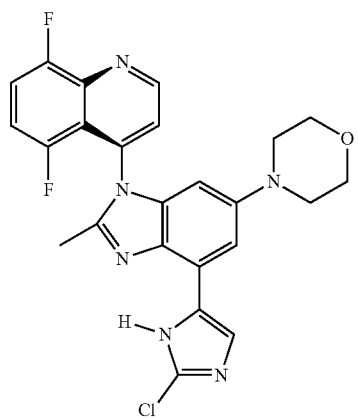 |
| 373 | 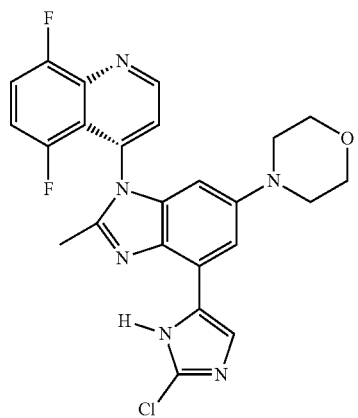 |
386
-continued
| Example | Image |
|---------|-------|
| 374 | 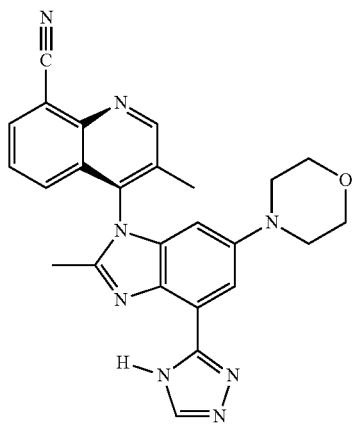 |
| 375 | |
| 376 | 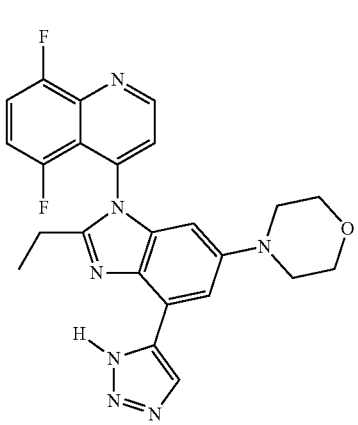 [SMILES: CCc1nc2c(-c3cnn[nH]3)cc(N3CCOCC3)cc2n1-c1ccnc2c(F)ccc(F)c12] |

387
-continued
| Example | Image |
|---|---|
| 377 | 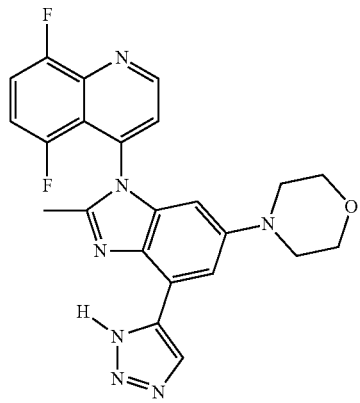 [SMILES: Cc1nc2c(-c3cnn[nH]3)cc(N3CCOCC3)cc2n1-c1ccnc2c(F)ccc(F)c12] |
| 378 | 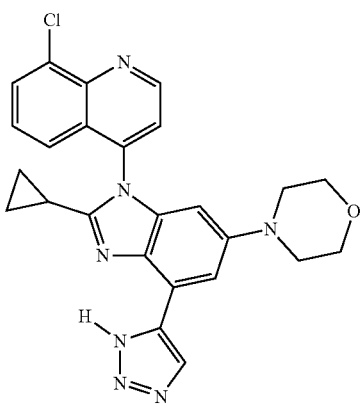 [SMILES: Clc1cccc2c(-n3c(C4CC4)nc4c(-c5cnn[nH]5)cc(N5CCOCC5)cc43)ccnc12] |
| 379 | 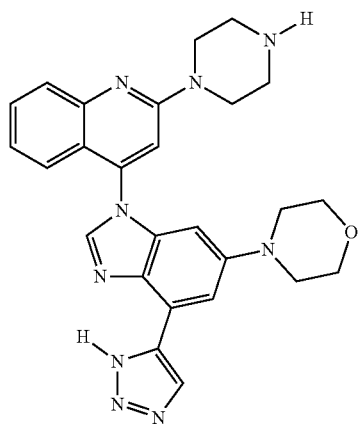 [SMILES: c1ccc2c(-n3cnc4c(-c5cnn[nH]5)cc(N5CCOCC5)cc43)cc(N3CCNCC3)nc2c1] |
388
-continued
| Example | Image |
|---|---|
| 380 | 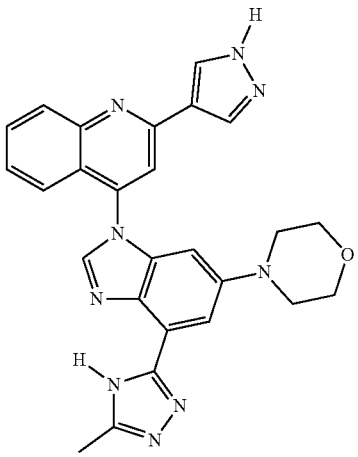 [SMILES: Cc1nnc(-c2cc(N3CCOCC3)cc3c2ncn3-c2cc(-c3cn[nH]c3)nc3ccccc23)[nH]1] |
| 381 | 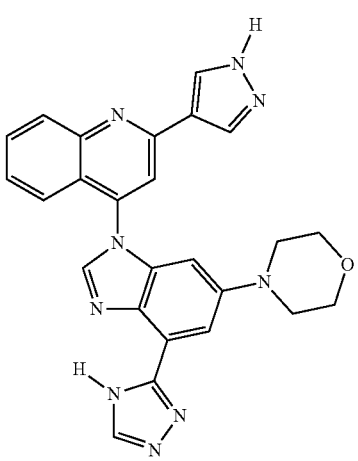 [SMILES: c1ccc2c(-n3cnc4c(-c5nnc[nH]5)cc(N5CCOCC5)cc43)cc(-c3cn[nH]c3)nc2c1] |
| 382 | 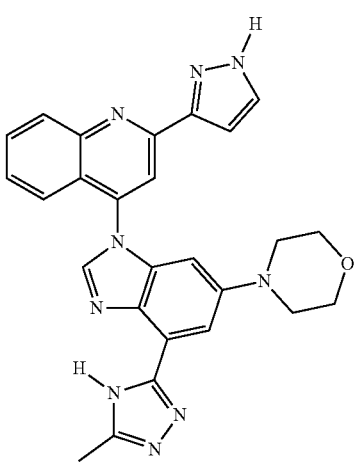 [SMILES: Cc1nnc(-c2cc(N3CCOCC3)cc3c2ncn3-c2cc(-c3cc[nH]n3)nc3ccccc23)[nH]1] |

| Example | Image |
|---|---|
| 383 | (structure) |
| 387 | (structure) |
| 388 | (structure) |
| 389 | (structure) |
| 390 | (structure) |
| 391 | (structure) |
| 392 | (structure) |

| Example | Image |
|---------|-------|
| 393 | 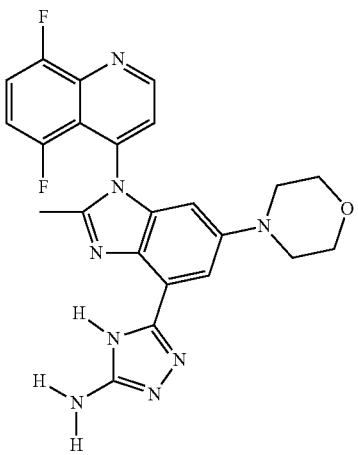 [SMILES: Cc1nc2c(-c3nnc(N)[nH]3)cc(N3CCOCC3)cc2n1-c1ccnc2c(F)ccc(F)c12] |
| 394 | 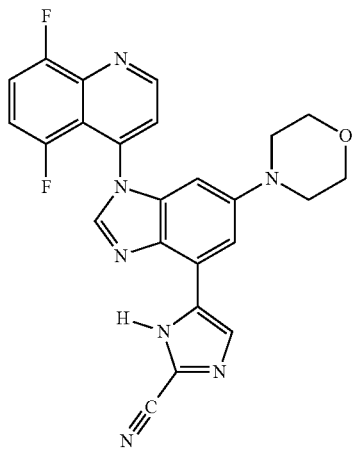 [SMILES: N#Cc1ncc(-c2cc(N3CCOCC3)cc3c2ncn3-c2ccnc3c(F)ccc(F)c23)[nH]1] |
or a pharmaceutically acceptable salt, isomer, or a mixture thereof.
20. A pharmaceutical composition comprising the compound of claim 1, or a pharmaceutically acceptable salt, isomer, or a mixture thereof, and at least one pharmaceutically acceptable vehicle.
\* \* \* \* \*